(12) United States Patent
DiPersio et al.

(10) Patent No.: US 12,304,941 B2
(45) Date of Patent: May 20, 2025

(54) SUPPRESSION OF CYTOKINE RELEASE SYNDROME IN CHIMERIC ANTIGEN RECEPTOR CELL THERAPY

(71) Applicant: Washington University, St. Louis, MO (US)

(72) Inventors: John DiPersio, St. Louis, MO (US); Matthew Cooper, St. Louis, MO (US); Alun Carter, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 17/746,645

(22) Filed: May 17, 2022

(65) Prior Publication Data

US 2023/0074186 A1    Mar. 9, 2023

Related U.S. Application Data

(63) Continuation of application No. 16/428,362, filed on May 31, 2019, now abandoned.

(60) Provisional application No. 62/679,597, filed on Jun. 1, 2018.

(51) Int. Cl.
| | |
|---|---|
| C07K 14/725 | (2006.01) |
| A61K 39/00 | (2006.01) |
| A61K 40/11 | (2025.01) |
| A61K 40/15 | (2025.01) |
| A61K 40/22 | (2025.01) |
| A61K 40/31 | (2025.01) |
| A61K 40/41 | (2025.01) |
| A61K 40/42 | (2025.01) |
| A61P 35/00 | (2006.01) |
| C07K 16/28 | (2006.01) |
| C12N 5/0783 | (2010.01) |
| C12N 15/90 | (2006.01) |

(52) U.S. Cl.
CPC .......... *C07K 14/7051* (2013.01); *A61K 40/11* (2025.01); *A61K 40/15* (2025.01); *A61K 40/22* (2025.01); *A61K 40/31* (2025.01); *A61K 40/418* (2025.01); *A61K 40/4202* (2025.01); *A61K 40/421* (2025.01); *A61K 40/4211* (2025.01); *A61P 35/00* (2018.01); *C07K 16/28* (2013.01); *C12N 5/0636* (2013.01); *C12N 5/0638* (2013.01); *C12N 15/907* (2013.01); *A61K 2239/29* (2023.05); *A61K 2239/31* (2023.05); *A61K 2239/38* (2023.05); *A61K 2239/48* (2023.05); *C12N 2310/20* (2017.05)

(58) Field of Classification Search
CPC ..... A61K 35/17; A61P 35/00; C07K 14/7051; C07K 16/28; C12N 15/907
See application file for complete search history.

(56) References Cited

U.S. PATENT DOCUMENTS

| | | |
|---|---|---|
| 10,494,434 B2 | 12/2019 | Riddell et al. |
| 2015/0202286 A1 | 7/2015 | June et al. |
| 2017/0334964 A1 | 11/2017 | Pulé et al. |
| 2017/0356010 A1 | 12/2017 | Frost et al. |
| 2018/0008638 A1 | 1/2018 | Campana et al. |
| 2018/0371052 A1 | 12/2018 | Ma et al. |
| 2020/0061116 A1 | 2/2020 | Novik et al. |

FOREIGN PATENT DOCUMENTS

| | | | |
|---|---|---|---|
| WO | WO-2015066262 A1 * | 5/2015 | ........... C12N 5/0636 |
| WO | 2017180989 A2 | 10/2017 | |
| WO | 2018027036 A1 | 2/2018 | |
| WO | 2018064602 A1 | 4/2018 | |
| WO | 2018068354 A1 | 4/2018 | |
| WO | 2018073391 A1 | 4/2018 | |
| WO | 2018073393 A2 | 4/2018 | |
| WO | WO-2018132513 A1 * | 7/2018 | ............. A61K 35/17 |
| WO | 2019070680 A2 | 4/2019 | |
| WO | 2019076489 A1 | 4/2019 | |
| WO | 2019099993 A1 | 5/2019 | |
| WO | 2019232425 A1 | 12/2019 | |

OTHER PUBLICATIONS

Giavridis et al. "CAR T cell-induced cytokine release syndrome is mediated by macrophages and abated by IL-1 blockade", Nat Med. Jun. 2018;24(6):731-738 (Year: 2018).*
Eyquem et al. "Targeting a CAR to the TRAC locus with CRISPR/Cas9 enhances tumour rejection", Nature. Mar. 2, 2017;543(7643):113-117 (Year: 2017).*
Ran et al. "Genome engineering using the CRISPR-Cas9 system", Nat Protoc. Nov. 2013; 8(11): 2281-2308 (Year: 2013).*
Rooney et al. "Modeling cytokine release syndrome", Nat Med. Jun. 2018;24(6):705-706 (Year: 2018).*
Cherkassky L., et al., "Human CAR T Cells With Cell-intrinsic PD-1 Checkpoint Blockade Resist Tumor-mediated Inhibition," Journal of clinical investigation, Aug. 2016, vol. 126, No. 8, pp. 3130-3144.
Extended European Search Report for European Application No. 19810633.8, mailed Feb. 21, 2022, 06 Pages.

(Continued)

*Primary Examiner* — Amy E Juedes
*Assistant Examiner* — Peter Johansen
(74) *Attorney, Agent, or Firm* — Polsinelli PC

(57) ABSTRACT

Disclosed herein are methods of gene editing, or endogenous suppression, of cytokines/chemokines/transcription factors secreted from chimeric antigen receptor (CAR)-bearing immune effector cell such as CAR-T cells for the mitigation of cytokine release syndrome and/or CAR-T associated neuropathy. These methods involve insertion of the CAR into a locus of a cytokine gene, blocking its expression. Also disclosed herein are (CAR)-bearing immune effector cells with CARs inserted into a locus of a cytokine gene, and methods of treatment of diseases with immunotherapy with a reduced incidence of cytokine release syndrome and/or CAR-T associated neuropathy.

15 Claims, 11 Drawing Sheets

Specification includes a Sequence Listing.

(56) References Cited

OTHER PUBLICATIONS

Giavridis T., et al., "CAR T Cell-induced Cytokine Release Syndrome is Mediated by Macrophages and Abated by IL-1 Blockade," Nature Medicine, May 28, 2018, Nature Publishing Co., New York, Jun. 2018, vol. 24, No. 6, pp. 731-738, 19 Pages, DOI: 10.1038/S41591-018-0041-7, ISSN 1078-8956, XP036519593.
Heczey A., et al., "Invariant NKT Cells with Chimeric Antigen Receptor Provide a Novel Platform for Safe and Effective Cancer Immunotherapy," Blood, Oct. 30, 2014, vol. 124 (18), pp. 2824-2833.
International Preliminary Report on Patentability for International Application No. PCT/US2019/034981, mailed Dec. 10, 2020, 13 Pages.
International Search Report and Written Opinion for International Application No. PCT/US2019/034981, mailed Oct. 1, 2019, 16 pages.
Karschnia P., et al., "Clinical Presentation, Management, and Biomarkers of Neurotoxicity After Adoptive Immunotherapy with CAR T Cells," Blood, May 16, 2019, vol. 133, No. 20, pp. 2212-2221.
Lee D.W., et al., "Current Concepts in the Diagnosis and Management of Cytokine Release Syndrome," Blood, Jul. 10, 2014, vol. 124, No. 2, pp. 188-195.
Lee D.W., et al., "The Future Is Now: Chimeric Antigen Receptors as New Targeted Therapies for Childhood Cancer," Clinical Cancer Research, May 15, 2012, vol. 18, No. 10, pp. 2780-2790.
Macleod T.D., et al., "Integration of a CD19 CAR into the TCR Alpha Chain Locus Streamlines Production of Allogeneic Gene-Edited CAR T Cells," Molecular Therapy, Apr. 2017, vol. 25 (4), pp. 949-961.
NCBI Reference Sequence NP_001139345.1: "T-Cell Surface Glycoprotein Cd8 Alpha Chain Isoform 1 Precursor [*Homo sapiens*]," NCBI, 3 Pages, [Retrieved on Jun. 7, 2020] Retrieved from URL: https://www.ncbi.nlm.nih.gov/protein/NP_001139345.1.
Neelapu S.S., et al., "Axicabtagene Ciloleucel CAR T-Cell Therapy in Refractory Large B-Cell Lymphoma," New England Journal of Medicine, Dec. 28, 2017, vol. 377, No. 26, pp. 2531-2544.
Norelli M., et al., "Monocyte-Derived IL-1 and IL-6 Are Differentially Required for Cytokine-Release Syndrome and Neurotoxicity Due to CAR T Cells," Nature Medicine, Jun. 2018, vol. 24, pp. 739-748, 16 Pages.
Parajuli B., et al., "GM-CSF Increases LPS-induced Production of Proinflammatory Mediators via Upregulation of TLR4 and CD14 in Murine Microglia," Journal of Neuroinflammation, Dec. 13, 2012, vol. 9, No. 268, 12 Pages.
Prudent V., et al., "Chimeric Antigen Receptor T-cell Neuropsychiatric Toxicity in Acute Lymphoblastic Leukemia," Published in final edited form as: Palliat Support Care, HHS Public Access Author Manuscript, Aug. 1, 2017, vol. 15, No. 4, pp. 499-503, 7 Pages.
Sachdeva M., et al., "Granulocyte-macrophage Colony-stimulating Factor Inactivation in CAR T-Cells Prevents Monocyte-dependent Release of Key Cytokine Release Syndrome Mediators," Journal of Biological Chemistry, Feb. 25, 2019, vol. 294, No. 14, pp. 5430-5437.
Santomasso B., et al., "Biomarkers Associated with Neurotoxicity in Adult Patients with Relapsed or Refractory B-ALL (R/R B-ALL) Treated with CD19 CAR T Cells," Journal of Clinical Oncology, May 30, 2017, vol. 35, No. 15, p. 3019 (2 Pages).
Shearer R.F., et al., "Experimental Design for Stable Genetic Manipulation in Mammalian Cell Lines: Lentivirus and Alternatives," Genes to Cells, 2015, vol. 20, pp. 1-10.
Sterner R.M., et al., "GM-CSF Blockade during Chimeric Antigen Receptor T Cell Therapy Reduces Cytokine Release Syndrome and Neurotoxicity and May Enhance Their Effector Functions," American Society of Hematology Annual Meeting, Oral and Poster Abstracts, Session 703, Adoptive Immunotherapy: Preclinical Studies to Improve Safety and Efficacy of CAR-T Cells, Dec. 3, 2018, 3 Pages.
Sterner R.M., et al., "GM-CSF Inhibition Reduces Cytokine Release Syndrome and Neuroinflammation but Enhances CAR-T Cell Function in Xenografts," Blood, Feb. 14, 2019, vol. 133, No. 7, pp. 697-709.
U.S. Department of Health and Human Services, "Common Terminology Criteria for Adverse Events (CTCAE)," National Institutes of Health, National Cancer Institute, NIH Publication 09-5410, Version 4.03, Jun. 14, 2010, 196 pages.
Xu X-J., et al., "Cytokine Release Syndrome in Cancer Immunotherapy with Chimeric Antigen Receptor Engineered T cells," Cancer Letters, Feb. 28, 2014, vol. 343, No. 2, pp. 172-178.
Zheng W., et al., "Modulation of PI3K Signaling to Improve CAR T Cell Function," Oncotarget, 2018, vol. 9 (88), pp. 35807-35808.

* cited by examiner

FIG. 11

ELISA plate layout - IL6 CAR GMCSF KO experiment 24 hr

| | Standard | | Controls | | | | CAR19 Control | | | CAR19 GM-CSF KO | | |
|---|---|---|---|---|---|---|---|---|---|---|---|---|
| | 1 | 2 | 3 | 4 | 5 | 6 | 7 | 8 | 9 | 10 | 11 | 12 |
| A | STD1 300 | STD1 300 | CAR19 T cells (50K) | | CAR19 (50K) + Act MQ (5K) | CAR19 (50K) + Act MQ | CAR19 (50K) + iDC + Beads | | | CAR19 GM-CSF (50K) + iDC + Beads | | |
| B | STD2 100 | STD2 100 | iDC (1K) | | CAR19 (50K) + RAMOS (5K) | CAR19 (50K) + MQ | CAR19 (50K) + iDC + RAMOS | | | CAR19 GM-CSF (50K) + iDC + RAMOS | | |
| C | STD3 50 | STD3 50 | Beads (50K) | | CAR19 (50K) + RAMOS (50K) | | CAR19 (50K) + Act MQ + RAMOS | | | CAR19 GM-CSF (50K) + Act MQ + RAMOS | | |
| D | STD4 25 | STD4 25 | Activated MQ (5K) | | iDC (1K) + Beads (50K) | | CAR19 (50K) + MQ + RAMOS | | | CAR19 GM-CSF (50K) + MQ + RAMOS | | |
| E | STD5 12.5 | STD5 12.5 | MQ (5K) | | Act MQ (5K) + Beads (50K) | | CAR19 (12.5K) + iDC + Beads | | | CAR19 GM-CSF (12.5K) + iDC + Beads | | |
| F | STD6 6.25 | STD6 6.25 | RAMOS (50K) | | MQ (5K) + Beads (50K) | | CAR19 (12.5K) + iDC + RAMOS | | | CAR19 GM-CSF (12.5K) + iDC + RAMOS | | |
| G | STD7 3.125 | STD7 3.125 | CAR19 (50K) + iDC (1K) | | CAR19 (50K) + iDC (1K) | | CAR19 (12.5K) + Act MQ + RAMOS | | | CAR19 GM-CSF (12.5K) + Act MQ + RAMOS | | |
| H | STD8 0 | STD8 0 | CAR19 (50K) + Beads (50K) | | CAR19 (50K) + Beads (50K) | | CAR19 (12.5K) + MQ + RAMOS | | | CAR19 GM-CSF (12.5K) + MQ + RAMOS | | |

FIG. 12a results of ELISA (top half) - IL6 CAR GMCSF KO experiment 24 hr

|   | 1 | 2 | 3 | 4 | 5 | 6 | 7 | 8 | 9 | 10 | 11 | 12 |   |
|---|---|---|---|---|---|---|---|---|---|----|----|----|---|
| A | 2.139 | 2.206 | 0.084 | 0.079 | 0.1 | 0.099 | 0.782 | 0.871 | 0.738 | 0.452 | 0.475 | 0.472 | 450 [test] |
|   | 0.082 | 0.076 | 0.055 | 0.048 | 0.044 | 0.046 | 0.055 | 0.058 | 0.055 | 0.079 | 0.05 | 0.051 | 540 [test] |
|   | 11.427 | 11.833 | 0.162 | 0.171 | 0.308 | 0.296 | 4.043 | 4.517 | 3.797 | 2.07 | 2.363 | 2.341 | pathlength |
|   | 2.141 | 2.202 | 0.084 | 0.079 | 0.1 | 0.099 | 0.782 | 0.87 | 0.742 | 0.453 | 0.478 | 0.476 | 450 |
|   | 0.083 | 0.076 | 0.054 | 0.048 | 0.044 | 0.046 | 0.054 | 0.058 | 0.055 | 0.079 | 0.05 | 0.051 | 540 |
|   | 0.187 | 0.186 | 0.52 | 0.462 | 0.325 | 0.335 | 0.193 | 0.192 | 0.195 | 0.219 | 0.202 | 0.203 | corrected [450] |
|   | 0.007 | 0.006 | 0.335 | 0.281 | 0.144 | 0.154 | 0.013 | 0.013 | 0.015 | 0.038 | 0.021 | 0.022 | corrected [540] |
| B | 0.806 | 0.833 | 0.083 | 0.073 | 0.081 | 0.084 | 0.274 | 0.301 | 0.324 | 0.248 | 0.235 | 0.236 | 630 [test] |
|   | 0.054 | 0.053 | 0.054 | 0.044 | 0.044 | 0.046 | 0.053 | 0.046 | 0.049 | 0.047 | 0.047 | 0.049 | 720 [test] |
|   | 4.177 | 4.331 | 0.159 | 0.164 | 0.206 | 0.21 | 1.226 | 1.416 | 1.532 | 1.116 | 1.047 | 1.041 | pathlength |
|   | 0.805 | 0.835 | 0.083 | 0.073 | 0.081 | 0.084 | 0.275 | 0.301 | 0.338 | 0.249 | 0.236 | 0.238 | 630 |
|   | 0.054 | 0.053 | 0.054 | 0.044 | 0.044 | 0.046 | 0.054 | 0.046 | 0.062 | 0.047 | 0.047 | 0.049 | 720 |
|   | 0.193 | 0.193 | 0.522 | 0.447 | 0.395 | 0.4 | 0.224 | 0.213 | 0.221 | 0.223 | 0.226 | 0.229 | corrected [450] |
|   | 0.013 | 0.012 | 0.342 | 0.267 | 0.215 | 0.217 | 0.044 | 0.033 | 0.04 | 0.042 | 0.045 | 0.047 | corrected [540] |
| C | 0.47 | 0.458 | 0.076 | 0.097 | 0.112 | 0.119 | 0.187 | 0.195 | 0.205 | 0.193 | 0.226 | 0.217 | 810 [test] |
|   | 0.049 | 0.048 | 0.048 | 0.045 | 0.045 | 0.044 | 0.046 | 0.045 | 0.052 | 0.047 | 0.047 | 0.047 | 900 [test] |
|   | 2.357 | 2.28 | 0.153 | 0.139 | 0.371 | 0.416 | 0.784 | 0.831 | 0.847 | 0.812 | 0.993 | 0.948 | pathlength |
|   | 0.469 | 0.458 | 0.076 | 0.07 | 0.112 | 0.119 | 0.187 | 0.195 | 0.205 | 0.194 | 0.226 | 0.218 | 810 |
|   | 0.049 | 0.048 | 0.049 | 0.045 | 0.046 | 0.044 | 0.046 | 0.046 | 0.053 | 0.047 | 0.048 | 0.049 | 900 |
|   | 0.291 | 0.201 | 0.496 | 0.507 | 0.302 | 0.286 | 0.239 | 0.235 | 0.242 | 0.239 | 0.228 | 0.23 | corrected [450] |
|   | 0.021 | 0.021 | 0.316 | 0.325 | 0.123 | 0.107 | 0.059 | 0.055 | 0.063 | 0.058 | 0.048 | 0.05 | corrected [540] |
| D | 0.271 | 0.277 | 0.087 | 0.086 | 0.071 | 0.079 | 0.252 | 0.267 | 0.291 | 0.234 | 0.242 | 0.254 | 990 [test] |
|   | 0.048 | 0.047 | 0.044 | 0.046 | 0.044 | 0.052 | 0.051 | 0.05 | 0.06 | 0.047 | 0.045 | 0.046 | 1080 [test] |
|   | 1.236 | 1.281 | 0.243 | 0.218 | 0.151 | 0.149 | 1.113 | 1.206 | 1.281 | 1.038 | 1.091 | 1.151 | pathlength |
|   | 0.272 | 0.277 | 0.087 | 0.085 | 0.071 | 0.079 | 0.252 | 0.268 | 0.292 | 0.234 | 0.242 | 0.253 | 990 |
|   | 0.049 | 0.047 | 0.044 | 0.046 | 0.045 | 0.053 | 0.051 | 0.051 | 0.062 | 0.048 | 0.046 | 0.047 | 1080 |
|   | 0.22 | 0.216 | 0.36 | 0.391 | 0.474 | 0.531 | 0.226 | 0.223 | 0.228 | 0.225 | 0.222 | 0.22 | corrected [450] |
|   | 0.039 | 0.037 | 0.182 | 0.212 | 0.298 | 0.354 | 0.046 | 0.042 | 0.048 | 0.046 | 0.042 | 0.041 | corrected [540] |

FIG. 12b results of ELISA (bottom half) - IL6 CAR GMCSF KO experiment 24 hr

| | 1 | 2 | 3 | 4 | 5 | 6 | 7 | 8 | 9 | 10 | 11 | 12 | |
|---|---|---|---|---|---|---|---|---|---|---|---|---|---|
| E | 0.172 | 0.17 | 0.073 | 0.075 | 0.085 | 0.084 | 0.492 | 0.557 | 0.42 | 0.18 | 0.247 | 0.19 | 450 [test] |
| | 0.046 | 0.045 | 0.044 | 0.046 | 0.045 | 0.045 | 0.05 | 0.053 | 0.05 | 0.048 | 0.048 | 0.047 | 540 [test] |
| | 0.698 | 0.691 | 0.161 | 0.161 | 0.222 | 0.216 | 2.46 | 2.796 | 2.054 | 0.735 | 1.107 | 0.794 | pathlength |
| | 0.171 | 0.17 | 0.073 | 0.075 | 0.085 | 0.084 | 0.496 | 0.558 | 0.42 | 0.181 | 0.249 | 0.19 | 450 |
| | 0.046 | 0.046 | 0.045 | 0.047 | 0.045 | 0.045 | 0.05 | 0.053 | 0.051 | 0.048 | 0.049 | 0.047 | 540 |
| | 0.245 | 0.246 | 0.454 | 0.468 | 0.533 | 0.399 | 0.202 | 0.2 | 0.204 | 0.246 | 0.225 | 0.239 | corrected [450] |
| | 0.066 | 0.066 | 0.277 | 0.291 | 0.203 | 0.209 | 0.02 | 0.019 | 0.025 | 0.066 | 0.044 | 0.059 | corrected [540] |
| F | 0.127 | 0.124 | 0.07 | 0.074 | 0.075 | 0.072 | 0.148 | 0.143 | 0.128 | 0.102 | 0.115 | 0.121 | 630 [test] |
| | 0.044 | 0.045 | 0.045 | 0.047 | 0.046 | 0.044 | 0.055 | 0.057 | 0.045 | 0.045 | 0.051 | 0.048 | 720 [test] |
| | 0.458 | 0.436 | 0.147 | 0.15 | 0.162 | 0.157 | 0.516 | 0.479 | 0.463 | 0.316 | 0.353 | 0.406 | pathlength |
| | 0.127 | 0.124 | 0.07 | 0.074 | 0.075 | 0.072 | 0.147 | 0.144 | 0.129 | 0.102 | 0.116 | 0.12 | 630 |
| | 0.045 | 0.045 | 0.046 | 0.047 | 0.046 | 0.044 | 0.055 | 0.057 | 0.045 | 0.045 | 0.052 | 0.048 | 720 |
| | 0.277 | 0.283 | 0.475 | 0.493 | 0.495 | 0.462 | 0.286 | 0.3 | 0.278 | 0.323 | 0.328 | 0.296 | corrected [450] |
| | 0.097 | 0.104 | 0.297 | 0.314 | 0.285 | 0.283 | 0.106 | 0.119 | 0.097 | 0.144 | 0.147 | 0.119 | corrected [540] |
| G | 0.098 | 0.1 | 0.078 | 0.073 | 0.104 | 0.122 | 0.143 | 0.169 | 0.144 | 0.125 | 0.134 | 0.131 | 810 [test] |
| | 0.044 | 0.044 | 0.046 | 0.044 | 0.045 | 0.05 | 0.049 | 0.049 | 0.05 | 0.05 | 0.045 | 0.046 | 900 [test] |
| | 0.301 | 0.313 | 0.179 | 0.161 | 0.326 | 0.398 | 0.523 | 0.667 | 0.523 | 0.415 | 0.493 | 0.469 | pathlength |
| | 0.099 | 0.101 | 0.078 | 0.073 | 0.103 | 0.122 | 0.144 | 0.169 | 0.144 | 0.125 | 0.133 | 0.13 | 810 |
| | 0.044 | 0.044 | 0.046 | 0.044 | 0.045 | 0.05 | 0.05 | 0.049 | 0.05 | 0.05 | 0.045 | 0.045 | 900 |
| | 0.328 | 0.322 | 0.437 | 0.452 | 0.317 | 0.306 | 0.275 | 0.254 | 0.275 | 0.301 | 0.269 | 0.277 | corrected [450] |
| | 0.148 | 0.142 | 0.259 | 0.272 | 0.138 | 0.127 | 0.095 | 0.074 | 0.096 | 0.12 | 0.091 | 0.096 | corrected [540] |
| H | 0.082 | 0.087 | 0.113 | 0.12 | 0.074 | 0.081 | 0.165 | 0.169 | 0.15 | 0.103 | 0.122 | 0.119 | 990 [test] |
| | 0.047 | 0.051 | 0.049 | 0.047 | 0.047 | 0.053 | 0.055 | 0.059 | 0.045 | 0.044 | 0.046 | 0.044 | 1080 [test] |
| | 0.197 | 0.336 | 0.356 | 0.406 | 0.15 | 0.157 | 0.611 | 0.607 | 0.579 | 0.329 | 0.422 | 0.412 | pathlength |
| | 0.082 | 0.087 | 0.113 | 0.12 | 0.074 | 0.081 | 0.165 | 0.169 | 0.15 | 0.103 | 0.122 | 0.118 | 990 |
| | 0.047 | 0.052 | 0.049 | 0.047 | 0.047 | 0.053 | 0.055 | 0.06 | 0.046 | 0.044 | 0.046 | 0.045 | 1080 |
| | 0.415 | 0.443 | 0.316 | 0.296 | 0.493 | 0.516 | 0.27 | 0.279 | 0.259 | 0.314 | 0.289 | 0.288 | corrected [450] |
| | 0.236 | 0.263 | 0.137 | 0.117 | 0.311 | 0.338 | 0.09 | 0.098 | 0.079 | 0.134 | 0.11 | 0.109 | corrected [540] |

SUPPRESSION OF CYTOKINE RELEASE SYNDROME IN CHIMERIC ANTIGEN RECEPTOR CELL THERAPY

This application claims the benefit of U.S. Provisional Application No. 62/679,597, filed Jun. 1, 2018, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Aug. 6, 2019, is named WGN0003-401-PC_SL.txt and is 956,834 bytes in size.

CAR-T cells have emerged as a promising therapy for the treatment of hematological malignancies. Despite remarkable clinical efficacy against B cell malignancies, the success of CAR-T therapy has been limited by severe, life-threatening toxicities, observed in over 50% of patients. These toxicities have resulted in several deaths leading to early termination of clinical trial. Toxicities primarily manifest as cytokine release syndrome (CRS, also referred to as "cytokine storm") characterized by high elevations of cytokines including INFγ, granulocyte-macrophage colony-stimulating factor, IL-10, and IL-6. These cytokine elevations result in a plethora of clinical symptoms including fever, hypotension, organ dysfunction, respiratory failure and coagulopathy. CRS can be fatal. Additionally, neurotoxicity often presents even after the initial symptoms of CRS have subsided. The pathogenesis of CRS and associated neurotoxicity is poorly understood and further understanding of the mechanism would be useful for the successful translation of CAR-T therapy. In the meanwhile, disrupting the pathogenesis of CRS by reducing the level of cytokine genes available for expression is one way to mitigate the condition.

Disclosed herein are methods of gene deletion and endogenous suppression, of cytokines/chemokines/transcription factors secreted from chimeric antigen receptor (CAR)-bearing immune effector cell, such as CAR-T cell, for the mitigation of cytokine release syndrome and/or CAR-T associated neuropathy. These gene deletion methods may include, but are not limited to, insertion of the CAR into a locus of a cytokine/chemokine/transcription factor gene, blocking its expression; gene editing with Transcription Activator-like Effector Nucleases (TALENs), Zinc Finger Nucleases (ZFNs), or CRISPR; expression of an scFv with an endoplasmic reticulum (ER) binding tether to bind the cytokine in the ER and prevent secretion; and transfection of small hairpin RNAs (shRNAs) or small interfering RNAs (siRNAs). Also disclosed herein are CAR-bearing immune effector cells modified with these described cytokine/chemokine/transcription factor gene deletion methods, and methods of treatment of diseases with immunotherapy with a reduced incidence of cytokine release syndrome (CRS) and/or CAR-T associated neuropathy (CAN).

BRIEF DESCRIPTION OF THE DRAWINGS

FIG. 11—Shows a set-up of an ELISA plate for detecting specific markers of CAR-T cells.

FIG. 12a and FIG. 12b—Shows the results for an ELISA assay detecting specific markers of the CAR-T cells. FIG. 12a shows the top half of the ELISA plate, and FIG. 12b shows the bottom half of the plate. In each of rows A-H, from top to bottom, the sub-rows indicate test, ref, Pathlength, 450, 540, Corrected [450], and Corrected [540].

DETAILED DESCRIPTION

Figure 1:
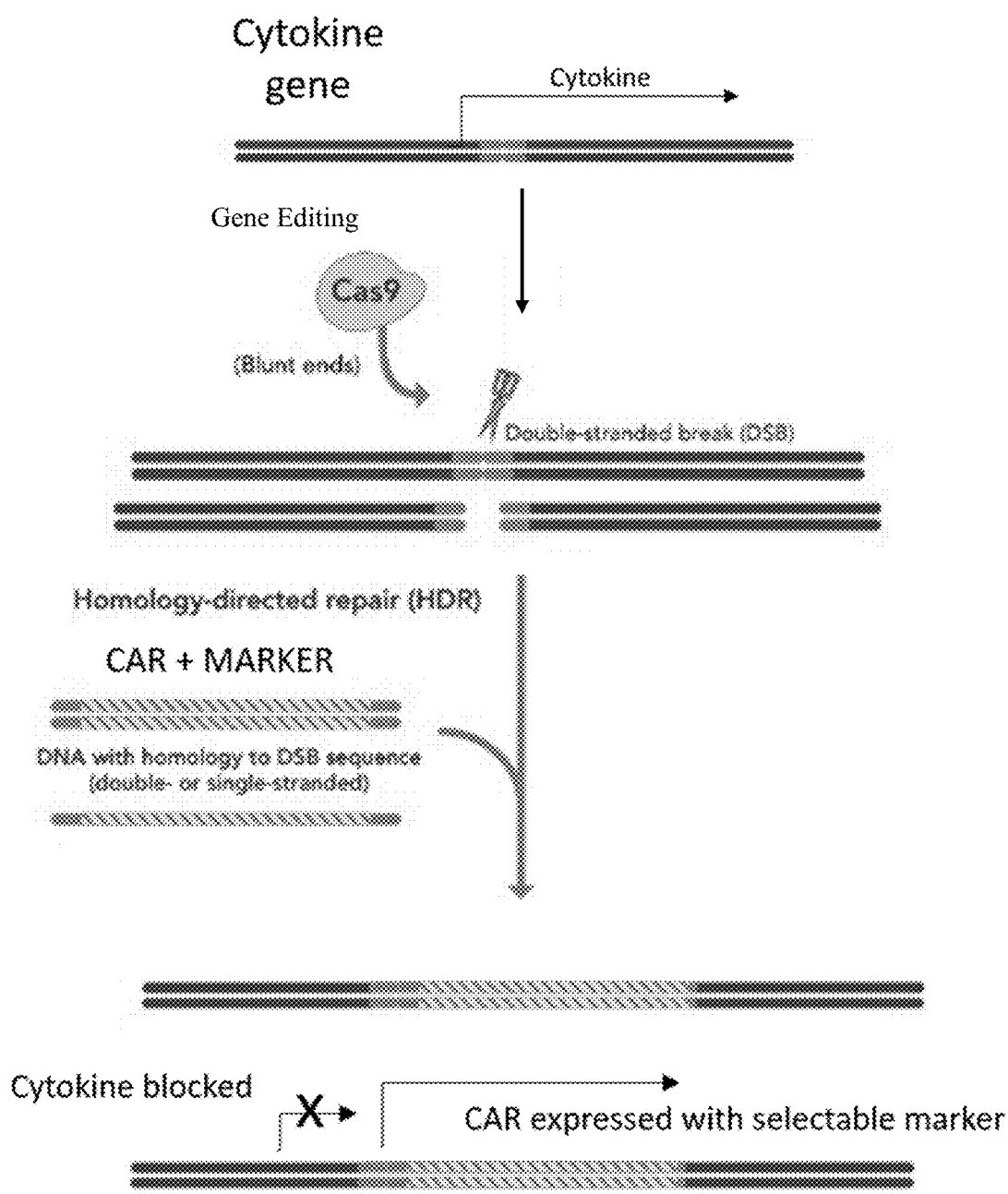
FIG. 1—Illustrates the concept of inserting a CAR into the gene for a cytokine in order to block its translation, thereby deleting it or reducing its level, thus preventing or reducing cytokine release syndrome and/or CAR-bearing immune effector cell associated neuropathy (CAR-T associated neuropathy).

Accordingly, disclosed herein as Embodiment 1 is a chimeric antigen receptor (CAR)-bearing immune effector cell that is deficient in a cytokine or in a chemokine or in a transcription factor that is involved in cytokine release syndrome.

The following disclosure will detail embodiments, alternatives, and uses of the cytokine-deficient cells, as well as the use of such cells in, for example, immunotherapy and adoptive cell transfer for the treatment of diseases. Accordingly, provided herein are the following additional embodiments.

Embodiment 2—The cell as recited in embodiment 1, wherein the cytokine or chemokine or transcription factor deficiency is effected by deletion or suppression of a gene encoding the cytokine or chemokine or transcription factor.

Embodiment 3—The cell as recited in any of embodiments 1 or 2, wherein the deletion or suppression is effected by inserting the CAR into a locus of the cytokine or chemokine or transcription factor gene.

Embodiment 4—The cell as recited in any of embodiments 1 to 3, wherein the CAR is part of a construct that also includes a selectable marker.

Embodiment 5—The cell as recited in any of embodiments 1 to 4, wherein the selectable marker comprises a green fluorescence (GFP) gene, a yellow fluorescent (YFP) gene, a truncated CD34 (tCD34) gene, or a truncated EGFR (tEGFR) gene.

Embodiment 6—The cell as recited in any of embodiments 1 to 5, wherein the cytokine or chemokine or transcription factor deficiency is effected by deletion or suppression of the cytokine or chemokine gene, by Transcription Activator-like Effector Nucleases (TALENs), Zinc Finger Nucleases (ZFNs), or Clustered Regularly Interspaced Short Palindromic Repeats (CRISPR) editing.

Embodiment 7—The cell as recited in any of embodiments 1 to 6, wherein deletion or suppression is effected using CRISPR.

Embodiment 8—The cell as recited in any of embodiments 1 to 7, wherein deletion or suppression is effected using Cas9-CRISPR.

Embodiment 9—The cell as recited in any of embodiments 1 to 8, wherein the Cas9 is delivered into the cell as mRNA or protein.

Embodiment 10—The cell as recited in any of embodiments 1 to 9, wherein the Cas9 is delivered into the cell as mRNA.

Embodiment 11—The cell as recited in any of embodiments 1 to 10, wherein the Cas9 is delivered into the cell as protein.

Embodiment 12—The cell as recited in any of embodiments 1 to 11, wherein a guide RNA (gRNA) targeting the gene to be deleted or suppressed is delivered contemporaneously with the Cas9.

Embodiment 13—The cell as recited in any of embodiments 1 to 12, wherein the delivery is by electroporation.

Embodiment 14—The cell as recited in any of embodiments 1 to 13, wherein the cytokine or chemokine or transcription factor deficiency is effected by suppression of the cytokine or chemokine or transcription factor gene transcript by transfection of one or more types of small interfering RNAs (siRNA).

Embodiment 15—The cell as recited in any of embodiments 1 to 14, wherein the cytokine or chemokine or transcription factor deficiency is effected by suppression of the cytokine or chemokine or transcription factor gene transcript by transduction of one or more types of short hairpin RNAs (shRNA).

Embodiment 16—A chimeric antigen receptor (CAR)-bearing immune effector cell expressing at least one CAR, wherein:
  the at least one CAR is inserted into a locus of a cytokine or chemokine or transcription factor gene or transcription factor gene;
  the cytokine or chemokine or transcription factor gene is deleted or suppressed by a method chosen from Transcription Activator-like Effector Nucleases (TALENs), Zinc Finger Nucleases (ZFNs), and Clustered Regularly Interspaces Short Palindromic Repeats (CRISPR) editing;
  the cytokine or chemokine or transcription factor is suppressed by expression of an scFv with an endoplasmic reticulum (ER) binding tether to bind the cytokine or chemokine in the ER and prevent secretion;
  the cytokine or chemokine or transcription factor gene transcript is suppressed by transfection of small interfering RNAs (siRNAs); or
  the cytokine or chemokine or transcription factor gene transcript is suppressed by transduction of short hairpin RNAs (shRNAs).

Embodiment 17—The cell as recited in any of embodiments 1 to 16, wherein the cell is chosen from a chimeric antigen receptor T cell (CAR-T), a CAR-bearing iNKT cell (INKT-CAR), and a CAR-bearing natural killer (NK) cell (NK-CAR), or a CAR-bearing macrophage.

Embodiment 18—The cell as recited in any of embodiments 1 to 17, wherein the cell is a CAR-T.

Embodiment 19—The cell as recited in any of embodiments 1 to 18, wherein the cell is a dual or tandem CAR-T.

Embodiment 20—The cell as recited in any of embodiments 1 to 17, wherein the cell is an iNKT-CAR.

Embodiment 21—The cell as recited in any of embodiments 1 to 20, wherein the cell is a dual or tandem iNKT-CAR.

Embodiment 22—The cell as recited in any of embodiments 1 to 17, wherein the cell is a CAR-macrophage.

Embodiment 23—The cell as recited in any of embodiments 1 to 22, wherein the cell is a dual or tandem CAR-macrophage.

Embodiment 24—The cell as recited in any of embodiments 1 to 23, wherein the cytokine or chemokine or transcription factor contributes to the development of cytokine release syndrome.

Embodiment 25—The cell as recited in any of embodiments 1 to 24, wherein the cytokine or chemokine or transcription factor is selected from among those recited in Table 10.

Embodiment 26—The cell as recited in any of embodiments 1 to 25, wherein the cytokine or chemokine or transcription factor is produced by T cells that activate or localize myeloid cells.

Embodiment 27—The cell as recited in any of embodiments 1 to 26, wherein the cytokine or chemokine or transcription factor is a T cell surface receptor gene that activates myeloid or CAR-T cells.

Embodiment 28—The cell as recited in any of embodiments 1 to 27, wherein the gene that is deleted or suppressed is a T cell surface receptor that is integrated into CAR-T cell signaling.

Embodiment 29—The cell as recited in any of embodiments 1 to 28, wherein the cytokine or chemokine or transcription factor drives T cell/CAR-T cell differentiation.

Embodiment 30—The cell as recited in any of embodiments 1 to 29, wherein the cytokine or chemokine is a transcription factor that drives T cell/CAR-T cell differentiation.

Embodiment 31—The cell as recited in any of embodiments 1 to 30, wherein the cytokine or chemokine or transcription factor is chosen from MCP1 (CCL2), MCP-2, GM-CSF, G-CSF, M-CSF, Il-4, and IFNγ.

Embodiment 32—The cell as recited in any of embodiments 1 to 31, wherein the cytokine or chemokine or transcription factor is GM-CSF.

Embodiment 33—The cell as recited in any of embodiments 1 to 32, wherein the cell is a GM-CSF deficient CAR-T cell.

Embodiment 34—The cell as recited in any of embodiments 1 to 33, wherein the cell is a GM-CSF deficient iNKT-CAR cell.

Embodiment 35—The cell as recited in any of embodiments 1 to 34, wherein the immune effector cells to be used are harvested from a healthy donor.

Embodiment 36—The cell as recited in any of embodiments 1 to 35, wherein the donor is a human.

Embodiment 37—The cell as recited in any of embodiments 1 to 36, wherein the chimeric antigen receptor(s) specifically binds at least one antigen expressed on a malignant cell.

Embodiment 38—The cell as recited in any of embodiments 1 to 37, wherein the one or more antigens expressed on a malignant cell is chosen from BCMA, CS1, CD38, CD138, CD19, CD33, CD123, CD371, CD117, CD135, Tim-3, CD5, CD7, CD2, CD4, CD3, CD79A, CD79B, APRIL, CD56, and CD1a.

Embodiment 39—The cell as recited in any of embodiments 1 to 38, wherein the chimeric antigen receptor specifically binds at least one antigen expressed on a malignant T cell.

Embodiment 40—The cell as recited in any of embodiments 1 to 39, wherein the antigen is selected from CD2, CD3&, CD4, CD5, CD7, TCRA, and TCRβ.

Embodiment 41—The cell as recited in any of embodiments 1 to 38, wherein the chimeric antigen receptor specifically binds at least one antigen expressed on a malignant B cell.

Embodiment 42—The cell as recited in any of embodiments 1 to 41, wherein the antigen is selected from CD19, CD20, CD21, CD22, CD23, CD24, CD25, CD27, CD38, and CD45.

Embodiment 43—The cell as recited in any of embodiments 1 to 42, wherein the antigen is selected from CD19 and CD20.

Embodiment 44—The cell as recited in any of embodiments 1 to 38, wherein the chimeric antigen receptor specifically binds at least one antigen expressed on a malignant mesothelial cell.

Embodiment 45—The cell as recited in any of embodiments 1 to 44, wherein the antigen is mesothelin.

Embodiment 46—The cell as recited in any of embodiments 1 to 38, wherein the chimeric antigen receptor specifically binds at least one antigen expressed on a malignant plasma cell.

Embodiment 47—The cell as recited in any of embodiments 1 to 46, wherein the antigen is selected from BCMA, CS1, CD38, and CD19.

Embodiment 48—The cell as recited in any of embodiments 1 to 47, wherein the chimeric antigen receptor expresses the extracellular portion of the APRIL protein, the ligand for BCMA and TACI, effectively co-targeting both BCMA and TACI.

Embodiment 49—The cell as recited in any of embodiments 1 to 48, wherein the CAR-T cell further comprises a suicide gene.

Embodiment 50—The cell as recited in any of embodiments 1 to 49, wherein endogenous T cell receptor mediated signaling is negligible in the cell.

Embodiment 51—The cell as recited in any of embodiments 1 to 50, wherein the cell does not induce alloreactivity or graft-versus-host disease.

Embodiment 52—The cell as recited in any of embodiments 1 to 51, wherein the cell does not induce fratricide.

Embodiment 53-A method of treatment of cancer in a patient, which has a reduced incidence of cytokine release syndrome and/or CAR-T associated neuropathy, comprising the administration of cells as recited in any of embodiments 1 to 52.

Embodiment 54—The method as recited in embodiment 53, wherein the cancer is a hematologic malignancy.

Embodiment 55—The method as recited in any of embodiments 53 to 54, wherein the hematologic malignancy is a T-cell malignancy.

Embodiment 56—The method as recited in any of embodiments 53 to 55, wherein the T cell malignancy is T-cell acute lymphoblastic leukemia (T-ALL).

Embodiment 57—The method as recited in any of embodiments 53 to 56, wherein the T cell malignancy is non-Hodgkin's lymphoma.

Embodiment 58—The method as recited in any of embodiments 53 to 57, wherein the hematologic malignancy is multiple myeloma.

Embodiment 59—The method as recited in any of embodiments 53 to 58, wherein the hematologic malignancy is AML.

Embodiment 60—The method as recited in any of embodiments 53 to 59, wherein the cancer is a solid tumor.

Embodiment 61—The method as recited any of embodiments 53 to 60, wherein the cancer is cervical cancer, pancreatic cancer, ovarian cancer, mesothelioma, and lung cancer.

Embodiment 62-A method of prevention or reduction of cytokine release syndrome or CAR-T associated neuropathy in a patient receiving chimeric antigen receptor T cell (CAR-T), CAR-bearing iNKT cell (INKT-CAR), CAR-bearing natural killer (NK) cell (NK-CAR), or CAR-bearing macrophage (CAR-macrophage) immunotherapy, comprising the administration of cells as recited in any of embodiments 53 to 61 as the immunotherapy.

Embodiment 63—The method of any of embodiments 53 to 62, wherein the patient is being treated for cancer.

Embodiment 64—The method as recited in any of embodiments 53 to 63, wherein the cancer is a hematologic malignancy.

Embodiment 65—The method as recited in any of embodiments 53 to 64, wherein the hematologic malignancy is a T-cell malignancy.

Embodiment 66—The method as recited in any of embodiments 53 to 65, wherein the T cell malignancy is T-cell acute lymphoblastic leukemia (T-ALL).

Embodiment 67—The method as recited in any of embodiments 53 to 66, wherein the T cell malignancy is non-Hodgkin's lymphoma.

Embodiment 68—The method as recited in any of embodiments 53 to 67, wherein the hematologic malignancy is multiple myeloma.

Embodiment 69—The method as recited in any of embodiments 53 to 68, wherein the hematologic malignancy is AML.

Embodiment 70—The method as recited in any of embodiments 53 to 69, wherein the cancer is a solid tumor.

Embodiment 71—The method as recited in any of embodiments 53 to 70, wherein the cancer is cervical cancer, pancreatic cancer, ovarian cancer, mesothelioma, and lung cancer.

Embodiment 72—A method of blocking the expression of a cytokine gene or chemokine gene or transcription factor gene in a chimeric antigen receptor T cell (CAR-T), CAR-bearing iNKT cell (INKT-CAR), CAR-bearing natural killer (NK) cell (NK-CAR), or CAR-bearing macrophage (CAR-macrophage) comprising the insertion of a CAR into a locus of the cytokine gene or chemokine gene or transcription factor gene.

Embodiment 73—The method of any of embodiments 53 to 72, wherein blocking the expression of the cytokine gene or chemokine gene or transcription factor gene does not reduce CAR-T cell-mediated killing.

Embodiment 74—A method of making a CAR-T (immune effector) cell that does not cause or contribute to CRS or CAR-T-associated neuropathy (CAN) comprising deleting or suppressing a cytokine or chemokine or transcription factor gene.

Embodiment 75—The method of any of embodiments 53 to 74, wherein deleting or suppressing the cytokine or chemokine or transcription factor gene does not reduce CAR-T cell-mediated killing.

Embodiment 76—The method as recited in any of embodiments 53 to 75, wherein the deletion or suppression is effected by inserting the CAR into a locus of the cytokine or chemokine or transcription factor gene.

Embodiment 77—The method as recited in any of embodiments 53 to 76, wherein the CAR is part of a construct that also includes a selectable marker.

Embodiment 78—The method as recited in any of embodiments 53 to 77, wherein the selectable marker comprises a green fluorescence (GFP) gene, a YFP gene, a tCD34 gene, or a tEGFR gene.

Embodiment 79—The method of any of embodiments 53 to 78, wherein the insertion of a CAR with a selectable marker into the cytokine or chemokine or transcription factor gene allows a single-step purification of TCR-negative cells.

Embodiment 80—The method of any of embodiments 53 to 79, wherein the insertion of a CAR with a selectable marker into the cytokine or chemokine or transcription factor gene allows a single step purification of CAR+ cytokine negative cells.

Embodiment 81—The method as recited in any of embodiments 53 to 80, wherein the deletion or suppression is effected using Transcription Activator-like Effector Nucleases (TALENs), Zinc Finger Nucleases (ZFNs), or Clustered Regularly Interspaced Short Palindromic Repeats (CRISPR) editing.

Embodiment 82—The method as recited in any of embodiments 53 to 81, wherein the deletion or suppression is effected using CRISPR.

Embodiment 83—The method as recited in any of embodiments 53 to 82, wherein the deletion or suppression is effected using Cas9-CRISPR.

Embodiment 84—The method as recited in any of embodiments 53 to 83, wherein the Cas9 is delivered into the cell as mRNA or protein.

Embodiment 85—The method as recited in any of embodiments 53 to 84, wherein the Cas9 is delivered into the cell as mRNA.

Embodiment 86—The method as recited in any of embodiments 53 to 85, wherein the Cas9 is delivered into the cell as protein.

Embodiment 87—The method as recited in any of embodiments 53 to 86, wherein a guide RNA (gRNA) targeting the gene to be deleted or suppressed is delivered contemporaneously with the Cas9.

Embodiment 88—The method as recited in any of embodiments 53 to 87, wherein the delivery is by electroporation.

Embodiment 89—The method as recited in any of embodiments 53 to 88, wherein the deletion or suppression is effected by suppression of the cytokine or chemokine or transcription factor gene transcript by transduction of one or more types of short hairpin RNAs (shRNA).

Embodiment 90—The method as recited in any of embodiments531 to 89, wherein the deletion or suppression is effected by transducing a construct encoding a protein expression blocker (PEBL).

Embodiment 91—The method of any of embodiments 53 to 90, wherein the construct encodes an antibody-derived single-chain variable fragment specific for the cytokine, chemokine or TF gene.

Embodiment 92—The method of any of embodiments 53 to 91, wherein deletion of the cytokine, chemokine, or transcription factor gene does not reduce CAR-T-mediated killing.

Embodiment 93—The method of any of embodiments 53 to 92, wherein the CAR to be inserted comprises a donor template.

Embodiment 94—The method of any of embodiments 53 to 93, wherein donor template comprises an adeno-associated virus (AAV), a single-stranded DNA, or a double-stranded DNA.

Disclosed herein is a chimeric antigen receptor (CAR)-bearing immune effector cell that is deficient in a cytokine.

In certain embodiments, the cytokine deficiency is effected by ablation of a cytokine gene or a chemokine gene, or a transcription factor gene.

In certain embodiments, the ablation is effected by inserting the CAR into a locus of the cytokine/chemokine/transcription factor gene.

In certain embodiments, the CAR is part of a construct that also includes a selectable marker.

In certain embodiments, the cytokine deficiency is effected by deletion or suppression of the cytokine/chemokine/transcription factor gene, by Transcription Activator-like Effector Nucleases (TALENs), Zinc Finger Nucleases (ZFNs), or Clustered Regularly Interspaces Short Palindromic Repeats (CRISPR) editing.

In certain embodiments, the cytokine deficiency is effected by suppression of the cytokine/chemokine/transcription factor gene transcript by transfection of small interfering RNAs (siRNAs).

Also disclosed herein is a chimeric antigen receptor (CAR)-bearing immune effector cell expressing at least one CAR, wherein:
  the at least one CAR is inserted into a locus of a cytokine/chemokine/transcription factor gene;
  the cytokine/chemokine/transcription factor gene is deleted or suppressed by a method chosen from Transcription Activator-like Effector Nucleases (TALENs), Zinc Finger Nucleases (ZFNs), and Clustered Regularly Interspaces Short Palindromic Repeats (CRISPR) editing;
  the cytokine is suppressed by expression of an scFv with an endoplasmic reticulum (ER) binding tether to bind the cytokine in the ER and prevent secretion; or
  the cytokine/chemokine/transcription factor gene transcript is suppressed by small interfering RNAs (siRNAs) transfection.

In certain embodiments, the cell is chosen from a chimeric antigen receptor T cell (CAR-T), a CAR-bearing iNKT cell (iNKT-CAR), and a CAR-bearing natural killer (NK) cell (NK-CAR).

In certain embodiments, the cell is a CAR-T.

In certain embodiments, the cell is a dual or tandem CAR-T.

In certain embodiments, the cell is an iNKT-CAR.

In certain embodiments, the cell is a dual or tandem iNKT-CAR.

In certain embodiments, the cytokine contributes to the development of cytokine release syndrome.

In certain embodiments, the cytokine is chosen from MCP1 (CCL2), MCP-2, GM-CSF, G-CSF, M-CSF, IL-4, and IFNγ.

In certain embodiments, the cytokine is GM-CSF.

In certain embodiments, the cell is a GM-CSF deficient CAR-T cell.

In certain embodiments, the cell is a GM-CSF deficient iNKT-CAR cell.

In certain embodiments, the chimeric antigen receptor specifically binds at least one antigen expressed on a malignant T cell.

In certain embodiments, the antigen is selected from CD2, CD3&, CD4, CD5, CD7, TCRA, and TCRβ.

In certain embodiments, the chimeric antigen receptor specifically binds at least one antigen expressed on a malignant B cell.

In certain embodiments, the antigen is selected from CD19 and CD20.

In certain embodiments, the chimeric antigen receptor specifically binds at least one antigen expressed on a malignant mesothelial cell.

In certain embodiments, the antigen is mesothelin.

In certain embodiments, the chimeric antigen receptor specifically binds at least one antigen expressed on a malignant plasma cell.

In certain embodiments, the antigen is selected from BCMA, CS1, CD38, and CD19.

In certain embodiments, the chimeric antigen receptor expresses the extracellular portion of the APRIL protein, the ligand for BCMA and TACI, effectively co-targeting both BCMA and TACI.

In certain embodiments, the CAR-T cell further comprises a suicide gene.

In certain embodiments, endogenous T cell receptor mediated signaling is negligible in the cell.

In certain embodiments, the cell does not induce alloreactivity or graft-versus-host disease.

In certain embodiments, the cell does not induce fratricide.

Also disclosed herein is a method of treatment of cancer in a patient, which has a reduced incidence of cytokine release syndrome and/or CAR-T associated neuropathy, comprising the administration of chimeric antigen receptor (CAR)-bearing immune effector cells as disclosed herein.

In certain embodiments, the cancer is a hematologic malignancy.

In certain embodiments, the hematologic malignancy is a T-cell malignancy.

In certain embodiments, the T cell malignancy is T-cell acute lymphoblastic leukemia (T-ALL).

In certain embodiments, the T cell malignancy is non-Hodgkin's lymphoma.

In certain embodiments, the hematologic malignancy is multiple myeloma.

In certain embodiments, the cancer is a solid tumor.

In certain embodiments, the cancer is cervical cancer, pancreatic cancer, ovarian cancer, mesothelioma, and lung cancer.

Also disclosed herein is a method of prevention or reduction of cytokine release syndrome, CAR-T associated neuropathy in a patient receiving chimeric antigen receptor T cell (CAR-T), CAR-bearing iNKT cell (INKT-CAR), or CAR-bearing natural killer (NK) cell (NK-CAR) immunotherapy, comprising the administration of chimeric antigen receptor (CAR)-bearing immune effector cells as disclosed herein as the immunotherapy.

Also disclosed herein is a method of blocking the expression of a cytokine/chemokine/transcription factor gene in a chimeric antigen receptor T cell (CAR-T), CAR-bearing iNKT cell (INKT-CAR), or CAR-bearing natural killer (NK) cell (NK-CAR), comprising the insertion of a CAR into a locus of the cytokine/chemokine/transcription factor gene.

CAR-Bearing Immune Effector Cells

A chimeric antigen receptor (CAR), is a recombinant fusion protein comprising: 1) an extracellular ligand-binding domain, i.e., an antigen-recognition domain, 2) a transmembrane domain, and 3) a signaling transducing domain.

Methods for CAR design, delivery and expression, and the manufacturing of clinical-grade CAR-T cell populations are known in the art. See, for example, Lee et al., *Clin. Cancer Res.*, 2012, 18 (10): 2780-90. An engineered chimeric antigen receptor polynucleotide that encodes for a CAR comprises: a signal peptide, an antigen recognition domain, at least one co-stimulatory domain, and a signaling domain.

The antigen-specific extracellular domain of a chimeric antigen receptor recognizes and specifically binds an antigen, typically a surface-expressed antigen of a malignancy. An "antigen-specific extracellular domain" (or, equivalently, "antigen-binding domain") specifically binds an antigen when, for example, it binds the antigen with an affinity constant or affinity of interaction (KD) between about 0.1 pM to about 10 µM, preferably about 0.1 pM to about 1 µM, more preferably about 0.1 pM to about 100 nM. Methods for determining the affinity of interaction are known in the art. An antigen-specific extracellular domain suitable for use in a CAR of the present disclosure may be any antigen-binding polypeptide, a wide variety of which are known in the art. In some instances, the antigen-binding domain is a single chain Fv (scFv). Other antibody based recognition domains (cAb VHH (camelid antibody variable domains) and humanized versions thereof, IgNAR VH (shark antibody variable domains) and humanized versions thereof, sdAb VH (single domain antibody variable domains) and "camelized" antibody variable domains are suitable for use. In some instances, T-cell receptor (TCR) based recognition domains such as single chain TCR (scTv, single chain two-domain TCR containing VαVβ) are also suitable for use.

A chimeric antigen receptor of the present disclosure also comprises an "intracellular domain" that provides an intracellular signal to the CAR-bearing immune effector cell upon antigen binding to the antigen-specific extracellular domain. The intracellular signaling domain of a chimeric antigen receptor of the present disclosure is responsible for activation of at least one of the effector functions of the T cell in which the chimeric receptor is expressed. The term "effector function" refers to a specialized function of a differentiated cell, such as an iNKT cell. An effector function of an iNKT cell, for example, may be NK transactivation, T cell activation and differentiation, B cell activation, dendritic cell activation and cross-presentation activity, and macrophage activation. Thus, the term "intracellular domain" refers to the portion of a CAR that transduces the effector function signal upon binding of an antigen to the extracellular domain and directs the iNKT cell to perform a specialized function. Non-limiting examples of suitable intracellular domains include the zeta chain of the T-cell receptor or any of its homologs (e.g., eta, delta, gamma, or epsilon), MB 1 chain, 829, Fe RIII, Fe R1, and combinations of signaling molecules, such as CD35 and CD28, CD27, 4-1 BB, DAP-1 0, OX40, and combinations thereof, as well as other similar molecules and fragments. Intracellular signaling portions of other members of the families of activating proteins may be used, such as FcγRIII and FcεRI. While usually the entire intracellular domain will be employed, in many cases it will not be necessary to use the entire intracellular polypeptide. To the extent that a truncated portion of the intracellular signaling domain may find use, such truncated portion may be used in place of the intact chain as long as it still transduces the effector function signal. The term intracellular domain is thus meant to include any truncated portion of the intracellular domain sufficient to transduce the effector function signal.

Typically, the antigen-specific extracellular domain is linked to the intracellular domain of the chimeric antigen receptor by a "transmembrane domain." A transmembrane domain traverses the cell membrane, anchors the CAR to the T cell surface, and connects the extracellular domain to the intracellular signaling domain, thus impacting expression of the CAR on the T cell surface. Chimeric antigen receptors may also further comprise one or more costimulatory domain and/or one or more spacer. A "costimulatory domain" is derived from the intracellular signaling domains of costimulatory proteins that enhance cytokine production, proliferation, cytotoxicity, and/or persistence in vivo. A "peptide hinge" connects the antigen-specific extracellular domain to the transmembrane domain. The transmembrane domain is fused to the costimulatory domain, optionally a costimulatory domain is fused to a second costimulatory domain, and the costimulatory domain is fused to a signaling domain, not limited to CD32. For example, inclusion of a spacer domain between the antigen-specific extracellular domain and the transmembrane domain, and between multiple scFvs in the case of tandem CAR, may affect flexibility of the antigen-binding domain(s) and thereby CAR function. Suitable transmembrane domains, costimulatory domains, and spacers are known in the art.

Engineered CARs may be introduced into CAR-bearing immune effector cells using retroviruses, which efficiently and stably integrate a nucleic acid sequence encoding the chimeric antigen receptor into the target cell genome. Other methods known in the art include, but are not limited to, lentiviral transduction, transposon-based systems, direct RNA transfection, and CRISPR/Cas systems (e.g., type I, type II, or type III systems using a suitable Cas protein such Cas3, Cas4, Cas5, Cas5e (or CasD), Cas6, Cas6e, Cas6f, Cas7, Cas8a1, Cas8a2, Cas8b, Cas8c, Cas9, Cas10, Cas1 0d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966, etc.). Zinc finger nucleases (ZFNs) and transcription activator-like effector nucleases (TALENs) may also be used. See, e.g., Shearer RF and Saunders DN, "Experimental design for stable genetic manipulation in mammalian cell lines: lentivirus and alternatives," *Genes Cells* 2015 January;20 (1): 1-10.

Manipulation of PI3K signaling can be used to prevent altered CAR-T cell differentiation due to constitutive CAR self-signaling and foster long-lived memory T cell development. pharmacologic blockade of PI3K during CAR-T manufacture and ex vivo expansion can abrogate preferential effector T cell development and restore CAR-T effector/memory ratio to that observed in empty vector transduced T cells, which can improve in vivo T cell persistence and therapeutic activity. Inhibition of p110δ PI3K can enhance efficacy and memory in tumor-specific therapeutic CD8 T cells, while inhibition of p110α PI3K can increase cytokine production and antitumor response.

This is proposed to be because the presence of a CAR on a T cell's surface can alter its activation and differentiation, even in the absence of ligand. Constitutive self-signaling through CAR, related to both the scFv framework and the signaling domains, can lead to aberrant T cell behavior, including altered differentiation and decreased survival. This is significant as the effectiveness of CAR-T cells in patients is directly associated with their in vivo longevity. The presence of the CD28 costimulatory domain increased CAR-T cell exhaustion induced by persistent CAR self-signaling; the 4-1BB costimulatory domain had a lesser effect. Furthermore, CD3-zeta significantly enhances the constitutive activation of the PI3K, AKT, mTOR, and glycolysis pathways, and fostered formation of short-lived effector cells over central/stem memory cells. See, e.g., Zhang W. et al., "Modulation of PI3K signaling to improve CAR T cell function," *Oncotarget*, 2018 Nov. 9; 9 (88): 35807-35808.

CAR Antigens. Suitable antigens to be genome-edited in the iNKT cells disclosed herein, and to be recognized by the CARs of INKT-CARs disclosed herein, include antigens specific to hematologic malignancies. These can include T cell-specific antigens and/or antigens that are not specific to T cells. The antigen may be specifically bound by the chimeric antigen receptor of an iNKT-CARs cell, and the antigen for which the iNKT-CARs cell is deficient, is an antigen expressed on a malignant T cell, preferably an antigen that is overexpressed on malignant T cell (i.e., a T cell derived from a T-cell malignancy) in comparison to a nonmalignant T cell. Examples of such antigens include CD2, CD3&, CD4, CD5, CD7, TRAC, and TCRβ.

T-cell malignancies comprise malignancies derived from T-cell precursors, mature T cells, or natural killer cells. Examples of T-cell malignancies include T-cell acute lymphoblastic leukemia/lymphoma (T-ALL), T-cell large granular lymphocyte (LGL) leukemia, human T-cell leukemia virus type 1-positive (HTLV-1+) adult T-cell leukemia/lymphoma (ATL), T-cell prolymphocytic leukemia (T-PLL), and various peripheral T-cell lymphomas (PTCLs), including but not limited to angioimmunoblastic T-cell lymphoma (AITL), ALK-positive anaplastic large cell lymphoma, and ALK-negative anaplastic large cell lymphoma.

Suitable CAR antigens can also include antigens found on the surface of a multiple myeloma cell, i.e., a malignant plasma cell, such as BCMA, CS1, CD38, and CD19. Alternatively, the CAR may be designed to express the extracellular portion of the APRIL protein, the ligand for BCMA and TACI, effectively co-targeting both BCMA and TACI for the treatment of multiple myeloma.

Additional examples of suitable antigens to be genome-edited in the iNKT cells disclosed herein, and to be recognized by the CARs of iNKT-CARs disclosed herein, are given below in Tables 1-10. These include CD2, CD38, CD4, CD5, CD7, TRAC, TCRβ, BCMA, CS1, and CD38.

Fratricide Resistance. The CAR-T, INKT, NK and other CAR-bearing immune effector cells encompassed by the present disclosure are optionally deficient in one or more antigens to which the chimeric antigen receptor specifically binds and are therefore fratricide-resistant. In some embodiments, the one or more antigens of the cell is modified such the chimeric antigen receptor no longer specifically binds the one or more modified antigens. For example, the epitope of the one or more antigens recognized by the chimeric antigen receptor may be modified by one or more amino acid changes (e.g., substitutions or deletions) or the epitope may be deleted from the antigen. In other embodiments, expression of the one or more antigens is reduced in the cell by at least 50%, at least 60%, at least 70%, at least 80%, at least 90% or more. Methods for decreasing the expression of a protein are known in the art and include, but are not limited to, modifying or replacing the promoter operably linked to the nucleic acid sequence encoding the protein. In still other embodiments, the cell is modified such that the one or more antigens is not expressed, e.g., by deletion or disruption of the gene encoding the one or more antigens. In each of the above embodiments, the CAR-bearing immune effector cell may be deficient in one or preferably all the antigens to which the chimeric antigen receptor specifically binds. Methods for genetically modifying a cell to be deficient in one or more antigens are well known in art, and non-limiting examples are provided above. In an exemplary embodiment, CRISPR/cas9 gene editing can be used to modify a cell to be deficient in one or more antigens. Zinc finger nucleases (ZFNs) and transcription activator-like effector nucleases (TALENs) may also be used. See, e.g., Shearer RF and Saunders DN, "Experimental design for stable genetic manipulation in mammalian cell lines: lentivirus and alternatives," *Genes Cells* 2015 January;20 (1): 1-10.

Avoidance of Allogenicity. CAR-T, INKT, NK and other CAR-bearing immune effector cells encompassed by the present disclosure may further be deficient in endogenous T cell receptor (TCR) signaling as a result of deleting a part of the T Cell Receptor (TCR)-CD3 complex. In various embodiments it may be desirable to eliminate or suppress endogenous TCR signaling in CAR-bearing immune effector cells disclosed herein. For example, decreasing or eliminating endogenous TCR signaling in CAR-T cells may prevent or reduce graft versus host disease (GvHD) when allogenic T cells are used to produce the CAR-T cells. Methods for eliminating or suppressing endogenous TCR signaling are known in the art and include, but are not limited to, deleting a part of the TCR-CD3 receptor complex, e.g., the TCR receptor alpha chain (TRAC), the TCR receptor beta chain (TRBC), CD3ε CD3γ CD3δ, and/or CD3ζ. Deleting a part of the TCR receptor complex may block TCR mediated signaling and may thus permit the safe use of allogeneic T cells as the source of CAR-T cells without inducing life-threatening GvHD.

Suicide Genes. Alternatively, or in addition, CAR-bearing immune effector cells encompassed by the present disclosure may further comprise one or more suicide genes. As used herein, "suicide gene" refers to a nucleic acid sequence introduced to a cell by standard methods known in the art that, when activated, results in the death of the cell. Suicide genes may facilitate effective tracking and elimination of the CAR-bearing immune effector cells in vivo if required. Facilitated killing by activating the suicide gene may occur by methods known in the art. Suitable suicide gene therapy systems known in the art include, but are not limited to, various the herpes simplex virus thymidine kinase (HSVtk)/ganciclovir (GCV) suicide gene therapy systems or inducible caspase 9 protein. In an exemplary embodiment, a suicide gene is a CD34/thymidine kinase chimeric suicide gene.

Components that may be included in a CAR as described herein are provided below in Tables 1 and 2.

TABLE 1

Amino acid sequences of different CAR components.

| Functional domains | SEQ ID NO: | Amino acid sequence |
| --- | --- | --- |
| CD8α signal peptide | SEQ ID NO: 1 | MALPVTALLLPLALLLHAARP |
| CD8α hinge | SEQ ID NO: 2 | TTTPAPRPPTPAPTIASQPLSLRPEACR PAAGGAVHTRGLDFACD |
| CD28 Transmembrane ($T_m$) domain | SEQ ID NO: 3 | FWVLVVVGGVLACYSLLVTVAFIIFWV |
| Surface glycoprotein CD8 alpha chain isoform 1 precursor (NP_001139345.1) | SEQ ID NO: 4 | MALPVTALLLPLALLLHAARPSQFRVSPLDRT WNLGETVELKCQVLLSNPTSGCSWLFQPRGAA ASPTFLLYLSQNKPKAAEGLDTQRFSGKRLGDT FVLTLSDFRRENEGYYFCSALSNSIMYFSHFVP VFLPAKPTTTPAPRPPTPAPTIASQPLSLRPEACR PAAGGAVHTRGLDFACDIYIWAPLAGTCGVLL LSLVITLYCNHRNRRRVCKCPRPVVKSGDKPSL SARYV |
| 4-1BB costimulatory domain | SEQ ID NO: 5 | KRGRKKLLYIFKQPFMRPVQTTQEEDGCSCRFP EEEEGGCEL |
| CD28 costimulatory domain | SEQ ID NO: 6 | RSKRSRLLHSDYMNMTPRRPGPTRKHYQPYAP PRDFAAYRS |
| CD3 zeta (ζ) | SEQ ID NO: 7 | RVKFSRSADAPAYKQGQNQLYNELNLGRREEY DVLDKRRGRDPEMGGKPRRKNPQEGLYNELQ KDKMAEAYSEIGMKGERRRGKGHDGLYQGLS TATKDTYDALHMQALPPR |
| P2A peptide | SEQ ID NO: 8 | GSGATNFSLLKQAGDVEENPGP |
| (GGGGS)₄ linker | SEQ ID NO: 9 | GGGGSGGGGSGGGGSGGGGS |
| hCD34 | SEQ ID NO: 10 | MPRGWTALCLLSLLPSGFMSLDNNGTATPELP TQGTFSNVSTNVSYQETTTPSTLGSTSLHPVSQ HGNEATTNITETTVKFTSTSVITSVYGNTNSSVQ SQTSVISTVFTTPANVSTPETTLKPSLSPGNVSD LSTTSTSLATSPTKPYTSSSPILSDIKAEIKCSG IREVKLTQGICLEQNKTSSCAEFKKDRGEGLARV LCGEEQADADAGAQVCSLLLAQSEVRPQCLLL |

TABLE 1-continued

Amino acid sequences of different CAR components.

| Functional domains | SEQ ID NO: | Amino acid sequence |
|---|---|---|
| | | VLANRTEISSKLQLMKKHQSDLKKLGILDFTEQ DVASHQSYSQKTLIALVTSGALLAVLGITGYFL MNRRSWSPI |
| Human-Herpes Simplex Virus-1 (HSV)- thymidine kinase (TK) | SEQ ID NO: 11 | MPRGWTALCLLSLLPSGFMSLDNNGTATPELP TQGTFSNVSTNVSYQETTTPSTLGSTSLHPVSQ HGNEATTNITETTVKFTSTSVITSVYGNTNSSVQ SQTSVISTVFTTPANVSTPETTLKPSLSPGNVSD LSTTSTSLATSPTKPYTSSSPILSDIKAEIKCSG IREVKLTQGICLEQNKTSSCAEFKKDRGEGLARV LCGEEQADADAGAQVCSLLLAQSEVRPQCLLL VLANRTEISSKLQLMKKHQSDLKKLGILDFTEQ DVASHQSYSQKTLIALVTSGALLAVLGITGYFL MNRRSWSPTGEGGGGGDLGGVKLPHLFGKRL VEARMASYPCHQHASAFDQAARSRGHSNRRT ALRPRRQQEATEVRLEQKMPTLLRVYIDGPHG MGKTTTTQLLVALGSRDDIVYVPEPMTYWQV LGASETIANIYTTQHRLDQGEISAGDAAVVMTS AQITMGMPYAVTDAVLAPHVGGEAGSSHAPPP ALTLLLDRHPIAVMLCYPAARYLMGSMTPQAV LAFVALIPPTLPGTNIVLGALPEDRHIDRLAKRQ RPGERLDLAMLAAIRRVYGLLANTVRYLQGGG SWWEDWGQLSGTAVPPQGAEPQSNAGPRPHIG DTLFTLFRAPELLAPNGDLYNVFAWALDVLAK RLRPMHVFILDYDQSPAGCRDALLQLTSGMVQ THVTTPGSIPTICDLARTFAREMGEAN |

TABLE 2

Amino acid sequences of the variable heavy ($V_H$) and variable light ($V_L$) chains of the scFvs.

| ScFv sequences | SEQ ID NO: | Amino acid sequence |
|---|---|---|
| CD2 heavy chain variable region (35.1 ATCC®HB-222™) | SEQ ID NO: 12 | EVKLEESGAELVKPGASVKLSCRTSGFNIKDTI HWVKQRPEQGLKWIGRIDPANGNTKYDPKFQ DKATVTADTSSNTAYLQLSSLTSEDTAVYYCV TYAYDGNWYFDVWGAGTAVTVSS |
| CD2 light chain variable region (35.1 ATCC®HB-222™) | SEQ ID NO: 13 | DIKNITQSPSSMYVSLGERVTITCKASQDINSFL SWFQQKPGKSPKTLIYRANRLVDGVPSRFSGS GSGQDYSLTISSLEYEDMEIYYCLQYDEFPYTF GGGTKLEMKR |
| CD2 heavy chain variable region (OKT 11 ATCC®CRL-8027™) | SEQ ID NO: 14 | EVQLEESGAELVRPGTSVKLSCKASGYTFTSY WMHWIKQRPEQGLEWIGRIDPYDSETHYNEK FKDKAILSVDKSSSTAYIQLSSLTSDDSAVYYC SRRDAKYDGYALDYWGQGTSVTVSS |
| CD2 light chain variable region (OKT 11 ATCC®CRL-8027™) | SEQ ID NO: 15 | DIVMTQAAPSVPVTPGESVSISCRSSKTLLHSN GNTYLYWFLQRPGQSPQVLIYRMSNLASGVP NRFSGSGSETTFTLRISRVEAEDVGIYYCMQHL EYPYTFGGGTKLEIER |
| CD3 heavy chain variable region (OKT 3) | SEQ ID NO: 16 | GSQVQLQQSGAELARPGASVKMSCKASGYTF TRYTMHWVKQRPGQGLEWIGYINPSRGYTNY NQKFKDKATLTTDKSSSTAYMQLSSLTSEDSA VYYCARYYDDHYCLDYWGQGTTLTVSS |
| CD3 light chain variable region (OKT 3) | SEQ ID NO: 17 | QIVLTQSPAIMSASPGEKVTMTCSASSSVSYM NWYQQKSGTSPKRWIYDTSKLASGVPAHFRG SGSGTSYSLTISGMEAEDAATYYCQQWSSNPF TFGSGTKLEINR |
| CD3 heavy chain variable region (UCHT1) | SEQ ID NO: 18 | EVQLVESGGGLVQPGGSLRLSCAASGYSFTGY TMNWVRQAPGKCLEWVALINPYKGVSTYNQ KFKDRFTISVDKSKNTAYLQMNSLRAEDTAV YYCARSGYYGDSDWYFDVWGQGTLVTVSS |

TABLE 2-continued

Amino acid sequences of the variable heavy (V$_H$)
and variable light (V$_L$) chains of the scFvs.

| ScFv sequences | SEQ ID NO: | Amino acid sequence |
|---|---|---|
| CD3 heavy chain variable region (UCHT1) | SEQ ID NO: 19 | DIQMTQSPSSLSASVGDRVTITCRASQDIRNYL NWYQQKPGKAPKLLIYYTSRLESGVPSRFSGS GSGTDYTLTISSLQPEDFATYYCQQGNTLPWT FGCGTKVEIK |
| CD7 heavy chain variable region | SEQ ID NO: 20 | EVQLVESGGGLVKPGGSLKLSCAASGLTFSSY AMSWVRQTPEKRLEWVASISSGGFTYYPDSV KGRFTISRDNARNILYLQMSSLRSEDTAMYYC ARDEVRGYLDVWGAGTTVTVS |
| CD7 light chain variable region | SEQ ID NO: 21 | DIQMTQTTSSLSASLGDRVTISCSASQGISNYL NWYQQKPDGTVKLLIYYTSSLHSGVPSRFSGS GSGTDYSLTISNLEPEDIATYYCQQYSKLPYTF GGGTKLEIKR |
| FTL3 heavy chain variable region (EB10) | SEQ ID NO: 22 | EVQLVQSGAEVKKPGASVKVSCKASGYTFTS YYMHWVRQAPGQGLEWMGIINPSGGSTSYAQ KFQGRVTMTRDTSTSTVYMELSSLRSEDTAVY YCARGVGAHDAFDIWGQGTTVTVSS |
| FTL3 light chain variable region (EB10) | SEQ ID NO: 23 | DVVMTQSPLSLPVTPGEPASISCRSSQSLLHSN GNNYLDWYLQKPGQSPQLLIYLGSNRASGVP DRFSGSGSDTDFTLQISRVEAEDVGVYYCMQG THPAISFGQGTRLEIK |
| FTL3 heavy chain variable region (NC7) | SEQ ID NO: 24 | EVQLVQSGAEVKKPGSSVKVSCKASGGTFSSY AISWVRQAPGQGLEWMGGIIPIFGTANYAQKF QGRVTITADKSTSTAYMELSSLRSEDTAVYYC ATFALFGFREQAFDIWGQGTTVTVSS |
| FTL3 light chain variable region (NC7) | SEQ ID NO: 25 | DIQMTQSPSSLSASVGDRVTITCRASQSISSYLN WYQQKPGKAPKLLIYAASSLQSGVPSRFSGSG SGTDFTLTISSLQPEDLATYYCQQSYSTPFTFGP GTKVDIK |
| FTL3 heavy chain variable region (D3-D4) | SEQ ID NO: 26 | EVQLVQSGAEVKKPGASVKVSCKASGYTFTS YYMHWARQAPGQGLEWMGIINPSGGSTSYAQ KFQGRVTMTRDTSTSTVYMELSSLRSEDTAVY YCARVVAAAVADYWGQGTLVTVSS |
| FTL3 light chain variable region (D3-D4) | SEQ ID NO: 27 | DVVMTQSPLSLPVTPGEPASISCRSSQSLLHSN GYNYLDWYLQKPGQSPQLLIYLGSNRASGVP DRFSGSGSGTDFTLKISRVEAEDVGVYYCMQS LQTPFTFGPGTKVDIK |
| CS1 heavy chain variable region | SEQ ID NO: 28 | QVQLQQPGAELVRPGASVKLSCKASGYSFTTY WMNWVKQRPGQGLEWIGMIHPSDSETRL NQKFKDKATLTVDKSSSTAYMQLSSPTSEDSA VYYCARSTMIATRAMDYWGQGTSVTVSS |
| CS1 light chain variable region | SEQ ID NO: 29 | DIVMTQSQKSMSTSVGDRVSITCKASQDVITG VAWYQQKPGQSPKLLIYSASYRYTGVPD RFTGSGSGTDFTFTISNVQAEDLAVYYCQQHY STPLTFGAGTKLELK |
| CD33 heavy chain variable region | SEQ ID NO: 30 | QVQLQQPGAEVVKPGASVKMSCKASGYTFTS YYIHWIKQTPGQGLEWVGVIYPGNDDISYNQK FQGKATLTADKSSTTAYMQLSSLTSEDSAVYY CAREVRLRYFDVWGQGTTVTVSSSG |
| CD33 light chain variable region | SEQ ID NO: 31 | GSEIVLTQSPGSLAVSPGERVTMSCKSSQSVFF SSSQKNYLAWYQQIPGQSPRLLIYWASTRESG VPDRFTGSGSGTDFTLTISSVQPEDLAIYYCHQ YLSSRTFGQGTKLEIKR |

Mono CAR-T Cells

In certain embodiments, the disclosure provides an engineered T cell comprising a single CAR, that specifically binds an antigen or cell surface protein, wherein the T cell is optionally deficient in that antigen or cell surface protein (e.g., CD7CARTΔCD7 cell). In non-limiting examples, the deficiency in the antigen or cell surface protein resulted from (a) modification of antigen or cell surface protein expressed by the T cell such that the chimeric antigen receptors no longer specifically binds the modified antigen or cell surface protein (e.g., the epitope of the one or more antigens recognized by the chimeric antigen receptor may be modified by one or more amino acid changes (e.g., substitutions or deletions) or the epitope may be deleted from the antigen), (b) modification of the T cell such that expression of antigen or cell surface protein is reduced in the T cell by at least 50%, at least 60%, at least 70%, at least 80%, at least 90% or more, or (c) modification of the T cell such that antigen or cell surface protein is not expressed (e.g., by deletion or disruption of the gene encoding antigen or cell surface protein). In each of the above embodiments, the CAR-T cell may be deficient in one or preferably all the antigens or cell surface proteins to which the chimeric antigen receptor specifically binds. The methods to genetically modify a T cell to be deficient in one or more antigens or cell surface proteins are well known in art and non-limiting examples are provided herein. In embodiments described below, the CRISPR-Cas9 system is used to modify a T cell to be deficient in one or more antigens. Any of these may be accomplished by the methods disclosed herein. In further embodiments, the T cell comprises a suicide gene.

For example, the CAR for a CD7 specific CAR-T cell may be generated by cloning a commercially synthesized anti-CD7 single chain variable fragment (scFv) into a 3rd generation CAR backbone with CD28 and/or 4-1BB internal signaling domains. An extracellular hCD34 domain may be added after a P2A peptide to enable both detection of CAR following viral transduction and purification using anti-hCD34 magnetic beads. A similar method may be followed for making CARs specific for other malignant T cell antigens.

CAR-T cells encompassed by the present disclosure may further be deficient in endogenous T cell receptor (TCR) signaling as a result of deleting a part of the T Cell Receptor (TCR)-CD3 complex. In various embodiments it may be desirable to eliminate or suppress endogenous TCR signaling in CAR-T cells disclosed herein. For example, decreasing or eliminating endogenous TCR signaling in CAR-T cells may prevent or reduce graft versus host disease (GvHD) when allogenic T cells are used to produce the CAR-T cells. Methods for eliminating or suppressing endogenous TCR signaling are known in the art and include, but are not limited to, deleting a part of the TCR-CD3 receptor complex, e.g., the TCR receptor alpha chain (TRAC), the TCR receptor beta chain (TCRβ) or subtypes thereof, TCRδ, TCRγ, CD3ε, CD3γ, and/or CD3δ. Deleting a part of the TCR receptor complex may block TCR mediated signaling and may thus permit the safe use of allogeneic T cells as the source of CAR-T cells without inducing life-threatening GvHD.

In addition, the CAR-T cells encompassed by the present disclosure may further comprise one or more suicide genes as described herein.

In a similar manner, other mono-CAR-T cells may be constructed and are given below in Table 3.

TABLE 3

Mono CARs and CAR-Ts

| Example | Antigen Target of CAR-T cells | Antigen Deletion/Suppression |
|---|---|---|
| M1 | APRIL | — |
| M2 | APRIL | APRIL |
| M3 | APRIL | APRIL + TRAC |
| M4 | APRIL | APRIL + CD3ε |
| M5 | APRIL | CD3ε |
| M6 | BCMA | — |
| M7 | CD117 | — |
| M8 | CD117 | CD117 |
| M9 | CD123 | — |
| M10 | CD123 | CD123 |

TABLE 3-continued

Mono CARs and CAR-Ts

| Example | Antigen Target of CAR-T cells | Antigen Deletion/Suppression |
|---|---|---|
| M11 | CD135 | — |
| M12 | CD135 | CD135 |
| M13 | CD138 | — |
| M14 | CD19 | — |
| M15 | CD1a | — |
| M16 | CD1a | CD3ε |
| M17 | CD1a | TRAC |
| M18 | CD1a | CD1a + TRAC |
| M19 | CD1a | CD1a + CD3ε |
| M20 | CD2 | — |
| M21 | CD2 | CD2 |
| M22 | CD2 | CD2 + TRAC |
| M23 | CD2 | CD2 + CD3ε |
| M24 | CD20 | |
| M25 | CD21 | |
| M26 | CD22 | |
| M27 | CD23 | |
| M28 | CD3 | — |
| M29 | CD3 | CD3ε |
| M30 | CD3 | CD3ε + TRAC |
| M31 | CD33 | — |
| M32 | CD33 | CD33 |
| M33 | CD371 | — |
| M34 | CD371 | CD371 |
| M35 | CD38 | — |
| M36 | CD38 | CD38 |
| M37 | CD4 | — |
| M38 | CD4 | CD4 |
| M39 | CD4 | CD4 + TRAC |
| M40 | CD4 | CD4 + CD3ε |
| M41 | CD5 | — |
| M42 | CD5 | CD5 |
| M43 | CD5 | CD5 + TRAC |
| M44 | CD5 | CD5 + CD3ε |
| M45 | CD56 | — |
| M46 | CD56 | CD56 |
| M47 | CD56 | CD56 + TRAC |
| M48 | CD56 | CD56 + CD3ε |
| M49 | CD56 | CD3ε |
| M50 | CD56 | TRAC |
| M51 | CD7 | — |
| M52 | CD7 | CD7 |
| M53 | CD7 | CD7 + TRAC |
| M54 | CD7 | CD7 + CD3ε |
| M55 | CD79A | — |
| M56 | CD79B | — |
| M57 | CS1 | — |
| M58 | CS1 | CS1 |
| M59 | Tim-3 | — |
| M60 | Tim-3 | Tim-3 |
| M61 | Tim-3 | Tim-3 + TRAC |
| M62 | Tim-3 | TRAC |
| M63 | Tim-3 | CD3ε |
| M64 | Tim-3 | Tim-3 + CD3ε |

Disclosed are embodiments of CAR amino acid sequences that can be expressed on the surface of a genome-edited CAR-T cell derived from a cytotoxic T cell, a memory T cell, or a gamma delta (γδ) T cell.

TABLE 4

Amino Acid Sequences of Mono Chimeric Antigen Receptors (CARs).

| Mono CAR Constructs | SEQ ID NO: | Amino acid sequence |
|---|---|---|
| CD7-CAR-4-1BB_CD34 | SEQ ID NO: 32 | MALPVTALLLPLALLLHAARPDIQMTQTTSSLSASLGDRVT ISCSASQGISNYLNWYQQKPDGTVKLLIYYTSSLHSGVPSRF SGSGSGTDYSLTISNLEPEDIATYYCQQYSKLPYTFGGGTKL EIKRGGGGSGGGGSGGGGSGGGGSEVQLVESGGGLVKPG GSLKLSCAASGLTFSSYAMSWVRQTPEKRLEWVASISSGGF TYYPDSVKGRFTISRDNARNILYLQMSSLRSEDTAMYYCA RDEVRGYLDVWGAGTTVTVSPRASTTTPAPRPPTPAPTIAS QPLSLRPEACRPAAGGAVHTRGLDFACDFWVLVVVGGVL ACYSLLVTVAFIIFWVKRGRKKLLYIFKQPFMRPVQTTQEE DGCSCRFPEEEEGGCELRVKFSRSADAPAYKQGQNQLYNE LNLGRREEYDVLDKRRGRDPEMGGKPRRKNPQEGLYNEL QKDKMAEAYSEIGMKGERRRGKGHDGLYQGLSTATKDTY DALHMQALPPRRTDGSGATNFSLLKQAGDVEENPGPVSEA MPRGWTALCLLSLLPSGFMSLDNNGTATPELPTQGTFSNVS TNVSYQETTTPSTLGSTSLHPVSQHGNEATTNITETTVKFTS TSVITSVYGNTNSSVQSQTSVISTVFTTPANVSTPETTLKPSL SPGNVSDLSTTSTSLATSPTKPYTSSSPILSDIKAEIKCSGI REVKLTQGICLEQNKTSSCAEFKKDRGEGLARVLCGEEQADA DAGAQVCSLLLAQSEVRPQCLLLVLANRTEISSKLQLMKK HQSDLKKLGILDFTEQDVASHQSYSQKTLIALVTSGALLAV LGITGYFLMNRRSWSPI |
| CD7-CAR-4-1BB_CD34_TK | SEQ ID NO: 33 | MALPVTALLLPLALLLHAARPDIQMTQTTSSLSASLGDRVT ISCSASQGISNYLNWYQQKPDGTVKLLIYYTSSLHSGVPSRF SGSGSGTDYSLTISNLEPEDIATYYCQQYSKLPYTFGGGTKL EIKRGGGGSGGGGSGGGGSGGGGSEVQLVESGGGLVKPG GSLKLSCAASGLTFSSYAMSWVRQTPEKRLEWVASISSGGF TYYPDSVKGRFTISRDNARNILYLQMSSLRSEDTAMYYCA RDEVRGYLDVWGAGTTVTVSPRASTTTPAPRPPTPAPTIAS QPLSLRPEACRPAAGGAVHTRGLDFACDFWVLVVVGGVL ACYSLLVTVAFIIFWVKRGRKKLLYIFKQPFMRPVQTTQEE DGCSCRFPEEEEGGCELRVKFSRSADAPAYKQGQNQLYNE LNLGRREEYDVLDKRRGRDPEMGGKPRRKNPQEGLYNEL QKDKMAEAYSEIGMKGERRRGKGHDGLYQGLSTATKDTY DALHMQALPPRRTDGSGATNFSLLKQAGDVEENPGPVSEA MPRGWTALCLLSLLPSGFMSLDNNGTATPELPTQGTFSNVS TNVSYQETTTPSTLGSTSLHPVSQHGNEATTNITETTVKFTS TSVITSVYGNTNSSVQSQTSVISTVFTTPANVSTPETTLKPSL SPGNVSDLSTTSTSLATSPTKPYTSSSPILSDIKAEIKCSGIRE VKLTQGICLEQNKTSSCAEFKKDRGEGLARVLCGEEQADA DAGAQVCSLLLAQSEVRPQCLLLVLANRTEISSKLQLMKK HQSDLKKLGILDFTEQDVASHQSYSQKTLIALVTSGALLAV LGITGYFLMNRRSWSPTGEGGGGDLGGVKLPHLFGKRLV EARMASYPCHQHASAFDQAARSRGHSNRRTALRPRRQQE ATEVRLEQKMPTLLRVYIDGPHGMGKTTTTQLLVALGSRD DIVYVPEPMTYWQVLGASETIANIYTTQHRLDQGEISAGDA AVVMTSAQITMGMPYAVTDAVLAPHVGGEAGSSHAPPPA LTLLLLDRHPIAVMLCYPAARYLMGSMTPQAVLAFVALIPPT LPGTNIVLGALPEDRHIDRLAKRQRPGERLDLAMLAAIRRV YGLLANTVRYLQGGGSWWEDWGQLSGTAVPPQGAEPQS NAGPRPHIGDTLFTLFRAPELLAPNGDLYNVFAWALDVLA KRLRPMHVFILDYDQSPAGCRDALLQLTSGMVQTHVTTPG SIPTICDLARTFAREMGEAN |
| CD7-CAR-CD28_CD34 | SEQ ID NO: 34 | MALPVTALLLPLALLLHAARPDIQMTQTTSSLSASLGDRVT ISCSASQGISNYLNWYQQKPDGTVKLLIYYTSSLHSGVPSRF SGSGSGTDYSLTISNLEPEDIATYYCQQYSKLPYTFGGGTKL EIKRGGGGSGGGGSGGGGSGGGGSEVQLVESGGGLVKPG GSLKLSCAASGLTFSSYAMSWVRQTPEKRLEWVASISSGGF TYYPDSVKGRFTISRDNARNILYLQMSSLRSEDTAMYYCA RDEVRGYLDVWGAGTTVTVSPRASTTTPAPRPPTPAPTIAS QPLSLRPEACRPAAGGAVHTRGLDFACDFWVLVVVGGVL ACYSLLVTVAFIIFWVRSKRSRLLHSDYMNMTPRRPGPTRK HYQPYAPPRDFAAYRSRVKFSRSADAPAYKQGQNQLYNE LNLGRREEYDVLDKRRGRDPEMGGKPRRKNPQEGLYNEL QKDKMAEAYSEIGMKGERRRGKGHDGLYQGLSTATKDTY DALHMQALPPRRTDGSGATNFSLLKQAGDVEENPGPVSEA MPRGWTALCLLSLLPSGFMSLDNNGTATPELPTQGTFSNVS TNVSYQETTTPSTLGSTSLHPVSQHGNEATTNITETTVKFTS TSVITSVYGNTNSSVQSQTSVISTVFTTPANVSTPETTLKPSL SPGNVSDLSTTSTSLATSPTKPYTSSSPILSDIKAEIKCSGIRE VKLTQGICLEQNKTSSCAEFKKDRGEGLARVLCGEEQADA DAGAQVCSLLLAQSEVRPQCLLLVLANRTEISSKLQLMKK HQSDLKKLGILDFTEQDVASHQSYSQKTLIALVTSGALLAV LGITGYFLMNRRSWSPI |

TABLE 4-continued

Amino Acid Sequences of Mono Chimeric Antigen Receptors (CARs).

| Mono CAR Constructs | SEQ ID NO: | Amino acid sequence |
|---|---|---|
| CD7-CAR-CD28_CD34_TK | SEQ ID NO: 35 | MALPVTALLLPLALLLHAARPDIQMTQTTSSLSASLGDRVT ISCSASQGISNYLNWYQQKPDGTVKLLIYYTSSLHSGVPSRF SGSGSGTDYSLTISNLEPEDIATYYCQQYSKLPYTFGGGTKL EIKRGGGGSGGGGSGGGGSGGGGSEVQLVESGGGLVKPG GSLKLSCAASGLTFSSYAMSWVRQTPEKRLEWVASISSGGF TYYPDSVKGRFTISRDNARNILYLQMSSLRSEDTAMYYCA RDEVRGYLDVWGAGTTVTVSPRASTTTPAPRPPTPAPTIAS QPLSLRPEACRPAAGGAVHTRGLDFACDFWVLVVVGGVL ACYSLLVTVAFIIFWVRSKRSRLLHSDYMNMTPRRPGPTRK HYQPYAPPRDFAAYRSRVKFSRSADAPAYKQGQNQLYNE LNLGRREEYDVLDKRRGRDPEMGGKPRRKNPQEGLYNEL QKDKMAEAYSEIGMKGERRRGKGHDGLYQGLSTATKDTY DALHMQALPPRRTDGSGATNFSLLKQAGDVEENPGPVSEA MPRGWTALCLLSLLPSGFMSLDNNGTATPELPTQGTFSNVS TNVSYQETTTPSTLGSTSLHPVSQHGNEATTNITETTVKFTS TSVITSVYGNTNSSVQSQTSVISTVFTTPANVSTPETTLKPSL SPGNVSDLSTTSTSLATSPTKPYTSSSPILSDIKAEIKCSGIRE VKLTQGICLEQNKTSSCAEFKKDRGEGLARVLCGEEQADA DAGAQVCSLLLAQSEVRPQCLLLVLANRTEISSKLQLMKK HQSDLKKLGILDFTEQDVASHQSYSQKTLIALVTSGALLAV LGITGYFLMNRRSWSPTGEGGGGDLGGVKLPHLFGKRLV EARMASYPCHQHASAFDQAARSRGHSNRRTALRPRRQQE ATEVRLEQKMPTLLRVYIDGPHGMGKTTTTQLLVALGSRD DIVYVPEPMTYWQVLGASETIANIYTTQHRLDQGEISAGDA AVVMTSAQITMGMPYAVTDAVLAPHVGGEAGSSHAPPPA LTLLLDRHPIAVMLCYPAARYLMGSMTPQAVLAFVALIPPT LPGTNIVLGALPEDRHIDRLAKRQRPGERLDLAMLAAIRRV YGLLANTVRYLQGGGSWWEDWGQLSGTAVPPQGAEPQS NAGPRPHIGDTLFTLFRAPELLAPNGDLYNVFAWALDVLA KRLRPMHVFILDYDQSPAGCRDALLQLTSGMVQTHVTTPG SIPTICDLARTFAREMGEAN |
| CD79B-CAR-CD28_CD34 | SEQ ID NO: 36 | MALPVTALLLPLALLLHAARPGSDIQLTQSPSSLSASVGDR VTITCKASQSVDYEGDSFLNWYQQKPGKAPKLLIYAASNL ESGVPSRFSGSGSGTDFTLTISSLQPEDFATYYCQQSNEDPL TFGQGTKVEIKRGGGGSGGGGSGGGGSGGGGSGGGGSEV QLVESGGGLVQPGGSLRLSCAASGYTFSSYWIEWVRQAPG KGLEWIGEILPGGGDTNYNEIFKGRATFSADTSKNTAYLQM NSLRAEDTAVYYCTRRVPIRLDYWGQGTLVTVSSPRASTT TPAPRPPTPAPTIASQPLSLRPEACRPAAGGAVHTRGLDFAC DFWVLVVVGGVLACYSLLVTVAFIIFWVRSKRSRLLHSDY MNMTPRRPGPTRKHYQPYAPPRDFAAYRSRVKFSRSADAP AYKQGQNQLYNELNLGRREEYDVLDKRRGRDPEMGGKPR RKNPQEGLYNELQKDKMAEAYSEIGMKGERRRGKGHDGL YQGLSTATKDTYDALHMQALPPRRTDGSGATNFSLLKQAG DVEENPGPVSEAMPRGWTALCLLSLLPSGFMSLDNNGTAT PELPTQGTFSNVSTNVSYQETTTPSTLGSTSLHPVSQHGNEA TTNITETTVKFTSTSVITSVYGNTNSSVQSQTSVISTVFTTPA NVSTPETTLKPSLSPGNVSDLSTTSTSLATSPTKPYTSSSPILS DIKAEIKCSGIREVKLTQGICLEQNKTSSCAEFKKDRGEGLA RVLCGEEQADADAGAQVCSLLLAQSEVRPQCLLLVLANRT EISSKLQLMKKHQSDLKKLGILDFTEQDVASHQSYSQKTLI ALVTSGALLAVLGITGYFLMNRRSWSPTGEGGGGGFKRDL GGVKLPHLFGKRLVEARMASYPCHQHASAFDQAARSRGH SNRRTALRPRRQQEATEVRLEQKMPTLLRVYIDGPHGMGK TTTTQLLVALGSRDDIVYVPEPMTYWQVLGASETIANIYTT QHRLDQGEISAGDAAVVMTSAQITMGMPYAVTDAVLAPH VGGEAGSSHAPPPALTLLLDRHPIAVMLCYPAARYLMGSM TPQAVLAFVALIPPTLPGTNIVLGALPEDRHIDRLAKRQRPG ERLDLAMLAAIRRVYGLLANTVRYLQGGGSWWEDWGQL SGTAVPPQGAEPQSNAGPRPHIGDTLFTLFRAPELLAPNGD LYNVFAWALDVLAKRLRPMHVFILDYDQSPAGCRDALLQ LTSGMVQTHVTTPGSIPTICDLARTFAREMGEAN |
| CD2-CAR-CD28_CD34 | SEQ ID NO: 37 | MALPVTALLLPLALLLHAARPDIVMTQAAPSVPVTPGESVS ISCRSSKTLLHSNGNTYLYWFLQRPGQSPQVLIYRMSNLAS GVPNRFSGSGSETTFTLRISRVEAEDVGIYYCMQHLEYPYT FGGGTKLEIERGGGGSGGGGSGGGGSGGGGSEVQLEESGA ELVRPGTSVKLSCKASGYTFTSYWMHWIKQRPEQGLEWIG RIDPYDSETHYNEKFKDKAILSVDKSSSTAYIQLSSLTSDDS AVYYCSRRDAKYDGYALDYWGQGTSVTVSSPRASTTTPA PRPPTPAPTIASQPLSLRPEACRPAAGGAVHTRGLDFACDF WVLVVVGGVLACYSLLVTVAFIIFWVRSKRSRLLHSDYMN MTPRRPGPTRKHYQPYAPPRDFAAYRSRVKFSRSADAPAY |

TABLE 4-continued

Amino Acid Sequences of Mono Chimeric Antigen Receptors (CARs).

| Mono CAR Constructs | SEQ ID NO: | Amino acid sequence |
|---|---|---|
| | | KQGQNQLYNELNLGRREEYDVLDKRRGRDPEMGGKPRRK<br>NPQEGLYNELQKDKMAEAYSEIGMKGERRRGKGHDGLYQ<br>GLSTATKDTYDALHMQALPPRRTDGSGATNFSLLKQAGDV<br>EENPGPVSEAMPRGWTALCLLSLLPSGFMSLDNNGTATPEL<br>PTQGTFSNVSTNVSYQETTTPSTLGSTSLHPVSQHGNEATT<br>NITETTVKFTSTSVITSVYGNTNSSVQSQTSVISTVFTTPANV<br>STPETTLKPSLSPGNVSDLSTTSTSLATSPTKPYTSSSPILSDI<br>KAEIKCSGIREVKLTQGICLEQNKTSSCAEFKKDRGEGLAR<br>VLCGEEQADADAGAQVCSLLLAQSEVRPQCLLLVLANRTE<br>ISSKLQLMKKHQSDLKKLGILDFTEQDVASHQSYSQKTLIA<br>LVTSGALLAVLGITGYFLMNRRSWSPI |
| CD2-CAR-4-1BB_CD34 | SEQ ID NO: 38 | MALPVTALLLPLALLLHAARPDIVMTQAAPSVPVTPGESVS<br>ISCRSSKTLLHSNGNTYLYWFLQRPGQSPQVLIYRMSNLAS<br>GVPNRFSGSGSETTFTLRISRVEAEDVGIYYCMQHLEYPYT<br>FGGGTKLEIERGGGGSGGGGSGGGGSGGGGSEVQLEESGA<br>ELVRPGTSVKLSCKASGYTFTSYWMHWIKQRPEQGLEWIG<br>RIDPYDSETHYNEKFKDKAILSVDKSSSTAYIQLSSLTSDDS<br>AVYYCSRRDAKYDGYALDYWGQGTSVTVSSPRASTTTPA<br>PRPPTPAPTIASQPLSLRPEACRPAAGGAVHTRGLDFACDF<br>WVLVVVGGVLACYSLLVTVAFIIFWVKRGRKKLLYIFKQP<br>FMRPVQTTQEEDGCSCRFPEEEEGGCELRVKFSRSADAPAY<br>KQGQNQLYNELNLGRREEYDVLDKRRGRDPEMGGKPRRK<br>NPQEGLYNELQKDKMAEAYSEIGMKGERRRGKGHDGLYQ<br>GLSTATKDTYDALHMQALPPRRTDGSGATNFSLLKQAGDV<br>EENPGPVSEAMPRGWTALCLLSLLPSGFMSLDNNGTATPEL<br>PTQGTFSNVSTNVSYQETTTPSTLGSTSLHPVSQHGNEATT<br>NITETTVKFTSTSVITSVYGNTNSSVQSQTSVISTVFTTPANV<br>STPETTLKPSLSPGNVSDLSTTSTSLATSPTKPYTSSSPILSDI<br>KAEIKCSGIREVKLTQGICLEQNKTSSCAEFKKDRGEGLAR<br>VLCGEEQADADAGAQVCSLLLAQSEVRPQCLLLVLANRTE<br>ISSKLQLMKKHQSDLKKLGILDFTEQDVASHQSYSQKTLIA<br>LVTSGALLAVLGITGYFLMNRRSWSPI |
| CD3-CD28-CD34 | SEQ ID NO: 39 | MALPVTALLLPLALLLHAARPGSQVQLQQSGAELARPGAS<br>VKMSCKASGYTFTRYTMHWVKQRPGQGLEWIGYINPSRG<br>YTNYNQKFKDKATLTTDKSSSTAYMQLSSLTSEDSAVYYC<br>ARYYDDHYCLDYWGQGTTLTVSSGGGGSGGGGSGGGGS<br>GGGGSQIVLTQSPAIMSASPGEKVTMTCSASSSVSYMNWY<br>QQKSGTSPKRWIYDTSKLASGVPAHFRGSGSGTSYSLTISG<br>MEAEDAATYYCQQWSSNPFTFGSGTKLEINRPRASTTTPAP<br>RPPPTPAPTIASQPLSLRPEACRPAAGGAVHTRGLDFACDFW<br>VLVVVGGVLACYSLLVTVAFIIFWVRSKRSRLLHSDYMNM<br>TPRRPGPTRKHYQPYAPPRDFAAYRSRVKFSRSADAPAYK<br>QGQNQLYNELNLGRREEYDVLDKRRGRDPEMGGKPRRKN<br>PQEGLYNELQKDKMAEAYSEIGMKGERRRGKGHDGLYQG<br>LSTATKDTYDALHMQALPPRRTDGSGATNFSLLKQAGDVE<br>ENPGPVSEAMPRGWTALCLLSLLPSGFMSLDNNGTATPELP<br>TQGTFSNVSTNVSYQETTTPSTLGSTSLHPVSQHGNEATTNI<br>TETTVKFTSTSVITSVYGNTNSSVQSQTSVISTVFTTPANVST<br>PETTLKPSLSPGNVSDLSTTSTSLATSPTKPYTSSSPILSDI<br>KAEIKCSGIREVKLTQGICLEQNKTSSCAEFKKDRGEGLARVL<br>CGEEQADADAGAQVCSLLLAQSEVRPQCLLLVLANRTEISS<br>KLQLMKKHQSDLKKLGILDFTEQDVASHQSYSQKTLIALV<br>TSGALLAVLGITGYFLMNRRSWSPI |

Tandem CAR-T Cells

A tandem CAR-T cell (tCAR-T), is a T cell with a single chimeric antigen polypeptide comprising two distinct extracellular ligand-binding (antigen/protein recognition) domains capable of interacting with two different cell surface molecules (e.g., antigen/protein), wherein the extracellular ligand-binding domains are linked together by one or more flexible linkers and share one or more costimulatory domains, wherein the binding of the first or second extracellular ligand-binding domain will signal through one or more the costimulatory domains(s) and a signaling transducing domain.

In certain embodiments, the T cell is deficient in one or more antigens or cell surface proteins (e.g., CD7 and CD2 for a CD7*CD2-tCARΔCD7ΔCD2 cell, or CD2 for a CD3*CD2-tCARΔCD3ΔCD2 cell). In non-limiting examples, the deficiency in the antigen(s) or cell surface protein(s) resulted from (a) modification of antigen or cell surface protein expressed by the T cell such that the chimeric antigen receptor no longer specifically binds the modified antigen(s) or cell surface protein(s) (e.g., the epitope of the one or more antigens recognized by the chimeric antigen receptor may be modified by one or more amino acid changes (e.g., substitutions or deletions) or the epitope may be deleted from the antigen), (b) modification of the T cell such that expression of antigen(s) or cell surface protein(s) is/are reduced in the T cell by at least 50%, at least 60%, at least 70%, at least 80%, at least 90% or more, or (c) modification of the T cell such that antigen(s) or cell surface protein(s) is/are not expressed (e.g., by deletion or disruption of the gene encoding antigen or cell surface protein). In each of the above embodiments, the CAR-T cell may be deficient in one or preferably all the antigens or cell surface proteins to which the chimeric antigen receptor specifically binds. The methods to genetically modify a T cell to be deficient in one or more antigens or cell surface proteins are well known in art and non-limiting examples are provided herein. In embodiments described below, the CRISPR-Cas9 system is used to modify a T cell to be deficient in one or more antigen(s) or cell surface protein(s). Any of these may be accomplished by the methods disclosed herein. In further embodiments, the T cell comprises a suicide gene.

A tCAR for a genome-edited, tandem CAR-T cell, i.e., CD2*CD3-tCARTΔCD2ΔCD38, may be generated by cloning a commercially synthesized anti-CD2 single chain variable fragment (scFv) and an anti-CD3 single chain variable fragment (scFv), separated by a peptide linker, into a lentiviral vector containing, e.g., a $2^{nd}$ or $3^{rd}$ generation CAR backbone with CD28 and/or 4-1BB internal signaling domains. An extracellular hCD34 domain may be added after a P2A peptide to enable both detection of CAR following viral transduction and purification using anti-hCD34 magnetic beads. A similar method may be followed for making tCARs specific for other malignant T cell antigens.

Tandem CARs may have different linker structures, i.e., be linear or hairpin, and the hairpin linker may optionally comprise a (Cys=Cys) double-stranded bond (DSB).

A linear tandem CAR-T cell comprises a chimeric antigen receptor (CAR) polypeptide comprising a first signal peptide, a first extracellular ligand-binding domain, a second extracellular ligand-binding domain, a hinge region, a transmembrane domain, one or more co-stimulatory domains, and a signaling transducing domain, wherein the first extracellular ligand-binding antigen recognition domain and the second extracellular ligand-binding antigen recognition domain have affinities for different cell surface molecules, i.e., antigens on a cancer cell, for example, a malignant T cell, B cell, or plasma cell; and wherein the linear tandem CAR-T cell possesses one or more genetic modifications, deletions, or disruptions resulting in reduced expression of the cell surface molecules in the linear tandem CAR-T cell.

In another embodiment, the signal peptide is the signal peptide from human CD8a.

In a third embodiment, the first extracellular ligand-binding domain comprises a single chain antibody fragment (scFv), comprising the light ($V_L$) and the heavy ($V_H$) variable fragment, designated $V_H1$ and $V_L1$ and joined by a linker (e.g., GGGGS (SEQ ID NO: 3065)). In some embodiments, this linker peptide is repeated 2, 3, 4, 5 or 6 times. In some embodiments, the first antigen recognition domain can be selected from: 1) $V_H1$-(GGGGS)$_{3-4}$ (SEQ ID NO: 3066)-$V_L1$ or 2) $V_L1$-(GGGGS)$_{3-4}$ (SEQ ID NO: 3066)-$V_H1$.

In some embodiments, the second extracellular ligand-binding domain comprises a single chain antibody fragment (scFv), comprising the light ($V_L$) and the heavy ($V_H$) variable fragment, designated $V_H2$ and $V_L2$ and joined by a linker (e.g., GGGGS (SEQ ID NO: 3065)). In some embodiments, this linker peptide is repeated 2, 3, 4, 5 or 6 times. In some embodiments, the first antigen recognition domain can be selected from: 1) $V_H2$-(GGGGS)$_{3-4}$ (SEQ ID NO: 3066)-$V_L2$ or 2) $V_L2$-(GGGGS)$_{3-4}$ (SEQ ID NO: 3066)-$V_H2$.

In further embodiments, the first antigen recognition domain and second antigen recognition domain are connected by a short linker peptide of 5 amino acids (GGGGS (SEQ ID NO: 3065)). In some embodiments, this linker peptide is repeated 2, 3, 4, 5, or 6 times.

Tandem CAR Constructs

In one embodiment, the first extracellular ligand-binding domain antigen recognition comprises a single chain antibody fragment (scFv), comprising the heavy ($V_H$) and the light ($V_L$) variable fragment, designated $V_H1$ and $V_L1$, and joined by a linker (e.g., GGGGS (SEQ ID NO: 3065)), targets a cell surface molecule, i.e., an antigen expressed on a malignant cell.

In certain embodiments, the heavy ($V_H$) and the light ($V_L$) variable fragment, designated $V_H1$ and $V_L1$, targeting an antigen expressed on a malignant T cell is selected from BCMA, CS1, CD38, CD138, CD19, CD33, CD123, CD371, CD117, CD135, Tim-3, CD5, CD7, CD2, CD4, CD3, CD79A, CD79B, APRIL, CD56, and CD1a.

In certain embodiments, the second extracellular ligand-binding domain antigen recognition comprises a single chain antibody fragment (scFv), comprising the heavy ($V_H$) and the light ($V_L$) variable fragment, designated $V_H2$ and $V_L2$, and joined by a linker (e.g., GGGGS (SEQ ID NO: 3065)), and targets a cell surface molecule, i.e., an antigen, expressed on a malignant cell.

In certain embodiments, the heavy ($V_H$) and the light ($V_L$) variable fragments, designated $V_H2$ and $V_L2$, targeting an antigen expressed on a malignant T cell is selected from BCMA, CS1, CD38, CD138, CD19, CD33, CD123, CD371, CD117, CD135, Tim-3, CD5, CD7, CD2, CD4, CD3, CD79A, CD79B, APRIL, CD56, and CD1a and differs from the variable heavy ($V_H1$) and light sequences ($V_L1$) of the first extracellular ligand-binding domain of the CAR molecule.

Additional examples of tandem CARs are given below in Table 5.

TABLE 5

Tandem CARs and CAR-Ts

| Example | Antigen Target CAR-T cell | Antigen Deletion/Suppression |
| --- | --- | --- |
| T1 | APRILxBCMA | — |
| T2 | APRILxCD19 | — |
| T3 | APRILxCD38 | — |
| T4 | APRILxCD38 | CD38 |
| T5 | APRILxCS1 | — |
| T6 | APRILxCS1 | CS1 |
| T7 | BCMAxCD19 | — |
| T8 | BCMAxCD38 | — |
| T9 | BCMAxCD38 | CD38 |
| T10 | BCMAxCS1 | — |
| T11 | BCMAxCS1 | CS1 |
| T12 | CD138xAPRIL | |
| T13 | CD138xBCMA | |
| T14 | CD138xCD19 | |
| T15 | CD138xCD38 | |
| T16 | CD138xCD38 | CD38 |
| T17 | CD138xCD79A | |
| T18 | CD138xCD79B | |
| T19 | CD138xCS1 | |
| T20 | CD138xCS1 | CS1 |
| T21 | CD19xCD38 | — |
| T22 | CD19xCD38 | CD38 |
| T23 | CD2xCD3ε | — |
| T24 | CD2xCD3ε | CD2 |
| T25 | CD2xCD3ε | CDε |
| T26 | CD2xCD3ε | CD2 and CD3ε |
| T27 | CD2xCD4 | — |
| T28 | CD2xCD4 | CD2 |
| T29 | CD2xCD4 | CD4 |
| T30 | CD2xCD4 | CD2 and CD4 |
| T31 | CD2xCD4 | CD2 and TRAC |
| T32 | CD2xCD4 | CD4 and TRAC |
| T33 | CD2xCD4 | CD2 and CD4 and TRAC |
| T34 | CD2xCD5 | — |
| T35 | CD2xCD5 | CD2 |

TABLE 5-continued

Tandem CARs and CAR-Ts

| Example | Antigen Target CAR-T cell | Antigen Deletion/Suppression |
|---|---|---|
| T36 | CD2xCD5 | CD5 |
| T37 | CD2xCD5 | CD2 and CD5 |
| T38 | CD2xCD5 | CD2 and TRAC |
| T39 | CD2xCD5 | CD5 and TRAC |
| T40 | CD2xCD5 | CD2 and CD5 and TRAC |
| T41 | CD2xCD7 | — |
| T42 | CD2xCD7 | CD2 |
| T43 | CD2xCD7 | CD7 |
| T44 | CD2xCD7 | CD2 and CD7 |
| T45 | CD2xCD7 | CD2 and TRAC |
| T46 | CD2xCD7 | CD7 and TRAC |
| T47 | CD2xCD7 | CD2 and CD7 and TRAC |
| T48 | CD3εxCD4 | — |
| T49 | CD3εxCD4 | CD3ε |
| T50 | CD3εxCD4 | CD4 |
| T51 | CD3εxCD4 | CD3ε and CD4 |
| T52 | CD3εxCD5 | — |
| T53 | CD3εxCD5 | CD3ε |
| T54 | CD3εxCD5 | CD5 |
| T55 | CD3εxCD5 | CD3ε and CD5 |
| T56 | CD3εxCD7 | — |
| T57 | CD3εxCD7 | CD3ε |
| T58 | CD3εxCD7 | CD7 |
| T59 | CD3εxCD7 | CD3ε and CD7 |
| T60 | CD4xCD5 | — |
| T61 | CD4xCD5 | CD4 |
| T62 | CD4xCD5 | CD5 |
| T63 | CD4xCD5 | CD4 and CD5 |
| T64 | CD4xCD5 | CD4 and TRAC |
| T65 | CD4xCD5 | CD5 and TRAC |
| T66 | CD4xCD5 | CD4 and CD5 and TRAC |
| T67 | CD4xCD7 | — |
| T68 | CD4xCD7 | CD4 |
| T69 | CD4xCD7 | CD7 |
| T70 | CD4xCD7 | CD4 and CD7 |
| T71 | CD4xCD7 | CD4 and TRAC |
| T72 | CD4xCD7 | CD4 and TRAC |
| T73 | CD4xCD7 | CD4 and CD7 and TRAC |
| T74 | CD5xCD7 | — |
| T75 | CD5xCD7 | CD5 |
| T76 | CD5xCD7 | CD7 |
| T77 | CD5xCD7 | CD5 and CD7 |
| T78 | CD5xCD7 | CD5 and TRAC |
| T79 | CD5xCD7 | CD7 and TRAC |
| T80 | CD5xCD7 | CD5 and CD7 and TRAC |
| T81 | CD79AxAPRIL | |
| T82 | CD79AxBCMA | |
| T83 | CD79AxCD19 | |
| T84 | CD79AxCD38 | |
| T85 | CD79AxCD38 | CD38 |
| T86 | CD79AxCD79B | |
| T87 | CD79AxCS1 | |
| T88 | CD79AxCS1 | CS1 |
| T89 | CD79BxAPRIL | |
| T90 | CD79BxBCMA | |
| T91 | CD79BxCD19 | |
| T92 | CD79BxCD38 | |
| T93 | CD79BxCD38 | CD38 |
| T94 | CD79BxCD79A | |
| T95 | CD79BxCS1 | |
| T96 | CD79BxCS1 | CS1 |
| T97 | CS1xCD19 | — |
| T98 | CS1xCD19 | CS1 |
| T99 | CS1xCD38 | — |
| T100 | CS1xCD38 | CS1 |
| T101 | CS1xCD38 | CD38 |
| T102 | CS1xCD38 | CS1 and CD38 |
| T103 | TCRβxCD2 | — |
| T104 | TCRβxCD2 | TCRβ |
| T105 | TCRβxCD2 | CD2 |
| T106 | TCRβxCD2 | TCRβ and CD2 |
| T107 | TCRβxCD3ε | — |
| T108 | TCRβxCD3ε | TCRβ |
| T109 | TCRβxCD3ε | CD3ε |
| T110 | TCRβxCD3ε | TCRβ and CD3ε |
| T111 | TCRβxCD4 | — |
| T112 | TCRβxCD4 | TCRβ |
| T113 | TCRβxCD4 | CD4 |
| T114 | TCRβxCD4 | TCRβ and CD4 |
| T115 | TCRβxCD5 | — |
| T116 | TCRβxCD5 | TCRβ |
| T117 | TCRβxCD5 | CD5 |
| T118 | TCRβxCD5 | TCRβ and CD5 |
| T119 | TCRβxCD7 | — |
| T120 | TCRβxCD7 | TCRβ |
| T121 | TCRβxCD7 | CD7 |
| T122 | TCRβxCD7 | TCRβ and CD7 |
| T123 | TRACxCD2 | — |
| T124 | TRACxCD2 | TRAC |
| T125 | TRACxCD2 | CD2 |
| T126 | TRACxCD2 | TRAC and CD2 |
| T127 | TRACxCD3ε | — |
| T128 | TRACxCD3ε | TRAC |
| T129 | TRACxCD3ε | CD3ε |
| T130 | TRACxCD3ε | TRAC and CD3ε |
| T131 | TRACxCD4 | — |
| T132 | TRACxCD4 | TRAC |
| T133 | TRACxCD4 | CD4 |
| T134 | TRACxCD4 | TRAC and CD4 |
| T135 | TRACxCD5 | — |
| T136 | TRACxCD5 | TRAC |
| T137 | TRACxCD5 | CD5 |
| T138 | TRACxCD5 | TRAC and CD5 |
| T139 | TRACxCD7 | — |
| T140 | TRACxCD7 | TRAC |
| T141 | TRACxCD7 | CD7 |
| T142 | TRACxCD7 | TRAC and CD7 |

In some embodiments, hairpin tandem CAR constructs may be provided herein, such as including, but not limited to, a construct incorporating the $V_H$ and $V_L$ domains of CD2 and CD3 scFvs (Table 6).

TABLE 6

Hairpin Tandem CAR Constructs Targeting CD2 and CD3.

| Clone 5 | Clone 6 | Clone 7 | Clone 8 | Clone 13 | Clone 14 | Clone 15 | Clone 16 |
|---|---|---|---|---|---|---|---|
| CD8a | CD8a | CD8a | CD8a | CD8a | CD8a | CD8a | CD8a |
| CD3-$V_L$ | CD3-$V_L$ | CD3-$V_L$ | CD3-$V_L$ | CD2-$V_L$ | CD2-$V_L$ | CD3-$V_L$ | CD3-$V_L$ |
| GGGGS$_4$ (SEQ ID NO: 9) | GGGGS$_4$ (SEQ ID NO: 9) | GGGGS$_4$ (SEQ ID NO: 9) | GGGGS$_4$ (SEQ ID NO: 9) | GGGGS$_4$ (SEQ ID NO: 9) | GGGGS$_4$ (SEQ ID NO: 9) | GGGGS$_4$ (SEQ ID NO: 9) | GGGGS$_4$ (SEQ ID NO: 9) |

TABLE 6-continued

Hairpin Tandem CAR Constructs Targeting CD2 and CD3.

| CD2-$V_L$ | CD2-$V_L$ | CD2-$V_L$ | CD2-$V_L$ | CD3-$V_L$ | CD3-$V_L$ | CD2-$V_L$ | CD2-$V_L$ |
|---|---|---|---|---|---|---|---|
| (GGGGS)$_{10}$ (SEQ ID NO: 3067) | (GGGGS)$_4$ GGGGP(GGGGS)$_4$ (SEQ ID NO: 3068) | (GGGGS)$_{10}$ (SEQ ID NO: 3067) | (GGGGS)$_4$ GGGGP(GGGGS)$_4$ (SEQ ID NO: 3068) | (GGGGS)$_{10}$ (SEQ ID NO: 3067) | (GGGGS)$_4$ GGGGP(GGGS)$_4$ (SEQ ID NO: 3068) | (GGGGS)$_{10}$ (SEQ ID NO: 3067) | (GGGGS)$_4$ GGGGP(GGGS)$_4$ (SEQ ID NO: 3068) |
| CD2-$V_H$ | CD2-$V_H$ | CD2-$V_H$ | CD2-$V_H$ | CD3-$V_H$ | CD3-$V_H$ | CD2-$V_H$ | CD2-$V_H$ |
| GGGGS$_4$ (SEQ ID NO: 9) | GGGGS$_4$ (SEQ ID NO: 9) | GGGGS$_4$ (SEQ ID NO: 9) | GGGGS$_4$ (SEQ ID NO: 9) | GGGGS$_4$ (SEQ ID NO: 9) | GGGGS$_4$ (SEQ ID NO: 9) | GGGGS$_4$ (SEQ ID NO: 9) | GGGGS$_4$ (SEQ ID NO: 9) |
| CD3-$V_H$ | CD3-$V_H$ | CD3-$V_H$ | CD3-$V_H$ | CD2-$V_H$ | CD2-$V_H$ | CD3-$V_H$ | CD3-$V_H$ |
| CD28 Tm CD28 CD3z$_{(1-2)}$ P2A CD34 | CD28 Tm CD28 CD3z$_{(1-2)}$ P2A CD34 | CD28 Tm CD28 CD3z$_{(1-2)}$ P2A CD34 | CD28 Tm CD28 CD3z$_{(1-2)}$ P2A CD34 | CD28 Tm CD28 CD3z$_{(1-2)}$ P2A CD34 | CD28 Tm CD28 CD3z$_{(1-2)}$ P2A CD34 | CD28 Tm CD28 CD3z$_{(1-2)}$ P2A CD34 | CD28 Tm CD28 CD3z$_{(1-2)}$ P2A CD34 |

Dual CAR-T Cells

In certain embodiments, the disclosure provides an engineered T cell with two distinct chimeric antigen receptor polypeptides with affinity to different antigen(s) or cell surface protein(s) expressed within the same effector cell, wherein each CAR functions independently. The CAR may be expressed from single or multiple polynucleotide sequences that specifically bind different antigen(s) or cell surface protein(s), wherein the T cell is deficient in the antigen(s) or cell surface protein(s) to which the CARs bind (e.g., CD7*CD2-dCARΔCD7ΔCD2 cell). In non-limiting examples, the deficiency in the antigen(s) or cell surface protein(s) resulted from (a) modification of antigen or cell surface protein expressed by the T cell such that the chimeric antigen receptor no longer specifically binds the modified antigen(s) or cell surface protein(s) (e.g., the epitope of the one or more antigens recognized by the chimeric antigen receptor may be modified by one or more amino acid changes (e.g., substitutions or deletions) or the epitope may be deleted from the antigen), (b) modification of the T cell such that expression of antigen(s) or cell surface protein(s) is/are reduced in the T cell by at least 50%, at least 60%, at least 70%, at least 80%, at least 90% or more, or (c) modification of the T cell such that antigen(s) or cell surface protein(s) is/are not expressed (e.g., by deletion or disruption of the gene encoding antigen or cell surface protein). In each of the above embodiments, the CAR-T cell may be deficient in one or preferably all the antigens or cell surface proteins to which the chimeric antigen receptor specifically binds. The methods to genetically modify a T cell to be deficient in one or more antigens or cell surface proteins are well known in art and non-limiting examples are provided herein. In embodiments described below, the CRISPR-Cas9 system is used to modify a T cell to be deficient in one or more antigen(s) or cell surface protein(s). Any of these may be accomplished by the methods disclosed herein. In further embodiments, the T cell comprises a suicide gene.

A dCAR for a genome-edited, dual CAR-T cell, i.e., CD2*CD3&-dCARTΔCD2ΔCD38, may be generated by cloning a commercially synthesized anti-CD2 single chain variable fragment into a lentiviral vector containing, e.g., a $2^{nd}$ or $3^{rd}$ generation CAR backbone with CD28 and/or 4-1BB internal signaling domains and cloning a commercially synthesized anti-CD3& single chain variable into the same lentiviral vector containing an additional $2^{nd}$ or $3^{rd}$ generation CAR backbone with CD28 and/or 4-1BB internal signaling domains resulting in a plasmid from which the two CAR constructs are expressed from the same vector. An extracellular hCD34 domain may be added after a P2A peptide to enable both detection of CAR following viral transduction and purification using anti-hCD34 magnetic beads. A similar method may be followed for making tCARs specific for other malignant T cell antigens.

In a similar manner, other dual CARs may be constructed and are given below in Tables 5-7.

In one embodiment, a dual CAR-T cell comprises (i) a first chimeric antigen receptor (CAR) polypeptide comprising a first signal peptide, a first antigen recognition domain, a first hinge region, a first transmembrane domain, a first co-stimulatory domain, and a first signaling domain; and (ii) a second chimeric antigen receptor polypeptide comprising a second signaling peptide, a second antigen recognition domain, a second hinge region, a second transmembrane domain, a second co-stimulatory domain, and a second signaling domain; wherein the first antigen recognition domain and the second antigen recognition domain have affinities for different target antigens; and wherein the dual CAR-T cell possesses one or more genetic disruptions resulting in reduced expression of the target antigen in the dual CAR-T cell.

In a second embodiment, the first signal peptide is a CD8a signal sequence.

In a third embodiment, the first antigen recognition domain is fusion protein of the variable regions of immunoglobulin heavy and light chains, designated $V_H1$ and $V_L1$, for the first antigen recognition domain, connected by a short linker peptide of 5 amino acids (GGGGS (SEQ ID NO: 3065)). In some embodiments, this linker peptide is repeated 3 or 4 times. In some embodiments, the first antigen recognition domain can be selected from $V_H1$-(GGGGS)$_{3-4}$ (SEQ ID NO: 3066)-$V_L1$ or $V_L1$-(GGGGS)$_{3-4}$ (SEQ ID NO: 3066)-$V_H1$.

In some embodiments, the first hinge region comprises CD8a.

In some embodiments, the first transmembrane domain is CD8 or CD28.

In some embodiments, the first co-stimulatory domain comprises 4-1BB, CD28, or a combination of both, in either order, i.e., 4-1BB-CD28 or CD28-4-1BB.

In some embodiments, the first signaling domain is CD3ζ or a CD3 ζ bi-peptide., i.e., CD3ζ-CD3ζ.

In some embodiments, the second signal peptide is a CD8a signal sequence of SEQ NO: 1.

In some embodiments, the second antigen recognition domain is fusion protein of the variable regions of immunoglobulin heavy and light chains, designated $V_H2$ and $V_L2$, for the second antigen recognition domain, connected by a short linker peptide of 5 amino acids (GGGGS (SEQ ID NO: 3065)). In some embodiments, this linker peptide is repeated 3 or 4 times. In some embodiments, the second antigen recognition domain can be selected from $V_H2\text{-}(GGGGS)_{3-4}$ (SEQ ID NO: 3066)-V1.2 or $V_L2\text{-}(GGGGS)_{3-4}$ (SEQ ID NO: 3066)-$V_H2$.

In some embodiments, the second hinge region comprises CD8a.

In some embodiments, the second transmembrane domain is CD8 or CD28.

In some embodiments, the second co-stimulatory domain comprises 4-1BB, CD28, or a combination of both, in either order, i.e., 4-1BB-CD28 or CD28-4-1BB.

In some embodiments, the second signaling domain is CD3ζ or a CD3ζ bi-peptide, i.e., CD3ζ-CD3ζ.

In some embodiments, the CAR polypeptide comprises a first antigen recognition domain fusion protein of $V_H1\text{-}(GGGGS)_{3-4}$ (SEQ ID NO: 3066)-$V_L1$ and a second antigen recognition domain fusion protein of $V_H2\text{-}(GGGGS)_{3-4}$ (SEQ ID NO: 3066)-$V_L2$.

In some embodiments, the CAR polypeptide comprises a first antigen recognition domain fusion protein of $V_L1\text{-}(GGGGS)_{3-4}$ (SEQ ID NO: 3066)-$V_H1$ and a second antigen recognition domain fusion protein of $V_L2\text{-}(GGGGS)_{3-4}$ (SEQ ID NO: 3066)-$V_H2$.

In some embodiments, the CAR polypeptide comprises a first antigen recognition domain fusion protein of $V_H2\text{-}(GGGGS)3.4$ (SEQ ID NO: 3066)-$V_L2$ and a second antigen recognition domain fusion protein of $V_H1\text{-}(GGGGS)_{3-4}$ (SEQ ID NO: 3066)-$V_L1$.

In some embodiments, the CAR polypeptide comprises a first antigen recognition domain fusion protein of $V_L2\text{-}(GGGGS)_{3-4}$ (SEQ ID NO: 3066)-$V_H2$ and a second antigen recognition domain fusion protein of $V_L1\text{-}(GGGGS)_{3-4}$ (SEQ ID NO: 3066)-$V_H1$.

In some embodiments, the CAR polypeptide comprises a first antigen recognition domain fusion protein of $V_H1\text{-}(GGGGS)_{3-4}$ (SEQ ID NO: 3066)-$V_L1$ and a second antigen recognition domain fusion protein of $V_L2\text{-}(GGGGS)_{3-4}$ (SEQ ID NO: 3066)-$V_H2$.

In some embodiments, the CAR polypeptide comprises a first antigen recognition domain fusion protein of $V_L1\text{-}(GGGGS)_{3-4}$ (SEQ ID NO: 3066)-$V_H1$ and a second antigen recognition domain fusion protein of $V_H2\text{-}(GGGGS)_{3-4}$ (SEQ ID NO: 3066)-$V_L2$.

In some embodiments, the CAR polypeptide comprises a first antigen recognition domain fusion protein of $V_H2\text{-}(GGGGS)_{3-4}$ (SEQ ID NO: 3066)-$V_L2$ and a second antigen recognition domain fusion protein of $V_L1\text{-}(GGGGS)_{3-4}$ (SEQ ID NO: 3066)-$V_H1$.

In some embodiments, the CAR polypeptide comprises a first antigen recognition domain fusion protein of V12-$(GGGGS)_{3-4}$ (SEQ ID NO: 3066)-$V_H2$ and a second antigen recognition domain fusion protein of $V_H1\text{-}(GGGGS)_{3-4}$ (SEQ ID NO: 3066)-$V_L1$.

In some embodiments, the CAR polypeptide comprises at least one high efficiency cleavage site, wherein the high efficiency cleavage site is selected from P2A, T2A, E2A, and F2A.

In some embodiments, the CAR polypeptide comprises a suicide gene.

In some embodiments, the CAR polypeptide comprises a mutant cytokine receptor.

In some embodiments, the dual CAR-T cell targets two antigens selected from CD5, CD7, CD2, CD4, CD3, CD33, CD123 (IL3RA), CD371 (CLL-1; CLEC12A), CD117 (c-kit), CD135 (FLT3), BCMA, CS1, CD38, CD79A, CD79B, CD138, and CD19, APRIL, and TACI.

Additional examples of dual CARs are given below in Table 7.

TABLE 7

Dual CARs and dCAR-Ts

| Example | Antigen Targets of CARs in dCAR-T cell | Antigen Deletion/Suppression |
|---|---|---|
| D1 | APRILxBCMA | — |
| D2 | APRILxCD19 | — |
| D3 | APRILxCD38 | — |
| D4 | APRILxCD38 | CD38 |
| D5 | APRILxCS1 | — |
| D6 | APRILxCS1 | CS1 |
| D7 | BCMAxCD19 | — |
| D8 | BCMAxCD38 | — |
| D9 | BCMAxCD38 | CD38 |
| D10 | BCMAxCS1 | — |
| D11 | BCMAxCS1 | CS1 |
| D12 | CD138xAPRIL | |
| D13 | CD138xBCMA | |
| D14 | CD138xCD19 | |
| D15 | CD138xCD38 | |
| D16 | CD138xCD38 | CD38 |
| D17 | CD138xCD79A | |
| D18 | CD138xCD79B | |
| D19 | CD138xCS1 | |
| D20 | CD138xCS1 | CS1 |
| D21 | CD19xCD38 | — |
| D22 | CD19xCD38 | CD38 |
| D23 | CD2xCD3ε | — |
| D24 | CD2xCD3ε | CD2 |
| D25 | CD2xCD3ε | CD3ε |
| D26 | CD2xCD3ε | CD2 and CD3ε |
| D27 | CD2xCD4 | — |
| D28 | CD2xCD4 | CD2 |
| D29 | CD2xCD4 | CD4 |
| D30 | CD2xCD4 | CD2 and CD4 |
| D31 | CD2xCD4 | CD2 and TRAC |
| D32 | CD2xCD4 | CD4 and TRAC |
| D33 | CD2xCD4 | CD2 and CD4 and TRAC |
| D34 | CD2xCD5 | — |
| D35 | CD2xCD5 | CD2 |
| D36 | CD2xCD5 | CD5 |
| D37 | CD2xCD5 | CD2 and CD5 |
| D38 | CD2xCD5 | CD2 and TRAC |
| D39 | CD2xCD5 | CD5 and TRAC |
| D40 | CD2xCD5 | CD2 and CD5 and TRAC |
| D41 | CD2xCD7 | — |
| D42 | CD2xCD7 | CD2 |
| D43 | CD2xCD7 | CD7 |
| D44 | CD2xCD7 | CD2 and CD7 |
| D45 | CD2xCD7 | CD2 and TRAC |
| D46 | CD2xCD7 | CD7 and TRAC |
| D47 | CD2xCD7 | CD2 and CD7 and TRAC |
| D48 | CD3εxCD4 | — |
| D49 | CD3εxCD4 | CD3ε |
| D50 | CD3εxCD4 | CD4 |
| D51 | CD3εxCD4 | CD3ε and CD4 |
| D52 | CD3εxCD5 | — |
| D53 | CD3εxCD5 | CD3ε |
| D54 | CD3εxCD5 | CD5 |
| D55 | CD3εxCD5 | CD3ε and CD5 |

TABLE 7-continued

Dual CARs and dCAR-Ts

| Example | Antigen Targets of CARs in dCAR-T cell | Antigen Deletion/Suppression |
|---|---|---|
| D56 | CD3εxCD7 | — |
| D57 | CD3εxCD7 | CD3ε |
| D58 | CD3εxCD7 | CD7 |
| D59 | CD3εxCD7 | CD3ε and CD7 |
| D60 | CD4xCD5 | — |
| D61 | CD4xCD5 | CD4 |
| D62 | CD4xCD5 | CD5 |
| D63 | CD4xCD5 | CD4 and CD5 |
| D64 | CD4xCD5 | CD4 and TRAC |
| D65 | CD4xCD5 | CD5 and TRAC |
| D66 | CD4xCD5 | CD4 and CD5 and TRAC |
| D67 | CD4xCD7 | — |
| D68 | CD4xCD7 | CD4 |
| D69 | CD4xCD7 | CD7 |
| D70 | CD4xCD7 | CD4 and CD7 |
| D71 | CD4xCD7 | CD4 and TRAC |
| D72 | CD4xCD7 | CD7 and TRAC |
| D73 | CD4xCD7 | CD4 and CD7 and TRAC |
| D74 | CD5xCD7 | — |
| D75 | CD5xCD7 | CD5 |
| D76 | CD5xCD7 | CD7 |
| D77 | CD5xCD7 | CD5 and CD7 |
| D78 | CD5xCD7 | CD5 and TRAC |
| D79 | CD5xCD7 | CD7 and TRAC |
| D80 | CD5xCD7 | CD5 and CD7 and TRAC |
| D81 | CD79AxAPRIL | |
| D82 | CD79AxBCMA | |
| D83 | CD79AxCD19 | |
| D84 | CD79AxCD38 | |
| D85 | CD79AxCD38 | CD38 |
| D86 | CD79AxCD79B | |
| D87 | CD79AxCS1 | |
| D88 | CD79AxCS1 | CS1 |
| D89 | CD79BxAPRIL | |
| D90 | CD79BxBCMA | |
| D91 | CD79BxCD19 | |
| D92 | CD79BxCD38 | |
| D93 | CD79BxCD38 | CD38 |
| D94 | CD79BxCD79A | |
| D95 | CD79BxCS1 | |
| D96 | CD79BxCS1 | CS1 |
| D97 | CS1xCD19 | — |
| D98 | CS1xCD19 | CS1 |
| D99 | CS1xCD38 | — |
| D100 | CS1xCD38 | CS1 |
| D101 | CS1xCD38 | CD38 |
| D102 | CS1xCD38 | CS1 and CD38 |
| D103 | TCRβxCD2 | — |
| D104 | TCRβxCD2 | TCRβ |
| D105 | TCRβxCD2 | CD2 |
| D106 | TCRβxCD2 | TCRβ and CD2 |
| D107 | TCRβxCD3ε | — |
| D108 | TCRβxCD3ε | TCRβ |
| D109 | TCRβxCD3ε | CD3ε |
| D110 | TCRβxCD3ε | TCRβ and CD3ε |
| D111 | TCRβxCD4 | — |
| D112 | TCRβxCD4 | TCRβ |
| D113 | TCRβxCD4 | CD4 |
| D114 | TCRβxCD4 | TCRβ and CD4 |
| D115 | TCRβxCD5 | — |
| D116 | TCRβxCD5 | TCRβ |
| D117 | TCRβxCD5 | CD5 |
| D118 | TCRβxCD5 | TCRβ and CD5 |
| D119 | TCRβxCD7 | — |
| D120 | TCRβxCD7 | TCRβ |
| D121 | TCRβxCD7 | CD7 |
| D122 | TCRβxCD7 | TCRβ and CD7 |
| D123 | TRACxCD2 | — |
| D124 | TRACxCD2 | TRAC |
| D125 | TRACxCD2 | CD2 |
| D126 | TRACxCD2 | TRAC and CD2 |
| D127 | TRACxCD3ε | — |
| D128 | TRACxCD3ε | TRAC |
| D129 | TRACxCD3ε | CD3ε |
| D130 | TRACxCD3ε | TRAC and CD3ε |
| D131 | TRACxCD4 | — |
| D132 | TRACxCD4 | TRAC |
| D133 | TRACxCD4 | CD4 |
| D134 | TRACxCD4 | TRAC and CD4 |
| D135 | TRACxCD5 | — |
| D136 | TRACxCD5 | TRAC |
| D137 | TRACxCD5 | CD5 |
| D138 | TRACxCD5 | TRAC and CD5 |
| D139 | TRACxCD7 | — |
| D140 | TRACxCD7 | TRAC |
| D141 | TRACxCD7 | CD7 |
| D142 | TRACxCD7 | TRAC and CD7 |

Cytokine/Chemokine/Transcription Factor Gene Deletion or Suppression

Cytokine release syndrome (CRS) is caused by a large, rapid release of cytokines from immune cells in response to immunotherapy (or other immunological stimulus). Accordingly, reducing the level of cytokines released would prevent or reduce the development and/or maintenance of CRS. As disclosed herein, this can be accomplished by modifying, disrupting, or deleting one or more cytokine/chemokine/transcription factor genes. One method to accomplish this is genetic ablation (gene silencing) in which gene expression is abolished through the alteration or deletion of genetic sequence information. This can be accomplished using known genetic engineering tools in the art such as Transcription Activator-like Effector Nucleases (TALENs), Zinc Finger Nucleases (ZFNs), CRISPR, and also by transfection of small interfering RNAs (siRNAs).

Another technique is expression of an scFv with an endoplasmic reticulum (ER) binding tether to bind the cytokine in the ER and prevent secretion. Specific constructs, named protein expression blockers (PEBLs), prevent transport of targeted proteins to the cell membrane. PEBL constructs can be readily combined with other gene modification systems for ex vivo cell processing of immune cells. A short hairpin RNA or small hairpin RNA (shRNA/Hairpin Vector) is an artificial RNA molecule with a tight hairpin turn that can be used to silence target gene expression, i.e., of antigens, via RNA interference (RNAi). Expression of shRNA in cells is typically accomplished by delivery of plasmids or through viral or bacterial vectors.

Cytokines or chemokines that can be deleted from immune effector cells as disclosed herein, e.g., by targeted transduction of a CAR into the gene sequence of the cytokine, include without limitation the following: XCL1, XCL2, CCL1, CCL2, CCL3, CCL4, CCL5, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27, CXCL1, CXCL2, CXCL3, CXCL4, CXCL5, CXCL6, CXCL7, CXCL8, CXCL9, CXCL10, CXCL11, CXCL12, CXCL13, CXCL14, CX3CL1, IL-1a, IL-1B, IL-1RA, IL-18, IL-2, IL-4, IL-7, IL-9, IL-13, IL-15, IL-3, IL-5, GM-CSF, IL-6, IL-11, G-CSF, IL-12, LIF, OSM, IL-10, IL-20, IL-14, IL-16, IL-17, IFN-α, IFN-β, IFN-γ, CD154, LT-β, TNF-α,TNF-β, 4-1BBL, APRIL, CD70, CD153, CD178, GITRL, LIGHT, OX40L, TALL-1, TRAIL, TWEAK, TRANCE, TGF-β1, TGF-β2, TGF-β3, Epo, Tpo, Flt-3L, SCF, M-CSF, MSP, A2M, ACKR1, ACKR2, ACKR3, ACVR1, ACVR2B, ACVRL1, ADIPOQ, AGER, AGRN, AIMP1, AREG, BMP1, BMP10, BMP15, BMP2, BMP3, BMP4, BMP5, BMP6, BMP7, BMP8A, BMP8B, BMPR2, C10orf99, C1QTNF4, C5, CCL28, CCR1, CCR2, CCR3, CCR5, CCR6, CCR7, CD109, CD36, CD4, CD40LG, CD74, CER1, CHRD, CKLF, CLCF1, CMTM1, CMTM2, CMTM3, CMTM4, CMTM5, CMTM6, CMTM7, CMTM8, CNTF, CNTFR, COPS5, CRLF1, CSF1, CSF1R, CSF2, CSF3, CSF3R, CTF1, CX3CR1, CXCL16, CXCL17, CXCR1, CXCR2, CXCR3, CXCR4, CXCR6, EBI3, EDNI, ELANE, ENG, FAM3B, FAM3C, FAM3D, FAS, FASLG, FGF2, FLT3LG, FZD4, GBP1, GDF1, GDF10, GDF11, GDF15, GDF2, GDF3, GDF5, GDF6, GDF7, GDF9, GPI, GREM1, GREM2, GRN, HAX1, HFE2, HMGB1, HYAL2, IFNA10, IFNA14, IFNA16, IFNA2, IFNA5, IFNA6, IFNA8, IFNAR1, IFNAR2, IFNB1, IFNE, IFNG, IFNGR1, IFNK, IFNL1, IFNL3, IFNW1, IL1ORA, IL11RA, IL12A, IL12B, IL12RB1, IL17A, IL17B, IL17C, IL17D, IL17F, IL18BP, IL-19, IL1F10, ILIR1, ILIR2, ILIRAPLI, ILIRLI, ILIRN, IL20RA, IL20RB, IL21, IL22, IL22RA1, IL22RA2, IL23A, IL23R, IL24, IL25, IL26, IL27, IL2RA, IL2RB, IL2RG, IL31, IL31RA, IL32, IL33, IL34, IL36A, IL36B, IL36G, IL36RN, IL37, IL6R, IL6ST, INHA, INHBA, INHBB, INHBC, INHBE, ITGA4, ITGAV, ITGB1, ITGB3, KIT, KITLG, KLHL20, LEFTY1, LEFTY2, LIFR, LTA, LTB, LTBP1, LTBP3, LTBP4, MIF, MINOS1-, MSTN, NAMPT, NBL1, NDP, NLRP7, NODAL, NOG, NRG1, NRP1, NRP2, OSMR, PARK7, PDPN, PF4, PF4V1, PGLYRP1, PLP2, PPBP, PXDN, SCG2, SCGB3A1, SECTM1, SLURP1, SOSTDC1, SP100, SPP1, TCAP, TGFBR1, TGFBR2, TGFBR3, THBS1, THNSL2, THPO, TIMP1, TNF, TNFRSF11, TNFRSF1A, TNFRSF9, TNFRSF10, TNFSF11, TNFSF12, TNFSF12-, TNFSF13, TNFSF13B, TNFSF14, TNFSF15, TNFSF18, TNFSF4, TNFSF8, TNFSF9, TRIM16, TSLP, TWSG1, TXLNA, VASN, VEGFA, VSTMI, WFIKKN1, WFIKKN2, WNT1, WNT2, WNT5A, WNT7A, and ZFP36.

In some embodiments, the cytokine is chosen from cytokine is chosen from MCP1 (CCL2), MCP-2, GM-CSF, G-CSF, M-CSF, Il-4, and IFNγ.

In certain embodiments, transcription factors that can be deleted from immune effector cells as disclosed herein include AHR, BCL6, FOXP3, GATA3, MAF, RORC, SPII, and TBX21.

The sequences of these genes are known and available in the art and can include, for example, those provided in Table 10.

Selection of Priority Target Genes

Cytokine/chemokine gene targets of specific interest for deletion or suppression (e.g., ablation, knock-out, KO) in CAR-T cells for the mitigation of CRS have been categorized into groups based on biological function. CRS development is dependent upon CAR-T cell activation and subsequent cytokine release, which initiates a dysregulated immune system in the recipient of the CAR-T cell therapy. Several studies have indicated that recipient myeloid activation is necessary for the development of CRS.

The first group of potential genes to KO in CAR-T are surface receptors that, when engaged with myeloid cells in normal immunological responses activate the myeloid cells (e.g., CD40L). The second group are cytokines that are released from CAR-T cells that activate myeloid cells (e.g., GM-CSF). In both these categories, the goal is to prevent CAR-T cell signaling, which will activate recipient myeloid cells and initiate CRS.

The third category of targets are endogenous T cell receptors that increase T cell activation (potentially in the absence of tumor target) that are integrated into the CAR-T receptor (e.g., endogenous CD28). The aim is to curtail activation of the CAR-T from non-tumor interactions, such as activated myeloid cells that could engage with CD28 on activated T cells, thus amplifying T cell cytokine production and subsequent myeloid activation.

The fourth and fifth categories of gene KO targets are transcription factors and cytokines that drive CAR-T cell differentiation and subsequent functional characteristics. CAR-T cells that are phenotypically similar to normal cytotoxic T cells (CTL, typically identified by CD8 expression) are capable of direct tumor killing through T cell mediated effector functions. CTL are supported and maintained by T helper cells (expressing CD4). Importantly, subsets of T helper cells can support CTL (i.e., Th1 cells) or inhibit (i.e., Th2 cells). Other T cells, such as Tregs can also inhibit CTL development and function. The aim is to target cytokines or transcription factors in the CAR-T population that would lead to CAR-T differentiation into non-cytotoxic T cell populations. Additionally, Th2 cells produce cytokines (such as GM-CSF and IL-4), which are indicative markers of CRS. It is likely that CAR-T phenotypes, which cannot optimally kill tumor cells, will be activated via CAR-T receptors, produce signals that drive CRS in the host, increase the time required for tumor killing, and require higher CAR-T cell doses than optimized "killing" products. Thus, knocking out or ablating (or suppressing) transcription factors (such as GATA3) or cytokines (such as IL-4) will prevent (or reduce) Th2 bias and reduce CRS.

Of additional interest regarding both myeloid activating cytokines and optimized CAR-T cell differentiation is the potential to mitigate CAR-T neurotoxicity. Neurotoxicity occurs in a small population of CAR-T recipients with CRS. Research has shown that CRS patients that progress to develop neurotoxicity have increased IL-5 and ferritin levels (Santomasso et al., 2017 and Philip et al., 2019). These two biomarkers indicate that mast cell activation may be involved with CNS complications. IL-5 is a key cytokine produced by Th2 cells, eosinophils and mast cells. Excessive levels of ferritin are observed in mastocytosis and several diseases involving mast cell dysregulation. Additionally, many mast cell diseases include neurological dysregulation. Given raised levels of IL-5, ferritin, and neurological toxicity in some patients, reducing mast cell activation by cytokines such as IL-5, or preventing Th2 cell development which drives IL-5-dependent mast cell activation, may also mitigate neurological complications seen in CRS recipients. With respect to CNS complications, CX3CR1 and OX40 were also highlighted, due to previously demonstrated high T cell burden in the CNS. CX3CR1 is a T cell chemokine receptor that principally directs T cells and potentially CAR-T cells into the CNS. OX40 is the T cell receptor which facilitates activation by cell-cell interaction with OX40L on eosinophils and mast cells.

Thus, in certain embodiments, the cytokine is chosen from CCL2 (MCP1), MCP-2, GM-CSF, G-CSF, M-CSF, Il-4, and IFNγ.

Indications and Standards of Care in CAR-T Therapy

In some embodiment, the genome-edited immune effector cells disclosed herein, and/or generated using the methods disclosed herein, express one or more chimeric antigen receptors (CARs) and can be used as a medicament, i.e., for the treatment of disease. In many embodiments, the cells are CAR-T cells.

Cells disclosed herein, and/or generated using the methods disclosed herein, may be used in immunotherapy and adoptive cell transfer, for the treatment, or the manufacture of a medicament for treatment, of cancers, autoimmune diseases, infectious diseases, and other conditions.

The cancer may be a hematologic malignancy or solid tumor. Hematologic malignancies include leukemias, lymphomas, multiple myeloma, and subtypes thereof. Lymphomas can be classified various ways, often based on the underlying type of malignant cell, including Hodgkin's lymphoma (often cancers of Reed-Sternberg cells, but also sometimes originating in B cells; all other lymphomas are non-Hodgkin's lymphomas), B-cell lymphomas, T-cell lymphomas, mantle cell lymphomas, Burkitt's lymphoma, follicular lymphoma, and others as defined herein and known in the art.

B-cell lymphomas include, but are not limited to, diffuse large B-cell lymphoma (DLBCL), chronic lymphocytic leukemia (CLL)/small lymphocytic lymphoma (SLL), and others as defined herein and known in the art.

T-cell lymphomas include T-cell acute lymphoblastic leukemia/lymphoma (T-ALL),, peripheral T-cell lymphoma (PTCL), T-cell chronic lymphocytic leukemia (T-CLL) Sezary syndrome, and others as defined herein and known in the art.

Leukemias include Acute myeloid (or myelogenous) leukemia (AML), chronic myeloid (or myelogenous) leukemia (CML), acute lymphocytic (or lymphoblastic) leukemia (ALL), chronic lymphocytic leukemia (CLL) hairy cell leukemia (sometimes classified as a lymphoma), and others as defined herein and known in the art.

Plasma cell malignancies include lymphoplasmacytic lymphoma, plasmacytoma, and multiple myeloma.

In some embodiments, the medicament can be used for treating cancer in a patient, particularly for the treatment of solid tumors such as melanomas, neuroblastomas, gliomas or carcinomas such as tumors of the brain, head and neck, breast, lung (e.g., non small cell lung cancer, NSCLC), reproductive tract (e.g., ovary), upper digestive tract, pancreas, liver, renal system (e.g., kidneys), bladder, prostate and colorectum.

In another embodiment, the medicament can be used for treating cancer in a patient, particularly for the treatment of hematologic malignancies selected from multiple myeloma and acute myeloid leukemia (AML) and for T-cell malignancies selected from T-cell acute lymphoblastic leukemia (T-ALL), non-Hodgkin's lymphoma, and T-cell chronic lymphocytic leukemia (T-CLL).

In some embodiments, the cells may be used in the treatment of autoimmune diseases such as lupus, autoimmune (rheumatoid) arthritis, multiple sclerosis, transplant rejection, Crohn's disease, ulcerative colitis, dermatitis, and the like. In some embodiments, the cells are chimeric autoantibody receptor T-cells, or CAAR-Ts displaying antigens or fragments thereof, instead of antibody fragments; in this version of adoptive cell transfer, the B cells that cause autoimmune diseases will attempt to attack the engineered T cells, which will respond by killing them.

In some embodiments, the cells may be used in the treatment of infectious diseases such as HIV and tuberculosis.

In another embodiment, the CAR-T cells of the present disclosure can undergo robust in vivo T cell expansion and can persist for an extended amount of time.

In some embodiments, the treatment of a patient with CAR-T cells of the present disclosure can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic, is meant that the cells or population of cells used for treating patients are not originating from the patient but from a donor.

The treatment of cancer with CAR-T cells of the present disclosure may be in combination with one or more therapies selected from antibody therapy, chemotherapy, cytokine therapy, dendritic cell therapy, gene therapy, hormone therapy, radiotherapy, laser light therapy, and radiation therapy.

The administration of CAR-T cells or a population of CAR-T cells of the present disclosure of the present disclosure be carried out by aerosol inhalation, injection, ingestion, transfusion, implantation or transplantation. The CAR-T cells compositions described herein, i.e., mono CAR, dual CAR, tandem CARs, may be administered to a patient subcutaneously, intradermally, intratumorally, intranodally, intramedullary, intramuscularly, by intravenous or intralymphatic injection, or intraperitoneally. In one embodiment, the cell compositions of the present disclosure are preferably administered by intravenous injection.

The administration of CAR-T cells or a population of CAR-T cells can consist of the administration of $10^4$-$10^9$ cells per kg body weight, preferably $10^5$ to $10^6$ cells/kg body weight including all integer values of cell numbers within those ranges. The CAR-T cells or a population of CAR-T cells can be administrated in one or more doses. In another embodiment, the effective amount of CAR-T cells or a population of CAR-T cells are administrated as a single dose. In another embodiment, the effective amount of cells are administered as more than one dose over a period time. Timing of administration is within the judgment of a health care provider and depends on the clinical condition of the patient. The CAR-T cells or a population of CAR-T cells may be obtained from any source, such as a blood bank or a donor. While the needs of a patient vary, determination of optimal ranges of effective amounts of a given CAR-T cell population(s) for a particular disease or conditions are within the skill of the art. An effective amount means an amount which provides a therapeutic or prophylactic benefit. The dosage administered will be dependent upon the age, health and weight of the patient recipient, type of concurrent treatment, if any, frequency of treatment, and the nature of the effect desired.

In another embodiment, the effective amount of CAR-T cells or a population of CAR-T cells or composition comprising those CAR-T cells are administered parenterally. The administration can be an intravenous administration. The administration of CAR-T cells or a population of CAR-T cells or composition comprising those CAR-T cells can be directly done by injection within a tumor.

In one embodiment of the present disclosure, the CAR-T cells or a population of the CAR-T cells are administered to a patient in conjunction with, e.g., before, simultaneously or following, any number of relevant treatment modalities, including but not limited to, treatment with cytokines, or expression of cytokines from within the CAR-T, that enhance T-cell proliferation and persistence and, include but not limited to, IL-2, IL-7, and IL-15.

In a second embodiment, the CAR-T cells or a population of CAR-T cells of the present disclosure may be used in combination with agents that inhibit immunosuppressive pathways, including but not limited to, inhibitors of TGF-β, interleukin 10 (IL-10), adenosine, VEGF, indoleamine 2,3 dioxygenase 1 (IDO1), indoleamine 2,3-dioxygenase 2 (IDO2), tryptophan 2-3-dioxygenase (TDO), lactate, hypoxia, arginase, and prostaglandin E2.

In another embodiment, the CAR-T cells or a population of CAR-T cells of the present disclosure may be used in combination with T-cell checkpoint inhibitors, including but not limited to, anti-CTLA4 (Ipilimumab) anti-PDI (Pembrolizumab, Nivolumab, Cemiplimab), anti-PDL1 (Atezolizumab, Avelumab, Durvalumab), anti-PDL2, anti-BTLA, anti-LAG3, anti-TIM3, anti-VISTA, anti-TIGIT, and anti-KIR.

In another embodiment, the CAR-T cells or a population of CAR-T cells of the present disclosure may be used in combination with T cell agonists, including but not limited to, antibodies that stimulate CD28, ICOS, OX-40, CD27, 4-1BB, CD137, GITR, and HVEM In another embodiment, the CAR-T cells or a population of CAR-T cells of the present disclosure may be used in combination with therapeutic oncolytic viruses, including but not limited to, retroviruses, picornaviruses, rhabdoviruses, paramyxoviruses, reoviruses, parvoviruses, adenoviruses, herpesviruses, and poxviruses.

In another embodiment, the CAR-T cells or a population of CAR-T cells of the present disclosure may be used in combination with immunostimulatory therapies, such as toll-like receptors agonists, including but not limited to, TLR3, TLR4, TLR7 and TLR9 agonists.

In another embodiment, the CAR-T cells or a population of CAR-T cells of the present disclosure may be used in combination with stimulator of interferon gene (STING) agonists, such as cyclic GMP-AMP synthase (cGAS).

Immune effector cell aplasia, particularly T cell aplasia is also a concern after adoptive cell transfer therapy. When the malignancy treated is a T-cell malignancy, and CAR-T cells target a T cell antigen, normal T cells and their precursors expressing the antigen will become depleted, and the immune system will be compromised. Accordingly, methods for managing these side effects are attendant to therapy. Such methods include selecting and retaining non-malignant T cells or precursors, either autologous or allogeneic (optionally engineered not to cause rejection or be rejected), for later expansion and re-infusion into the patient, after CAR-T cells are exhausted or deactivated. Alternatively, CAR-T cells which recognize and kill subsets of TCR-bearing cells, such as normal and malignant TRBC1+, but not TRBC2+ cells, or alternatively, TRBC2+, but not TRBC1+ cells, may be used to eradicate a T cell malignancy while preserving sufficient normal T cells to maintain normal immune system function.

Definitions

As used herein, the terms below have the meanings indicated. Other definitions may occur throughout the specification.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "activation" (and other conjugations thereof) in reference to cells is generally understood to be synonymous with "stimulating" and as used herein refers to treatment of cells that results in expansion of cell populations. In T cells, activation is often accomplished by exposure to CD2 and CD28 (and sometimes CD2 as well) agonists, typically antibodies, optionally coated onto magnetic beads or conjugated to a colloidal polymeric matrix.

The term "antigen" as used herein is a cell surface protein recognized by (i.e., that is the target of) T cell receptor or chimeric antigen receptor. In the classical sense antigens are substances, typically proteins, that are recognized by antibodies, but the definitions overlap insofar as the CAR comprises antibody-derived domains such as light ($V_L$) and heavy ($V_H$) chains recognizing one or more antigen(s).

The term "cancer" refers to a malignancy or abnormal growth of cells in the body. Many different cancers can be characterized or identified by particular cell surface proteins or molecules. Thus, in general terms, cancer in accordance with the present disclosure may refer to any malignancy that may be treated with an immune effector cell, such as a CAR-T cell as described herein, in which the immune effector cell recognizes and binds to the cell surface protein on the cancer cell. As used herein, cancer may refer to a hematologic malignancy, such as multiple myeloma, a T-cell malignancy, or a B cell malignancy. T cell malignancies may include, but are not limited to, T-cell acute lymphoblastic leukemia (T-ALL) or non-Hodgkin's lymphoma. A cancer may also refer to a solid tumor, such as including, but not limited to, cervical cancer, pancreatic cancer, ovarian cancer, mesothelioma, and lung cancer.

A "cell surface protein" as used herein is a protein (or protein complex) expressed by a cell at least in part on the surface of the cell. Examples of cell surface proteins include the TCR (and subunits thereof) and CD7.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "composition" as used herein refers to an immunotherapeutic cell population combination with one or more therapeutically acceptable carriers.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "donor template" refers to the reference genomic material that the cell uses as a template to repair the a double-stranded break through the homology-directed repair (HDR) DNA repair pathway. The donor template contains the piece of DNA to be inserted into the genome (containing the gene to be expressed, CAR, or marker) with two homology arms flanking the site of the double-stranded break. In some embodiments, a donor template may be an adeno-associated virus, a single-stranded DNA, or a double-stranded DNA.

The term "fratricide" as used herein means a process which occurs when a CAR-T cell (or other CAR-bearing immune effector cell) becomes the target of, and is killed by, another CAR-T cell comprising the same chimeric antigen receptor as the target of CAR-T cell, because the targeted cell expresses the antigen specifically recognized by the chimeric antigen receptor on both cells. CAR-T comprising a chimeric antigen receptor which are deficient in an antigen to which the chimeric antigen receptor specifically binds will be "fratricide-resistant."

The term "genome-edited" or "gene-edited" as used herein means having a gene or potion of the genome added, deleted, or modified (e.g., disrupted) to be non-functional. Thus, in certain embodiments, a "genome-edited T cell" is a T cell that has had a gene such as a CAR recognizing at least one antigen added; and/or has had a gene such as the gene(s) to the antigen(s) that are recognized by the CAR deleted, and/or has had the gene to the TCR or a subunit thereof disrupted.

A "healthy donor," as used herein, is one who does not have a malignancy (particularly a hematologic malignancy, e.g., a T-cell malignancy).

As used herein, an "immature dendritic cell" or "iDC" refers to an immature dendritic cell.

The term "therapeutically acceptable" refers to substances which are suitable for use in contact with the tissues of patients without undue toxicity, irritation, and allergic response, are commensurate with a reasonable benefit/risk ratio, and/or are effective for their intended use.

The term "therapeutically effective" is intended to qualify the amount of active ingredients used in the treatment of a disease or disorder or on the effecting of a clinical endpoint.

The term "patient" is generally synonymous with the term "subject" and includes all mammals including humans.

A "malignant B cell" is a B cell derived from a B-cell malignancy. B cell malignancies include, without limitation, (DLBCL), chronic lymphocytic leukemia (CLL)/small lymphocytic lymphoma (SLL), and B cell-precursor acute lymphoblastic leukemia (ALL).

The term "exposing to," as used herein, in the context of bringing compositions of matter (such as antibodies) into intimate contact with other compositions of matter (such as cells), is intended to be synonymous with "incubated with," and no lengthier period of time in contact is intended by the use of one term instead of the other.

A "malignant T cell" is a T cell derived from a T-cell malignancy. The term "T-cell malignancy" refers to a broad, highly heterogeneous grouping of malignancies derived from T-cell precursors, mature T cells, or natural killer cells. Non-limiting examples of T-cell malignancies include T-cell acute lymphoblastic leukemia/lymphoma (T-ALL),, human T-cell leukemia virus type 1-positive (HTLV-1+) adult T-cell leukemia/lymphoma (ATL), T-cell prolymphocytic leukemia (T-PLL), Adult T-cell lymphoma/leukemia (HTLV-1 associated), Aggressive NK-cell leukemia, Anaplastic large-cell lymphoma (ALCL), ALK positive, Anaplastic large-cell lymphoma (ALCL), ALK negative, Angioimmunoblastic T-cell lymphoma (AITL), Breast implant-associated anaplastic large-cell lymphoma, Chronic lymphoproliferative disorder of NK cells, Extra nodal NK/T-cell lymphoma, nasal type, Enteropathy-type T-cell lymphoma, Follicular T-cell lymphoma, Hepatosplenic T-cell lymphoma, Indolent T-cell lymphoproliferative disorder of the GI tract, Monomorphic epitheliotrophic intestinal T-cell lymphoma, Mycosis fungoides, Nodal peripheral T-cell lymphoma with TFH phenotype, Peripheral T-cell lymphoma (PTCL), NOS, Primary cutaneous α/β T-cell lymphoma, Primary cutaneous CD8+ aggressive epidermotropic cytotoxic T-cell lymphoma, Primary cutaneous acral CD8+ T-cell lymphoma, Primary cutaneous CD4+ small/medium T-cell lymphoproliferative disorders [Primary cutaneous anaplastic large-cell lymphoma (C-ALCL), lymphoid papulosis], Sezary syndrome, Subcutaneous, panniculitis-like T-cell lymphoma, Systemic EBV+ T-cell lymphoma of childhood, and T-cell large granular lymphocytic leukemia (LGL).

A "malignant plasma cell" is a plasma cell derived from a plasma cell malignancy. The term "plasma-cell malignancy" refers to a malignancy in which abnormal plasma cells are overproduced. Non-limiting examples of plasma cell malignancies include lymphoplasmacytic lymphoma, plasmacytoma, and multiple myeloma.

As used herein, "suicide gene" refers to a nucleic acid sequence introduced to a CAR-T cell by standard methods known in the art, that when activated result in the death of the CAR-T cell. If required suicide genes may facilitate the tracking and elimination, i.e., killing, of CAR-T cells in vivo. Facilitated killing of CAR-T cells by activating a suicide gene can be accomplished by standard methods known in the art. Suicide gene systems known in the art include, but are not limited to, several herpes simplex virus thymidine kinase (HSVtk)/ganciclovir (GCV) suicide gene therapy systems and inducible caspase 9 proteins. In one embodiment, the suicide gene is a chimeric CD34/thymidine kinase.

As used herein, an "immune effector cell" is a leukocyte that can modulate an immune response. Immune effector cells include T cells, B cells, natural killer (NK) cells, iNKT cells (invariant T-cell receptor alpha natural killer T cells), and macrophages. T cell receptor (TCR)-bearing immune effector cells include, of course, T cells, but also cells which have been engineered to express a T cell receptor. Immune effector cells may be obtained or derived/generated from any appropriate source, such as including, but not limited to, healthy donors, peripheral blood mononuclear cells, cord blood, and induced pluripotent stem cells (iPSC).

As used herein, a "CAR-bearing immune effector cell" is an immune effector cell which has been transduced with at least one CAR. A "CAR-T cell" is a T cell which has been transduced with at least one CAR; CAR-T cells can be mono, dual, or tandem CAR-T cells. CAR-T cells can be autologous, meaning that they are engineered from a subject's own cells, or allogeneic, meaning that the cells are sourced from a healthy donor, and in many cases, engineered so as not to provoke a host-vs-graft or graft-vs-host reaction.

A "chimeric antigen receptor" or "CAR" as used herein and generally used in the art, refers to a recombinant fusion protein that has an extracellular ligand-binding domain, a transmembrane domain, and a signaling transducing domain that directs the cell to perform a specialized function upon binding of the extracellular ligand-binding domain to a component present on the target cell. For example, a CAR can have an antibody-based specificity for a desired antigen (e.g., tumor antigen) with a T cell receptor-activating intracellular domain to generate a chimeric protein that exhibits specific anti-target cellular immune activity. First-generation CARs include an extracellular ligand-binding domain and signaling transducing domain, commonly CD3ζ or FcεRIγ. Second generation CARs are built upon first generation CAR constructs by including an intracellular costimulatory domain, commonly 4-1BB or CD28. These costimulatory domains help enhance CAR-T cell cytotoxicity and proliferation compared to first generation CARs. The third generation CARs include multiple costimulatory domains, primarily to increase CAR-T cell proliferation and persistence. Chimeric antigen receptors are distinguished from other antigen binding agents by their ability both to bind MHC-independent antigens and transduce activation signals via their intracellular domain.

The term "CAR-iNKT cell" (equivalently, iNKT-CAR) means an iNKT cell that expresses a chimeric antigen receptor. A dual iNKT-CAR cell (equivalently, iNKT-dCAR) is an iNKT-CAR cell that expresses two distinct chimeric antigen receptor polypeptides with affinity to different target antigens expressed within the same effector cell, wherein each CAR functions independently. The CAR may be expressed from a single or multiple polynucleotide sequences. A tandem INKT-CAR cell (equivalently, iNKT-tCAR) is an iNKT-CAR cell with a single chimeric antigen polypeptide containing two distinct antigen recognition domains with affinity to different targets, wherein the antigen recognition domains are linked through a peptide linker and share common costimulatory domain(s), and wherein binding of either antigen recognition domain will signal though a common costimulatory domains(s) and signaling domain.

The term "chimeric antigen receptor T cell" (equivalently, CAR-T) means an T cell that expresses a chimeric antigen receptor.

The term dual CAR-T (dCAR-T), means a CAR-T cell that expresses cells two distinct chimeric antigen receptor polypeptides with affinity to different target antigen expressed within the same effector cell, wherein each CAR functions independently. The CAR may be expressed from single or multiple polynucleotide sequences.

The term tandem CAR-T (tCAR-T) means a single chimeric antigen polypeptide containing two distinct antigen recognition domains with affinity to different targets wherein the antigen recognition domain is linked through a peptide linker and share common costimulatory domain(s), wherein the binding of either antigen recognition domain will signal through a common co-stimulatory domains(s) and signaling domain.

As used herein, a chimeric antigen receptor natural killer (NK) cell (equivalently, NK-CAR) would have a meaning analogous to the definitions of CAR-T and iNKT-CAR.

As used herein, a chimeric antigen receptor macrophage (equivalently, CAR-macrophage) would have a meaning analogous to the definitions of CAR-T, INKT-CAR, and NK-CAR.

As used herein, the term "cytokine release syndrome" refers to a condition that may occur after treatment with some types of immunotherapy, such as monoclonal antibodies and CAR-T or other CAR-bearing immune effector cells. Cytokine release syndrome is caused by a large, rapid release of cytokines into the blood from immune cells affected by the immunotherapy. Symptoms of CRS include fever, fatigue, loss of appetite, muscle and joint pain, nausea, vomiting, diarrhea, rashes, fast breathing, rapid heartbeat, low blood pressure, seizures, headache, confusion, delirium, hallucinations, tremor, and loss of coordination. CRS can manifest along a spectrum of mild to fatal, and can be ranked by severity as follows:

Grade 1: Mild reaction, infusion interruption not indicated; intervention not indicated Grade 2: Therapy or infusion interruption indicated but responds promptly to symptomatic treatment (e.g., anti-histamines, NSAIDS, narcotics, IV fluids); prophylactic medications indicated for <=24 hrs Grade 3: Prolonged (e.g., not rapidly responsive to symptomatic medication and/or brief interruption of infusion); recurrence of symptoms following initial improvement; hospitalization indicated for clinical sequelae (e.g., renal impairment, pulmonary infiltrates)

Grade 4: Life-threatening consequences; pressor or ventilatory support indicated Grade 5: Death See, e.g., "Common Terminology Criteria for Adverse Events (CTCAE) Version v4.03," National Institutes of Health and National Cancer Institute, Jun. 14, 2010; Lee D W et al., "Current concepts in the diagnosis and management of cytokine release syndrome," *Blood* 2014 124 (2): 188-95.

As used herein, the term "CAR-T associated neuropathy" means neuropathy that arises subsequent to administration of CAR-T therapy to a patient, often after intervening cytokine release syndrome has occurred and subsided. The term is relatively new, mainly because CAR-T therapy is relatively new; see, e.g., Vasthie P and Breitbart W S, "Chimeric antigen receptor T-cell neuropsychiatric toxicity in acute lymphoblastic leukemia," Palliat Support Care. 2017 August; 15 (4): 499-503. Accordingly, CAR-T associated neuropathy should be understood at this time to be equivalent to the term "CAR-bearing immune effector cell associated neuropathy," since similar neuropathy could arise from therapy with, e.g., iNKT-CARs or NK-CARs.

As used herein, a "cytokine" is one of a class of small (~5-20 kDa), soluble signaling proteins that are that are synthesized and secreted by certain cells of the immune system at variable, and occasionally locally high, concentrations and by binding to receptors on other cells, send signals to and have an effect on those cells. A "chemokine" is a chemotactic cytokine, i.e., a subspecies of cytokine that is able to induce chemotaxis in nearby responsive cells.

As used herein, to be "deficient" in a cytokine or protein means to lack sufficient quantity of the cytokine or protein for the cytokine or protein to elicit its normal effect. A cell that is "deficient" in GM-CSF, for example, (a "GM-CSF deficient" cell) could be entirely lacking in GM-CSF, but it also could express such a negligible quantity of GM-CSF that the GM-CSF present could not contribute in any meaningful way to the development or maintenance of cytokine release syndrome.

The term "deletion" as used herein in reference to the effect of editing on a gene or its protein product, means alteration or loss of part the sequence of DNA encoding the protein so as to reduce or prevent expression of the protein product. The term "suppression" in the same context means to reduce expression of the protein product; and the term "ablation" in the same context means to knock out (KO) or prevent expression of the protein product. Deletion encompasses suppression and ablation.

As used herein, a "secretable protein" is s protein secreted by a cell which has an effect on other cells. By way of example, secretable proteins include cytokines, chemokines, and transcription factors.

As used herein, a "selectable marker" refers to a marker that allows distinguishing between different cell types, such as a cell into which a CAR has been successfully inserted (i.e., a gene-edited or modified cell). Selectable markers are well known in the art and materials and methods for their use are readily available. In some embodiments, a selectable marker appropriate in accordance with the present disclosure may be a fluorescent protein gene, such as including, but not limited to, a green fluorescence (GFP) gene or a yellow fluorescent protein (YFP) gene. In some embodiments, a selectable marker may be a splice variant of a CD34 gene, such as a truncated CD34 (tCD34) gene or a truncated EGFR (tEGFR) gene. In some embodiments, a selectable marker described herein, such as GFP, or others known and available in the art, may be inserted alone into a gene as described herein (i.e., without a CAR), or may be inserted as a component of a construct comprising the selectable marker and a CAR.

As used herein, a "short hairpin RNA" or "small hairpin RNA" (shRNA) is an artificial RNA molecule, often about 80 base pairs in length and with a tight hairpin turn, that can be used to silence target gene expression via processing within the cell into siRNA which in turn knocks down gene expression. ShRNAs can be incorporated into genomic DNA, and provide stable and long-lasting expression.

As used herein, "transduction" is the process by which foreign DNA is introduced into a cell by a virus or viral vector such as a plasmid, for example by short hairpin RNAs (shRNAs); it often provides long-lasting or permanent silencing of a gene. It may be accomplished by methods known in the art, including electroporation.

Transfection is the process of deliberately introducing purified nucleic acids into eukaryotic cells, for example small interfering RNAs (siRNAs); it produces transient silencing of a gene by RNA interference with mRNA transcripts. Transduction is the process by which foreign DNA is introduced into a cell by a virus or viral vector such as a plasmid, for example by short hairpin RNAs (shRNAs); it often provides long-lasting or permanent silencing of a gene. Both may be accomplished by methods known in the art, including electroporation.

EXAMPLES

The invention is further illustrated by the following examples.

Example 1—Method of Blocking Gene Translation by CAR Insertion

FIG. 1 shows the deletion of a cytokine gene by using Cas9/CRISPR to target a locus in a cytokine gene, then use homology-directed repair to insert the CAS construct. Optionally, the CAS construct would contain a marker, such as a selectable marker as described herein. One challenge with this concept is that is hard to select and sort out the cells have been edited from those that still express the cytokine/chemokine. One way to overcome this is to insert the CAR construct containing a marker, into gene that has been deleted. It has previously been demonstrated that inserting CAR19 into the TRAC gene allows the selection of TRAC-negative, CAR-positive cells. This would allow sorting of cells that have both expression of the car and have the cytokine deleted. Another alternative would be to express a shRNA from the CAR construct that would degrade the RNA encoding for the cytokine without altering the genome. A marker on the CAR construct (such as the truncated CD34 marker) could be used to select cells that downregulate the cytokine and express the CAR, i.e., CAR+=Cytokine negative.

Figure 2:
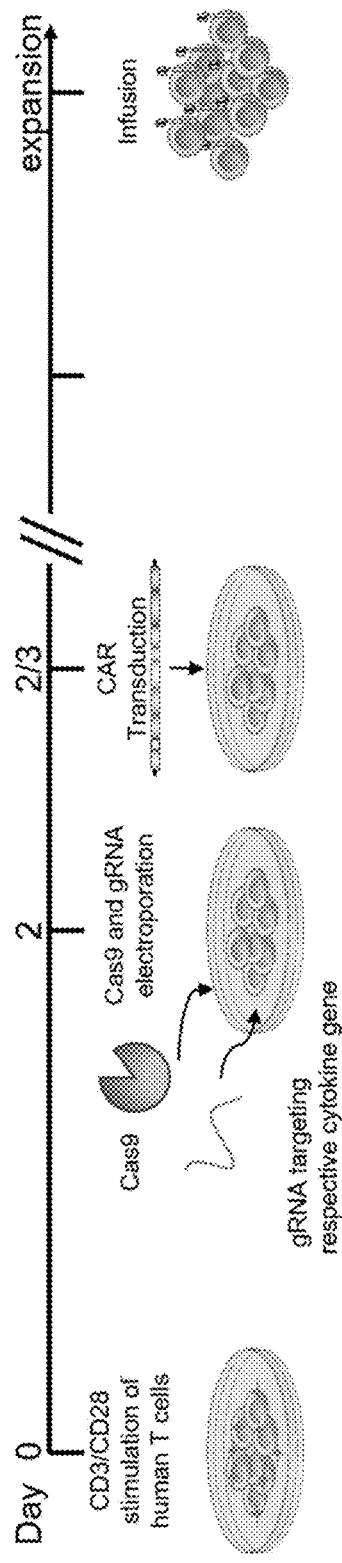
FIG. 2—Shows a timeline for a method of treatment of hematologic malignancies using the CAR-T cells disclosed herein. Those of skill in the art will appreciate that some flexibility is possible in the time frames shown.

As shown in FIG. 2, CAR-bearing immune effector cells (e.g., CAR-T) would be activated for two days prior to gene editing to delete the target cytokine gene and transduction of CAR.

Example 2—General Method of Making Genome-Edited CAR-Bearing Immune Effector Cells Further details regarding the manner of making CAR-bearing immune effector cells are known in the art, e.g., as disclosed in WO2018027036A1.

The following general steps may be taken to provide CAR-bearing immune effector cells. As those of skill in the art will recognize, certain of the steps may be conducted sequentially or out of the order listed below, though perhaps leading to different efficiency.

Step 1. Cells are harvested, isolated, and purified, for example using magnetic selection with a labelled antibody-coated magnetic beads that bind to a cell-specific protein (available from, e.g., Miltenyi Biotec). For T cells, anti-CD3/CD28 beads could be used. Other purification techniques are known in the art and could be used.

Step 3. Cells are thereafter activated. There are several ways to activate immune effector cells. For example, T cells may be activated using antiCD3/CD28 beads for two days prior to bead removal. Alternatively, an antibody could be used.

Step 4. The antigen that is the target of the CAR may be deleted from the cell surface or its expression suppressed to prevent subsequent fratricide. Target deletion may be accomplished by electroporation with Cas9 mRNA and gRNA against the target(s). Other techniques, however, could be used to suppress expression of the target. These include other genome editing techniques such as TALENs, ZFNs, RNA interference, and eliciting of internal binding of the antigen to prevent cell surface expression. Deletion of the target may not be required in every circumstance. Examples of gRNAs that may be used include those shown in Tables 8-10, as well as others known in the art.

TABLE 8

Guide RNA sequences for use in removing surface antigens on immune effector cells

| Target gene | gRNA sequence |
|---|---|
| CD7 | 5'_2'OMe(A(ps)U(pS)C(ps))ACGGAGGUCAAUGUCUAGUUUUAGAGCUAGA AAUAGCAAGUUAAAAUAAGGCUAGUCCGUUAUCAACUUGAAAAAGUG GCACCGAGUCGGUGC2'OMe(U(ps)U(ps)U(ps)U_3' (SEQ ID NO: 40) |
| CD7g10 | 5'_2'OMe(G(ps)U(ps)A(ps))GACAUUGACCUCCGUGAGUUUUAGAGCUAGA AAUAGCAAGUUAAAAUAAGGCUAGUCCGUUAUCAACUUGAAAAAGUG GCACCGAGUCGGUGC2'OMe(U(ps)U(ps)U(ps)U_3' (SEQ ID NO: 41) |

TABLE 8-continued

Guide RNA sequences for use in removing surface
antigens on immune effector cells

| Target gene | gRNA sequence |
|---|---|
| CD7g4 | 5'_2'OMe(A(ps)U(ps)C(ps))ACGGAGGUCAAUGUCUAGUUUUAGAGCUAGA<br>AAUAGCAAGUUAAAAUAAGGCUAGUCCGUUAUCAACUUGAAAAAGUG<br>GCACCGAGUCGGUGC2'OMe(U(ps)U(ps)U(ps)U_3' (SEQ ID NO: 42) |
| TRACg | 5'_2'OMe(G(ps)A(ps)G(ps))AAUCAAAAUCGGUGAAUGUUUUAGAGCUAGA<br>AAUAGCAAGUUAAAAUAAGGCUAGUCCGUUAUCAACUUGAAAAAGUG<br>GCACCGAGUCGGUGC2'OMe(U(ps)U(ps)U(ps)U_3' (SEQ ID NO: 43) |
| CS1 | 5'_2'OMe(G(ps)A(ps)C(ps))CAAUCUGACAUGCUGCAGUUUUAGAGCUAGA<br>AAUAGCAAGUUAAAAUAAGGCUAGUCCGUUAUCAACUUGAAAAAGUG<br>GCACCGAGUCGGUGC2'OMe(U(ps)U(ps)U(ps)U_3' (SEQ ID NO: 44) |
| CD2 | 5'_2'OMe(A(ps)C(ps)A(ps))GCUGACAGGCUCGACACGUUUUAGAGCUAGA<br>AAUAGCAAGUUAAAAUAAGGCUAGUCCGUUAUCAACUUGAAAAAGUG<br>GCACCGAGUCGGUGC2'OMe(U(ps)U(ps)U(ps) U_3' (SEQ ID NO: 45) |
| CD2g | 5'_2'OMe(G(ps)A(ps)G(ps))AAUCAAAAUCGGUGAAUGUUUUAGAGCUAGA<br>AAUAGCAAGUUAAAAUAAGGCUAGUCCGUUAUCAACUUGAAAAAGUG<br>GCACCGAGUCGGUGC2'OMe(U(ps)U(ps)U(ps) U 3' (SEQ ID NO: 46) |
| CD3εg | 5'_2'OMe(A(ps)G(ps)G(ps))GCAUGUCAAUAUUACUGGUUUUAGAGCUAGA<br>AAUAGCAAGUUAAAAUAAGGCUAGUCCGUUAUCAACUUGAAAAAGUG<br>GCACCGAGUCGGUGC2'OMe(U(ps)U(ps)U(ps) U 3' (SEQ ID NO: 47) |
| CD5 | 5'_2'OMe(C(ps)G(ps)U(ps))UCCAACUCGAAGUGCCAGUUUUAGAGCUAGA<br>AAUAGCAAGUUAAAAUAAGGCUAGUCCGUUAUCAACUUGAAAAAGUG<br>GCACCGAGUCGGUGC2'OMe(U(ps)U(ps)U(ps))U3' (SEQ ID NO: 48) |
| CD5g | 5'_2'OMe(C(ps)G(ps)U(ps))uCCAACUCGAAGUGCCAGUUUUAGAGCUAGA<br>AAUAGCAAGUUAAAAUAAGGCUAGUCCGUUAUCAACUUGAAAAAGUG<br>GCACCGAGUCGGUGC2'OMe(U(ps)U(ps)U(ps)U_3' (SEQ ID NO: 49) |

RNA; (ps) indicate phosphorothioate.
Underlined bases denote target sequence.

Step 5. Cells may then be transduced with a CAR targeted to (i.e., that recognizes) one or more antigen or protein targets, for example with a lentivirus containing a CAR construct. Any other suitable method of transduction/transfection may be used, for example transfection using DNA-integrating viral or non-viral vectors containing transposable elements, or transient expressing of non-DNA integrating polynucleotides, such as mRNA, or insertion of CAR polynucleotide into site of nuclease activity using homologous or non-homologous recombination.

Step 6. CAR-bearing immune effector cells are then cultured to expand their population.

Example 3—Method of Making Genome-Edited Tandem CAR-Bearing Immune Effector Cells In a variation of the protocol in the example above, a tCAR cell recognizing two antigens can be made. In Step 4, the two antigens can be deleted from the cell surface, or suppressed as described above, but electroporation with gRNA for each of the two targets and Cas9 mRNA. In Step 5, cells are then transduced with a CAR that recognizes two targets.

Example 4—Method of Making Genome-Edited Dual CAR-Bearing Immune Effector Cells

In a variation of the protocol in the example above, a dCAR cell targeting two antigens can be made. This variation would contain two separate CARs, each recognizing a different antigen.

Example 5—Method of Making and Testing a Genome-Edited CAR-T Cell with Suppressed Expression of Cytokine or Chemokine The following steps may be taken to provide a genome-edited CAR-T cell with suppressed expression and/or secretion of a specific cytokine or chemokine. This example describes the making of a CD19 targeting CAR-T which is deficient in expression of GM-CSF. As those of skill in the art will recognize, certain of the steps may be conducted sequentially or out of the order listed below, though perhaps leading to different efficiency.

Tumor is injected into SCID-Beige mice (3e6 Raji containing Luciferase) if performing in vivo CRS experiment. This should be completed 3 weeks prior to infusion of CAR-T into mice.

T Cell Activation (Day 0).

T cells are purified via leukapheresis chamber using a Miltenyi human PanT isolation kit, then resuspended in media. Cells are counted and the number of human T cell activation CD3/CD28 beads required to obtain 3:1 bead: cell ratio determined. Beads are washed 2× with T cell media, then cells diluted at 1.256 cells/mL in hXcyte media. Human T cell activation CD3/CD28 beads are added. Into each well of a 6-well plate are aliquoted 4 mL/well of 1.256 cell/mL solution. Cells are incubated at 37° C.

CRISPR (Day 2).

Target deletion may be accomplished by electroporating with Cas9 mRNA and gRNA against the target(s). Other techniques, however, could be used to suppress expression of the target. These include other genome editing techniques such as TALENs, RNA interference, and eliciting of internal binding of the antigen to prevent cell surface expression. Examples of gRNAs that may be used include those shown in Tables 8-10, as well as others known in the art.

| Sample ID | gRNA#1 | Cas9 | Nucleofection Buffer P3 |
|---|---|---|---|
| | 20 μg gGM-CSF | 15 μg Cas9 mRNA | 100 μl |

TABLE 9

Guide RNA sequences for use in reducing CRS

| Target gene | gRNA sequence |
|---|---|
| GM-CSF | 5' 2'OMe(U(ps)A(ps)C(ps))UCAGGUU CAGGAGACGCGUUUUAGAGCUAGAAAUAGCAA GUUAAAAUAAGGCUAGUCCGUUAUCAACUUGA AAAAGUGGCACCGAGUCGGUGC 2'OMe (U(ps)U(ps)U(ps)U_3' (SEQ ID NO: 50) |

RNA; (ps) indicate phosphorothioate.
Underlined bases denote target sequence.

TABLE 10

Additional guide RNA sequences for use in reducing the incidence of CRS

| Target Gene Symbol | Guide RNA Sequence | SEQ ID NO: | Location | Gene ID No. |
|---|---|---|---|---|
| A2M | GACAAAUCAAUCUACAAACC | 56 | chr12 | ENST00000318602.11 |
| A2M | GGUCCGCUUCUUAAAUUCUU | 57 | chr12 | ENST00000318602.11 |
| A2M | UCCUCAUUGGAUGAAGACUU | 58 | chr12 | ENST00000318602.11 |
| ACKR1 | AACUGAGAACUCAAGUCAGC | 59 | chr1 | ENST00000368122.2 |
| ACKR1 | GAAGGAAUCAUUCACACCAU | 60 | chr1 | ENST00000368122.2 |
| ACKR1 | ACACUGGUGAGGAUGAAGAA | 61 | chr1 | ENST00000368122.2 |
| ACKR2 | UCGGCAUCCUCAGUGGCGAG | 62 | chr3 | ENST00000422265.5 |
| ACKR2 | GCAUGAAGGCCACUUCAUCC | 63 | chr3 | ENST00000422265.5 |
| ACKR2 | AAAUCAGGCUAUAGAAGACU | 64 | chr3 | ENST00000422265.5 |
| ACKR3 | UAGAGCAGGACGCUUUUGUU | 65 | chr2 | ENST00000272928.3 |
| ACKR3 | CGGCAUGAUUGCCAACUCCG | 66 | chr2 | ENST00000272928.3 |
| ACKR3 | CCCACAGGUCGGCAAUGGCC | 67 | chr2 | ENST00000272928.3 |
| ACVR1 | UCUUUCCCUGCUCAUAAACC | 68 | chr2 | ENST00000263640.7 |
| ACVR1 | UCCUCACUGAGCAUCAACGA | 69 | chr2 | ENST00000263640.7 |
| ACVR1 | CUCUACAUGUGUGUGUGUGA | 70 | chr2 | ENST00000263640.7 |
| ACVR2B | CUACAACGCCAACUGGGAGC | 71 | chr3 | ENST00000352511.4 |
| ACVR2B | GCCAGAGCUGUUGCGCCAGG | 72 | chr3 | ENST00000352511.4 |
| ACVR2B | AUGACUUCAACUGCUACGAU | 73 | chr3 | ENST00000352511.4 |

TABLE 10-continued

Additional guide RNA sequences for use in reducing the incidence of CRS

| Target Gene Symbol | Guide RNA Sequence | SEQ ID NO: | Location | Gene ID No. |
|---|---|---|---|---|
| ACVRL1 | AGACCCUGUGAAGCCGUCUC | 74 | chr12 | ENST00000388922.8 |
| ACVRL1 | GGCCUACCUGCCGGGGGGCC | 75 | chr12 | ENST00000388922.8 |
| ACVRL1 | GGGGCUGCGGGAACUUGCAC | 76 | chr12 | ENST00000388922.8 |
| ADIPOQ | GGGCUCAGGAUGCUGUUGCU | 77 | chr3 | ENST00000320741.6 |
| ADIPOQ | CGUGGUUUCCUGGUCAUGAC | 78 | chr3 | ENST00000320741.6 |
| ADIPOQ | GGGGGCCUGCACAGGUUGGA | 79 | chr3 | ENST00000320741.6 |
| AGER | ACGGACUCGGUAGUUGGACU | 80 | chr6 | ENST00000375076.8 |
| AGER | CUGUCGGGAUCCAGGAUGAG | 81 | chr6 | ENST00000375076.8 |
| AGER | UCCCCAGGGAGGAGGCCCCU | 82 | chr6 | ENST00000375076.8 |
| AGRN | CGGGGAAUGCUGUGCGGCUU | 83 | chr1 | ENST00000379370.6 |
| AGRN | GAAGAGCCCGUGCCCCAGCG | 84 | chr1 | ENST00000379370.6 |
| AGRN | GCAUUCGUUGCUGUAGGUGG | 85 | chr1 | ENST00000379370.6 |
| AHR | UUGAUUCCUUCAGCUGGGAU | 86 | chr7 | ENST00000242057.8 |
| AHR | GUAAAGCCAAUCCCAGCUGA | 87 | chr7 | ENST00000242057.8 |
| AHR | UUGACUUGAUUCCUUCAGCU | 88 | chr7 | ENST00000242057.8 |
| AHR | UUUGACUUGAUUCCUUCAGC | 89 | chr7 | ENST00000242057.8 |
| AIMP1 | AACCAAUUCGAAGAUCCAGA | 90 | chr4 | ENST00000358008.7 |
| AIMP1 | UAUGUGGAAGAAGUAGAUGU | 91 | chr4 | ENST00000358008.7 |
| AIMP1 | CAAGAGGAACAUGAUUCACC | 92 | chr4 | ENST00000358008.7 |
| AREG | GGUCCAAUCCAGCAGCAUAA | 93 | chr4 | ENST00000395748.7 |
| AREG | CCACAGUGCUGAUGGAUUUG | 94 | chr4 | ENST00000395748.7 |
| AREG | AGAAGGCAUUUCACUCACAG | 95 | chr4 | ENST00000395748.7 |
| BCL6 | CUGUAAAGAUGCUAUAGAAC | 96 | chr3 | ENST00000406870.6 |
| BCL6 | CACUAAGGUUGCAUUUCAAC | 97 | chr3 | ENST00000406870.6 |
| BCL6 | GAUCUAGAUUGAUCACACUA | 98 | chr3 | ENST00000406870.6 |
| BCL6 | AAUCCCUCAGGGUUGAUCUC | 99 | chr3 | ENST00000406870.6 |
| BMP1 | CAGCGGCAGGCGGGCCACGC | 100 | chr8 | ENST00000306385.9 |
| BMP1 | GGCCGACUACACCUAUGACC | 101 | chr8 | ENST00000306385.9 |
| BMP1 | GGCGCUCACCCGCCUUGCAG | 102 | chr8 | ENST00000306385.9 |
| BMP10 | GAAACUCAUCCUUCAUGCUC | 103 | chr2 | ENST00000295379.1 |
| BMP10 | AGGGACAUAUCUUCUUCCAG | 104 | chr2 | ENST00000295379.1 |
| BMP10 | CAGAAACCAAGUAAGCUGCC | 105 | chr2 | ENST00000295379.1 |
| BMP15 | CGUGCUUUUCAUGGAACACA | 106 | chrX | ENST00000252677.3 |
| BMP15 | CCCUACUUUGCCCCUGAUUG | 107 | chrX | ENST00000252677.3 |
| BMP15 | AGUGAAUGCCCUAGGAGCCG | 108 | chrX | ENST00000252677.3 |
| BMP2 | CGCAGGUCGACCAUGGUGGC | 109 | chr20 | ENST00000378827.4 |

TABLE 10-continued

Additional guide RNA sequences for use in
reducing the incidence of CRS

| Target Gene Symbol | Guide RNA Sequence | SEQ ID NO: | Location | Gene ID No. |
|---|---|---|---|---|
| BMP2 | GGGCCGCAGGAAGUUCGCGG | 110 | chr20 | ENST00000378827.4 |
| BMP2 | GCCGCAACUCGAACUCGCUC | 111 | chr20 | ENST00000378827.4 |
| BMP3 | AGGCUGCUCUUUCUGUGGCU | 112 | chr4 | ENST00000282701.2 |
| BMP3 | GGCACAGCUUUGCGGAGCUC | 113 | chr4 | ENST00000282701.2 |
| BMP3 | CGAGCUGCAGCCGCAAGACA | 114 | chr4 | ENST00000282701.2 |
| BMP4 | UUCGUGGUGGAAGCUCCUCA | 115 | chr14 | ENST00000245451.8 |
| BMP4 | GAAGAGCAGAUCCACAGCAC | 116 | chr14 | ENST00000245451.8 |
| BMP4 | CACUCUUGCUAGGCUGCGGG | 117 | chr14 | ENST00000245451.8 |
| BMP5 | ACUGAGUACUCCGACUCUUC | 118 | chr6 | ENST00000370830.3 |
| BMP5 | AGACCCAGACCAUUUUCACC | 119 | chr6 | ENST00000370830.3 |
| BMP5 | CGAAAGACGGGAAAUACAAA | 120 | chr6 | ENST00000370830.3 |
| BMP6 | GAUGCAGAAGGAGAUCUUGU | 121 | chr6 | ENST00000283147.6 |
| BMP6 | GGCUGUUGGAGGCCGUGCAG | 122 | chr6 | ENST00000283147.6 |
| BMP6 | CCUCGCGGAGAGCCCCCUCC | 123 | chr6 | ENST00000283147.6 |
| BMP7 | UCUCAUUGUCGAAGCGUUCC | 124 | chr20 | ENST00000395863.7 |
| BMP7 | GCCGUGACAGCUUCCCCUUC | 125 | chr20 | ENST00000395863.7 |
| BMP7 | UCUUCCAGUGGAACAUGACA | 126 | chr20 | ENST00000395863.7 |
| BMP8A | CCAGAAGCCAGAGCGGUCCG | 127 | chr1 | ENST00000331593.5 |
| BMP8A | UGGCGGUGCUCGGGCUACCC | 128 | chr1 | ENST00000331593.5 |
| BMP8A | UGGCGGUGCUCGGGCUACCC | 129 | chr1 | ENST00000331593.5 |
| BMP8B | CGGUGCUCGGGCUGCCUGGG | 130 | chr1 | ENST00000372827.7 |
| BMP8B | CCCAGGAGCCAGAGCGGGCC | 131 | chr1 | ENST00000372827.7 |
| BMP8B | CCCAGGAGCCAGAGCGGGCC | 132 | chr1 | ENST00000372827.7 |
| BMPR2 | CACUUGCAGCUGAUUGGCCG | 133 | chr2 | ENST00000374580.8 |
| BMPR2 | UUUCGUUGAUAAAAUUCUGA | 134 | chr2 | ENST00000374580.8 |
| BMPR2 | CUCAUCUCCAACUAUAAAGC | 135 | chr2 | ENST00000374580.8 |
| C10orf99 | GGAAAGGACUAGAAGCCUCA | 136 | chr10 | ENST00000372126.3 |
| C10orf99 | CCUACCUUCUGUGGAGAAGA | 137 | chr10 | ENST00000372126.3 |
| C10orf99 | CUCUGAUCAGGAUUUGUUGG | 138 | chr10 | ENST00000372126.3 |
| C1QTNF4 | CCAUCUCCGACGUGCCCUCC | 139 | chr11 | ENST00000302514.3 |
| C1QTNF4 | CAGCUCAGAGGAUCCCGGGC | 140 | chr11 | ENST00000302514.3 |
| C1QTNF4 | CCCAGCAGGCCCAGCAGAAG | 141 | chr11 | ENST00000302514.3 |
| C5* | UCCAGCACCGUCACUCCAGA | 142 | chr9 | ENST00000223642.2 |
| C5* | ACACGUGUUACACUUUUGCU | 143 | chr9 | ENST00000223642.2 |
| C5* | GAUUCGCUUGACCAGUUGGU | 144 | chr9 | ENST00000223642.2 |
| CCL1* | AGAAACGUGGUCAGCCACUC | 145 | chr17 | ENST00000225842.3 |
| CCL1* | CUCUUGCUGUCCACAUCUUC | 146 | chr17 | ENST00000225842.3 |

TABLE 10-continued

Additional guide RNA sequences for use in
reducing the incidence of CRS

| Target Gene Symbol | Guide RNA Sequence | SEQ ID NO: | Location | Gene ID No. |
| --- | --- | --- | --- | --- |
| CCL1* | GCAGAUCAUCACCACAGCCC | 147 | chr17 | ENST00000225842.3 |
| CCL11 | AGGUCUCCGCAGCACUUCUG | 148 | chr17 | ENST00000305869.3 |
| CCL11 | CUGGCCCAGCGAGCCCCUGG | 149 | chr17 | ENST00000305869.3 |
| CCL11 | UAACCACCUCCAGAGCUACU | 150 | chr17 | ENST00000305869.3 |
| CCL13* | AUGUGAAGCAGCAAGUAGAU | 151 | chr17 | ENST00000225844.6 |
| CCL13* | CUUCUGGGGACACCUGCUGG | 152 | chr17 | ENST00000225844.6 |
| CCL13* | AACUUUGGAUGGGGAAUGU | 153 | chr17 | ENST00000225844.6 |
| CCL14 | CAGGAGUGAGGUUGGGGCUC | 154 | chr17 | ENST00000618404.4 |
| CCL14 | GGCAUUGCACUCACGUGAGG | 155 | chr17 | ENST00000618404.4 |
| CCL14 | CCACAGCAUGAAGAUCUCCG | 156 | chr17 | ENST00000618404.4 |
| CCL15* | UCCCAGAGCUUGAGUUACCA | 157 | chr17 | ENST00000617897.1 |
| CCL15* | CACCAUUUGUGAACUGGGCC | 158 | chr17 | ENST00000617897.1 |
| CCL15* | CACCAUUUGUGAACUGGGCC | 159 | chr17 | ENST00000617897.1 |
| CCL16 | GGACGUGCUUACAUGAUUGC | 160 | chr17 | ENST00000611905.1 |
| CCL16 | GUUGCCAAGGAGACUAGUGG | 161 | chr17 | ENST00000611905.1 |
| CCL16 | UCCUUCAGAAGUUCCUGAGU | 162 | chr17 | ENST00000611905.1 |
| CCL17 | GCUCCUCUCCCUGCAGCUCG | 163 | chr16 | ENST00000219244.8 |
| CCL17 | UGGCUCCCUUGAAGUACUCC | 164 | chr16 | ENST00000219244.8 |
| CCL17 | UGGAGCAGUCCUCAGAUGUC | 165 | chr16 | ENST00000219244.8 |
| CCL18 | GAGGCAGCAGAGCUCUUUGU | 166 | chr17 | ENST00000616054.1 |
| CCL18 | UGGCUUGGGGCACUGGGGGC | 167 | chr17 | ENST00000616054.1 |
| CCL18 | CCAUCCUCCCUCCCGAGGGG | 168 | chr17 | ENST00000616054.1 |
| CCL19 | CCCACAACUCACACUACAGC | 169 | chr9 | ENST00000311925.6 |
| CCL19 | AAGUUCCUCACGAUGUACCC | 170 | chr9 | ENST00000311925.6 |
| CCL19 | CAUUGGUGCCACUCAGAGUU | 171 | chr9 | ENST00000311925.6 |
| CCL2 | GUUAUAACAGCAGGUGACUG | 172 | chr17 | ENST00000225831.4 |
| CCL2 | UUCUUUGGGACACUUGCUGC | 173 | chr17 | ENST00000225831.4 |
| CCL2 | GGCUUGUCCCUUGCUCCACA | 174 | chr17 | ENST00000225831.4 |
| CCL20 | CAAACUCUUGGUACAGCACA | 175 | chr2 | ENST00000358813.4 |
| CCL20 | CACCUCUGCGGCGAAUCAGA | 176 | chr2 | ENST00000358813.4 |
| CCL20 | CAGUUGAGCUCAAGGCUAAA | 177 | chr2 | ENST00000358813.4 |
| CCL21 | CCCUGCAGGCAGUGAUGGAG | 178 | chr9 | ENST00000259607.6 |
| CCL21 | CCUCCCUGCCUUGGUACCUU | 179 | chr9 | ENST00000259607.6 |
| CCL21 | GGCUCUGAGCCUCCUUAUCC | 180 | chr9 | ENST00000259607.6 |
| CCL22 | ACCCCUCCCCUAGGCCCCUA | 181 | chr16 | ENST00000219235.4 |
| CCL22 | GACGGUAACGGACGUAAUCA | 182 | chr16 | ENST00000219235.4 |

TABLE 10-continued

Additional guide RNA sequences for use in reducing the incidence of CRS

| Target Gene Symbol | Guide RNA Sequence | SEQ ID NO: | Location | Gene ID No. |
|---|---|---|---|---|
| CCL22 | AGGCCUCGGGCAGGAGUCUG | 183 | chr16 | ENST00000219235.4 |
| CCL23* | UCGUUUCAAAGUAACUCUCC | 184 | chr17 | ENST00000615050.1 |
| CCL23* | AGCAGUCAGCACUAGUAGCA | 185 | chr17 | ENST00000615050.1 |
| CCL23* | GUGCUCUGGAGGAGAAAGAU | 186 | chr17 | ENST00000615050.1 |
| CCL24 | CCUCAAGGCAGGAGUGAUGU | 187 | chr7 | ENST00000222902.6 |
| CCL24 | GAGAAUUCCUGAGAACCGAG | 188 | chr7 | ENST00000222902.6 |
| CCL24 | CUCUCCUCUUCUAGGCUCUG | 189 | chr7 | ENST00000222902.6 |
| CCL25 | UGUGGUUGCAGGUGUCUUUG | 190 | chr19 | ENST00000390669.7 |
| CCL25 | GGGCUGUGCUCCGGCGCGCC | 191 | chr19 | ENST00000390669.7 |
| CCL25 | GGCCCCACUCACAUCGCAGC | 192 | chr19 | ENST00000390669.7 |
| CCL26 | CCAUCCUGUUGCAUGACUGA | 193 | chr7 | ENST00000005180.8 |
| CCL26 | CCAGUAACAGCUGCUCCCAG | 194 | chr7 | ENST00000005180.8 |
| CCL26 | GUAUUGGAAGCAGCAGGUCU | 195 | chr7 | ENST00000005180.8 |
| CCL27 | GAGCUCACACGAAAGCCUGG | 196 | chr9 | ENST00000259631.4 |
| CCL27 | ACUGAGGAAGGUCAUCCAGG | 197 | chr9 | ENST00000259631.4 |
| CCL27 | AGGCAGUGCUGGGUGGCAGU | 198 | chr9 | ENST00000259631.4 |
| CCL28 | AAUCCUUCCAGCACAGAUUU | 199 | chr5 | ENST00000361115.4 |
| CCL28 | GUGCCCCACUCACCUUCUG | 200 | chr5 | ENST00000361115.4 |
| CCL28 | CAGGCAGGAAUGCAGCAGAG | 201 | chr5 | ENST00000361115.4 |
| CCL3 | GCCACAAGAAAAGAUUGAUG | 202 | chr17 | ENST00000613922.1 |
| CCL3 | ACUCACGUGAUGCAGAGAAC | 203 | chr17 | ENST00000613922.1 |
| CCL3 | UCACCUGCUCAGAAUCAUGC | 204 | chr17 | ENST00000613922.1 |
| CCL4* | UGAGAGCGCUGGAGAGCAGA | 205 | chr17 | ENST00000615863.1 |
| CCL4* | UGAGAGCGCUGGAGAGCAGA | 206 | chr17 | ENST00000615863.1 |
| CCL4* | UGAGAGCGCUGGAGAGCAGA | 207 | chr17 | ENST00000615863.1 |
| CCL5 | GACUCACACGACUGCUGGGU | 208 | chr17 | ENST00000603197.5 |
| CCL5 | UGAUGUGGGCACGGGGCAGU | 209 | chr17 | ENST00000603197.5 |
| CCL5 | CUUUCCUCUUCCAGAUUCCU | 210 | chr17 | ENST00000603197.5 |
| CCL7 | AUUGAUAAAUCUGUAGCAGC | 211 | chr17 | ENST00000378569.2 |
| CCL7 | CCACAUACAUUACAGCUUCC | 212 | chr17 | ENST00000378569.2 |
| CCL7 | CUAGUCCUAUUCCCUGCCCA | 213 | chr17 | ENST00000378569.2 |
| CCL8* | AAAGCAGCAGGUGAUUGGAA | 214 | chr17 | ENST00000394620.1 |
| CCL8* | CACCAACAUCCAAUGUCCCA | 215 | chr17 | ENST00000394620.1 |
| CCL8* | CCCCCAUUCAAAAGUUCUGA | 216 | chr17 | ENST00000394620.1 |
| CCR1 | CCUGGUUGGAAACAUCCUGG | 217 | chr3 | ENST00000296140.3 |
| CCR1 | AGGCCCUCUCGUUCACCUUC | 218 | chr3 | ENST00000296140.3 |
| CCR1 | UCAUAGUCCUCUGUGGUGUU | 219 | chr3 | ENST00000296140.3 |

TABLE 10-continued

Additional guide RNA sequences for use in reducing the incidence of CRS

| Target Gene Symbol | Guide RNA Sequence | SEQ ID NO: | Location | Gene ID No. |
|---|---|---|---|---|
| CCR2 | GAUAAACCGAGAACGAGAUG | 220 | chr3 | ENST00000445132.2 |
| CCR2 | ACCUUUUUGAUUAUGAUUA | 221 | chr3 | ENST00000445132.2 |
| CCR2 | GUAGAGCGGAGGCAGGAGUU | 222 | chr3 | ENST00000445132.2 |
| CCR3 | CUAGAUACAGUUGAGACCUU | 223 | chr3 | ENST00000357422.2 |
| CCR3 | UAUCAGCUUUUUCACAGAGC | 224 | chr3 | ENST00000357422.2 |
| CCR3 | GGUGUUCACUGUGGGCCUCU | 225 | chr3 | ENST00000357422.2 |
| CCR5 | UUUUGCAGUUUAUCAGGAUG | 226 | chr3 | ENST00000292303.4 |
| CCR5 | AAAACAGGUCAGAGAUGGCC | 227 | chr3 | ENST00000292303.4 |
| CCR5 | UGUAUUCCAAAGUCCCACU | 228 | chr3 | ENST00000292303.4 |
| CCR6 | UUGUUCUUACUCUCCCAUUC | 229 | chr6 | ENST00000341935.9 |
| CCR6 | GCCUUUUAGCAACUUGCACG | 230 | chr6 | ENST00000341935.9 |
| CCR6 | CCGGUACAUCGCCAUUGUAC | 231 | chr6 | ENST00000341935.9 |
| CCR7 | GGCCGCGCUGUAGGCCCAGA | 232 | chr17 | ENST00000246657.2 |
| CCR7 | GAGCAGGUAGGUAUCGGUCA | 233 | chr17 | ENST00000246657.2 |
| CCR7 | UAGGCCCACGAAACAAAUGA | 234 | chr17 | ENST00000246657.2 |
| CD109 | UCCGGGCCUGAUGAUCCCUG | 235 | chr6 | ENST00000287097.5 |
| CD109 | GCCUUCACAGUCACCUGUGA | 236 | chr6 | ENST00000287097.5 |
| CD109 | CAAAGACUCCUUCUGCUUCC | 237 | chr6 | ENST00000287097.5 |
| CD27** | CCUUCACGAGGAAUGUUCCU | 238 | chr12 | ENST00000266557.3 |
| CD27** | UCCUUCACGAGGAAUGUUCC | 239 | chr12 | ENST00000266557.3 |
| CD27** | GCUGGUCACAGUCCUUCACG | 240 | chr12 | ENST00000266557.3 |
| CD27** | ACUGAGCAGCCUUUCUAUGC | 241 | chr12 | ENST00000266557.3 |
| CD28*** | CACCAAAAUCUUGUUUCCUG | 242 | ch2 | ENST00000458610.6 |
| CD28*** | UCACCAAAAUCUUGUUUCCU | 243 | ch2 | ENST00000458610.6 |
| CD28*** | UUGUCGUACGCUACAAGCAU | 244 | ch2 | ENST00000458610.6 |
| CD28*** | AUUGUCGUACGCUACAAGCA | 245 | ch2 | ENST00000458610.6 |
| CD36 | CAAGAAAAAUGGGCUGUGAC | 246 | chr7 | ENST00000309881.11 |
| CD36 | GGUGCUGUCCUGGCUGUGUU | 247 | chr7 | ENST00000309881.11 |
| CD36 | UAUCCAGAAGACAAUUAAAA | 248 | chr7 | ENST00000309881.11 |
| CD4** | AGUGCAAUGUAGGAGUCCAA | 249 | chr12 | ENST00000011653.8 |
| CD4** | CUGGAGCUCCAGCUGAGACA | 250 | chr12 | ENST00000011653.8 |
| CD4** | UUUUGAACUCCACCUUCUUC | 251 | chr12 | ENST00000011653.8 |
| CD40LG** | CAAAAUAGAUAGAAGAUGAA | 252 | chrX | ENST00000370629.6 |
| CD40LG** | ACGAUACAGAGAUGCAACAC | 253 | chrX | ENST00000370629.6 |
| CD40LG** | CCAGUUUGAAGGCUUUGUGA | 254 | chrX | ENST00000370629.6 |
| CD70 | AGCGCUGGAUGCACACCACG | 255 | chr19 | ENST00000245903.3 |

TABLE 10-continued

Additional guide RNA sequences for use in
reducing the incidence of CRS

| Target Gene Symbol | Guide RNA Sequence | SEQ ID NO: | Location | Gene ID No. |
|---|---|---|---|---|
| CD70 | AGCCCGCAGGACGCACCCAU | 256 | chr19 | ENST00000245903.3 |
| CD70 | CGCCGCGGCGAUGCCGGAGG | 257 | chr19 | ENST00000245903.3 |
| CD74 | UGCUCACACAUACCUCUCCG | 258 | chr5 | ENST00000009530.11 |
| CD74 | UGUUGGAGAUAAGGUCGCGC | 259 | chr5 | ENST00000009530.11 |
| CD74 | AGAUGCACAGGAGGAGAAGC | 260 | chr5 | ENST00000009530.11 |
| CD8A** | CCGGAACUGGCUCGGCCUGG | 261 | ch2 | ENST00000409511.6 |
| CD8A** | CACCCGGAACUGGCUCGGCC | 262 | ch2 | ENST00000409511.6 |
| CD8A** | GGCGACACCCGGAACUGGCU | 263 | ch2 | ENST00000409511.6 |
| CD8A** | CGCCAGGCCGAGCCAGUUCC | 264 | ch2 | ENST00000409511.6 |
| CER1 | GGCACUGCGACAAACAGAUC | 265 | chr9 | ENST00000380911.3 |
| CER1 | AAAGAGAACUCUGAUUCUGG | 266 | chr9 | ENST00000380911.3 |
| CER1 | CUGCUGGUACUCCUGCCUCU | 267 | chr9 | ENST00000380911.3 |
| CHRD | GCCGGCGGGGCCGGGAGGCU | 268 | chr3 | ENST00000204604.5 |
| CHRD | UCCCGGCCGGCCCGCGGCGC | 269 | chr3 | ENST00000204604.5 |
| CHRD | CUGCCCGUUCGGGGAGCGGC | 270 | chr3 | ENST00000204604.5 |
| CKLF | GUGAUAACAAUAUAUGGUUC | 271 | chr16 | ENST00000264001.8 |
| CKLF | GACUUGAUCGAUUAAUGAAG | 272 | chr16 | ENST00000264001.8 |
| CKLF | GUAGGAAAAGUAAAAUUUA | 273 | chr16 | ENST00000264001.8 |
| CLCF1 | CAUAGGUCCCAGCCAAGCUG | 274 | chr11 | ENST00000312438.7 |
| CLCF1 | CAUAGGUUUUCUGGAUGGAG | 275 | chr11 | ENST00000312438.7 |
| CLCF1 | GGUGCCAGAGCACCGUGCAC | 276 | chr11 | ENST00000312438.7 |
| CMTM1 | GACUCAGGUUUGGCUGUUUC | 277 | chr16 | ENST00000379500.6 |
| CMTM1 | UACGCUGCCGCUACUUGCCA | 278 | chr16 | ENST00000379500.6 |
| CMTM1 | UGCGGGGUGCUUCCGGGGUG | 279 | chr16 | ENST00000379500.6 |
| CMTM2 | CGAGUCAGUCAUGGCACCUA | 280 | chr16 | ENST00000268595.2 |
| CMTM2 | UCCACCCGGGGCCAAACCCG | 281 | chr16 | ENST00000268595.2 |
| CMTM2 | AAAGGCGGUGCAGGACCAUA | 282 | chr16 | ENST00000268595.2 |
| CMTM3 | CCGGACCCCGAGCCUGCCGG | 283 | chr16 | ENST00000361909.8 |
| CMTM3 | GGAAAGCCCGCGCCGGCAGC | 284 | chr16 | ENST00000361909.8 |
| CMTM3 | UCCCGCCGCACUCACCGACU | 285 | chr16 | ENST00000361909.8 |
| CMTM4 | CCGCCCGGCACCUACCACUU | 286 | chr16 | ENST00000394106.6 |
| CMTM4 | GGUAGUCGGGGUCGCAGCGC | 287 | chr16 | ENST00000394106.6 |
| CMTM4 | GCUGCUGGCGCCCGAGAUCA | 288 | chr16 | ENST00000394106.6 |
| CMTM5 | GCUCAGUGCUCGAGAUCGCC | 289 | chr14 | ENST00000359320.7 |
| CMTM5 | CCAGGGCUUCGCGGUGGACA | 290 | chr14 | ENST00000359320.7 |
| CMTM5 | UUACCAGCUCGGUUUCCAGC | 291 | chr14 | ENST00000359320.7 |
| CMTM6 | UUGAGAACGCGCCGGAGCAA | 292 | chr3 | ENST00000205636.3 |

TABLE 10-continued

Additional guide RNA sequences for use in reducing the incidence of CRS

| Target Gene Symbol | Guide RNA Sequence | SEQ ID NO: | Location | Gene ID No. |
|---|---|---|---|---|
| CMTM6 | CGCUCCGGGGCCUCUGGCG | 293 | chr3 | ENST00000205636.3 |
| CMTM6 | CGGCCCGAGGCGAUGGAGAA | 294 | chr3 | ENST00000205636.3 |
| CMTM7 | GGAGCUCCGCACACAGAUGA | 295 | chr3 | ENST00000334983.9 |
| CMTM7 | AAUGAUCCUCGCCUUUUACC | 296 | chr3 | ENST00000334983.9 |
| CMTM7 | CGACAGGGGCCAGCUGAUAC | 297 | chr3 | ENST00000334983.9 |
| CMTM8 | GUGUGCGAGCGGGCGCGCUG | 298 | chr3 | ENST00000307526.3 |
| CMTM8 | CAGCAGCUUCGCCUACGACC | 299 | chr3 | ENST00000307526.3 |
| CMTM8 | CCCGUCGGCACUCACGAUCU | 300 | chr3 | ENST00000307526.3 |
| CNTF | AUCAACCUGGACUCUGCGGA | 301 | chr11 | ENST00000361987.5 |
| CNTF | GGAAGGUACGAUAAGCUUGA | 302 | chr11 | ENST00000361987.5 |
| CNTF | GUGCAUUUUACCCCAACCGA | 303 | chr11 | ENST00000361987.5 |
| CNTFR | CCAGCUGAGAGCCGUUGAGC | 304 | chr9 | ENST00000351266.8 |
| CNTFR | GGGAUGCUGCGGUGACGUGG | 305 | chr9 | ENST00000351266.8 |
| CNTFR | CAGGCGCUCGUACUGCACAU | 306 | chr9 | ENST00000351266.8 |
| COPS5 | UAGUCCAGGGCUUCGCCGCC | 307 | chr8 | ENST00000357849.8 |
| COPS5 | CUGAGCUUCCUGCAUGUUGU | 308 | chr8 | ENST00000357849.8 |
| COPS5 | CCUCGGCGAUGGCGGCGUCC | 309 | chr8 | ENST00000357849.8 |
| CRLF1 | CCAGCGUGAGUACAUCGGAG | 310 | chr19 | ENST00000392386.7 |
| CRLF1 | CAUAGGGCGUAAAGAGAGCC | 311 | chr19 | ENST00000392386.7 |
| CRLF1 | ACUCCUCACAUGUGUUGUCC | 312 | chr19 | ENST00000392386.7 |
| CSF1* | GCCUUCUUAAGGUAGCACAC | 313 | chr1 | ENST00000329608.10 |
| CSF1* | GGUGUUAUCUCUGAAGCGCA | 314 | chr1 | ENST00000329608.10 |
| CSF1* | GUCAUGCUCUUCAUAAUCCU | 315 | chr1 | ENST00000329608.10 |
| CSF1R | CACCUUUCUGCACUUUCAGC | 316 | chr5 | ENST00000286301.7 |
| CSF1R | CAAUGCAGUGCCCUGAUGGG | 317 | chr5 | ENST00000286301.7 |
| CSF1R | CCAGGGCGAGAAGGAGUAGU | 318 | chr5 | ENST00000286301.7 |
| CSF2* | CCACAGUGCCCAAGAGCAGC | 319 | chr5 | ENST00000296871.3 |
| CSF2* | CAGGGCUGCGUGCUGGGGCU | 320 | chr5 | ENST00000296871.3 |
| CSF2* | UAGAGACACUGCUGCUGAGA | 321 | chr5 | ENST00000296871.3 |
| CSF3 | UGUGCCACAGCAGCAGCUGC | 322 | chr17 | ENST00000225474.6 |
| CSF3 | GAAGCUCUGGGGCAGGGAGC | 323 | chr17 | ENST00000225474.6 |
| CSF3 | GGGCGAUGGCGCAGCGCUCC | 324 | chr17 | ENST00000225474.6 |
| CSF3R | GCAAUAGCAACAAGACCUGG | 325 | chr1 | ENST00000361632.8 |
| CSF3R | AUAGCCCUGAGGCCAUGGAU | 326 | chr1 | ENST00000361632.8 |
| CSF3R | GCAUGGAGUCUGGUCAGAGC | 327 | chr1 | ENST00000361632.8 |
| CTF1 | UCUCCGCAGGUGCAGCUCCA | 328 | chr16 | ENST00000279804.2 |

TABLE 10-continued

Additional guide RNA sequences for use in reducing the incidence of CRS

| Target Gene Symbol | Guide RNA Sequence | SEQ ID NO: | Location | Gene ID No. |
|---|---|---|---|---|
| CTF1 | CCGGCCACCGGCAGCCGCGG | 329 | chr16 | ENST00000279804.2 |
| CTF1 | AGCCGCAGCCGCUCGUGCAC | 330 | chr16 | ENST00000279804.2 |
| CX3CL1 | GUGCCGACCCGAAGGAGCAA | 331 | chr16 | ENST00000006053.6 |
| CX3CL1 | CUUCGAGAAGCAGAUCGGCG | 332 | chr16 | ENST00000006053.6 |
| CX3CL1 | CGCCUGUGGCUUCGGGCUCC | 333 | chr16 | ENST00000006053.6 |
| CX3CR1** | CUACCAACAAAUUUCCCACC | 334 | chr3 | ENST00000399220.2 |
| CX3CR1** | UUGGGGACAUCGUGGUCUUU | 335 | chr3 | ENST00000399220.2 |
| CX3CR1** | AAGUUUUCUGUCACUGAUUC | 336 | chr3 | ENST00000399220.2 |
| CXCL1 | GGAGAGAGCAGCGCGGGCCA | 337 | chr4 | ENST00000395761.3 |
| CXCL1 | CUGGCCGGCGCGCAGCAGGU | 338 | chr4 | ENST00000395761.3 |
| CXCL1 | GUGCCUACCCCAGCCGCGUC | 339 | chr4 | ENST00000395761.3 |
| CXCL10 | UACAGUAUAUAAUUACAACC | 340 | chr4 | ENST00000306602.2 |
| CXCL10 | CGUGGACAAAAUUGGCUUGC | 341 | chr4 | ENST00000306602.2 |
| CXCL10 | UUGAUUACUAAUGCUGAUGC | 342 | chr4 | ENST00000306602.2 |
| CXCL11 | GCUGAAGAUGACAAUGGUGC | 343 | chr4 | ENST00000306621.7 |
| CXCL11 | GUUGUUACUUGGGUACAUUA | 344 | chr4 | ENST00000306621.7 |
| CXCL11 | AGCGUCCUCUUUUGAACAUG | 345 | chr4 | ENST00000306621.7 |
| CXCL12 | CUACACCUUUAAUAAGACUC | 346 | chr10 | ENST00000343575.10 |
| CXCL12 | UCAAGACUUACACAAUCUGA | 347 | chr10 | ENST00000343575.10 |
| CXCL12 | UGACGUUGGCUCUGGCAACA | 348 | chr10 | ENST00000343575.10 |
| CXCL13 | AGGUCUAUUACACAAGCUUG | 349 | chr4 | ENST00000286758.4 |
| CXCL13 | UUCGAUCAAUGAAGCGUCUA | 350 | chr4 | ENST00000286758.4 |
| CXCL13 | ACUUACAUGAUUUCUUUUCU | 351 | chr4 | ENST00000286758.4 |
| CXCL14 | AAUUGGCGCUUGGGUUCCCC | 352 | chr5 | ENST00000337225.5 |
| CXCL14 | CUGUACACCGCGCUGUGGA | 353 | chr5 | ENST00000337225.5 |
| CXCL14 | GAGGGGCGCGGCGUGGGAGC | 354 | chr5 | ENST00000337225.5 |
| CXCL16 | GCGCUGAGUGGACUGCAAGG | 355 | chr17 | ENST00000293778.10 |
| CXCL16 | UACCAGCCCCCCAAUUUCUC | 356 | chr17 | ENST00000293778.10 |
| CXCL16 | AAUGUGGACAUGCUUACUCG | 357 | chr17 | ENST00000293778.10 |
| CXCL17 | AUUGGUCUCAGAGGGGCCCA | 358 | chr19 | ENST00000601181.5 |
| CXCL17 | GACCUUUGCACUCACAUUCU | 359 | chr19 | ENST00000601181.5 |
| CXCL17 | CUUCCGACAGGGGUCGCCAG | 360 | chr19 | ENST00000601181.5 |
| CXCL2 | GCAGUGGCAGCGGCAGCGAU | 361 | chr4 | ENST00000508487.2 |
| CXCL2 | UUCUUCCCUAGGAGCGCCCC | 362 | chr4 | ENST00000508487.2 |
| CXCL2 | UUCUUCCCUAGGAGCGCCCC | 363 | chr4 | ENST00000508487.2 |
| CXCL3* | UGGCAGCGGAAGCGCGGGGC | 364 | chr4 | ENST00000296026.4 |
| CXCL3* | GGGACCUUACAUUCACACUU | 365 | chr4 | ENST00000296026.4 |

TABLE 10-continued

Additional guide RNA sequences for use in
reducing the incidence of CRS

| Target Gene Symbol | Guide RNA Sequence | SEQ ID NO: | Location | Gene ID No. |
| --- | --- | --- | --- | --- |
| CXCL3* | GGGACCUUACAUUCACACUU | 366 | chr4 | ENST00000296026.4 |
| CXCL5 | CCCUUUAUAGGGCAGGUUGC | 367 | chr4 | ENST00000296027.4 |
| CXCL5 | GCGCCAUGCGCUCUCACCGC | 368 | chr4 | ENST00000296027.4 |
| CXCL5 | GAGCUCCUUGUGCGCGCUGU | 369 | chr4 | ENST00000296027.4 |
| CXCL6* | GCCCGAAGGACCCGGGACAC | 370 | chr4 | ENST00000226317.9 |
| CXCL6* | GGGGCCCCGGCGGCGUCAGC | 371 | chr4 | ENST00000226317.9 |
| CXCL6* | UUUUUAUAGGGCAGGUUGCU | 372 | chr4 | ENST00000226317.9 |
| CXCL8 | CAACAGGUGCAGUUUUGCCA | 373 | chr4 | ENST00000307407.7 |
| CXCL8 | AAAUUUGGGGUGGAAAGGUU | 374 | chr4 | ENST00000307407.7 |
| CXCL8 | UACUUACAUAAUUUCUGUGU | 375 | chr4 | ENST00000307407.7 |
| CXCL9* | UUUCAAUUUCUCGCAGGAA | 376 | chr4 | ENST00000264888.5 |
| CXCL9* | AUUGUAGGUGGAUAGUCCCU | 377 | chr4 | ENST00000264888.5 |
| CXCL9* | GGAACCCCAGUAGUGAGAAA | 378 | chr4 | ENST00000264888.5 |
| CXCR1 | GAUGGUAAGCCUGGCGGAAA | 379 | chr2 | ENST00000295683.2 |
| CXCR1 | UUGGUCAAGUUUGUUUGUCU | 380 | chr2 | ENST00000295683.2 |
| CXCR1 | CUACAGUGGCAUCCUGCUGU | 381 | chr2 | ENST00000295683.2 |
| CXCR2 | GUGACAGCUUUGAAGAUUUC | 382 | chr2 | ENST00000318507.6 |
| CXCR2 | AUCUAGUAGAAAAGGGGCA | 383 | chr2 | ENST00000318507.6 |
| CXCR2 | UGUGGUCAUUAUCUAUGCCC | 384 | chr2 | ENST00000318507.6 |
| CXCR3^ | GCAGAAAGAGGAGGCUGUAG | 385 | chrX | ENST00000373693.3 |
| CXCR3^ | UACCUCCCCGCCCUGCCCAC | 386 | chrX | ENST00000373693.3 |
| CXCR3^ | AAGAGCUGAAGUUCUCCAGG | 387 | chrX | ENST00000373693.3 |
| CXCR4^ | CCCAAAGUACCAGUUUGCCA | 388 | chr2 | ENST00000409817.1 |
| CXCR4^ | AGAGGAGGUCGGCCACUGAC | 389 | chr2 | ENST00000409817.1 |
| CXCR4^ | UGGAUUGGUCAUCCUGGUCA | 390 | chr2 | ENST00000409817.1 |
| CXCR6** | GGAAGUCUUGAUGCUCCUCC | 391 | chr3 | ENST00000304552.4 |
| CXCR6** | GGUGUUUGUCUGUGGUCUGG | 392 | chr3 | ENST00000304552.4 |
| CXCR6** | CCGUCAGGCUCUGCAACUUA | 393 | chr3 | ENST00000304552.4 |
| EBI3 | CACCCUGUGCAGGCUCGGCA | 394 | chr19 | ENST00000221847.5 |
| EBI3 | GGAUGUCCAGCUGUUCUCCA | 395 | chr19 | ENST00000221847.5 |
| EBI3 | AGCUGCUGCUGGAGCCCCAG | 396 | chr19 | ENST00000221847.5 |
| EDN1 | UUUCUCUCCCCAGCAGUCUU | 397 | chr6 | ENST00000379375.5 |
| EDN1 | CCACUCCCAGUCCACCCUGG | 398 | chr6 | ENST00000379375.5 |
| EDN1 | UCUGCCACCUGGACAUCAUU | 399 | chr6 | ENST00000379375.5 |
| ELANE | CACAAUCUCCGAGGCCAGCG | 400 | chr19 | ENST00000263621.1 |
| ELANE | GUGUCCCUGCAGCUGCGCGG | 401 | chr19 | ENST00000263621.1 |

TABLE 10-continued

Additional guide RNA sequences for use in reducing the incidence of CRS

| Target Gene Symbol | Guide RNA Sequence | SEQ ID NO: | Location | Gene ID No. |
|---|---|---|---|---|
| ELANE | GCGGCCGACAUGACGAAGUU | 402 | chr19 | ENST00000263621.1 |
| ENG | CCGGGCCACUCGGCCGGGUA | 403 | chr9 | ENST00000344849.4 |
| ENG | CGCCUUCCAAGUGGCAGCCC | 404 | chr9 | ENST00000344849.4 |
| ENG | CGUGCGGCCCAUGUCCUGGC | 405 | chr9 | ENST00000344849.4 |
| EPO | CUGUUCUAGAAUGUCCUGCC | 406 | chr7 | ENST00000252723.2 |
| EPO | CCCUCUGGGCCUCCCAGUCC | 407 | chr7 | ENST00000252723.2 |
| EPO | CCUGGAGAGGUACCUCUUGG | 408 | chr7 | ENST00000252723.2 |
| FAM3B | UUACAGCUCCAGUCCCCAAA | 409 | chr21 | ENST00000357985.6 |
| FAM3B | UGUAGGCAUAGGUGUCAGAU | 410 | chr21 | ENST00000357985.6 |
| FAM3B | GUUAUCCUCAAAGCAGAUUU | 411 | chr21 | ENST00000357985.6 |
| FAM3C | CUGAUAGUGCAUUUUACUUU | 412 | chr7 | ENST00000359943.7 |
| FAM3C | AUUGUUCUUACCAUUUGCCA | 413 | chr7 | ENST00000359943.7 |
| FAM3C | UCCCCCUUCAGUUUAAUGAG | 414 | chr7 | ENST00000359943.7 |
| FAM3D | GUGUCUUAGGUACUUACAUG | 415 | chr3 | ENST00000358781.6 |
| FAM3D | UUUGCGUUUAAAAUCUGCAG | 416 | chr3 | ENST00000358781.6 |
| FAM3D | GAGGUUAAAAAGUACAAGUG | 417 | chr3 | ENST00000358781.6 |
| FAS | CACUUGGGCAUUAACACUUU | 418 | chr10 | ENST00000355740.6 |
| FAS | UACAGUUGAGACUCAGAACU | 419 | chr10 | ENST00000355740.6 |
| FAS | GUGUAACAUACCUGGAGGAC | 420 | chr10 | ENST00000355740.6 |
| FASLG | UGGGGAUAUGGGUAAUUGAA | 421 | chr1 | ENST00000367721.2 |
| FASLG | AACUGUGCCUGGAGGGGCCC | 422 | chr1 | ENST00000367721.2 |
| FASLG | GGUGGUGGCCUCCUUUGACC | 423 | chr1 | ENST00000367721.2 |
| FGF2 | CCGCAGGGACCAUGGCAGCC | 424 | chr4 | ENST00000608478.1 |
| FGF2 | GGGUCCUUGAAGUGGCCGGG | 425 | chr4 | ENST00000608478.1 |
| FGF2 | ACGCCGAGUUGACGGGGUC | 426 | chr4 | ENST00000608478.1 |
| FLT3LG | CUCUAGGAGGAGCUCUGCGG | 427 | chr19 | ENST00000594009.5 |
| FLT3LG | GAGCGGCUCAAGACUGUCGC | 428 | chr19 | ENST00000594009.5 |
| FLT3LG | GCUGACCUGAAAGGCACAUU | 429 | chr19 | ENST00000594009.5 |
| FOXP3 | AGGACCCGAUGCCCAACCCC | 430 | chrX | ENST00000376207.8 |
| FOXP3 | CCGAGGGCUUGCCAGGCCUG | 431 | chrX | ENST00000376207.8 |
| FOXP3 | CCGAUGCCCAACCCCAGGCC | 432 | chrX | ENST00000376207.8 |
| FOXP3 | CCCCAGGCCUGGCAAGCCCU | 433 | chrX | ENST00000376207.8 |
| FZD4 | UCGUCCCCGAAGCCCCGCGC | 434 | chr11 | ENST00000531380.1 |
| FZD4 | CAGACUGAGACCGACGCCCC | 435 | chr11 | ENST00000531380.1 |
| FZD4 | CGAUGCUGGCCAUGGCCUGG | 436 | chr11 | ENST00000531380.1 |
| GATA3 | GAGCACAGCCGAGGCCAUGG | 437 | chr10 | ENST00000346208.4 |
| GATA3 | CUGGUCCGCCGUCACCUCCA | 438 | chr10 | ENST00000346208.4 |

TABLE 10-continued

Additional guide RNA sequences for use in reducing the incidence of CRS

| Target Gene Symbol | Guide RNA Sequence | SEQ ID NO: | Location | Gene ID No. |
|---|---|---|---|---|
| GATA3 | AGCCGAGGCCAUGGAGGUGA | 439 | chr10 | ENST00000346208.4 |
| GATA3 | CGAGGCCAUGGAGGUGACGG | 440 | chr10 | ENST00000346208.4 |
| GBP1 | UCCUCACAUCUUCAUAAUGG | 441 | chr1 | ENST00000370473.4 |
| GBP1 | CAAGCUGGCUGGAAAGAAAA | 442 | chr1 | ENST00000370473.4 |
| GBP1 | UUCUGCCAUUACACAGCCUA | 443 | chr1 | ENST00000370473.4 |
| GDF1 | CGUCCGCCGCGAGCCAGACC | 444 | chr19 | ENST00000247005.7 |
| GDF1 | GGCCGGUUCCCCCGGUCAUG | 445 | chr19 | ENST00000247005.7 |
| GDF1 | GGGGCACGGGGCGCGGGUC | 446 | chr19 | ENST00000247005.7 |
| GDF10 | CCAUGGCUCAUGUCCCCGCU | 447 | chr10 | ENST00000580279.1 |
| GDF10 | CGUUGUUUCUGCUGUUGCUC | 448 | chr10 | ENST00000580279.1 |
| GDF10 | CGCGGGCAGUGCGGACCAGG | 449 | chr10 | ENST00000580279.1 |
| GDF11 | ACGGGGCAGCCGUCCGGCUC | 450 | chr12 | ENST00000257868.9 |
| GDF11 | UCUGCGACUUGAUGCUCUCU | 451 | chr12 | ENST00000257868.9 |
| GDF11 | CACCACCUCGCGGCUGAUGU | 452 | chr12 | ENST00000257868.9 |
| GDF15 | CACCGUCCUGAGUUCUUGCC | 453 | chr19 | ENST00000252809.3 |
| GDF15 | GCUCGCCUCGGCCAGAGACA | 454 | chr19 | ENST00000252809.3 |
| GDF15 | CUCUCGGAAUCUGGAGUCUU | 455 | chr19 | ENST00000252809.3 |
| GDF2 | GCGGGCCUAAGAUGUGUCCU | 456 | chr10 | ENST00000581492.2 |
| GDF2 | CUGCAGUGGCUUCCCCUGUA | 457 | chr10 | ENST00000581492.2 |
| GDF2 | AGGCACCCCCAGUGGGCUGU | 458 | chr10 | ENST00000581492.2 |
| GDF3 | AAAAUUUCUUCAAGAUAUA | 459 | chr12 | ENST00000329913.3 |
| GDF3 | CCUUAUCUAAGCCCAGAAAU | 460 | chr12 | ENST00000329913.3 |
| GDF3 | GUUAAUUCUGGCUUUGGGCC | 461 | chr12 | ENST00000329913.3 |
| GDF5 | CCCUGGCCUGAAGACGUUCC | 462 | chr20 | ENST00000374369.7 |
| GDF5 | UGACUUGGGCCAGAGACCCC | 463 | chr20 | ENST00000374369.7 |
| GDF5 | GGUACCAAAGCAAGAAAGUG | 464 | chr20 | ENST00000374369.7 |
| GDF6 | GCGGCUUCGCAUGCCCUUGG | 465 | chr8 | ENST00000287020.6 |
| GDF6 | GGAUUUGCCCGGUUUCCAGC | 466 | chr8 | ENST00000287020.6 |
| GDF6 | GCCCGCCAUGGAUACUCCCA | 467 | chr8 | ENST00000287020.6 |
| GDF7 | AGCGCCUGCCGCCCCCGCGA | 468 | chr2 | ENST00000272224.4 |
| GDF7 | GCUGGGCCGGUCCGGAGCCC | 469 | chr2 | ENST00000272224.4 |
| GDF7 | UGCGGGCGCCGCGGCUGUCC | 470 | chr2 | ENST00000272224.4 |
| GDF9 | AUACCUGUUACCUGGUCUCC | 471 | chr5 | ENST00000378673.2 |
| GDF9 | AGAGCCGAACAGUGUUGUAG | 472 | chr5 | ENST00000378673.2 |
| GDF9 | CUAUAAGACAUAUGCUACCA | 473 | chr5 | ENST00000378673.2 |
| GPI | GUCCCGGGUGAGAGCGGCCA | 474 | chr19 | ENST00000356487.9 |

TABLE 10-continued

Additional guide RNA sequences for use in
reducing the incidence of CRS

| Target Gene Symbol | Guide RNA Sequence | SEQ ID NO: | Location | Gene ID No. |
|---|---|---|---|---|
| GPI | UCAGCUCGGAGCGGUGCUCG | 475 | chr19 | ENST00000356487.9 |
| GPI | CGGCCCGCCCGCACCUGAAG | 476 | chr19 | ENST00000356487.9 |
| GREM1 | UAUGAGCCGCACAGCCUACA | 477 | chr15 | ENST00000622074.1 |
| GREM1 | CCCUUCAGCAGCCGGCAGCA | 478 | chr15 | ENST00000622074.1 |
| GREM1 | UUGUGCUGGGCCUUGUCUGG | 479 | chr15 | ENST00000622074.1 |
| GREM2 | CGGUGACCACCAGGGCCUCC | 480 | chr1 | ENST00000318160.4 |
| GREM2 | GCAGCAACAACUCGGAGAGA | 481 | chr1 | ENST00000318160.4 |
| GREM2 | GCUUUCCCUGUCCUUGUUCC | 482 | chr1 | ENST00000318160.4 |
| GRN | CAGGCAGACCAUGUGGACCC | 483 | chr17 | ENST00000053867.7 |
| GRN | GCUGGAACGCGGUGCCCAGA | 484 | chr17 | ENST00000053867.7 |
| GRN | AGCUGGCUCCUCCGGGGUCC | 485 | chr17 | ENST00000053867.7 |
| HAX1 | CACCUUUCUGCAGAACUUCC | 486 | chr1 | ENST00000328703.11 |
| HAX1 | UACGGGAGGGACAGACACUU | 487 | chr1 | ENST00000328703.11 |
| HAX1 | CCAGUCUGGUGCUGGUUGGG | 488 | chr1 | ENST00000328703.11 |
| HFE2 | AGGAGCGGAGGGCUCGACAG | 489 | chr1 | ENST00000336751.10 |
| HFE2 | UCAUCAGGAGCACUUCGAGG | 490 | chr1 | ENST00000336751.10 |
| HFE2 | CGUACUCAGCAUUGCAGCGG | 491 | chr1 | ENST00000336751.10 |
| HMGB1* | GAUACUCACGGAGGCCUCUU | 492 | chr13 | ENST00000339872.8 |
| HMGB1* | GAUACUCACGGAGGCCUCUU | 493 | chr13 | ENST00000339872.8 |
| HMGB1* | GAUACUCACGGAGGCCUCUU | 494 | chr13 | ENST00000339872.8 |
| HYAL2 | GCGUGGGCCACAGUCCUGUG | 495 | chr3 | ENST00000357750.8 |
| HYAL2 | UGCUGUGGGCUUGAGCUCCA | 496 | chr3 | ENST00000357750.8 |
| HYAL2 | GCAGCCCCAGCAUGCGGGC | 497 | chr3 | ENST00000357750.8 |
| ICAM3** | UCAUGUUCCUGAAGGUGUCC | 498 | chr19 | ENST00000160262.9 |
| ICAM3** | CAUGUUCCUGAAGGUGUCCA | 499 | chr19 | ENST00000160262.9 |
| ICAM3** | AUGUUCCUGAAGGUGUCCAG | 500 | chr19 | ENST00000160262.9 |
| ICAM3** | UCCUGAAGGUGUCCAGGGGC | 501 | chr19 | ENST00000160262.9 |
| ICOS** | UUUUAUGCAGGAGAAAUCAA | 502 | ch2 | ENST00000316386.10 |
| ICOS** | GAGAUGUUUAUAUUUCACAA | 503 | ch2 | ENST00000316386.10 |
| ICOS** | AUGUUUAUAUUUCACAACGG | 504 | ch2 | ENST00000316386.10 |
| ICOS** | UUUAAAAUGCAGUUGCUGAA | 505 | ch2 | ENST00000316386.10 |
| IFNA10 | CAAACUCCUCCUGGGGGAUU | 506 | chr9 | ENST00000357374.2 |
| IFNA10 | CAAACUCCUCCUGGGGGAUU | 507 | chr9 | ENST00000357374.2 |
| IFNA10 | CAAACUCCUCCUGGGGGAUU | 508 | chr9 | ENST00000357374.2 |
| IFNA14 | CAGGAGGACUUUGAUGCUCA | 509 | chr9 | ENST00000380222.3 |
| IFNA14 | AAGCAAAGGGCAAUGCCAUU | 510 | chr9 | ENST00000380222.3 |
| IFNA14 | AAGCAAAGGGCAAUGCCAUU | 511 | chr9 | ENST00000380222.3 |

TABLE 10-continued

Additional guide RNA sequences for use in
reducing the incidence of CRS

| Target Gene Symbol | Guide RNA Sequence | SEQ ID NO: | Location | Gene ID No. |
|---|---|---|---|---|
| IFNA16 | CAUCUCAUGGAAGGCAGAGA | 512 | chr9 | ENST00000380216.1 |
| IFNA16 | AUAUGAUUUCGGAUUCCCCC | 513 | chr9 | ENST00000380216.1 |
| IFNA16 | AUAUGAUUUCGGAUUCCCCC | 514 | chr9 | ENST00000380216.1 |
| IFNA2 | UCAAGGUCCUCCUGCUACCC | 515 | chr9 | ENST00000380206.3 |
| IFNA2 | CACCAGUAAAGCAAAGGUCA | 516 | chr9 | ENST00000380206.3 |
| IFNA2 | CACCAGUAAAGCAAAGGUCA | 517 | chr9 | ENST00000380206.3 |
| IFNA5 | UUGAUGAUAAUGGCACAAAU | 518 | chr9 | ENST00000610521.1 |
| IFNA5 | CUUGCCCUUUGUUUUACUGA | 519 | chr9 | ENST00000610521.1 |
| IFNA5 | CUUGCCCUUUGUUUUACUGA | 520 | chr9 | ENST00000610521.1 |
| IFNA6 | AGGUCUGCUGAAUCACCUCA | 521 | chr9 | ENST00000380210.1 |
| IFNA6 | ACAUGACUUCAGAUUUCCCC | 522 | chr9 | ENST00000380210.1 |
| IFNA6 | UCAUGGUCCUCCUGUGACCC | 523 | chr9 | ENST00000380210.1 |
| IFNA8 | UACAAGUCAUUCAGCUCUCU | 524 | chr9 | ENST00000380205.1 |
| IFNA8 | GUUUAUCAUCAAACUCCUCC | 525 | chr9 | ENST00000380205.1 |
| IFNA8 | GUUUAUCAUCAAACUCCUCC | 526 | chr9 | ENST00000380205.1 |
| IFNAR1 | UUUACUUUAAAGAACUGGGA | 527 | chr21 | ENST00000270139.7 |
| IFNAR1 | GAGUGAAGAAAAGUUGCAUU | 528 | chr21 | ENST00000270139.7 |
| IFNAR1 | AAACACUUCUUCAUGGUAUG | 529 | chr21 | ENST00000270139.7 |
| IFNAR2 | UAAACCAGAAGAUUUGAAGG | 530 | chr21 | ENST00000342136.8 |
| IFNAR2 | UGAGUGGAGAAGCACACACG | 531 | chr21 | ENST00000342136.8 |
| IFNAR2 | UCAGUUGCUCACACAAUUUC | 532 | chr21 | ENST00000342136.8 |
| IFNB1 | UUGAAUACUGCCUCAAGGAC | 533 | chr9 | ENST00000380232.3 |
| IFNB1 | GAAAAUUGCUGCUUCUUUGU | 534 | chr9 | ENST00000380232.3 |
| IFNB1 | AGCACAACAGGAGAGCAAUU | 535 | chr9 | ENST00000380232.3 |
| IFNE | UGGCCAGAGUGUGUCCUUUU | 536 | chr9 | ENST00000448696.4 |
| IFNE | UAGACACUGCUGAAUUGACA | 537 | chr9 | ENST00000448696.4 |
| IFNE | CUUGAUUCACUUGUCUUUGC | 538 | chr9 | ENST00000448696.4 |
| IFNG* | UUUUUAAUAGUACUUGUUUG | 539 | chr12 | ENST00000229135.3 |
| IFNG* | CUUCUUUUACAUAUGGGUCC | 540 | chr12 | ENST00000229135.3 |
| IFNG* | GAAAUAUACAAGUUAUAUCU | 541 | chr12 | ENST00000229135.3 |
| IFNGR1** | AUUGUACACCCUAAUGUAAC | 542 | chr6 | ENST00000367739.8 |
| IFNGR1** | CUCCAUUUACAAAAACUGAA | 543 | chr6 | ENST00000367739.8 |
| IFNGR1** | UUUCUGAUAUCCAGUUUAGG | 544 | chr6 | ENST00000367739.8 |
| IFNK | UUGUGGCUUGAGAUCCUUAU | 545 | chr9 | ENST00000276943.2 |
| IFNK | CGUUCAGUAAGUUACAGUCC | 546 | chr9 | ENST00000276943.2 |
| IFNK | UUUUCUCGUAGACAUUCUAC | 547 | chr9 | ENST00000276943.2 |

TABLE 10-continued

Additional guide RNA sequences for use in reducing the incidence of CRS

| Target Gene Symbol | Guide RNA Sequence | SEQ ID NO: | Location | Gene ID No. |
| --- | --- | --- | --- | --- |
| IFNL1 | AUUUAGCCAUGGCUGCAGCU | 548 | chr19 | ENST00000333625.2 |
| IFNL1 | GUGGCAGCCCUUCCCAGUUG | 549 | chr19 | ENST00000333625.2 |
| IFNL1 | UAGCGAGCUUCAAGAAGGCC | 550 | chr19 | ENST00000333625.2 |
| IFNL3 | CGGGCCUGUGUGAGUCGUCA | 551 | chr19 | ENST00000413851.2 |
| IFNL3 | CCAAGACAUCCCCCAGGGCU | 552 | chr19 | ENST00000413851.2 |
| IFNL3 | CCAAGACAUCCCCCAGGGCU | 553 | chr19 | ENST00000413851.2 |
| IFNW1 | CUCCCUUUUACCAUCUCCUG | 554 | chr9 | ENST00000380229.3 |
| IFNW1 | CAUUUGGUGCAGAAGCACCA | 555 | chr9 | ENST00000380229.3 |
| IFNW1 | AGAUCCAACAGGGCUAUAGC | 556 | chr9 | ENST00000380229.3 |
| IL10* | CGGAGAUCUCGAAGCAUGUU | 557 | chr1 | ENST00000423557.1 |
| IL10* | UCAGACUGGGUGCCCUGGCC | 558 | chr1 | ENST00000423557.1 |
| IL10* | CUCAGCACUGCUCUGUUGCC | 559 | chr1 | ENST00000423557.1 |
| IL10RA** | GGUCUGGCUACAGUUGGAGA | 560 | chr11 | ENST00000227752.7 |
| IL10RA** | GGUAGCCAUUGCUGUGGUAC | 561 | chr11 | ENST00000227752.7 |
| IL10RA** | GGUGUUGGUGACGGUCCAGU | 562 | chr11 | ENST00000227752.7 |
| IL11 | CGUGCCGCAGGUAGGACAGU | 563 | chr19 | ENST00000264563.6 |
| IL11 | CGGCUCUAUCCCCAGCUCCC | 564 | chr19 | ENST00000264563.6 |
| IL11 | CACUGGGAGCUCUACAGGUA | 565 | chr19 | ENST00000264563.6 |
| IL11RA | AGUGUCCUGGUUUCGGGAUG | 566 | chr9 | ENST00000318041.13 |
| IL11RA | GCUAGGGCAUGAACUGGUCC | 567 | chr9 | ENST00000318041.13 |
| IL11RA | UGCCCCAAGUGCACCAUCC | 568 | chr9 | ENST00000318041.13 |
| IL12A | CCAGGGUAGCCACAAGGAGG | 569 | chr3 | ENST00000305579.6 |
| IL12A | GGUCUGGAGUGGCCACGGGG | 570 | chr3 | ENST00000305579.6 |
| IL12A | UGACGGCCCUCAGCAGGUUU | 571 | chr3 | ENST00000305579.6 |
| IL12B | ACUCUUUGACUUGGAUGGUC | 572 | chr5 | ENST00000231228.2 |
| IL12B | GGUGAUACCAUCUUCUUCAG | 573 | chr5 | ENST00000231228.2 |
| IL12B | UUUAUGUCGUAGAAUUGGAU | 574 | chr5 | ENST00000231228.2 |
| IL12RB1^ | CACUUCCUGCGGUGUUGGUG | 575 | chr19 | ENST00000593993.6 |
| IL12RB1^ | GGAGCACUCGUAACGAUCAC | 576 | chr19 | ENST00000593993.6 |
| IL12RB1^ | AUCUCUUCCAGGCUCGGCCU | 577 | chr19 | ENST00000593993.6 |
| IL13* | CAUGGCGCUUUUGUUGACCA | 578 | chr5 | ENST00000304506.7 |
| IL13* | GCCUCCCUCUACAGCCCUCA | 579 | chr5 | ENST00000304506.7 |
| IL13* | CGACACUCACCUUCUGGUUC | 580 | chr5 | ENST00000304506.7 |
| IL15 | AUGGAAAUACUUCUCAAAUG | 581 | chr4 | ENST00000296545.11 |
| IL15 | GGCAUUCAUGUCUUCAUUUU | 582 | chr4 | ENST00000296545.11 |
| IL15 | AUGGUCAUGAUGAUUGUCCU | 583 | chr4 | ENST00000296545.11 |
| IL16 | CAAAAUUUCGGUCCAUCUCC | 584 | chr15 | ENST00000302987.8 |

TABLE 10-continued

Additional guide RNA sequences for use in reducing the incidence of CRS

| Target Gene Symbol | Guide RNA Sequence | SEQ ID NO: | Location | Gene ID No. |
|---|---|---|---|---|
| IL16 | AGGGCUAGAGCCAUCAUCAC | 585 | chr15 | ENST00000302987.8 |
| IL16 | GGAAAAUUCCCUCCUUGCCC | 586 | chr15 | ENST00000302987.8 |
| IL17A^ | GCUACUGCUGCUGAGCCUGG | 587 | chr6 | ENST00000340057.1 |
| IL17A^ | UCAACCUGAACAUCCAUAAC | 588 | chr6 | ENST00000340057.1 |
| IL17A^ | GGAUCGGUUGUAGUAAUCUG | 589 | chr6 | ENST00000340057.1 |
| IL17B^ | GCUCUGAGCUGUUCCUCAGC | 590 | chr5 | ENST00000261796.3 |
| IL17B^ | GAAACCGUAUGCCCGCAUGG | 591 | chr5 | ENST00000261796.3 |
| IL17B^ | CUCUUGCUUUUGGGGCUCCU | 592 | chr5 | ENST00000261796.3 |
| IL17C^ | UCAGAAACAGGAGGCCGGGG | 593 | chr16 | ENST00000244241.4 |
| IL17C^ | CGGUACCCCACACUGCUACU | 594 | chr16 | ENST00000244241.4 |
| IL17C^ | GCACCUCGAGCCAGCAGGUG | 595 | chr16 | ENST00000244241.4 |
| IL17D^ | CGGCAGCGCCAGCAGGAAGC | 596 | chr13 | ENST00000304920.3 |
| IL17D^ | GGACCGGCCGGAGGAGCUAC | 597 | chr13 | ENST00000304920.3 |
| IL17D^ | GUGGAAGGCACUGAGCACGC | 598 | chr13 | ENST00000304920.3 |
| IL17F^ | GGUAGUAUGAAGCUUGACAU | 599 | chr6 | ENST00000336123.4 |
| IL17F^ | GAAAAAGUAUGUCCUACUU | 600 | chr6 | ENST00000336123.4 |
| IL17F^ | UACUUGCUGCUGUCGAUAUU | 601 | chr6 | ENST00000336123.4 |
| IL18 | GGAAAUAAUUUUGUUCUCAC | 602 | chr11 | ENST00000280357.11 |
| IL18 | UUACAGCCAUACCUCUAGGC | 603 | chr11 | ENST00000280357.11 |
| IL18 | UUAUUUCAGAUAAUGCACCC | 604 | chr11 | ENST00000280357.11 |
| IL18BP | GCAGGACCCACAAAGGGCUG | 605 | chr11 | ENST00000260049.9 |
| IL18BP | UGUGCUUCUAACUGAGGCAG | 606 | chr11 | ENST00000260049.9 |
| IL18BP | GCUGGACACUGCUUAGCUGC | 607 | chr11 | ENST00000260049.9 |
| IL19 | AGUUACAGUGUGUUUCCCUU | 608 | chr1 | ENST00000270218.10 |
| IL19 | CAGUAGACAACCACGGUCUC | 609 | chr1 | ENST00000270218.10 |
| IL19 | CUUGGAAACUCUCUUCUAUA | 610 | chr1 | ENST00000270218.10 |
| IL1A | GGAAGGUUCUGAAGAAGAGA | 611 | chr2 | ENST00000263339.3 |
| IL1A | GGUAAGCUUGGAUGUUUUAG | 612 | chr2 | ENST00000263339.3 |
| IL1A | GCCAUAGCUUACAUGAUAGA | 613 | chr2 | ENST00000263339.3 |
| IL1B* | CAUUCUCCUGGAAGGUCUGU | 614 | chr2 | ENST00000263341.6 |
| IL1B* | CAUGGCCACAACAACUGACG | 615 | chr2 | ENST00000263341.6 |
| IL1B* | CUCUCCGCAGUGCUCCUUCC | 616 | chr2 | ENST00000263341.6 |
| IL1F10 | AUCUGCAUACUUCCUAACAG | 617 | chr2 | ENST00000341010.6 |
| IL1F10 | CCAGGCAGCGGCUCCCUCCC | 618 | chr2 | ENST00000341010.6 |
| IL1F10 | GGCCUCUCACCUCCAGCUGU | 619 | chr2 | ENST00000341010.6 |
| IL1R1** | UCCUUUUAAAGAUAAAUGCA | 620 | chr2 | ENST00000410023.5 |

TABLE 10-continued

Additional guide RNA sequences for use in
reducing the incidence of CRS

| Target Gene Symbol | Guide RNA Sequence | SEQ ID NO: | Location | Gene ID No. |
|---|---|---|---|---|
| IL1R1** | CUUAACCCAAAUGAACACAA | 621 | chr2 | ENST00000410023.5 |
| IL1R1** | UAUCUACAGAACAAGCCUCC | 622 | chr2 | ENST00000410023.5 |
| IL1R2** | CCAGAAGCUGCCGGUUUCGU | 623 | chr2 | ENST00000332549.7 |
| IL1R2** | UGUAGCCCUGAGGUGCCCCC | 624 | chr2 | ENST00000332549.7 |
| IL1R2** | UAAAAAUGACUCUGCUAGGA | 625 | chr2 | ENST00000332549.7 |
| IL1RAPL1** | AAUUCUUAAGGAGCAUCUUG | 626 | chrX | ENST00000378993.5 |
| IL1RAPL1** | CUCUGUGGAAGAAGGUGACU | 627 | chrX | ENST00000378993.5 |
| IL1RAPL1** | UACACUCACCUCGUUUAUGA | 628 | chrX | ENST00000378993.5 |
| IL1RL1** | UUUCUUAUUUCAGAAUUGUC | 629 | chr2 | ENST00000233954.5 |
| IL1RL1** | AAUGUGAUGACUGAGGACGC | 630 | chr2 | ENST00000233954.5 |
| IL1RL1** | ACCCUUGACCGUGAAGGACC | 631 | chr2 | ENST00000233954.5 |
| IL1RN** | UUCCCCAGAAAAGAUAGAUG | 632 | chr2 | ENST00000409930.3 |
| IL1RN** | ACAGGCACAUCUUCCCUCCA | 633 | chr2 | ENST00000409930.3 |
| IL1RN** | AGCAUGUUUUUACCUCCAGC | 634 | chr2 | ENST00000409930.3 |
| IL2 | UGUAAUAAUUUUAGUAAGAA | 635 | chr4 | ENST00000226730.4 |
| IL2 | ACAACUGGAGCAUUUACUGC | 636 | chr4 | ENST00000226730.4 |
| IL2 | GACUUAGUGCAAUGCAAGAC | 637 | chr4 | ENST00000226730.4 |
| IL20 | AAGGCUGAAGGCAAGACUAG | 638 | chr1 | ENST00000367096.7 |
| IL20 | UGGACUGAAGACACUCAAUU | 639 | chr1 | ENST00000367096.7 |
| IL20 | UUCUGAGAUACGGGGCAGUG | 640 | chr1 | ENST00000367096.7 |
| IL20RA | CAUCCCCGACCCGCACCUGG | 641 | chr6 | ENST00000316649.9 |
| IL20RA | UGUUGCUCCUGGCGGCGCCU | 642 | chr6 | ENST00000316649.9 |
| IL20RA | CCGCCGCCCAUGCGGGCUCC | 643 | chr6 | ENST00000316649.9 |
| IL20RB | AGUGAGUGAGCACCAGCUGC | 644 | chr3 | ENST00000329582.8 |
| IL20RB | UGCCAUACAACCUUCGUGUC | 645 | chr3 | ENST00000329582.8 |
| IL20RB | UUCUAUUAAAGGGAUGCUUC | 646 | chr3 | ENST00000329582.8 |
| IL21 | GAAAAAUUAUGUGAAUGACU | 647 | chr4 | ENST00000264497.7 |
| IL21 | UCAUGUGGCGAUCUUGACCU | 648 | chr4 | ENST00000264497.7 |
| IL21 | ACAAUCCUCUCCAUGUUGCC | 649 | chr4 | ENST00000264497.7 |
| IL22^ | UGGACUUGUCAAGCCUGCAG | 650 | chr12 | ENST00000328087.5 |
| IL22^ | UCUCUUGGCCCUCUUGGUAC | 651 | chr12 | ENST00000328087.5 |
| IL22^ | AAGAGCUCACAGAUUUCUGC | 652 | chr12 | ENST00000328087.5 |
| IL22RA1^ | GAUGUCUGGCUGCCCUAAGU | 653 | chr1 | ENST00000270800.1 |
| IL22RA1^ | UCUGGACCCAGGGAGCCCGC | 654 | chr1 | ENST00000270800.1 |
| IL22RA1^ | CAGGGAUCAGGACGUGCUCC | 655 | chr1 | ENST00000270800.1 |
| IL22RA2^ | UUCUGAGUAGCUCCCAGCCG | 656 | chr6 | ENST00000349184.8 |
| IL22RA2^ | CUGUAUGUCUGAGGUUUCAC | 657 | chr6 | ENST00000349184.8 |

TABLE 10-continued

Additional guide RNA sequences for use in reducing the incidence of CRS

| Target Gene Symbol | Guide RNA Sequence | SEQ ID NO: | Location | Gene ID No. |
|---|---|---|---|---|
| IL22RA2^ | ACAGAUAUGGACAGAGACAA | 658 | chr6 | ENST00000349184.8 |
| IL23A* | CUGCUGCCCUGGACAGCUCA | 659 | chr12 | ENST00000228534.5 |
| IL23A* | AAGCUGCUGGCACUGAGUCC | 660 | chr12 | ENST00000228534.5 |
| IL23A* | CUCACCAUGUGUCCCACUAG | 661 | chr12 | ENST00000228534.5 |
| IL23R** | CUGUUGCACAUAUGUAAAAU | 662 | chr1 | ENST00000347310.9 |
| IL23R** | GAUGUCAAGAAACAGGCAAA | 663 | chr1 | ENST00000347310.9 |
| IL23R** | UAAGUACACUCACCUGUUUC | 664 | chr1 | ENST00000347310.9 |
| IL24 | UGAGAGGCUGUCGCCAGCAA | 665 | chr1 | ENST00000294984.6 |
| IL24 | CUUCUCUGGAGCCAGGUAUC | 666 | chr1 | ENST00000294984.6 |
| IL24 | ACAACCCCCUUCACUUGGCA | 667 | chr1 | ENST00000294984.6 |
| IL25 | CCUACAGGUGGUUGCAUUCU | 668 | chr14 | ENST00000329715.2 |
| IL25 | GAGGUGUCCUGCCCUUUGCU | 669 | chr14 | ENST00000329715.2 |
| IL25 | UGCCUCCCCUAGAGCCUGCU | 670 | chr14 | ENST00000329715.2 |
| IL26 | AUAGAGAGCGUCAACAGCUU | 671 | chr12 | ENST00000229134.4 |
| IL26 | AGAUUGCUUGUGCUUGGCAA | 672 | chr12 | ENST00000229134.4 |
| IL26 | UGCUGGUGAAUUUCAUUUUG | 673 | chr12 | ENST00000229134.4 |
| IL27 | CAUUAGGGGGACUUACAAAG | 674 | chr16 | ENST00000356897.1 |
| IL27 | GCAGCUCCUGCAGGCUCAGC | 675 | chr16 | ENST00000356897.1 |
| IL27 | ACCAGCUUGAACCAGGAGCA | 676 | chr16 | ENST00000356897.1 |
| IL2RA | CAGAGCUUGUGCAUUGACAU | 677 | chr10 | ENST00000379959.7 |
| IL2RA | GUGACCCGCUUUUUAUUCUG | 678 | chr10 | ENST00000379959.7 |
| IL2RA | AUGGCUUUGAAUGUGGCGUG | 679 | chr10 | ENST00000379959.7 |
| IL2RB | UGUGGCCUGGGGACAGCGUC | 680 | chr22 | ENST00000216223.9 |
| IL2RB | CCCACAGAUGCAACAUAAGC | 681 | chr22 | ENST00000216223.9 |
| IL2RB | GUUGUCUCCAGUUCGCCUGA | 682 | chr22 | ENST00000216223.9 |
| IL2RG | CAUACCAAUAAUGCAGAGUG | 683 | chrX | ENST00000374202.6 |
| IL2RG | UCGAGUACAUGAAUUGCACU | 684 | chrX | ENST00000374202.6 |
| IL2RG | GAAACACUGAGGGAGUCAGU | 685 | chrX | ENST00000374202.6 |
| IL3* | GCAGGAGCAGGACGGGCAGG | 686 | chr5 | ENST00000296870.2 |
| IL3* | CAACGCCCUUGAAGACAAGC | 687 | chr5 | ENST00000296870.2 |
| IL3* | CUACUCACCAGCAAAGGCAA | 688 | chr5 | ENST00000296870.2 |
| IL31 | CUUUCAAAAGCAUCUUCGAG | 689 | chr12 | ENST00000377035.1 |
| IL31 | GUAACGGACGGGCAACGUG | 690 | chr12 | ENST00000377035.1 |
| IL31 | AGAAAGAGCACAGACGUCGA | 691 | chr12 | ENST00000377035.1 |
| IL31RA | CAACUUCGCUAAGAACCGUA | 692 | chr5 | ENST00000447346.6 |
| IL31RA | AGCUCUGCGAUGUGCGGUCA | 693 | chr5 | ENST00000447346.6 |

TABLE 10-continued

Additional guide RNA sequences for use in reducing the incidence of CRS

| Target Gene Symbol | Guide RNA Sequence | SEQ ID NO: | Location | Gene ID No. |
|---|---|---|---|---|
| IL31RA | CAGUCAUUCCCAUUUUUUCU | 694 | chr5 | ENST00000447346.6 |
| IL32 | CUGCCUCUCUUCACAGCACC | 695 | chr16 | ENST00000325568.9 |
| IL32 | AGAAUCAGGACGUGGACAGG | 696 | chr16 | ENST00000325568.9 |
| IL32 | UCAGGGUGAGAAGGAUGAAG | 697 | chr16 | ENST00000325568.9 |
| IL33 | UUGUUUAGAAUCCCAACAGA | 698 | chr9 | ENST00000381434.7 |
| IL33 | CUCUGGCCUUAUGAUAAAAA | 699 | chr9 | ENST00000381434.7 |
| IL33 | UUUCAGUGAAGGCCUUUUGG | 700 | chr9 | ENST00000381434.7 |
| IL34 | UCUUGGGAUCUUCCUUGGCG | 701 | chr16 | ENST00000288098.6 |
| IL34 | GCACUCCUCAUUCUGCGUCA | 702 | chr16 | ENST00000288098.6 |
| IL34 | CAGGAGCCGACUUCAGUACA | 703 | chr16 | ENST00000288098.6 |
| IL36A | CACAUGUCGGCAUGAGAUUA | 704 | chr2 | ENST00000259211.6 |
| IL36A | GAUUGAGUCCAUUCAGGCCC | 705 | chr2 | ENST00000259211.6 |
| IL36A | ACUCACCUUCAGCUGCAGUG | 706 | chr2 | ENST00000259211.6 |
| IL36B | CAAGCCUACUUUGCAGCUUA | 707 | chr2 | ENST00000327407.2 |
| IL36B | UAUGGUUUACCUGGGAAUCA | 708 | chr2 | ENST00000327407.2 |
| IL36B | GCUAUUAAAUGAAGAGUGAC | 709 | chr2 | ENST00000327407.2 |
| IL36G | UCAGUGUGUAAACCUAUUAC | 710 | chr2 | ENST00000259205.4 |
| IL36G | CACAAGGUUCUGACCCUGAA | 711 | chr2 | ENST00000259205.4 |
| IL36G | CUGUUUGCACUGCUGUGGCU | 712 | chr2 | ENST00000259205.4 |
| IL36RN | CACAGGUGAAGAGAUCAGCG | 713 | chr2 | ENST00000346807.7 |
| IL36RN | CACCCAGGAUGACGGGGGAC | 714 | chr2 | ENST00000346807.7 |
| IL36RN | GGAGCCGACUCUAACACUAG | 715 | chr2 | ENST00000346807.7 |
| IL37 | GCUAAUGCAAAGAAGAUCUC | 716 | chr2 | ENST00000263326.7 |
| IL37 | AUUCUCCUGGGGGUCUCUAA | 717 | chr2 | ENST00000263326.7 |
| IL37 | AACUCUCACCUUCAGCUGAA | 718 | chr2 | ENST00000263326.7 |
| IL4* | CAGAGGGGGAAGCAGUUGGG | 719 | chr5 | ENST00000231449.6 |
| IL4* | UGAUAUCGCACUUGUGUCCG | 720 | chr5 | ENST00000231449.6 |
| IL4* | UACUCACCUUCUGCUCUGUG | 721 | chr5 | ENST00000231449.6 |
| IL5* | CAUAAAGAAAAUUACCUCAU | 722 | chr5 | ENST00000231454.5 |
| IL5* | UGCAUUGGUGAAAGAGACCU | 723 | chr5 | ENST00000231454.5 |
| IL5* | CAUUUGAGUUUGCUAGCUCU | 724 | chr5 | ENST00000231454.5 |
| IL6* | CCCUCCGGCACAGGCGCCUU | 725 | chr7 | ENST00000258743.9 |
| IL6* | ACAUCUUUGGAAUCUUCUCC | 726 | chr7 | ENST00000258743.9 |
| IL6* | AACGAAUUGACAAACAAAUU | 727 | chr7 | ENST00000258743.9 |
| IL6R** | CAGUCCGGCCGAAGACUUCC | 728 | chr1 | ENST00000368485.7 |
| IL6R** | UAACUGGCAGGAGAACUUCU | 729 | chr1 | ENST00000368485.7 |
| IL6R** | CAGCAAAACUCAAACCUUUC | 730 | chr1 | ENST00000368485.7 |

TABLE 10-continued

Additional guide RNA sequences for use in reducing the incidence of CRS

| Target Gene Symbol | Guide RNA Sequence | SEQ ID NO: | Location | Gene ID No. |
|---|---|---|---|---|
| IL6ST | AUUUACCUGGCUCCAAGUUG | 731 | chr5 | ENST00000336909.9 |
| IL6ST | UUAUAACACUCUUAAUACUU | 732 | chr5 | ENST00000336909.9 |
| IL6ST | UGAUAAAUUAUGUGGCGGAU | 733 | chr5 | ENST00000336909.9 |
| IL7 | GGUCAGCAUCGAUCAAUUAU | 734 | chr8 | ENST00000263851.8 |
| IL7 | AUGCUACUGGCAACAGAACA | 735 | chr8 | ENST00000263851.8 |
| IL7 | UGUCAAAUUUAGUUUCUUUU | 736 | chr8 | ENST00000263851.8 |
| IL9^ | CUACCUGCAUCUUGUUGAUG | 737 | chr5 | ENST00000274520.1 |
| IL9^ | UGGACACCCCUGGCCUGCCA | 738 | chr5 | ENST00000274520.1 |
| IL9^ | UGUCAAGAUGCUUCUGGCCA | 739 | chr5 | ENST00000274520.1 |
| INHA | UCAGCAGCAAGAAGAGCAGU | 740 | chr2 | ENST00000243786.2 |
| INHA | CCGGGAACUUGUUCUGGCCA | 741 | chr2 | ENST00000243786.2 |
| INHA | CCGCGGUGACCAGGGAAGGU | 742 | chr2 | ENST00000243786.2 |
| INHBA | UGAACUUAUGGAGCAGACCU | 743 | chr7 | ENST00000242208.4 |
| INHBA | GAACGGGUAUGUGGAGAUAG | 744 | chr7 | ENST00000242208.4 |
| INHBA | GGGUACCGGCUGGGUGACAU | 745 | chr7 | ENST00000242208.4 |
| INHBB | GGCGGCGGCGCGGCAGGCGU | 746 | chr2 | ENST00000295228.3 |
| INHBB | GUACGUCGUGCGGCGGCUUC | 747 | chr2 | ENST00000295228.3 |
| INHBB | UGUGCCGCUUCACCGCCUCC | 748 | chr2 | ENST00000295228.3 |
| INHBC | AAAGGCCAGAAGCAAUGAGG | 749 | chr12 | ENST00000309668.2 |
| INHBC | UGGACACUGACCGCCAGCUC | 750 | chr12 | ENST00000309668.2 |
| INHBC | GCGGGAGCUGCUUCUUGAUC | 751 | chr12 | ENST00000309668.2 |
| INHBE | AAAGUGAGCAGGGAGCUGU | 752 | chr12 | ENST00000266646.2 |
| INHBE | CAAGCAAAGAGUGCCAGGAA | 753 | chr12 | ENST00000266646.2 |
| INHBE | CCAGGAGAGUGCGGGACCCU | 754 | chr12 | ENST00000266646.2 |
| ITGA4** | CCACCGAGAGCGCAUGGCUU | 755 | chr2 | ENST00000397033.6 |
| ITGA4** | GACCGGCCGCCCCUACAACG | 756 | chr2 | ENST00000397033.6 |
| ITGA4** | AGCCGAACAGCGUGUUGUGG | 757 | chr2 | ENST00000397033.6 |
| ITGAV** | CGGCGAUGGCUUUUCCGCCG | 758 | chr2 | ENST00000261023.7 |
| ITGAV** | GUCCCGAGAGAAGAAGCGGG | 759 | chr2 | ENST00000261023.7 |
| ITGAV** | GACAGUCCUGCCGAGUACUC | 760 | chr2 | ENST00000261023.7 |
| ITGB1** | UGCUGUUCCUUUGCUACGGU | 761 | chr10 | ENST00000302278.7 |
| ITGB1** | GAUGACAUAGAAAAUCCCAG | 762 | chr10 | ENST00000302278.7 |
| ITGB1** | AUUUAGACAUUUUUACAGGA | 763 | chr10 | ENST00000302278.7 |
| ITGB3** | GCGAGGUGAGCCCAGAGGCA | 764 | chr17 | ENST00000559488.5 |
| ITGB3** | AGGCCCGAGUACUAGAGGAC | 765 | chr17 | ENST00000559488.5 |
| ITGB3** | GGGGACUGACUUGAGUGACC | 766 | chr17 | ENST00000559488.5 |

TABLE 10-continued

Additional guide RNA sequences for use in reducing the incidence of CRS

| Target Gene Symbol | Guide RNA Sequence | SEQ ID NO: | Location | Gene ID No. |
|---|---|---|---|---|
| KIT** | CUCAACCAUCUGUGAGUCCA | 767 | chr4 | ENST00000288135.5 |
| KIT** | AUCAGACUUAAUAGUCCGCG | 768 | chr4 | ENST00000288135.5 |
| KIT** | AAAGUCCAUUUGACAAAGCC | 769 | chr4 | ENST00000288135.5 |
| KITLG | UUUCUUUCACGCACUCCACA | 770 | chr12 | ENST00000228280.9 |
| KITLG | AAGUUUUCAAAUAUUUCUGA | 771 | chr12 | ENST00000228280.9 |
| KITLG | UCUUGCAGCCAAGUCAUUGU | 772 | chr12 | ENST00000228280.9 |
| KLHL20 | GCACCGGGAGCUAUGUGAUG | 773 | chr1 | ENST00000209884.4 |
| KLHL20 | UACUUCCGAGCUAUGUUUAC | 774 | chr1 | ENST00000209884.4 |
| KLHL20 | UAGCCCUCUCGUCAAUGUCU | 775 | chr1 | ENST00000209884.4 |
| LEFTY1 | GCUGCAGCAGGGCCACGUAC | 776 | chr1 | ENST00000272134.5 |
| LEFTY1 | CCUCCAUGUCGGCCCUGUCC | 777 | chr1 | ENST00000272134.5 |
| LEFTY1 | GUGUUGCCCCUGGCCAGCCC | 778 | chr1 | ENST00000272134.5 |
| LEFTY2 | AUGUCGGCCCUGUCCAGUAC | 779 | chr1 | ENST00000366820.9 |
| LEFTY2 | CUCCUCGGUCAGGGCCGCCC | 780 | chr1 | ENST00000366820.9 |
| LEFTY2 | GCAGCACCAUGUGGCCCCUG | 781 | chr1 | ENST00000366820.9 |
| LIF | GUCCCGGGUGAUGUUGCCCA | 782 | chr22 | ENST00000249075.3 |
| LIF | UGCCGUUGGCGUGGAAGGGC | 783 | chr22 | ENST00000249075.3 |
| LIF | UGUUGGGGAACGGCUCCCCC | 784 | chr22 | ENST00000249075.3 |
| LIFR | UGAUGCACUUACCCUUUUUC | 785 | chr5 | ENST00000263409.8 |
| LIFR | UAAAUGUUGAUAACAGCCAC | 786 | chr5 | ENST00000263409.8 |
| LIFR | GAAACGACCAUCCUGGAUGG | 787 | chr5 | ENST00000263409.8 |
| LTA | CCCUAGGGGCUCCCUGGUGU | 788 | chr6 | ENST00000418386.2 |
| LTA | GAUGCAUCUUGGGGUGCUGA | 789 | chr6 | ENST00000418386.2 |
| LTA | CAGGUGGAUGUUUACCAAUG | 790 | chr6 | ENST00000418386.2 |
| LTB | UAUCACUGUCCUGGCUGUGC | 791 | chr6 | ENST00000429299.2 |
| LTB | UCCCUCCUGCUAGCUGUGGC | 792 | chr6 | ENST00000429299.2 |
| LTB | UUCAGUCUCAAUGGGGCAC | 793 | chr6 | ENST00000429299.2 |
| LTBP1 | AUGGUGGCCAGUGCAGUUCA | 794 | chr2 | ENST00000407925.5 |
| LTBP1 | GUUUAGGCACGCUGGCACCA | 795 | chr2 | ENST00000407925.5 |
| LTBP1 | GAGGCAAGGUAUGUGUUGAA | 796 | chr2 | ENST00000407925.5 |
| LTBP3 | GCCCUCACCCACGCGGAAGC | 797 | chr11 | ENST00000322147.8 |
| LTBP3 | AUGACGCUCAUCGGAGAGAA | 798 | chr11 | ENST00000322147.8 |
| LTBP3 | CUGCAAGCGGACCUGUCUCA | 799 | chr11 | ENST00000322147.8 |
| LTBP4 | CCCUUGAUCUGUCACAAUGG | 800 | chr19 | ENST00000308370.11 |
| LTBP4 | GGCCGGGGCCGGGCGCCCG | 801 | chr19 | ENST00000308370.11 |
| LTBP4 | GUGCUCGUCGUCGCGGUGGU | 802 | chr19 | ENST00000308370.11 |
| MAF | CAGGAGAAUGGCAUCAGAAC | 803 | chr16 | ENST00000326043.4 |

TABLE 10-continued

Additional guide RNA sequences for use in reducing the incidence of CRS

| Target Gene Symbol | Guide RNA Sequence | SEQ ID NO: | Location | Gene ID No. |
|---|---|---|---|---|
| MAF | CAGGGGACUGGUGGGCAGGU | 804 | chr16 | ENST00000326043.4 |
| MAF | UCCAUGGCCAGGGGACUGGU | 805 | chr16 | ENST00000326043.4 |
| MAF | CGACCUGCCCACCAGUCCCC | 806 | chr16 | ENST00000326043.4 |
| MIF | UUGGUGUUUACGAUGAACAU | 807 | chr22 | ENST00000215754.7 |
| MIF | CAGCAGCUGGCGCAGGCCAC | 808 | chr22 | ENST00000215754.7 |
| MIF | GCGCGGAACCCCUCGUCCGG | 809 | chr22 | ENST00000215754.7 |
| MINOS1- | GGCCACGGGCAUGAUGCUUC | 810 | chr1 | ENST00000602662.1 |
| MINOS1- | GAACAGUGCCAGCUUGUUGA | 811 | chr1 | ENST00000602662.1 |
| MINOS1- | AGCCGCUGUGGCCCACGAUC | 812 | chr1 | ENST00000602662.1 |
| MSTN | UGACGAUUAUCACGCUACAA | 813 | chr2 | ENST00000260950.4 |
| MSTN | UUCCCGGAGUGGAGGAGCUU | 814 | chr2 | ENST00000260950.4 |
| MSTN | AAUCCUCAGUAAACUUCGUC | 815 | chr2 | ENST00000260950.4 |
| NAMPT | GCUGGGGACGAGCGCGCGGC | 816 | chr7 | ENST00000222553.7 |
| NAMPT | CUUUACCUUGUAGGAGUCGG | 817 | chr7 | ENST00000222553.7 |
| NAMPT | CCGGCCCGAGAUGAAUCCUG | 818 | chr7 | ENST00000222553.7 |
| NBL1 | GGCCACGGGCAUGAUGCUUC | 819 | chr1 | ENST00000375136.7 |
| NBL1 | GAACAGUGCCAGCUUGUUGA | 820 | chr1 | ENST00000375136.7 |
| NBL1 | AGCCGCUGUGGCCCACGAUC | 821 | chr1 | ENST00000375136.7 |
| NDP | UUGAGCUACACUUGUACAAU | 822 | chrX | ENST00000378062.5 |
| NDP | CAGCUCAUUCAUAAUGGACU | 823 | chrX | ENST00000378062.5 |
| NDP | CAGCAGGGAGAGCAUAGAAA | 824 | chrX | ENST00000378062.5 |
| NLRP7 | GCCUCUUCCACCUCAGACCA | 825 | chr19 | ENST00000328092.9 |
| NLRP7 | GAGUUUCAAAUCCCUUUUAU | 826 | chr19 | ENST00000328092.9 |
| NLRP7 | CUGCAGAGUCCACUCUAGCU | 827 | chr19 | ENST00000328092.9 |
| NODAL | UGACCAGGCCUCUCUCCAAG | 828 | chr10 | ENST00000287139.7 |
| NODAL | GGGACAAAGUGACAGUGAAU | 829 | chr10 | ENST00000287139.7 |
| NODAL | CUGUGUCGGGCUUUGGCUGG | 830 | chr10 | ENST00000287139.7 |
| NOG | GACCACCACCAGGGCGUAGA | 831 | chr17 | ENST00000332822.4 |
| NOG | GGCGGAUGUGGAGAUAGUGC | 832 | chr17 | ENST00000332822.4 |
| NOG | UUGGGGUCAAAGAUAGGGUC | 833 | chr17 | ENST00000332822.4 |
| NRG1 | GCUACAUCUACAUCCACCAC | 834 | chr8 | ENST00000287842.7 |
| NRG1 | AAACUUUCUGUGUGAAUGGA | 835 | chr8 | ENST00000287842.7 |
| NRG1 | UUACUUGCACAAGUAUCUCG | 836 | chr8 | ENST00000287842.7 |
| NRP1 | UUGCAGAGCAGUGUCUCAGA | 837 | chr10 | ENST00000265371.8 |
| NRP1 | GCUGUCGGUGUAAAAAACCA | 838 | chr10 | ENST00000265371.8 |
| NRP1 | CCACAGUAACGCCCAAUGUG | 839 | chr10 | ENST00000265371.8 |

TABLE 10-continued

Additional guide RNA sequences for use in reducing the incidence of CRS

| Target Gene Symbol | Guide RNA Sequence | SEQ ID NO: | Location | Gene ID No. |
|---|---|---|---|---|
| NRP2 | CUUUCAGACCCACCGUGCGG | 840 | chr2 | ENST00000357785.9 |
| NRP2 | UCUGGUGGGAGGGGUAGUCC | 841 | chr2 | ENST00000357785.9 |
| NRP2 | UUGAGGACAAUCUUCUGGUU | 842 | chr2 | ENST00000357785.9 |
| OSM | AGGGCCCAGGUGCUUACAUA | 843 | chr22 | ENST00000215781.2 |
| OSM | GAUCUGUCUGCUUCUGGAGC | 844 | chr22 | ENST00000215781.2 |
| OSM | GUUUCCAAGCAUGGCGAGCA | 845 | chr22 | ENST00000215781.2 |
| OSMR | AUUACAGCACCACUGUGAAG | 846 | chr5 | ENST00000274276.7 |
| OSMR | CUUUGUAAGAAUAAAGAGUU | 847 | chr5 | ENST00000274276.7 |
| OSMR | GAGCAACUGGAGUUCCUGGG | 848 | chr5 | ENST00000274276.7 |
| PARK7 | UAGAUUAAGGUCACCGUUGC | 849 | chr1 | ENST00000338639.9 |
| PARK7 | CAGGACAAAUGACCACAUCA | 850 | chr1 | ENST00000338639.9 |
| PARK7 | CAUGGAGUUAUUCCUUCAUA | 851 | chr1 | ENST00000338639.9 |
| PDPN | CAACUGCAAAGUUUGCUGUC | 852 | chr1 | ENST00000294489.10 |
| PDPN | CCCCACCGUCGCGCUCCUCC | 853 | chr1 | ENST00000294489.10 |
| PDPN | CAGCUCAGAAUCUUGCUGCU | 854 | chr1 | ENST00000294489.10 |
| PF4 | UGUGAGGGCUGGCAGCGGCG | 855 | chr4 | ENST00000296029.3 |
| PF4 | GUGGCAGGAGCAGCAACCCC | 856 | chr4 | ENST00000296029.3 |
| PF4 | CGCAGCAUGAGCUCCGCAGC | 857 | chr4 | ENST00000296029.3 |
| PF4V1 | GGCGCGGGUGAGGCGGGACC | 858 | chr4 | ENST00000226524.3 |
| PF4V1 | AGAGCAGAAACCAGGCUGGG | 859 | chr4 | ENST00000226524.3 |
| PF4V1 | AGAGCAGAAACCAGGCUGGG | 860 | chr4 | ENST00000226524.3 |
| PGLYRP1 | CGAUACCACCACAUAGCGUA | 861 | chr19 | ENST00000008938.4 |
| PGLYRP1 | CAGGGCCUUCCACUCGUUCC | 862 | chr19 | ENST00000008938.4 |
| PGLYRP1 | GCCGCUCUAUGCUGCUUGCC | 863 | chr19 | ENST00000008938.4 |
| PLP2 | ACCCUUCCAGAUAUUAUGCC | 864 | chrX | ENST00000376327.5 |
| PLP2 | ACCGACAGGGAGGAGUAGCC | 865 | chrX | ENST00000376327.5 |
| PLP2 | GGACCCCUUCUCACACUCCA | 866 | chrX | ENST00000376327.5 |
| PPBP | UUGGCGAAAGGCAAAGGUAG | 867 | chr4 | ENST00000296028.3 |
| PPBP | GUCAUUGCUGCUGACUGCUC | 868 | chr4 | ENST00000296028.3 |
| PPBP | AAGGGGUGGUAUCAAGUCUG | 869 | chr4 | ENST00000296028.3 |
| PXDN | ACCACAGUUCAGCUCUUCCG | 870 | chr2 | ENST00000252804.8 |
| PXDN | GCGUCUGGGAUAUUCACAGA | 871 | chr2 | ENST00000252804.8 |
| PXDN | ACUGCGACUGUGAAAUCCUG | 872 | chr2 | ENST00000252804.8 |
| RORC | CCGCGUUACAGCGCUGGCUC | 873 | chr1 | ENST00000318247.6 |
| RORC | AGUAGGCCGCGUUACAGCGC | 874 | chr1 | ENST00000318247.6 |
| RORC | CUGCUGACGGGUGCAGGAGU | 875 | chr1 | ENST00000318247.6 |
| RORC | GCAGUUCUGCUGACGGGUGC | 876 | chr1 | ENST00000318247.6 |

TABLE 10-continued

Additional guide RNA sequences for use in reducing the incidence of CRS

| Target Gene Symbol | Guide RNA Sequence | SEQ ID NO: | Location | Gene ID No. |
|---|---|---|---|---|
| SCG2 | AGCCCUGAUCAUUUCAGGAC | 877 | chr2 | ENST00000305409.2 |
| SCG2 | CUGGUUCUUUCUGAAGCAGC | 878 | chr2 | ENST00000305409.2 |
| SCG2 | UGGCUGAAGCAAAGACCCAC | 879 | chr2 | ENST00000305409.2 |
| SCGB3A1 | CCUCUAUGAGGUGGUUCACG | 880 | chr5 | ENST00000292641.3 |
| SCGB3A1 | GGUGCCGAGGGGGUUGGCCA | 881 | chr5 | ENST00000292641.3 |
| SCGB3A1 | UGCAGCUGCUGCUUUCUUAG | 882 | chr5 | ENST00000292641.3 |
| SECTM1 | ACAGCCCAGCAUGGGAGUCC | 883 | chr17 | ENST00000269389.7 |
| SECTM1 | CUGGAGCUGCCAGCCGUCCC | 884 | chr17 | ENST00000269389.7 |
| SECTM1 | CUUGAUGUUGACAUGGGAGA | 885 | chr17 | ENST00000269389.7 |
| SLURP1 | CCCUGACUCCAGUGCACCCA | 886 | chr8 | ENST00000246515.1 |
| SLURP1 | CGUCACCAGCGUGGUCAUGC | 887 | chr8 | ENST00000246515.1 |
| SLURP1 | CUUGCAGGUGUAGCACUUGA | 888 | chr8 | ENST00000246515.1 |
| SOSTDC1 | AUCAAGCCAGAAAUGGAGGC | 889 | chr7 | ENST00000307068.4 |
| SOSTDC1 | AGAAAUCCUUUAUUCACAUG | 890 | chr7 | ENST00000307068.4 |
| SOSTDC1 | UUAGGAUGCAUGCAAGGGGA | 891 | chr7 | ENST00000307068.4 |
| SP100 | UCUGAGAGUCCAUUUUCAGG | 892 | chr2 | ENST00000340126.8 |
| SP100 | AGUGACAAAGAUGAUUCGCU | 893 | chr2 | ENST00000340126.8 |
| SP100 | ACCCAGUCAGUCUUACCUGU | 894 | chr2 | ENST00000340126.8 |
| SPI1 | GUCCCCCACAGACCAUUACU | 895 | chr11 | ENST00000378538.7 |
| SPI1 | GGGGGUGGAAGUCCCAGUAA | 896 | chr11 | ENST00000378538.7 |
| SPI1 | CGCUGUGCACGUGGUGGGGG | 897 | chr11 | ENST00000378538.7 |
| SPI1 | ACUCGCUGUGCACGUGGUGG | 898 | chr11 | ENST00000378538.7 |
| SPP1 | AAUGGUGAGACUCAUCAGAC | 899 | chr4 | ENST00000237623.11 |
| SPP1 | UCGGUUGCUGGCAGGUCCGU | 900 | chr4 | ENST00000237623.11 |
| SPP1 | UGAUGGCCGAGGUGAUAGUG | 901 | chr4 | ENST00000237623.11 |
| TBX21 | CCCGCCCCGGAUGGGCAUCG | 902 | ch17 | ENST00000177694.1 |
| TBX21 | GGCAUCGUGGAGCCGGGUUG | 903 | ch17 | ENST00000177694.1 |
| TBX21 | GGGUUGCGGAGACAUGCUGA | 904 | ch17 | ENST00000177694.1 |
| TBX21 | GUCGCUCCCCGGCAUCGGCU | 905 | ch17 | ENST00000177694.1 |
| TCAP | GCACUGCCCCUGCUGGUGGU | 906 | chr17 | ENST00000309889.2 |
| TCAP | AGUACCAGCUGCCCUACCAG | 907 | chr17 | ENST00000309889.2 |
| TCAP | CUCCUUGGUGGCGCCCAUCU | 908 | chr17 | ENST00000309889.2 |
| TGFB1* | GCCGCAGCUUGGACAGGAUC | 909 | chr19 | ENST00000221930.5 |
| TGFB1* | CUCCAUGUCGAUAGUCUUGC | 910 | chr19 | ENST00000221930.5 |
| TGFB1* | AGCAGCCGCAGCCCGGAGGG | 911 | chr19 | ENST00000221930.5 |
| TGFB2* | UACCUGCAGCACACUCGAUA | 912 | chr1 | ENST00000366930.8 |

TABLE 10-continued

Additional guide RNA sequences for use in reducing the incidence of CRS

| Target Gene Symbol | Guide RNA Sequence | SEQ ID NO: | Location | Gene ID No. |
|---|---|---|---|---|
| TGFB2* | UCGGGCUCAGGAUAGUCUUC | 913 | chr1 | ENST00000366930.8 |
| TGFB2* | CUUCUCCUGGAGCAAGUCCC | 914 | chr1 | ENST00000366930.8 |
| TGFB3* | GACAGAUCUUGAGCAAGCUC | 915 | chr14 | ENST00000238682.7 |
| TGFB3* | UGGUGCAAGUGGACAGAGAG | 916 | chr14 | ENST00000238682.7 |
| TGFB3* | GCACUUGCAAAGGGCUCUGG | 917 | chr14 | ENST00000238682.7 |
| TGFBR1** | UUUUCAGUAAAGUCAUCACC | 918 | chr9 | ENST00000374994.8 |
| TGFBR1** | CUGCAUCUCACUCAUGUUGA | 919 | chr9 | ENST00000374994.8 |
| TGFBR1** | CCUCUUCAUUUGGCACUCGA | 920 | chr9 | ENST00000374994.8 |
| TGFBR2** | UCUACUGCUACCGCGUUAAC | 921 | chr3 | ENST00000295754.9 |
| TGFBR2** | CGAGCACUGUGCCAUCAUCC | 922 | chr3 | ENST00000295754.9 |
| TGFBR2** | GUUGAUGUUGUUGGCACACG | 923 | chr3 | ENST00000295754.9 |
| TGFBR3** | CAGCCCAGUUGUGCCUCUGC | 924 | chr1 | ENST00000212355.8 |
| TGFBR3** | CAUCAAGGCCUGGACAGGAU | 925 | chr1 | ENST00000212355.8 |
| TGFBR3** | CCCUUGGCAGGUCCAGAGCC | 926 | chr1 | ENST00000212355.8 |
| THBS1 | UCCUGUCUAACAGAGUCUGG | 927 | chr15 | ENST00000260356.5 |
| THBS1 | GUCGGCGCCCAGACCCCUUG | 928 | chr15 | ENST00000260356.5 |
| THBS1 | UCAGGUUGGCAUCCUCGAUG | 929 | chr15 | ENST00000260356.5 |
| THNSL2 | GAGAAGUGGUCCAUCUGUCC | 930 | chr2 | ENST00000324166.6 |
| THNSL2 | UGGCGUCACAUAUGCAUUUA | 931 | chr2 | ENST00000324166.6 |
| THNSL2 | UCUUCUCCAGGAAGUACUGC | 932 | chr2 | ENST00000324166.6 |
| THPO | CCUGUCCAGAAAGCUGCCCC | 933 | chr3 | ENST00000204615.11 |
| THPO | CCAUCACUCCCUCCAGCAGA | 934 | chr3 | ENST00000204615.11 |
| THPO | UCUUUCUCAGGAGGAGACCA | 935 | chr3 | ENST00000204615.11 |
| TIMP1 | CAGGGGCUCAAAGGGGGCCA | 936 | chrX | ENST00000218388.8 |
| TIMP1 | GACACAGGUGCAGGCCCUGC | 937 | chrX | ENST00000218388.8 |
| TIMP1 | GGGUGAGGACUCACCGAGGU | 938 | chrX | ENST00000218388.8 |
| TNF* | GAUCAUGCUUUCAGUGCUCA | 939 | chr6 | ENST00000449264.2 |
| TNF* | CAAGAAGACAGGGGGGCCCC | 940 | chr6 | ENST00000449264.2 |
| TNF* | GGCGCCUGCCACGAUCAGGA | 941 | chr6 | ENST00000449264.2 |
| TNFRSF4** | CCGGCCCCUGCUCAGGAAGU | 942 | chr1 | ENST00000379236.3 |
| TNFRSF4** | UGAGCGGAAGCAGCUGUGCA | 943 | chr1 | ENST00000379236.3 |
| TNFRSF4** | GCAGCUGUGCACGGCCACAC | 944 | chr1 | ENST00000379236.3 |
| TNFRSF4** | GCGGCAGACUGUGUCCUGUG | 945 | chr1 | ENST00000379236.3 |
| TNFRSF11** | GUCUCCCGCAGGCAAGGCCC | 946 | chr18 | ENST00000586569.2 |
| TNFRSF11** | CCCCCGGCGCUGCGCGUGCA | 947 | chr18 | ENST00000586569.2 |
| TNFRSF11** | CCGCAACACCGAGUGCGCGC | 948 | chr18 | ENST00000586569.2 |
| TNFRSF11** | GCCAGCUGUCUGUGUAGUAG | 949 | chr8 | ENST00000297350.8 |

TABLE 10-continued

Additional guide RNA sequences for use in reducing the incidence of CRS

| Target Gene Symbol | Guide RNA Sequence | SEQ ID NO: | Location | Gene ID No. |
|---|---|---|---|---|
| TNFRSF11** | AACAACACUGUACAGCAAAG | 950 | chr8 | ENST00000297350.8 |
| TNFRSF11** | ACUUUGGAGGAAACGUUUCC | 951 | chr8 | ENST00000297350.8 |
| TNFRSF1A | AGCAAAUCGAAUUAUUUUGA | 952 | chr12 | ENST00000162749.6 |
| TNFRSF1A | UUCUCCCUGUCCCCUAGGUG | 953 | chr12 | ENST00000162749.6 |
| TNFRSF1A | CCAGGUGCUCCUGGAGCUGU | 954 | chr12 | ENST00000162749.6 |
| TNFRSF9** | UGUGAACAGGAUUGUAAACA | 955 | chr1 | ENST00000377507.7 |
| TNFRSF9** | CAGAGUGUGACUGCACUCCA | 956 | chr1 | ENST00000377507.7 |
| TNFRSF9** | GGGACUUUGUAGGUGUUUUC | 957 | chr1 | ENST00000377507.7 |
| TNFSF9*** | GGGGUCCAGUGAAGCGUCAG | 958 | chr19 | ENST00000245817.4 |
| TNFSF9*** | AUACGCCUCUGACGCUUCAC | 959 | chr19 | ENST00000245817.4 |
| TNFSF9*** | CGGGAGGCCACGGGGCUUCG | 960 | chr19 | ENST00000245817.4 |
| TNFSF9*** | CACUGGACCCCGAAGCCCCG | 961 | chr19 | ENST00000245817.4 |
| TNFSF10 | CUACCUUUCUAACGAGCUGA | 962 | chr3 | ENST00000241261.6 |
| TNFSF10 | GUUCAUACUCUCUUCGUCAU | 963 | chr3 | ENST00000241261.6 |
| TNFSF10 | GAAACAAGCAAUGCCACUUU | 964 | chr3 | ENST00000241261.6 |
| TNFSF11 | CCAUCUUCUGAUAUUCUAUU | 965 | chr13 | ENST00000398795.6 |
| TNFSF11 | AGAUUUCAAGACACAACUC | 966 | chr13 | ENST00000398795.6 |
| TNFSF11 | UUCAUGUAGGAGAAUUAAAC | 967 | chr13 | ENST00000398795.6 |
| TNFSF12 | CCGCCCCAUGGCCGCCCGU | 968 | chr17 | ENST00000293825.10 |
| TNFSF12 | CCUGCUGGUCCCGCUCGCGC | 969 | chr17 | ENST00000293825.10 |
| TNFSF12 | CCGGGCAUCGCUGUCCGCCC | 970 | chr17 | ENST00000293825.10 |
| TNFSF12- | CCGCCCCAUGGCCGCCCGU | 971 | chr17 | ENST00000293826.4 |
| TNFSF12- | CCUGCUGGUCCCGCUCGCGC | 972 | chr17 | ENST00000293826.4 |
| TNFSF12- | CCGGGCAUCGCUGUCCGCCC | 973 | chr17 | ENST00000293826.4 |
| TNFSF13 | GGGGGGCCCAGUCAGAGAGC | 974 | chr17 | ENST00000338784.8 |
| TNFSF13 | CAGAGCCAUGGCACAAGCCA | 975 | chr17 | ENST00000338784.8 |
| TNFSF13 | AGAGAGGUGAGCCGGCUGCA | 976 | chr17 | ENST00000338784.8 |
| TNFSF13B | UCAUUUCUUCUCUUUUCUUA | 977 | chr13 | ENST00000375887.8 |
| TNFSF13B | CUCCAAAGACGGAAAGCUGC | 978 | chr13 | ENST00000375887.8 |
| TNFSF13B | CACGGUGGUGUCUUUCUACC | 979 | chr13 | ENST00000375887.8 |
| TNFSF14 | CACACCGCCCAGCUGCACCU | 980 | chr19 | ENST00000599359.1 |
| TNFSF14 | GGGCCCCAUCGUGGUAGCUG | 981 | chr19 | ENST00000599359.1 |
| TNFSF14 | GCUGCCGGUCAAGCUGGAGU | 982 | chr19 | ENST00000599359.1 |
| TNFSF15 | UCAUCCCACGGAAUGUGACC | 983 | chr9 | ENST00000374045.4 |
| TNFSF15 | AUUUGUUGGUAUAGUUCAUU | 984 | chr9 | ENST00000374045.4 |
| TNFSF15 | UGAUUUUUAAAGUGCUGUGU | 985 | chr9 | ENST00000374045.4 |

TABLE 10-continued

Additional guide RNA sequences for use in reducing the incidence of CRS

| Target Gene Symbol | Guide RNA Sequence | SEQ ID NO: | Location | Gene ID No. |
|---|---|---|---|---|
| TNFSF18 | AAUAAAGAUUAGCCAACUGA | 986 | chr1 | ENST00000404377.3 |
| TNFSF18 | GCAAAAGAGCCACAGCUUCC | 987 | chr1 | ENST00000404377.3 |
| TNFSF18 | AAGUGGCUCAAACACAUUUU | 988 | chr1 | ENST00000404377.3 |
| TNFSF4 | CCUCAUCCUUCUGGUAAUGA | 989 | chr1 | ENST00000281834.3 |
| TNFSF4 | GUUUUAUCUCAUCUCCCUGA | 990 | chr1 | ENST00000281834.3 |
| TNFSF4 | CUAGAAUAUAAGAAGGAGAA | 991 | chr1 | ENST00000281834.3 |
| TNFSF8 | UCUGUGCCUUGUCUUCACGG | 992 | chr9 | ENST00000223795.2 |
| TNFSF8 | GCUCGUGGUCCCCAGGUGGC | 993 | chr9 | ENST00000223795.2 |
| TNFSF8 | UGAGUGCUUGCUGCAGCCCU | 994 | chr9 | ENST00000223795.2 |
| TNFSF9 | AUACGCCUCUGACGCUUCAC | 995 | chr19 | ENST00000245817.4 |
| TNFSF9 | ACGCGGCAGGCGCGAGCGCG | 996 | chr19 | ENST00000245817.4 |
| TNFSF9 | CGUCUUCCUCGCCUGCCCCU | 997 | chr19 | ENST00000245817.4 |
| TRIM16 | CUCCUCGGAGAAGCUUGGCA | 998 | chr17 | ENST00000336708.11 |
| TRIM16 | GGUCACCCAGCCCAGAUUCU | 999 | chr17 | ENST00000336708.11 |
| TRIM16 | AGCCUCCCAGAUGGCUGAGU | 1000 | chr17 | ENST00000336708.11 |
| TSLP | UGGAUUUCAGUAAGGCAAUG | 1001 | chr5 | ENST00000344895.3 |
| TSLP | AAUGUUCGCCAUGAAAACUA | 1002 | chr5 | ENST00000344895.3 |
| TSLP | CAAGGUACAGCAAACGUCUG | 1003 | chr5 | ENST00000344895.3 |
| TWSG1 | GUGAGUGCCCGGAAGAGAGA | 1004 | chr18 | ENST00000262120.9 |
| TWSG1 | UGUGAAAGUUCUUCUGCAAC | 1005 | chr18 | ENST00000262120.9 |
| TWSG1 | ACAGACACAUUCUGGUGGUG | 1006 | chr18 | ENST00000262120.9 |
| TXLNA | UAACCAGGGGGCCCCGGCG | 1007 | chr1 | ENST00000373609.1 |
| TXLNA | AGAGAAGUCCCGGACCUAUG | 1008 | chr1 | ENST00000373609.1 |
| TXLNA | UGUGUUUGGAUCCCCCUUGG | 1009 | chr1 | ENST00000373609.1 |
| VASN | GGCAGCUUUGCCGGCCUGCC | 1010 | chr16 | ENST00000304735.3 |
| VASN | ACUCGCCAACCUCAGCAACC | 1011 | chr16 | ENST00000304735.3 |
| VASN | AUGAGACCUUCCGUGGCCUG | 1012 | chr16 | ENST00000304735.3 |
| VEGFA | CAGGGGCCGGAGCCCGCGCC | 1013 | chr6 | ENST00000425836.6 |
| VEGFA | UUCUCGCUUCGGAGGAGCCG | 1014 | chr6 | ENST00000425836.6 |
| VEGFA | AAGUGCUAGCUCGGGCCGGG | 1015 | chr6 | ENST00000425836.6 |
| VSTM1 | CGAAGCUGAAUUCCCCUUCA | 1016 | chr19 | ENST00000338372.6 |
| VSTM1 | UGCGCAAGGUGAACGACUCU | 1017 | chr19 | ENST00000338372.6 |
| VSTM1 | UUCAACCACCGAGCUGGGCC | 1018 | chr19 | ENST00000338372.6 |
| WFIKKN1 | GCUCCUUCUCACAGCGGUCG | 1019 | chr16 | ENST00000319070.2 |
| WFIKKN1 | CCGCUGCUAUAUGGACGCCG | 1020 | chr16 | ENST00000319070.2 |
| WFIKKN1 | CCUGCAAGCACGUGCUCAGC | 1021 | chr16 | ENST00000319070.2 |
| WFIKKN2 | GUGCAAAGACCGCUGUGAGA | 1022 | chr17 | ENST00000311378.4 |

TABLE 10-continued

Additional guide RNA sequences for use in reducing the incidence of CRS

| Target Gene Symbol | Guide RNA Sequence | SEQ ID NO: | Location | Gene ID No. |
|---|---|---|---|---|
| WFIKKN2 | CCGCUGCUACAUGGAUGCCG | 1023 | chr17 | ENST00000311378.4 |
| WFIKKN2 | CCUGCCGCUAUCACUUCACC | 1024 | chr17 | ENST00000311378.4 |
| WNT1 | AGACUCCAAGAGUCUGCAAC | 1025 | chr12 | ENST00000293549.3 |
| WNT1 | GCGUCUGAUACGCCAAAAUC | 1026 | chr12 | ENST00000293549.3 |
| WNT1 | GGCAGUUCCGGAAUCGCCGC | 1027 | chr12 | ENST00000293549.3 |
| WNT2 | UGUUGCAAUUCCAGCGGUGC | 1028 | chr7 | ENST00000265441.7 |
| WNT2 | CUAAUGGCACGCAUCACAUC | 1029 | chr7 | ENST00000265441.7 |
| WNT2 | GAGCUACAGGUGGCUCCUCC | 1030 | chr7 | ENST00000265441.7 |
| WNT5A | UGCAGUUCCACCUUCGAUGU | 1031 | chr3 | ENST00000264634.8 |
| WNT5A | CUUCUCCGAUGUACUGCAUG | 1032 | chr3 | ENST00000264634.8 |
| WNT5A | CCUGCCAGUUGGCUGCAGAG | 1033 | chr3 | ENST00000264634.8 |
| WNT7A | AGAGCGCACCGUCUUCGGGA | 1034 | chr3 | ENST00000285018.4 |
| WNT7A | ACUGAAACUGACACUCGUCC | 1035 | chr3 | ENST00000285018.4 |
| WNT7A | UGGCAGAUCGCCCGCUGUCU | 1036 | chr3 | ENST00000285018.4 |
| XCL1* | GGAGUGAAGUCUCAGAUAAG | 1037 | chr1 | ENST00000367818.3 |
| XCL1* | GGAGUGAAGUCUCAGAUAAG | 1038 | chr1 | ENST00000367818.3 |
| XCL1* | GGAGUGAAGUCUCAGAUAAG | 1039 | chr1 | ENST00000367818.3 |
| XCL2* | GAGUGUAUUUCUAUACCUCU | 1040 | chr1 | ENST00000367819.2 |
| XCL2* | UAGGGAGUGAAGUCUCACAU | 1041 | chr1 | ENST00000367819.2 |
| XCL2* | UAGGGAGUGAAGUCUCACAU | 1042 | chr1 | ENST00000367819.2 |
| ZFP36 | CCUCCAUGGUCGGAUGGCAC | 1043 | chr19 | ENST00000597629.1 |
| ZFP36 | UCGGAGGGGCUCAGGCUCCA | 1044 | chr19 | ENST00000597629.1 |
| ZFP36 | GGAGGGCCGCAGCUGUGGCU | 1045 | chr19 | ENST00000597629.1 |

*indicates cytokines/chemokines produced by T cells that activate or localize myeloid cells
**indicates T cell surface receptor genes that activate myeloid or CAR-T cells
***indicates T cell surface receptors that are integrated into CAR-T cell signaling thus endogenous receptors are redundant
^indicates cytokines that drive T cell/CAR-T cell differentiation
Bold rows indicate transcription factors that drive T cell/CAR-T cell differentiation Example 6-Protocol-Nucleofection Using Nucleofector 4D $4 \times 10^6$ cells per reaction are used. EO-115-100 µl transfection volume is programmed, and the entire supplement added to the Nucleofector™ Solution P3. Cell culture plates are prepared by filling appropriate number of wells with desired volume of recommended culture media (2 ml in 6 well plate) and pre-incubating/equilibrating plates in a humidified 37° C./5% $CO_2$ incubator. Beads are magnetically removed (twice to ensure complete removal), then cells counted and cell density determined. The required number of cells are centrifuged at 90×g for 10 minutes at room temperature, the supernatant removed completely. Cells are then resuspended in PBS (1 ml) and transferred to a microcentrifuge tube, and the required number of cells centrifuged at 90×g for 10 minutes at room temperature. The supernatant is removed completely, and the cell pellet resuspended carefully in complete room temperature 4D Nucleofector™ Solution P3, $4 \times 10^6$ per 100 µl). Twenty µg of gRNA (gGM-CSF) is added to each tube of 15 µg Cas9 mRNA. Then 100 µl of cells is added to each tube of Cas9/gRNA, gently mixed and everything transferred into the Nucleocuvette™. The cuvette is gently tapped to remove bubbles. Electroporation is carried out using program (Human T cell stim EO-115). After run completion, the Nucleocuvette™ is carefully removed from the vessel from the retainer using a specialized tool. Cells are resuspended with pre-warmed medium. The media is then taken up from destination well, added to cuvette, and gently pipetted up and down two to three times. This is then transferred to well. This procedure is repeated with media from same well and incubated at 37° C.

CAR Transduction (Day 2).

Genome-edited CAR-T cells may then be transduced with one or more CARs targeted to (i.e., that recognizes) one or more targets, for example with a lentivirus containing a CAR construct. Any other suitable method of transduction may be used.

Protocol—To transduce T cells with lentivirus: One μl of polybrene is added for each ml media (8 mg/ml stock). The required amount of virus is then added to give required M.O.I. Cells and virus are mixed and placed back in incubator at 37° C.

Assessment of Transduction Efficiency (Day 10).

Samples of cells may then be assessed for transduction efficiency by taking a $5 \times 10^5$ cells from each sample and analyzing by flow cytometry. Samples are washed with RB, and 3 μl of anti-CD34 PE antibody added (to detect the CAR as the construct contains human truncated CD34). Thereafter, 5 μl of CD3 APC is added, the cells washed, and flow cytometry performed. CAR-T cells should be CD38 positive, CD34 positive.

Assessment of Genetic Deletion.

To assess genetic deletion, $5 \times 10^5$ cells are harvested from each sample and their DNA extracted. Gene editing efficiency is assessed using target sequencing of the target loci using TIDE-analysis or deep sequencing.

Assessment of Tumor Burden and Cytokine Level.

T cells are harvested (Day 11). Tumor burden may be imaged in mouse using bioluminescent imaging. $3 \times 10^7$ CAR-T are injected per mouse I.P.

Serum cytokine levels (Day 12) are measured, e.g., using the Luminex multiplex cytokine profiling assay to check for elevations in CRS-related cytokines. A 4-hr chromium release assay against targets cells (Raji) may be performed to assess in vitro activity (Day 11).

Example 7—Additional Examples of CAR-Bearing Immune Effector Cells

Several types of chimeric antigen receptor (CAR)-bearing immune effector cells that are deficient in a cytokine may be made using the methods above. Tables 11-13 below give Examples.

TABLE 11

| Example | Cell | Mono, Dual, or Tandem | CAR Target(s) | Antigen Deletion(s) | TCR Modifications | Gene Deleted/ Suppressed |
|---|---|---|---|---|---|---|
| 1 | T-Cell | Mono | CD19 | — | — | GM-CSF |
| 2 | T-Cell | Mono | CD19 | — | — | CCL2 |
| 3 | T-Cell | Mono | CD19 | — | — | MCP-2 |
| 4 | T-Cell | Mono | CD19 | — | — | G-CSF |
| 5 | T-Cell | Mono | CD19 | — | — | M-CSF |
| 6 | T-Cell | Mono | CD19 | — | — | Il-4 |
| 7 | T-Cell | Mono | CD19 | — | — | IFNγ |
| 8 | T-Cell | Mono | CD19 | — | TRAC | GM-CSF |
| 9 | T-Cell | Mono | CD19 | — | TRAC | CCL2 |
| 10 | T-Cell | Mono | CD19 | — | TRAC | MCP-2 |
| 11 | T-Cell | Mono | CD19 | — | TRAC | G-CSF |
| 12 | T-Cell | Mono | CD19 | — | TRAC | M-CSF |
| 13 | T-Cell | Mono | CD19 | — | TRAC | Il-4 |
| 14 | T-Cell | Mono | CD19 | — | TRAC | IFNγ |
| 15 | T-Cell | Mono | CD20 | — | — | GM-CSF |
| 16 | T-Cell | Mono | CD20 | — | — | CCL2 |
| 17 | T-Cell | Mono | CD20 | — | — | MCP-2 |
| 18 | T-Cell | Mono | CD20 | — | — | G-CSF |
| 19 | T-Cell | Mono | CD20 | — | — | M-CSF |
| 20 | T-Cell | Mono | CD20 | — | — | Il-4 |
| 21 | T-Cell | Mono | CD20 | — | — | IFNγ |
| 22 | T-Cell | Mono | CD20 | — | TRAC | GM-CSF |
| 23 | T-Cell | Mono | CD20 | — | TRAC | CCL2 |
| 24 | T-Cell | Mono | CD20 | — | TRAC | MCP-2 |
| 25 | T-Cell | Mono | CD20 | — | TRAC | G-CSF |
| 26 | T-Cell | Mono | CD20 | — | TRAC | M-CSF |
| 27 | T-Cell | Mono | CD20 | — | TRAC | Il-4 |
| 28 | T-Cell | Mono | CD20 | — | TRAC | IFNγ |
| 29 | T-Cell | Mono | BCMA | — | — | GM-CSF |
| 30 | T-Cell | Mono | BCMA | — | — | CCL2 |
| 31 | T-Cell | Mono | BCMA | — | — | MCP-2 |
| 32 | T-Cell | Mono | BCMA | — | — | G-CSF |
| 33 | T-Cell | Mono | BCMA | — | — | M-CSF |
| 34 | T-Cell | Mono | BCMA | — | — | Il-4 |
| 35 | T-Cell | Mono | BCMA | — | — | IFNγ |
| 36 | T-Cell | Mono | BCMA | — | TRAC | GM-CSF |
| 37 | T-Cell | Mono | BCMA | — | TRAC | CCL2 |
| 38 | T-Cell | Mono | BCMA | — | TRAC | MCP-2 |
| 39 | T-Cell | Mono | BCMA | — | TRAC | G-CSF |
| 40 | T-Cell | Mono | BCMA | — | TRAC | M-CSF |
| 41 | T-Cell | Mono | BCMA | — | TRAC | Il-4 |
| 42 | T-Cell | Mono | BCMA | — | TRAC | IFNγ |
| 43 | T-Cell | Mono | Mesothelin | — | — | GM-CSF |
| 44 | T-Cell | Mono | Mesothelin | — | — | CCL2 |
| 45 | T-Cell | Mono | Mesothelin | — | — | MCP-2 |
| 46 | T-Cell | Mono | Mesothelin | — | — | G-CSF |
| 47 | T-Cell | Mono | Mesothelin | — | — | M-CSF |
| 48 | T-Cell | Mono | Mesothelin | — | — | Il-4 |
| 49 | T-Cell | Mono | Mesothelin | — | — | IFNγ |

TABLE 11-continued

| Example | Cell | Mono, Dual, or Tandem | CAR Target(s) | Antigen Deletion(s) | TCR Modifications | Gene Deleted/ Suppressed |
|---|---|---|---|---|---|---|
| 50 | T-Cell | Mono | Mesothelin | — | TRAC | GM-CSF |
| 51 | T-Cell | Mono | Mesothelin | — | TRAC | CCL2 |
| 52 | T-Cell | Mono | Mesothelin | — | TRAC | MCP-2 |
| 53 | T-Cell | Mono | Mesothelin | — | TRAC | G-CSF |
| 54 | T-Cell | Mono | Mesothelin | — | TRAC | M-CSF |
| 55 | T-Cell | Mono | Mesothelin | — | TRAC | Il-4 |
| 56 | T-Cell | Mono | Mesothelin | — | TRAC | IFNγ |
| 57 | T-Cell | Mono | CD7 | CD7 | TRAC | GM-CSF |
| 58 | T-Cell | Mono | CD7 | CD7 | TRAC | CCL2 |
| 59 | T-Cell | Mono | CD7 | CD7 | TRAC | MCP-2 |
| 60 | T-Cell | Mono | CD7 | CD7 | TRAC | G-CSF |
| 61 | T-Cell | Mono | CD7 | CD7 | TRAC | M-CSF |
| 62 | T-Cell | Mono | CD7 | CD7 | TRAC | Il-4 |
| 63 | T-Cell | Mono | CD7 | CD7 | TRAC | IFNγ |
| 64 | T-Cell | Mono | CD3ε | CD3ε | — | GM-CSF |
| 65 | T-Cell | Mono | CD3ε | CD3ε | — | CCL2 |
| 66 | T-Cell | Mono | CD3ε | CD3ε | — | MCP-2 |
| 67 | T-Cell | Mono | CD3ε | CD3ε | — | G-CSF |
| 68 | T-Cell | Mono | CD3ε | CD3ε | — | M-CSF |
| 69 | T-Cell | Mono | CD3ε | CD3ε | — | Il-4 |
| 70 | T-Cell | Mono | CD3ε | CD3ε | — | IFNγ |
| 71 | T-Cell | Mono | CD2 | CD2 | TRAC | GM-CSF |
| 72 | T-Cell | Mono | CD2 | CD2 | TRAC | CCL2 |
| 73 | T-Cell | Mono | CD2 | CD2 | TRAC | MCP-2 |
| 74 | T-Cell | Mono | CD2 | CD2 | TRAC | G-CSF |
| 75 | T-Cell | Mono | CD2 | CD2 | TRAC | M-CSF |
| 76 | T-Cell | Mono | CD2 | CD2 | TRAC | Il-4 |
| 77 | T-Cell | Mono | CD2 | CD2 | TRAC | IFNγ |
| 78 | T-Cell | Mono | CD5 | — | TRAC | GM-CSF |
| 79 | T-Cell | Mono | CD5 | — | TRAC | CCL2 |
| 80 | T-Cell | Mono | CD5 | — | TRAC | MCP-2 |
| 81 | T-Cell | Mono | CD5 | — | TRAC | G-CSF |
| 82 | T-Cell | Mono | CD5 | — | TRAC | M-CSF |
| 83 | T-Cell | Mono | CD5 | — | TRAC | Il-4 |
| 84 | T-Cell | Mono | CD5 | — | TRAC | IFNγ |
| 85 | T-Cell | Mono | CD5 | CD5 | TRAC | GM-CSF |
| 86 | T-Cell | Mono | CD5 | CD5 | TRAC | CCL2 |
| 87 | T-Cell | Mono | CD5 | CD5 | TRAC | MCP-2 |
| 88 | T-Cell | Mono | CD5 | CD5 | TRAC | G-CSF |
| 89 | T-Cell | Mono | CD5 | CD5 | TRAC | M-CSF |
| 90 | T-Cell | Mono | CD5 | CD5 | TRAC | Il-4 |
| 91 | T-Cell | Mono | CD5 | CD5 | TRAC | IFNγ |
| 92 | T-Cell | Tandem | CD7 × CD2 | CD7 & CD2 | TRAC | GM-CSF |
| 93 | T-Cell | Tandem | CD7 × CD2 | CD7 & CD2 | TRAC | CCL2 |
| 94 | T-Cell | Tandem | CD7 × CD2 | CD7 & CD2 | TRAC | MCP-2 |
| 95 | T-Cell | Tandem | CD7 × CD2 | CD7 & CD2 | TRAC | G-CSF |
| 96 | T-Cell | Tandem | CD7 × CD2 | CD7 & CD2 | TRAC | M-CSF |
| 97 | T-Cell | Tandem | CD7 × CD2 | CD7 & CD2 | TRAC | Il-4 |
| 98 | T-Cell | Tandem | CD7 × CD2 | CD7 & CD2 | TRAC | IFNγ |
| 99 | T-Cell | Tandem | CD3ε × CD2 | CD3 & CD2 | — | GM-CSF |
| 100 | T-Cell | Tandem | CD3ε × CD2 | CD3 & CD2 | — | CCL2 |
| 101 | T-Cell | Tandem | CD3ε × CD2 | CD3 & CD2 | — | MCP-2 |
| 102 | T-Cell | Tandem | CD3ε × CD2 | CD3 & CD2 | — | G-CSF |
| 103 | T-Cell | Tandem | CD3ε × CD2 | CD3 & CD2 | — | M-CSF |
| 104 | T-Cell | Tandem | CD3ε × CD2 | CD3 & CD2 | — | Il-4 |
| 105 | T-Cell | Tandem | CD3ε × CD2 | CD3 & CD2 | — | IFNγ |
| 106 | T-Cell | Tandem | CD19 × CD20 | — | TRAC | GM-CSF |
| 107 | T-Cell | Tandem | CD19 × CD20 | — | TRAC | CCL2 |
| 108 | T-Cell | Tandem | CD19 × CD20 | — | TRAC | MCP-2 |
| 109 | T-Cell | Tandem | CD19 × CD20 | — | TRAC | G-CSF |
| 110 | T-Cell | Tandem | CD19 × CD20 | — | TRAC | M-CSF |
| 111 | T-Cell | Tandem | CD19 × CD20 | — | TRAC | Il-4 |
| 112 | T-Cell | Tandem | CD19 × CD20 | — | TRAC | IFNγ |
| 113 | T-Cell | Dual | CD7 × CD2 | CD7 & CD2 | TRAC | GM-CSF |
| 114 | T-Cell | Dual | CD7 × CD2 | CD7 & CD2 | TRAC | CCL2 |
| 115 | T-Cell | Dual | CD7 × CD2 | CD7 & CD2 | TRAC | MCP-2 |
| 116 | T-Cell | Dual | CD7 × CD2 | CD7 & CD2 | TRAC | G-CSF |
| 117 | T-Cell | Dual | CD7 × CD2 | CD7 & CD2 | TRAC | M-CSF |
| 118 | T-Cell | Dual | CD7 × CD2 | CD7 & CD2 | TRAC | Il-4 |
| 119 | T-Cell | Dual | CD7 × CD2 | CD7 & CD2 | TRAC | IFNγ |
| 120 | T-Cell | Dual | CD3ε × CD2 | CD3 & CD2 | — | GM-CSF |
| 121 | T-Cell | Dual | CD3ε × CD2 | CD3 & CD2 | — | CCL2 |
| 122 | T-Cell | Dual | CD3ε × CD2 | CD3 & CD2 | — | MCP-2 |
| 123 | T-Cell | Dual | CD3ε × CD2 | CD3 & CD2 | — | G-CSF |
| 124 | T-Cell | Dual | CD3ε × CD2 | CD3 & CD2 | — | M-CSF |
| 125 | T-Cell | Dual | CD3ε × CD2 | CD3 & CD2 | — | Il-4 |

TABLE 11-continued

| Example | Cell | Mono, Dual, or Tandem | CAR Target(s) | Antigen Deletion(s) | TCR Modifications | Gene Deleted/Suppressed |
|---|---|---|---|---|---|---|
| 126 | T-Cell | Dual | CD3ε × CD2 | CD3 & CD2 | — | IFNγ |
| 127 | T-Cell | Dual | CD19 × CD20 | — | TRAC | GM-CSF |
| 128 | T-Cell | Dual | CD19 × CD20 | — | TRAC | CCL2 |
| 129 | T-Cell | Dual | CD19 × CD20 | — | TRAC | MCP-2 |
| 130 | T-Cell | Dual | CD19 × CD20 | — | TRAC | G-CSF |
| 131 | T-Cell | Dual | CD19 × CD20 | — | TRAC | M-CSF |
| 132 | T-Cell | Dual | CD19 × CD20 | — | TRAC | Il-4 |
| 133 | T-Cell | Dual | CD19 × CD20 | — | TRAC | IFNγ |

TABLE 12

| Example | Cell | Mono, Dual, or Tandem | CAR Target(s) | Antigen Deletion(s) | Gene Deleted/Suppressed |
|---|---|---|---|---|---|
| 134 | NK Cell | Mono | CD19 | — | GM-CSF |
| 135 | NK Cell | Mono | CD19 | — | CCL2 |
| 136 | NK Cell | Mono | CD19 | — | MCP-2 |
| 137 | NK Cell | Mono | CD19 | — | G-CSF |
| 138 | NK Cell | Mono | CD19 | — | M-CSF |
| 139 | NK Cell | Mono | CD19 | — | Il-4 |
| 140 | NK Cell | Mono | CD19 | — | IFNγ |
| 141 | NK Cell | Mono | CD19 | — | GM-CSF |
| 142 | NK Cell | Mono | CD19 | — | CCL2 |
| 143 | NK Cell | Mono | CD19 | — | MCP-2 |
| 144 | NK Cell | Mono | CD19 | — | G-CSF |
| 145 | NK Cell | Mono | CD19 | — | M-CSF |
| 146 | NK Cell | Mono | CD19 | — | Il-4 |
| 147 | NK Cell | Mono | CD19 | — | IFNγ |
| 148 | NK Cell | Mono | CD20 | — | GM-CSF |
| 149 | NK Cell | Mono | CD20 | — | CCL2 |
| 150 | NK Cell | Mono | CD20 | — | MCP-2 |
| 151 | NK Cell | Mono | CD20 | — | G-CSF |
| 152 | NK Cell | Mono | CD20 | — | M-CSF |
| 153 | NK Cell | Mono | CD20 | — | Il-4 |
| 154 | NK Cell | Mono | CD20 | — | IFNγ |
| 155 | NK Cell | Mono | CD20 | — | GM-CSF |
| 156 | NK Cell | Mono | CD20 | — | CCL2 |
| 157 | NK Cell | Mono | CD20 | — | MCP-2 |
| 158 | NK Cell | Mono | CD20 | — | G-CSF |
| 159 | NK Cell | Mono | CD20 | — | M-CSF |
| 160 | NK Cell | Mono | CD20 | — | Il-4 |
| 161 | NK Cell | Mono | CD20 | — | IFNγ |
| 162 | NK Cell | Mono | BCMA | — | GM-CSF |
| 163 | NK Cell | Mono | BCMA | — | CCL2 |
| 164 | NK Cell | Mono | BCMA | — | MCP-2 |
| 165 | NK Cell | Mono | BCMA | — | G-CSF |
| 166 | NK Cell | Mono | BCMA | — | M-CSF |
| 167 | NK Cell | Mono | BCMA | — | Il-4 |
| 168 | NK Cell | Mono | BCMA | — | IFNγ |
| 169 | NK Cell | Mono | BCMA | — | GM-CSF |
| 170 | NK Cell | Mono | BCMA | — | CCL2 |
| 171 | NK Cell | Mono | BCMA | — | MCP-2 |
| 172 | NK Cell | Mono | BCMA | — | G-CSF |
| 173 | NK Cell | Mono | BCMA | — | M-CSF |
| 174 | NK Cell | Mono | BCMA | — | Il-4 |
| 175 | NK Cell | Mono | BCMA | — | IFNγ |
| 176 | NK Cell | Mono | Mesothelin | — | GM-CSF |
| 177 | NK Cell | Mono | Mesothelin | — | CCL2 |
| 178 | NK Cell | Mono | Mesothelin | — | MCP-2 |
| 179 | NK Cell | Mono | Mesothelin | — | G-CSF |
| 180 | NK Cell | Mono | Mesothelin | — | M-CSF |
| 181 | NK Cell | Mono | Mesothelin | — | Il-4 |
| 182 | NK Cell | Mono | Mesothelin | — | IFNγ |
| 183 | NK Cell | Mono | Mesothelin | — | GM-CSF |
| 184 | NK Cell | Mono | Mesothelin | — | CCL2 |
| 185 | NK Cell | Mono | Mesothelin | — | MCP-2 |
| 186 | NK Cell | Mono | Mesothelin | — | G-CSF |
| 187 | NK Cell | Mono | Mesothelin | — | M-CSF |
| 188 | NK Cell | Mono | Mesothelin | — | Il-4 |
| 189 | NK Cell | Mono | Mesothelin | — | IFNγ |
| 190 | NK Cell | Mono | CD7 | CD7 | GM-CSF |
| 191 | NK Cell | Mono | CD7 | CD7 | CCL2 |
| 192 | NK Cell | Mono | CD7 | CD7 | MCP-2 |
| 193 | NK Cell | Mono | CD7 | CD7 | G-CSF |
| 194 | NK Cell | Mono | CD7 | CD7 | M-CSF |
| 195 | NK Cell | Mono | CD7 | CD7 | Il-4 |
| 196 | NK Cell | Mono | CD7 | CD7 | IFNγ |
| 197 | NK Cell | Mono | CD3ε | CD3ε | GM-CSF |
| 198 | NK Cell | Mono | CD3ε | CD3ε | CCL2 |
| 199 | NK Cell | Mono | CD3ε | CD3ε | MCP-2 |
| 200 | NK Cell | Mono | CD3ε | CD3ε | G-CSF |
| 201 | NK Cell | Mono | CD3ε | CD3ε | M-CSF |
| 202 | NK Cell | Mono | CD3ε | CD3ε | Il-4 |
| 203 | NK Cell | Mono | CD3ε | CD3ε | IFNγ |
| 204 | NK Cell | Mono | CD2 | CD2 | GM-CSF |
| 205 | NK Cell | Mono | CD2 | CD2 | CCL2 |
| 206 | NK Cell | Mono | CD2 | CD2 | MCP-2 |
| 207 | NK Cell | Mono | CD2 | CD2 | G-CSF |
| 208 | NK Cell | Mono | CD2 | CD2 | M-CSF |
| 209 | NK Cell | Mono | CD2 | CD2 | Il-4 |
| 210 | NK Cell | Mono | CD2 | CD2 | IFNγ |
| 211 | NK Cell | Mono | CD5 | — | GM-CSF |
| 212 | NK Cell | Mono | CD5 | — | CCL2 |
| 213 | NK Cell | Mono | CD5 | — | MCP-2 |
| 214 | NK Cell | Mono | CD5 | — | G-CSF |
| 215 | NK Cell | Mono | CD5 | — | M-CSF |
| 216 | NK Cell | Mono | CD5 | — | Il-4 |
| 217 | NK Cell | Mono | CD5 | — | IFNγ |
| 218 | NK Cell | Tandem | CD7xCD2 | CD7 & CD2 | GM-CSF |
| 219 | NK Cell | Tandem | CD7xCD2 | CD7 & CD2 | CCL2 |
| 220 | NK Cell | Tandem | CD7xCD2 | CD7 & CD2 | MCP-2 |
| 221 | NK Cell | Tandem | CD7xCD2 | CD7 & CD2 | G-CSF |
| 222 | NK Cell | Tandem | CD7xCD2 | CD7 & CD2 | M-CSF |
| 223 | NK Cell | Tandem | CD7xCD2 | CD7 & CD2 | Il-4 |
| 224 | NK Cell | Tandem | CD7xCD2 | CD7 & CD2 | IFNγ |
| 225 | NK Cell | Tandem | CD3εxCD2 | CD3 & CD2 | GM-CSF |
| 226 | NK Cell | Tandem | CD3εxCD2 | CD3 & CD2 | CCL2 |
| 227 | NK Cell | Tandem | CD3εxCD2 | CD3 & CD2 | MCP-2 |
| 228 | NK Cell | Tandem | CD3εxCD2 | CD3 & CD2 | G-CSF |
| 229 | NK Cell | Tandem | CD3εxCD2 | CD3 & CD2 | M-CSF |
| 230 | NK Cell | Tandem | CD3εxCD2 | CD3 & CD2 | Il-4 |
| 231 | NK Cell | Tandem | CD3εxCD2 | CD3 & CD2 | IFNγ |
| 232 | NK Cell | Tandem | CD19xCD20 | — | GM-CSF |
| 233 | NK Cell | Tandem | CD19xCD20 | — | CCL2 |
| 234 | NK Cell | Tandem | CD19xCD20 | — | MCP-2 |
| 235 | NK Cell | Tandem | CD19xCD20 | — | G-CSF |
| 236 | NK Cell | Tandem | CD19xCD20 | — | M-CSF |
| 237 | NK Cell | Tandem | CD19xCD20 | — | Il-4 |
| 238 | NK Cell | Tandem | CD19xCD20 | — | IFNγ |
| 239 | NK Cell | Dual | CD7xCD2 | CD7 & CD2 | GM-CSF |
| 240 | NK Cell | Dual | CD7xCD2 | CD7 & CD2 | CCL2 |
| 241 | NK Cell | Dual | CD7xCD2 | CD7 & CD2 | MCP-2 |
| 242 | NK Cell | Dual | CD7xCD2 | CD7 & CD2 | G-CSF |
| 243 | NK Cell | Dual | CD7xCD2 | CD7 & CD2 | M-CSF |
| 244 | NK Cell | Dual | CD7xCD2 | CD7 & CD2 | Il-4 |
| 245 | NK Cell | Dual | CD7xCD2 | CD7 & CD2 | IFNγ |
| 246 | NK Cell | Dual | CD3εxCD2 | CD3 & CD2 | GM-CSF |
| 247 | NK Cell | Dual | CD3εxCD2 | CD3 & CD2 | CCL2 |
| 248 | NK Cell | Dual | CD3εxCD2 | CD3 & CD2 | MCP-2 |
| 249 | NK Cell | Dual | CD3εxCD2 | CD3 & CD2 | G-CSF |

TABLE 12-continued

| Example | Cell | Mono, Dual, or Tandem | CAR Target(s) | Antigen Deletion(s) | Gene Deleted/ Suppressed |
|---|---|---|---|---|---|
| 250 | NK Cell | Dual | CD3εxCD2 | CD3 & CD2 | M-CSF |
| 251 | NK Cell | Dual | CD3εxCD2 | CD3 & CD2 | Il-4 |
| 252 | NK Cell | Dual | CD3εxCD2 | CD3 & CD2 | IFNγ |
| 253 | NK Cell | Dual | CD19xCD20 | — | GM-CSF |
| 254 | NK Cell | Dual | CD19xCD20 | — | CCL2 |
| 255 | NK Cell | Dual | CD19xCD20 | — | MCP-2 |
| 256 | NK Cell | Dual | CD19xCD20 | — | G-CSF |
| 257 | NK Cell | Dual | CD19xCD20 | — | M-CSF |
| 258 | NK Cell | Dual | CD19xCD20 | — | Il-4 |
| 259 | NK Cell | Dual | CD19xCD20 | — | IFNγ |

TABLE 13

| Example | Cell | Mono, Dual, or Tandem | CAR Target(s) | Antigen Deletion(s) | Gene Deleted/ Suppressed |
|---|---|---|---|---|---|
| 260 | iNKT | Mono | CD19 | — | GM-CSF |
| 261 | iNKT | Mono | CD19 | — | CCL2 |
| 262 | iNKT | Mono | CD19 | — | MCP-2 |
| 263 | iNKT | Mono | CD19 | — | G-CSF |
| 264 | iNKT | Mono | CD19 | — | M-CSF |
| 265 | iNKT | Mono | CD19 | — | Il-4 |
| 266 | iNKT | Mono | CD19 | — | IFNγ |
| 267 | iNKT | Mono | CD19 | — | GM-CSF |
| 268 | iNKT | Mono | CD19 | — | CCL2 |
| 269 | iNKT | Mono | CD19 | — | MCP-2 |
| 270 | iNKT | Mono | CD19 | — | G-CSF |
| 271 | iNKT | Mono | CD19 | — | M-CSF |
| 272 | iNKT | Mono | CD19 | — | Il-4 |
| 273 | iNKT | Mono | CD19 | — | IFNγ |
| 274 | iNKT | Mono | CD20 | — | GM-CSF |
| 275 | iNKT | Mono | CD20 | — | CCL2 |
| 276 | iNKT | Mono | CD20 | — | MCP-2 |
| 277 | iNKT | Mono | CD20 | — | G-CSF |
| 278 | iNKT | Mono | CD20 | — | M-CSF |
| 279 | iNKT | Mono | CD20 | — | Il-4 |
| 280 | iNKT | Mono | CD20 | — | IFNγ |
| 281 | iNKT | Mono | CD20 | — | GM-CSF |
| 282 | iNKT | Mono | CD20 | — | CCL2 |
| 283 | iNKT | Mono | CD20 | — | MCP-2 |
| 284 | iNKT | Mono | CD20 | — | G-CSF |
| 285 | iNKT | Mono | CD20 | — | M-CSF |
| 286 | iNKT | Mono | CD20 | — | Il-4 |
| 287 | iNKT | Mono | CD20 | — | IFNγ |
| 288 | iNKT | Mono | BCMA | — | GM-CSF |
| 289 | iNKT | Mono | BCMA | — | CCL2 |
| 290 | iNKT | Mono | BCMA | — | MCP-2 |
| 291 | iNKT | Mono | BCMA | — | G-CSF |
| 292 | iNKT | Mono | BCMA | — | M-CSF |
| 293 | iNKT | Mono | BCMA | — | Il-4 |
| 294 | iNKT | Mono | BCMA | — | IFNγ |
| 295 | iNKT | Mono | BCMA | — | GM-CSF |
| 296 | iNKT | Mono | BCMA | — | CCL2 |
| 297 | iNKT | Mono | BCMA | — | MCP-2 |
| 298 | iNKT | Mono | BCMA | — | G-CSF |
| 299 | iNKT | Mono | BCMA | — | M-CSF |
| 300 | iNKT | Mono | BCMA | — | Il-4 |
| 301 | iNKT | Mono | BCMA | — | IFNγ |
| 302 | iNKT | Mono | Mesothelin | — | GM-CSF |
| 303 | iNKT | Mono | Mesothelin | — | CCL2 |
| 304 | iNKT | Mono | Mesothelin | — | MCP-2 |
| 305 | iNKT | Mono | Mesothelin | — | G-CSF |
| 306 | iNKT | Mono | Mesothelin | — | M-CSF |
| 307 | iNKT | Mono | Mesothelin | — | Il-4 |
| 308 | iNKT | Mono | Mesothelin | — | IFNγ |
| 309 | iNKT | Mono | Mesothelin | — | GM-CSF |
| 310 | iNKT | Mono | Mesothelin | — | CCL2 |
| 311 | iNKT | Mono | Mesothelin | — | MCP-2 |
| 312 | iNKT | Mono | Mesothelin | — | G-CSF |
| 313 | iNKT | Mono | Mesothelin | — | M-CSF |
| 314 | iNKT | Mono | Mesothelin | — | Il-4 |
| 315 | iNKT | Mono | Mesothelin | — | IFNγ |

TABLE 13-continued

| Example | Cell | Mono, Dual, or Tandem | CAR Target(s) | Antigen Deletion(s) | Gene Deleted/ Suppressed |
|---|---|---|---|---|---|
| 316 | iNKT | Mono | CD7 | CD7 | GM-CSF |
| 317 | iNKT | Mono | CD7 | CD7 | CCL2 |
| 318 | iNKT | Mono | CD7 | CD7 | MCP-2 |
| 319 | iNKT | Mono | CD7 | CD7 | G-CSF |
| 320 | iNKT | Mono | CD7 | CD7 | M-CSF |
| 321 | iNKT | Mono | CD7 | CD7 | Il-4 |
| 322 | iNKT | Mono | CD7 | CD7 | IFNγ |
| 323 | iNKT | Mono | CD3ε | CD3ε | GM-CSF |
| 324 | iNKT | Mono | CD3ε | CD3ε | CCL2 |
| 325 | iNKT | Mono | CD3ε | CD3ε | MCP-2 |
| 326 | iNKT | Mono | CD3ε | CD3ε | G-CSF |
| 327 | iNKT | Mono | CD3ε | CDε | M-CSF |
| 328 | iNKT | Mono | CD3ε | CD3ε | Il-4 |
| 329 | iNKT | Mono | CD3ε | CD3ε | IFNγ |
| 330 | iNKT | Mono | CD2 | CD2 | GM-CSF |
| 331 | iNKT | Mono | CD2 | CD2 | CCL2 |
| 332 | iNKT | Mono | CD2 | CD2 | MCP-2 |
| 333 | iNKT | Mono | CD2 | CD2 | G-CSF |
| 334 | iNKT | Mono | CD2 | CD2 | M-CSF |
| 335 | iNKT | Mono | CD2 | CD2 | Il-4 |
| 336 | iNKT | Mono | CD2 | CD2 | IFNγ |
| 337 | iNKT | Mono | CD5 | — | GM-CSF |
| 338 | iNKT | Mono | CD5 | — | CCL2 |
| 339 | iNKT | Mono | CD5 | — | MCP-2 |
| 340 | iNKT | Mono | CD5 | — | G-CSF |
| 341 | iNKT | Mono | CD5 | — | M-CSF |
| 342 | iNKT | Mono | CD5 | — | Il-4 |
| 343 | iNKT | Mono | CD5 | — | IFNγ |
| 344 | iNKT | Mono | CD5 | CD5 | GM-CSF |
| 345 | iNKT | Mono | CD5 | CD5 | CCL2 |
| 346 | iNKT | Mono | CD5 | CD5 | MCP-2 |
| 347 | iNKT | Mono | CD5 | CD5 | G-CSF |
| 348 | iNKT | Mono | CD5 | CD5 | M-CSF |
| 349 | iNKT | Mono | CD5 | CD5 | Il-4 |
| 350 | iNKT | Mono | CD5 | CD5 | IFNγ |
| 351 | iNKT | Tandem | CD7xCD2 | CD7 & CD2 | GM-CSF |
| 352 | iNKT | Tandem | CD7xCD2 | CD7 & CD2 | CCL2 |
| 353 | iNKT | Tandem | CD7xCD2 | CD7 & CD2 | MCP-2 |
| 354 | iNKT | Tandem | CD7xCD2 | CD7 & CD2 | G-CSF |
| 355 | iNKT | Tandem | CD7xCD2 | CD7 & CD2 | M-CSF |
| 356 | iNKT | Tandem | CD7xCD2 | CD7 & CD2 | Il-4 |
| 357 | iNKT | Tandem | CD7xCD2 | CD7 & CD2 | IFNγ |
| 358 | iNKT | Tandem | CD3εxCD2 | CD3 & CD2 | GM-CSF |
| 359 | iNKT | Tandem | CD3εxCD2 | CD3 & CD2 | CCL2 |
| 360 | iNKT | Tandem | CD3εxCD2 | CD3 & CD2 | MCP-2 |
| 361 | iNKT | Tandem | CD3εxCD2 | CD3 & CD2 | G-CSF |
| 362 | iNKT | Tandem | CD3εxCD2 | CD3 & CD2 | M-CSF |
| 363 | iNKT | Tandem | CD3εxCD2 | CD3 & CD2 | Il-4 |
| 364 | iNKT | Tandem | CD3εxCD2 | CD3 & CD2 | IFNγ |
| 365 | iNKT | Tandem | CD19xCD20 | — | GM-CSF |
| 366 | iNKT | Tandem | CD19xCD20 | — | CCL2 |
| 367 | iNKT | Tandem | CD19xCD20 | — | MCP-2 |
| 368 | iNKT | Tandem | CD19xCD20 | — | G-CSF |
| 369 | iNKT | Tandem | CD19xCD20 | — | M-CSF |
| 370 | iNKT | Tandem | CD19xCD20 | — | Il-4 |
| 371 | iNKT | Tandem | CD19xCD20 | — | IFNγ |
| 372 | iNKT | Dual | CD7xCD2 | CD7 & CD2 | GM-CSF |
| 373 | iNKT | Dual | CD7xCD2 | CD7 & CD2 | CCL2 |
| 374 | iNKT | Dual | CD7xCD2 | CD7 & CD2 | MCP-2 |
| 375 | iNKT | Dual | CD7xCD2 | CD7 & CD2 | G-CSF |
| 376 | iNKT | Dual | CD7xCD2 | CD7 & CD2 | M-CSF |
| 377 | iNKT | Dual | CD7xCD2 | CD7 & CD2 | Il-4 |
| 378 | iNKT | Dual | CD7xCD2 | CD7 & CD2 | IFNγ |
| 379 | iNKT | Dual | CD3εxCD2 | CD3 & CD2 | GM-CSF |
| 380 | iNKT | Dual | CD3εxCD2 | CD3 & CD2 | CCL2 |
| 381 | iNKT | Dual | CD3εxCD2 | CD3 & CD2 | MCP-2 |
| 382 | iNKT | Dual | CD3εxCD2 | CD3 & CD2 | G-CSF |
| 383 | iNKT | Dual | CD3εxCD2 | CD3 & CD2 | M-CSF |
| 384 | iNKT | Dual | CD3εxCD2 | CD3 & CD2 | Il-4 |
| 385 | iNKT | Dual | CD3εxCD2 | CD3 & CD2 | IFNγ |
| 386 | iNKT | Dual | CD19xCD20 | — | GM-CSF |
| 387 | iNKT | Dual | CD19xCD20 | — | CCL2 |
| 388 | iNKT | Dual | CD19xCD20 | — | MCP-2 |
| 389 | iNKT | Dual | CD19xCD20 | — | G-CSF |

TABLE 13-continued

| Example | Cell | Mono, Dual, or Tandem | CAR Target(s) | Antigen Deletion(s) | Gene Deleted/ Suppressed |
|---|---|---|---|---|---|
| 390 | iNKT | Dual | CD19xCD20 | — | M-CSF |
| 391 | iNKT | Dual | CD19xCD20 | — | Il-4 |
| 392 | iNKT | Dual | CD19xCD20 | — | IFNγ |

Example 8—Biological Assays

The following assays, or variations thereon, may be used to assess efficacy of the cytokine-deficient chimeric antigen receptor (CAR)-bearing immune effector cells disclosed herein.

T-ALL. Testing efficacy of cells in a xenogeneic model of T-ALL: $1 \times 10^5$ Click Beetle Red luciferase (CBR) labeled CCRF-CEM T-ALL (99% CD7+ by FACS) cells will be injected I.V. into NSG recipients prior to infusion of $2 \times 10^6$ to $1 \times 10^7$ CAR7-bearing immune effector cells or non-targeting CAR19-bearing immune effector cells control cells i.v. on day +4. In contrast to mice receiving CART19-bearing immune effector cells or mice injected with tumor only, mice receiving CAR7-bearing immune effector cells will demonstrate significantly prolonged survival and reduced tumor burden as determined by bioluminescent imaging.

Multiple Myeloma. Testing efficacy of INKT-CAR-CSI in a xenogeneic model of multiple myeloma: $5 \times 10^5$ Click Beetle Red luciferase (CBR) labeled MM.1S (99% CS1+ by FACS) cells will be injected I.V. into NSG recipients prior to infusion of $2 \times 10^6$ to $1 \times 10^7$ iNKT-CAR-CS1 or non-targeting iNKT-CAR19 control cells i.v. on day +4, or +14 or +28. In contrast to mice receiving iNKT-CAR19 or mice injected with tumor only, mice receiving iNKT-CAR-CS1 will demonstrate significantly prolonged survival and reduced tumor burden as determined by bioluminescent imaging.

In Vivo Models of Cytokine Release Syndrome and Neurotoxicity.

An in vivo mouse model of CRS is disclosed in Giavridis et al., "CAR T cell-induced cytokine release syndrome is mediated by macrophages and abated by IL-1 blockade," Nat Med 2018 May 28. For example, in order to initiate CRS as a model system, tumor cells are injected intraperitoneally into immune deficient mice and allowed to develop into a tumor. The mice are then given CAR-T cells targeting the cancerous cells and monitored for several days to induce the onset of CRS, after which mice are sacrificed and cells and tissue obtained for analysis. Mice may also be treated for CRS and monitored for success or failure of treatment (i.e., administering antibodies against cytokines produces as a result of administration of CAR-T cells).

Analyses appropriate for monitoring CRS in such a model may include monitoring of weight change in the mice after administration of CAR-T cells, percent survival of mice, serum levels of inflammatory factors, i.e., murine SAA3 (equivalent to human C-reactive protein), cytokine levels before and after administration of CAR-T cells, species of origin of pro-inflammatory cytokines (i.e., human versus murine cytokines; and/or percent survival of mice treated with CAR-T cells that received antibodies against specific cytokines.

Mice that eventually die from CRS symptoms or complications may be classified as having severe CRS, while mice that survive but suffer greater than 10% weight loss may be classified as having non-severe CRS. Using this model, it was discovered that monocytes and macrophages are the main source for IL-6 in CRS.

Another model useful for assessing both CRS and CAR-T associated neuropathy is disclosed in Norelli, "Monocyte-derived IL-1 and IL-6 are differentially required for cytokine-release syndrome and neurotoxicity due to CAR T cells," Nat Med 2018 May 28. In this model, human stem cells, such as hematopoietic stem and progenitor cells (HSPCs), are injected into humanized NSG mice, which are immunocompromised transgenic mice expressing human stem cell factor, GM-CSF, and IL-3 to support and enhance hematopoiesis from the injected human stem cells. The mice are given tumor cells to serve as targets for subsequently administered CAR-T cells, and then monitored for CRS symptoms. Following injection of CAR-T cells, these mice exhibit typical symptoms of CRS, including high fever and elevated levels of certain cytokines implicated in CRS, such as IL-1 and/or IL-6. Control of CRS in these mice may be accomplished by blocking the receptor for the cytokine using, for example, antibodies, depletion of cell types expressing the cytokine, or administration of an antagonist of the cytokine. As above, it was determined that monocytes are the main source of the pro-CRS cytokine IL-6, and depletion of monocytes eliminated CRS and protected the mice from death from CRS.

Other CRS animal models are known in the art and may also be used as deemed appropriate.

Methods for Inducing and Testing Cytokine Release Syndrome for Control Purposes

In one model, IL-7 may be directly injected into a mouse or other animal model to induce or initiate CRS for control purposes, as described herein. In yet another example, recombinant or transgenic IL-7 may be expressed in a cell to result in increased IL-7 signaling.

In a still further example, a constitutively signaling cytokine receptor, such as an IL-7 receptor, may be engineered into an immune effector cell such that the immune effector cell itself triggers IL-7 signaling, but is unresponsive to extracellular IL-7, and initiation of IL-7 signaling of surrounding lymphocytes is avoided. Additionally, co-expressing a constitutively signaling IL-7 receptor with a CAR recognizing a specific disease or tumor antigen results in increased T-cell proliferation, survival, and antitumor activity. A constitutively expressing IL-7 receptor is able to transmit IL-7 signaling without the need for IL-7 ligand or the common gamma $\gamma_c$ chain, a component of the native IL-7 receptor, along with IL-7Rα. This can be accomplished by engineering cysteine and/or proline into the transmembrane domain of the IL-7Rα chain, which results in homodimerization of IL-7Rα and subsequent phosphorylation of JAK1/JAK1, which then activates downstream signaling of IL-7.

An example of a method for making and testing a genome-edited CAR-T cell deficient at inducing CRS by insertion of selectable marker into gene edited locus is provided below.

Example 9—Insertion of CAR into T Cell Receptor Gene

A CAR or any protein of interest may be inserted into the gene for the T cell receptor. Macleod et al. ("Integration of a CD19 CAR into the TCR Alpha Chain Locus Streamlines Production of Allogeneic Gene-Edited CAR T Cells," Molec Therapy 25 (4): P949-961, 2017) reports the generation of allogeneic CAR T cells by targeting the insertion of a CAR transgene directly into the native TCR locus using an engineered homing endonuclease and an AAV donor template. Anti-CD19 CAR T cells produced in this manner do not express the endogenous cell-surface TCR, exhibit potent effector functions in vitro, and mediate clearance of CD19+ tumors in an in vivo mouse model. The resulting gene-edited CAR T cells exhibit potent anti-tumor activity in vitro and in vivo in preclinical models, suggesting that these cells have potential for safe and efficacious use as adoptive cellular therapy in unrelated patients with CD19+ hematological malignancies.

Example 10—Anti-Cytokine/Chemokine Antibodies to Reduce CRS

Introduction of immune effector cells to a patient or subject for treatment of cancer often results in CRS due to the production and secretion of cytokines and/or chemokines by the immune effector cells. One way to prevent CRS is to administer antibodies recognizing a specific CRS-inducing cytokine or chemokine to the patient or subject such that the amount of circulating cytokine/chemokine is reduced. For example, as reported by Sachdeva et al., (*J Biol Chem* 294 (14): 5430-5437, 2019), administration of anti-GMCSF antibodies reduced the GMCSF secretion thereby effectively reducing CRS. Therefore, administering antibodies recognizing a specific cytokine and/or chemokine can prevent or reduce the occurrence of CRS in a patient or subject.

Example 11—Insertion of CAR into GMCSF Gene

One exemplary way to prevent CRS is to insert a CAR into a gene for a cytokine or chemokine that is involved in initiation or prolonging of CRS. Disruption or ablation of a cytokine or chemokine gene in a CAR-T or other immune effector cell prevents the initiation of CRS by that particular cytokine or chemokine. One example of such a gene is GMCSF, although other genes involved in initiating or prolonging CRS may also be disrupted in this or a similar manner as described herein. Disruption of the GMCSF gene is described at least in Sachdeva et al. (*J Biol Chem* 294 (14): 5430-5437, 2019) and a description of making and testing a CAR-T cell inserted into the GM-CSF gene is provided below. Briefly, a TALEN or other gene-editing enzyme may be designed or engineered to target a cytokine or chemokine gene of choice in a CAR-T cell, and the expression of the gene monitored by methods known in the art. Significant reduction in the expression and secretion of the cytokine or chemokine gene by the CAR-T cell was reported, which implies that the occurrence of CRS would be reduced. Additionally, this approach was found to simultaneously maintain both the proliferation capability and the anti-tumor activity of the CAR-T cell, as assessed by transwell assays and serial killing assays.

In addition to the use of gene editing to delete a gene such as GM-CSF, antibodies to a cytokine or chemokine causing or contributing to CRS may also be used. For example, an antibody recognizing the GM-CSF protein may be administered to a patient or subject receiving CAR-T therapy. This practice is known in the art, particularly for reduction of CRS as a result of IL-6 signaling using the IL-6R antagonist tocilizumab, however other antibodies or antagonists recognizing cytokines or chemokines, or antagonists of their receptors, may be used as deemed appropriate by a clinician. Appropriate antibodies will bind to the circulating cytokine or chemokine, and antagonists will bind to the native receptors for the cytokine or chemokine, thus preventing downstream CRS-promoting activities in the subject. In some instances, both of these approaches may be employed in a subject, i.e., insertion of a CAR into the gene for a cytokine or chemokine to inactivate the gene, and also administering antibodies against the same cytokine or chemokine to the subject. This approach has been shown to be effective while conferring no negative effects on the activity of the CAR-T cells in vivo or in vitro (Sterner et al., "GM-CSF inhibition reduces cytokine release syndrome and neuroinflammation but enhances CAR-T cell function in xenografts," *Blood* 133:697-709, 2019).

Example 12—Method of Making and Testing Genome-Edited CAR-T Cells Deficient at Inducing CRS by Insertion of Selectable Marker into Gene Edited Loci Inject tumor in SCID-Beige mice (3e6 Raji containing Luciferase) if performing in vivo CRS experiment. This should be completed 3 weeks prior to infusion of CAR-T into mice.

The following steps may be taken to provide a genome-edited, CRS-resistant, CAR-T cell in which the CAR is expressed from the gene edited loci with a selectable marker disclosed herein. It is not possible to select and purify edited cells based on the deletion of genes that encode internal or secreted proteins, thus a selectable marker is required to enrich for this gene modification. This example describes the making of a CD19CARTΔGMCSFΔCD3ε cell, in which the deletion of GM-CSF mitigates risk of CRS and deletion of CD3ε prevents TCR signaling and graft vs host disease (GvHD). As those of skill in the art will recognize, certain of the steps may be conducted sequentially or out of the order listed below, though perhaps leading to different efficiency.

Step 1: T Cell Activation (Day 0)

Purify T cells from leukapheresis chamber using a Miltenyi human PanT isolation kit. Resuspend in media. Count cells. Determine number of human T cell activation CD3/CD28 beads required to obtain 3:1 bead: cell ratio. Wash beads 2× with T cell media. Dilute cells at 1.256 cells/mL in hXcyte media. Add human T cell activation CD3/CD28 beads. Aliquot 4 mL/well of 1.256 cell/mL solution into 6 well plate. Incubate cells at 37° C.

Step 2: CRISPR (Day 2)

The target gene is genetically deleted and the CAR inserted into the gene edited loci. The DNA double-stranded break can be repaired using homology directed repair using a donor template to repair the break and insert the desired sequence into the edited loci. Target deletion may be accomplished by electroporating with Cas9 mRNA and gRNA against the target(s). The donor template may be a DNA plasmid, or a double-stranded linear DNA, or a single stranded-stranded linear DNA containing homology to the DNA surrounding the double-stranded breaks electroplated with the Cas9/gRNA. In this example the homology arms align to either side of the double-stranded break induced by gRNA GM-CSF. Additionally, a viral vector such as AAV may be used as the source of the donor template. Other techniques, however, could be used to induce DNA double strand breaks. These include other genome editing techniques such as TALENs and mega-nucleases.

The sequences of the gRNAs for GM-CSF and CD38 are as follows:

hGMCSF gRNA:
(SEQ ID NO: 50)
5'_2'OMe(U(ps)A(ps)C(ps))UCAGGUUCAGGAGACGCGUUUUA

GAGCUAGAAAUAGCAAGUUAAAAUAAGGCUAGUCCGUUAUCAACUUGA

AAAAGUGGCACCGAGUCGGUGC2'OMe(U(ps)U(ps)U(ps)U_3'

CD3ε gRNA:
(SEQ ID NO: 47)
5'_2'OMe(A(ps)G(ps)G(ps))GCAUGUCAAUAUUACUGGUUUUA

GAGCUAGAAAUAGCAAGUUAAAAUAAGGCUAGUCCGUUAUCAACUUGA

AAAAGUGGCACCGAGUCGGUGC2'OMe(U(ps)U(ps)U(ps)U 3'

| Sample ID | gRNA#1 | gRNA#2 | Cas9 | Nucleofection Buffer P3 |
|---|---|---|---|---|
| UCART19 | 20 μg gGM-CSF | 20 μg gCD3ε | 15 μg Cas9 mRNA | 100 μl |

Nucleofection Using Nucleofector 4D:

Perform nucleofection protocol as described above (Example 6), using 20 μg of each gRNA (gGM-CSF and gCD38) to each tube of 15 μg cas9 mRNA.

Figure 3:
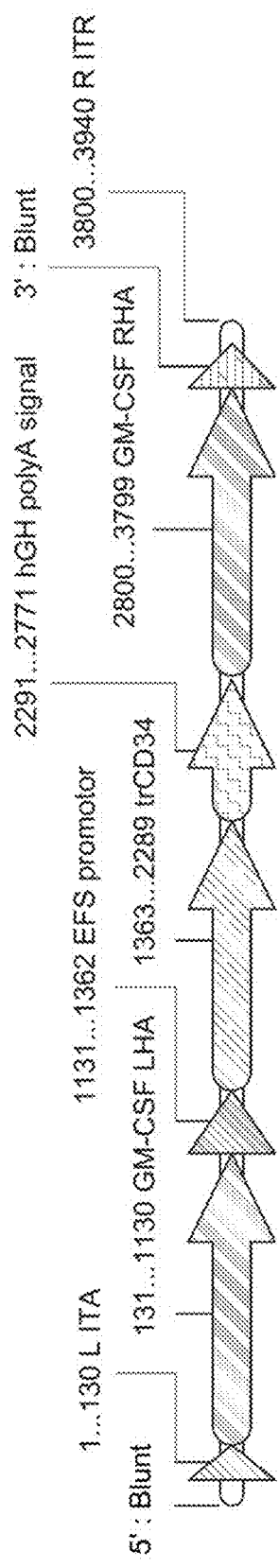
FIG. 3—Shows the AAV donor construct for insertion of CD34 into the GM-CSF locus.

Step 3: Transduction of T Cells with AAV Vector Containing HDR Repair Construct to Introduce CAR and a Selectable Marker into GM-CSF Loci Sequences for components of vectors described herein are provided in the sequence listing, such as including, but not limited to, SEQ ID NOs: 3048-3064. For example, recombinant AAV6 donor vector (FIG. 3, containing ITR-Right homology arm (SEQ ID NO: 51), EF1a promotor (SEQ ID NO:52), CAR19 p2a trCD34 (SEQ ID NO:53), Left homology arm (SEQ ID NO:54), ITR (SEQ ID NO:55), is added to the cell culture 2-4 hrs after electroporation with a MOI between $1 \times 10^4$ and $1 \times 10^6$.

Step 4: Assessment of CRISPR Activity and Td Efficiency (Day 10)

Take $5 \times 10^5$ cells from each sample and analyze by flow cytometry. Wash samples with RB. Add 3 μl of anti-CD34 PE antibody (This detects the insertion TrCD34 tag into GM-CSF loci). Add 5 μl of CD3 APC and 2 μl of anti-FAB BV421 (detects CAR transduction). Wash. Perform Flow cytometry. Cells should be CD38-negative, CD34-positive and FAB+. Harvest T cells (Day 11).

Purification of CAR-T cells. TCR-negative cells can be purified using TCRa/b negative selection to remove TCR positive cells. GM-CSF deleted cells can be enriched using a CD34-positive selection on the Miltenyi Automacs. This enriches the GM-SCF-cells and removes TCR+ cells.

Step 5: Assessment of CAR-T Activity In Vivo

Inject $3 \times 10^7$ CAR-T per mouse I.P. Assess serum cytokine levels. (Day 12, Day 13, Day 14) Measure serum cytokine levels using Luminex multiplex cytokine profiling assay to check for elevations in CRS related cytokines. Perform a 4 hr chromium release assay against targets cells (Raji) to assess in vitro activity (Day 11).

Example 13—Confirmation of GFP Expression with EGFP Integration into CD3e Locus of Jurkats Under Control of CD3e Promotor Direct insertion of GFP into the CD3e locus of a Jurkat cell line may be performed using the method details below.

Figure 4:
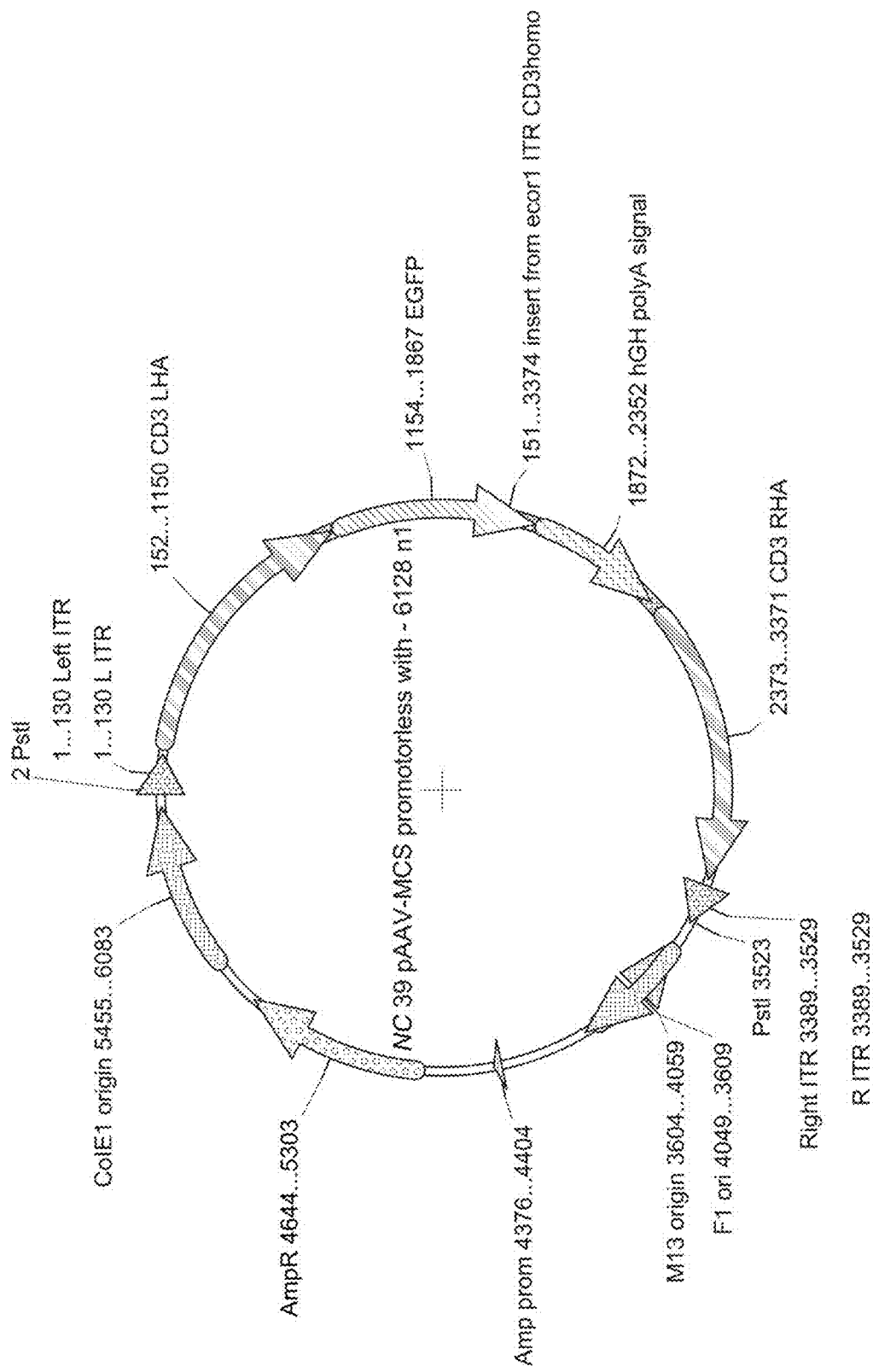
FIG. 4—Shows the WC40 plasmid vector for use in inserting GFP into the CD3ε locus.
Figures 5, 6:
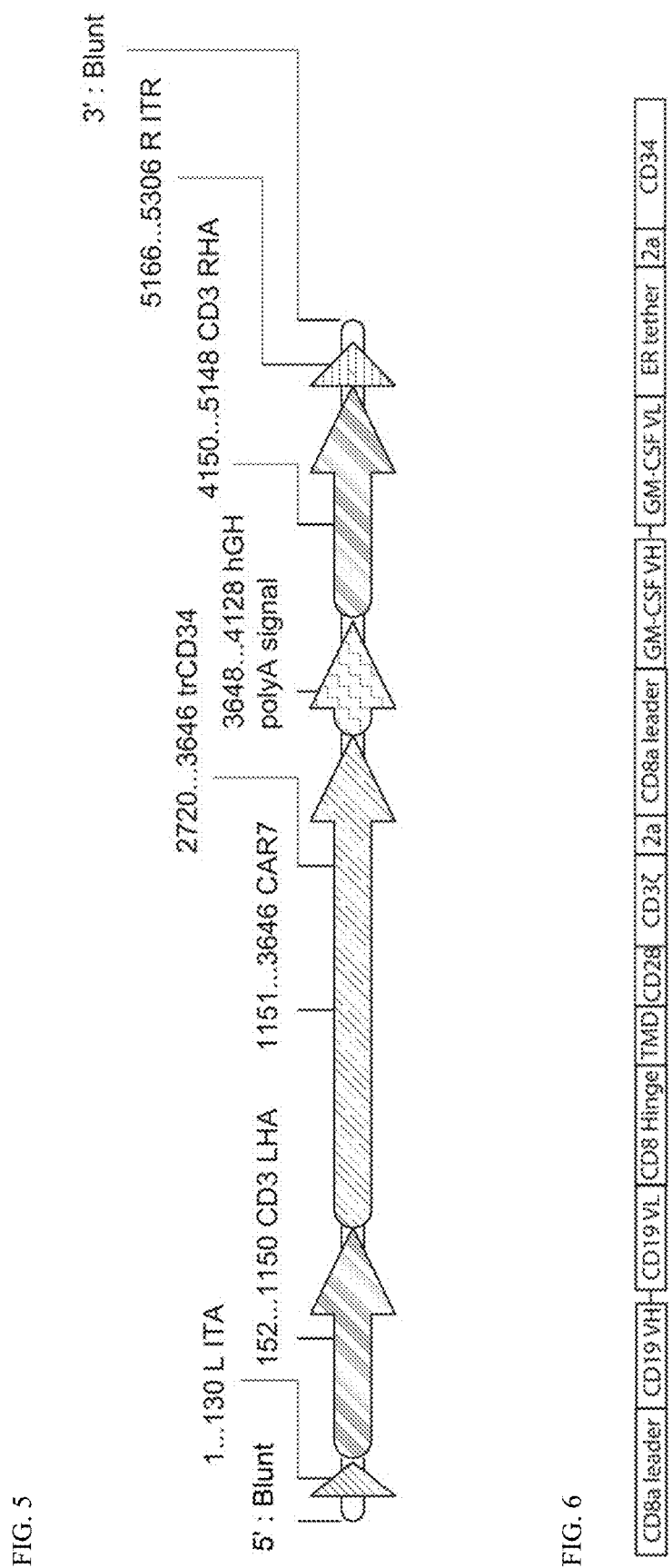
FIG. 5—Shows the AAV donor construct for insertion of GFP into the CD3ε locus.
FIG. 6—Shows a CAR19-GM-CSF PEBL-trCD34 construct.

Days prior: Digest plasmid with PST1 (FIG. 4). Two fragments (3.5 kb and 2.6 kb) are generated upon digestion. Purify using gel extraction kit and ethanol precipitate. Resuspend at 500 ng/μl. This generates donor template 'DNA' in table below Make and titre AAV. The sequence of the AAV is shown in FIG. 5 and provided in SEQ ID NOs:306. This generates donor template 'AAV' in the Table below.

Donor template 'plasmid' is shown in the table below.

Day 0:

Harvest jurkats and count. Spin cells down @100 g for 10 mins. Transfer cells to 1.5 m microcentrifuge tube and wash in PBS. Spin cells down @100×g for 10 mins. Resuspend in pre-warmed buffer SE. Add 100 μl to tube containing gRNA/Cas9. Transfer to nucleocuvette and zap using the Jurkat program on 4D. Transfer to pre-warmed media in 2 ml respective media in a 6-well plate. Return to incubator and expand for 4 days.

TABLE 14

| | Name | Nucleofector Solution | Cell line | Cell number | Cas9 mRNA | gRNA | Donor template |
|---|---|---|---|---|---|---|---|
| 1 | WT | — | Jurkat | 4 × 10⁶ | — | 20 μg CD3e | — |
| 2 | 3Δ | SE | Jurkat | 4 × 10⁶ | 15 μg | 20 μg CD3e | — |
| 3 | P-1ug | SE | Jurkat | 4 × 10⁶ | 15 μg | 20 μg CD3e | Plasmid 1ug |
| 4 | P-2ug | SE | Jurkat | 4 × 10⁶ | 15 μg | 20 μg CD3e | Plasmid 2ug |
| 5 | P-2ug | SE | Jurkat | 4 × 10⁶ | 15 μg | 20 μg CD3e | Plasmid 3ug |
| 6 | D-1ug | SE | Jurkat | 4 × 10⁶ | 15 μg | 20 μg CD3e | DNA 1ug |
| 7 | D-2ug | SE | Jurkat | 4 × 10⁶ | 15 μg | 20 μg CD3e | DNA 2ug |
| 8 | D-4ug | SE | Jurkat | 4 × 10⁶ | 15 μg | 20 μg CD3e | DNA 3ug |
| 9 | AAV Td | SE | Jurkat | 4 × 10⁶ | 15 μg | 20 μg CD3e | AAV 1e4 |
| 10 | AAV Td | SE | Jurkat | 4 × 10⁶ | 15 μg | 20 μg CD3e | AAV 1e5 |
| 11 | AAV Td | SE | Jurkat | 4 × 10⁶ | 15 μg | 20 μg CD3e | AAV 1e6 |

Day 4: FACS cells for GFP and CD3 APC. Assess editing efficiency by loss of CD3 and integration of the AAV-GFP donor by GFP fluorescence.

Example 14—Method of Making and Testing a Genome-Edited CAR-T Cells by Insertion of CAR into CD3e Loci The following steps may be taken to provide a genome-edited CAR-T cell in which the car is expressed from the gene edited loci (CAR-T) disclosed herein. This example describes the making of a CD7CART ΔCD7 ΔCD3ε cell. As those of skill in the art will recognize, certain of the steps may be conducted sequentially or out of the order listed below, though perhaps leading to different efficiency.
Step 1: T Cell Activation (Day 0)
Purify T cells from leukapheresis chamber using Miltenyi human PanT isolation kit. Resuspend in media. Count cells. Determine number of human T cell activation CD3/CD28 beads required to obtain 3:1 bead: cell ratio. Wash beads 2× with T cell media. Dilute cells at 1.256 cells/mL in hXcyte media. Add human T cell activation CD3/CD28 beads. Aliquot 4 mL/well of 1.256 cell/mL solution into 6 well plate. Incubate cells at 37° C.
Step 2: CRISPR (Day 2)
The target gene is genetically deleted and the CAR inserted into the gene edited loci. The DNA double-stranded break can be repaired using homology-directed repair using a donor template to repair the break and insert the desired sequence into the edited loci. Target deletion may be accomplished by electroporating with Cas9 mRNA and gRNA against the target(s). The donor template may be a DNA plasmid, or double-stranded linear DNA, or single-stranded linear DNA containing homology to the DNA surrounding the double-stranded breaks electroporated with the Cas9/gRNA. Additionally, a viral vector such as AAV may be used as the source of the donor template. Other techniques, however, could be used to induce DNA double-stranded breaks. These include other genome editing techniques, such as TALENs and mega-nucleases.

| Sample ID | gRNA#1 | gRNA#2 | Cas9 | Nucleofection Buffer P3 |
|---|---|---|---|---|
| UCART7 | 20 μg gCD7 | 20 μg gCD3ε | 15 μg Cas9 mRNA | 100 μl |

Nucleofection Using Nucleofector 4D:
Perform nucleofection protocol as described above (Example 6), using 20 μg of each gRNA (gCD7 and gCD38) to each tube of 15 μg Cas9.
Step 3: Transduction of T Cells with AAV Vector Containing HDR Repair Construct
Recombinant AAV6 (or other serotypes of AAV) donor vector is added to the cell culture 2-4 hrs after electroporation with an MOI between $1 \times 10^4$ and $1 \times 10^6$.
Step 4: Assessment of CRISPR Activity and Td Efficiency (Day 10)
Take $5 \times 10^5$ cells from each sample and analyze by flow cytometry. Wash samples with RB. Add 3 μl of anti-CD34 PE antibody (This detects the CAR, as the construct contains human truncated CD34). Add 5 μl of CD3 APC and 2 μl of CD7 BV421. Wash. Perform Flow cytometry. Cells should be CD38-negative, CD7-negative and CD34-positive. Harvest T cells (Day 11).
Purification of CAR-T cells. CD34+ (CAR+) and TCR-negative cells can be purified in a single step using a positive selection of CD34+ cells on a Miltenyi Automacs. This enriches the CAR+ cells and removes and TCR+ cells (as CAR insertion disrupts TCR signaling).
Step 5: Assessment of CAR-T Activity In Vivo
Inject tumor in NSG mice ($5 \times 10^5$ MOLT3 or HH: containing Luciferase) if performing in vivo imaging experiment (Day 7).
Image tumor burden in mouse using bioluminescent imaging. Inject $2 \times 10^6$ CD34+CAR-T per mouse I.V. via tail vein or perform a 4 hr chromium release assay against targets cell (MOLT3 or HH) (Day 11). Those of skill in the art will appreciate that some flexibility is possible in the specified time frames.

Example 15—Cytokine/Chemokine Gene Silencing Using shRNA

Similar to siRNAs, short hairpin RNA can be used to knock down or eliminate expression of a cytokine/chemokine/transcription factor gene in an immune effector cell.
Cherkassky et al. ("Human CAR T cells with cell-intrinsic PD-1 checkpoint blockade resist tumor-mediated inhibition," *J Clin Investig* 2016; 126:3130-3144) reported use of shRNA to knock down expression of immune checkpoint PD-1 in CD28 mesothelin-specific CAR-T cells, which showed enhanced proliferative function upon antigen stimulation, augmented cytotoxicity, and enhanced cytokine secretion. In addition, a CD19-specific CAR with a PD-1 shRNA lentiviral cassette has been tested for use in CD19-positive B-cell lymphoma. A list of useful shRNAs and their sequences is provided in Tables 15 and 16.

TABLE 15

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| A2M | CCGGAGGCGTCCCTATACCAAA TAACTCGAGTTATTTGGTATAG GGACGCCTTTTTTG | 1046 | chr12 | ENST00000318602.11 |
| A2M | CCGGAGACTGCATCAATCGTCA TAACTCGAGTTATGACGATTGA TGCAGTCTTTTTTG | 1047 | chr12 | ENST00000318602.11 |
| A2M | CCGGCCTCCAGACATCCTTGAA ATACTCGAGTATTTCAAGGATG TCTGGAGGTTTTTG | 1048 | chr12 | ENST00000318602.11 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| ACKR1 | CCGGATCCTGTGGGCCTGGTTTATTCTCGAGAATAAACCAGGCCCACAGGATTTTTTG | 1049 | chr1 | ENST00000368122.2 |
| ACKR1 | CCGGTGGCAGAAGCCCTGGCAATTTCTCGAGAAATTGCCAGGGCTTCTGCCATTTTTG | 1050 | chr1 | ENST00000368122.2 |
| ACKR1 | CCGGGGCGGATGGTTGAGATCTATCCTCGAGGATAGATCTCAACCATCCGCCTTTTTG | 1051 | chr1 | ENST00000368122.2 |
| ACKR2 | CCGGGAGCACTCTTTATACTATTAACTCGAGTTAATAGTATAAAGAGTGCTCTTTTTG | 1052 | chr3 | ENST00000422265.5 |
| ACKR2 | CCGGGTGGAACTGCCACGCAGATTTCTCGAGAAATCTGCGTGGCAGTTCCACTTTTTG | 1053 | chr3 | ENST00000422265.5 |
| ACKR2 | CCGGCATTGGGTCTTCGGGAGTTTCCTCGAGGAAACTCCCGAAGACCCAATGTTTTTG | 1054 | chr3 | ENST00000422265.5 |
| ACKR3 | CCGGCACTATTGGTGTACCTTATAACTCGAGTTATAAGGTACACCAATAGTGTTTTTG | 1055 | chr2 | ENST00000272928.3 |
| ACKR3 | CCGGGGCATAGTGCTGACATATATTCTCGAGAATATATGTCAGCACTATGCCTTTTTG | 1056 | chr2 | ENST00000272928.3 |
| ACKR3 | CCGGGCCGTTCCCTTCTCCATTATCCTCGAGGATAATGGAGAAGGGAACGGCTTTTTG | 1057 | chr2 | ENST00000272928.3 |
| ACVR1 | CCGGTGATAATTCCCTCGACAAATTCTCGAGAATTTGTCGAGGGAATTATCATTTTTG | 1058 | chr2 | ENST00000263640.7 |
| ACVR1 | CCGGGCAGAACGTATTTAGCCATTACTCGAGTAATGGCTAAATACGTTCTGCTTTTTG | 1059 | chr2 | ENST00000263640.7 |
| ACVR1 | CCGGCTGGTCTGTCTTTGGATAATACTCGAGTATTATCCAAAGACAGACCAGTTTTTG | 1060 | chr2 | ENST00000263640.7 |
| ACVR2B | CCGGATGTCACGAGGCCTCTCATACCTCGAGGTATGAGAGGCCTCGTGACATTTTTG | 1061 | chr3 | ENST00000352511.4 |
| ACVR2B | CCGGCCCAGCTCATGAATGACTTTGCTCGAGCAAAGTCATTCATGAGCTGGGTTTTG | 1062 | chr3 | ENST00000352511.4 |
| ACVR2B | CCGGCTTTGGCTTGGCTGTTCGATTCTCGAGAATCGAACAGCCAAGCCAAAGTTTTTG | 1063 | chr3 | ENST00000352511.4 |
| ACVRL1 | CCGGCCGGGAGACTGAGATCTATAACTCGAGTTATAGATCTCAGTCTCCCGGTTTTTG | 1064 | chr12 | ENST00000388922.8 |
| ACVRL1 | CCGGCAGGAGCACCTGATTCCTTTCCTCGAGGAAAGGAATCAGGTGCTCCTGTTTTTG | 1065 | chr12 | ENST00000388922.8 |
| ACVRL1 | CCGGCGTGGAGATCTTCGGTACACACTCGAGTGTGTACCGAAGATCTCCACGTTTTTG | 1066 | chr12 | ENST00000388922.8 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
| --- | --- | --- | --- | --- |
| ADIPOQ | CCGGGTTGGAGGCCTTTAGATATTACTCGAGTAATATCTAAAGGCCTCCAACTTTTTG | 1067 | chr3 | ENST00000320741.6 |
| ADIPOQ | CCGGATGCTCATATCAATCCTATAACTCGAGTTATAGGATTGATATGAGCATTTTTG | 1068 | chr3 | ENST00000320741.6 |
| ADIPOQ | CCGGACGGTTAGGAAGTTGATTATTCTCGAGAATAATCAACTTCCTAACCGTTTTTG | 1069 | chr3 | ENST00000320741.6 |
| AGER | CCGGCACACTGCAGTCGGAGCTAATCTCGAGATTAGCTCCGACTGCAGTGTGTTTTTG | 1070 | chr6 | ENST00000375076.8 |
| AGER | CCGGGAAGCCAGAAATTGTAGATTCCTCGAGGAATCTACAATTTCTGGCTTCTTTTTG | 1071 | chr6 | ENST00000375076.8 |
| AGER | CCGGTGCTGATCCTCCCTGAGATAGCTCGAGCTATCTCAGGGAGGATCAGCATTTTTG | 1072 | chr6 | ENST00000375076.8 |
| AGRN | CCGGGAGTTCTGTGTGGAAGATAAACTCGAGTTTATCTTCCACACAGAACTCTTTTTG | 1073 | chr1 | ENST00000379370.6 |
| AGRN | CCGGGCGCACGTATGACAGTGATTGCTCGAGCAATCACTGTCATACGTGCGCTTTTTG | 1074 | chr1 | ENST00000379370.6 |
| AGRN | CCGGACGACGGAGTCACCTACGAAACTCGAGTTTCGTAGGTGACTCCGTCGTTTTTG | 1075 | chr1 | ENST00000379370.6 |
| AHR | CCGGCGGCATAGAGACCGACTTAATCTCGAGATTAAGTCGGTCTCTATGCCGTTTTTG | 1076 | chr7 | ENST00000242057.8 |
| AHR | CCGGGCGGCATAGAGACCGACTTAACTCGAGTTAAGTCGGTCTCTATGCCGCTTTTTG | 1077 | chr7 | ENST00000242057.8 |
| AHR | CCGGATCCACAGTCAGCCATAATAACTCGAGTTATTATGGCTGACTGTGGATTTTTG | 1078 | chr7 | ENST00000242057.8 |
| AHR | CCGGACTGCTTAAAGTTGGTATTAACTCGAGTTAATACCAACTTTAAGCAGTTTTTG | 1079 | chr7 | ENST00000242057.8 |
| AIMP1 | CCGGCAGCCTGATCTTCACACTAATCTCGAGATTAGTGTGAAGATCAGGCTGTTTTTG | 1080 | chr4 | ENST00000358008.7 |
| AIMP1 | CCGGAGAAGTAGATGTCGGAGAAATCTCGAGATTTCTCCGACATCTACTTCTTTTTTG | 1081 | chr4 | ENST00000358008.7 |
| AIMP1 | CCGGGCCAGAGTAACCCTGACTAATCTCGAGATTAGTCAGGGTTACTCTGGCTTTTTG | 1082 | chr4 | ENST00000358008.7 |
| AREG | CCGGCCTCTTTCCAGTGGATCATAACTCGAGTTATGATCCACTGGAAAGAGGTTTTG | 1083 | chr4 | ENST00000395748.7 |
| AREG | CCGGTACTCGGCTCAGGCCATTATGCTCGAGCATAATGGCCTGAGCCGAGTATTTTG | 1084 | chr4 | ENST00000395748.7 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| AREG | CCGGATTCACGGAGAATGCAAA TATCTCGAGATATTTGCATTCTC CGTGAATTTTTG | 1085 | chr4 | ENST00000395748.7 |
| BCL6 | CCGGTGTGCCACAGCAATATCT ATTCTCGAGAATAGATATTGCT GTGGCACATTTTTG | 1086 | chr3 | ENST00000406870.6 |
| BCL6 | CCGGACTGCGTTAAAGGCTCGA TTTCTCGAGAAATCGAGCCTTT AACGCAGTTTTTG | 1087 | chr3 | ENST00000406870.6 |
| BCL6 | CCGGCCGGCTCAATAACATCGT TAACTCGAGTTAACGATGTTAT TGAGCCGGTTTTTG | 1088 | chr3 | ENST00000406870.6 |
| BCL6 | CCGGACAAGCCAGCCGGCTCAA TAACTCGAGTTATTGAGCCGGC TGGCTTGTTTTTG | 1089 | chr3 | ENST00000406870.6 |
| BMP1 | CCGGACTGACGAGGACAGCTAT ATTCTCGAGAATATAGCTGTCC TCGTCAGTTTTTG | 1090 | chr8 | ENST00000306385.9 |
| BMP1 | CCGGGCTCGTAAGTCCTCCATC AAACTCGAGTTTGATGGAGGAC TTACGAGCTTTTTG | 1091 | chr8 | ENST00000306385.9 |
| BMP1 | CCGGACAGCTGTGCCTACGACT ATCCTCGAGGATAGTCGTAGGC ACAGCTGTTTTTG | 1092 | chr8 | ENST00000306385.9 |
| BMP10 | CCGGAGCAAGACGGTGTCGACT TTACTCGAGTAAAGTCGACACC GTCTTGCTTTTTG | 1093 | chr2 | ENST00000295379.1 |
| BMP10 | CCGGGCGTCGTCACCTACAAGT TTACTCGAGTAAACTTGTAGGT GACGACGCTTTTTG | 1094 | chr2 | ENST00000295379.1 |
| BMP10 | CCGGCATGGCTGAACTTAGGCT ATACTCGAGTATAGCCTAAGTT CAGCCATGTTTTTG | 1095 | chr2 | ENST00000295379.1 |
| BMP15 | CCGGTACTACGCGATGGTCTCA ATTCTCGAGAATTGAGACCATC GCGTAGTATTTTTG | 1096 | chrX | ENST00000252677.3 |
| BMP15 | CCGGGCCTTCTTGTTACTCTATT TCCTCGAGGAAATAGAGTAACA AGAAGGCTTTTTG | 1097 | chrX | ENST00000252677.3 |
| BMP15 | CCGGATGGAACACAGGGCCCA AATGCTCGAGCATTTGGGCCCT GTGTTCCATTTTTG | 1098 | chrX | ENST00000252677.3 |
| BMP2 | CCGGGATCATCTGAACTCCACT AATCTCGAGATTAGTGGAGTTC AGATGATCTTTTTG | 1099 | chr20 | ENST00000378827.4 |
| BMP2 | CCGGCCGGAGATTCTTCTTTAA TTTCTCGAGAAATTAAAGAAGA ATCTCCGGTTTTTG | 1100 | chr20 | ENST00000378827.4 |
| BMP2 | CCGGCAAGATGCTTTAGGAAAC AATCTCGAGATTGTTTCCTAAA GCATCTTGTTTTTG | 1101 | chr20 | ENST00000378827.4 |
| BMP3 | CCGGCTTACAGGGACACCGGAA TTTCTCGAGAAATTCCGGTGTC CCTGTAAGTTTTTG | 1102 | chr4 | ENST00000282701.2 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| BMP3 | CCGGGGCCAAATCTCATCGAGATATCTCGAGATATCTCGATGAGATTTGGCCTTTTTG | 1103 | chr4 | ENST00000282701.2 |
| BMP3 | CCGGGTGGATTGAACCTCGGAATTGCTCGAGCAATTCCGAGGTTCAATCCACTTTTTG | 1104 | chr4 | ENST00000282701.2 |
| BMP4 | CCGGCCCTGGTCAATTCTGTCAATTCTCGAGAATTGACAGAATTGACCAGGGTTTTTG | 1105 | chr14 | ENST00000245451.8 |
| BMP4 | CCGGTCCTTGAGGATAGACAGATATCTCGAGATATCTGTCTATCCTCAAGGATTTTTG | 1106 | chr14 | ENST00000245451.8 |
| BMP4 | CCGGAGGGCCAGCATGTCAGGATTACTCGAGTAATCCTGACATGCTGGCCCTTTTTG | 1107 | chr14 | ENST00000245451.8 |
| BMP5 | CCGGTGGACGCAGTATCAACGTAAACTCGAGTTTACGTTGATACTGCGTCCATTTTTG | 1108 | chr6 | ENST00000370830.3 |
| BMP5 | CCGGCCAGAAGGATACGCTGCATTTCTCGAGAAATGCAGCGTATCCTTCTGGTTTTTG | 1109 | chr6 | ENST00000370830.3 |
| BMP5 | CCGGATGCCACCAACCACGCTATAGCTCGAGCTATAGCGTGGTTGGTGGCATTTTTG | 1110 | chr6 | ENST00000370830.3 |
| BMP6 | CCGGATACAGGAATATGGTTGTAAGCTCGAGCTTACAACCATATTCCTGTATTTTTG | 1111 | chr6 | ENST00000283147.6 |
| BMP6 | CCGGCGCCGACAACAGAGTCGTAATCTCGAGATTACGACTCTGTTGTCGGCGTTTTTG | 1112 | chr6 | ENST00000283147.6 |
| BMP6 | CCGGCTGTCTATCAAAGGTAGATTTCTCGAGAAATCTACCTTTGATAGACAGTTTTTG | 1113 | chr6 | ENST00000283147.6 |
| BMP7 | CCGGACGTTCCGGATCAGCGTTTATCTCGAGATAAACGCTGATCCGGAACGTTTTTG | 1114 | chr20 | ENST00000395863.7 |
| BMP7 | CCGGACTCGTTTCCAGAGGTAATTACTCGAGTAATTACCTCTGGAAACGAGTTTTTG | 1115 | chr20 | ENST00000395863.7 |
| BMP7 | CCGGACCATCGAGAGTTCCGGTTTGCTCGAGCAAACCGGAACTCTCGATGGTTTTTG | 1116 | chr20 | ENST00000395863.7 |
| BMP8A | CCGGAGGGTGCAGTTAGCATATTAGCTCGAGCTAATATGCTAACTGCACCCTTTTTG | 1117 | chr1 | ENST00000331593.5 |
| BMP8A | CCGGAGCACAGAAGTCCTATCTTAGCTCGAGCTAAGATAGGACTTCTGTGCTTTTTG | 1118 | chr1 | ENST00000331593.5 |
| BMP8A | CCGGAGGTACAACACTGGCCATTTCCTCGAGGAAATGGCAGTGTTGTACCTTTTTG | 1119 | chr1 | ENST00000331593.5 |
| BMP8B | CCGGCCAAGGCTACTCGGCCTATTACTCGAGTAATAGGCCGAGTAGCCTTGGTTTTTG | 1120 | chr1 | ENST00000372827.7 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| BMP8B | CCGGGACCCTCACAACCACGTACATCTCGAGATGTACGTGGTTGTGAGGGTCTTTTTG | 1121 | chr1 | ENST00000372827.7 |
| BMP8B | CCGGCGTTAACATGGTGGAGCGAGACTCGAGTCTCGCTCCACCATGTTAACGTTTTTG | 1122 | chr1 | ENST00000372827.7 |
| BMPR2 | CCGGGAACGGCTATGTGCGTTTAAACTCGAGTTTAAACGCACATAGCCGTTCTTTTTG | 1123 | chr2 | ENST00000374580.8 |
| BMPR2 | CCGGGCCTATGGAGTGAAATTATTTCTCGAGAAATAATTTCACTCCATAGGCTTTTTG | 1124 | chr2 | ENST00000374580.8 |
| BMPR2 | CCGGATTACCACGAGGAGATCATTACTCGAGTAATGATCTCCTCGTGGTAATTTTTG | 1125 | chr2 | ENST00000374580.8 |
| C10orf99 | CCGGCATCATGTGAGGCTCTGTAAACTCGAGTTTACAGAGCCTCACATGATGTTTTTG | 1126 | chr10 | ENST00000372126.3 |
| C10orf99 | CCGGCCCAACTCAACAAACCTGAAACTCGAGTTTCAGGTTTGTTGAGTTGGGTTTTTG | 1127 | chr10 | ENST00000372126.3 |
| C10orf99 | CCGGGCCATCAACTTTCAGAGCTATCTCGAGATAGCTCTGAAAGTTGATGGCTTTTTG | 1128 | chr10 | ENST00000372126.3 |
| C1QTNF4 | CCGGACACCGAGTTCGTCAACATTGCTCGAGCAATGTTGACGAACTCGGTGTTTTTG | 1129 | chr11 | ENST00000302514.3 |
| C1QTNF4 | CCGGGCGTAAGACGCTGTCGGTTAACTCGAGTTAACCGACAGCGTCTTACGCTTTTTG | 1130 | chr11 | ENST00000302514.3 |
| C1QTNF4 | CCGGCGAGGTGCAGGCCATGATTTACTCGAGTAAATCATGGCCTGCACCTCGTTTTTG | 1131 | chr11 | ENST00000302514.3 |
| C5 | CCGGACGATGGAGCCTGCGTTAATACTCGAGTATTAACGCAGGCTCCATCGTTTTTG | 1132 | chr9 | ENST00000223642.2 |
| C5 | CCGGTCCCGACTTCTGGTCTATTACCTCGAGGTAATAGACCAGAAGTCGGGATTTTTG | 1133 | chr9 | ENST00000223642.2 |
| C5 | CCGGGCCCGAGAGAACAGCTTATATCTCGAGATATAAGCTGTTCTCTCGGGCTTTTTG | 1134 | chr9 | ENST00000223642.2 |
| CCL1 | CCGGGCAATCCTGTGTTACAGAAATCTCGAGATTTCTGTAACACAGGATTGCTTTTTG | 1135 | chr17 | ENST00000225842.3 |
| CCL1 | CCGGCTGCTCCAATGAGGGCTTAATCTCGAGATTAAGCCCTCATTGGAGCAGTTTTTG | 1136 | chr17 | ENST00000225842.3 |
| CCL1 | CCGGCCTGAGGGCAATCCTGTGTTACTCGAGTAACACAGGATTGCCCTCAGGTTTTTG | 1137 | chr17 | ENST00000225842.3 |
| CCL11 | CCGGCCAACTCCAAAGCCATAAATACTCGAGTATTTATGGCTTTGGAGTTGGTTTTTG | 1138 | chr17 | ENST00000305869.3 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| CCL11 | CCGGCATTCTGAGGTAACCTCATTACTCGAGTAATGAGGTTACCTCAGAATGTTTTTG | 1139 | chr17 | ENST00000305869.3 |
| CCL11 | CCGGTCCTCCATGAATATCAGTTATCTCGAGATAACTGATATTCATGGAGGATTTTTG | 1140 | chr17 | ENST00000305869.3 |
| CCL13 | CCGGTGGAATACTTCTACCATAATTCTCGAGAATTATGGTAGAAGTATTCCATTTTTG | 1141 | chr17 | ENST00000225844.6 |
| CCL13 | CCGGTCAAGCTGGAGTACGTGAAATCTCGAGATTTCACGTACTCCAGCTTGATTTTTG | 1142 | chr17 | ENST00000225844.6 |
| CCL13 | CCGGACTCAACGTCCCATCTACTTGCTCGAGCAAGTAGATGGGACGTTGAGTTTTTG | 1143 | chr17 | ENST00000225844.6 |
| CCL14 | CCGGCCTAGGGACCAAGACTGAATCCTCGAGGATTCAGTCTTGGTCCCTAGGTTTTTG | 1144 | chr17 | ENST00000618404.4 |
| CCL14 | CCGGCAGCGGATTATGGATTACTATCTCGAGATAGTAATCCATAATCCGCTGTTTTTG | 1145 | chr17 | ENST00000618404.4 |
| CCL14 | CCGGCAAGCCCGGAATTGTCTTCATCTCGAGATGAAGACAATTCCGGGCTTGTTTTTG | 1146 | chr17 | ENST00000618404.4 |
| CCL15 | CCGGGCTGAAGCCCTACTCAATATACTCGAGTATATTGAGTAGGGCTTCAGCTTTTTG | 1147 | chr17 | ENST00000617897.1 |
| CCL15 | CCGGACAGAGTTAATGATGTCAAAGCTCGAGCTTTGACATCATTAACTCTGTTTTTG | 1148 | chr17 | ENST00000617897.1 |
| CCL15 | CCGGATCCCGTGTTCACTCATGAAACTCGAGTTTCATGAGTGAACACGGGATTTTTG | 1149 | chr17 | ENST00000617897.1 |
| CCL16 | CCGGAGGAGAAGTATTTCGAATATTCTCGAGAATATTCGAAATACTTCTCCTTTTTG | 1150 | chr17 | ENST00000611905.1 |
| CCL16 | CCGGAGGAACTTGTCCACGGTTAAACTCGAGTTTAACCGTGGACAAGTTCCTTTTTG | 1151 | chr17 | ENST00000611905.1 |
| CCL16 | CCGGCTGCCTGAAGTATTATGAGAACTCGAGTTCTCATAATACTTCAGGCAGTTTTTG | 1152 | chr17 | ENST00000611905.1 |
| CCL17 | CCGGGAGAGTGAAGAATGCAGTTAACTCGAGTTAACTGCATTCTTCACTCTCTTTTTG | 1153 | chr16 | ENST00000219244.8 |
| CCL17 | CCGGGAGTACTTCAAGGGAGCCATTCTCGAGAATGGCTCCCTTGAAGTACTCTTTTTG | 1154 | chr16 | ENST00000219244.8 |
| CCL17 | CCGGGCAAAGCCTTGAGAGGTCTTGCTCGAGCAAGACCTCTCAAGGCTTTGCTTTTTG | 1155 | chr16 | ENST00000219244.8 |
| CCL18 | CCGGTCTATTGTTGAGCTGCATTATCTCGAGATAATGCAGCTCAACAATAGATTTTTG | 1156 | chr17 | ENST00000616054.1 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| CCL18 | CCGGCCTTCAACTCTTCGTACAT TCCTCGAGGAATGTACGAAGAG TTGAAGGTTTTTG | 1157 | chr17 | ENST00000616054.1 |
| CCL18 | CCGGGTCTATACCTCCTGGCAG ATTCTCGAGAATCTGCCAGGAG GTATAGACTTTTTG | 1158 | chr17 | ENST00000616054.1 |
| CCL19 | CCGGGAGTCAAGCATTGTGAAT TATCTCGAGATAATTCACAATG CTTGACTCTTTTTG | 1159 | chr9 | ENST00000311925.6 |
| CCL19 | CCGGGCCGCAGCAGTTAACCTA TGACTCGAGTCATAGGTTAACT GCTGCGGCTTTTTG | 1160 | chr9 | ENST00000311925.6 |
| CCL19 | CCGGCCAACTCTGAGTGGCACC AATCTCGAGATTGGTGCCACTC AGAGTTGGTTTTTG | 1161 | chr9 | ENST00000311925.6 |
| CCL2 | CCGGCCCAGTCACCTGCTGTTA TAACTCGAGTTATAACAGCAGG TGACTGGGTTTTTG | 1162 | chr17 | ENST00000225831.4 |
| CCL2 | CCGGCCCAGTCACCTGCTGTTA TAACTCGAGTTATAACAGCAGG TGACTGGGTTTTTG | 1163 | chr17 | ENST00000225831.4 |
| CCL2 | CCGGGCTCGCGAGCTATAGAAG AATCTCGAGATTCTTCTATAGCT CGCGAGCTTTTTG | 1164 | chr17 | ENST00000225831.4 |
| CCL20 | CCGGAGTTGTCTGTGTGCGCAA ATCCTCGAGGATTTGCGCACAC AGACAACTTTTTG | 1165 | chr2 | ENST00000358813.4 |
| CCL20 | CCGGGACCGTATTCTTCATCCT AAACTCGAGTTTAGGATGAAGA ATACGGTCTTTTTG | 1166 | chr2 | ENST00000358813.4 |
| CCL20 | CCGGAGGGTTTAGTGCTTATCT AATCTCGAGATTAGATAAGCAC TAAACCCTTTTTG | 1167 | chr2 | ENST00000358813.4 |
| CCL21 | CCGGCACTCTTTCTCCTGCTTTA ACCTCGAGGTTAAAGCAGGAGA AAGAGTGTTTTTG | 1168 | chr9 | ENST00000259607.6 |
| CCL21 | CCGGGAGCTATGTGCAGACCCA AAGCTCGAGCTTTGGGTCTGCA CATAGCTCTTTTTG | 1169 | chr9 | ENST00000259607.6 |
| CCL21 | CCGGCCATCCCAGCTATCCTGT TCTCTCGAGAGAACAGGATAGC TGGGATGGTTTTTG | 1170 | chr9 | ENST00000259607.6 |
| CCL22 | CCGGCCCTACCTCCCTGCCATT ATACTCGAGTATAATGGCAGGG AGGTAGGGTTTTTG | 1171 | chr16 | ENST00000219235.4 |
| CCL22 | CCGGGCGTGGTGAAACACTTCT ACTCTCGAGAGTAGAAGTGTTT CACCACGCTTTTTG | 1172 | chr16 | ENST00000219235.4 |
| CCL22 | CCGGATGTTGCTGACACCCAGA AAGCTCGAGCTTTCTGGGTGTC AGCAACATTTTTG | 1173 | chr16 | ENST00000219235.4 |
| CCL23 | CCGGCACTCCTGGAGAGTTACT TTGCTCGAGCAAAGTAACTCTC CAGGAGTGTTTTTG | 1174 | chr17 | ENST00000615050.1 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| CCL23 | CCGGCCTTTCTCATGCTGCAGG ATTCTCGAGAATCCTGCAGCAT GAGAAAGGTTTTTG | 1175 | chr17 | ENST00000615050.1 |
| CCL23 | CCGGGAAGCTGGACACACGGAT CAACTCGAGTTGATCCGTGTGT CCAGCTTCTTTTTG | 1176 | chr17 | ENST00000615050.1 |
| CCL24 | CCGGAGTGATCTTCACCACCAA GAACTCGAGTTCTTGGTGGTGA AGATCACTTTTTG | 1177 | chr7 | ENST00000222902.6 |
| CCL24 | CCGGGTTCTTTGTTTCCAAGAG AATCTCGAGATTCTCTTGGAAA CAAAGAACTTTTTG | 1178 | chr7 | ENST00000222902.6 |
| CCL24 | CCGGCCTGCTGCATGTTCTTTGT TTCTCGAGAAACAAAGAACATG CAGCAGGTTTTTG | 1179 | chr7 | ENST00000222902.6 |
| CCL25 | CCGGGCCGGATCTTTCTCCGAT AAACTCGAGTTTATCGGAGAAA GATCCGGCTTTTTG | 1180 | chr19 | ENST00000390669.7 |
| CCL25 | CCGGGCTCCTGGATGCTCGAAA TAACTCGAGTTATTTCGAGCAT CCAGGAGCTTTTTG | 1181 | chr19 | ENST00000390669.7 |
| CCL25 | CCGGCCCTCCTGATATCAGCTA ATTCTCGAGAATTAGCTGATAT CAGGAGGGTTTTTG | 1182 | chr19 | ENST00000390669.7 |
| CCL26 | CCGGCACACGTGGGAGTGACAT ATCCTCGAGGATATGTCACTCC CACGTGTGTTTTTG | 1183 | chr7 | ENST00000005180.8 |
| CCL26 | CCGGTCCGAAACAATTGTGACT CAGCTCGAGCTGAGTCACAATT GTTTCGGATTTTTG | 1184 | chr7 | ENST00000005180.8 |
| CCL26 | CCGGGCTGTGATATTCACTACC AAACTCGAGTTTGGTAGTGAAT ATCACAGCTTTTTG | 1185 | chr7 | ENST00000005180.8 |
| CCL27 | CCGGTTCGTGCTTCACCTGGCTC AACTCGAGTTGAGCCAGGTGAA GCACGAATTTTTG | 1186 | chr9 | ENST00000259631.4 |
| CCL27 | CCGGCCGAAAGCCACTCTCAGA CAACTCGAGTTGTCTGAGAGTG GCTTTCGGTTTTTG | 1187 | chr9 | ENST00000259631.4 |
| CCL27 | CCGGCAAGCTACTGAGGAAGGT CATCTCGAGATGACCTTCCTCA GTAGCTTGTTTTTG | 1188 | chr9 | ENST00000259631.4 |
| CCL28 | CCGGCGGAGGTTTCACATCATA TTTCTCGAGAAATATGATGTGA AACCTCCGTTTTTG | 1189 | chr5 | ENST00000361115.4 |
| CCL28 | CCGGCACGAAACATACGGCCAT AAACTCGAGTTTATGGCCGTAT GTTTCGTGTTTTTG | 1190 | chr5 | ENST00000361115.4 |
| CCL28 | CCGGTTAGAGAGTCTACAGATA AATCTCGAGATTTATCTGTAGA CTCTCTAATTTTTG | 1191 | chr5 | ENST00000361115.4 |
| CCL3 | CCGGCCGGCAGATTCCACAGAA TTTCTCGAGAAATTCTGTGGAA TCTGCCGGTTTTTG | 1192 | chr17 | ENST00000613922.1 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| CCL3 | CCGGTTCGATTTCACAGTGTGTTTGCTCGAGCAAACACACTGTGAAATCGAATTTTTG | 1193 | chr17 | ENST00000613922.1 |
| CCL3 | CCGGCAACCAGTTCTCTGCATCACTCTCGAGAGTGATGCAGAGAACTGGTTGTTTTTG | 1194 | chr17 | ENST00000613922.1 |
| CCL4 | CCGGATGTGCCGTGTTATTGTATTACTCGAGTAATACAATAACACGGCACATTTTTG | 1195 | chr17 | ENST00000615863.1 |
| CCL4 | CCGGTCCTGTCCCTTCTCTTAATTTCTCGAGAAATTAAGAGAAGGGACAGGATTTTTG | 1196 | chr17 | ENST00000615863.1 |
| CCL4 | CCGGCTGTGCTGATCCCAGTGAATCCTCGAGGATTCACTGGGATCAGCACAGTTTTTG | 1197 | chr17 | ENST00000615863.1 |
| CCL5 | CCGGTGAACCTGAACTTACACAAATCTCGAGATTTGTGTAAGTTCAGGTTCATTTTTG | 1198 | chr17 | ENST00000603197.5 |
| CCL5 | CCGGCCTGCTGCTTTGCCTACATTGCTCGAGCAATGTAGGCAAAGCAGCAGGTTTTTG | 1199 | chr17 | ENST00000603197.5 |
| CCL5 | CCGGCTACCACACAGCAGCAGTTACCTCGAGGTAACTGCTGCTGTGTGGTAGTTTTTG | 1200 | chr17 | ENST00000603197.5 |
| CCL7 | CCGGCATAAAGCCTTGGATGTATATCTCGAGATATACATCCAAGGCTTTATGTTTTTG | 1201 | chr17 | ENST00000378569.2 |
| CCL7 | CCGGGCTGCTACAGATTATCAATACTCGAGTATTGATAATCTGTAGCAGCTTTTTG | 1202 | chr17 | ENST00000378569.2 |
| CCL7 | CCGGTCTAAGGAATATGAGCTTTATCTCGAGATAAAGCTCATATTCCTTAGATTTTTG | 1203 | chr17 | ENST00000378569.2 |
| CCL8 | CCGGGCTGCTTTAACGTGATCAATACTCGAGTATTGATCACGTTAAAGCAGCTTTTTG | 1204 | chr17 | ENST00000394620.1 |
| CCL8 | CCGGCAGGTGCAGTGTGACATTATTCTCGAGAATAATGTCACACTGCACCTGTTTTTG | 1205 | chr17 | ENST00000394620.1 |
| CCL8 | CCGGTTGTACTGCTGTTGTTGAAATCTCGAGATTTCAACAACAGCAGTACAATTTTTG | 1206 | chr17 | ENST00000394620.1 |
| CCR1 | CCGGATTCTGCTAAGACGACCAAATCTCGAGATTTGGTCGTCTTAGCAGAATTTTTG | 1207 | chr3 | ENST00000296140.3 |
| CCR1 | CCGGATCTGCTACACAGGGATTATACTCGAGTATAATCCCTGTGTAGCAGATTTTTG | 1208 | chr3 | ENST00000296140.3 |
| CCR1 | CCGGCCTCTGTACTCCTTGGTATTTCTCGAGAAATACCAAGGAGTACAGAGGTTTTTG | 1209 | chr3 | ENST00000296140.3 |
| CCR2 | CCGGACGGTGCTCCCTGTCATAAATCTCGAGATTTATGACAGGGAGCACCGTTTTTG | 1210 | chr3 | ENST00000445132.2 |

TABLE 15-continued

5' to 3' (Forward) shRNA sequences for Silencing of Cytokine/Chemokine
Genes to Reduce the Incidence of CRS

| Target Gene Symbol | shRNA Forward Oligo Sequence | SEQ ID NO: | Location | Gene ID No. |
| --- | --- | --- | --- | --- |
| CCR2 | CCGGCTTCTGGACTCCCTATAATATCTCGAGATATTATAGGGAGTCCAGAAGTTTTTG | 1211 | chr3 | ENST00000445132.2 |
| CCR2 | CCGGGCTGTATCACATCGGTTATTTCTCGAGAAATAACCGATGTGATACAGCTTTTTG | 1212 | chr3 | ENST00000445132.2 |
| CCR3 | CCGGATACAGGAGGCTCCGAATTATCTCGAGATAATTCGGAGCCTCCTGTATTTTTG | 1213 | chr3 | ENST00000357422.2 |
| CCR3 | CCGGCCCAGAGGATACAGTATATAGCTCGAGCTATATACTGTATCCTCTGGGTTTTTG | 1214 | chr3 | ENST00000357422.2 |
| CCR3 | CCGGTAGCAGCTCTTCCTGAATTTACTCGAGTAAATTCAGGAAGAGCTGCTATTTTTG | 1215 | chr3 | ENST00000357422.2 |
| CCR5 | CCGGACTCTTGACAGGGCTCTATTTCTCGAGAAATAGAGCCCTGTCAAGAGTTTTTG | 1216 | chr3 | ENST00000292303.4 |
| CCR5 | CCGGCGAGCGAGCAAGCTCAGTTTACTCGAGTAAACTGAGCTTGCTCGCTCGTTTTTG | 1217 | chr3 | ENST00000292303.4 |
| CCR5 | CCGGTCCATACAGTCAGTATCAATTCTCGAGAATTGATACTGACTGTATGGATTTTTG | 1218 | chr3 | ENST00000292303.4 |
| CCR6 | CCGGGGTCTATGACAGACGTCTATCCTCGAGGATAGACGTCGTCATAGACCTTTTTG | 1219 | chr6 | ENST00000341935.9 |
| CCR6 | CCGGCGACTCCAGTGAAGATTATTTCTCGAGAAATAATCTTCACTGGAGTCGTTTTTG | 1220 | chr6 | ENST00000341935.9 |
| CCR6 | CCGGTCGACTCCAGTGAAGATTATCTCGAGAATAATCTTCACTGGAGTCGATTTTTG | 1221 | chr6 | ENST00000341935.9 |
| CCR7 | CCGGGATGAGGTCACGGACGATTACCTCGAGGTAATCGTCCGTGACCTCATCTTTTTG | 1222 | chr17 | ENST00000246657.2 |
| CCR7 | CCGGGCTGGTCGTGTTGACCTATATCTCGAGATATAGGTCAACACGACCAGCTTTTTG | 1223 | chr17 | ENST00000246657.2 |
| CCR7 | CCGGCGTGTTGACCTATATCTATTTCTCGAGAAATAGATATAGGTCAACACGTTTTTG | 1224 | chr17 | ENST00000246657.2 |
| CD109 | CCGGGCCGATCCTTACATAGATATTCTCGAGAATATCTATGTAAGGATCGGCTTTTTG | 1225 | chr6 | ENST00000287097.5 |
| CD109 | CCGGCCCGGAGGAAATGTGACTATTCTCGAGAATAGTCACATTTCCTCCGGGTTTTTG | 1226 | chr6 | ENST00000287097.5 |
| CD109 | CCGGCCGCTTATCATTTGAGACCAACTCGAGTTGGTCTCAAATGATAAGCGGTTTTTG | 1227 | chr6 | ENST00000287097.5 |
| CD27 | CCGGCTTACCTTATGTCAGTGAGATCTCGAGATCTCACTGACATAAGGTAAGTTTTTG | 1228 | chr12 | ENST00000266557.3 |

TABLE 15-continued

5' to 3' (Forward) shRNA sequences for Silencing of Cytokine/Chemokine
Genes to Reduce the Incidence of CRS

| Target Gene Symbol | shRNA Forward Oligo Sequence | SEQ ID NO: | Location | Gene ID No. |
|---|---|---|---|---|
| CD27 | CCGGGCACTGTAACTCTGGTCTTCTCTCGAGAGAAGACCAGAGTTACAGTGCTTTTTG | 1229 | chr12 | ENST00000266557.3 |
| CD27 | CCGGCCACCCACTTACCTTATGTCACTCGAGTGACATAAGGTAAGTGGGTGGTTTTTG | 1230 | chr12 | ENST00000266557.3 |
| CD27 | CCGGGCCAGATGTGTGAGCCAGGAACTCGAGTTCCTGGCTCACACATCTGGCTTTTTG | 1231 | chr12 | ENST00000266557.3 |
| CD28 | CCGGCCTCCAGAATTTGTATGTTAACTCGAGTTAACATACAAATTCTGGAGGTTTTTG | 1232 | ch2 | ENST00000458610.6 |
| CD28 | CCGGCAACCTTAGCTGCAAGTATTCCTCGAGGAATACTTGCAGCTAAGGTTGTTTTTG | 1233 | ch2 | ENST00000458610.6 |
| CD28 | CCGGTGGAGTCCTGGCTTGCTATAGCTCGAGCTATAGCAAGCCAGGACTCCATTTTTG | 1234 | ch2 | ENST00000458610.6 |
| CD28 | CCGGCCTCCTCCTTACCTAGACAATCTCGAGATTGTCTAGGTAAGGAGGAGGTTTTTG | 1235 | ch2 | ENST00000458610.6 |
| CD36 | CCGGAGAACCTATTGATGGATTAAACTCGAGTTTAATCCATCAATAGGTTCTTTTTG | 1236 | chr7 | ENST00000309881.11 |
| CD36 | CCGGGCCATAATCGACACATATAAACTCGAGTTTATATGTGTCGATTATGGCTTTTTG | 1237 | chr7 | ENST00000309881.11 |
| CD36 | CCGGACGGCTGCAGGTCAACCTATTCTCGAGAATAGGTTGACCTGCAGCCGTTTTTG | 1238 | chr7 | ENST00000309881.11 |
| CD4 | CCGGCCTGATCATCAAGAATCTTAACTCGAGTTAAGATTCTTGATGATCAGGTTTTTG | 1239 | chr12 | ENST00000011653.8 |
| CD4 | CCGGAGAGCGGATGTCTCAGATCAACTCGAGTTGATCTGAGACATCCGCTCTTTTTG | 1240 | chr12 | ENST00000011653.8 |
| CD4 | CCGGCCACTCGCCTTTACAGTTGAACTCGAGTTCAACTGTAAAGGCGAGTGGTTTTTG | 1241 | chr12 | ENST00000011653.8 |
| CD40LG | CCGGGGGAAACAGCTGACCGTTAAACTCGAGTTTAACGGTCAGCTGTTTCCTTTTTG | 1242 | chrX | ENST00000370629.6 |
| CD40LG | CCGGTTCGAGTCAAGCTCCATTTATCTCGAGATAAATGGAGCTTGACTCGAATTTTTG | 1243 | chrX | ENST00000370629.6 |
| CD40LG | CCGGTGACGCTGGGAGTCTTCATAACTCGAGTTATGAAGACTCCCAGCGTCATTTTTG | 1244 | chrX | ENST00000370629.6 |
| CD70 | CCGGCCATCGTGATGGCATCTACATCTCGAGATGTAGATGCCATCACGATGGTTTTTG | 1245 | chr19 | ENST00000245903.3 |
| CD70 | CCGGCAGCTACGTATCCATCGTGATCTCGAGATCACGATGGATACGTAGCTGTTTTTG | 1246 | chr19 | ENST00000245903.3 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| CD70 | CCGGCCAACCTCACTGGGACAC TTTCTCGAGAAAGTGTCCCAGT GAGGTTGGTTTTTG | 1247 | chr19 | ENST00000245903.3 |
| CD74 | CCGGCAAGTCGGAACAGCAGAT AACCTCGAGGTTATCTGCTGTT CCGACTTGTTTTTG | 1248 | chr5 | ENST00000009530.11 |
| CD74 | CCGGGAGAACCTGAGACACCTT AAGCTCGAGCTTAAGGTGTCTC AGGTTCTCTTTTTG | 1249 | chr5 | ENST00000009530.11 |
| CD74 | CCGGCACACAGCTACAGCTTT CTTCTCGAGAAGAAAGCTGTAG CTGTGTGGTTTTTG | 1250 | chr5 | ENST00000009530.11 |
| CD8A | CCGGGCTGGACTTCGCCTGTGA TATCTCGAGATATCACAGGCGA AGTCCAGCTTTTTG | 1251 | ch2 | ENST00000409511.6 |
| CD8A | CCGGGTGTATTCATTCTCATGAT TACTCGAGTAATCATGAGAATG AATACACTTTTTG | 1252 | ch2 | ENST00000409511.6 |
| CD8A | CCGGCCAGAGACAGCTTGATCA AGCTCGAGCTTTGATCAAGCT GTCTCTGGTTTTTG | 1253 | ch2 | ENST00000409511.6 |
| CD8A | CCGGCCTTCTCCTGTCACTGGTT ATCTCGAGATAACCAGTGACAG GAGAAGGTTTTTG | 1254 | ch2 | ENST00000409511.6 |
| CER1 | CCGGGAGAAGATGCTGTCCAGA TTTCTCGAGAAATCTGGACAGC ATCTTCTCTTTTTG | 1255 | chr9 | ENST00000380911.3 |
| CER1 | CCGGCCAGCCGATAGATGGAAT GAACTCGAGTTCATTCCATCTA TCGGCTGGTTTTTG | 1256 | chr9 | ENST00000380911.3 |
| CER1 | CCGGCAAGAAATTCTGGCACCA CTTCTCGAGAAGTGGTGCCAGA ATTTCTTGTTTTTG | 1257 | chr9 | ENST00000380911.3 |
| CHRD | CCGGACGTCCTGCAAAGTGTCC TTTCTCGAGAAAGGACACTTTG CAGGACGTTTTTG | 1258 | chr3 | ENST00000204604.5 |
| CHRD | CCGGACTGATCCAGAGCTGGAG AAACTCGAGTTTCTCCAGCTCT GGATCAGTTTTTG | 1259 | chr3 | ENST00000204604.5 |
| CHRD | CCGGCGGCTGCTGAAGGGATTC TATCTCGAGATAGAATCCCTTC AGCAGCCGTTTTTG | 1260 | chr3 | ENST00000204604.5 |
| CKLF | CCGGCCTTTGCTTGTGTTTGCAC TTCTCGAGAAGTGCAAACACAA GCAAAGGTTTTTG | 1261 | chr16 | ENST00000264001.8 |
| CKLF | CCGGCCCTGAACCATATATTGT TATCTCGAGATAACAATATATG GTTCAGGGTTTTTG | 1262 | chr16 | ENST00000264001.8 |
| CKLF | CCGGTGGATTTGAAGTCACCGT TATCTCGAGATAACGGTGACTT CAAATCCATTTTTG | 1263 | chr16 | ENST00000264001.8 |
| CLCF1 | CCGGGAAACAAACATGGTGGC AATTCTCGAGAATTGCCACCAT GTTTGTTTCTTTTTG | 1264 | chr11 | ENST00000312438.7 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| CLCF1 | CCGGCCACAGGATTTCCTGAAAGTTCTCGAGAACTTTCAGGAAATCCTGTGGTTTTTG | 1265 | chr11 | ENST00000312438.7 |
| CLCF1 | CCGGCATGGTGGCAATTCTACACAACTCGAGTTGTGTAGAATTGCCACCATGTTTTTG | 1266 | chr11 | ENST00000312438.7 |
| CMTM1 | CCGGCACCACTTGCTGACCTATTTACTCGAGTAAATAGGTCAGCAAGTGGTGTTTTTG | 1267 | chr16 | ENST00000379500.6 |
| CMTM1 | CCGGGACCTATTTACATTGGCCCTTCTCGAGAAGGGCCAATGTAAATAGGTCTTTTTG | 1268 | chr16 | ENST00000379500.6 |
| CMTM1 | CCGGGCTGTGTTCCTTTCAGTAGTTCTCGAGAACTACTGAAAGGAACACAGCTTTTTG | 1269 | chr16 | ENST00000379500.6 |
| CMTM2 | CCGGGTAAGGAGCCATCGGACAAACCTCGAGGTTTGTCCGATGGCTCCTTACTTTTTG | 1270 | chr16 | ENST00000268595.2 |
| CMTM2 | CCGGCTTACTTGCTGTGATCCTTATCTCGAGATAAGGATCACAGCAAGTAAGTTTTTG | 1271 | chr16 | ENST00000268595.2 |
| CMTM2 | CCGGCATAAGGAGCCATCGGACAAACTCGAGTTTGTCCGATGGCTCCTTATGTTTTTG | 1272 | chr16 | ENST00000268595.2 |
| CMTM3 | CCGGCATCGTGTTTGCAACTGATTTCTCGAGAAATCAGTTGCAAACACGATGTTTTTG | 1273 | chr16 | ENST00000361909.8 |
| CMTM3 | CCGGGCTTCTTAACAGATGGCATTTCTCGAGAAATGCCATCTGTTAAGAAGCTTTTTG | 1274 | chr16 | ENST00000361909.8 |
| CMTM3 | CCGGGCTTCTTAACAGATGGCATTTCTCGAGAAATGCCATCTGTTAAGAAGCTTTTTG | 1275 | chr16 | ENST00000361909.8 |
| CMTM4 | CCGGCAACTGGAATCTGACAGATTTCTCGAGAAATCTGTCAGATTCCAGTTGTTTTTG | 1276 | chr16 | ENST00000394106.6 |
| CMTM4 | CCGGGACTGGCGTCTTGCTGATTATCTCGAGATAATCAGCAAGACGCCAGTCTTTTTG | 1277 | chr16 | ENST00000394106.6 |
| CMTM4 | CCGGGCAGAAATTGCTGCCGTGATACTCGAGTATCACGGCAGCAATTTCTGCTTTTTG | 1278 | chr16 | ENST00000394106.6 |
| CMTM5 | CCGGCAAGATCTACCGGACTGAGATCTCGAGATCTCAGTCCGGTAGATCTTGTTTTTG | 1279 | chr14 | ENST00000359320.7 |
| CMTM5 | CCGGCCTGACCCTCATCATCTTCATCTCGAGATGAAGATGATGAGGGTCAGGTTTTTG | 1280 | chr14 | ENST00000359320.7 |
| CMTM5 | CCGGCTTCCTCTATGCCACCCAGTACTCGAGTACTGGGTGGCATAGAGGAAGTTTTTG | 1281 | chr14 | ENST00000359320.7 |
| CMTM6 | CCGGGCCCTCACTGAGCCACTTAATCTCGAGATTAAGTGGCTCAGTGAGGGCTTTTTG | 1282 | chr3 | ENST00000205636.3 |

TABLE 15-continued

5' to 3' (Forward) shRNA sequences for Silencing of Cytokine/Chemokine
Genes to Reduce the Incidence of CRS

| Target Gene Symbol | shRNA Forward Oligo Sequence | SEQ ID NO: | Location | Gene ID No. |
|---|---|---|---|---|
| CMTM6 | CCGGCCCAAGACAGTGAAAGTAATTCTCGAGAATTACTTTCACTGTCTTGGGTTTTTG | 1283 | chr3 | ENST00000205636.3 |
| CMTM6 | CCGGCCCAAGACAGTGAAAGTAATTCTCGAGAATTACTTTCACTGTCTTGGGTTTTTG | 1284 | chr3 | ENST00000205636.3 |
| CMTM7 | CCGGCTGCTGAAAGTGGCGCAAATGCTCGAGCATTTGCGCCACTTTCAGCAGTTTTTG | 1285 | chr3 | ENST00000334983.9 |
| CMTM7 | CCGGCAAAGCCCTGTCCTAATTTATCTCGAGATAAATTAGGACAGGGCTTTGTTTTTG | 1286 | chr3 | ENST00000334983.9 |
| CMTM7 | CCGGCCTGTCGATCTTTGGTTTCATCTCGAGATGAAACCAAAGATCGACAGGTTTTTG | 1287 | chr3 | ENST00000334983.9 |
| CMTM8 | CCGGTGCTGGTATGGACGCTTATTGCTCGAGCAATAAGCGTCCATACCAGCATTTTTG | 1288 | chr3 | ENST00000307526.3 |
| CMTM8 | CCGGGCAAAGTGTTGTAGCTTATAACTCGAGTTATAAGCTACAACACTTTGCTTTTTG | 1289 | chr3 | ENST00000307526.3 |
| CMTM8 | CCGGATATTCCCAGAGAATTGTATTCTCGAGAATACAATTCTCTGGGAATATTTTTG | 1290 | chr3 | ENST00000307526.3 |
| CNTF | CCGGGTAACCTCTACAGGCATTTAACTCGAGTTAAATGCCTGTAGAGGTTACTTTTTG | 1291 | chr11 | ENST00000361987.5 |
| CNTF | CCGGGTTGAAGGACTACAGGTATTTCTCGAGAAATACCTGTAGTCCTTCAACTTTTTG | 1292 | chr11 | ENST00000361987.5 |
| CNTF | CCGGGGTGACTTCCATCAAGCTATACTCGAGTATAGCTTGATGGAAGTCACCTTTTTG | 1293 | chr11 | ENST00000361987.5 |
| CNTFR | CCGGCATTCTCTTCAGACACAATTTCTCGAGAAATTGTGTCTGAAGAGAATGTTTTTG | 1294 | chr9 | ENST00000351266.8 |
| CNTFR | CCGGGCATTCTCTTCAGACACAATTCTCGAGAATTGTGTCTGAAGAGAATGCTTTTTG | 1295 | chr9 | ENST00000351266.8 |
| CNTFR | CCGGGCCGGGAAGGAGTACATTATCCTCGAGGATAATGTACTCCTTCCCGGCTTTTTG | 1296 | chr9 | ENST00000351266.8 |
| COPS5 | CCGGCTAAGGATCACCATTACTTTACTCGAGTAAAGTAATGGTGATCCTTAGTTTTTG | 1297 | chr8 | ENST00000357849.8 |
| COPS5 | CCGGCCAGACTATTCCACTTAATAACTCGAGTTATTAAGTGGAATAGTCTGGTTTTTG | 1298 | chr8 | ENST00000357849.8 |
| COPS5 | CCGGCAGTCTCTGAGAAGTACTTTACTCGAGTAAAGTACTTCTCAGAGACTGTTTTTG | 1299 | chr8 | ENST00000357849.8 |
| CRLF1 | CCGGCGATGTACTCACGCTGGATATCTCGAGATATCCAGCGTGAGTACATCGTTTTTG | 1300 | chr19 | ENST00000392386.7 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| CRLF1 | CCGGCGATGTACTCACGCTGGATATCTCGAGATATCCAGCGTGAGTACATCGTTTTTG | 1301 | chr19 | ENST00000392386.7 |
| CRLF1 | CCGGCCCAGAGAAACCCGTCAACATCTCGAGATGTTGACGGGTTTCTCTGGGTTTTTG | 1302 | chr19 | ENST00000392386.7 |
| CSF1 | CCGGTCTCCTGGTACAAGACATAATCTCGAGATTATGTCTTGTACCAGGAGATTTTTG | 1303 | chr1 | ENST00000329608.10 |
| CSF1 | CCGGGTCGGCCTGATTTCCCGTAAACTCGAGTTTACGGGAAATCAGGCCGACTTTTTG | 1304 | chr1 | ENST00000329608.10 |
| CSF1 | CCGGTTGACAAGGACTGGAATATTTCTCGAGAAATATTCCAGTCCTTGTCAATTTTTG | 1305 | chr1 | ENST00000329608.10 |
| CSF1R | CCGGGTGAACAGCAAGTTCTATAAACTCGAGTTTATAGAACTTGCTGTTCACTTTTTG | 1306 | chr5 | ENST00000286301.7 |
| CSF1R | CCGGACAGGAGAGAGCGGGACTATACTCGAGTATAGTCCCGCTCTCTCCTGTTTTTTG | 1307 | chr5 | ENST00000286301.7 |
| CSF1R | CCGGGCTGCTATTGTACAAGTATAACTCGAGTTATACTTGTACAATAGCAGCTTTTTG | 1308 | chr5 | ENST00000286301.7 |
| CSF2 | CCGGGGAGCTGCTCTCTCATGAAACCTCGAGGTTTCATGAGAGAGCAGCTCCTTTTTG | 1309 | chr5 | ENST00000296871.3 |
| CSF2 | CCGGCCCAGATTATCACCTTTGAAACTCGAGTTTCAAAGGTGATAATCTGGGTTTTTG | 1310 | chr5 | ENST00000296871.3 |
| CSF2 | CCGGGAAGTCATCTCAGAAATGTTTCTCGAGAAACATTTCTGAGATGACTTCTTTTTG | 1311 | chr5 | ENST00000296871.3 |
| CSF3 | CCGGGTCTATTTAAGCCTCATATTTCTCGAGAAATATGAGGCTTAAATAGACTTTTTG | 1312 | chr17 | ENST00000225474.6 |
| CSF3 | CCGGGATAGGTAAATACCAAGTATTCTCGAGAATACTTGGTATTTACCTATCTTTTTG | 1313 | chr17 | ENST00000225474.6 |
| CSF3 | CCGGGCTTAGAGCAAGTGAGGAAGACTCGAGTCTTCCTCACTTGCTCTAAGCTTTTTG | 1314 | chr17 | ENST00000225474.6 |
| CSF3R | CCGGCAGCCAGGCCTGCACATAAATCTCGAGATTATGTGCAGGCCTGGCTGTTTTTG | 1315 | chr1 | ENST00000361632.8 |
| CSF3R | CCGGCTATGCCTACTCTCAAGAAATCTCGAGATTTCTTGAGAGTAGGCATAGTTTTTG | 1316 | chr1 | ENST00000361632.8 |
| CSF3R | CCGGCCAGCTTCACTCTGAAGAGTTCTCGAGAACTCTTCAGAGTGAAGCTGGTTTTTG | 1317 | chr1 | ENST00000361632.8 |
| CTF1 | CCGGGAGCAGCTGCTCCAGGAATATCTCGAGATATTCCTGGAGCAGCTGCTCTTTTTG | 1318 | chr16 | ENST00000279804.2 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| CTF1 | CCGGGTCTCTCCTTCCGCTTCTT TGCTCGAGCAAAGAAGCGGAA GGAGAGACTTTTTG | 1319 | chr16 | ENST00000279804.2 |
| CTF1 | CCGGTGTCTGTCTGTCTGCTCTT AGCTCGAGCTAAGAGCAGACA GACAGACATTTTTG | 1320 | chr16 | ENST00000279804.2 |
| CX3CL1 | CCGGCCCGGAGCTGTGGTAGTA ATTCTCGAGAATTACTACCACA GCTCCGGGTTTTTG | 1321 | chr16 | ENST00000006053.6 |
| CX3CL1 | CCGGGCTGCTGCCCTAACTCGA AATCTCGAGATTTCGAGTTAGG GCAGCAGCTTTTTG | 1322 | chr16 | ENST00000006053.6 |
| CX3CL1 | CCGGCGGTGTGACGAAATGCAA CATCTCGAGATGTTGCATTTCGT CACACCGTTTTTG | 1323 | chr16 | ENST00000006053.6 |
| CX3CR1 | CCGGTGGCCTGTGTCTAGTTGTT TGCTCGAGCAAACAACTAGACA CAGGCCATTTTTG | 1324 | chr3 | ENST00000399220.2 |
| CX3CR1 | CCGGTGGGATCCCTCATCCTCA TACCTCGAGGTATGAGGATGAG GGATCCCATTTTTG | 1325 | chr3 | ENST00000399220.2 |
| CX3CR1 | CCGGGCTTTGCTCATCCACTATC AACTCGAGTTGATAGTGGATGA GCAAAGCTTTTTG | 1326 | chr3 | ENST00000399220.2 |
| CXCL1 | CCGGACCTGCACACTGTCCTAT TATCTCGAGATAATAGGACAGT GTGCAGGTTTTTG | 1327 | chr4 | ENST00000395761.3 |
| CXCL1 | CCGGAGATGCTGAACAGTGACA AATCTCGAGATTTGTCACTGTTC AGCATCTTTTTG | 1328 | chr4 | ENST00000395761.3 |
| CXCL1 | CCGGGTTCTCCAGTCATTATGTT AACTCGAGTTAACATAATGACT GGAGAACTTTTTG | 1329 | chr4 | ENST00000395761.3 |
| CXCL10 | CCGGGTATATGTCAAGCCATAA TTGCTCGAGCAATTATGGCTTG ACATATACTTTTTG | 1330 | chr4 | ENST00000306602.2 |
| CXCL10 | CCGGACTCTACCCTGGCACTAT AATCTCGAGATTATAGTGCCAG GGTAGAGTTTTTG | 1331 | chr4 | ENST00000306602.2 |
| CXCL10 | CCGGCCTGTTAATCCAAGGTCT TTACTCGAGTAAAGACCTTGGA TTAACAGGTTTTTG | 1332 | chr4 | ENST00000306602.2 |
| CXCL11 | CCGGGCTGGTTACCATCGGAGT TTACTCGAGTAAACTCCGATGG TAACCAGCTTTTTG | 1333 | chr4 | ENST00000306621.7 |
| CXCL11 | CCGGGCAGTGAAAGTGGCAGAT ATTCTCGAGAATATCTGCCACT TTCACTGCTTTTTG | 1334 | chr4 | ENST00000306621.7 |
| CXCL11 | CCGGGAAGCAAGCAAGGCTTAT AATCTCGAGATTATAAGCCTTG CTTGCTTCTTTTTG | 1335 | chr4 | ENST00000306621.7 |
| CXCL12 | CCGGGCTTAGACTAAGGCCATT ATTCTCGAGAATAATGGCCTTA GTCTAAGCTTTTTG | 1336 | chr10 | ENST00000343575.10 |

TABLE 15-continued

5' to 3' (Forward) shRNA sequences for Silencing of Cytokine/Chemokine
Genes to Reduce the Incidence of CRS

| Target Gene Symbol | shRNA Forward Oligo Sequence | SEQ ID NO: | Location | Gene ID No. |
|---|---|---|---|---|
| CXCL12 | CCGGCTCTCACTATACCAGTAT AATCTCGAGATTATACTGGTAT AGTGAGAGTTTTTG | 1337 | chr10 | ENST00000343575.10 |
| CXCL12 | CCGGCAAACTGTGCCCTTCAGA TTGCTCGAGCAATCTGAAGGGC ACAGTTTGTTTTTG | 1338 | chr10 | ENST00000343575.10 |
| CXCL13 | CCGGGATTCCCTGATGCTGATA TTTCTCGAGAAATATCAGCATC AGGGAATCTTTTTG | 1339 | chr4 | ENST00000286758.4 |
| CXCL13 | CCGGAGGAATCCATGTAGTAGA TATCTCGAGATATCTACTACAT GGATTCCTTTTTG | 1340 | chr4 | ENST00000286758.4 |
| CXCL13 | CCGGAGGTGTTCTGGAGGTCTA TTACTCGAGTAATAGACCTCCA GAACACCTTTTTG | 1341 | chr4 | ENST00000286758.4 |
| CXCL14 | CCGGATTTGTCCATACGTCACT ATACTCGAGTATAGTGACGTAT GGACAAATTTTTG | 1342 | chr5 | ENST00000337225.5 |
| CXCL14 | CCGGCAAAGGACTTTGCAGATT AAACTCGAGTTTAATCTGCAAA GTCCTTTGTTTTTG | 1343 | chr5 | ENST00000337225.5 |
| CXCL14 | CCGGGCGCAGGGTCTACGAAGA ATACTCGAGTATTCTTCGTAGA CCCTGCGCTTTTTG | 1344 | chr5 | ENST00000337225.5 |
| CXCL16 | CCGGACATCCAGCCTACACGTA TTTCTCGAGAAATACGTGTAGG CTGGATGTTTTTG | 1345 | chr17 | ENST00000293778.10 |
| CXCL16 | CCGGTCTGAAGGTGCGAGGATT ATACTCGAGTATAATCCTCGCA CCTTCAGATTTTTG | 1346 | chr17 | ENST00000293778.10 |
| CXCL16 | CCGGTCCAGATCTGCCGGTTCA TTACTCGAGTAATGAACCGGCA GATCTGGATTTTTG | 1347 | chr17 | ENST00000293778.10 |
| CXCL17 | CCGGGCGCCCACTCTTCCAATT AAACTCGAGTTTAATTGGAAGA GTGGGCGCTTTTTG | 1348 | chr19 | ENST00000601181.5 |
| CXCL17 | CCGGTCCAGAGCCTGCCAGCAA TTTCTCGAGAAATTGCTGGCAG GCTCTGGATTTTTG | 1349 | chr19 | ENST00000601181.5 |
| CXCL17 | CCGGAGAATGTGAGTGCAAAG ATTGCTCGAGCAATCTTTGCAC TCACATTCTTTTTG | 1350 | chr19 | ENST00000601181.5 |
| CXCL2 | CCGGCTTGCACACTCTCCCATT ATACTCGAGTATAATGGGAGAG TGTGCAAGTTTTTG | 1351 | chr4 | ENST00000508487.2 |
| CXCL2 | CCGGGCAGATATTCTCTAGTCA TTTCTCGAGAAATGACTAGAGA ATATCTGCTTTTTG | 1352 | chr4 | ENST00000508487.2 |
| CXCL2 | CCGGATTTCTTCGTGATGACAT ATCCTCGAGGATATGTCATCAC GAAGAAATTTTTG | 1353 | chr4 | ENST00000508487.2 |
| CXCL3 | CCGGTTACGAGGGTTCTACTTA TTTCTCGAGAAATAAGTAGAAC CCTCGTAATTTTTG | 1354 | chr4 | ENST00000296026.4 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
| --- | --- | --- | --- | --- |
| CXCL3 | CCGGATTTAGTGGGAGACCATA ATGCTCGAGCATTATGGTCTCC CACTAAATTTTTG | 1355 | chr4 | ENST00000296026.4 |
| CXCL3 | CCGGACTGACAGGAGAGAAGT AAGACTCGAGTCTTACTTCTCTC CTGTCAGTTTTTG | 1356 | chr4 | ENST00000296026.4 |
| CXCL5 | CCGGTGAATTGTAGGTGACTAT TATCTCGAGATAATAGTCACCT ACAATTCATTTTTG | 1357 | chr4 | ENST00000296026.4 |
| CXCL5 | CCGGCAGACCACGCAAGGAGTT CATCTCGAGATGAACTCCTTGC GTGGTCTGTTTTTG | 1358 | chr4 | ENST00000296026.4 |
| CXCL5 | CCGGCGGGAAGGAAATTTGTCT TGACTCGAGTCAAGACAAATTT CCTTCCCGTTTTTG | 1359 | chr4 | ENST00000296026.4 |
| CXCL6 | CCGGTTTACCCTAGGATGCTAT TTACTCGAGTAAATAGCATCCT AGGGTAAATTTTTG | 1360 | chr4 | ENST00000226317.9 |
| CXCL6 | CCGGGTTGCACTTGTTTACGCG TTACTCGAGTAACGCGTAAACA AGTGCAACTTTTTG | 1361 | chr4 | ENST00000226317.9 |
| CXCL6 | CCGGGCTGTGGATTTCGTATGG AAACTCGAGTTTCCATACGAAA TCCACAGCTTTTTG | 1362 | chr4 | ENST00000226317.9 |
| CXCL8 | CCGGTGCGCCAACACAGAAATT ATTCTCGAGAATAATTTCTGTGT TGGCGCATTTTTG | 1363 | chr4 | ENST00000307407.7 |
| CXCL8 | CCGGCAAGAGAATATCCGAACT TTACTCGAGTAAAGTTCGGATA TTCTCTTGTTTTTG | 1364 | chr4 | ENST00000307407.7 |
| CXCL8 | CCGGTGCACGGGAGAATATACA AATCTCGAGATTTGTATATTCTC CCGTGCATTTTTG | 1365 | chr4 | ENST00000307407.7 |
| CXCL9 | CCGGCCAAAGGAGGATGGCAT ATAACTCGAGTTATATGCCATC CTCCTTTGGTTTTTG | 1366 | chr4 | ENST00000264888.5 |
| CXCL9 | CCGGCCAAACGTTAAGAATTGT TAACTCGAGTTAACAATTCTTA ACGTTTGGTTTTTG | 1367 | chr4 | ENST00000264888.5 |
| CXCL9 | CCGGGATGTGAAGGAACTGATT AAACTCGAGTTTAATCAGTTCC TTCACATCTTTTTG | 1368 | chr4 | ENST00000264888.5 |
| CXCR1 | CCGGCTTGGCACGTCATCGTGT TACCTCGAGGTAACACGATGAC GTGCCAAGTTTTTG | 1369 | chr2 | ENST00000295683.2 |
| CXCR1 | CCGGACCCACTAACTGGCTAAT TAGCTCGAGCTAATTAGCCAGT TAGTGGGTTTTTG | 1370 | chr2 | ENST00000295683.2 |
| CXCR1 | CCGGGAGACACTCAACAAGTAT GTTCTCGAGAACATACTTGTTG AGTGTCTCTTTTTG | 1371 | chr2 | ENST00000295683.2 |
| CXCR2 | CCGGGAAGCGCTACTTGGTCAA ATTCTCGAGAATTTGACCAAGT AGCGCTTCTTTTTG | 1372 | chr2 | ENST00000318507.6 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
| --- | --- | --- | --- | --- |
| CXCR2 | CCGGGCCACTAAATTGACACTTAAACTCGAGTTTAAGTGTCAATTTAGTGGCTTTTTG | 1373 | chr2 | ENST00000318507.6 |
| CXCR2 | CCGGCCCTGGAAATCAACAAGTATTCTCGAGAATACTTGTTGATTTCCAGGGTTTTTG | 1374 | chr2 | ENST00000318507.6 |
| CXCR3 | CCGGCCTTCTCATTTGGAAACTAAACTCGAGTTTAGTTTCCAAATGAGAAGGTTTTTG | 1375 | chrX | ENST00000373693.3 |
| CXCR3 | CCGGCGCTACCTGAACATAGTTCATCTCGAGATGAACTATGTTCAGGTAGCGTTTTTG | 1376 | chrX | ENST00000373693.3 |
| CXCR3 | CCGGGAGTACAAGGCATGGCGTAGACTCGAGTCTACGCCATGCCTTGTACTCTTTTTG | 1377 | chrX | ENST00000373693.3 |
| CXCR4 | CCGGCTATTCCCGACTTCATCTTTGCTCGAGCAAAGATGAAGTCGGGAATAGTTTTTG | 1378 | chr2 | ENST00000409817.1 |
| CXCR4 | CCGGGCGTGTAGTGAATCACGTAAACTCGAGTTTACGTGATTCACTACACGCTTTTTG | 1379 | chr2 | ENST00000409817.1 |
| CXCR4 | CCGGCCTGTTCTTAAGACGTGATTTCTCGAGAAATCACGTCTTAAGAACAGGTTTTTG | 1380 | chr2 | ENST00000409817.1 |
| CXCR6 | CCGGGCTTGCTCATCTGGGTGATATCTCGAGATATCACCCAGATGAGCAAGCTTTTTG | 1381 | chr3 | ENST00000304552.4 |
| CXCR6 | CCGGTACTGGGCATCTACACTATTACTCGAGTAATAGTGTAGATGCCCAGTATTTTTG | 1382 | chr3 | ENST00000304552.4 |
| CXCR6 | CCGGTTATCTATGGCAATGTCTTTACTCGAGTAAAGACATTGCCATAGATAATTTTTG | 1383 | chr3 | ENST00000304552.4 |
| EBI3 | CCGGTGAACTGTCACTGTGAGATATCTCGAGATATCTCACAGTGACAGTTCATTTTTG | 1384 | chr19 | ENST00000221847.5 |
| EBI3 | CCGGATGTACTACTCTCTCCTTTACCTCGAGGTAAAGGAGAGAGTAGTACATTTTTG | 1385 | chr19 | ENST00000221847.5 |
| EBI3 | CCGGGCCTTTCATAACAGAGCACATCTCGAGATGTGCTCTGTTATGAAAGGCTTTTG | 1386 | chr19 | ENST00000221847.5 |
| EDN1 | CCGGCCATGAGAAACAGCGTCAAATCTCGAGATTTGACGCTGTTTCTCATGGTTTTTG | 1387 | chr6 | ENST00000379375.5 |
| EDN1 | CCGGGCTCGTCCCTGATGGATAAGCTCGAGCTTATCCATCAGGGACGAGCTTTTTG | 1388 | chr6 | ENST00000379375.5 |
| EDN1 | CCGGAGACAAGAAGTGCTGGAATTTCTCGAGAAATTCCAGCACTTCTTGTCTTTTTG | 1389 | chr6 | ENST00000379375.5 |
| ELANE | CCGGGCACTGCGTGGCGAATGTAAACTCGAGTTTACATTCGCCACGCAGTGCTTTTTG | 1390 | chr19 | ENST00000263621.1 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| ELANE | CCGGTGCTCAACGACATCGTGATTCCTCGAGGAATCACGATGTCGTTGAGCATTTTTG | 1391 | chr19 | ENST00000263621.1 |
| ELANE | CCGGCAACGGGCTAATCCACGGAATCTCGAGATTCCGTGGATTAGCCCGTTGTTTTTG | 1392 | chr19 | ENST00000263621.1 |
| ENG | CCGGGCAGGTGTCAGCAAGTATGATCTCGAGATCATACTTGCTGACACCTGCTTTTTG | 1393 | chr9 | ENST00000344849.4 |
| ENG | CCGGGCAGGTGTCAGCAAGTATGATCTCGAGATCATACTTGCTGACACCTGCTTTTTG | 1394 | chr9 | ENST00000344849.4 |
| ENG | CCGGGTCTTGCAGAAACAGTCCATTCTCGAGAATGGACTGTTTCTGCAAGACTTTTTG | 1395 | chr9 | ENST00000344849.4 |
| EPO | CCGGCCCAGACACCAAAGTTAATTTCTCGAGAAATTAACTTTGGTGTCTGGGTTTTTG | 1396 | chr7 | ENST00000252723.2 |
| EPO | CCGGTGCAGCTGCATGTGGATAAAGCTCGAGCTTTATCCACATGCAGCTGCATTTTTG | 1397 | chr7 | ENST00000252723.2 |
| EPO | CCGGAGAGCAACTCTGAGATCTAAGCTCGAGCTTAGATCTCAGAGTTGCTCTTTTTG | 1398 | chr7 | ENST00000252723.2 |
| FAM3B | CCGGTTGGAACTCCCTTCCGAAATTCTCGAGAATTTCGGAAGGGAGTTCCAATTTTTG | 1399 | chr21 | ENST00000357985.6 |
| FAM3B | CCGGTAAATCCAACAGCCCATATTTCTCGAGAAATATGGGCTGTTGGATTTATTTTTG | 1400 | chr21 | ENST00000357985.6 |
| FAM3B | CCGGTCAGGTCTAGCTGGGTATTTACTCGAGTAAATACCCAGCTAGACCTGATTTTTG | 1401 | chr21 | ENST00000357985.6 |
| FAM3C | CCGGCTTGGTGTGTGCATGAGTATTCTCGAGAATACTCATGCACACACCAAGTTTTTG | 1402 | chr7 | ENST00000359943.7 |
| FAM3C | CCGGGAGGAGATGTGGCACCATTTACTCGAGTAAATGGTGCCACATCTCCTCTTTTTG | 1403 | chr7 | ENST00000359943.7 |
| FAM3C | CCGGGCCATACAAGATGGAACAATACTCGAGTATTGTTCCATCTTGTATGGCTTTTTG | 1404 | chr7 | ENST00000359943.7 |
| FAM3D | CCGGCACCTAGTGAAATTCCTTAAACTCGAGTTTAAGGAATTTCACTAGGTGTTTTTG | 1405 | chr3 | ENST00000358781.6 |
| FAM3D | CCGGCATGTACTCTGGAGATGTTATCTCGAGATAACATCTCCAGAGTACATGTTTTTG | 1406 | chr3 | ENST00000358781.6 |
| FAM3D | CCGGCAATGTGGGCAGAGGCCTAAACTCGAGTTTAGGCCTCTGCCCACATTGTTTTTG | 1407 | chr3 | ENST00000358781.6 |
| FAS | CCGGGCGTATGACACATTGATTAAACTCGAGTTTAATCAATGTGTCATACGCTTTTTG | 1408 | chr10 | ENST00000355740.6 |

TABLE 15-continued

5' to 3' (Forward) shRNA sequences for Silencing of Cytokine/Chemokine
Genes to Reduce the Incidence of CRS

| Target Gene Symbol | shRNA Forward Oligo Sequence | SEQ ID NO: | Location | Gene ID No. |
|---|---|---|---|---|
| FAS | CCGGCCTGAAACAGTGGCAATA AATCTCGAGATTATTGCCACT GTTTCAGGTTTTTG | 1409 | chr10 | ENST00000355740.6 |
| FAS | CCGGCTATCATCCTCAAGGACA TTACTCGAGTAATGTCCTTGAG GATGATAGTTTTTG | 1410 | chr10 | ENST00000355740.6 |
| FASLG | CCGGGACTAGAGGCTTGCATAA TAACTCGAGTTATTATGCAAGC CTCTAGTCTTTTTG | 1411 | chr1 | ENST00000367721.2 |
| FASLG | CCGGACTGGGCTGTACTTTGTA TATCTCGAGATATACAAAGTAC AGCCCAGTTTTTG | 1412 | chr1 | ENST00000367721.2 |
| FASLG | CCGGTGAGCTCTCTCTGGTCAA TTTCTCGAGAAATTGACCAGAG AGAGCTCATTTTTG | 1413 | chr1 | ENST00000367721.2 |
| FGF2 | CCGGGAAACGAACTGGGCAGT ATAACTCGAGTTATACTGCCCA GTTCGTTTCTTTTTG | 1414 | chr4 | ENST00000608478.1 |
| FGF2 | CCGGTATAGCTCAGTTTGGATA ATTCTCGAGAATTATCCAAACT GAGCTATATTTTTG | 1415 | chr4 | ENST00000608478.1 |
| FGF2 | CCGGTGAACGATTGGAATCTAA TAACTCGAGTTATTAGATTCCA ATCGTTCATTTTTG | 1416 | chr4 | ENST00000608478.1 |
| FLT3LG | CCGGCTGTCTGACTACCTGCTTC AACTCGAGTTGAAGCAGGTAGT CAGACAGTTTTTG | 1417 | chr19 | ENST00000594009.5 |
| FLT3LG | CCGGTCCTCCGACTTCGCTGTC AAAACTCGAGTTTGACAGCGAAG TCGGAGGATTTTTG | 1418 | chr19 | ENST00000594009.5 |
| FLT3LG | CCGGGCTTCGTCCAGACCAACA TCTCTCGAGAGATGTTGGTCTG GACGAAGCTTTTTG | 1419 | chr19 | ENST00000594009.5 |
| FOXP3 | CCGGAGCTGGAGTTCCGCAAGA AACCTCGAGGTTTCTTGCGGAA CTCCAGCTTTTTG | 1420 | chrX | ENST00000376207.8 |
| FOXP3 | CCGGTCCTACCCACTGCTGGCA AATCTCGAGATTTGCCAGCAGT GGGTAGGATTTTTG | 1421 | chrX | ENST00000376207.8 |
| FOXP3 | CCGGTGTCCCTCACTCAACACA AACCTCGAGGTTTGTGTTGAGT GAGGGACATTTTTG | 1422 | chrX | ENST00000376207.8 |
| FOXP3 | CCGGCACACGCATGTTTGCCTT CTTCTCGAGAAGAAGGCAAACA TGCGTGTGTTTTTG | 1423 | chrX | ENST00000376207.8 |
| FZD4 | CCGGCGTGTGTGATTGCCTGTT ATTCTCGAGAATAACAGGCAAT CACACACGTTTTTG | 1424 | chr11 | ENST00000531380.1 |
| FZD4 | CCGGTCTCAGTATGTGCTATAA TATCTCGAGATATTATAGCACA TACTGAGATTTTTG | 1425 | chr11 | ENST00000531380.1 |
| FZD4 | CCGGTTCTCAGTATGTGCTATA ATACTCGAGTATTATAGCACAT ACTGAGAATTTTTG | 1426 | chr11 | ENST00000531380.1 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| GATA3 | CCGGAGCCTAAACGCGATGGAT ATACTCGAGTATATCCATCGCG TTTAGGCTTTTTG | 1427 | chr10 | ENST00000346208.4 |
| GATA3 | CCGGCCCAAGAACAGCTCGTTT AACCTCGAGGTTAAACGAGCTG TTCTTGGGTTTTTG | 1428 | chr10 | ENST00000346208.4 |
| GATA3 | CCGGGCCAAGAAGTTTAAGGAA TATCTCGAGATATTCCTTAAACT TCTTGGCTTTTTG | 1429 | chr10 | ENST00000346208.4 |
| GATA3 | CCGGCCCTGTAATTGTTGTTTGT ATCTCGAGATACAAACAACAAT TACAGGGTTTTTG | 1430 | chr10 | ENST00000346208.4 |
| GBP1 | CCGGCCAGATGAGTACCTGACA TACCTCGAGGTATGTCAGGTAC TCATCTGGTTTTTG | 1431 | chr1 | ENST00000370473.4 |
| GBP1 | CCGGCGACGAAAGGCATGTACC ATACTCGAGTATGGTACATGCC TTTCGTCGTTTTTG | 1432 | chr1 | ENST00000370473.4 |
| GBP1 | CCGGCGACGAAAGGCATGTACC ATACTCGAGTATGGTACATGCC TTTCGTCGTTTTTG | 1433 | chr1 | ENST00000370473.4 |
| GDF1 | CCGGGTTCACCAAGCTCAACAT TTACTCGAGTAAATGTTGAGCT TGGTGAACTTTTTG | 1434 | chr19 | ENST00000247005.7 |
| GDF1 | CCGGGAGTTCACCAAGCTCAAC ATTCTCGAGAATGTTGAGCTTG GTGAACTCTTTTTG | 1435 | chr19 | ENST00000247005.7 |
| GDF1 | CCGGCCCTTATGAACCTCTACT GGTCTCGAGACCAGTAGAGGTT CATAAGGGTTTTTG | 1436 | chr19 | ENST00000247005.7 |
| GDF10 | CCGGCAGGATAATCGTGGTGTA AATCTCGAGATTTACACCACGA TTATCCTGTTTTTG | 1437 | chr10 | ENST00000580279.1 |
| GDF10 | CCGGCGACCAGAAGGCCGTGTA TTTCTCGAGAAATACACGGCCT TCTGGTCGTTTTTG | 1438 | chr10 | ENST00000580279.1 |
| GDF10 | CCGGCTGTCCGCCAGTGCATCA TTACTCGAGTAATGATGCACTG GCGGACAGTTTTTG | 1439 | chr10 | ENST00000580279.1 |
| GDF11 | CCGGCCTGCAGATCTTGCGACT AAACTCGAGTTTAGTCGCAAGA TCTGCAGGTTTTTG | 1440 | chr12 | ENST00000257868.9 |
| GDF11 | CCGGGATCGCTGTGGCTGCTCT TAACTCGAGTTAAGAGCAGCCA CAGCGATCTTTTTG | 1441 | chr12 | ENST00000257868.9 |
| GDF11 | CCGGGAGATGTAGAGACAGTG ATAGCTCGAGCTATCACTGTCT CTACATCTCTTTTTG | 1442 | chr12 | ENST00000257868.9 |
| GDF15 | CCGGAGACTCCAGATTCCGAGA GTTCTCGAGAACTCTCGGAATC TGGAGTCTTTTTG | 1443 | chr19 | ENST00000252809.3 |
| GDF15 | CCGGGCTCCAGACCTATGATGA CTTCTCGAGAAGTCATCATAGG TCTGGAGCTTTTTG | 1444 | chr19 | ENST00000252809.3 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| GDF15 | CCGGAGAGCTGGGAAGATTCGAACACTCGAGTGTTCGAATCTTCCCAGCTCTTTTTTG | 1445 | chr19 | ENST00000252809.3 |
| GDF2 | CCGGCAACAGGTACACGTCCGATAACTCGAGTTATCGGACGTGTACCTGTTGTTTTTG | 1446 | chr10 | ENST00000581492.2 |
| GDF2 | CCGGTGAAAGGAAGCGTGGTCATTTCTCGAGAAATGACCACGCTTCCTTTCATTTTTG | 1447 | chr10 | ENST00000581492.2 |
| GDF2 | CCGGTATGAAGCCTACGAGTGTAAGCTCGAGCTTACACTCGTAGGCTTCATATTTTTG | 1448 | chr10 | ENST00000581492.2 |
| GDF3 | CCGGACCGTCACCAGCTATTCATTACTCGAGTAATGAATAGCTGGTGACGGTTTTTG | 1449 | chr12 | ENST00000329913.3 |
| GDF3 | CCGGCTCTCAACAGCTCCAATTATGCTCGAGCATAATTGGAGCTGTTGAGAGTTTTTG | 1450 | chr12 | ENST00000329913.3 |
| GDF3 | CCGGTTGGGCCAGGCAGTCCAATTTCTCGAGAAATTGGACTGCCTGGCCCAATTTTTG | 1451 | chr12 | ENST00000329913.3 |
| GDF5 | CCGGCAACACCATCACCAGCTTTATCTCGAGATAAAGCTGGTGATGGTGTTGTTTTTG | 1452 | chr20 | ENST00000374369.7 |
| GDF5 | CCGGATGAGACTCAGCCCACCATTTCTCGAGAAATGGTGGGCTGAGTCTCATTTTTG | 1453 | chr20 | ENST00000374369.7 |
| GDF5 | CCGGTGAGTGTGACTTGGGCTAAAGCTCGAGCTTTAGCCCAAGTCACACTCATTTTTG | 1454 | chr20 | ENST00000374369.7 |
| GDF6 | CCGGGACTCCCATCAGCATTCTATACTCGAGTATAGAATGCTGATGGGAGTCTTTTTG | 1455 | chr8 | ENST00000287020.6 |
| GDF6 | CCGGCGAGTACATGCTGTCAATCTACTCGAGTAGATTGACAGCATGTACTCGTTTTTG | 1456 | chr8 | ENST00000287020.6 |
| GDF6 | CCGGCAGTCTTCCAAGTCGGCTAATCTCGAGATTAGCCGACTTGGAAGACTGTTTTTG | 1457 | chr8 | ENST00000287020.6 |
| GDF7 | CCGGGCAGAGGAAAGAGAGCTTATTCTCGAGAATAAGCTCTCTTTCCTCTGCTTTTTG | 1458 | chr2 | ENST00000272224.4 |
| GDF7 | CCGGGTTCGACGTGTCCAGCCTTAACTCGAGTTAAGGCTGGACACGTCGAACTTTTTG | 1459 | chr2 | ENST00000272224.4 |
| GDF7 | CCGGCCACTTCATGATGTCGCTTTACTCGAGTAAAGCGACATCATGAAGTGGTTTTTG | 1460 | chr2 | ENST00000272224.4 |
| GDF9 | CCGGGATGGCTCAATTGCCTATAAACTCGAGTTTATAGGCAATTGAGCCATCTTTTTG | 1461 | chr5 | ENST00000378673.2 |
| GDF9 | CCGGCCATCAGTGGAACTGCTATTTCTCGAGAAATAGCAGTTCCACTGATGGTTTTTG | 1462 | chr5 | ENST00000378673.2 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| GDF9 | CCGGGAGTGAATACTTCAGACAATTCTCGAGAATTGTCTGAAGTATTCACTCTTTTTG | 1463 | chr5 | ENST00000378673.2 |
| GPI | CCGGCGTCTGGTATGTCTCCAACATCTCGAGATGTTGGAGACATACCAGACGTTTTTG | 1464 | chr19 | ENST00000356487.9 |
| GPI | CCGGCGTCTGGTATGTCTCCAACATCTCGAGATGTTGGAGACATACCAGACGTTTTTG | 1465 | chr19 | ENST00000356487.9 |
| GPI | CCGGGCGGATGTTCAATGGTGAGAACTCGAGTTCTCACCATTGAACATCCGCTTTTTG | 1466 | chr19 | ENST00000356487.9 |
| GREM1 | CCGGGCAGTGTCGTTGCATATCCATCTCGAGATGGATATGCAACGACACTGCTTTTTG | 1467 | chr15 | ENST00000622074.1 |
| GREM1 | CCGGACAGCCACCTACCAAGAAGAACTCGAGTTCTTCTTGGTAGGTGGCTGTTTTTTG | 1468 | chr15 | ENST00000622074.1 |
| GREM1 | CCGGCAACAGTCGCACCATCATCAACTCGAGTTGATGATGGTGCGACTGTTGTTTTTG | 1469 | chr15 | ENST00000622074.1 |
| GREM2 | CCGGGCTGTGAAGGAAGGAAATTTACTCGAGTAAATTTCCTTCCTTCACAGCTTTTTG | 1470 | chr1 | ENST00000318160.4 |
| GREM2 | CCGGCAAGGTGCATTTCTGTCATTTCTCGAGAAATGACAGAAATGCACCTTGTTTTTG | 1471 | chr1 | ENST00000318160.4 |
| GREM2 | CCGGCGGAAGTAGACGTAACTTATTCTCGAGAATAAGTTACGTCTACTTCCGTTTTTG | 1472 | chr1 | ENST00000318160.4 |
| GRN | CCGGGCCCTGATAGTCAGTTCGAATCTCGAGATTCGAACTGACTATCAGGGCTTTTTG | 1473 | chr17 | ENST00000053867.7 |
| GRN | CCGGGCCCTGATAGTCAGTTCGAATCTCGAGATTCGAACTGACTATCAGGGCTTTTTG | 1474 | chr17 | ENST00000053867.7 |
| GRN | CCGGCTTCCAAAGATCAGGTAACAACTCGAGTTGTTACCTGATCTTTGGAAGTTTTTG | 1475 | chr17 | ENST00000053867.7 |
| HAX1 | CCGGACAGACACTTCGGGACTCAATCTCGAGATTGAGTCCCGAAGTGTCTGTTTTTTG | 1476 | chr1 | ENST00000328703.11 |
| HAX1 | CCGGCCAGCCCAAATCCTATTTCAACTCGAGTTGAAATAGGATTTGGGCTGGTTTTTG | 1477 | chr1 | ENST00000328703.11 |
| HAX1 | CCGGCCAGAGGCCATTTCATAGGTTCTCGAGAACCTATGAAATGGCCTCTGGTTTTTG | 1478 | chr1 | ENST00000328703.11 |
| HFE2 | CCGGGACATGATCATTAGCCATAAGCTCGAGCTTATGGCTAATGATCATGTCTTTTTG | 1479 | chr1 | ENST00000336751.10 |
| HFE2 | CCGGGCCTACATTGGCACAACTATACTCGAGTATAGTTGTGCCAATGTAGGCTTTTTG | 1480 | chr1 | ENST00000336751.10 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| HFE2 | CCGGGAAGCTCACCATCATATT TAACTCGAGTTAAATATGATGG TGAGCTTCTTTTTG | 1481 | chr1 | ENST00000336751.10 |
| HMGB1 | CCGGGATGCAGCTTATACGAAA TAACTCGAGTTATTTCGTATAA GCTGCATCTTTTTG | 1482 | chr13 | ENST00000339872.8 |
| HMGB1 | CCGGGTTGGTGCACAGCACAAA TTACTCGAGTAATTTGTGCTGTG CACCAACTTTTTG | 1483 | chr13 | ENST00000339872.8 |
| HMGB1 | CCGGAGAAGATGATGATGATGA ATACTCGAGTATTCATCATCAT CATCTTCTTTTTG | 1484 | chr13 | ENST00000339872.8 |
| HYAL2 | CCGGCCTGCCAGTACCTCAAAG ATTCTCGAGAATCTTTGAGGTA CTGGCAGGTTTTTG | 1485 | chr3 | ENST00000357750.8 |
| HYAL2 | CCGGCCTGCCAGTACCTCAAAG ATTCTCGAGAATCTTTGAGGTA CTGGCAGGTTTTTG | 1486 | chr3 | ENST00000357750.8 |
| HYAL2 | CCGGCTGGACCTGAATGCCTTT GATCTCGAGATCAAAGGCATTC AGGTCCAGTTTTTG | 1487 | chr3 | ENST00000357750.8 |
| ICAM3 | CCGGGTCCAGCTCACGAGGCAA ATACTCGAGTATTTGCCTCGTG AGCTGGACTTTTTG | 1488 | chr19 | ENST00000160262.9 |
| ICAM3 | CCGGCCAGCTCAACTTCAGCTA AATCTCGAGATTTAGCTGAAGT TGAGCTGGTTTTTG | 1489 | chr19 | ENST00000160262.9 |
| ICAM3 | CCGGGCACTTGAAATGGAAAGA TAACTCGAGTTATCTTTCCATTT CAAGTGCTTTTTG | 1490 | chr19 | ENST00000160262.9 |
| ICAM3 | CCGGGAGCGGCAGTTACCATGT TAGCTCGAGCTAACATGGTAAC TGCCGCTCTTTTTG | 1491 | chr19 | ENST00000160262.9 |
| ICOS | CCGGGCACGACCCTAACGGTGA ATACTCGAGTATTCACCGTTAG GGTCGTGCTTTTTG | 1492 | ch2 | ENST00000316386.10 |
| ICOS | CCGGGTCCGCATTTCACTATCA TACCTCGAGGTATGATAGTGAA ATGCGGACTTTTTG | 1493 | ch2 | ENST00000316386.10 |
| ICOS | CCGGCCATTCTCATGCCAACTA TTACTCGAGTAATAGTTGGCAT GAGAATGGTTTTTG | 1494 | ch2 | ENST00000316386.10 |
| ICOS | CCGGCACAGATGTGACCCTATA ATACTCGAGTATTATAGGGTCA CATCTGTGTTTTTG | 1495 | ch2 | ENST00000316386.10 |
| IFNA10 | CCGGTGTAAAGAAGTGTCGTGT ATACTCGAGTATACACGACACT TCTTTACATTTTTG | 1496 | chr9 | ENST00000357374.2 |
| IFNA10 | CCGGATAACCACGACGCGTTGA ATCCTCGAGGATTCAACGCGTC GTGGTTATTTTTTG | 1497 | chr9 | ENST00000357374.2 |
| IFNA10 | CCGGCCTGGGACAAATGGGAA GAATCTCGAGATTCTTCCCATTT GTCCCAGGTTTTTG | 1498 | chr9 | ENST00000357374.2 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| IFNA14 | CCGGCTGGGCTGTAATCTGTCTCAACTCGAGTTGAGACAGATTACAGCCCAGTTTTTG | 1499 | chr9 | ENST00000380222.3 |
| IFNA14 | CCGGCCTGAATAACAGGAGGACTTTCTCGAGAAAGTCCTCCTGTTATTCAGGTTTTTG | 1500 | chr9 | ENST00000380222.3 |
| IFNA14 | CCGGGCAGCAGACCTTCAATCTCTTCTCGAGAAGAGATTGAAGGTCTGCTGCTTTTTG | 1501 | chr9 | ENST00000380222.3 |
| IFNA16 | CCGGTGTAAAGAAGCATCGTGTTTACTCGAGTAAACACGATGCTTCTTTACATTTTTG | 1502 | chr9 | ENST00000380216.1 |
| IFNA16 | CCGGATGATCCTCATTGATTAATACCTCGAGGTATTAATCAATGAGGATCATTTTTG | 1503 | chr9 | ENST00000380216.1 |
| IFNA16 | CCGGCCTGAAGGACAGATATGATTTCTCGAGAAATCATATCTGTCCTTCAGGTTTTTG | 1504 | chr9 | ENST00000380216.1 |
| IFNA2 | CCGGGCACAGTGGTTAATGTAATAACTCGAGTTATTACATTAACCACTGTGCTTTTTG | 1505 | chr9 | ENST00000380206.3 |
| IFNA2 | CCGGTATGACCATGACACGATTTAACTCGAGTTAAATCGTGTCATGGTCATATTTTTG | 1506 | chr9 | ENST00000380206.3 |
| IFNA2 | CCGGCCATGCTGACTGATCCATTATCTCGAGATAATGGATCAGTCAGCATGGTTTTTG | 1507 | chr9 | ENST00000380206.3 |
| IFNA5 | CCGGACTTGGGATGAGACACTTCTACTCGAGTAGAAGTGTCTCATCCCAAGTTTTTG | 1508 | chr9 | ENST00000610521.1 |
| IFNA5 | CCGGAGTGGAAGACACTCCTCTGATCTCGAGATCAGAGGAGTGTCTTCCACTTTTTG | 1509 | chr9 | ENST00000610521.1 |
| IFNA5 | CCGGTCAACTGCAAGTCAATCTGTTCTCGAGAACAGATTGACTTGCAGTTGATTTTTG | 1510 | chr9 | ENST00000610521.1 |
| IFNA6 | CCGGGACAGACATGACTTCAGATTTCTCGAGAAATCTGAAGTCATGTCTGTCTTTTTG | 1511 | chr9 | ENST00000380210.1 |
| IFNA6 | CCGGCTGTCCTCCATGAGGTGATTCCTCGAGGAATCACCTCATGGAGGACAGTTTTTG | 1512 | chr9 | ENST00000380210.1 |
| IFNA6 | CCGGAGGCTTCTAGACAAACTCTATCTCGAGATAGAGTTTGTCTAGAAGCCTTTTTG | 1513 | chr9 | ENST00000380210.1 |
| IFNA8 | CCGGTAACTATCTATAGGGCTTAAACTCGAGTTTAAGCCCTATAGATAGTTATTTTTG | 1514 | chr9 | ENST00000380210.1 |
| IFNA8 | CCGGCCAGGAGGAGTTTGATGATAACTCGAGTTATCATCAAACTCCTCCTGGTTTTTG | 1515 | chr9 | ENST00000380205.1 |
| IFNA8 | CCGGGACCTGGTACAACACGGAAATCTCGAGATTTCCGTGTTGTACCAGGTCTTTTTG | 1516 | chr9 | ENST00000380205.1 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| IFNAR1 | CCGGGCCAAGATTCAGGAAATTATTCTCGAGAATAATTTCCTGAATCTTGGCTTTTTG | 1517 | chr21 | ENST00000270139.7 |
| IFNAR1 | CCGGGCTCTCCCGTTTGTCATTTATCTCGAGATAAATGACAAACGGGAGAGCTTTTTG | 1518 | chr21 | ENST00000270139.7 |
| IFNAR1 | CCGGATGAACTGTGTCAAGTATAAGCTCGAGCTTATACTTGACACAGTTCATTTTTG | 1519 | chr21 | ENST00000270139.7 |
| IFNAR2 | CCGGGAGTGGAAATTTCACCTATATCTCGAGATATAGGTGAAATTTCCACTCTTTTTG | 1520 | chr21 | ENST00000342136.8 |
| IFNAR2 | CCGGTGTATATCAGCCTCGTGTTTGCTCGAGCAAACACGAGGCTGATATACATTTTTG | 1521 | chr21 | ENST00000342136.8 |
| IFNAR2 | CCGGGCAAATACCACAAGATCATTTCTCGAGAAATGATCTTGTGGTATTTGCTTTTTG | 1522 | chr21 | ENST00000342136.8 |
| IFNB1 | CCGGATTGAATGGGAGGCTTGAATACTCGAGTATTCAAGCCTCCCATTCAATTTTTG | 1523 | chr9 | ENST00000380232.3 |
| IFNB1 | CCGGCCTACAAAGAAGCAGCAATTTCTCGAGAAATTGCTGCTTCTTTGTAGGTTTTTG | 1524 | chr9 | ENST00000380232.3 |
| IFNB1 | CCGGCTAATGTCTATCATCAGATAACTCGAGTTATCTGATGATAGACATTAGTTTTTG | 1525 | chr9 | ENST00000380232.3 |
| IFNE | CCGGGGTAGTGATAACCTTAGATTACTCGAGTAATCTAAGGTTATCACTACCTTTTTG | 1526 | chr9 | ENST00000448696.4 |
| IFNE | CCGGAGCCTCTTCAGGGCAAATATTCTCGAGAATATTTGCCCTGAAGAGGCTTTTTG | 1527 | chr9 | ENST00000448696.4 |
| IFNE | CCGGCATAGAGTGGTAATACAATTTCTCGAGAAATTGTATTACCACTCTATGTTTTTG | 1528 | chr9 | ENST00000448696.4 |
| IFNG | CCGGGGTTGTCCTGCCTGCAATATTCTCGAGAATATTGCAGGCAGGACAACCTTTTTG | 1529 | chr12 | ENST00000229135.3 |
| IFNG | CCGGCATTCAGATGTAGCGGATAATCTCGAGATTATCCGCTACATCTGAATGTTTTTG | 1530 | chr12 | ENST00000229135.3 |
| IFNG | CCGGTGTTACTGCCAGGACCCATATCTCGAGATATGGGTCCTGGCAGTAACATTTTTG | 1531 | chr12 | ENST00000229135.3 |
| IFNGR1 | CCGGACGAGCAGGAAGTCGATTATGCTCGAGCATAATCGACTTCCTGCTCGTTTTTG | 1532 | chr6 | ENST00000367739.8 |
| IFNGR1 | CCGGCATGAACCCTATCGTATATTGCTCGAGCAATATACGATAGGGTTCATGTTTTTG | 1533 | chr6 | ENST00000367739.8 |
| IFNGR1 | CCGGCGGAAGTGAGATCCAGTATAACTCGAGTTATACTGGATCTCACTTCCGTTTTTG | 1534 | chr6 | ENST00000367739.8 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| IFNK | CCGGGAGATTGTGGCTACGCAAATGCTCGAGCATTTGCGTAGCCACAATCTCTTTTTG | 1535 | chr9 | ENST00000276943.2 |
| IFNK | CCGGCTGTTCAGATTCAAGATTATTCTCGAGAATAATCTTGAATCTGAACAGTTTTTG | 1536 | chr9 | ENST00000276943.2 |
| IFNK | CCGGTCAGCCAACACACCTTCAAATCTCGAGATTTGAAGGTGTGTTGGCTGATTTTTG | 1537 | chr9 | ENST00000276943.2 |
| IFNL1 | CCGGCTCACGCGAGACCTCAAATATCTCGAGATATTTGAGGTCTCGCGTGAGTTTTTG | 1538 | chr19 | ENST00000333625.2 |
| IFNL1 | CCGGGCCACATTGGCAGGTTCAAATCTCGAGATTTGAACCTGCCAATGTGGCTTTTTG | 1539 | chr19 | ENST00000333625.2 |
| IFNL1 | CCGGGAGTTGCAGCTCTCCTGTCTTCTCGAGAAGACAGGAGAGCTGCAACTCTTTTTG | 1540 | chr19 | ENST00000333625.2 |
| IFNL3 | CCGGAGGGCCAAAGATGCCTTAGAACTCGAGTTCTAAGGCATCTTTGGCCCTTTTTG | 1541 | chr19 | ENST00000413851.2 |
| IFNL3 | CCGGGCCTTTAAGAGGGCCAAAGATCTCGAGATCTTTGGCCCTCTTAAAGGCTTTTTG | 1542 | chr19 | ENST00000413851.2 |
| IFNL3 | CCGGTGCCACATAGCCCAGTTCAAGCTCGAGCTTGAACTGGGCTATGTGGCATTTTG | 1543 | chr19 | ENST00000413851.2 |
| IFNW1 | CCGGAGACTCTTATTTCGGCTTTAACTCGAGTTAAAGCCGAAATAAGAGTCTTTTTG | 1544 | chr9 | ENST00000380229.3 |
| IFNW1 | CCGGTCAGTCCCTAAGATGTTATTTCTCGAGAAATAACATCTTAGGGACTGATTTTTG | 1545 | chr9 | ENST00000380229.3 |
| IFNW1 | CCGGCGGTATATTAAGCCAGTATATCTCGAGATATACTGGCTTAATATACCGTTTTTG | 1546 | chr9 | ENST00000380229.3 |
| IL10 | CCGGAGCTTCTCTGTGAACGATTTACTCGAGTAAATCGTTCACAGAGAAGCTTTTTG | 1547 | chr | ENST00000423557.1 |
| IL10 | CCGGGCAGGTGAAGAATGCCTTTAACTCGAGTTAAAGGCATTCTTCACCTGCTTTTTG | 1548 | chr1 | ENST00000423557.1 |
| IL10 | CCGGGCTGGACAACTTGTTGTTAAACTCGAGTTTAACAACAAGTTGTCCAGCTTTTTG | 1549 | chr1 | ENST00000423557.1 |
| IL10RA | CCGGTCTGTCGCTTCCCGAAGTAACCTCGAGGTTACTTCGGGAAGCGACAGATTTTTG | 1550 | chr11 | ENST00000227752.7 |
| IL10RA | CCGGGAAACAGGATCCTCTAGAATCTCGAGATTTCTAGAGGATCCTGTTTCTTTTTG | 1551 | chr11 | ENST00000227752.7 |
| IL10RA | CCGGGAACTCTTTCCTGTATCATAACTCGAGTTATGATACAGGAAAGAGTTCTTTTTG | 1552 | chr11 | ENST00000227752.7 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| IL11 | CCGGATATCCACTTGAGGGCGATTTCTCGAGAAATCGCCCTCAAGTGGATATTTTTTG | 1553 | chr19 | ENST00000264563.6 |
| IL11 | CCGGCCTTCCAAAGCCAGATCTTATCTCGAGATAAGATCTGGCTTTGGAAGGTTTTTG | 1554 | chr19 | ENST00000264563.6 |
| IL11 | CCGGTGCACAGCTGAGGGACAAATTCTCGAGAATTTGTCCCTCAGCTGTGCATTTTTG | 1555 | chr19 | ENST00000264563.6 |
| IL11RA | CCGGCGGCAGATTCCACCTATAATTCTCGAGAATTATAGGTGGAATCTGCCGTTTTTG | 1556 | chr9 | ENST00000318041.13 |
| IL11RA | CCGGTCGGCAGATTCCACCTATAATCTCGAGATTATAGGTGGAATCTGCCGATTTTTG | 1557 | chr9 | ENST00000318041.13 |
| IL11RA | CCGGTGGAGCCAGTACCGGATTAATCTCGAGATTAATCCGGTACTGGCTCCATTTTTG | 1558 | chr9 | ENST00000318041.13 |
| IL12A | CCGGTGATACCTCTGATCAAGTATTCTCGAGAATACTTGATCAGAGGTATCATTTTTG | 1559 | chr3 | ENST00000305579.6 |
| IL12A | CCGGCCTGTGCCTTAGTAGTATTTACTCGAGTAAATACTACTAAGGCACAGGTTTTTG | 1560 | chr3 | ENST00000305579.6 |
| IL12A | CCGGCCTGTTTACCATTGGAATTAACTCGAGTTAATTCCAATGGTAAACAGGTTTTTG | 1561 | chr3 | ENST00000305579.6 |
| IL12B | CCGGGAATTTGGTCCACTGATATTTCTCGAGAAATATCAGTGGACCAAATTCTTTTTG | 1562 | chr5 | ENST00000231228.2 |
| IL12B | CCGGCCATGGGCCTTCATGCTATTTCTCGAGAAATAGCATGAAGGCCCATGGTTTTTG | 1563 | chr5 | ENST00000231228.2 |
| IL12B | CCGGTTAGATGCTAAATGCTCATTGCTCGAGCAATGAGCATTTAGCATCTAATTTTTG | 1564 | chr5 | ENST00000231228.2 |
| IL12RB1 | CCGGCAGCTCTACAACTCAGTTAAACTCGAGTTTAACTGAGTTGTAGAGCTGTTTTTG | 1565 | chr19 | ENST00000593993.6 |
| IL12RB1 | CCGGGTCATCTCCTCGAACCAATTTCTCGAGAAATTGGTTCGAGGAGATGACTTTTTG | 1566 | chr19 | ENST00000593993.6 |
| IL12RB1 | CCGGCCAACGGGACCACCATGTATTCTCGAGAATACATGGTGGTCCCGTTGGTTTTTG | 1567 | chr19 | ENST00000593993.6 |
| IL13 | CCGGACTTCGAAAGCATCATTATTTCTCGAGAAATAATGATGCTTTCGAAGTTTTTG | 1568 | chr5 | ENST00000304506.7 |
| IL13 | CCGGATTGAAGTTGCAGATTCATTTCTCGAGAAATGAATCTGCAACTTCAATTTTTG | 1569 | chr5 | ENST00000304506.7 |
| IL13 | CCGGCCTGCTCTTACATTTAAAGAACTCGAGTTCTTTAAATGTAAGAGCAGGTTTTTG | 1570 | chr5 | ENST00000304506.7 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| IL15 | CCGGGAAGATCTTATTCAATCTATGCTCGAGCATAGATTGAATAAGATCTTCTTTTTG | 1571 | chr4 | ENST00000296545.11 |
| IL15 | CCGGTAAGGGTGATAGTCAAATTATCTCGAGATAATTTGACTATCACCCTTATTTTTG | 1572 | chr4 | ENST00000296545.11 |
| IL15 | CCGGCACTCTGCTGCTTAGACATAACTCGAGTTATGTCTAAGCAGCAGAGTGTTTTTG | 1573 | chr4 | ENST00000296545.11 |
| IL16 | CCGGTGGGACCACGTGAGATCATTCCTCGAGGAATGATCTCACGTGGTCCCATTTTTG | 1574 | chr15 | ENST00000302987.8 |
| IL16 | CCGGGTTCTGGATGAAGCAACATTACTCGAGTAATGTTGCTTCATCCAGAACTTTTTG | 1575 | chr15 | ENST00000302987.8 |
| IL16 | CCGGCCCAAACAGTGACATTTATTTCTCGAGAAATAAATGTCACTGTTTGGGTTTTTG | 1576 | chr15 | ENST00000302987.8 |
| IL17A | CCGGATCAGTTCTGCCTAGGTAAATCTCGAGATTTACCTAGGCAGAACTGATTTTTTG | 1577 | chr6 | ENST00000340057.1 |
| IL17A | CCGGGAGCTATTTAAGGATCTATTTCTCGAGAAATAGATCCTTAAATAGCTCTTTTTG | 1578 | chr6 | ENST00000340057.1 |
| IL17A | CCGGGGTCAACCTGAACATCCATAACTCGAGTTATGGATGTTCAGGTTGACCTTTTTG | 1579 | chr6 | ENST00000340057.1 |
| IL17B | CCGGTATGCCCGCATGGAGGAGTATCTCGAGATACTCCTCCATGCGGGCATATTTTTG | 1580 | chr5 | ENST00000261796.3 |
| IL17B | CCGGGTGTCACGGATGAAACCGTATCTCGAGATACGGTTTCATCCGTGACACTTTTTG | 1581 | chr5 | ENST00000261796.3 |
| IL17B | CCGGGCAGCTGTGGATGTCCAACAACTCGAGTTGTTGGACATCCACAGCTGCTTTTTG | 1582 | chr5 | ENST00000261796.3 |
| IL17C | CCGGGCACCTCTTCCAGCCCTTAAACTCGAGTTTAAGGGCTGGAAGAGGTGCTTTTTG | 1583 | chr16 | ENST00000244241.4 |
| IL17C | CCGGCTTTGCCTTCCACACCGAGTTCTCGAGAACTCGGTGTGGAAGGCAAAGTTTTTG | 1584 | chr16 | ENST00000244241.4 |
| IL17C | CCGGATCTCCAGCCTCAGTAGTTGGCTCGAGCCAACTACTGAGGCTGGAGATTTTTG | 1585 | chr16 | ENST00000244241.4 |
| IL17D | CCGGAGAGCTACTCTGTTACATTTCCTCGAGGAAATGTAACAGAGTAGCTCTTTTTG | 1586 | chr13 | ENST00000304920.3 |
| IL17D | CCGGCAAAGAGATAGGGACGCATATCTCGAGATATGCGTCCCTATCTCTTTGTTTTTG | 1587 | chr13 | ENST00000304920.3 |
| IL17D | CCGGAGACAGCATCAACTCCAGCATCTCGAGATGCTGGAGTTGATGCTGTCTTTTTTG | 1588 | chr13 | ENST00000304920.3 |

TABLE 15-continued

5' to 3' (Forward) shRNA sequences for Silencing of Cytokine/Chemokine
Genes to Reduce the Incidence of CRS

| Target Gene Symbol | shRNA Forward Oligo Sequence | SEQ ID NO: | Location | Gene ID No. |
|---|---|---|---|---|
| IL17F | CCGGTCATCCACCATGTGCAGT AAGCTCGAGCTTACTGCACATG GTGGATGATTTTTG | 1589 | chr6 | ENST00000336123.4 |
| IL17F | CCGGGTACTTGCTGCTGTCGAT ATTCTCGAGAATATCGACAGCA GCAAGTACTTTTTG | 1590 | chr6 | ENST00000336123.4 |
| IL17F | CCGGCGTTTCCATGTCACGTAA CATCTCGAGATGTTACGTGACA TGGAAACGTTTTTG | 1591 | chr6 | ENST00000336123.4 |
| IL18 | CCGGCCCGGACCATATTTATTA TAACTCGAGTTATAATAAATAT GGTCCGGGTTTTTG | 1592 | chr11 | ENST00000280357.11 |
| IL18 | CCGGTGATTCTGACTGTAGAGA TAACTCGAGTTATCTCTACAGT CAGAATCATTTTTG | 1593 | chr11 | ENST00000280357.11 |
| IL18 | CCGGTGGCAAGCTTGAATCTAA ATTCTCGAGAATTTAGATTCAA GCTTGCCATTTTTG | 1594 | chr11 | ENST00000280357.11 |
| IL18BP | CCGGGGTCCCTTCTCTCACCAA ATTCTCGAGAATTTGGTGAGAG AAGGGACCTTTTTG | 1595 | chr11 | ENST00000260049.9 |
| IL18BP | CCGGTCCCATGTCTCTGCTCATT TACTCGAGTAAATGAGCAGAGA CATGGGATTTTTG | 1596 | chr11 | ENST00000260049.9 |
| IL18BP | CCGGCTGGGCAATGGTTCCTTC ATTCTCGAGAATGAAGGAACCA TTGCCCAGTTTTTG | 1597 | chr11 | ENST00000260049.9 |
| IL19 | CCGGGTCCACGCTGCTGCCATT AAACTCGAGTTTAATGGCAGCA GCGTGGACTTTTTG | 1598 | chr | ENST00000270218.10 |
| IL19 | CCGGTCCACAGACATGCACCAT ATACTCGAGTATATGGTGCATG TCTGTGGATTTTTG | 1599 | chr1 | ENST00000270218.10 |
| IL19 | CCGGTGATGACAAGGAACCTGT ATACTCGAGTATACAGGTTCCT TGTCATCATTTTTG | 1600 | chr1 | ENST00000270218.10 |
| IL1A | CCGGGTGGAACCAACACTAACA TATCTCGAGATATGTTAGTGTT GGTTCCACTTTTTG | 1601 | chr2 | ENST00000263339.3 |
| IL1A | CCGGGCCCTCAATCAAAGTATA ATTCTCGAGAATTATACTTTGAT TGAGGGCTTTTTG | 1602 | chr2 | ENST00000263339.3 |
| IL1A | CCGGTATTACAGATGGGCAAAT TAACTCGAGTTAATTTGCCCAT CTGTAATATTTTTG | 1603 | chr2 | ENST00000263339.3 |
| IL1B | CCGGATCAATAACAAGCTGGAA TTTCTCGAGAAATTCCAGCTTGT TATTGATTTTTG | 1604 | chr2 | ENST00000263341.6 |
| IL1B | CCGGAGCAACCGCTTCCCTATT TATCTCGAGATAAATAGGGAAG CGGTTGCTTTTTG | 1605 | chr2 | ENST00000263341.6 |
| IL1B | CCGGCTGACTTCACCATGCAAT TGCTCGAGCAAATTGCATGGT GAAGTCAGTTTTTG | 1606 | chr2 | ENST00000263341.6 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| IL1F10 | CCGGTCCTTGTGGGCTCAGTTT AATCTCGAGATTAAACTGAGCC CACAAGGATTTTTG | 1607 | chr2 | ENST00000341010.6 |
| IL1F10 | CCGGGGTCTATGGTAGGCAGAA TAACTCGAGTTATTCTGCCTACC ATAGACCTTTTTG | 1608 | chr2 | ENST00000341010.6 |
| IL1F10 | CCGGTGCAGACCAGAAGGCTCT ATACTCGAGTATAGAGCCTTCT GGTCTGCATTTTTG | 1609 | chr2 | ENST00000341010.6 |
| IL1R1 | CCGGGCCAAGAATACACATGGT ATACTCGAGTATACCATGTGTA TTCTTGGCTTTTTG | 1610 | chr2 | ENST00000410023.5 |
| IL1R1 | CCGGATAATGCACAAGCCATAT TTACTCGAGTAAATATGGCTTG TGCATTATTTTTG | 1611 | chr2 | ENST00000410023.5 |
| IL1R1 | CCGGTGGTATAGATGCAGCATA TATCTCGAGATATATGCTGCAT CTATACCATTTTTG | 1612 | chr2 | ENST00000410023.5 |
| IL1R2 | CCGGCAATCCCGTGTAAGGTGT TTCCTCGAGGAAACACCTTACA CGGGATTGTTTTTG | 1613 | chr2 | ENST00000332549.7 |
| IL1R2 | CCGGGACCATTCCTGTGATCAT TTCCTCGAGGAAATGATCACAG GAATGGTCTTTTTG | 1614 | chr2 | ENST00000332549.7 |
| IL1R2 | CCGGCGTTCATCTCATACCCGC AAACTCGAGTTTGCGGGTATGA GATGAACGTTTTTG | 1615 | chr2 | ENST00000332549.7 |
| IL1RAPL1 | CCGGCAAAGCAAGCGGCTGATT ATTCTCGAGAATAATCAGCCGC TTGCTTTGTTTTTG | 1616 | chrX | ENST00000378993.5 |
| IL1RAPL1 | CCGGGCCAGCGTTCTCCTTCAT AAACTCGAGTTTATGAAGGAGA ACGCTGGCTTTTTG | 1617 | chrX | ENST00000378993.5 |
| IL1RAPL1 | CCGGTCAAGCTCCTGACGGTCA TTACTCGAGTAATGACCGTCAG GAGCTTGATTTTTG | 1618 | chrX | ENST00000378993.5 |
| IL1RL1 | CCGGTTACACCGTGGATTGGTA TTACTCGAGTAATACCAATCCA CGGTGTAATTTTTG | 1619 | chr2 | ENST00000233954.5 |
| IL1RL1 | CCGGAGTTGCTGATTCTGGTAT TTACTCGAGTAAATACCAGAAT CAGCAACTTTTTG | 1620 | chr2 | ENST00000233954.5 |
| IL1RL1 | CCGGCGTGAAGGAAGAGGATTT ATTCTCGAGAATAAATCCTCTT CCTTCACGTTTTTG | 1621 | chr2 | ENST00000233954.5 |
| IL1RN | CCGGGCAAGGACCAAATGTCAA TTTCTCGAGAAATTGACATTTG GTCCTTGCTTTTTG | 1622 | chr2 | ENST00000409930.3 |
| IL1RN | CCGGCGTCATGGTCACCAAATT CTACTCGAGTAGAATTTGGTGA CCATGACGTTTTTG | 1623 | chr2 | ENST00000409930.3 |
| IL1RN | CCGGCTGCCTCCAGAATGGTCT TTCCTCGAGGAAAGACCATTCT GGAGGCAGTTTTTG | 1624 | chr2 | ENST00000409930.3 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
| --- | --- | --- | --- | --- |
| IL2 | CCGGGCTACCTATTGTAACTAT TATCTCGAGATAATAGTTACAA TAGGTAGCTTTTTG | 1625 | chr4 | ENST00000226730.4 |
| IL2 | CCGGCAGCTACAACTGGAGCAT TTACTCGAGTAAATGCTCCAGT TGTAGCTGTTTTTG | 1626 | chr4 | ENST00000226730.4 |
| IL2 | CCGGTGCTGGATTTACAGATGA TTTCTCGAGAAATCATCTGTAA ATCCAGCATTTTTG | 1627 | chr4 | ENST00000226730.4 |
| IL20 | CCGGCTGATGCTCTGTGAGATA TTTCTCGAGAAATATCTCACAG AGCATCAGTTTTTG | 1628 | chr1 | ENST00000367096.7 |
| IL20 | CCGGTGGTCACAGTGTATCTTA TTTCTCGAGAAATAAGATACAC TGTGACCATTTTTG | 1629 | chr1 | ENST00000367096.7 |
| IL20 | CCGGGGACTGAAGACACTCAAT TGCTCGAGCAAATTGAGTGTC TTCAGTCCTTTTTG | 1630 | chr1 | ENST00000367096.7 |
| IL20RA | CCGGCCAGTATTATGCCAAAGT TAACTCGAGTTAACTTTGGCAT AATACTGGTTTTTG | 1631 | chr6 | ENST00000316649.9 |
| IL20RA | CCGGGAGGGTCTTCAAGGAGTT AAACTCGAGTTTAACTCCTTGA AGACCCTCTTTTTG | 1632 | chr6 | ENST00000316649.9 |
| IL20RA | CCGGGCTTCGCATTTGATGGAA ATTCTCGAGAATTTCCATCAAA TGCGAAGCTTTTTG | 1633 | chr6 | ENST00000316649.9 |
| IL20RB | CCGGCAGTGTACTATTCTGTCG AATCTCGAGATTCGACAGAATA GTACACTGTTTTTG | 1634 | chr3 | ENST00000329582.8 |
| IL20RB | CCGGCCAGAATAATCCTTGAGA GAACTCGAGTTCTCTCAAGGAT TATTCTGGTTTTTG | 1635 | chr3 | ENST00000329582.8 |
| IL20RB | CCGGCTCTGTACTCTCAACCAA CATCTCGAGATGTTGGTTGAGA GTACAGAGTTTTTG | 1636 | chr3 | ENST00000329582.8 |
| IL21 | CCGGAGGAAACCACCTTCCACA AATCTCGAGATTTGTGGAAGGT GGTTTCCTTTTTG | 1637 | chr4 | ENST00000264497.7 |
| IL21 | CCGGATGACTTGGTCCCTGAAT TCCTCGAGGAAATTCAGGGAC CAAGTCATTTTTG | 1638 | chr4 | ENST00000264497.7 |
| IL21 | CCGGCTTTCAGAAGGCCCAACT AAACTCGAGTTTAGTTGGGCCT TCTGAAAGTTTTTG | 1639 | chr4 | ENST00000264497.7 |
| IL22 | CCGGAGGCTAAGCACATGTCAT ATTCTCGAGAATATGACATGTG CTTAGCCTTTTTG | 1640 | chr12 | ENST00000328087.5 |
| IL22 | CCGGGTTTCCATAATCAGTACT TTACTCGAGTAAAGTACTGATT ATGGAAACTTTTTG | 1641 | chr12 | ENST00000328087.5 |
| IL22 | CCGGAGACTTTCTAAGCATAGA TATCTCGAGATATCTATGCTTA GAAAGTCTTTTTTG | 1642 | chr12 | ENST00000328087.5 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| IL22RA1 | CCGGGGACACTTTCTAGTCCTAAACCTCGAGGTTTAGGACTAGAAAGTGTCCTTTTTG | 1643 | chr1 | ENST00000270800.1 |
| IL22RA1 | CCGGAGGGACACCACAGTACCTAAACTCGAGTTTAGGTACTGTGGTGTCCCTTTTTG | 1644 | chr1 | ENST00000270800.1 |
| IL22RA1 | CCGGCTGTCCGAGATCACCTACTTACTCGAGTAAGTAGGTGATCTCGGACAGTTTTTG | 1645 | chr1 | ENST00000270800.1 |
| IL22RA2 | CCGGAGACATACAGGAACCTTATTACTCGAGTAATAAGGTTCCTGTATGTCTTTTTG | 1646 | chr6 | ENST00000349184.8 |
| IL22RA2 | CCGGCTCGTGTTTGAAGGATCTTATCTCGAGATAAGATCCTTCAAACACGAGTTTTTG | 1647 | chr6 | ENST00000349184.8 |
| IL22RA2 | CCGGTGCTCCAAATTTACCATATAGCTCGAGCTATATGGTAAATTTGGAGCATTTTTG | 1648 | chr6 | ENST00000349184.8 |
| IL23A | CCGGAGCTGCTAGGATCGGATATTTCTCGAGAAATATCCGATCCTAGCAGCTTTTTG | 1649 | chr12 | ENST00000228534.5 |
| IL23A | CCGGCTGTGAGCCAACAGGTTAATTCTCGAGAATTAACCTGTTGGCTCACAGTTTTTG | 1650 | chr12 | ENST00000228534.5 |
| IL23A | CCGGGGATCCACCAGGGTCTGATTTCTCGAGAAATCAGACCCTGGTGGATCCTTTTTG | 1651 | chr12 | ENST00000228534.5 |
| IL23R | CCGGCTTTCTTTGATTGGGATATTTCTCGAGAAATATCCCAATCAAAGAAAGTTTTTG | 1652 | chr1 | ENST00000347310.9 |
| IL23R | CCGGTATCTCACCTCAAGCTATATTCTCGAGAATATAGCTTGAGGTGAGATATTTTTG | 1653 | chr1 | ENST00000347310.9 |
| IL23R | CCGGCGACAATACTACAGTTGTATACTCGAGTATACAACTGTAGTATTGTCGTTTTTG | 1654 | chr1 | ENST00000347310.9 |
| IL24 | CCGGCACAGGCGGTTTCTGCTATTCCTCGAGGAATAGCAGAAACCGCCTGTGTTTTTG | 1655 | chr1 | ENST00000294984.6 |
| IL24 | CCGGGTCAGGACTCTGAAGTCATTCCTCGAGGAATGACTTCAGAGTCCTGACTTTTTG | 1656 | chr1 | ENST00000294984.6 |
| IL24 | CCGGTCGGATGCTGAGAGCTGTTACCTCGAGGTAACAGCTCTCAGCATCCGATTTTTG | 1657 | chr1 | ENST00000294984.6 |
| IL25 | CCGGACAGGCACTTTCTAGATATTTCTCGAGAAATATCTAGAAAGTGCCTGTTTTTG | 1658 | chr14 | ENST00000329715.2 |
| IL25 | CCGGCCACAACCAGACTGTCTTCTACTCGAGTAGAAGACAGTCTGGTTGTGGTTTTTG | 1659 | chr14 | ENST00000329715.2 |
| IL25 | CCGGTCCTGTAGGGCCAGTGAAGATCTCGAGATCTTCACTGGCCCTACAGGATTTTTG | 1660 | chr14 | ENST00000329715.2 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| IL26 | CCGGAGCTGTTGACGCTCTCTATATCTCGAGATATAGAGAGCGTCAACAGCTTTTTG | 1661 | chr12 | ENST00000229134.4 |
| IL26 | CCGGAGTACATTGTGTCAACTTAATCTCGAGATTAAGTTGACACAATGTACTTTTTG | 1662 | chr12 | ENST00000229134.4 |
| IL26 | CCGGCGATTCCAGAAGACCGCATAACTCGAGTTATGCGGTCTTCTGGAATCGTTTTTG | 1663 | chr12 | ENST00000229134.4 |
| IL27 | CCGGACTCCTTGGAGCTCGTCTTATCTCGAGATAAGACGAGCTCCAAGGAGTTTTTG | 1664 | chr16 | ENST00000356897.1 |
| IL27 | CCGGACTTTAGGACTGGAGTCTTGGCTCGAGCCAAGACTCCAGTCCTAAAGTTTTTG | 1665 | chr16 | ENST00000356897.1 |
| IL27 | CCGGCATCATCAGCCTTGGACAAGGCTCGAGCCTTGTCCAAGGCTGATGATGTTTTTG | 1666 | chr16 | ENST00000356897.1 |
| IL2RA | CCGGCCTCGTCACAACAACAGATTTCTCGAGAAATCTGTTGTTGTGACGAGGTTTTTG | 1667 | chr10 | ENST00000379959.7 |
| IL2RA | CCGGACCCTATACAACTGGACATTGCTCGAGCAATGTCCAGTTGTATAGGGTTTTTG | 1668 | chr10 | ENST00000379959.7 |
| IL2RA | CCGGACTCGGAACACAACGAAACAACTCGAGTTGTTTCGTTGTGTTCCGAGTTTTTG | 1669 | chr10 | ENST00000379959.7 |
| IL2RB | CCGGAGTCCCAGACCTGGTGGATTTCTCGAGAAATCCACCAGGTCTGGGACTTTTTG | 1670 | chr22 | ENST00000216223.9 |
| IL2RB | CCGGGACCCACAGATGCAACATAAGCTCGAGCTTATGTTGCATCTGTGGGTCTTTTTG | 1671 | chr22 | ENST00000216223.9 |
| IL2RB | CCGGCCAGACACCCAGTATGAGTTTCTCGAGAAACTCATACTGGGTGTCTGGTTTTTG | 1672 | chr22 | ENST00000216223.9 |
| IL2RG | CCGGTCGTGTTCGGAGCCGCTTTAACTCGAGTTAAAGCGGCTCCGAACACGATTTTTG | 1673 | chrX | ENST00000374202.6 |
| IL2RG | CCGGCCAACCTCACTCTGCATTATTCTCGAGAATAATGCAGAGTGAGGTTGGTTTTTG | 1674 | chrX | ENST00000374202.6 |
| IL2RG | CCGGTTGGCTCCATGGGATTGATTACTCGAGTAATCAATCCCATGGAGCCAATTTTTG | 1675 | chrX | ENST00000374202.6 |
| IL3 | CCGGTTATCCCATTGAGACTATTTACTCGAGTAAATAGTCTCAATGGGATAATTTTTG | 1676 | chr5 | ENST00000296870.2 |
| IL3 | CCGGCGGCATCAGATGAATTGTTAACTCGAGTTAACAATTCATCTGATGCCGTTTTTG | 1677 | chr5 | ENST00000296870.2 |
| IL3 | CCGGGCAATTGAGAGCATTCTTAAACTCGAGTTTAAGAATGCTCTCAATTGCTTTTTG | 1678 | chr5 | ENST00000296870.2 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| IL31 | CCGGGCATATCTCAAGACAATCAGACTCGAGTCTGATTGTCTTGAGATATGCTTTTTG | 1679 | chr12 | ENST00000377035.1 |
| IL31 | CCGGCCAAGTGATGATGTACAGAAACTCGAGTTTCTGTACATCATCACTTGGTTTTTG | 1680 | chr12 | ENST00000377035.1 |
| IL31 | CCGGCCTGACTATTTCTCAACAGTTCTCGAGAACTGTTGAGAAATAGTCAGGTTTTTG | 1681 | chr12 | ENST00000377035.1 |
| IL31RA | CCGGCATCAAACGAATGATTCAAATCTCGAGATTTGAATCATTCGTTTGATGTTTTTG | 1682 | chr5 | ENST00000447346.6 |
| IL31RA | CCGGCGCCTGTTTCATCTGATTTAACTCGAGTTAAATCAGATGAAACAGGCGTTTTTG | 1683 | chr5 | ENST00000447346.6 |
| IL31RA | CCGGTTTCCTGTGTCTACTACTATACTCGAGTATAGTAGTAGACACAGGAAATTTTTG | 1684 | chr5 | ENST00000447346.6 |
| IL32 | CCGGTGTCGCCCTGGCATCTTAATACTCGAGTATTAAGATGCCAGGGCGACATTTTTG | 1685 | chr16 | ENST00000325568.9 |
| IL32 | CCGGAGAGCTCACTCCTCTACTTGACTCGAGTCAAGTAGAGGAGTGAGCTCTTTTTG | 1686 | chr16 | ENST00000325568.9 |
| IL32 | CCGGAGAGCTGGAGGACGACTTCAACTCGAGTTGAAGTCGTCCTCCAGCTCTTTTTG | 1687 | chr16 | ENST00000325568.9 |
| IL33 | CCGGGAGTGCTTTGCCTTTGGTATACTCGAGTATACCAAAGGCAAAGCACTCTTTTTG | 1688 | chr9 | ENST00000381434.7 |
| IL33 | CCGGGCACTCCAACTGTGTTTCATTCTCGAGAATGAAACACAGTTGGAGTGCTTTTTG | 1689 | chr9 | ENST00000381434.7 |
| IL33 | CCGGCCTGTTACTTTAGGAGAGAAACTCGAGTTTCTCTCCTAAAGTAACAGGTTTTTG | 1690 | chr9 | ENST00000381434.7 |
| IL34 | CCGGGCCGACTTCAGTACATGAAACCTCGAGGTTTCATGTACTGAAGTCGGCTTTTTG | 1691 | chr16 | ENST00000288098.6 |
| IL34 | CCGGCAGAGCCCTCATTGCAGTATGCTCGAGCATACTGCAATGAGGGCTCTGTTTTTG | 1692 | chr16 | ENST00000288098.6 |
| IL34 | CCGGCCGTGTTGTCCCTCTTGAATGCTCGAGCATTCAAGAGGGACAACACGGTTTTTG | 1693 | chr16 | ENST00000288098.6 |
| IL36A | CCGGCTCCAGTCACTATTGCCTTAACTCGAGTTAAGGCAATAGTGACTGGAGTTTTTG | 1694 | chr2 | ENST00000259211.6 |
| IL36A | CCGGTTCAGGACCAGACGCTCATAGCTCGAGCTATGAGCGTCTGGTCCTGAATTTTTG | 1695 | chr2 | ENST00000259211.6 |
| IL36A | CCGGCTCTGCCTGATGTGTGCTAAACTCGAGTTTAGCACACATCAGGCAGAGTTTTTG | 1696 | chr2 | ENST00000259211.6 |

TABLE 15-continued

5' to 3' (Forward) shRNA sequences for Silencing of Cytokine/Chemokine
Genes to Reduce the Incidence of CRS

| Target Gene Symbol | shRNA Forward Oligo Sequence | SEQ ID NO: | Location | Gene ID No. |
|---|---|---|---|---|
| IL36B | CCGGATCCTATGCTATTCGTGATTCCTCGAGGAATCACGAATAGCATAGGATTTTTTG | 1697 | chr2 | ENST00000327407.2 |
| IL36B | CCGGCCTGAGTGGAAATTCTTTAATCTCGAGATTAAAGAATTTCCACTCAGGTTTTTG | 1698 | chr2 | ENST00000327407.2 |
| IL36B | CCGGTTGGACTACATAACCTGTAAACTCGAGTTTACAGGTTATGTAGTCCAATTTTTG | 1699 | chr2 | ENST00000327407.2 |
| IL36G | CCGGTGATATCATCCAGTCTTTATACTCGAGTATAAAGACTGGATGATATCATTTTTG | 1700 | chr2 | ENST00000259205.4 |
| IL36G | CCGGCAGGAGAGCTGGGTGGTATAACTCGAGTTATACCACCCAGCTCTCCTGTTTTTG | 1701 | chr2 | ENST00000259205.4 |
| IL36G | CCGGGGGAATCCAGAATCCAGAAATCTCGAGATTTCTGGATTCTGGATTCCCTTTTTG | 1702 | chr2 | ENST00000259205.4 |
| IL36RN | CCGGCTCGGCATTGAAGGTGCTTTACTCGAGTAAAGCACCTTCAATGCCGAGTTTTTG | 1703 | chr2 | ENST00000346807.7 |
| IL36RN | CCGGTGGTTCCCAGTTTGGATAAATCTCGAGATTTATCCAAACTGGGAACCATTTTTG | 1704 | chr2 | ENST00000346807.7 |
| IL36RN | CCGGGGGAATCATTCCTGCTTAATGCTCGAGCATTAAGCAGGAATGATTCCCTTTTTG | 1705 | chr2 | ENST00000346807.7 |
| IL37 | CCGGCTCTACTGTGACAAGGATAAACTCGAGTTTATCCTTGTCACAGTAGAGTTTTTG | 1706 | chr2 | ENST00000263326.7 |
| IL37 | CCGGTGCACCTCCTGCAATTGTAATCTCGAGATTACAATTGCAGGAGGTGCATTTTTG | 1707 | chr2 | ENST00000263326.7 |
| IL37 | CCGGGTTCACACAAAGATCTTCTTTCTCGAGAAAGAAGATCTTTGTGTGAACTTTTTG | 1708 | chr2 | ENST00000263326.7 |
| IL4 | CCGGAGCTGATCCGATTCCTGAAACCTCGAGGTTTCAGGAATCGGATCAGCTTTTTG | 1709 | chr5 | ENST00000231449.6 |
| IL4 | CCGGCCACGGACACAAGTGCGATATCTCGAGATATCGCACTTGTGTCCGTGGTTTTTG | 1710 | chr5 | ENST00000231449.6 |
| IL4 | CCGGTAGCATGTGCCGGCAACTTGCTCGAGCAAAGTTGCCGGCACATGCTATTTTTG | 1711 | chr5 | ENST00000231449.6 |
| IL5 | CCGGGCAAGAGTTTCTTGGTGTAATCTCGAGATTACACCAAGAAACTCTTGCTTTTTG | 1712 | chr5 | ENST00000231454.5 |
| IL5 | CCGGGGGTACTGTGGAAAGACTATTCTCGAGAATAGTCTTTCCACAGTACCCTTTTTG | 1713 | chr5 | ENST00000231454.5 |
| IL5 | CCGGGAAAGAGTCAGGCCTTAATTTCTCGAGAAATTAAGGCCTGACTCTTTCTTTTTG | 1714 | chr5 | ENST00000231454.5 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| IL6 | CCGGATGAGCGTTAGGACACTA TTTCTCGAGAAATAGTGTCCTA ACGCTCATTTTTTG | 1715 | chr7 | ENST00000258743.9 |
| IL6 | CCGGGAGTACCTCCAGAACAGA TTTCTCGAGAAATCTGTTCTGG AGGTACTCTTTTTG | 1716 | chr7 | ENST00000258743.9 |
| IL6 | CCGGATGTGAAGCTGAGTTAAT TTACTCGAGTAAATTAACTCAG CTTCACATTTTTTG | 1717 | chr7 | ENST00000258743.9 |
| IL6R | CCGGGCAGGCACTTACTACTAA TAACTCGAGTTATTAGTAGTAA GTGCCTGCTTTTTG | 1718 | chr1 | ENST00000368485.7 |
| IL6R | CCGGTATCGGGCTGAACGGTCA AAGCTCGAGCTTTGACCGTTCA GCCCGATATTTTTG | 1719 | chr1 | ENST00000368485.7 |
| IL6R | CCGGCTGGACCCTGTGGATGAT AAACTCGAGTTTATCATCCACA GGGTCCAGTTTTTG | 1720 | chr1 | ENST00000368485.7 |
| IL6ST | CCGGACCGTGCATCGCACCTAT TTACTCGAGTAAATAGGTGCGA TGCACGGTTTTTG | 1721 | chr5 | ENST00000336909.9 |
| IL6ST | CCGGACTTCAGCAGTACCTATA AAGCTCGAGCTTTATAGGTACT GCTGAAGTTTTTG | 1722 | chr5 | ENST00000336909.9 |
| IL6ST | CCGGCGGCCAGAAGATCTACAA TTACTCGAGTAATTGTAGATCTT CTGGCCGTTTTTG | 1723 | chr5 | ENST00000336909.9 |
| IL7 | CCGGGCTCGCAAGTTGAGGCAA TTTCTCGAGAAATTGCCTCAAC TTGCGAGCTTTTTG | 1724 | chr8 | ENST00000263851.8 |
| IL7 | CCGGGCTCACTATGAATCTATT ATACTCGAGTATAATAGATTCA TAGTGAGCTTTTTG | 1725 | chr8 | ENST00000263851.8 |
| IL7 | CCGGGTGTTTCCTAAAGAGACT ATTCTCGAGAATAGTCTCTTTA GGAAACACTTTTTG | 1726 | chr8 | ENST00000263851.8 |
| IL9 | CCGGACCACCATGCAAACAAGA TACCTCGAGGTATCTTGTTTGCA TGGTGGTTTTTTG | 1727 | chr5 | ENST00000274520.1 |
| IL9 | CCGGGAACAACAAGTGTCCATA TTTCTCGAGAAATATGGACACT TGTTGTTCTTTTTG | 1728 | chr5 | ENST00000274520.1 |
| IL9 | CCGGCTGAAGAGTCTTCTGGAA ATTCTCGAGAATTTCCAGAAGA CTCTTCAGTTTTTG | 1729 | chr5 | ENST00000274520.1 |
| INHA | CCGGCCTCGGATGGAGGTTACT CTTCTCGAGAAGAGTAACCTCC ATCCGAGGTTTTTG | 1730 | chr2 | ENST00000243786.2 |
| INHA | CCGGGCAGCACTGTGCTTGTAT CTACTCGAGTAGATACAAGCAC AGTGCTGCTTTTTG | 1731 | chr2 | ENST00000243786.2 |
| INHA | CCGGTGGAGGTTACTCTTTCAA GTACTCGAGTACTTGAAAGAGT AACCTCCATTTTTG | 1732 | chr2 | ENST00000243786.2 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| INHBA | CCGGAGGCACTTTCCTACCCAA TTACTCGAGTAATTGGGTAGGA AAGTGCCTTTTTG | 1733 | chr7 | ENST00000242208.4 |
| INHBA | CCGGGAGAATGGTGTACCCTTT ATTCTCGAGAATAAAGGGTACA CCATTCTCTTTTTG | 1734 | chr7 | ENST00000242208.4 |
| INHBA | CCGGAGACGCTGCACTTCGAGA TTTCTCGAGAAATCTCGAAGTG CAGCGTCTTTTTG | 1735 | chr7 | ENST00000242208.4 |
| INHBB | CCGGCAAATGGATGCGGTGACA AATCTCGAGATTTGTCACCGCA TCCATTTGTTTTTG | 1736 | chr2 | ENST00000295228.3 |
| INHBB | CCGGGCTGGAACGACTGGATCA TAGCTCGAGCTATGATCCAGTC GTTCCAGCTTTTTG | 1737 | chr2 | ENST00000295228.3 |
| INHBB | CCGGTGATGAGTACAACATCGT CAACTCGAGTTGACGATGTTGT ACTCATCATTTTTG | 1738 | chr2 | ENST00000295228.3 |
| INHBC | CCGGTCAACCAGACTCGTCTTG ATTCTCGAGAATCAAGACGAGT CTGGTTGATTTTTG | 1739 | chr12 | ENST00000309668.2 |
| INHBC | CCGGCAAGACTGACATACCTGA CATCTCGAGATGTCAGGTATGT CAGTCTTGTTTTTG | 1740 | chr12 | ENST00000309668.2 |
| INHBC | CCGGCAGGCCAGTCTCATGTTC TTTCTCGAGAAAGAACATGAGA CTGGCCTGTTTTTG | 1741 | chr12 | ENST00000309668.2 |
| INHBE | CCGGCTCCTCTACCTGGATCAT AATCTCGAGATTATGATCCAGG TAGAGGAGTTTTTG | 1742 | chr12 | ENST00000266646.2 |
| INHBE | CCGGACCTGGGCTGGCATACCT TAACTCGAGTTAAGGTATGCCA GCCCAGGTTTTTG | 1743 | chr12 | ENST00000266646.2 |
| INHBE | CCGGGCAGCCCTTCCTAGAGCT TAACTCGAGTTAAGCTCTAGGA AGGGCTGCTTTTTG | 1744 | chr12 | ENST00000266646.2 |
| ITGA4 | CCGGCCAACGCTTCAGTGATCA ATCCTCGAGGATTGATCACTGA AGCGTTGGTTTTTG | 1745 | chr2 | ENST00000397033.6 |
| ITGA4 | CCGGTGTAGAACACATCAAGCA TTTCTCGAGAAATGCTTGATGT GTTCTACATTTTTG | 1746 | chr2 | ENST00000397033.6 |
| ITGA4 | CCGGCATGATCTTGTGACATAT TATCTCGAGATAATATGTCACA AGATCATGTTTTTG | 1747 | chr2 | ENST00000397033.6 |
| ITGAV | CCGGTTGAAGTGTACCCTAGCA TTTCTCGAGAAATGCTAGGGTA CACTTCAATTTTTG | 1748 | chr2 | ENST00000261023.7 |
| ITGAV | CCGGCACTCCAAGAACATGACT ATTCTCGAGAATAGTCATGTTC TTGGAGTGTTTTTG | 1749 | chr2 | ENST00000261023.7 |
| ITGAV | CCGGGTGAGGTCGAAACAGGAT AAACTCGAGTTTATCCTGTTTCG ACCTCACTTTTTG | 1750 | chr2 | ENST00000261023.7 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
| --- | --- | --- | --- | --- |
| ITGB1 | CCGGTTTGTAGGAAGAGGGATAATACTCGAGTATTATCCCTCTTCCTACAAATTTTTG | 1751 | chr10 | ENST00000302278.7 |
| ITGB1 | CCGGGCCTTGCATTACTGCTGATATCTCGAGATATCAGCAGTAATGCAAGGCTTTTTG | 1752 | chr10 | ENST00000302278.7 |
| ITGB1 | CCGGGCCTTGCATTACTGCTGATATCTCGAGATATCAGCAGTAATGCAAGGCTTTTTG | 1753 | chr10 | ENST00000302278.7 |
| ITGB3 | CCGGGTCGTCAGATTCCAGTACTATCTCGAGATAGTACTGGAATCTGACGACTTTTTG | 1754 | chr17 | ENST00000559488.5 |
| ITGB3 | CCGGGTCGTCAGATTCCAGTACTATCTCGAGATAGTACTGGAATCTGACGACTTTTTG | 1755 | chr17 | ENST00000559488.5 |
| ITGB3 | CCGGCCACGTCTACCTTCACCAATACTCGAGTATTGGTGAAGGTAGACGTGGTTTTTG | 1756 | chr17 | ENST00000559488.5 |
| KIT | CCGGACTTCATCTAACGAGATTAAACTCGAGTTTAATCTCGTTAGATGAAGTTTTTG | 1757 | chr4 | ENST00000288135.5 |
| KIT | CCGGGCGACGAGATTAGGCTGTTATCTCGAGATAACAGCCTAATCTCGTCGCTTTTTG | 1758 | chr4 | ENST00000288135.5 |
| KIT | CCGGACGAGTTGGCCCTAGACTTAGCTCGAGCTAAGTCTAGGGCCAACTCGTTTTTG | 1759 | chr4 | ENST00000288135.5 |
| KITLG | CCGGGCAGGAATCGTGTGACTAATACTCGAGTATTAGTCACACGATTCCTGCTTTTTG | 1760 | chr12 | ENST00000228280.9 |
| KITLG | CCGGGCAGGAATCGTGTGACTAATACTCGAGTATTAGTCACACGATTCCTGCTTTTTG | 1761 | chr12 | ENST00000228280.9 |
| KITLG | CCGGCCTATTTAATCCTCTCGTCAACTCGAGTTGACGAGAGGATTAAATAGGTTTTTG | 1762 | chr12 | ENST00000228280.9 |
| KLHL20 | CCGGGCCAATACATGGAGGTTATATCTCGAGATATAACCTCCATGTATTGGCTTTTTG | 1763 | chr1 | ENST00000209884.4 |
| KLHL20 | CCGGGCCGCAAGAACGACCACTAATCTCGAGATTAGTGGTCGTTCTTGCGGCTTTTTG | 1764 | chr1 | ENST00000209884.4 |
| KLHL20 | CCGGCACATTGTGAATCCCATATTTCTCGAGAAATATGGGATTCACAATGTGTTTTTG | 1765 | chr1 | ENST00000209884.4 |
| LEFTY1 | CCGGACAAGTTACCTCACCTAATTTCTCGAGAAATTAGGTGAGGTAACTTGTTTTTG | 1766 | chr1 | ENST00000272134.5 |
| LEFTY1 | CCGGAGCCCAATGTGTCATTGTTTACTCGAGTAAACAATGACACATTGGGCTTTTTG | 1767 | chr1 | ENST00000272134.5 |
| LEFTY1 | CCGGTCTCTAGTGAGCCCTGAATTTCTCGAGAAATTCAGGGCTCACTAGAGATTTTTG | 1768 | chr1 | ENST00000272134.5 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
| --- | --- | --- | --- | --- |
| LEFTY2 | CCGGAGTTACTCCATCCCAATTTAGCTCGAGCTAAATTGGGATGGAGTAACTTTTTG | 1769 | chr1 | ENST00000366820.9 |
| LEFTY2 | CCGGCTAAGCACTTACGTGAGTAAACTCGAGTTTACTCACGTAAGTGCTTAGTTTTTG | 1770 | chr1 | ENST00000366820.9 |
| LEFTY2 | CCGGTAGGCGCCTGGTGTATCCATTCTCGAGAATGGATACACCAGGCGCCTATTTTTG | 1771 | chr1 | ENST00000366820.9 |
| LIF | CCGGGCAGTGCCAATGCCCTCTTTACTCGAGTAAAGAGGGCATTGGCACTGCTTTTTG | 1772 | chr22 | ENST00000249075.3 |
| LIF | CCGGACCGCATAGTCGTGTACCTTGCTCGAGCAAGGTACACGACTATGCGGTTTTTG | 1773 | chr22 | ENST00000249075.3 |
| LIF | CCGGCAACAACCTGGACAAGCTATGCTCGAGCATAGCTTGTCCAGGTTGTTGTTTTTG | 1774 | chr22 | ENST00000249075.3 |
| LIFR | CCGGTGACTTGCGACTACGTCATTACTCGAGTAATGACGTAGTCGCAAGTCATTTTTG | 1775 | chr5 | ENST00000263409.8 |
| LIFR | CCGGACTTCTGCAGATTCGATATTACTCGAGTAATATCGAATCTGCAGAAGTTTTTG | 1776 | chr5 | ENST00000263409.8 |
| LIFR | CCGGGTAGGCTCAGACATAACATTTCTCGAGAAATGTTATGTCTGAGCCTACTTTTTG | 1777 | chr5 | ENST00000263409.8 |
| LTA | CCGGGCCCTAGTACTGTCTTCTTTGCTCGAGCAAAGAAGACAGTACTAGGGCTTTTTG | 1778 | chr6 | ENST00000418386.2 |
| LTA | CCGGGATCAAGTCACCGGAGCTTCCTCGAGGAAAGCTCCGGTGACTTGATCTTTTTG | 1779 | chr6 | ENST00000418386.2 |
| LTA | CCGGGCTCCCAGAAGATGGTGTATCCTCGAGGATACACCATCTTCTGGGAGCTTTTTG | 1780 | chr6 | ENST00000418386.2 |
| LTB | CCGGGCGAGAGGGAAGACCTTCTTTCTCGAGAAAGAAGGTCTTCCCTCTCGCTTTTTG | 1781 | chr6 | ENST00000429299.2 |
| LTB | CCGGCGAGAGGGTGTACGTCAACATCTCGAGATGTTGACGTACACCCTCTCGTTTTTG | 1782 | chr6 | ENST00000429299.2 |
| LTB | CCGGGACGAAGGAACAGGCGTTTCTCTCGAGAGAAACGCCTGTTCCTTCGTCTTTTTG | 1783 | chr6 | ENST00000429299.2 |
| LTBP1 | CCGGGATGACCTGTGTCGATGTAAACTCGAGTTTACATCGACACAGGTCATCTTTTTG | 1784 | chr2 | ENST00000407925.5 |
| LTBP1 | CCGGGGTGGAACAGTGCTGTTATTTCTCGAGAAATAACAGCACTGTTCCACCTTTTTG | 1785 | chr2 | ENST00000407925.5 |
| LTBP1 | CCGGCCGTTGAATACCGCCTTGAATCTCGAGATTCAAGGCGGTATTCAACGGTTTTTG | 1786 | chr2 | ENST00000407925.5 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| LTBP3 | CCGGGCATCCTCAATGGATGTGAAACTCGAGTTTCACATCCATTGAGGATGCTTTTTG | 1787 | chr11 | ENST00000322147.8 |
| LTBP3 | CCGGTGTTGTTCGGGTCGGAGATTTCTCGAGAAATCTCCGACCCGAACAACATTTTTG | 1788 | chr11 | ENST00000322147.8 |
| LTBP3 | CCGGAGCGCTTCAAGGTGGTCTTTGCTCGAGCAAAGACCACCTTGAAGCGCTTTTTG | 1789 | chr11 | ENST00000322147.8 |
| LTBP4 | CCGGGCTTCGACATGCCAGACTTTGCTCGAGCAAAGTCTGGCATGTCGAAGCTTTTTG | 1790 | chr19 | ENST00000308370.11 |
| LTBP4 | CCGGTGAAACACTACAGGGTGTATGCTCGAGCATACACCCTGTAGTGTTTCATTTTTG | 1791 | chr19 | ENST00000308370.11 |
| LTBP4 | CCGGCAACCGGCTTTGAAAGAGTTACTCGAGTAACTCTTTCAAAGCCGGTTGTTTTG | 1792 | chr19 | ENST00000308370.11 |
| MAF | CCGGTCAGTGGGATACGCCACATTTCTCGAGAAATGTGGCGTATCCCACTGATTTTTG | 1793 | chr16 | ENST00000326043.4 |
| MAF | CCGGTTTATGGTGTGTGCAAGTAAACTCGAGTTTACTTGCACACACCATAAATTTTTG | 1794 | chr16 | ENST00000326043.4 |
| MAF | CCGGGTTAGAGAAGAAGGCTATTAACTCGAGTTAATAGCCTTCTTCTCTAACTTTTTG | 1795 | chr16 | ENST00000326043.4 |
| MAF | CCGGTGTTAATGACTTCGATCTGATCTCGAGATCAGATCGAAGTCATTAACATTTTTG | 1796 | chr16 | ENST00000326043.4 |
| MIF | CCGGCTACATCAACTATTACGACATCTCGAGATGTCGTAATAGTTGATGTAGTTTTTG | 1797 | chr22 | ENST00000215754.7 |
| MIF | CCGGCTACATCAACTATTACGACATCTCGAGATGTCGTAATAGTTGATGTAGTTTTTG | 1798 | chr22 | ENST00000215754.7 |
| MIF | CCGGGACAGGGTCTACATCAACTATCTCGAGATAGTTGATGTAGACCCTGTCTTTTTG | 1799 | chr22 | ENST00000215754.7 |
| MINOS1- | CCGGGCCAAGCTGCACAATTTAATACTCGAGTATTAAATTGTGCAGCTTGGCTTTTTG | 1800 | chr1 | ENST00000602662.1 |
| MINOS1- | CCGGGCTGGCACTGTTCCCAGATAACTCGAGTTATCTGGGAACAGTGCCAGCTTTTTG | 1801 | chr1 | ENST00000602662.1 |
| MINOS1- | CCGGAGAAAGACCACTGGCAGAAACCTCGAGGTTTCTGCCAGTGGTCTTTCTTTTTTG | 1802 | chr | ENST00000602662.1 |
| MSTN | CCGGAGGCCCAACTATGGATATATTCTCGAGAATATATCCATAGTTGGGCCTTTTTG | 1803 | chr2 | ENST00000260950.4 |
| MSTN | CCGGGAGCTAGAAGGAGATCAAATTCTCGAGAATTTGATCTCCTTCTAGCTCTTTTTG | 1804 | chr2 | ENST00000260950.4 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| MSTN | CCGGGTATGCTTTAAAGTCTATTTCCTCGAGGAAATAGACTTTAAAGCATACTTTTTG | 1805 | chr2 | ENST00000260950.4 |
| NAMPT | CCGGAGCGATAGCTATGACATTTATCTCGAGATAAATGTCATAGCTATCGCTTTTTG | 1806 | chr7 | ENST00000222553.7 |
| NAMPT | CCGGGTGAAGATCTAAGACATTTAACTCGAGTTAAATGTCTTAGATCTTCACTTTTTG | 1807 | chr7 | ENST00000222553.7 |
| NAMPT | CCGGTACAAGGTTACTCACTATAAACTCGAGTTTATAGTGAGTAACCTTGTATTTTTG | 1808 | chr7 | ENST00000222553.7 |
| NBL1 | CCGGGCCAAGCTGCACAATTTAATACTCGAGTATTAAATTGTGCAGCTTGGCTTTTTG | 1809 | chr1 | ENST00000375136.7 |
| NBL1 | CCGGGCTGGCACTGTTCCCAGATAACTCGAGTTATCTGGGAACAGTGCCAGCTTTTTG | 1810 | chr1 | ENST00000375136.7 |
| NBL1 | CCGGAGAAAGACCACTGGCAGAAACCTCGAGGTTTCTGCCAGTGGTCTTTCTTTTTG | 1811 | chr1 | ENST00000375136.7 |
| NDP | CCGGCTGCTAAAGGTTACCGATTTCCTCGAGGAAATCGGTAACCTTTAGCAGTTTTTG | 1812 | chrX | ENST00000378062.5 |
| NDP | CCGGCTCTGCATATTCTAGTAATAACTCGAGTTATTACTAGAATATGCAGAGTTTTTG | 1813 | chrX | ENST00000378062.5 |
| NDP | CCGGACGGACAGCTCATTCATAATGCTCGAGCATTATGAATGAGCTGTCCGTTTTTG | 1814 | chrX | ENST00000378062.5 |
| NLRP7 | CCGGCCGTTCAAGGAAATTTCTATTCTCGAGAATAGAAATTTCCTTGAACGGTTTTTG | 1815 | chr19 | ENST00000328092.9 |
| NLRP7 | CCGGCGGGTCTCTAAGATGTCTTATCTCGAGATAAGACATCTTAGAGACCCGTTTTTG | 1816 | chr19 | ENST00000328092.9 |
| NLRP7 | CCGGACCTGCTCAGAAATCATAAATCTCGAGATTTATGATTTCTGAGCAGGTTTTTG | 1817 | chr19 | ENST00000328092.9 |
| NODAL | CCGGGTGCTCCTAGATCACCATAAACTCGAGTTTATGGTGATCTAGGAGCACTTTTTG | 1818 | chr10 | ENST00000287139.7 |
| NODAL | CCGGCACCTATAGCTTTCATGTATTCTCGAGAATACATGAAAGCTATAGGTGTTTTTG | 1819 | chr10 | ENST00000287139.7 |
| NODAL | CCGGGCATGCTGTATGTGGATAATGCTCGAGCATTATCCACATACAGCATGCTTTTTG | 1820 | chr10 | ENST00000287139.7 |
| NOG | CCGGAGGTCAGTATTATACGTTAAACTCGAGTTTAACGTATAATACTGACCTTTTTG | 1821 | chr17 | ENST00000332822.4 |
| NOG | CCGGATTCTGGTTGTTGCTAATAATCTCGAGATTATTAGCAACAACCAGAATTTTTG | 1822 | chr17 | ENST00000332822.4 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| NOG | CCGGTGCGGAGGAAGTTACAGATGTCTCGAGACATCTGTAACTTCCTCCGCATTTTTG | 1823 | chr17 | ENST00000332822.4 |
| NRG1 | CCGGGATATCACAGAGGCCTATAACCTCGAGGTTATAGGCCTCTGTGATATCTTTTTG | 1824 | chr8 | ENST00000287842.7 |
| NRG1 | CCGGGGCTGATTCTGGAGAGTATATCTCGAGATATACTCTCCAGAATCAGCCTTTTTG | 1825 | chr8 | ENST00000287842.7 |
| NRG1 | CCGGGACAGTGCCTCTGCCAATATCCTCGAGGATATTGGCAGAGGCACTGTCTTTTTG | 1826 | chr8 | ENST00000287842.7 |
| NRP1 | CCGGTATACTAGAATCACCGCATTTCTCGAGAAATGCGGTGATTCTAGTATATTTTTG | 1827 | chr10 | ENST00000265371.8 |
| NRP1 | CCGGCAGCCTTGAATGCACTTATATCTCGAGATATAAGTGCATTCAAGGCTGTTTTTG | 1828 | chr10 | ENST00000265371.8 |
| NRP1 | CCGGCAGCCTTGAATGCACTTATATCTCGAGATATAAGTGCATTCAAGGCTGTTTTTG | 1829 | chr10 | ENST00000265371.8 |
| NRP2 | CCGGCGACTGCAAGTATGACTTTATCTCGAGATAAAGTCATACTTGCAGTCGTTTTTG | 1830 | chr2 | ENST00000357785.9 |
| NRP2 | CCGGCCGGATTGCTAATGAACAGATCTCGAGATCTGTTCATTAGCAATCCGGTTTTTG | 1831 | chr2 | ENST00000357785.9 |
| NRP2 | CCGGCCTCAACTTCAACCCTCACTTCTCGAGAAGTGAGGGTTGAAGTTGAGGTTTTTG | 1832 | chr2 | ENST00000357785.9 |
| OSM | CCGGACTTCCTCCTTTCCGTGTTTCCTCGAGGAAACACGGAAAGGAGGAAGTTTTTG | 1833 | chr22 | ENST00000215781.2 |
| OSM | CCGGGGACCGACTTTCCATTGATTCCTCGAGGAATCAATGGAAAGTCGGTCCTTTTTG | 1834 | chr22 | ENST00000215781.2 |
| OSM | CCGGTGGTCCTTGCACTCCTGTTTCCTCGAGGAAACAGGAGTGCAAGGACCATTTTTG | 1835 | chr22 | ENST00000215781.2 |
| OSMR | CCGGTAACCTGACTCATCGAGTTTACTCGAGTAAACTCGATGAGTCAGGTTATTTTTG | 1836 | chr5 | ENST00000274276.7 |
| OSMR | CCGGAGGAGAACCCTCACCTAATAACTCGAGTTATTAGGTGAGGGTTCTCCTTTTTTG | 1837 | chr5 | ENST00000274276.7 |
| OSMR | CCGGGCACTCCATAAGGAATAATTTCTCGAGAAATTATTCCTTATGGAGTGCTTTTTG | 1838 | chr5 | ENST00000274276.7 |
| PARK7 | CCGGGTAGCCGTGATGTGGTCATTTCTCGAGAAATGACCACATCACGGCTACTTTTTG | 1839 | chr1 | ENST00000338639.9 |
| PARK7 | CCGGGCAATTGTTGAAGCCCTGAATCTCGAGATTCAGGGCTTCAACAATTGCTTTTTG | 1840 | chr1 | ENST00000338639.9 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| PARK7 | CCGGACTCTGAGAATCGTGTGG AAACTCGAGTTTCCACACGATT CTCAGAGTTTTTG | 1841 | chr1 | ENST00000338639.9 |
| PDPN | CCGGGCCTCTGGTATGAGAAAT AAACTCGAGTTTATTTCTCATAC CAGAGGCTTTTTG | 1842 | chr1 | ENST00000294489.10 |
| PDPN | CCGGAGTCCACGCGCAAGAACA AAGCTCGAGCTTTGTTCTTGCG CGTGGACTTTTTG | 1843 | chr1 | ENST00000294489.10 |
| PDPN | CCGGTGACCCTGGTTGGAATCA TAGCTCGAGCTATGATTCCAAC CAGGGTCATTTTTG | 1844 | chr1 | ENST00000294489.10 |
| PF4 | CCGGACGCTGAAGAATGGAAG GAAACTCGAGTTTCCTTCCATTC TTCAGCGTTTTTG | 1845 | chr4 | ENST00000296029.3 |
| PF4 | CCGGCCAACTGATAGCCACGCT GAACTCGAGTTCAGCGTGGCTA TCAGTTGGTTTTTG | 1846 | chr4 | ENST00000296029.3 |
| PF4 | CCGGCACGCTGAAGAATGGAA GGAACTCGAGTTCCTTCCATTCT TCAGCGTGTTTTTG | 1847 | chr4 | ENST00000296029.3 |
| PF4V1 | CCGGGTTGTGGTATAGTCAATC TATCTCGAGATAGATTGACTAT ACCACAACTTTTTG | 1848 | chr4 | ENST00000226524.3 |
| PF4V1 | CCGGAGCTGCCTAAGTGTGCAC TTTCTCGAGAAAGTGCACACTT AGGCAGCTTTTTG | 1849 | chr4 | ENST00000226524.3 |
| PF4V1 | CCGGCTGACACATCACAATTTC ATACTCGAGTATGAAATTGTGA TGTGTCAGTTTTTG | 1850 | chr4 | ENST00000226524.3 |
| PGLYRP1 | CCGGGTGCCCACTCAGGTCACT TATCTCGAGATAAGTGACCTGA GTGGGCACTTTTTG | 1851 | chr19 | ENST00000008938.4 |
| PGLYRP1 | CCGGCTTACGCTATGTGGTGGT ATCCTCGAGGATACCACCACAT AGCGTAAGTTTTTG | 1852 | chr19 | ENST00000008938.4 |
| PGLYRP1 | CCGGCATCAGCTTCATGGGCAA CTACTCGAGTAGTTGCCCATGA AGCTGATGTTTTTG | 1853 | chr19 | ENST00000008938.4 |
| PLP2 | CCGGCCTGTCGGTGATTGAGAT GATCTCGAGATCATCTCAATCA CCGACAGGTTTTTG | 1854 | chrX | ENST00000376327.5 |
| PLP2 | CCGGCCTGTCGGTGATTGAGAT GATCTCGAGATCATCTCAATCA CCGACAGGTTTTTG | 1855 | chrX | ENST00000376327.5 |
| PLP2 | CCGGCGAAAGGGAATCCTCCTG TTTCTCGAGAAACAGGAGGATT CCCTTTCGTTTTTG | 1856 | chrX | ENST00000376327.5 |
| PPBP | CCGGAGGTGATGAATCTGCTGA TTACTCGAGTAATCAGCAGATT CATCACCTTTTTG | 1857 | chr4 | ENST00000296028.3 |
| PPBP | CCGGTGTTTCTGCCAAACTTCTT TACTCGAGTAAAGAAGTTTGGC AGAAACATTTTTG | 1858 | chr4 | ENST00000296028.3 |

TABLE 15-continued

5' to 3' (Forward) shRNA sequences for Silencing of Cytokine/Chemokine
Genes to Reduce the Incidence of CRS

| Target Gene Symbol | shRNA Forward Oligo Sequence | SEQ ID NO: | Location | Gene ID No. |
|---|---|---|---|---|
| PPBP | CCGGCTCCCAGGAAGGGTAGAATTTCTCGAGAAATTCTACCCTTCCTGGGAGTTTTTG | 1859 | chr4 | ENST00000296028.3 |
| PXDN | CCGGAGATTGCGACTGGACTCAAACCTCGAGGTTTGAGTCCAGTCGCAATCTTTTTG | 1860 | chr2 | ENST00000252804.8 |
| PXDN | CCGGGTTCCTGACGTCAGTCGAAATCTCGAGATTTCGACTGACGTCAGGAACTTTTTG | 1861 | chr2 | ENST00000252804.8 |
| PXDN | CCGGGAAGGATTCTTGACCATCAATCTCGAGATTGATGGTCAAGAATCCTTCTTTTTG | 1862 | chr2 | ENST00000252804.8 |
| RORC | CCGGCACCTCACAAATTGAAGTGATCTCGAGATCACTTCAATTTGTGAGGTGTTTTTG | 1863 | chr1 | ENST00000318247.6 |
| RORC | CCGGGCCCTCATATTCCAACAACTTCTCGAGAAGTTGTTGGAATATGAGGGCTTTTTG | 1864 | chr1 | ENST00000318247.6 |
| RORC | CCGGGCTTCTCAAAGCAGGAGCAATCTCGAGATTGCTCCTGCTTTGAGAAGCTTTTTG | 1865 | chr1 | ENST00000318247.6 |
| RORC | CCGGCGAGGATGAGATTGCCCTCTACTCGAGTAGAGGGCAATCTCATCCTCGTTTTTG | 1866 | chr1 | ENST00000318247.6 |
| SCG2 | CCGGACGACAAGGATCAAGAATTAGCTCGAGCTAATTCTTGATCCTTGTCGTTTTTG | 1867 | chr2 | ENST00000305409.2 |
| SCG2 | CCGGCCTGTCTCTTATCCCTTTAATCTCGAGATTAAAGGGATAAGAGACAGGTTTTTG | 1868 | chr2 | ENST00000305409.2 |
| SCG2 | CCGGGAAAGCAGCCCAGATTATAATCTCGAGATTATAATCTGGGCTGCTTTCTTTTTG | 1869 | chr2 | ENST00000305409.2 |
| SCGB3A1 | CCGGTCATAGAGGGCTCCCAGAAGTCTCGAGACTTCTGGGAGCCCTCTATGATTTTTG | 1870 | chr5 | ENST00000292641.3 |
| SCGB3A1 | CCGGCCCGTGAACCACCTCATAGAGCTCGAGCTCTATGAGGTGGTTCACGGGTTTTTG | 1871 | chr5 | ENST00000292641.3 |
| SCGB3A1 | CCGGGACTGGAGCATCTACACCTGACTCGAGTCAGGTGTAGATGCTCCAGTCTTTTTG | 1872 | chr5 | ENST00000292641.3 |
| SECTM1 | CCGGCACCAGAGAAATAACAGACAACTCGAGTTGTCTGTTATTTCTCTGGTGTTTTTG | 1873 | chr17 | ENST00000269389.7 |
| SECTM1 | CCGGCCATGACTCGAATATCTGAAACTCGAGTTTCAGATATTCGAGTCATGGTTTTTG | 1874 | chr17 | ENST00000269389.7 |
| SECTM1 | CCGGCCATGACTCGAATATCTGAAACTCGAGTTTCAGATATTCGAGTCATGGTTTTTG | 1875 | chr17 | ENST00000269389.7 |
| SLURP1 | CCGGGTGCTTCCTGCAGGACCATTACTCGAGTAATGGTCCTGCAGGAAGCACTTTTTG | 1876 | chr8 | ENST00000246515.1 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| SLURP1 | CCGGAGACCTCTGCAACTCGGAACTCTCGAGAGTTCCGAGTTGCAGAGGTCTTTTTG | 1877 | chr8 | ENST00000246515.1 |
| SLURP1 | CCGGCTCAAGTGCTACACCTGCAAGCTCGAGCTTGCAGGTGTAGCACTTGAGTTTTTG | 1878 | chr8 | ENST00000246515.1 |
| SOSTDC1 | CCGGGATGCCACAGAAATCCTTTATCTCGAGATAAAGGATTTCTGTGGCATCTTTTTG | 1879 | chr7 | ENST00000307068.4 |
| SOSTDC1 | CCGGGGAACTGCGTTCCACCAAATACTCGAGTATTGGTGGAACGCAGTTCCTTTTTG | 1880 | chr7 | ENST00000307068.4 |
| SOSTDC1 | CCGGTGAATCTTCACAGTAACATTTCTCGAGAAATGTTACTGTGAAGATTCATTTTTG | 1881 | chr7 | ENST00000307068.4 |
| SP100 | CCGGGAAGTGAGCCTGTGATCAATACTCGAGTATTGATCACAGGCTCACTTCTTTTTG | 1882 | chr2 | ENST00000340126.8 |
| SP100 | CCGGTATACGCTGCGGTGGATATACCTCGAGGTATATCCACCGCAGCGTATATTTTTG | 1883 | chr2 | ENST00000340126.8 |
| SP100 | CCGGTCGTGATCTCATCACAAATAACTCGAGTTATTTGTGATGAGATCACGATTTTTG | 1884 | chr2 | ENST00000340126.8 |
| SPI1 | CCGGGCCCTATGACACGGATCTATACTCGAGTATAGATCCGTGTCATAGGGCTTTTTG | 1885 | chr11 | ENST00000378538.7 |
| SPI1 | CCGGAGAGCTTCGCCGAGAACAACTCTCGAGAGTTGTTCTCGGCGAAGCTCTTTTTG | 1886 | chr11 | ENST00000378538.7 |
| SPI1 | CCGGCGGATCTATACCAACGCCAAACTCGAGTTTGGCGTTGGTATAGATCCGTTTTTG | 1887 | chr11 | ENST00000378538.7 |
| SPI1 | CCGGCCGTATGTAAATCAGATCTCCCTCGAGGGAGATCTGATTTACATACGGTTTTTG | 1888 | chr11 | ENST00000378538.7 |
| SPP1 | CCGGCCACAAGCAGTCCAGATTATACTCGAGTATAATCTGGACTGCTTGTGGTTTTTG | 1889 | chr4 | ENST00000237623.11 |
| SPP1 | CCGGCCGAGGTGATAGTGTGGTTTACTCGAGTAAACCACACTATCACCTCGGTTTTTG | 1890 | chr4 | ENST00000237623.11 |
| SPP1 | CCGGCTTCAGGGTTATGTCTATGTTCTCGAGAACATAGACATAACCCTGAAGTTTTTG | 1891 | chr4 | ENST00000237623.11 |
| TBX21 | CCGGGCCCTAACTACAGTCGTTTACCTCGAGGTAAACGACTGTAGTTAGGGCTTTTTG | 1892 | ch17 | ENST00000177694.1 |
| TBX21 | CCGGCCTGTTGTGGTCCAAGTTTAACTCGAGTTAAACTTGGACCACAACAGGTTTTTG | 1893 | ch17 | ENST00000177694.1 |
| TBX21 | CCGGCGCTTCCAACACGCATATCTTCTCGAGAAGATATGCGTGTTGGAAGCGTTTTTG | 1894 | ch17 | ENST00000177694.1 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| TBX21 | CCGGACAATGTGACCCAGATGA TTGCTCGAGCAATCATCTGGGT CACATTGTTTTTG | 1895 | ch17 | ENST00000177694.1 |
| TCAP | CCGGCTTTGTAGTTTGCCCAGA GTTCTCGAGAACTCTGGGCAAA CTACAAAGTTTTTG | 1896 | chr17 | ENST00000309889.2 |
| TCAP | CCGGGCCATGGCTGCTTTGTA GTTCTCGAGAACTACAAAGCAG CCATGGCCTTTTTG | 1897 | chr17 | ENST00000309889.2 |
| TCAP | CCGGGGTGGCTGAGATCACAAA GCACTCGAGTGCTTTGTGATCT CAGCCACCTTTTTG | 1898 | chr17 | ENST00000309889.2 |
| TGFB1 | CCGGACTGCGGATCTCTGTGTC ATTCTCGAGAATGACACAGAGA TCCGCAGTTTTTG | 1899 | chr19 | ENST00000221930.5 |
| TGFB1 | CCGGCCACAACGAAATCTATGA CAACTCGAGTTGTCATAGATTT CGTTGTGGTTTTTG | 1900 | chr19 | ENST00000221930.5 |
| TGFB1 | CCGGCCACAACGAAATCTATGA CAACTCGAGTTGTCATAGATTT CGTTGTGGTTTTTG | 1901 | chr19 | ENST00000221930.5 |
| TGFB2 | CCGGGCGGCCTATTGCTTTAGA AATCTCGAGATTTCTAAAGCAA TAGGCCGCTTTTTG | 1902 | chr1 | ENST00000366930.8 |
| TGFB2 | CCGGGCTGGAGCATGCCCGTAT TTACTCGAGTAAATACGGGCAT GCTCCAGCTTTTTG | 1903 | chr1 | ENST00000366930.8 |
| TGFB2 | CCGGTTGCTGCCTACGTCCACTT TACTCGAGTAAAGTGGACGTAG GCAGCAATTTTTG | 1904 | chr1 | ENST00000366930.8 |
| TGFB3 | CCGGCATTGCCAAACAGCGCTA TATCTCGAGATATAGCGCTGTT TGGCAATGTTTTTG | 1905 | chr14 | ENST00000238682.7 |
| TGFB3 | CCGGGCTCTAGGGAATCTGGAT TATCTCGAGATAATCCAGATTC CCTAGAGCTTTTTG | 1906 | chr14 | ENST00000238682.7 |
| TGFB3 | CCGGCGGAATACTATGCCAAAG AAACTCGAGTTTCTTTGGCATA GTATTCCGTTTTTG | 1907 | chr14 | ENST00000238682.7 |
| TGFBR1 | CCGGGCCTTGAGAGTAATGGCT AAACTCGAGTTTAGCCATTACT CTCAAGGCTTTTTG | 1908 | chr9 | ENST00000374994.8 |
| TGFBR1 | CCGGCTCATGTTGATGGTCTAT ATCCTCGAGGATATAGACCATC AACATGAGTTTTTG | 1909 | chr9 | ENST00000374994.8 |
| TGFBR1 | CCGGGAAGTTGCTGTTAAGATA TTCCTCGAGGAATATCTTAACA GCAACTTCTTTTTG | 1910 | chr9 | ENST00000374994.8 |
| TGFBR2 | CCGGCGTTCAGAAGTCGGTTAA TAACTCGAGTTATTAACCGACT TCTGAACGTTTTTG | 1911 | chr3 | ENST00000295754.9 |
| TGFBR2 | CCGGCTCTAGGCTTTATCGTGTT TACTCGAGTAAACACGATAAAG CCTAGAGTTTTTG | 1912 | chr3 | ENST00000295754.9 |

TABLE 15-continued

5' to 3' (Forward) shRNA sequences for Silencing of Cytokine/Chemokine
Genes to Reduce the Incidence of CRS

| Target Gene Symbol | shRNA Forward Oligo Sequence | SEQ ID NO: | Location | Gene ID No. |
| --- | --- | --- | --- | --- |
| TGFBR2 | CCGGCTCAGGAAATGAGATTGA TTTCTCGAGAAATCAATCTCATT TCCTGAGTTTTTG | 1913 | chr3 | ENST00000295754.9 |
| TGFBR3 | CCGGGGAGTTGGTAAAGGGTTA ATACTCGAGTATTAACCCTTTA CCAACTCCTTTTTG | 1914 | chr1 | ENST00000212355.8 |
| TGFBR3 | CCGGTAATGGATTTCCGGGAGA TATCTCGAGATATCTCCCGGAA ATCCATTATTTTTG | 1915 | chr1 | ENST00000212355.8 |
| TGFBR3 | CCGGCACACCCAGGGCTAGTAT AAACTCGAGTTTATACTAGCCC TGGGTGTGTTTTTG | 1916 | chr1 | ENST00000212355.8 |
| THBS1 | CCGGGTAGGTTATGATGAGTTT AATCTCGAGATTAAACTCATCA TAACCTACTTTTTG | 1917 | chr15 | ENST00000260356.5 |
| THBS1 | CCGGCGTGACTGTAAGATTGTA AATCTCGAGATTTACAATCTTA CAGTCACGTTTTTG | 1918 | chr15 | ENST00000260356.5 |
| THBS1 | CCGGGAGATCCCTAATCATCAA ATTCTCGAGAATTTGATGATTA GGGATCTCTTTTTG | 1919 | chr15 | ENST00000260356.5 |
| THNSL2 | CCGGGAGCCGATCAAGACTGTG TTTCTCGAGAAACACAGTCTTG ATCGGCTCTTTTTG | 1920 | chr2 | ENST00000324166.6 |
| THNSL2 | CCGGGCTGCCATTGAGAGTGTT CAACTCGAGTTGAACACTCTCA ATGGCAGCTTTTTG | 1921 | chr2 | ENST00000324166.6 |
| THNSL2 | CCGGGCTGCCATTGAGAGTGTT CAACTCGAGTTGAACACTCTCA ATGGCAGCTTTTTG | 1922 | chr2 | ENST00000324166.6 |
| THPO | CCGGGACCTCCGAGTCCTCAGT AAACTCGAGTTTACTGAGGACT CGGAGGTCTTTTTG | 1923 | chr3 | ENST00000204615.11 |
| THPO | CCGGAGCTAGCTCTTTGGTCTA TTTCTCGAGAAATAGACCAAAG AGCTAGCTTTTTG | 1924 | chr3 | ENST00000204615.11 |
| THPO | CCGGCAACCTCCAGCCTGGATA TTCCTCGAGGAATATCCAGGCT GGAGGTTGTTTTTG | 1925 | chr3 | ENST00000204615.11 |
| TIMP1 | CCGGGCACAGTGTTTCCCTGTTT ATCTCGAGATAAACAGGGAAAC ACTGTGCTTTTTG | 1926 | chrX | ENST00000218388.8 |
| TIMP1 | CCGGGCACAGTGTTTCCCTGTTT ATCTCGAGATAAACAGGGAAAC ACTGTGCTTTTTG | 1927 | chrX | ENST00000218388.8 |
| TIMP1 | CCGGACAGACGGCCTTCTGCAA TTCCTCGAGGAATTGCAGAAGG CCGTCTGTTTTTG | 1928 | chrX | ENST00000218388.8 |
| TNF | CCGGGAACCCAAGCTTAGAACT TTACTCGAGTAAAGTTCTAAGC TTGGGTTCTTTTTG | 1929 | chr6 | ENST00000449264.2 |
| TNF | CCGGGGAGCCAGCTCCCTCTAT TTACTCGAGTAAATAGAGGGAG CTGGCTCCTTTTTG | 1930 | chr6 | ENST00000449264.2 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
| --- | --- | --- | --- | --- |
| TNF | CCGGTGGCGTGGAGCTGAGAGATAACTCGAGTTATCTCTCAGCTCCACGCCATTTTTG | 1931 | chr6 | ENST00000449264.2 |
| TNFRSF4 | CCGGGCACGTGGTGTAACCTCAGAACTCGAGTTCTGAGGTTACACCACGTGCTTTTTG | 1932 | chr1 | ENST00000379236.3 |
| TNFRSF4 | CCGGCAGCAATAGCTCGGACGCAATCTCGAGATTGCGTCCGAGCTATTGCTGTTTTTG | 1933 | chr1 | ENST00000379236.3 |
| TNFRSF4 | CCGGGACAGCTACAAGCCTGGAGTTCTCGAGAACTCCAGGCTTGTAGCTGTCTTTTTG | 1934 | chr1 | ENST00000379236.3 |
| TNFRSF4 | CCGGGCTTCTACAACGACGTGGTCACTCGAGTGACCACGTCGTTGTAGAAGCTTTTTG | 1935 | chr1 | ENST00000379236.3 |
| TNFRSF11 | CCGGTGTTTACTTGCCCGGTTTAATCTCGAGATTAAACCGGGCAAGTAAACATTTTTG | 1936 | chr18 | ENST00000586569.2 |
| TNFRSF11 | CCGGTGTACCAGTGAGAAGCATTATCTCGAGATAATGCTTCTCACTGGTACATTTTTG | 1937 | chr18 | ENST00000586569.2 |
| TNFRSF11 | CCGGTGGGACGGTGCTGTAACAAATCTCGAGATTTGTTACAGCACCGTCCCATTTTTG | 1938 | chr18 | ENST00000586569.2 |
| TNFRSF11 | CCGGGAAAGCACTCACAGCTAATTTCTCGAGAAATTAGCTGTGAGTGCTTTCTTTTTG | 1939 | chr8 | ENST00000297350.8 |
| TNFRSF11 | CCGGGATAAATGCTTGCTGCATAAACTCGAGTTTATGCAGCAAGCATTTATCTTTTTG | 1940 | chr8 | ENST00000297350.8 |
| TNFRSF11 | CCGGCCAGTGTGTGTTCATTGTAAACTCGAGTTTACAATGAACACACACTGGTTTTTG | 1941 | chr8 | ENST00000297350.8 |
| TNFRSF1A | CCGGAGAACCAGTACCGGCATTATTCTCGAGAATAATGCCGGTACTGGTTCTTTTTG | 1942 | chr12 | ENST00000162749.6 |
| TNFRSF1A | CCGGGGAGCTGTTGGTGGGAATATACTCGAGTATATTCCCACCAACAGCTCCTTTTTG | 1943 | chr12 | ENST00000162749.6 |
| TNFRSF1A | CCGGCTTGAAGGAACTACTACTAAGCTCGAGCTTAGTAGTAGTTCCTTCAAGTTTTTG | 1944 | chr12 | ENST00000162749.6 |
| TNFRSF9 | CCGGGCTCCGTTTCTCTGTTGTTAACTCGAGTTAACAACAGAGAAACGGAGCTTTTTG | 1945 | chr1 | ENST00000377507.7 |
| TNFRSF9 | CCGGCAAGAACACCATCCTACATAACTCGAGTTATGTAGGATGGTGTTCTTGTTTTTG | 1946 | chr1 | ENST00000377507.7 |
| TNFRSF9 | CCGGCAGTCCCTGTCCTCCAAATAGCTCGAGCTATTTGGAGGACAGGGACTGTTTTTG | 1947 | chr1 | ENST00000377507.7 |
| TNFSF9 | CCGGCAAGTTGGACCTTGATATTTACTCGAGTAAATATCAAGGTCCAACTTGTTTTTG | 1948 | chr19 | ENST00000245817.4 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| TNFSF9 | CCGGCTACTATGTCTTCTTTCAA CTCTCGAGAGTTGAAAGAAGAC ATAGTAGTTTTTG | 1949 | chr19 | ENST00000245817.4 |
| TNFSF9 | CCGGCCCTTCACCGAGGTCGGA ATACTCGAGTATTCCGACCTCG GTGAAGGGTTTTTG | 1950 | chr19 | ENST00000245817.4 |
| TNFSF9 | CCGGTGAGCTACAAAGAGGAC ACGACTCGAGTCGTGTCCTCTTT GTAGCTCATTTTTG | 1951 | chr19 | ENST00000245817.4 |
| TNFSF10 | CCGGAGAAATAGTTGTTGGTCT AAACTCGAGTTTAGACCAACAA CTATTTCTTTTTG | 1952 | chr3 | ENST00000241261.6 |
| TNFSF10 | CCGGAGTTATCCTGACCCTATA TTGCTCGAGCAATATAGGGTCA GGATAACTTTTTG | 1953 | chr3 | ENST00000241261.6 |
| TNFSF10 | CCGGGACAAACAAATGGTCCAA TATCTCGAGATATTGGACCATT TGTTTGTCTTTTTG | 1954 | chr3 | ENST00000241261.6 |
| TNFSF11 | CCGGCTAATGGTGTACGTCACT AAACTCGAGTTTAGTGACGTAC ACCATTAGTTTTTG | 1955 | chr13 | ENST00000398795.6 |
| TNFSF11 | CCGGCCGGATCAGGATGCAACA TACCTCGAGGTATGTTGCATCC TGATCCGGTTTTTG | 1956 | chr13 | ENST00000398795.6 |
| TNFSF11 | CCGGGCAGTATATTTCTTCGTTC TTCTCGAGAAGAACGAAGAAAT ATACTGCTTTTTG | 1957 | chr13 | ENST00000398795.6 |
| TNFSF12 | CCGGGTATTCCCACTCTTATCTT ACCTCGAGGTAAGATAAGAGTG GGAATACTTTTTG | 1958 | chr17 | ENST00000293825.10 |
| TNFSF12 | CCGGGGGCATTGTGTTCACTGT ACTCTCGAGAGTACAGTGAACA CAATGCCCTTTTTG | 1959 | chr17 | ENST00000293825.10 |
| TNFSF12 | CCGGCAGATGGAGGTTACACAA CTTCTCGAGAAGTTGTGTAACC TCCATCTGTTTTTG | 1960 | chr17 | ENST00000293825.10 |
| TNFSF12- | CCGGCCTCACCTACTTCGGACT CTTCTCGAGAAGAGTCCGAAGT AGGTGAGGTTTTTG | 1961 | chr17 | ENST00000293826.4 |
| TNFSF12- | CCGGCTGTACTGTCAGGTGCAC TTTCTCGAGAAAGTGCACCTGA CAGTACAGTTTTTG | 1962 | chr17 | ENST00000293826.4 |
| TNFSF12- | CCGGGCGCAGGCAGATGGAGG TTACCTCGAGGTAACCTCCATC TGCCTGCGCTTTTTG | 1963 | chr17 | ENST00000293826.4 |
| TNFSF13 | CCGGCAGTTGCCCTCTGGTTGA GTTCTCGAGAACTCAACCAGAG GGCAACTGTTTTTG | 1964 | chr17 | ENST00000338784.8 |
| TNFSF13 | CCGGATGGCTCTGCTGACCCAA CAACTCGAGTTGTTGGGTCAGC AGAGCCATTTTTG | 1965 | chr17 | ENST00000338784.8 |
| TNFSF13 | CCGGCCCAACAAACAGAGCTGC AGACTCGAGTCTGCAGCTCTGT TTGTTGGGTTTTTG | 1966 | chr17 | ENST00000338784.8 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| TNFSF13B | CCGGCCTGAAACACTACCCAAT AATCTCGAGATTATTGGGTAGT GTTTCAGGTTTTTG | 1967 | chr13 | ENST00000375887.8 |
| TNFSF13B | CCGGCTACGCCATGGGACATCT AATCTCGAGATTAGATGTCCCA TGGCGTAGTTTTTG | 1968 | chr13 | ENST00000375887.8 |
| TNFSF13B | CCGGGTGACTTTGTTTCGATGT ATTCTCGAGAATACATCGAAAC AAAGTCACTTTTTG | 1969 | chr13 | ENST00000375887.8 |
| TNFSF14 | CCGGTCCTGGGAGCAGCTGATA CAACTCGAGTTGTATCAGCTGC TCCCAGGATTTTTG | 1970 | chr19 | ENST00000599359.1 |
| TNFSF14 | CCGGGACAGACCGACATCCCAT TCACTCGAGTGAATGGGATGTC GGTCTGTCTTTTTG | 1971 | chr19 | ENST00000599359.1 |
| TNFSF14 | CCGGATGGGTCTGACACGTGGA GAACTCGAGTTCTCCACGTGTC AGACCCATTTTTG | 1972 | chr19 | ENST00000599359.1 |
| TNFSF15 | CCGGATTAAGACACTGATCACT AAACTCGAGTTTAGTGATCAGT GTCTTAATTTTTG | 1973 | chr9 | ENST00000374045.4 |
| TNFSF15 | CCGGGTCGGGAGACTACTTCAT TTACTCGAGTAAATGAAGTAGT CTCCCGACTTTTTG | 1974 | chr9 | ENST00000374045.4 |
| TNFSF15 | CCGGACTATAGGAGGAGAGCA AATACTCGAGTATTTGCTCTCCT CCTATAGTTTTTG | 1975 | chr9 | ENST00000374045.4 |
| TNFSF18 | CCGGCCTTCAGTTGGCTAATCTT TACTCGAGTAAAGATTAGCCAA CTGAAGGTTTTTG | 1976 | chr1 | ENST00000404377.3 |
| TNFSF18 | CCGGCTGAACCTCCTTGCGTGA ATACTCGAGTATTCACGCAAGG AGGTTCAGTTTTTG | 1977 | chr1 | ENST00000404377.3 |
| TNFSF18 | CCGGATGATACAAACTCTAACA AACCTCGAGGTTTGTTAGAGTT TGTATCATTTTTG | 1978 | chr1 | ENST00000404377.3 |
| TNFSF4 | CCGGGTGGCCTCTCTGACTTAC AAACTCGAGTTTGTAAGTCAGA GAGGCCACTTTTTG | 1979 | chr1 | ENST00000281834.3 |
| TNFSF4 | CCGGGCAGAACAACTCAGTCAT CATCTCGAGATGATGACTGAGT TGTTCTGCTTTTTG | 1980 | chr1 | ENST00000281834.3 |
| TNFSF4 | CCGGGCCAAGATTCGAGAGGA ACAACTCGAGTTGTTCCTCTCG AATCTTGGCTTTTTG | 1981 | chr1 | ENST00000281834.3 |
| TNFSF8 | CCGGACTGTATGGTCTTGATCT ATTCTCGAGAATAGATCAAGAC CATACAGTTTTTG | 1982 | chr9 | ENST00000223795.2 |
| TNFSF8 | CCGGCAAACTACACAGGGTATT AAACTCGAGTTTAATACCCTGT GTAGTTTGTTTTTG | 1983 | chr9 | ENST00000223795.2 |
| TNFSF8 | CCGGGTGGATACATTCCAGTAC ATACTCGAGTATGTACTGGAAT GTATCCACTTTTTG | 1984 | chr9 | ENST00000223795.2 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| TNFSF9 | CCGGCAAGTTGGACCTTGATAT TTACTCGAGTAAATATCAAGGT CCAACTTGTTTTTG | 1985 | chr19 | ENST00000245817.4 |
| TNFSF9 | CCGGCTACTATGTCTTCTTTCAA CTCTCGAGAGTTGAAAGAAGAC ATAGTAGTTTTTG | 1986 | chr19 | ENST00000245817.4 |
| TNFSF9 | CCGGCCCTTCACCGAGGTCGGA ATACTCGAGTATTCCGACCTCG GTGAAGGGTTTTTG | 1987 | chr19 | ENST00000245817.4 |
| TRIM16 | CCGGGCCGTTGTTCAGCGCAAA TATCTCGAGATATTTGCGCTGA ACAACGGCTTTTTG | 1988 | chr17 | ENST00000336708.11 |
| TRIM16 | CCGGGCCGTTGTTCAGCGCAAA TATCTCGAGATATTTGCGCTGA ACAACGGCTTTTTG | 1989 | chr17 | ENST00000336708.11 |
| TRIM16 | CCGGCCGCATCAGGTGAACATC AAACTCGAGTTTGATGTTCACC TGATGCGGTTTTTG | 1990 | chr17 | ENST00000336708.11 |
| TSLP | CCGGACTCAATGATAGCACCTA AACCTCGAGGTTTAGGTGCTAT CATTGAGTTTTTG | 1991 | chr5 | ENST00000344895.3 |
| TSLP | CCGGCGTCGCTTCAATCGACCT TTACTCGAGTAAAGGTCGATTG AAGCGACGTTTTTG | 1992 | chr5 | ENST00000344895.3 |
| TSLP | CCGGCCATCTTTATTATGGTCAT ATCTCGAGATATGACCATAATA AAGATGGTTTTTG | 1993 | chr5 | ENST00000344895.3 |
| TWSG1 | CCGGGACTGTGTTGGTATGTGT AATCTCGAGATTACACATACCA ACACAGTCTTTTTG | 1994 | chr18 | ENST00000262120.9 |
| TWSG1 | CCGGGCGCCTTATTCCAGTGAC AAACTCGAGTTTGTCACTGGAA TAAGGCGCTTTTTG | 1995 | chr18 | ENST00000262120.9 |
| TWSG1 | CCGGGAATCACTGAGCTGTAAC AAACTCGAGTTTGTTACAGCTC AGTGATTCTTTTTG | 1996 | chr18 | ENST00000262120.9 |
| TXLNA | CCGGGCACATACTGTGTGGACA ATACTCGAGTATTGTCCACACA GTATGTGCTTTTTG | 1997 | chr1 | ENST00000373609.1 |
| TXLNA | CCGGTGCTGATGCAGACATTGA ATACTCGAGTATTCAATGTCTG CATCAGCATTTTTG | 1998 | chr1 | ENST00000373609.1 |
| TXLNA | CCGGAGCGAGGTATTCACCACA TTCCTCGAGGAATGTGGTGAAT ACCTCGCTTTTTG | 1999 | chr1 | ENST00000373609.1 |
| VASN | CCGGAGCTTGACTACGCCGACT TTGCTCGAGCAAAGTCGGCGTA GTCAAGCTTTTTG | 2000 | chr16 | ENST00000304735.3 |
| VASN | CCGGAGCCAACAGGCTGCATGA AATCTCGAGATTTCATGCAGCC TGTTGGCTTTTTG | 2001 | chr16 | ENST00000304735.3 |
| VASN | CCGGGAGATCCTTTCCCATTTAT TCCTCGAGGAATAAATGGGAAA GGATCTCTTTTTG | 2002 | chr16 | ENST00000304735.3 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| VEGFA | CCGGCAAGATCCGCAGACGTGTAAACTCGAGTTTACACGTCTGCGGATCTTGTTTTTG | 2003 | chr6 | ENST00000425836.6 |
| VEGFA | CCGGCAAGATCCGCAGACGTGTAAACTCGAGTTTACACGTCTGCGGATCTTGTTTTTG | 2004 | chr6 | ENST00000425836.6 |
| VEGFA | CCGGGCGCAAGAAATCCCGGTATAACTCGAGTTATACCGGGATTTCTTGCGCTTTTTG | 2005 | chr6 | ENST00000425836.6 |
| VSTM1 | CCGGATGAATATGCGGCACTGAAAGCTCGAGCTTTCAGTGCCGCATATTCATTTTTTG | 2006 | chr19 | ENST00000338372.6 |
| VSTMI | CCGGCATTCCCAGAATGTGACATTTCTCGAGAAATGTCACATTCTGGGAATGTTTTTG | 2007 | chr19 | ENST00000338372.6 |
| VSTM1 | CCGGGAGTGACCTATGCTGAGCTAACTCGAGTTAGCTCAGCATAGGTCACTCTTTTTG | 2008 | chr19 | ENST00000338372.6 |
| WFIKKN1 | CCGGTGCGCCCTGATCAGATGTATGCTCGAGCATACATCTGATCAGGGCGCATTTTTG | 2009 | chr16 | ENST00000319070.2 |
| WFIKKN1 | CCGGGGACGTGCTCAAGGATGACAACTCGAGTTGTCATCCTTGAGCACGTCCTTTTTG | 2010 | chr16 | ENST00000319070.2 |
| WFIKKN1 | CCGGAGTGCTGCATCAACGTGTGTGCTCGAGCACACACGTTGATGCAGCACTTTTTG | 2011 | chr16 | ENST00000319070.2 |
| WFIKKN2 | CCGGTCAAGTTCTTGGGCACCAAGTCTCGAGACTTGGTGCCCAAGAACTTGATTTTTG | 2012 | chr17 | ENST00000311378.4 |
| WFIKKN2 | CCGGTACAACCGCTGCTATATGGACCTCGAGGTCCATATAGCAGCGGTTGTATTTTTG | 2013 | chr17 | ENST00000311378.4 |
| WFIKKN2 | CCGGCACCAGCTTGCTCAGATATTCCTCGAGGAATATCTGAGCAAGCTGGTGTTTTTG | 2014 | chr17 | ENST00000311378.4 |
| WNT1 | CCGGCTGTCGAGAAACGGCGTTTATCTCGAGATAAACGCCGTTTCTCGACAGTTTTTG | 2015 | chr12 | ENST00000293549.3 |
| WNT1 | CCGGGACCTCGTCTACTTCGAGAAACTCGAGTTTCTCGAAGTAGACGAGGTCTTTTTG | 2016 | chr12 | ENST00000293549.3 |
| WNT1 | CCGGGCCACGAGTTTGGATGTTGTACTCGAGTACAACATCCAAACTCGTGGCTTTTTG | 2017 | chr12 | ENST00000293549.3 |
| WNT2 | CCGGCCACAAATGGTCCCAATTAAGCTCGAGCTTAATTGGGACCATTTGTGGTTTTTG | 2018 | chr7 | ENST00000265441.7 |
| WNT2 | CCGGTCGGGAATCTGCCTTTGTTTACTCGAGTAAACAAAGGCAGATTCCCGATTTTTG | 2019 | chr7 | ENST00000265441.7 |
| WNT2 | CCGGTTGACTATGGGATCAAATTTGCTCGAGCAAATTTGATCCCATAGTCAATTTTTG | 2020 | chr7 | ENST00000265441.7 |

TABLE 15-continued

5' to 3' (Forward) shRNA sequences for Silencing of Cytokine/Chemokine Genes to Reduce the Incidence of CRS

| Target Gene Symbol | shRNA Forward Oligo Sequence | SEQ ID NO: | Location | Gene ID No. |
|---|---|---|---|---|
| WNT5A | CCGGCTCCCAGGACCCGCTTAT TTACTCGAGTAAATAAGCGGGT CCTGGGAGTTTTTG | 2021 | chr3 | ENST00000264634.8 |
| WNT5A | CCGGCAAAGAATGCCAGTATCA ATTCTCGAGAATTGATACTGGC ATTCTTTGTTTTTG | 2022 | chr3 | ENST00000264634.8 |
| WNT5A | CCGGCCTGTTCAGATGTCAGAA GTACTCGAGTACTTCTGACATC TGAACAGGTTTTTG | 2023 | chr3 | ENST00000264634.8 |
| WNT7A | CCGGCATAGGAGAAGGCTCACA AATCTCGAGATTTGTGAGCCTT CTCCTATGTTTTTG | 2024 | chr3 | ENST00000285018.4 |
| WNT7A | CCGGGGCGCAAGCATCATCTGT AACCTCGAGGTTACAGATGATG CTTGCGCCTTTTTG | 2025 | chr3 | ENST00000285018.4 |
| WNT7A | CCGGTCTTCGGGAAGGAGCTCA AAGCTCGAGCTTTGAGCTCCTT CCCGAAGATTTTTG | 2026 | chr3 | ENST00000285018.4 |
| XCL1 | CCGGGCTGTGACAATGGCAACA ATTCTCGAGAATTGTTGCCATT GTCACAGCTTTTTG | 2027 | chr1 | ENST00000367818.3 |
| XCL1 | CCGGTTCAACTTGTCTCTATAAT AGCTCGAGCTATTATAGAGACA AGTTGAATTTTTG | 2028 | chr1 | ENST00000367818.3 |
| XCL1 | CCGGAGATTCTGGCTAGTGTCT ATCCTCGAGGATAGACACTAGC CAGAATCTTTTTG | 2029 | chr1 | ENST00000367818.3 |
| XCL2 | CCGGACTGCCAGTTAGCAGAAT CAACTCGAGTTGATTCTGCTAA CTGGCAGTTTTTG | 2030 | chr1 | ENST00000367819.2 |
| XCL2 | CCGGGTAGGGAGTGAAGTCTCA CATCTCGAGATGTGAGACTTCA CTCCCTACTTTTTG | 2031 | chr1 | ENST00000367819.2 |
| XCL2 | CCGGGAAATCCAACACCAGAA ATAACTCGAGTTATTTCTGGTGT TGGATTTCTTTTTG | 2032 | chr1 | ENST00000367819.2 |
| ZFP36 | CCGGGATCCGACCCTGATGAAT ATGCTCGAGCATATTCATCAGG GTCGGATCTTTTTG | 2033 | chr19 | ENST00000597629.1 |
| ZFP36 | CCGGATCTGTCTCCTAGAATCTT ATCTCGAGATAAGATTCTAGGA GACAGATTTTTTG | 2034 | chr19 | ENST00000597629.1 |
| ZFP36 | CCGGCCCTTTATTTATGACGACT TTCTCGAGAAAGTCGTCATAAA TAAAGGGTTTTTG | 2035 | chr19 | ENST00000597629.1 |

TABLE 16

3' to 5' (Reverse) shRNA sequences for Silencing of Cytokine/Chemokine
Genes to Reduce the Incidence of CRS

| Target Gene Symbol | shRNA Reverse Oligo Sequence | SEQ ID NO: | Location | Gene ID No. |
|---|---|---|---|---|
| A2M | AATTCAAAAAGGCGTCCCTATACCAAATAACTCGAGTTATTTGGTATAGGGACGCCT | 2036 | chr12 | ENST00000318602.11 |
| A2M | AATTCAAAAAGACTGCATCAATCGTCATAACTCGAGTTATGACGATTGATGCAGTCT | 2037 | chr12 | ENST00000318602.11 |
| A2M | AATTCAAAAACCTCCAGACATCCTTGAAATACTCGAGTATTTCAAGGATGTCTGGAGG | 2038 | chr12 | ENST00000318602.11 |
| ACKR1 | AATTCAAAAATCCTGTGGGCCTGGTTTATTCTCGAGAATAAACCAGGCCCACAGGAT | 2039 | chr1 | ENST00000368122.2 |
| ACKR1 | AATTCAAAAATGGCAGAAGCCCTGGCAATTTCTCGAGAAATTGCCAGGGCTTCTGCCA | 2040 | chr1 | ENST00000368122.2 |
| ACKR1 | AATTCAAAAAGGCGGATGGTTGAGATCTATCCTCGAGGATAGATCTCAACCATCCGCC | 2041 | chr1 | ENST00000368122.2 |
| ACKR2 | AATTCAAAAAGAGCACTCTTTATACTATTAACTCGAGTTAATAGTATAAAGAGTGCTC | 2042 | chr3 | ENST00000422265.5 |
| ACKR2 | AATTCAAAAAGTGGAACTGCCACGCAGATTTCTCGAGAAATCTGCGTGGCAGTTCCAC | 2043 | chr3 | ENST00000422265.5 |
| ACKR2 | AATTCAAAAACATTGGGTCTTCGGGAGTTTCCTCGAGGAAACTCCCGAAGACCCAATG | 2044 | chr3 | ENST00000422265.5 |
| ACKR3 | AATTCAAAAACACTATTGGTGTACCTTATAACTCGAGTTATAAGGTACACCAATAGTG | 2045 | chr2 | ENST00000272928.3 |
| ACKR3 | AATTCAAAAAGGCATAGTGCTGACATATATTCTCGAGAATATATGTCAGCACTATGCC | 2046 | chr2 | ENST00000272928.3 |
| ACKR3 | AATTCAAAAAGCCGTTCCCTTCTCCATTATCCTCGAGGATAATGGAGAAGGGAACGGC | 2047 | chr2 | ENST00000272928.3 |
| ACVR1 | AATTCAAAAATGATAATTCCCTCGACAAATTCTCGAGAATTTGTCGAGGGAATTATCA | 2048 | chr2 | ENST00000263640.7 |
| ACVR1 | AATTCAAAAAGCAGAACGTATTTAGCCATTACTCGAGTAATGGCTAAATACGTTCTGC | 2049 | chr2 | ENST00000263640.7 |
| ACVR1 | AATTCAAAAACTGGTCTGTCTTTGGATAATACTCGAGTATTATCCAAAGACAGACCAG | 2050 | chr2 | ENST00000263640.7 |
| ACVR2B | AATTCAAAAATGTCACGAGGCCTCTCATACCTCGAGGTATGAGAGGCCTCGTGACAT | 2051 | chr3 | ENST00000352511.4 |
| ACVR2B | AATTCAAAAACCCAGCTCATGAATGACTTTGCTCGAGCAAAGTCATTCATGAGCTGGG | 2052 | chr3 | ENST00000352511.4 |
| ACVR2B | AATTCAAAAACTTTGGCTTGGCTGTTCGATTCTCGAGAATCGAACAGCCAAGCCAAAG | 2053 | chr3 | ENST00000352511.4 |
| ACVRL1 | AATTCAAAAACCGGGAGACTGAGATCTATAACTCGAGTTATAGATCTCAGTCTCCCGG | 2054 | chr12 | ENST00000388922.8 |
| ACVRL1 | AATTCAAAAACAGGAGCACCTGATTCCTTTCCTCGAGGAAAGGAATCAGGTGCTCCTG | 2055 | chr12 | ENST00000388922.8 |
| ACVRL1 | AATTCAAAAACGTGGAGATCTTCGGTACACACTCGAGTGTGTACCGAAGATCTCCACG | 2056 | chr12 | ENST00000388922.8 |
| ADIPOQ | AATTCAAAAAGTTGGAGGCCTTTAGATATTACTCGAGTAATATCTAAAGGCCTCCAAC | 2057 | chr3 | ENST00000320741.6 |
| ADIPOQ | AATTCAAAAAATGCTCATATCAATCCTATAACTCGAGTTATAGGATTGATATGAGCAT | 2058 | chr3 | ENST00000320741.6 |
| ADIPOQ | AATTCAAAAACGGTTAGGAAGTTGATTATTCTCGAGAATAATCAACTTCCTAACCGT | 2059 | chr3 | ENST00000320741.6 |
| AGER | AATTCAAAAACACACTGCAGTCGGAGCTAATCTCGAGATTAGCTCCGACTGCAGTGTG | 2060 | chr6 | ENST00000375076.8 |
| AGER | AATTCAAAAAGAAGCCAGAAATTGTAGATTCCTCGAGGAATCTACAATTTCTGGCTTC | 2061 | chr6 | ENST00000375076.8 |
| AGER | AATTCAAAAATGCTGATCCTCCCTGAGATAGCTCGAGCTATCTCAGGGAGGATCAGCA | 2062 | chr6 | ENST00000375076.8 |
| AGRN | AATTCAAAAAGAGTTCTGTGTGGAAGATAAACTCGAGTTTATCTTCCACACAGAACTC | 2063 | chr1 | ENST00000379370.6 |
| AGRN | AATTCAAAAAGCGCACGTATGACAGTGATTGCTCGAGCAATCACTGTCATACGTGCGC | 2064 | chr1 | ENST00000379370.6 |
| AGRN | AATTCAAAAACGACGGAGTCACCTACGAAACTCGAGTTTCGTAGGTGACTCCGTCGT | 2065 | chr1 | ENST00000379370.6 |
| AHR | AATTCAAAAACGGCATAGAGACCGACTTAATCTCGAGATTAAGTCGGTCTCTATGCCG | 2066 | chr7 | ENST00000242057.8 |
| AHR | AATTCAAAAAGCGGCATAGAGACCGACTTACTCGAGTTAAGTCGGTCTCTATGCCGC | 2067 | chr7 | ENST00000242057.8 |
| AHR | AATTCAAAAATCCACAGTCAGCCATAATAACTCGAGTTATTATGGCTGACTGTGGAT | 2068 | chr7 | ENST00000242057.8 |
| AHR | AATTCAAAAACTGCTTAAAGTTGGTATTAACTCGAGTTAATACCAACTTTAAGCAGT | 2069 | chr7 | ENST00000242057.8 |
| AIMP1 | AATTCAAAAACAGCCTGATCTTCACACTAATCTCGAGATTAGTGTGAAGATCAGGCTG | 2070 | chr4 | ENST00000358008.7 |
| AIMP1 | AATTCAAAAAGAAGTAGATGTCGGAGAAATCTCGAGATTTCTCCGACATCTACTTCT | 2071 | chr4 | ENST00000358008.7 |
| AIMP1 | AATTCAAAAAGCCAGAGTAACCCTGACTAATCTCGAGATTAGTCAGGGTTACTCTGGC | 2072 | chr4 | ENST00000358008.7 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
|---|---|---|---|---|
| AREG | AATTCAAAAACCTCTTTCCAGTGGATCATAACTCGAGTTATGATCCACTGGAAAGAGG | 2073 | chr4 | ENST00000395748.7 |
| AREG | AATTCAAAAATACTCGGCTCAGGCCATTATGCTCGAGCATAATGGCCTGAGCCGAGTA | 2074 | chr4 | ENST00000395748.7 |
| AREG | AATTCAAAAAATTCACGGAGAATGCAAATATCTCGAGATATTTGCATTCTCCGTGAAT | 2075 | chr4 | ENST00000395748.7 |
| BCL6 | AATTCAAAAATGTGCCACAGCAATATCTATTCTCGAGAATAGATATTGCTGTGGCACA | 2076 | chr3 | ENST00000406870.6 |
| BCL6 | AATTCAAAAACTGCGTTAAAGGCTCGATTTCTCGAGAAATCGAGCCTTTAACGCAGT | 2077 | chr3 | ENST00000406870.6 |
| BCL6 | AATTCAAAAACCGGCTCAATAACATCGTTAACTCGAGTTAACGATGTTATTGAGCCGG | 2078 | chr3 | ENST00000406870.6 |
| BCL6 | AATTCAAAAACAAGCCAGCCGGCTCAATAACTCGAGTTATTGAGCCGGCTGGCTTGT | 2079 | chr3 | ENST00000406870.6 |
| BMP1 | AATTCAAAAACTGACGAGGACAGCTATATTCTCGAGAATATAGCTGTCCTCGTCAGT | 2080 | chr8 | ENST00000306385.9 |
| BMP1 | AATTCAAAAAGCTCGTAAGTCCTCCATCAAACTCGAGTTTGATGGAGGACTTACGAGC | 2081 | chr8 | ENST00000306385.9 |
| BMP1 | AATTCAAAAACAGCTGTGCCTACGACTATCCTCGAGGATAGTCGTAGGCACAGCTGT | 2082 | chr8 | ENST00000306385.9 |
| BMP10 | AATTCAAAAAGCAAGACGGTGTCGACTTTACTCGAGTAAAGTCGACACCGTCTTGCT | 2083 | chr2 | ENST00000295379.1 |
| BMP10 | AATTCAAAAAGCGTCGTCACCTACAAGTTTACTCGAGTAAACTTGTAGGTGACGACGC | 2084 | chr2 | ENST00000295379.1 |
| BMP10 | AATTCAAAAACATGGCTGAACTTAGGCTATACTCGAGTATAGCCTAAGTTCAGCCATG | 2085 | chr2 | ENST00000295379.1 |
| BMP15 | AATTCAAAAATACTACGCGATGGTCTCAATTCTCGAGAATTGAGACCATCGCGTAGTA | 2086 | chrX | ENST00000252677.3 |
| BMP15 | AATTCAAAAAGCCTTCTTGTTACTCTATTTCCTCGAGGAAATAGAGTAACAAGAAGGC | 2087 | chrX | ENST00000252677.3 |
| BMP15 | AATTCAAAAATGGAACACAGGGCCCAAATGCTCGAGCATTTGGGCCCTGTGTTCCAT | 2088 | chrX | ENST00000252677.3 |
| BMP2 | AATTCAAAAAGATCATCTGAACTCCACTAATCTCGAGATTAGTGGAGTTCAGATGATC | 2089 | chr20 | ENST00000378827.4 |
| BMP2 | AATTCAAAAACCGGAGATTCTTCTTTAATTTCTCGAGAAATTAAAGAAGAATCTCCGG | 2090 | chr20 | ENST00000378827.4 |
| BMP2 | AATTCAAAAACAAGATGCTTTAGGAAACAATCTCGAGATTGTTTCCTAAAGCATCTTG | 2091 | chr20 | ENST00000378827.4 |
| BMP3 | AATTCAAAAACTTACAGGGACACCGGAATTTCTCGAGAAATTCCGGTGTCCCTGTAAG | 2092 | chr4 | ENST00000282701.2 |
| BMP3 | AATTCAAAAAGGCCAAATCTCATCGAGATATCTCGAGATATCTCGATGAGATTTGGCC | 2093 | chr4 | ENST00000282701.2 |
| BMP3 | AATTCAAAAAGTGGATTGAACCTCGGAATTGCTCGAGCAATTCCGAGGTTCAATCCAC | 2094 | chr4 | ENST00000282701.2 |
| BMP4 | AATTCAAAAACCCTGGTCAATTCTGTCAATTCTCGAGAATTGACAGAATTGACCAGGG | 2095 | chr14 | ENST00000245451.8 |
| BMP4 | AATTCAAAAATCCTTGAGGATAGACAGATATCTCGAGATATCTGTCTATCCTCAAGGA | 2096 | chr14 | ENST00000245451.8 |
| BMP4 | AATTCAAAAAGGGCCAGCATGTCAGGATTACTCGAGTAATCCTGACATGCTGGCCCT | 2097 | chr14 | ENST00000245451.8 |
| BMP5 | AATTCAAAAATGGACGCAGTATCAACGTAAACTCGAGTTTACGTTGATACTGCGTCCA | 2098 | chr6 | ENST00000370830.3 |
| BMP5 | AATTCAAAAACCAGAAGGATACGCTGCATTTCTCGAGAAATGCAGCGTATCCTTCTGG | 2099 | chr6 | ENST00000370830.3 |
| BMP5 | AATTCAAAAATGCCACCAACCACGCTATAGCTCGAGCTATAGCGTGGTTGGTGGCAT | 2100 | chr6 | ENST00000370830.3 |
| BMP6 | AATTCAAAAATACAGGAATATGGTTGTAAGCTCGAGCTTACAACCATATTCCTGTAT | 2101 | chr6 | ENST00000283147.6 |
| BMP6 | AATTCAAAAACGCCGACAACAGAGTCGTAATCTCGAGATTACGACTCTGTTGTCGGCG | 2102 | chr6 | ENST00000283147.6 |
| BMP6 | AATTCAAAAACTGTCTATCAAAGGTAGATTTCTCGAGAAATCTACCTTTGATAGACAG | 2103 | chr6 | ENST00000283147.6 |
| BMP7 | AATTCAAAAACGTTCCGGATCAGCGTTTATCTCGAGATAAACGCTGATCCGGAACGT | 2104 | chr20 | ENST00000395863.7 |
| BMP7 | AATTCAAAAACTCGTTTCCAGAGGTAATTACTCGAGTAATTACCTCTGGAAACGAGT | 2105 | chr20 | ENST00000395863.7 |
| BMP7 | AATTCAAAAACCATCGAGAGTTCCGGTTTGCTCGAGCAAACCGGAACTCTCGATGGT | 2106 | chr20 | ENST00000395863.7 |
| BMP8A | AATTCAAAAAGGGTGCAGTTAGCATATTAGCTCGAGCTAATATGCTAACTGCACCCT | 2107 | chr1 | ENST00000331593.5 |
| BMP8A | AATTCAAAAAGCACAGAAGTCCTATCTTAGCTCGAGCTAAGATAGGACTTCTGTGCT | 2108 | chr1 | ENST00000331593.5 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
|---|---|---|---|---|
| BMP8A | AATTCAAAAAGGTACAACACTGGCCATTTCCTCGAGGAAATGGCCAGTGTTGTACCT | 2109 | chr1 | ENST00000331593.5 |
| BMP8B | AATTCAAAAACCAAGGCTACTCGGCCTATTACTCGAGTAATAGGCCGAGTAGCCTTGG | 2110 | chr1 | ENST00000372827.7 |
| BMP8B | AATTCAAAAAGACCCTCACAACCACGTACATCTCGAGATGTACGTGGTTGTGAGGGTC | 2111 | chr1 | ENST00000372827.7 |
| BMP8B | AATTCAAAAACGTTAACATGGTGGAGCGAGACTCGAGTCTCGCTCCACCATGTTAACG | 2112 | chr1 | ENST00000372827.7 |
| BMPR2 | AATTCAAAAAGAACGGCTATGTGCGTTTAAACTCGAGTTTAAACGCACATAGCCGTTC | 2113 | chr2 | ENST00000374580.8 |
| BMPR2 | AATTCAAAAAGCCTATGGAGTGAAATTATTTCTCGAGAAATAATTTCACTCCATAGGC | 2114 | chr2 | ENST00000374580.8 |
| BMPR2 | AATTCAAAAAATTACCACGAGGAGATCATTACTCGAGTAATGATCTCCTCGTGGTAAT | 2115 | chr2 | ENST00000374580.8 |
| C10orf99 | AATTCAAAAACATCATGTGAGGCTCTGTAAACTCGAGTTTACAGAGCCTCACATGATG | 2116 | chr10 | ENST00000372126.3 |
| C10orf99 | AATTCAAAAACCCAACTCAACAAACCTGAAACTCGAGTTTCAGGTTTGTTGAGTTGGG | 2117 | chr10 | ENST00000372126.3 |
| C10orf99 | AATTCAAAAAGCCATCAACTTTCAGAGCTATCTCGAGATAGCTCTGAAAGTTGATGGC | 2118 | chr10 | ENST00000372126.3 |
| C1QTNF4 | AATTCAAAAAACACCGAGTTCGTCAACATTGCTCGAGCAATGTTGACGAACTCGGTGT | 2119 | chr11 | ENST00000302514.3 |
| C1QTNF4 | AATTCAAAAAGCGTAAGACGCTGTCGGTTAACTCGAGTTAACCGACAGCGTCTTACGC | 2120 | chr11 | ENST00000302514.3 |
| C1QTNF4 | AATTCAAAAACGAGGTGCAGGCCATGATTTACTCGAGTAAATCATGGCCTGCACCTCG | 2121 | chr11 | ENST00000302514.3 |
| C5 | AATTCAAAAAACGATGGAGCCTGCGTTAATACTCGAGTATTAACGCAGGCTCCATCGT | 2122 | chr9 | ENST00000223642.2 |
| C5 | AATTCAAAAATCCCGACTTCTGGTCTATTACCTCGAGGTAATAGACCAGAAGTCGGGA | 2123 | chr9 | ENST00000223642.2 |
| C5 | AATTCAAAAAGCCCGAGAGAACAGCTTATATCTCGAGATATAAGCTGTTCTCTCGGGC | 2124 | chr9 | ENST00000223642.2 |
| CCL1 | AATTCAAAAAGCAATCCTGTGTTACAGAAATCTCGAGATTTCTGTAACACAGGATTGC | 2125 | chr17 | ENST00000225842.3 |
| CCL1 | AATTCAAAAACTGCTCCAATGAGGGCTTAATCTCGAGATTAAGCCCTCATTGGAGCAG | 2126 | chr17 | ENST00000225842.3 |
| CCL1 | AATTCAAAAACCTGAGGGCAATCCTGTGTTACTCGAGTAACACAGGATTGCCCTCAGG | 2127 | chr17 | ENST00000225842.3 |
| CCL11 | AATTCAAAAACCAACTCCAAAGCCATAAATACTCGAGTATTTATGGCTTTGGAGTTGG | 2128 | chr17 | ENST00000305869.3 |
| CCL11 | AATTCAAAAACATTCTGAGGTAACCTCATTACTCGAGTAATGAGGTTACCTCAGAATG | 2129 | chr17 | ENST00000305869.3 |
| CCL11 | AATTCAAAAATCCTCCATGAATATCAGTTATCTCGAGATAACTGATATTCATGGAGGA | 2130 | chr17 | ENST00000305869.3 |
| CCL13 | AATTCAAAAATGGAATACTTCTACCATAATTCTCGAGAATTATGGTAGAAGTATTCCA | 2131 | chr17 | ENST00000225844.6 |
| CCL13 | AATTCAAAAATCAAGCTGGAGTACGTGAAATCTCGAGATTTCACGTACTCCAGCTTGA | 2132 | chr17 | ENST00000225844.6 |
| CCL13 | AATTCAAAAAACTCAACGTCCCATCTACTTGCTCGAGCAAGTAGATGGGACGTTGAGT | 2133 | chr17 | ENST00000225844.6 |
| CCL14 | AATTCAAAAACCTAGGGACCAAGACTGAATCCTCGAGGATTCAGTCTTGGTCCCTAGG | 2134 | chr17 | ENST00000618404.4 |
| CCL14 | AATTCAAAAACAGCGGATTATGGATTACTATCTCGAGATAGTAATCCATAATCCGCTG | 2135 | chr17 | ENST00000618404.4 |
| CCL14 | AATTCAAAAACAAGCCCGGAATTGTCTTCATCTCGAGATGAAGACAATTCCGGGCTTG | 2136 | chr17 | ENST00000618404.4 |
| CCL15 | AATTCAAAAAGCTGAAGCCCTACTCAATATACTCGAGTATATTGAGTAGGGCTTCAGC | 2137 | chr17 | ENST00000617897.1 |
| CCL15 | AATTCAAAAACAGAGTTAATGATGTCAAAGCTCGAGCTTTGACATCATTAACTCTGT | 2138 | chr17 | ENST00000617897.1 |
| CCL15 | AATTCAAAAATCCCGTGTTCACTCATGAAACTCGAGTTTCATGAGTGAACACGGGAT | 2139 | chr17 | ENST00000617897.1 |
| CCL16 | AATTCAAAAAGGAGAAGTATTTCGAATATTCTCGAGAATATTCGAAATACTTCTCCT | 2140 | chr17 | ENST00000611905.1 |
| CCL16 | AATTCAAAAAGGAACTTGTCCACGGTTAAACTCGAGTTTAACCGTGGACAAGTTCCT | 2141 | chr17 | ENST00000611905.1 |
| CCL16 | AATTCAAAAACTGCCTGAAGTATTATGAGAACTCGAGTTCTCATAATACTTCAGGCAG | 2142 | chr17 | ENST00000611905.1 |
| CCL17 | AATTCAAAAAGAGAGTGAAGAATGCAGTTAACTCGAGTTAACTGCATTCTTCACTCTC | 2143 | chr16 | ENST00000219244.8 |
| CCL17 | AATTCAAAAAGAGTACTTCAAGGGAGCCATTCTCGAGAATGGCTCCCTTGAAGTACTC | 2144 | chr16 | ENST00000219244.8 |
| CCL17 | AATTCAAAAAGCAAAGCCTTGAGAGGTCTTGCTCGAGCAAGACCTCTCAAGGCTTTGC | 2145 | chr16 | ENST00000219244.8 |

TABLE 16-continued

3' to 5' (Reverse) shRNA sequences for Silencing of Cytokine/Chemokine
Genes to Reduce the Incidence of CRS

| Target Gene Symbol | shRNA Reverse Oligo Sequence | SEQ ID NO: | Location | Gene ID No. |
|---|---|---|---|---|
| CCL18 | AATTCAAAAATCTATTGTTGAGCTGCATTATCTCGAGATAATGCAGCTCAACAATAGA | 2146 | chr17 | ENST00000616054.1 |
| CCL18 | AATTCAAAAACCTTCAACTCTTCGTACATTCCTCGAGGAATGTACGAAGAGTTGAAGG | 2147 | chr17 | ENST00000616054.1 |
| CCL18 | AATTCAAAAAGTCTATACCTCCTGGCAGATTCTCGAGAATCTGCCAGGAGGTATAGAC | 2148 | chr17 | ENST00000616054.1 |
| CCL19 | AATTCAAAAAGAGTCAAGCATTGTGAATTATCTCGAGATAATTCACAATGCTTGACTC | 2149 | chr9 | ENST00000311925.6 |
| CCL19 | AATTCAAAAAGCCGCAGCAGTTAACCTATGACTCGAGTCATAGGTTAACTGCTGCGGC | 2150 | chr9 | ENST00000311925.6 |
| CCL19 | AATTCAAAAACCAACTCTGAGTGGCACCAATCTCGAGATTGGTGCCACTCAGAGTTGG | 2151 | chr9 | ENST00000311925.6 |
| CCL2 | AATTCAAAAACCCAGTCACCTGCTGTTATAACTCGAGTTATAACAGCAGGTGACTGGG | 2152 | chr17 | ENST00000225831.4 |
| CCL2 | AATTCAAAAACCCAGTCACCTGCTGTTATAACTCGAGTTATAACAGCAGGTGACTGGG | 2153 | chr17 | ENST00000225831.4 |
| CCL2 | AATTCAAAAAGCTCGCGAGCTATAGAAGAATCTCGAGATTCTTCTATAGCTCGCGAGC | 2154 | chr17 | ENST00000225831.4 |
| CCL20 | AATTCAAAAAGTTGTCTGTGTGCGCAAATCCTCGAGGATTTGCGCACACAGACAACT | 2155 | chr2 | ENST00000358813.4 |
| CCL20 | AATTCAAAAAGACCGTATTCTTCATCCTAAACTCGAGTTTAGGATGAAGAATACGGTC | 2156 | chr2 | ENST00000358813.4 |
| CCL20 | AATTCAAAAAGGGTTTAGTGCTTATCTAATCTCGAGATTAGATAAGCACTAAACCCT | 2157 | chr2 | ENST00000358813.4 |
| CCL21 | AATTCAAAAACACTCTTTCTCCTGCTTTAACCTCGAGGTTAAAGCAGGAGAAAGAGTG | 2158 | chr9 | ENST00000259607.6 |
| CCL21 | AATTCAAAAAGAGCTATGTGCAGACCCAAAGCTCGAGCTTTGGGTCTGCACATAGCTC | 2159 | chr9 | ENST00000259607.6 |
| CCL21 | AATTCAAAAACCATCCCAGCTATCCTGTTCTCTCGAGAGAACAGGATAGCTGGGATGG | 2160 | chr9 | ENST00000259607.6 |
| CCL22 | AATTCAAAAACCCTACCTCCCTGCCATTATACTCGAGTATAATGGCAGGGAGGTAGGG | 2161 | chr16 | ENST00000219235.4 |
| CCL22 | AATTCAAAAAGCGTGGTGAAACACTTCTACTCTCGAGAGTAGAAGTGTTTCACCACGC | 2162 | chr16 | ENST00000219235.4 |
| CCL22 | AATTCAAAAATGTTGCTGACACCCAGAAAGCTCGAGCTTTCTGGGTGTCAGCAACAT | 2163 | chr16 | ENST00000219235.4 |
| CCL23 | AATTCAAAAACACTCCTGGAGAGTTACTTTGCTCGAGCAAAGTAACTCTCCAGGAGTG | 2164 | chr17 | ENST00000615050.1 |
| CCL23 | AATTCAAAAACCTTTCTCATGCTGCAGGATTCTCGAGAATCCTGCAGCATGAGAAAGG | 2165 | chr17 | ENST00000615050.1 |
| CCL23 | AATTCAAAAAGAAGCTGGACACACGGATCAACTCGAGTTGATCCGTGTGTCCAGCTTC | 2166 | chr17 | ENST00000615050.1 |
| CCL24 | AATTCAAAAAAGTGATCTTCACCACCAAGAACTCGAGTTCTTGGTGGTGAAGATCACT | 2167 | chr7 | ENST00000222902.6 |
| CCL24 | AATTCAAAAAGTTCTTTGTTTCCAAGAGAATCTCGAGATTCTCTTGGAAACAAAGAAC | 2168 | chr7 | ENST00000222902.6 |
| CCL24 | AATTCAAAAACCTGCTGCATGTTCTTTGTTTCTCGAGAAACAAAGAACATGCAGCAGG | 2169 | chr7 | ENST00000222902.6 |
| CCL25 | AATTCAAAAAGCCGGATCTTTCTCCGATAAACTCGAGTTTATCGGAGAAAGATCCGGC | 2170 | chr19 | ENST00000390669.7 |
| CCL25 | AATTCAAAAAGCTCCTGGATGCTCGAAATAACTCGAGTTATTTCGAGCATCCAGGAGC | 2171 | chr19 | ENST00000390669.7 |
| CCL25 | AATTCAAAAACCCTCCTGATATCAGCTAATTCTCGAGAATTAGCTGATATCAGGAGGG | 2172 | chr19 | ENST00000390669.7 |
| CCL26 | AATTCAAAAACACACGTGGGAGTGACATATCCTCGAGGATATGTCACTCCCACGTGTG | 2173 | chr7 | ENST00000005180.8 |
| CCL26 | AATTCAAAAATCCGAAACAATTGTGACTCAGCTCGAGCTGAGTCACAATTGTTTCGGA | 2174 | chr7 | ENST00000005180.8 |
| CCL26 | AATTCAAAAAGCTGTGATATTCACTACCAAACTCGAGTTTGGTAGTGAATATCACAGC | 2175 | chr7 | ENST00000005180.8 |
| CCL27 | AATTCAAAAATTCGTGCTTCACCTGGCTCAACTCGAGTTGAGCCAGGTGAAGCACGAA | 2176 | chr9 | ENST00000259631.4 |
| CCL27 | AATTCAAAAACCGAAAGCCACTCTCAGACAACTCGAGTTGTCTGAGAGTGGCTTTCGG | 2177 | chr9 | ENST00000259631.4 |
| CCL27 | AATTCAAAAACAAGCTACTGAGGAAGGTCATCTCGAGATGACCTTCCTCAGTAGCTTG | 2178 | chr9 | ENST00000259631.4 |
| CCL28 | AATTCAAAAACGGAGGTTTCACATCATATTTCTCGAGAAATATGATGTGAAACCTCCG | 2179 | chr5 | ENST00000361115.4 |
| CCL28 | AATTCAAAAACACGAAACATACGGCCATAAACTCGAGTTTATGGCCGTATGTTTCGTG | 2180 | chr5 | ENST00000361115.4 |
| CCL28 | AATTCAAAAATTAGAGAGTCTACAGATAAATCTCGAGATTTATCTGTAGACTCTCTAA | 2181 | chr5 | ENST00000361115.4 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
|---|---|---|---|---|
| CCL3 | AATTCAAAAACCGGCAGATTCCACAGAATTTCTCGAGAAATTCTGTGGAATCTGCCGG | 2182 | chr17 | ENST00000613922.1 |
| CCL3 | AATTCAAAAATTCGATTTCACAGTGTGTTTGCTCGAGCAAACACACTGTGAAATCGAA | 2183 | chr17 | ENST00000613922.1 |
| CCL3 | AATTCAAAAACAACCAGTTCTCTGCATCACTCTCGAGAGTGATGCAGAGAACTGGTTG | 2184 | chr17 | ENST00000613922.1 |
| CCL4 | AATTCAAAAATGTGCCGTGTTATTGTATTACTCGAGTAATACAATAACACGGCACAT | 2185 | chr17 | ENST00000615863.1 |
| CCL4 | AATTCAAAAATCCTGTCCCTTCTCTTAATTTCTCGAGAAATTAAGAGAAGGGACAGGA | 2186 | chr17 | ENST00000615863.1 |
| CCL4 | AATTCAAAAACTGTGCTGATCCCAGTGAATCCTCGAGGATTCACTGGGATCAGCACAG | 2187 | chr17 | ENST00000615863.1 |
| CCL5 | AATTCAAAAATGAACCTGAACTTACACAAATCTCGAGATTTGTGTAAGTTCAGGTTCA | 2188 | chr17 | ENST00000603197.5 |
| CCL5 | AATTCAAAAACCTGCTGCTTTGCCTACATTGCTCGAGCAATGTAGGCAAAGCAGCAGG | 2189 | chr17 | ENST00000603197.5 |
| CCL5 | AATTCAAAAACTACCACACAGCAGCAGTTACCTCGAGGTAACTGCTGCTGTGTGGTAG | 2190 | chr17 | ENST00000603197.5 |
| CCL7 | AATTCAAAAACATAAAGCCTTGGATGTATATCTCGAGATATACATCCAAGGCTTTATG | 2191 | chr17 | ENST00000378569.2 |
| CCL7 | AATTCAAAAAGCTGCTACAGATTTATCAATACTCGAGTATTGATAAATCTGTAGCAGC | 2192 | chr17 | ENST00000378569.2 |
| CCL7 | AATTCAAAAATCTAAGGAATATGAGCTTTATCTCGAGATAAAGCTCATATTCCTTAGA | 2193 | chr17 | ENST00000378569.2 |
| CCL8 | AATTCAAAAAGCTGCTTTAACGTGATCAATACTCGAGTATTGATCACGTTAAAGCAGC | 2194 | chr17 | ENST00000394620.1 |
| CCL8 | AATTCAAAAACAGGTGCAGTGTGACATTATTCTCGAGAATAATGTCACACTGCACCTG | 2195 | chr17 | ENST00000394620.1 |
| CCL8 | AATTCAAAAATTGTACTGCTGTTGTTGAAATCTCGAGATTTCAACAACAGCAGTACAA | 2196 | chr17 | ENST00000394620.1 |
| CCR1 | AATTCAAAAAATTCTGCTAAGACGACCAAATCTCGAGATTTGGTCGTCTTAGCAGAAT | 2197 | chr3 | ENST00000296140.3 |
| CCR1 | AATTCAAAAAATCTGCTACACAGGGATTATACTCGAGTATAATCCCTGTGTAGCAGAT | 2198 | chr3 | ENST00000296140.3 |
| CCR1 | AATTCAAAAACCTCTGTACTCCTTGGTATTTCTCGAGAAATACCAAGGAGTACAGAGG | 2199 | chr3 | ENST00000296140.3 |
| CCR2 | AATTCAAAAACGGTGCTCCCTGTCATAAATCTCGAGATTTATGACAGGGAGCACCGT | 2200 | chr3 | ENST00000445132.2 |
| CCR2 | AATTCAAAAACTTCTGGACTCCCTATAATATCTCGAGATATTATAGGGAGTCCAGAAG | 2201 | chr3 | ENST00000445132.2 |
| CCR2 | AATTCAAAAAGCTGTATCACATCGGTTATTTCTCGAGAAATAACCGATGTGATACAGC | 2202 | chr3 | ENST00000445132.2 |
| CCR3 | AATTCAAAAAATACAGGAGGCTCCGAATTATCTCGAGATAATTCGGAGCCTCCTGTAT | 2203 | chr3 | ENST00000357422.2 |
| CCR3 | AATTCAAAAACCCAGAGGATACAGTATATAGCTCGAGCTATATACTGTATCCTCTGGG | 2204 | chr3 | ENST00000357422.2 |
| CCR3 | AATTCAAAAATAGCAGCTCTTCCTGAATTTACTCGAGTAAATTCAGGAAGAGCTGCTA | 2205 | chr3 | ENST00000357422.2 |
| CCR5 | AATTCAAAAAACTCTTGACAGGGCTCTATTTCTCGAGAAATAGAGCCCTGTCAAGAGT | 2206 | chr3 | ENST00000292303.4 |
| CCR5 | AATTCAAAAACGAGCGAGCAAGCTCAGTTTACTCGAGTAAACTGAGCTTGCTCGCTCG | 2207 | chr3 | ENST00000292303.4 |
| CCR5 | AATTCAAAAATCCATACAGTCAGTATCAATTCTCGAGAATTGATACTGACTGTATGGA | 2208 | chr3 | ENST00000292303.4 |
| CCR6 | AATTCAAAAAGGTCTATGACAGACGTCTATCCTCGAGGATAGACGTCTGTCATAGACC | 2209 | chr6 | ENST00000341935.9 |
| CCR6 | AATTCAAAAACGACTCCAGTGAAGATTATTTCTCGAGAAATAATCTTCACTGGAGTCG | 2210 | chr6 | ENST00000341935.9 |
| CCR6 | AATTCAAAAATCGACTCCAGTGAAGATTATTCTCGAGAATAATCTTCACTGGAGTCGA | 2211 | chr6 | ENST00000341935.9 |
| CCR7 | AATTCAAAAAGATGAGGTCACGGACGATTACCTCGAGGTAATCGTCCGTGACCTCATC | 2212 | chr17 | ENST00000246657.2 |
| CCR7 | AATTCAAAAAGCTGGTCGTGTTGACCTATATCTCGAGATATAGGTCAACACGACCAGC | 2213 | chr17 | ENST00000246657.2 |
| CCR7 | AATTCAAAAACGTGTTGACCTATATCTATTTCTCGAGAAATAGATATAGGTCAACACG | 2214 | chr17 | ENST00000246657.2 |
| CD109 | AATTCAAAAAGCCGATCCTTACATAGATATTCTCGAGAATATCTATGTAAGGATCGGC | 2215 | chr6 | ENST00000287097.5 |
| CD109 | AATTCAAAAACCCGGAGGAAATGTGACTATTCTCGAGAATAGTCACATTTCCTCCGGG | 2216 | chr6 | ENST00000287097.5 |
| CD109 | AATTCAAAAACCGCTTATCATTTGAGACCAACTCGAGTTGGTCTCAAATGATAAGCGG | 2217 | chr6 | ENST00000287097.5 |
| CD27 | AATTCAAAAACTTACCTTATGTCAGTGAGATCTCGAGATCTCACTGACATAAGGTAAG | 2218 | chr12 | ENST00000266557.3 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
|---|---|---|---|---|
| CD27 | AATTCAAAAAGCACTGTAACTCTGGTCTTCTCTCGAGAGAAGACCAGAGTTACAGTGC | 2219 | chr12 | ENST00000266557.3 |
| CD27 | AATTCAAAAACCACCCACTTACCTTATGTCACTCGAGTGACATAAGGTAAGTGGGTGG | 2220 | chr12 | ENST00000266557.3 |
| CD27 | AATTCAAAAAGCCAGATGTGTGAGCCAGGAACTCGAGTTCCTGGCTCACACATCTGGC | 2221 | chr12 | ENST00000266557.3 |
| CD28 | AATTCAAAAACCTCCAGAATTTGTATGTTAACTCGAGTTAACATACAAATTCTGGAGG | 2222 | ch2 | ENST00000458610.6 |
| CD28 | AATTCAAAAACAACCTTAGCTGCAAGTATTCCTCGAGGAATACTTGCAGCTAAGGTTG | 2223 | ch2 | ENST00000458610.6 |
| CD28 | AATTCAAAAATGGAGTCCTGGCTTGCTATAGCTCGAGCTATAGCAAGCCAGGACTCCA | 2224 | ch2 | ENST00000458610.6 |
| CD28 | AATTCAAAAACCTCCTCCTTACCTAGACAATCTCGAGATTGTCTAGGTAAGGAGGAGG | 2225 | ch2 | ENST00000458610.6 |
| CD36 | AATTCAAAAAAGAACCTATTGATGGATTAAACTCGAGTTTAATCCATCAATAGGTTCT | 2226 | chr7 | ENST00000309881.11 |
| CD36 | AATTCAAAAAGCCATAATCGACACATATAAACTCGAGTTTATATGTGTCGATTATGGC | 2227 | chr7 | ENST00000309881.11 |
| CD36 | AATTCAAAAAACGGCTGCAGGTCAACCTATTCTCGAGAATAGGTTGACCTGCAGCCGT | 2228 | chr7 | ENST00000309881.11 |
| CD4 | AATTCAAAAACCTGATCATCAAGAATCTTAACTCGAGTTAAGATTCTTGATGATCAGG | 2229 | chr12 | ENST00000011653.8 |
| CD4 | AATTCAAAAAAGAGCGGATGTCTCAGATCAACTCGAGTTGATCTGAGACATCCGCTCT | 2230 | chr12 | ENST00000011653.8 |
| CD4 | AATTCAAAAACCACTCGCCTTTACAGTTGAACTCGAGTTCAACTGTAAAGGCGAGTGG | 2231 | chr12 | ENST00000011653.8 |
| CD40LG | AATTCAAAAAGGGAAACAGCTGACCGTTAAACTCGAGTTTAACGGTCAGCTGTTTCCC | 2232 | chrX | ENST00000370629.6 |
| CD40LG | AATTCAAAAATTCGAGTCAAGCTCCATTTATCTCGAGATAAATGGAGCTTGACTCGAA | 2233 | chrX | ENST00000370629.6 |
| CD40LG | AATTCAAAAATGACGCTGGGAGTCTTCATAACTCGAGTTATGAAGACTCCCAGCGTCA | 2234 | chrX | ENST00000370629.6 |
| CD70 | AATTCAAAAACCATCGTGATGGCATCTACATCTCGAGATGTAGATGCCATCACGATGG | 2235 | chr19 | ENST00000245903.3 |
| CD70 | AATTCAAAAACAGCTACGTATCCATCGTGATCTCGAGATCACGATGGATACGTAGCTG | 2236 | chr19 | ENST00000245903.3 |
| CD70 | AATTCAAAAACCAACCTCACTGGGACACTTTCTCGAGAAAGTGTCCCAGTGAGGTTGG | 2237 | chr19 | ENST00000245903.3 |
| CD74 | AATTCAAAAACAAGTCGGAACAGCAGATAACCTCGAGGTTATCTGCTGTTCCGACTTG | 2238 | chr5 | ENST00000009530.11 |
| CD74 | AATTCAAAAAGAGAACCTGAGACACCTTAAGCTCGAGCTTAAGGTGTCTCAGGTTCTC | 2239 | chr5 | ENST00000009530.11 |
| CD74 | AATTCAAAAACCACACAGCTACAGCTTTCTTCTCGAGAAGAAAGCTGTAGCTGTGTGG | 2240 | chr5 | ENST00000009530.11 |
| CD8A | AATTCAAAAAGCTGGACTTCGCCTGTGATATCTCGAGATATCACAGGCGAAGTCCAGC | 2241 | ch2 | ENST00000409511.6 |
| CD8A | AATTCAAAAAGTGTATTCATTCTCATGATTACTCGAGTAATCATGAGAATGAATACAC | 2242 | ch2 | ENST00000409511.6 |
| CD8A | AATTCAAAAACCAGAGACAGCTTGATCAAAGCTCGAGCTTTGATCAAGCTGTCTCTGG | 2243 | ch2 | ENST00000409511.6 |
| CD8A | AATTCAAAAACCTTCTCCTGTCACTGGTTATCTCGAGATAACCAGTGACAGGAGAAGG | 2244 | ch2 | ENST00000409511.6 |
| CER1 | AATTCAAAAAGAGAAGATGCTGTCCAGATTTCTCGAGAAATCTGGACAGCATCTTCTC | 2245 | chr9 | ENST00000380911.3 |
| CER1 | AATTCAAAAACCAGCCGATAGATGGAATGAACTCGAGTTCATTCCATCTATCGGCTGG | 2246 | chr9 | ENST00000380911.3 |
| CER1 | AATTCAAAAACAAGAAATTCTGGCACCACTTCTCGAGAAGTGGTGCCAGAATTTCTTG | 2247 | chr9 | ENST00000380911.3 |
| CHRD | AATTCAAAAACGTCCTGCAAAGTGTCCTTTCTCGAGAAAGGACACTTTGCAGGACGT | 2248 | chr3 | ENST00000204604.5 |
| CHRD | AATTCAAAAACTGATCCAGAGCTGGAGAAACTCGAGTTTCTCCAGCTCTGGATCAGT | 2249 | chr3 | ENST00000204604.5 |
| CHRD | AATTCAAAAACGGCTGCTGAAGGGATTCTATCTCGAGATAGAATCCCTTCAGCAGCCG | 2250 | chr3 | ENST00000204604.5 |
| CKLF | AATTCAAAAACCTTTGCTTGTGTTTGCACTTCTCGAGAAGTGCAAACACAAGCAAAGG | 2251 | chr16 | ENST00000264001.8 |
| CKLF | AATTCAAAAACCCTGAACCATATATTGTTATCTCGAGATAACAATATATGGTTCAGGG | 2252 | chr16 | ENST00000264001.8 |
| CKLF | AATTCAAAAATGGATTTGAAGTCACCGTTATCTCGAGATAACGGTGACTTCAAATCCA | 2253 | chr16 | ENST00000264001.8 |
| CLCF1 | AATTCAAAAAGAAACAAACATGGTGGCAATTCTCGAGAATTGCCACCATGTTTGTTTC | 2254 | chr11 | ENST00000312438.7 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
|---|---|---|---|---|
| CLCF1 | AATTCAAAAACCACAGGATTTCCTGAAAGTTCTCGAGAACTTTCAGGAAATCCTGTGG | 2255 | chr11 | ENST00000312438.7 |
| CLCF1 | AATTCAAAAACATGGTGGCAATTCTACACAACTCGAGTTGTGTAGAATTGCCACCATG | 2256 | chr11 | ENST00000312438.7 |
| CMTM1 | AATTCAAAAACACCACTTGCTGACCTATTTACTCGAGTAAATAGGTCAGCAAGTGGTG | 2257 | chr16 | ENST00000379500.6 |
| CMTM1 | AATTCAAAAAGACCTATTTACATTGGCCCTTCTCGAGAAGGGCCAATGTAAATAGGTC | 2258 | chr16 | ENST00000379500.6 |
| CMTM1 | AATTCAAAAAGCTGTGTTCCTTTCAGTAGTTCTCGAGAACTACTGAAAGGAACACAGC | 2259 | chr16 | ENST00000379500.6 |
| CMTM2 | AATTCAAAAAGTAAGGAGCCATCGGACAAACCTCGAGGTTTGTCCGATGGCTCCTTAC | 2260 | chr16 | ENST00000268595.2 |
| CMTM2 | AATTCAAAAACTTACTTGCTGTGATCCTTATCTCGAGATAAGGATCACAGCAAGTAAG | 2261 | chr16 | ENST00000268595.2 |
| CMTM2 | AATTCAAAAACATAAGGAGCCATCGGACAAACTCGAGTTTGTCCGATGGCTCCTTATG | 2262 | chr16 | ENST00000268595.2 |
| CMTM3 | AATTCAAAAACATCGTGTTTGCAACTGATTTCTCGAGAAATCAGTTGCAAACACGATG | 2263 | chr16 | ENST00000361909.8 |
| CMTM3 | AATTCAAAAAGCTTCTTAACAGATGGCATTTCTCGAGAAATGCCATCTGTTAAGAAGC | 2264 | chr16 | ENST00000361909.8 |
| CMTM3 | AATTCAAAAAGCTTCTTAACAGATGGCATTTCTCGAGAAATGCCATCTGTTAAGAAGC | 2265 | chr16 | ENST00000361909.8 |
| CMTM4 | AATTCAAAAACAACTGGAATCTGACAGATTTCTCGAGAAATCTGTCAGATTCCAGTTG | 2266 | chr16 | ENST00000394106.6 |
| CMTM4 | AATTCAAAAAGACTGGCGTCTTGCTGATTATCTCGAGATAATCAGCAAGACGCCAGTC | 2267 | chr16 | ENST00000394106.6 |
| CMTM4 | AATTCAAAAAGCAGAAATTGCTGCCGTGATACTCGAGTATCACGGCAGCAATTTCTGC | 2268 | chr16 | ENST00000394106.6 |
| CMTM5 | AATTCAAAAACAAGATCTACCGGACTGAGATCTCGAGATCTCAGTCCGGTAGATCTTG | 2269 | chr14 | ENST00000359320.7 |
| CMTM5 | AATTCAAAAACCTGACCCTCATCATCTTCATCTCGAGATGAAGATGATGAGGGTCAGG | 2270 | chr14 | ENST00000359320.7 |
| CMTM5 | AATTCAAAAACTTCCTCTATGCCACCCAGTACTCGAGTACTGGGTGGCATAGAGGAAG | 2271 | chr14 | ENST00000359320.7 |
| CMTM6 | AATTCAAAAAGCCCTCACTGAGCCACTTAATCTCGAGATTAAGTGGCTCAGTGAGGGC | 2272 | chr3 | ENST00000205636.3 |
| CMTM6 | AATTCAAAAACCCAAGACAGTGAAAGTAATTCTCGAGAATTACTTTCACTGTCTTGGG | 2273 | chr3 | ENST00000205636.3 |
| CMTM6 | AATTCAAAAACCCAAGACAGTGAAAGTAATTCTCGAGAATTACTTTCACTGTCTTGGG | 2274 | chr3 | ENST00000205636.3 |
| CMTM7 | AATTCAAAAACTGCTGAAAGTGGCGCAAATGCTCGAGCATTTGCGCCACTTTCAGCAG | 2275 | chr3 | ENST00000334983.9 |
| CMTM7 | AATTCAAAAACAAAGCCCTGTCCTAATTTATCTCGAGATAAATTAGGACAGGGCTTTG | 2276 | chr3 | ENST00000334983.9 |
| CMTM7 | AATTCAAAAACCTGTCGATCTTTGGTTTCATCTCGAGATGAAACCAAAGATCGACAGG | 2277 | chr3 | ENST00000334983.9 |
| CMTM8 | AATTCAAAAATGCTGGTATGGACGCTTATTGCTCGAGCAATAAGCGTCCATACCAGCA | 2278 | chr3 | ENST00000307526.3 |
| CMTM8 | AATTCAAAAAGCAAAGTGTTGTAGCTTATAACTCGAGTTATAAGCTACAACACTTTGC | 2279 | chr3 | ENST00000307526.3 |
| CMTM8 | AATTCAAAAAATATTCCCAGAGAATTGTATTCTCGAGAATACAATTCTCTGGGAATAT | 2280 | chr3 | ENST00000307526.3 |
| CNTF | AATTCAAAAAGTAACCTCTACAGGCATTTAACTCGAGTTAAATGCCTGTAGAGGTTAC | 2281 | chr11 | ENST00000361987.5 |
| CNTF | AATTCAAAAAGTTGAAGGACTACAGGTATTTCTCGAGAAATACCTGTAGTCCTTCAAC | 2282 | chr11 | ENST00000361987.5 |
| CNTF | AATTCAAAAAGGTGACTTCCATCAAGCTATACTCGAGTATAGCTTGATGGAAGTCACC | 2283 | chr11 | ENST00000361987.5 |
| CNTFR | AATTCAAAAACATTCTCTTCAGACACAATTTCTCGAGAAATTGTGTCTGAAGAGAATG | 2284 | chr9 | ENST00000351266.8 |
| CNTFR | AATTCAAAAAGCATTCTCTTCAGACACAATTCTCGAGAATTGTGTCTGAAGAGAATGC | 2285 | chr9 | ENST00000351266.8 |
| CNTFR | AATTCAAAAAGCCGGGAAGGAGTACATTATCCTCGAGGATAATGTACTCCTTCCCGGC | 2286 | chr9 | ENST00000351266.8 |
| COPS5 | AATTCAAAAACTAAGGATCACCATTACTTTACTCGAGTAAAGTAATGGTGATCCTTAG | 2287 | chr8 | ENST00000357849.8 |
| COPS5 | AATTCAAAAACCAGACTATTCCACTTAATAACTCGAGTTATTAAGTGGAATAGTCTGG | 2288 | chr8 | ENST00000357849.8 |
| COPS5 | AATTCAAAAACAGTCTCTGAGAAGTACTTTACTCGAGTAAAGTACTTCTCAGAGACTG | 2289 | chr8 | ENST00000357849.8 |
| CRLF1 | AATTCAAAAACGATGTACTCACGCTGGATATCTCGAGATATCCAGCGTGAGTACATCG | 2290 | chr19 | ENST00000392386.7 |
| CRLF1 | AATTCAAAAACGATGTACTCACGCTGGATATCTCGAGATATCCAGCGTGAGTACATCG | 2291 | chr19 | ENST00000392386.7 |

TABLE 16-continued

3' to 5' (Reverse) shRNA sequences for Silencing of Cytokine/Chemokine
Genes to Reduce the Incidence of CRS

| Target Gene Symbol | shRNA Reverse Oligo Sequence | SEQ ID NO: | Location | Gene ID No. |
|---|---|---|---|---|
| CRLF1 | AATTCAAAAACCCAGAGAAACCCGTCAACATCTCGAGATGTTGACGGGTTTCTCTGGG | 2292 | chr19 | ENST00000392386.7 |
| CSF1 | AATTCAAAAATCTCCTGGTACAAGACATAATCTCGAGATTATGTCTTGTACCAGGAGA | 2293 | chr1 | ENST00000329608.10 |
| CSF1 | AATTCAAAAAGTCGGCCTGATTTCCCGTAAACTCGAGTTTACGGGAAATCAGGCCGAC | 2294 | chr1 | ENST00000329608.10 |
| CSF1 | AATTCAAAAATTGACAAGGACTGGAATATTTCTCGAGAAATATTCCAGTCCTTGTCAA | 2295 | chr1 | ENST00000329608.10 |
| CSF1R | AATTCAAAAAGTGAACAGCAAGTTCTATAAACTCGAGTTTATAGAACTTGCTGTTCAC | 2296 | chr5 | ENST00000286301.7 |
| CSF1R | AATTCAAAAACAGGAGAGAGCGGGACTATACTCGAGTATAGTCCCGCTCTCTCCTGT | 2297 | chr5 | ENST00000286301.7 |
| CSF1R | AATTCAAAAAGCTGCTATTGTACAAGTATAACTCGAGTTATACTTGTACAATAGCAGC | 2298 | chr5 | ENST00000286301.7 |
| CSF2 | AATTCAAAAAGGAGCTGCTCTCTCATGAAACCTCGAGGTTTCATGAGAGAGCAGCTCC | 2299 | chr5 | ENST00000296871.3 |
| CSF2 | AATTCAAAAACCCAGATTATCACCTTTGAAACTCGAGTTTCAAAGGTGATAATCTGGG | 2300 | chr5 | ENST00000296871.3 |
| CSF2 | AATTCAAAAAGAAGTCATCTCAGAAATGTTTCTCGAGAAACATTTCTGAGATGACTTC | 2301 | chr5 | ENST00000296871.3 |
| CSF3 | AATTCAAAAAGTCTATTTAAGCCTCATATTTCTCGAGAAATATGAGGCTTAAATAGAC | 2302 | chr17 | ENST00000225474.6 |
| CSF3 | AATTCAAAAAGATAGGTAAATACCAAGTATTCTCGAGAATACTTGGTATTTACCTATC | 2303 | chr17 | ENST00000225474.6 |
| CSF3 | AATTCAAAAAGCTTAGAGCAAGTGAGGAAGACTCGAGTCTTCCTCACTTGCTCTAAGC | 2304 | chr17 | ENST00000225474.6 |
| CSF3R | AATTCAAAAACAGCCAGGCCTGCACATAAATCTCGAGATTTATGTGCAGGCCTGGCTG | 2305 | chr1 | ENST00000361632.8 |
| CSF3R | AATTCAAAAACTATGCCTACTCTCAAGAAATCTCGAGATTTCTTGAGAGTAGGCATAG | 2306 | chr1 | ENST00000361632.8 |
| CSF3R | AATTCAAAAACCAGCTTCACTCTGAAGAGTTCTCGAGAACTCTTCAGAGTGAAGCTGG | 2307 | chr1 | ENST00000361632.8 |
| CTF1 | AATTCAAAAAGAGCAGCTGCTCCAGGAATATCTCGAGATATTCCTGGAGCAGCTGCTC | 2308 | chr16 | ENST00000279804.2 |
| CTF1 | AATTCAAAAAGTCTCTCCTTCCGCTTCTTTGCTCGAGCAAAGAAGCGGAAGGAGAGAC | 2309 | chr16 | ENST00000279804.2 |
| CTF1 | AATTCAAAAATGTCTGTCTGTCGCTCTTAGCTCGAGCTAAGAGCAGACAGACAGACA | 2310 | chr16 | ENST00000279804.2 |
| CX3CL1 | AATTCAAAAACCCGGAGCTGTGGTAGTAATTCTCGAGAATTACTACCACAGCTCCGGG | 2311 | chr16 | ENST00000006053.6 |
| CX3CL1 | AATTCAAAAAGCTGCTGCCCTAACTCGAAATCTCGAGATTTCGAGTTAGGGCAGCAGC | 2312 | chr16 | ENST00000006053.6 |
| CX3CL1 | AATTCAAAAACGGTGTGACGAAATGCAACATCTCGAGATGTTGCATTTCGTCACACCG | 2313 | chr16 | ENST00000006053.6 |
| CX3CR1 | AATTCAAAAATGGCCTGTGTCTAGTTGTTTGCTCGAGCAAACAACTAGACACAGGCCA | 2314 | chr3 | ENST00000399220.2 |
| CX3CR1 | AATTCAAAAATGGGATCCCTCATCCTCATACCTCGAGGTATGAGGATGAGGGATCCCA | 2315 | chr3 | ENST00000399220.2 |
| CX3CR1 | AATTCAAAAAGCTTTGCTCATCCACTATCAACTCGAGTTGATAGTGGATGAGCAAAGC | 2316 | chr3 | ENST00000399220.2 |
| CXCL1 | AATTCAAAAACCTGCACACTGTCCTATTATCTCGAGATAATAGGACAGTGTGCAGGT | 2317 | chr4 | ENST00000395761.3 |
| CXCL1 | AATTCAAAAAGATGCTGAACAGTGACAAATCTCGAGATTTGTCACTGTTCAGCATCT | 2318 | chr4 | ENST00000395761.3 |
| CXCL1 | AATTCAAAAAGTTCTCCAGTCATTATGTTAACTCGAGTTAACATAATGACTGGAGAAC | 2319 | chr4 | ENST00000395761.3 |
| CXCL10 | AATTCAAAAAGTATATGTCAAGCCATAATTGCTCGAGCAATTATGGCTTGACATATAC | 2320 | chr4 | ENST00000306602.2 |
| CXCL10 | AATTCAAAAACTCTACCCTGGCACTATAATCTCGAGATTATAGTGCCAGGGTAGAGT | 2321 | chr4 | ENST00000306602.2 |
| CXCL10 | AATTCAAAAACCTGTTAATCCAAGGTCTTTACTCGAGTAAAGACCTTGGATTAACAGG | 2322 | chr4 | ENST00000306602.2 |
| CXCL11 | AATTCAAAAAGCTGGTTACCATCGGAGTTTACTCGAGTAAACTCCGATGGTAACCAGC | 2323 | chr4 | ENST00000306621.7 |
| CXCL11 | AATTCAAAAAGCAGTGAAAGTGGCAGATATTCTCGAGAATATCTGCCACTTTCACTGC | 2324 | chr4 | ENST00000306621.7 |
| CXCL11 | AATTCAAAAAGAAGCAAGCAAGGCTTATAATCTCGAGATTATAAGCCTTGCTTGCTTC | 2325 | chr4 | ENST00000306621.7 |
| CXCL12 | AATTCAAAAAGCTTAGACTAAGGCCATTATTCTCGAGAATAATGGCCTTAGTCTAAGC | 2326 | chr10 | ENST00000343575.10 |
| CXCL12 | AATTCAAAAACTCTCACTATACCAGTATAATCTCGAGATTATACTGGTATAGTGAGAG | 2327 | chr10 | ENST00000343575.10 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
|---|---|---|---|---|
| CXCL12 | AATTCAAAAACAAACTGTGCCCTTCAGATTGCTCGAGCAATCTGAAGGGCACAGTTTG | 2328 | chr10 | ENST00000343575.10 |
| CXCL13 | AATTCAAAAAGATTCCCTGATGCTGATATTTCTCGAGAAATATCAGCATCAGGGAATC | 2329 | chr4 | ENST00000286758.4 |
| CXCL13 | AATTCAAAAAGGAATCCATGTAGTAGATATCTCGAGATATCTACTACATGGATTCCT | 2330 | chr4 | ENST00000286758.4 |
| CXCL13 | AATTCAAAAAGGTGTTCTGGAGGTCTATTACTCGAGTAATAGACCTCCAGAACACCT | 2331 | chr4 | ENST00000286758.4 |
| CXCL14 | AATTCAAAAATTTGTCCATACGTCACTATACTCGAGTATAGTGACGTATGGACAAAT | 2332 | chr5 | ENST00000337225.5 |
| CXCL14 | AATTCAAAAACAAAGGACTTTGCAGATTAAACTCGAGTTTAATCTGCAAAGTCCTTTG | 2333 | chr5 | ENST00000337225.5 |
| CXCL14 | AATTCAAAAAGCGCAGGGTCTACGAAGAATACTCGAGTATTCTTCGTAGACCCTGCGC | 2334 | chr5 | ENST00000337225.5 |
| CXCL16 | AATTCAAAAACATCCAGCCTACACGTATTTCTCGAGAAATACGTGTAGGCTGGATGT | 2335 | chr17 | ENST00000293778.10 |
| CXCL16 | AATTCAAAAATCTGAAGGTGCGAGGATTATACTCGAGTATAATCCTCGCACCTTCAGA | 2336 | chr17 | ENST00000293778.10 |
| CXCL16 | AATTCAAAAATCCAGATCTGCCGGTTCATTACTCGAGTAATGAACCGGCAGATCTGGA | 2337 | chr17 | ENST00000293778.10 |
| CXCL17 | AATTCAAAAAGCGCCCACTCTTCCAATTAAACTCGAGTTTAATTGGAAGAGTGGGCGC | 2338 | chr19 | ENST00000601181.5 |
| CXCL17 | AATTCAAAAATCCAGAGCCTGCCAGCAATTTCTCGAGAAATTGCTGGCAGGCTCTGGA | 2339 | chr19 | ENST00000601181.5 |
| CXCL17 | AATTCAAAAAGAATGTGAGTGCAAAGATTGCTCGAGCAATCTTTGCACTCACATTCT | 2340 | chr19 | ENST00000601181.5 |
| CXCL2 | AATTCAAAAACTTGCACACTCTCCCATTATACTCGAGTATAATGGGAGAGTGTGCAAG | 2341 | chr4 | ENST00000508487.2 |
| CXCL2 | AATTCAAAAAGCAGATATTCTCTAGTCATTTCTCGAGAAATGACTAGAGAATATCTGC | 2342 | chr4 | ENST00000508487.2 |
| CXCL2 | AATTCAAAAAATTTCTTCGTGATGACATATCCTCGAGGATATGTCATCACGAAGAAAT | 2343 | chr4 | ENST00000508487.2 |
| CXCL3 | AATTCAAAAATTACGAGGGTTCTACTTATTTCTCGAGAAATAAGTAGAACCCTCGTAA | 2344 | chr4 | ENST00000296026.4 |
| CXCL3 | AATTCAAAAAATTTAGTGGGAGACCATAATGCTCGAGCATTATGGTCTCCCACTAAAT | 2345 | chr4 | ENST00000296026.4 |
| CXCL3 | AATTCAAAAAACTGACAGGAGAGAAGTAAGACTCGAGTCTTACTTCTCTCCTGTCAGT | 2346 | chr4 | ENST00000296026.4 |
| CXCL5 | AATTCAAAAATGAATTGTAGGTGACTATTATCTCGAGATAATAGTCACCTACAATTCA | 2347 | chr4 | ENST00000296027.4 |
| CXCL5 | AATTCAAAAACAGACCACGCAAGGAGTTCATCTCGAGATGAACTCCTTGCGTGGTCTG | 2348 | chr4 | ENST00000296027.4 |
| CXCL5 | AATTCAAAAACGGGAAGGAAATTTGTCTTGACTCGAGTCAAGACAAATTTCCTTCCCG | 2349 | chr4 | ENST00000296027.4 |
| CXCL6 | AATTCAAAAATTTACCCTAGGATGCTATTTACTCGAGTAAATAGCATCCTAGGGTAAA | 2350 | chr4 | ENST00000226317.9 |
| CXCL6 | AATTCAAAAAGTTGCACTTGTTTACGCGTTACTCGAGTAACGCGTAAACAAGTGCAAC | 2351 | chr4 | ENST00000226317.9 |
| CXCL6 | AATTCAAAAAGCTGTGGATTTCGTATGGAAACTCGAGTTTCCATACGAAATCCACAGC | 2352 | chr4 | ENST00000226317.9 |
| CXCL8 | AATTCAAAAATGCGCCAACACAGAAATTATTCTCGAGAATAATTTCTGTGTTGGCGCA | 2353 | chr4 | ENST00000307407.7 |
| CXCL8 | AATTCAAAAACAAGAGAATATCCGAACTTTACTCGAGTAAAGTTCGGATATTCTCTTG | 2354 | chr4 | ENST00000307407.7 |
| CXCL8 | AATTCAAAAATGCACGGGAGAATATACAAATCTCGAGATTTGTATATTCTCCCGTGCA | 2355 | chr4 | ENST00000307407.7 |
| CXCL9 | AATTCAAAAACCAAAGGAGGATGGCATATAACTCGAGTTATATGCCATCCTCCTTTGG | 2356 | chr4 | ENST00000264888.5 |
| CXCL9 | AATTCAAAAACCAAACGTTAAGAATTGTTAACTCGAGTTAACAATTCTTAACGTTTGG | 2357 | chr4 | ENST00000264888.5 |
| CXCL9 | AATTCAAAAAGATGTGAAGGAACTGATTAAACTCGAGTTTAATCAGTTCCTTCACATC | 2358 | chr4 | ENST00000264888.5 |
| CXCR1 | AATTCAAAAACTTGGCACGTCATCGTGTTACCTCGAGGTAACACGATGACGTGCCAAG | 2359 | chr2 | ENST00000295683.2 |
| CXCR1 | AATTCAAAAACCCACTAACTGGCTAATTAGCTCGAGCTAATTAGCCAGTTAGTGGGT | 2360 | chr2 | ENST00000295683.2 |
| CXCR1 | AATTCAAAAAGAGACACTCAACAAGTATGTTCTCGAGAACATACTTGTTGAGTGTCTC | 2361 | chr2 | ENST00000295683.2 |
| CXCR2 | AATTCAAAAAGAAGCGCTACTTGGTCAAATTCTCGAGAATTTGACCAAGTAGCGCTTC | 2362 | chr2 | ENST00000318507.6 |
| CXCR2 | AATTCAAAAAGCCACTAAATTGACACTTAAACTCGAGTTTAAGTGTCAATTTAGTGGC | 2363 | chr2 | ENST00000318507.6 |
| CXCR2 | AATTCAAAAACCCTGGAAATCAACAAGTATTCTCGAGAATACTTGTTGATTTCCAGGG | 2364 | chr2 | ENST00000318507.6 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
|---|---|---|---|---|
| CXCR3 | AATTCAAAAACCTTCTCATTTGGAAACTAAACTCGAGTTTAGTTTCCAAATGAGAAGG | 2365 | chrX | ENST00000373693.3 |
| CXCR3 | AATTCAAAAACGCTACCTGAACATAGTTCATCTCGAGATGAACTATGTTCAGGTAGCG | 2366 | chrX | ENST00000373693.3 |
| CXCR3 | AATTCAAAAAGAGTACAAGGCATGGCGTAGACTCGAGTCTACGCCATGCCTTGTACTC | 2367 | chrX | ENST00000373693.3 |
| CXCR4 | AATTCAAAAACTATTCCCGACTTCATCTTTGCTCGAGCAAAGATGAAGTCGGGAATAG | 2368 | chr2 | ENST00000409817.1 |
| CXCR4 | AATTCAAAAAGCGTGTAGTGAATCACGTAAACTCGAGTTTACGTGATTCACTACACGC | 2369 | chr2 | ENST00000409817.1 |
| CXCR4 | AATTCAAAAACCTGTTCTTAAGACGTGATTTCTCGAGAAATCACGTCTTAAGAACAGG | 2370 | chr2 | ENST00000409817.1 |
| CXCR6 | AATTCAAAAAGCTTGCTCATCTGGGTGATATCTCGAGATATCACCCAGATGAGCAAGC | 2371 | chr3 | ENST00000304552.4 |
| CXCR6 | AATTCAAAAATACTGGGCATCTACACTATTACTCGAGTAATAGTGTAGATGCCCAGTA | 2372 | chr3 | ENST00000304552.4 |
| CXCR6 | AATTCAAAAATTATCTATGGCAATGTCTTTACTCGAGTAAAGACATTGCCATAGATAA | 2373 | chr3 | ENST00000304552.4 |
| EBI3 | AATTCAAAAATGAACTGTCACTGTGAGATATCTCGAGATATCTCACAGTGACAGTTCA | 2374 | chr19 | ENST00000221847.5 |
| EBI3 | AATTCAAAAAATGTACTACTCTCTCCTTTACCTCGAGGTAAAGGAGAGAGTAGTACAT | 2375 | chr19 | ENST00000221847.5 |
| EBI3 | AATTCAAAAAGCCTTTCATAACAGAGCACATCTCGAGATGTGCTCTGTTATGAAAGGC | 2376 | chr19 | ENST00000221847.5 |
| EDN1 | AATTCAAAAACCATGAGAAACAGCGTCAAATCTCGAGATTTGACGCTGTTTCTCATGG | 2377 | chr6 | ENST00000379375.5 |
| EDN1 | AATTCAAAAAGCTCGTCCCTGATGGATAAAGCTCGAGCTTTATCCATCAGGGACGAGC | 2378 | chr6 | ENST00000379375.5 |
| EDN1 | AATTCAAAAAAGACAAGAAGTGCTGGAATTTCTCGAGAAATTCCAGCACTTCTTGTCT | 2379 | chr6 | ENST00000379375.5 |
| ELANE | AATTCAAAAAGCACTGCGTGGCGAATGTAAACTCGAGTTTACATTCGCCACGCAGTGC | 2380 | chr19 | ENST00000263621.1 |
| ELANE | AATTCAAAAATGCTCAACGACATCGTGATTCCTCGAGGAATCACGATGTCGTTGAGCA | 2381 | chr19 | ENST00000263621.1 |
| ELANE | AATTCAAAAACAACGGGCTAATCCACGGAATCTCGAGATTCCGTGGATTAGCCCGTTG | 2382 | chr19 | ENST00000263621.1 |
| ENG | AATTCAAAAAGCAGGTGTCAGCAAGTATGATCTCGAGATCATACTTGCTGACACCTGC | 2383 | chr9 | ENST00000344849.4 |
| ENG | AATTCAAAAAGCAGGTGTCAGCAAGTATGATCTCGAGATCATACTTGCTGACACCTGC | 2384 | chr9 | ENST00000344849.4 |
| ENG | AATTCAAAAAGTCTTGCAGAAACAGTCCATTCTCGAGAATGGACTGTTTCTGCAAGAC | 2385 | chr9 | ENST00000344849.4 |
| EPO | AATTCAAAAACCCAGACACCAAAGTTAATTTCTCGAGAAATTAACTTTGGTGTCTGGG | 2386 | chr7 | ENST00000252723.2 |
| EPO | AATTCAAAAATGCAGCTGCATGTGGATAAAGCTCGAGCTTTATCCACATGCAGCTGCA | 2387 | chr7 | ENST00000252723.2 |
| EPO | AATTCAAAAAAGAGCAACTCTGAGATCTAAGCTCGAGCTTAGATCTCAGAGTTGCTCT | 2388 | chr7 | ENST00000252723.2 |
| FAM3B | AATTCAAAAATTGGAACTCCCTTCCGAAATTCTCGAGAATTTCGGAAGGGAGTTCCAA | 2389 | chr21 | ENST00000357985.6 |
| FAM3B | AATTCAAAAATAAATCCAACAGCCCATATTTCTCGAGAAATATGGGCTGTTGGATTTA | 2390 | chr21 | ENST00000357985.6 |
| FAM3B | AATTCAAAAATCAGGTCTAGCTGGGTATTTACTCGAGTAAATACCCAGCTAGACCTGA | 2391 | chr21 | ENST00000357985.6 |
| FAM3C | AATTCAAAAACTTGGTGTGTGCATGAGTATTCTCGAGAATACTCATGCACACACCAAG | 2392 | chr7 | ENST00000359943.7 |
| FAM3C | AATTCAAAAAGAGGAGATGTGGCACCATTTACTCGAGTAAATGGTGCCACATCTCCTC | 2393 | chr7 | ENST00000359943.7 |
| FAM3C | AATTCAAAAAGCCATACAAGATGGAACAATACTCGAGTATTGTTCCATCTTGTATGGC | 2394 | chr7 | ENST00000359943.7 |
| FAM3D | AATTCAAAAACACCTAGTGAATTCTTAAACTCGAGTTTAAGGAATTTCACTAGGTG | 2395 | chr3 | ENST00000358781.6 |
| FAM3D | AATTCAAAAACATGTACTCTGGAGATGTTATCTCGAGATAACATCTCCAGAGTACATG | 2396 | chr3 | ENST00000358781.6 |
| FAM3D | AATTCAAAAACAATGTGGGCAGAGGCCTAAACTCGAGTTTAGGCCTCTGCCCACATTG | 2397 | chr3 | ENST00000358781.6 |
| FAS | AATTCAAAAAGCGTATGACACATTGATTAAACTCGAGTTTAATCAATGTGTCATACGC | 2398 | chr10 | ENST00000355740.6 |
| FAS | AATTCAAAAACCTGAAACAGTGGCAATAAATCTCGAGATTTATTGCCACTGTTTCAGG | 2399 | chr10 | ENST00000355740.6 |
| FAS | AATTCAAAAACTATCATCCTCAAGGACATTACTCGAGTAATGTCCTTGAGGATGATAG | 2400 | chr10 | ENST00000355740.6 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
|---|---|---|---|---|
| FASLG | AATTCAAAAAGACTAGAGGCTTGCATAATAACTCGAGTTATTATGCAAGCCTCTAGTC | 2401 | chr1 | ENST00000367721.2 |
| FASLG | AATTCAAAAAACTGGGCTGTACTTTGTATATCTCGAGATATACAAAGTACAGCCCAGT | 2402 | chr1 | ENST00000367721.2 |
| FASLG | AATTCAAAAATGAGCTCTCTCTGGTCAATTTCTCGAGAAATTGACCAGAGAGAGCTCA | 2403 | chr1 | ENST00000367721.2 |
| FGF2 | AATTCAAAAAGAAACGAACTGGGCAGTATAACTCGAGTTATACTGCCCAGTTCGTTTC | 2404 | chr4 | ENST00000608478.1 |
| FGF2 | AATTCAAAAATATAGCTCAGTTTGGATAATTCTCGAGAATTATCCAAACTGAGCTATA | 2405 | chr4 | ENST00000608478.1 |
| FGF2 | AATTCAAAAATGAACGATTGGAATCTAATAACTCGAGTTATTAGATTCCAATCGTTCA | 2406 | chr4 | ENST00000608478.1 |
| FLT3LG | AATTCAAAAACTGTCTGACTACCTGCTTCAACTCGAGTTGAAGCAGGTAGTCAGACAG | 2407 | chr19 | ENST00000594009.5 |
| FLT3LG | AATTCAAAAATCCTCCGACTTCGCTGTCAAACTCGAGTTTGACAGCGAAGTCGGAGGA | 2408 | chr19 | ENST00000594009.5 |
| FLT3LG | AATTCAAAAAGCTTCGTCCAGACCAACATCTCTCGAGAGATGTTGGTCTGGACGAAGC | 2409 | chr19 | ENST00000594009.5 |
| FOXP3 | AATTCAAAAAGCTGGAGTTCCGCAAGAAACCTCGAGGTTTCTTGCGGAACTCCAGCT | 2410 | chrX | ENST00000376207.8 |
| FOXP3 | AATTCAAAAATCCTACCCACTGCTGGCAAATCTCGAGATTTGCCAGCAGTGGGTAGGA | 2411 | chrX | ENST00000376207.8 |
| FOXP3 | AATTCAAAAATGTCCCTCACTCAACACAAACCTCGAGGTTTGTGTTGAGTGAGGGACA | 2412 | chrX | ENST00000376207.8 |
| FOXP3 | AATTCAAAAACACACGCATGTTTGCCTTCTTCTCGAGAAGAAGGCAAACATGCGTGTG | 2413 | chrX | ENST00000376207.8 |
| FZD4 | AATTCAAAAACGTGTGTGATTGCCTGTTATTCTCGAGAATAACAGGCAATCACACACG | 2414 | chr11 | ENST00000531380.1 |
| FZD4 | AATTCAAAAATCTCAGTATGTGCTATAATATCTCGAGATATTATAGCACATACTGAGA | 2415 | chr11 | ENST00000531380.1 |
| FZD4 | AATTCAAAAATTCTCAGTATGTGCTATAATACTCGAGTATTATAGCACATACTGAGAA | 2416 | chr11 | ENST00000531380.1 |
| GATA3 | AATTCAAAAAGCCTAAACGCGATGGATATACTCGAGTATATCCATCGCGTTTAGGCT | 2417 | chr10 | ENST00000346208.4 |
| GATA3 | AATTCAAAAACCCAAGAACAGCTCGTTTAACCTCGAGGTTAAACGAGCTGTTCTTGGG | 2418 | chr10 | ENST00000346208.4 |
| GATA3 | AATTCAAAAAGCCAAGAAGTTTAAGGAATATCTCGAGATATTCCTTAAACTTCTTGGC | 2419 | chr10 | ENST00000346208.4 |
| GATA3 | AATTCAAAAACCCTGTAATTGTTGTTTGTATCTCGAGATACAAACAACAATTACAGGG | 2420 | chr10 | ENST00000346208.4 |
| GBP1 | AATTCAAAAACCAGATGAGTACCTGACATACCTCGAGGTATGTCAGGTACTCATCTGG | 2421 | chr1 | ENST00000370473.4 |
| GBP1 | AATTCAAAAACGACGAAAGGCATGTACCATACTCGAGTATGGTACATGCCTTTCGTCG | 2422 | chr1 | ENST00000370473.4 |
| GBP1 | AATTCAAAAACGACGAAAGGCATGTACCATACTCGAGTATGGTACATGCCTTTCGTCG | 2423 | chr1 | ENST00000370473.4 |
| GDF1 | AATTCAAAAAGTTCACCAAGCTCAACATTTACTCGAGTAAATGTTGAGCTTGGTGAAC | 2424 | chr19 | ENST00000247005.7 |
| GDF1 | AATTCAAAAAGAGTTCACCAAGCTCAACATTCTCGAGAATGTTGAGCTTGGTGAACTC | 2425 | chr19 | ENST00000247005.7 |
| GDF1 | AATTCAAAAACCCTTATGAACCTCTACTGGTCTCGAGACCAGTAGAGGTTCATAAGGG | 2426 | chr19 | ENST00000247005.7 |
| GDF10 | AATTCAAAAACAGGATAATCGTGGTGTAAATCTCGAGATTTACACCACGATTATCCTG | 2427 | chr10 | ENST00000580279.1 |
| GDF10 | AATTCAAAAACGACCAGAAGGCCGTGTATTTCTCGAGAAATACACGGCCTTCTGGTCG | 2428 | chr10 | ENST00000580279.1 |
| GDF10 | AATTCAAAAACTGTCCGCCAGTGCATCATTACTCGAGTAATGATGCACTGGCGGACAG | 2429 | chr10 | ENST00000580279.1 |
| GDF11 | AATTCAAAAACCTGCAGATCTTGCGACTAAACTCGAGTTTAGTCGCAAGATCTGCAGG | 2430 | chr12 | ENST00000257868.9 |
| GDF11 | AATTCAAAAAGATCGCTGTGGCTGCTCTTAACTCGAGTTAAGAGCAGCCACAGCGATC | 2431 | chr12 | ENST00000257868.9 |
| GDF11 | AATTCAAAAAGAGATGTAGAGACAGTGATAGCTCGAGCTATCACTGTCTCTACATCTC | 2432 | chr12 | ENST00000257868.9 |
| GDF15 | AATTCAAAAAAGACTCCAGATTCCGAGAGTTCTCGAGAACTCTCGGAATCTGGAGTCT | 2433 | chr19 | ENST00000252809.3 |
| GDF15 | AATTCAAAAAGCTCCAGACCTATGATGACTTCTCGAGAAGTCATCATAGGTCTGGAGC | 2434 | chr19 | ENST00000252809.3 |
| GDF15 | AATTCAAAAAGAGCTGGGAAGATTCGAACACTCGAGTGTTCGAATCTTCCCAGCTCT | 2435 | chr19 | ENST00000252809.3 |
| GDF2 | AATTCAAAAACAACAGGTACACGTCCGATAACTCGAGTTATCGGACGTGTACCTGTTG | 2436 | chr10 | ENST00000581492.2 |
| GDF2 | AATTCAAAAATGAAAGGAAGCGTGGTCATTTCTCGAGAAATGACCACGCTTCCTTTCA | 2437 | chr10 | ENST00000581492.2 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
|---|---|---|---|---|
| GDF2 | AATTCAAAAATATGAAGCCTACGAGTGTAAGCTCGAGCTTACACTCGTAGGCTTCATA | 2438 | chr10 | ENST00000581492.2 |
| GDF3 | AATTCAAAAACCGTCACCAGCTATTCATTACTCGAGTAATGAATAGCTGGTGACGGT | 2439 | chr12 | ENST00000329913.3 |
| GDF3 | AATTCAAAAACTCTCAACAGCTCCAATTATGCTCGAGCATAATTGGAGCTGTTGAGAG | 2440 | chr12 | ENST00000329913.3 |
| GDF3 | AATTCAAAAATTGGGCCAGGCAGTCCAATTTCTCGAGAAATTGGACTGCCTGGCCCAA | 2441 | chr12 | ENST00000329913.3 |
| GDF5 | AATTCAAAAACAACACCATCACCAGCTTTATCTCGAGATAAAGCTGGTGATGGTGTTG | 2442 | chr20 | ENST00000374369.7 |
| GDF5 | AATTCAAAAAATGAGACTCAGCCCACCATTTCTCGAGAAATGGTGGGCTGAGTCTCAT | 2443 | chr20 | ENST00000374369.7 |
| GDF5 | AATTCAAAAATGAGTGTGACTTGGGCTAAAGCTCGAGCTTTAGCCCAAGTCACACTCA | 2444 | chr20 | ENST00000374369.7 |
| GDF6 | AATTCAAAAAGACTCCCATCAGCATTCTATACTCGAGTATAGAATGCTGATGGGAGTC | 2445 | chr8 | ENST00000287020.6 |
| GDF6 | AATTCAAAAACGAGTACATGCTGTCAATCTACTCGAGTAGATTGACAGCATGTACTCG | 2446 | chr8 | ENST00000287020.6 |
| GDF6 | AATTCAAAAACAGTCTTCCAAGTCGGCTAATCTCGAGATTAGCCGACTTGGAAGACTG | 2447 | chr8 | ENST00000287020.6 |
| GDF7 | AATTCAAAAAGCAGAGGAAAGAGAGCTTATTCTCGAGAATAAGCTCTCTTTCCTCTGC | 2448 | chr2 | ENST00000272224.4 |
| GDF7 | AATTCAAAAAGTTCGACGTGTCCAGCCTTAACTCGAGTTAAGGCTGGACACGTCGAAC | 2449 | chr2 | ENST00000272224.4 |
| GDF7 | AATTCAAAAACCACTTCATGATGTCGCTTTACTCGAGTAAAGCGACATCATGAAGTGG | 2450 | chr2 | ENST00000272224.4 |
| GDF9 | AATTCAAAAAGATGGCTCAATTGCCTATAAACTCGAGTTTATAGGCAATTGAGCCATC | 2451 | chr5 | ENST00000378673.2 |
| GDF9 | AATTCAAAAACCATCAGTGGAACTGCTATTTCTCGAGAAATAGCAGTTCCACTGATGG | 2452 | chr5 | ENST00000378673.2 |
| GDF9 | AATTCAAAAAGAGTGAATACTTCAGACAATTCTCGAGAATTGTCTGAAGTATTCACTC | 2453 | chr5 | ENST00000378673.2 |
| GPI | AATTCAAAAACGTCTGGTATGTCTCCAACATCTCGAGATGTTGGAGACATACCAGACG | 2454 | chr19 | ENST00000356487.9 |
| GPI | AATTCAAAAACGTCTGGTATGTCTCCAACATCTCGAGATGTTGGAGACATACCAGACG | 2455 | chr19 | ENST00000356487.9 |
| GPI | AATTCAAAAAGCGGATGTTCAATGGTGAGAACTCGAGTTCTCACCATTGAACATCCGC | 2456 | chr19 | ENST00000356487.9 |
| GREM1 | AATTCAAAAAGCAGTGTCGTTGCATATCCATCTCGAGATGGATATGCAACGACACTGC | 2457 | chr15 | ENST00000622074.1 |
| GREM1 | AATTCAAAAAACAGCCACCTACCAAGAAGAACTCGAGTTCTTCTTGGTAGGTGGCTGT | 2458 | chr15 | ENST00000622074.1 |
| GREM1 | AATTCAAAAACAACAGTCGCACCATCATCAACTCGAGTTGATGATGGTGCGACTGTTG | 2459 | chr15 | ENST00000622074.1 |
| GREM2 | AATTCAAAAAGCTGTGAAGGAAGGAAATTTACTCGAGTAAATTTCCTTCCTTCACAGC | 2460 | chr1 | ENST00000318160.4 |
| GREM2 | AATTCAAAAACAAGGTGCATTTCTGTCATTTCTCGAGAAATGACAGAAATGCACCTTG | 2461 | chr1 | ENST00000318160.4 |
| GREM2 | AATTCAAAAACGGAAGTAGACGTAACTTATTCTCGAGAATAAGTTACGTCTACTTCCG | 2462 | chr1 | ENST00000318160.4 |
| GRN | AATTCAAAAAGCCCTGATAGTCAGTTCGAATCTCGAGATTCGAACTGACTATCAGGGC | 2463 | chr17 | ENST00000053867.7 |
| GRN | AATTCAAAAAGCCCTGATAGTCAGTTCGAATCTCGAGATTCGAACTGACTATCAGGGC | 2464 | chr17 | ENST00000053867.7 |
| GRN | AATTCAAAAACTTCCAAAGATCAGGTAACAACTCGAGTTGTTACCTGATCTTTGGAAG | 2465 | chr17 | ENST00000053867.7 |
| HAX1 | AATTCAAAAAACAGACACTTCGGGACTCAATCTCGAGATTGAGTCCCGAAGTGTCTGT | 2466 | chr1 | ENST00000328703.11 |
| HAX1 | AATTCAAAAACCAGCCCAAATCCTATTTCAACPCGAGTTGAAATAGGATTTGGGCTGG | 2467 | chr1 | ENST00000328703.11 |
| HAX1 | AATTCAAAAACCAGAGGCCATTTCATAGGTTCTCGAGAACCTATGAAATGGCCTCTGG | 2468 | chr1 | ENST00000328703.11 |
| HFE2 | AATTCAAAAAGACATGATCATTAGCCATAAGCTCGAGCTTATGGCTAATGATCATGTC | 2469 | chr1 | ENST00000336751.10 |
| HFE2 | AATTCAAAAAGCCTACATTGGCACAACTATACTCGAGTATAGTTGTGCCAATGTAGGC | 2470 | chr1 | ENST00000336751.10 |
| HFE2 | AATTCAAAAAGAAGCTCACCATCATATTTAACTCGAGTTAAATATGATGGTGAGCTTC | 2471 | chr1 | ENST00000336751.10 |
| HMGB1 | AATTCAAAAAGATGCAGCTTATACGAAATAACTCGAGTTATTTCGTATAAGCTGCATC | 2472 | chr13 | ENST00000339872.8 |
| HMGB1 | AATTCAAAAAGTTGGTGCACAGCACAAATTACTCGAGTAATTTGTGCTGTGCACCAAC | 2473 | chr13 | ENST00000339872.8 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
|---|---|---|---|---|
| HMGB1 | AATTCAAAAAGAAGATGATGATGATGAATACTCGAGTATTCATCATCATCATCTTCT | 2474 | chr13 | ENST00000339872.8 |
| HYAL2 | AATTCAAAAACCTGCCAGTACCTCAAAGATTCTCGAGAATCTTTGAGGTACTGGCAGG | 2475 | chr3 | ENST00000357750.8 |
| HYAL2 | AATTCAAAAACCTGCCAGTACCTCAAAGATTCTCGAGAATCTTTGAGGTACTGGCAGG | 2476 | chr3 | ENST00000357750.8 |
| HYAL2 | AATTCAAAAACTGGACCTGAATGCCTTTGATCTCGAGATCAAAGGCATTCAGGTCCAG | 2477 | chr3 | ENST00000357750.8 |
| ICAM3 | AATTCAAAAAGTCCAGCTCACGAGGCAAATACTCGAGTATTTGCCTCGTGAGCTGGAC | 2478 | chr19 | ENST00000160262.9 |
| ICAM3 | AATTCAAAAACCAGCTCAACTTCAGCTAAATCTCGAGATTTAGCTGAAGTTGAGCTGG | 2479 | chr19 | ENST00000160262.9 |
| ICAM3 | AATTCAAAAAGCACTTGAAATGGAAAGATAACTCGAGTTATCTTTCCATTTCAAGTGC | 2480 | chr19 | ENST00000160262.9 |
| ICAM3 | AATTCAAAAAGAGCGGCAGTTACCATGTTAGCTCGAGCTAACATGGTAACTGCCGCTC | 2481 | chr19 | ENST00000160262.9 |
| ICOS | AATTCAAAAAGCACGACCCTAACGGTGAATACTCGAGTATTCACCGTTAGGGTCGTGC | 2482 | ch2 | ENST00000316386.10 |
| ICOS | AATTCAAAAAGTCCGCATTTCACTATCATACCTCGAGGTATGATAGTGAAATGCGGAC | 2483 | ch2 | ENST00000316386.10 |
| ICOS | AATTCAAAAACCATTCTCATGCCAACTATTACTCGAGTAATAGTTGGCATGAGAATGG | 2484 | ch2 | ENST00000316386.10 |
| ICOS | AATTCAAAAACACAGATGTGACCCTATAATACTCGAGTATTATAGGGTCACATCTGTG | 2485 | ch2 | ENST00000316386.10 |
| IFNA10 | AATTCAAAAATGTAAAGAAGTGTCGTGTATACTCGAGTATACACGACACTTCTTTACA | 2486 | chr9 | ENST00000357374.2 |
| IFNA10 | AATTCAAAAAATAACCACGACGCGTTGAATCCTCGAGGATTCAACGCGTCGTGGTTAT | 2487 | chr9 | ENST00000357374.2 |
| IFNA10 | AATTCAAAAACCTGGGACAAATGGGAAGAATCTCGAGATTCTTCCCATTTGTCCCAGG | 2488 | chr9 | ENST00000357374.2 |
| IFNA14 | AATTCAAAAACTGGGCTGTAATCTGTCTCAACTCGAGTTGAGACAGATTACAGCCCAG | 2489 | chr9 | ENST00000380222.3 |
| IFNA14 | AATTCAAAAACCTGAATAACAGGAGGACTTTCTCGAGAAAGTCCTCCTGTTATTCAGG | 2490 | chr9 | ENST00000380222.3 |
| IFNA14 | AATTCAAAAAGCAGCAGACCTTCAATCTCTTCTCGAGAAGAGATTGAAGGTCTGCTGC | 2491 | chr9 | ENST00000380222.3 |
| IFNA16 | AATTCAAAAATGTAAAGAAGCATCGTGTTTACTCGAGTAAACACGATGCTTCTTTACA | 2492 | chr9 | ENST00000380216.1 |
| IFNA16 | AATTCAAAAAATGATCCTCATTGATTAATACCTCGAGGTATTAATCAATGAGGATCAT | 2493 | chr9 | ENST00000380216.1 |
| IFNA16 | AATTCAAAAACCTGAAGGACAGATATGATTTCTCGAGAAATCATATCTGTCCTTCAGG | 2494 | chr9 | ENST00000380216.1 |
| IFNA2 | AATTCAAAAAGCACAGTGGTTAATGTAATAACTCGAGTTATTACATTAACCACTGTGC | 2495 | chr9 | ENST00000380206.3 |
| IFNA2 | AATTCAAAAATATGACCATGACACGATTTAACTCGAGTTAAATCGTGTCATGGTCATA | 2496 | chr9 | ENST00000380206.3 |
| IFNA2 | AATTCAAAAACCATGCTGACTGATCCATTATCTCGAGATAATGGATCAGTCAGCATGG | 2497 | chr9 | ENST00000380206.3 |
| IFNA5 | AATTCAAAAAACTTGGGATGAGACACTTCTACTCGAGTAGAAGTGTCTCATCCCAAGT | 2498 | chr9 | ENST00000610521.1 |
| IFNA5 | AATTCAAAAAGTGGAAGACACTCCTCTGATCTCGAGATCAGAGGAGTGTCTTCCACT | 2499 | chr9 | ENST00000610521.1 |
| IFNA5 | AATTCAAAAATCAACTGCAAGTCAATCTGTTCTCGAGAACAGATTGACTTGCAGTTGA | 2500 | chr9 | ENST00000610521.1 |
| IFNA6 | AATTCAAAAAGACAGACATGACTTCAGATTTCTCGAGAAATCTGAAGTCATGTCTGTC | 2501 | chr9 | ENST00000380210.1 |
| IFNA6 | AATTCAAAAACTGTCCTCCATGAGGTGATTCCTCGAGGAATCACCTCATGGAGGACAG | 2502 | chr9 | ENST00000380210.1 |
| IFNA6 | AATTCAAAAAGGCTTCTAGACAAACTCTATCTCGAGATAGAGTTTGTCTAGAAGCCT | 2503 | chr9 | ENST00000380210.1 |
| IFNA8 | AATTCAAAAATAACTATCTATAGGGCTTAAACTCGAGTTTAAGCCCTATAGATAGTTA | 2504 | chr9 | ENST00000380205.1 |
| IFNA8 | AATTCAAAAACCAGGAGGAGTTTGATGATAACTCGAGTTATCATCAAACTCCTCCTGG | 2505 | chr9 | ENST00000380205.1 |
| IFNA8 | AATTCAAAAAGACCTGGTACAACACGGAAATCTCGAGATTTCCGTGTTGTACCAGGTC | 2506 | chr9 | ENST00000380205.1 |
| IFNAR1 | AATTCAAAAAGCCAAGATTCAGGAAATTATTCTCGAGAATAATTTCCTGAATCTTGGC | 2507 | chr21 | ENST00000270139.7 |
| IFNAR1 | AATTCAAAAAGCTCTCCCGTTTGTCATTTATCTCGAGATAAATGACAAACGGGAGAGC | 2508 | chr21 | ENST00000270139.7 |
| IFNAR1 | AATTCAAAAATGAACTGTGTCAAGTATAAGCTCGAGCTTATACTTGACACAGTTCAT | 2509 | chr21 | ENST00000270139.7 |
| IFNAR2 | AATTCAAAAAGAGTGGAAATTTCACCTATATCTCGAGATATAGGTGAAATTTCCACTC | 2510 | chr21 | ENST00000342136.8 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
| --- | --- | --- | --- | --- |
| IFNAR2 | AATTCAAAAATGTATATCAGCCTCGTGTTTGCTCGAGCAAACACGAGGCTGATATACA | 2511 | chr21 | ENST00000342136.8 |
| IFNAR2 | AATTCAAAAAGCAAATACCACAAGATCATTTCTCGAGAAATGATCTTGTGGTATTTGC | 2512 | chr21 | ENST00000342136.8 |
| IFNB1 | AATTCAAAAATTGAATGGGAGGCTTGAATACTCGAGTATTCAAGCCTCCCATTCAAT | 2513 | chr9 | ENST00000380232.3 |
| IFNB1 | AATTCAAAAACCTACAAAGAAGCAGCAATTTCTCGAGAAATTGCTGCTTCTTTGTAGG | 2514 | chr9 | ENST00000380232.3 |
| IFNB1 | AATTCAAAAACTAATGTCTATCATCAGATAACTCGAGTTATCTGATGATAGACATTAG | 2515 | chr9 | ENST00000380232.3 |
| IFNE | AATTCAAAAAGGTAGTGATAACCTTAGATTACTCGAGTAATCTAAGGTTATCACTACC | 2516 | chr9 | ENST00000448696.4 |
| IFNE | AATTCAAAAAGCCTCTTCAGGGCAAATATTCTCGAGAATATTTGCCCTGAAGAGGCT | 2517 | chr9 | ENST00000448696.4 |
| IFNE | AATTCAAAAACATAGAGTGGTAATACAATTTCTCGAGAAATTGTATTACCACTCTATG | 2518 | chr9 | ENST00000448696.4 |
| IFNG | AATTCAAAAAGGTTGTCCTGCCTGCAATATTCTCGAGAATATTGCAGGCAGGACAACC | 2519 | chr12 | ENST00000229135.3 |
| IFNG | AATTCAAAAACATTCAGATGTAGCGGATAATCTCGAGATTATCCGCTACATCTGAATG | 2520 | chr12 | ENST00000229135.3 |
| IFNG | AATTCAAAAATGTTACTGCCAGGACCCATATCTCGAGATATGGGTCCTGGCAGTAACA | 2521 | chr12 | ENST00000229135.3 |
| IFNGR1 | AATTCAAAAAACGAGCAGGAAGTCGATTATGCTCGAGCATAATCGACTTCCTGCTCGT | 2522 | chr6 | ENST00000367739.8 |
| IFNGR1 | AATTCAAAAACATGAACCCTATCGTATATTGCTCGAGCAATATACGATAGGGTTCATG | 2523 | chr6 | ENST00000367739.8 |
| IFNGR1 | AATTCAAAAACGGAAGTGAGATCCAGTATAACTCGAGTTATACTGGATCTCACTTCCG | 2524 | chr6 | ENST00000367739.8 |
| IFNK | AATTCAAAAAGAGATTGTGGCTACGCAAATGCTCGAGCATTTGCGTAGCCACAATCTC | 2525 | chr9 | ENST00000276943.2 |
| IFNK | AATTCAAAAACTGTTCAGATTCAAGATTATTCTCGAGAATAATCTTGAATCTGAACAG | 2526 | chr9 | ENST00000276943.2 |
| IFNK | AATTCAAAAATCAGCCAACACACCTTCAAATCTCGAGATTTGAAGGTGTGTTGGCTGA | 2527 | chr9 | ENST00000276943.2 |
| IFNL1 | AATTCAAAAACTCACGCGAGACCTCAAATATCTCGAGATATTTGAGGTCTCGCGTGAG | 2528 | chr19 | ENST00000333625.2 |
| IFNL1 | AATTCAAAAAGCCACATTGGCAGGTTCAAATCTCGAGATTTGAACCTGCCAATGTGGC | 2529 | chr19 | ENST00000333625.2 |
| IFNL1 | AATTCAAAAAGAGTTGCAGCTCTCCTGTCTTCTCGAGAAGACAGGAGAGCTGCAACTC | 2530 | chr19 | ENST00000333625.2 |
| IFNL3 | AATTCAAAAAGGGCCAAAGATGCCTTAGAACTCGAGTTCTAAGGCATCTTTGGCCCT | 2531 | chr19 | ENST00000413851.2 |
| IFNL3 | AATTCAAAAAGCCTTTAAGAGGGCAAAGATCTCGAGATCTTTGGCCCTCTTAAAGGC | 2532 | chr19 | ENST00000413851.2 |
| IFNL3 | AATTCAAAAATGCCACATAGCCCAGTTCAAGCTCGAGCTTGAACTGGGCTATGTGGCA | 2533 | chr19 | ENST00000413851.2 |
| IFNW1 | AATTCAAAAAAGACTCTTATTTCGGCTTTAACTCGAGTTAAAGCCGAAATAAGAGTCT | 2534 | chr9 | ENST00000380229.3 |
| IFNW1 | AATTCAAAAATCAGTCCCTAAGATGTTATTTCTCGAGAAATAACATCTTAGGGACTGA | 2535 | chr9 | ENST00000380229.3 |
| IFNW1 | AATTCAAAAACGGTATATTAAGCCAGTATATCTCGAGATATACTGGCTTAATATACCG | 2536 | chr9 | ENST00000380229.3 |
| IL10 | AATTCAAAAAGCTTCTCTGTGAACGATTTACTCGAGTAAATCGTTCACAGAGAAGCT | 2537 | chr1 | ENST00000423557.1 |
| IL10 | AATTCAAAAAGCAGGTGAAGAATGCCTTTAACTCGAGTTAAAGGCATTCTTCACCTGC | 2538 | chr1 | ENST00000423557.1 |
| IL10 | AATTCAAAAAGCTGGACAACTTGTTGTTAAACTCGAGTTTAACAACAAGTTGTCCAGC | 2539 | chr1 | ENST00000423557.1 |
| IL10RA | AATTCAAAAATCTGTCGCTTCCCGAAGTAACCTCGAGGTTACTTCGGGAAGCGACAGA | 2540 | chr11 | ENST00000227752.7 |
| IL10RA | AATTCAAAAAGAAACAGGATCCTCTAGAAATCTCGAGATTTCTAGAGGATCCTGTTTC | 2541 | chr11 | ENST00000227752.7 |
| IL10RA | AATTCAAAAAGAACTCTTTCCTGTATCATAACTCGAGTTATGATACAGGAAAGAGTTC | 2542 | chr11 | ENST00000227752.7 |
| IL11 | AATTCAAAAAATATCCACTTGAGGGCGATTTCTCGAGAAATCGCCCTCAAGTGGATAT | 2543 | chr19 | ENST00000264563.6 |
| IL11 | AATTCAAAAACCTTCCAAAGCCAGATCTTATCTCGAGATAAGATCTGGCTTTGGAAGG | 2544 | chr19 | ENST00000264563.6 |
| IL11 | AATTCAAAAATGCACAGCTGAGGGACAAATTCTCGAGAATTTGTCCCTCAGCTGTGCA | 2545 | chr19 | ENST00000264563.6 |
| IL11RA | AATTCAAAAACGGCAGATTCCACCTATAATTCTCGAGAATTATAGGTGGAATCTGCCG | 2546 | chr9 | ENST00000318041.13 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
|---|---|---|---|---|
| IL11RA | AATTCAAAAATCGGCAGATTCCACCTATAATCTCGAGATTATAGGTGGAATCTGCCGA | 2547 | chr9 | ENST00000318041.13 |
| IL11RA | AATTCAAAAATGGAGCCAGTACCGGATTAATCTCGAGATTAATCCGGTACTGGCTCCA | 2548 | chr9 | ENST00000318041.13 |
| IL12A | AATTCAAAAATGATACCTCTGATCAAGTATTCTCGAGAATACTTGATCAGAGGTATCA | 2549 | chr3 | ENST00000305579.6 |
| IL12A | AATTCAAAAACCTGTGCCTTAGTAGTATTTACTCGAGTAAATACTACTAAGGCACAGG | 2550 | chr3 | ENST00000305579.6 |
| IL12A | AATTCAAAAACCTGTTTACCATTGGAATTAACTCGAGTTAATTCCAATGGTAAACAGG | 2551 | chr3 | ENST00000305579.6 |
| IL12B | AATTCAAAAAGAATTTGGTCCACTGATATTTCTCGAGAAATATCAGTGGACCAAATTC | 2552 | chr5 | ENST00000231228.2 |
| IL12B | AATTCAAAAACCATGGGCCTTCATGCTATTTCTCGAGAAATAGCATGAAGGCCCATGG | 2553 | chr5 | ENST00000231228.2 |
| IL12B | AATTCAAAAATTAGATGCTAAATGCTCATTGCTCGAGCAATGAGCATTTAGCATCTAA | 2554 | chr5 | ENST00000231228.2 |
| IL12RB1 | AATTCAAAAACAGCTCTACAACTCAGTTAAACTCGAGTTTAACTGAGTTGTAGAGCTG | 2555 | chr19 | ENST00000593993.6 |
| IL12RB1 | AATTCAAAAAGTCATCTCCTCGAACCAATTTCTCGAGAAATTGGTTCGAGGAGATGAC | 2556 | chr19 | ENST00000593993.6 |
| IL12RB1 | AATTCAAAAACCAACGGGACCACCATGTATTCTCGAGAATACATGGTGGTCCCGTTGG | 2557 | chr19 | ENST00000593993.6 |
| IL13 | AATTCAAAAAACTTCGAAAGCATCATTATTTCTCGAGAAATAATGATGCTTTCGAAGT | 2558 | chr5 | ENST00000304506.7 |
| IL13 | AATTCAAAAAATTGAAGTTGCAGATTCATTTCTCGAGAAATGAATCTGCAACTTCAAT | 2559 | chr5 | ENST00000304506.7 |
| IL13 | AATTCAAAAACCTGCTCTTACATTTAAAGAACTCGAGTTCTTTAAATGTAAGAGCAGG | 2560 | chr5 | ENST00000304506.7 |
| IL15 | AATTCAAAAAGAAGATCTTATTCAATCTATGCTCGAGCATAGATTGAATAAGATCTTC | 2561 | chr4 | ENST00000296545.11 |
| IL15 | AATTCAAAAATAAGGGTGATAGTCAAATTATCTCGAGATAATTTGACTATCACCCTTA | 2562 | chr4 | ENST00000296545.11 |
| IL15 | AATTCAAAAACACTCTGCTGCTTAGACATAACTCGAGTTATGTCTAAGCAGCAGAGTG | 2563 | chr4 | ENST00000296545.11 |
| IL16 | AATTCAAAAATGGGACCACGTGAGATCATTCCTCGAGGAATGATCTCACGTGGTCCCA | 2564 | chr15 | ENST00000302987.8 |
| IL16 | AATTCAAAAAGTTCTGGATGAAGCAACATTACTCGAGTAATGTTGCTTCATCCAGAAC | 2565 | chr15 | ENST00000302987.8 |
| IL16 | AATTCAAAAACCCAAACAGTGACATTTATTTCTCGAGAAATAAATGTCACTGTTTGGG | 2566 | chr15 | ENST00000302987.8 |
| IL17A | AATTCAAAAAATCAGTTCTGCCTAGGTAAATCTCGAGATTTACCTAGGCAGAACTGAT | 2567 | chr6 | ENST00000340057.1 |
| IL17A | AATTCAAAAAGAGCTATTTAAGGATCTATTTCTCGAGAAATAGATCCTTAAATAGCTC | 2568 | chr6 | ENST00000340057.1 |
| IL17A | AATTCAAAAAGGTCAACCTGAACATCCATAACTCGAGTTATGGATGTTCAGGTTGACC | 2569 | chr6 | ENST00000340057.1 |
| IL17B | AATTCAAAAATATGCCCGCATGGAGGAGTATCTCGAGATACTCCTCCATGCGGGCATA | 2570 | chr5 | ENST00000261796.3 |
| IL17B | AATTCAAAAAGTGTCACGGATGAAACCGTATCTCGAGATACGGTTTCATCCGTGACAC | 2571 | chr5 | ENST00000261796.3 |
| IL17B | AATTCAAAAAGCAGCTGTGGATGTCCAACAACTCGAGTTGTTGGACATCCACAGCTGC | 2572 | chr5 | ENST00000261796.3 |
| IL17C | AATTCAAAAAGCACCTCTTCCAGCCCTTAAACTCGAGTTTAAGGGCTGGAAGAGGTGC | 2573 | chr16 | ENST00000244241.4 |
| IL17C | AATTCAAAAACTTTGCCTTCCACACCGAGTTCTCGAGAACTCGGTGTGGAAGGCAAAG | 2574 | chr16 | ENST00000244241.4 |
| IL17C | AATTCAAAAAATCTCCAGCCTCAGTAGTTGGCTCGAGCCAACTACTGAGGCTGGAGAT | 2575 | chr16 | ENST00000244241.4 |
| IL17D | AATTCAAAAAGAGCTACTCTGTTACATTTCCTCGAGGAAATGTAACAGAGTAGCTCT | 2576 | chr13 | ENST00000304920.3 |
| IL17D | AATTCAAAAACAAAGAGATAGGGACGCATATCTCGAGATATGCGTCCCTATCTCTTTG | 2577 | chr13 | ENST00000304920.3 |
| IL17D | AATTCAAAAAGACAGCATCAACTCCAGCATCTCGAGATGCTGGAGTTGATGCTGTCT | 2578 | chr13 | ENST00000304920.3 |
| IL17F | AATTCAAAAATCATCCACCATGTGCAGTAAGCTCGAGCTTACTGCACATGGTGGATGA | 2579 | chr6 | ENST00000336123.4 |
| IL17F | AATTCAAAAAGTACTTGCTGCTGTCGATATTCTCGAGAATATCGACAGCAGCAAGTAC | 2580 | chr6 | ENST00000336123.4 |
| IL17F | AATTCAAAAACGTTTCCATGTCACGTAACATCTCGAGATGTTACGTGACATGGAAACG | 2581 | chr6 | ENST00000336123.4 |
| IL18 | AATTCAAAAACCCGGACCATATTTATTATAACTCGAGTTATAATAAATATGGTCCGGG | 2582 | chr11 | ENST00000280357.11 |
| IL18 | AATTCAAAAATGATTCTGACTGTAGAGATAACTCGAGTTATCTCTACAGTCAGAATCA | 2583 | chr11 | ENST00000280357.11 |

TABLE 16-continued

3' to 5' (Reverse) shRNA sequences for Silencing of Cytokine/Chemokine
Genes to Reduce the Incidence of CRS

| Target Gene Symbol | shRNA Reverse Oligo Sequence | SEQ ID NO: | Location | Gene ID No. |
|---|---|---|---|---|
| IL18 | AATTCAAAAATGGCAAGCTTGAATCTAAATTCTCGAGAATTTAGATTCAAGCTTGCCA | 2584 | chr11 | ENST00000280357.11 |
| IL18BP | AATTCAAAAAGGTCCCTTCTCTCACCAAATTCTCGAGAATTTGGTGAGAGAAGGGACC | 2585 | chr11 | ENST00000260049.9 |
| IL18BP | AATTCAAAAATCCCATGTCTCTGCTCATTTACTCGAGTAAATGAGCAGAGACATGGGA | 2586 | chr11 | ENST00000260049.9 |
| IL18BP | AATTCAAAAACTGGGCAATGGTTCCTTCATTCTCGAGAATGAAGGAACCATTGCCCAG | 2587 | chr11 | ENST00000260049.9 |
| IL19 | AATTCAAAAAGTCCACGCTGCTGCCATTAAACTCGAGTTTAATGGCAGCAGCGTGGAC | 2588 | chr1 | ENST00000270218.10 |
| IL19 | AATTCAAAAATCCACAGACATGCACCATATACTCGAGTATATGGTGCATGTCTGTGGA | 2589 | chr1 | ENST00000270218.10 |
| IL19 | AATTCAAAAATGATGACAAGGAACCTGTATACTCGAGTATACAGGTTCCTTGTCATCA | 2590 | chr1 | ENST00000270218.10 |
| IL1A | AATTCAAAAAGTGGAACCAACACTAACATATCTCGAGATATGTTAGTGTTGGTTCCAC | 2591 | chr2 | ENST00000263339.3 |
| IL1A | AATTCAAAAAGCCCTCAATCAAAGTATAATTCTCGAGAATTATACTTTGATTGAGGGC | 2592 | chr2 | ENST00000263339.3 |
| IL1A | AATTCAAAAATATTACAGATGGGCAAATTAACTCGAGTTAATTTGCCCATCTGTAATA | 2593 | chr2 | ENST00000263339.3 |
| IL1B | AATTCAAAAAATCAATAACAAGCTGGAATTTCTCGAGAAATTCCAGCTTGTTATTGAT | 2594 | chr2 | ENST00000263341.6 |
| IL1B | AATTCAAAAAAGCAACCGCTTCCCTATTTATCTCGAGATAAATAGGGAAGCGGTTGCT | 2595 | chr2 | ENST00000263341.6 |
| IL1B | AATTCAAAAACTGACTTCACCATGCAATTTGCTCGAGCAAATTGCATGGTGAAGTCAG | 2596 | chr2 | ENST00000263341.6 |
| IL1F10 | AATTCAAAAATCCTTGTGGGCTCAGTTTAATCTCGAGATTAAACTGAGCCCACAAGGA | 2597 | chr2 | ENST00000341010.6 |
| IL1F10 | AATTCAAAAAGGTCTATGGTAGGCAGAATAACTCGAGTTATTCTGCCTACCATAGACC | 2598 | chr2 | ENST00000341010.6 |
| IL1F10 | AATTCAAAAATGCAGACCAGAAGGCTCTATACTCGAGTATAGAGCCTTCTGGTCTGCA | 2599 | chr2 | ENST00000341010.6 |
| IL1R1 | AATTCAAAAAGCCAAGAATACACATGGTATACTCGAGTATACCATGTGTATTCTTGGC | 2600 | chr2 | ENST00000410023.5 |
| IL1R1 | AATTCAAAAAATAATGCACAAGCCATATTTACTCGAGTAAATATGGCTTGTGCATTAT | 2601 | chr2 | ENST00000410023.5 |
| IL1R1 | AATTCAAAAATGGTATAGATGCAGCATATATCTCGAGATATATGCTGCATCTATACCA | 2602 | chr2 | ENST00000410023.5 |
| IL1R2 | AATTCAAAAACAATCCCGTGTAAGGTGTTTCCTCGAGGAAACACCTTACACGGGATTG | 2603 | chr2 | ENST00000332549.7 |
| IL1R2 | AATTCAAAAAGACCATTCCTGTGATCATTTCCTCGAGGAAATGATCACAGGAATGGTC | 2604 | chr2 | ENST00000332549.7 |
| IL1R2 | AATTCAAAAACGTTCATCTCATACCCGCAAACTCGAGTTTGCGGGTATGAGATGAACG | 2605 | chr2 | ENST00000332549.7 |
| IL1RAPL1 | AATTCAAAAACAAAGCAAGCGGCTGATTATTCTCGAGAATAATCAGCCGCTTGCTTTG | 2606 | chrX | ENST00000378993.5 |
| IL1RAPL1 | AATTCAAAAAGCCAGCGTTCTCCTTCATAAACTCGAGTTTATGAAGGAGAACGCTGGC | 2607 | chrX | ENST00000378993.5 |
| IL1RAPL1 | AATTCAAAAATCAAGCTCCTGACGGTCATTACTCGAGTAATGACCGTCAGGAGCTTGA | 2608 | chrX | ENST00000378993.5 |
| IL1RL1 | AATTCAAAAATTACACCGTGGATTGGTATTACTCGAGTAATACCAATCCACGGTGTAA | 2609 | chr2 | ENST00000233954.5 |
| IL1RL1 | AATTCAAAAAGTTGCTGATTCTGGTATTTACTCGAGTAAATACCAGAATCAGCAACT | 2610 | chr2 | ENST00000233954.5 |
| IL1RL1 | AATTCAAAAACGTGAAGGAAGAGGATTTATTCTCGAGAATAAATCCTCTTCCTTCACG | 2611 | chr2 | ENST00000233954.5 |
| IL1RN | AATTCAAAAAGCAAGGACCCAAATGTCAATTTCTCGAGAAATTGACATTTGGTCCTTGC | 2612 | chr2 | ENST00000409930.3 |
| IL1RN | AATTCAAAAACGTCATGGTCACCAAATTCTACTCGAGTAGAATTTGGTGACCATGACG | 2613 | chr2 | ENST00000409930.3 |
| IL1RN | AATTCAAAAACTGCCTCCAGAATGGTCTTTCCTCGAGGAAAGACCATTCTGGAGGCAG | 2614 | chr2 | ENST00000409930.3 |
| IL2 | AATTCAAAAAGCTACCTATTGTAACTATTATCTCGAGATAATAGTTACAATAGGTAGC | 2615 | chr4 | ENST00000226730.4 |
| IL2 | AATTCAAAAACAGCTACAACTGGAGCATTTACTCGAGTAAATGCTCCAGTTGTAGCTG | 2616 | chr4 | ENST00000226730.4 |
| IL2 | AATTCAAAAATGCTGGATTTACAGATGATTTCTCGAGAAATCATCTGTAAATCCAGCA | 2617 | chr4 | ENST00000226730.4 |
| IL20 | AATTCAAAAACTGATGCTCTGTGAGATATTTCTCGAGAAATATCTCACAGAGCATCAG | 2618 | chr1 | ENST00000367096.7 |
| IL20 | AATTCAAAAATGGTCACAGTGTATCTTATTTCTCGAGAAATAAGATACACTGTGACCA | 2619 | chr1 | ENST00000367096.7 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
|---|---|---|---|---|
| IL20 | AATTCAAAAAGGACTGAAGACACTCAATTTGCTCGAGCAAATTGAGTGTCTTCAGTCC | 2620 | chr1 | ENST00000367096.7 |
| IL20RA | AATTCAAAAACCAGTATTATGCCAAAGTTAACTCGAGTTAACTTTGGCATAATACTGG | 2621 | chr6 | ENST00000316649.9 |
| IL20RA | AATTCAAAAAGAGGGTCTTCAAGGAGTTAAACTCGAGTTTAACTCCTTGAAGACCCTC | 2622 | chr6 | ENST00000316649.9 |
| IL20RA | AATTCAAAAAGCTTCGCATTTGATGGAAATTCTCGAGAATTTCCATCAAATGCGAAGC | 2623 | chr6 | ENST00000316649.9 |
| IL20RB | AATTCAAAAACAGTGTACTATTCTGTCGAATCTCGAGATTCGACAGAATAGTACACTG | 2624 | chr3 | ENST00000329582.8 |
| IL20RB | AATTCAAAAACCAGAATAATCCTTGAGAGAACTCGAGTTCTCTCAAGGATTATTCTGG | 2625 | chr3 | ENST00000329582.8 |
| IL20RB | AATTCAAAAACTCTGTACTCTCAACCAACATCTCGAGATGTTGGTTGAGAGTACAGAG | 2626 | chr3 | ENST00000329582.8 |
| IL21 | AATTCAAAAAAGGAAACCACCTTCCACAAATCTCGAGATTTGTGGAAGGTGGTTTCCT | 2627 | chr4 | ENST00000264497.7 |
| IL21 | AATTCAAAAAATGACTTGGTCCCTGAATTTCCTCGAGGAAATTCAGGGACCAAGTCAT | 2628 | chr4 | ENST00000264497.7 |
| IL21 | AATTCAAAAACTTTCAGAAGGCCCAACTAAACTCGAGTTTAGTTGGGCCTTCTGAAAG | 2629 | chr4 | ENST00000264497.7 |
| IL22 | AATTCAAAAAGGCTAAGCACATGTCATATTCTCGAGAATATGACATGTGCTTAGCCT | 2630 | chr12 | ENST00000328087.5 |
| IL22 | AATTCAAAAAGTTTCCATAATCAGTACTTTACTCGAGTAAAGTACTGATTATGGAAAC | 2631 | chr12 | ENST00000328087.5 |
| IL22 | AATTCAAAAAGACTTTCTAAGCATAGATATCTCGAGATATCTATGCTTAGAAAGTCT | 2632 | chr12 | ENST00000328087.5 |
| IL22RA1 | AATTCAAAAAGGACACTTTCTAGTCCTAAACCTCGAGGTTTAGGACTAGAAAGTGTCC | 2633 | chr1 | ENST00000270800.1 |
| IL22RA1 | AATTCAAAAAGGGACACCACAGTACCTAAACTCGAGTTTAGGTACTGTGGTGTCCCT | 2634 | chr1 | ENST00000270800.1 |
| IL22RA1 | AATTCAAAAACTGTCCGAGATCACCTACTTACTCGAGTAAGTAGGTGATCTCGGACAG | 2635 | chr1 | ENST00000270800.1 |
| IL22RA2 | AATTCAAAAAGACATACAGGAACCTTATTACTCGAGTAATAAGGTTCCTGTATGTCT | 2636 | chr6 | ENST00000349184.8 |
| IL22RA2 | AATTCAAAAACTCGTGTTTGAAGGATCTTATCTCGAGATAAGATCCTTCAAACACGAG | 2637 | chr6 | ENST00000349184.8 |
| IL22RA2 | AATTCAAAAATGCTCCAAATTTACCATATAGCTCGAGCTATATGGTAAATTTGGAGCA | 2638 | chr6 | ENST00000349184.8 |
| IL23A | AATTCAAAAAGCTGCTAGGATCGGATATTTCTCGAGAAATATCCGATCCTAGCAGCT | 2639 | chr12 | ENST00000228534.5 |
| IL23A | AATTCAAAAACTGTGAGCCAACAGGTTAATTCTCGAGAATTAACCTGTTGGCTCACAG | 2640 | chr12 | ENST00000228534.5 |
| IL23A | AATTCAAAAAGGATCCACCAGGGTCTGATTTCTCGAGAAATCAGACCCTGGTGGATCC | 2641 | chr12 | ENST00000228534.5 |
| IL23R | AATTCAAAAACTTTCTTTGATTGGGATATTTCTCGAGAAATATCCCAATCAAAGAAAG | 2642 | chr1 | ENST00000347310.9 |
| IL23R | AATTCAAAAATATCTCACCTCAAGCTATATTCTCGAGAATATAGCTTGAGGTGAGATA | 2643 | chr1 | ENST00000347310.9 |
| IL23R | AATTCAAAAACGACAATACTACAGTTGTATACTCGAGTATACAACTGTAGTATTGTCG | 2644 | chr1 | ENST00000347310.9 |
| IL24 | AATTCAAAAACACAGGCGGTTTCTGCTATTCCTCGAGGAATAGCAGAAACCGCCTGTG | 2645 | chr1 | ENST00000294984.6 |
| IL24 | AATTCAAAAAGTCAGGACTCTGAAGTCATTCCTCGAGGAATGACTTCAGAGTCCTGAC | 2646 | chr1 | ENST00000294984.6 |
| IL24 | AATTCAAAAATCGGATGCTGAGAGCTGTTACCTCGAGGTAACAGCTCTCAGCATCCGA | 2647 | chr1 | ENST00000294984.6 |
| IL25 | AATTCAAAAACAGGCACTTTCTAGATATTTCTCGAGAAATATCTAGAAAGTGCCTGT | 2648 | chr14 | ENST00000329715.2 |
| IL25 | AATTCAAAAACCACAACCAGACTGTCTTCTACTCGAGTAGAAGACAGTCTGGTTGTGG | 2649 | chr14 | ENST00000329715.2 |
| IL25 | AATTCAAAAATCCTGTAGGGCCAGTGAAGATCTCGAGATCTTCACTGGCCCTACAGGA | 2650 | chr14 | ENST00000329715.2 |
| IL26 | AATTCAAAAAGCTGTTGACGCTCTCTATATCTCGAGATATAGAGAGCGTCAACAGCT | 2651 | chr12 | ENST00000229134.4 |
| IL26 | AATTCAAAAAGTACATTGTGTCAACTTAATCTCGAGATTAAGTTGACACAATGTACT | 2652 | chr12 | ENST00000229134.4 |
| IL26 | AATTCAAAAACGATTCCAGAAGACCGCATAACTCGAGTTATGCGGTCTTCTGGAATCG | 2653 | chr12 | ENST00000229134.4 |
| IL27 | AATTCAAAAACTCCTTGGAGCTCGTCTTATCTCGAGATAAGACGAGCTCCAAGGAGT | 2654 | chr16 | ENST00000356897.1 |
| IL27 | AATTCAAAAACTTTAGGACTGGAGTCTTGGCTCGAGCCAAGACTCCAGTCCTAAAGT | 2655 | chr16 | ENST00000356897.1 |
| IL27 | AATTCAAAAACATCATCAGCCTTGGACAAGGCTCGAGCCTTGTCCAAGGCTGATGATG | 2656 | chr16 | ENST00000356897.1 |

TABLE 16-continued

3' to 5' (Reverse) shRNA sequences for Silencing of Cytokine/Chemokine
Genes to Reduce the Incidence of CRS

| Target Gene Symbol | shRNA Reverse Oligo Sequence | SEQ ID NO: | Location | Gene ID No. |
|---|---|---|---|---|
| IL2RA | AATTCAAAAACCTCGTCACAACAACAGATTTCTCGAGAAATCTGTTGTTGTGACGAGG | 2657 | chr10 | ENST00000379959.7 |
| IL2RA | AATTCAAAAACCCTATACAACTGGACATTGCTCGAGCAATGTCCAGTTGTATAGGGT | 2658 | chr10 | ENST00000379959.7 |
| IL2RA | AATTCAAAAACTCGGAACACAACGAAACAACTCGAGTTGTTTCGTTGTGTTCCGAGT | 2659 | chr10 | ENST00000379959.7 |
| IL2RB | AATTCAAAAAGTCCCAGACCTGGTGGATTTCTCGAGAAATCCACCAGGTCTGGGACT | 2660 | chr22 | ENST00000216223.9 |
| IL2RB | AATTCAAAAAGACCCACAGATGCAACATAAGCTCGAGCTTATGTTGCATCTGTGGGTC | 2661 | chr22 | ENST00000216223.9 |
| IL2RB | AATTCAAAAACCAGACACCCAGTATGAGTTTCTCGAGAAACTCATACTGGGTGTCTGG | 2662 | chr22 | ENST00000216223.9 |
| IL2RG | AATTCAAAAATCGTGTTCGGAGCCGCTTTAACTCGAGTTAAAGCGGCTCCGAACACGA | 2663 | chrX | ENST00000374202.6 |
| IL2RG | AATTCAAAAACCAACCTCACTCTGCATTATTCTCGAGAATAATGCAGAGTGAGGTTGG | 2664 | chrX | ENST00000374202.6 |
| IL2RG | AATTCAAAAATTGGCTCCATGGGATTGATTACTCGAGTAATCAATCCCATGGAGCCAA | 2665 | chrX | ENST00000374202.6 |
| IL3 | AATTCAAAAATTATCCCATTGAGACTATTTACTCGAGTAAATAGTCTCAATGGGATAA | 2666 | chr5 | ENST00000296870.2 |
| IL3 | AATTCAAAAACGGCATCAGATGAATTGTTAACTCGAGTTAACAATTCATCTGATGCCG | 2667 | chr5 | ENST00000296870.2 |
| IL3 | AATTCAAAAAGCAATTGAGAGCATTCTTAAACTCGAGTTTAAGAATGCTCTCAATTGC | 2668 | chr5 | ENST00000296870.2 |
| IL31 | AATTCAAAAAGCATATCTCAAGACAATCAGACTCGAGTCTGATTGTCTTGAGATATGC | 2669 | chr12 | ENST00000377035.1 |
| IL31 | AATTCAAAAACCAAGTGATGATGTACAGAAACTCGAGTTTCTGTACATCATCACTTGG | 2670 | chr12 | ENST00000377035.1 |
| IL31 | AATTCAAAAACCTGACTATTTCTCAACAGTTCTCGAGAACTGTTGAGAAATAGTCAGG | 2671 | chr12 | ENST00000377035.1 |
| IL31RA | AATTCAAAAACATCAAACGAATGATTCAAATCTCGAGATTTGAATCATTCGTTTGATG | 2672 | chr5 | ENST00000447346.6 |
| IL31RA | AATTCAAAAACGCCTGTTTCATCTGATTTAACTCGAGTTAAATCAGATGAAACAGGCG | 2673 | chr5 | ENST00000447346.6 |
| IL31RA | AATTCAAAAATTTCCTGTGTCTACTACTATACTCGAGTATAGTAGTAGACACAGGAAA | 2674 | chr5 | ENST00000447346.6 |
| IL32 | AATTCAAAAATGTCGCCCTGGCATCTTAATACTCGAGTATTAAGATGCCAGGGCGACA | 2675 | chr16 | ENST00000325568.9 |
| IL32 | AATTCAAAAAGAGCTCACTCCTCTACTTGACTCGAGTCAAGTAGAGGAGTGAGCTCT | 2676 | chr16 | ENST00000325568.9 |
| IL32 | AATTCAAAAAGAGCTGGAGGACGACTTCAACTCGAGTTGAAGTCGTCCTCCAGCTCT | 2677 | chr16 | ENST00000325568.9 |
| IL33 | AATTCAAAAAGAGTGCTTTGCCTTTGGTATACTCGAGTATACCAAAGGCAAAGCACTC | 2678 | chr9 | ENST00000381434.7 |
| IL33 | AATTCAAAAAGCACTCCAACTGTGTTTCATTCTCGAGAATGAAACACAGTTGGAGTGC | 2679 | chr9 | ENST00000381434.7 |
| IL33 | AATTCAAAAACCTGTTACTTTAGGAGAGAAACTCGAGTTTCTCTCCTAAAGTAACAGG | 2680 | chr9 | ENST00000381434.7 |
| IL34 | AATTCAAAAAGCCGACTTCAGTACATGAAACCTCGAGGTTTCATGTACTGAAGTCGGC | 2681 | chr16 | ENST00000288098.6 |
| IL34 | AATTCAAAAACAGAGCCCTCATTGCAGTATGCTCGAGCATACTGCAATGAGGGCTCTG | 2682 | chr16 | ENST00000288098.6 |
| IL34 | AATTCAAAAACCGTGTTGTCCCTCTTGAATGCTCGAGCATTCAAGAGGGACAACACG | 2683 | chr16 | ENST00000288098.6 |
| IL36A | AATTCAAAAACTCCAGTCACTATTGCCTTAACTCGAGTTAAGGCAATAGTGACTGGAG | 2684 | chr2 | ENST00000259211.6 |
| IL36A | AATTCAAAAATTCAGGACCAGACGCTCATAGCTCGAGCTATGAGCGTCTGGTCCTGAA | 2685 | chr2 | ENST00000259211.6 |
| IL36A | AATTCAAAAACTCTGCCTGATGTGTGCTAAACTCGAGTTTAGCACACATCAGGCAGAG | 2686 | chr2 | ENST00000259211.6 |
| IL36B | AATTCAAAAATCCTATGCTATTCGTGATTCCTCGAGGAATCACGAATAGCATAGGAT | 2687 | chr2 | ENST00000327407.2 |
| IL36B | AATTCAAAAACCTGAGTGGAAATTCTTTAATCTCGAGATTAAAGAATTTCCACTCAGG | 2688 | chr2 | ENST00000327407.2 |
| IL36B | AATTCAAAAATTGGACTACATAACCTGTAAACTCGAGTTTACAGGTTATGTAGTCCAA | 2689 | chr2 | ENST00000327407.2 |
| IL36G | AATTCAAAAATGATATCATCCAGTCTTTATACTCGAGTATAAAGACTGGATGATATCA | 2690 | chr2 | ENST00000259205.4 |
| IL36G | AATTCAAAAACAGGAGAGCTGGGTGGTATAACTCGAGTTATACCACCCAGCTCTCCTG | 2691 | chr2 | ENST00000259205.4 |
| IL36G | AATTCAAAAAGGGAATCCAGAATCCAGAAATCTCGAGATTTCTGGATTCTGGATTCCC | 2692 | chr2 | ENST00000259205.4 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
|---|---|---|---|---|
| IL36RN | AATTCAAAAACTCGGCATTGAAGGTGCTTTACTCGAGTAAAGCACCTTCAATGCCGAG | 2693 | chr2 | ENST00000346807.7 |
| IL36RN | AATTCAAAAATGGTTCCCAGTTTGGATAAATCTCGAGATTTATCCAAACTGGGAACCA | 2694 | chr2 | ENST00000346807.7 |
| IL36RN | AATTCAAAAAGGGAATCATTCCTGCTTAATGCTCGAGCATTAAGCAGGAATGATTCCC | 2695 | chr2 | ENST00000346807.7 |
| IL37 | AATTCAAAAACTCTACTGTGACAAGGATAAACTCGAGTTTATCCTTGTCACAGTAGAG | 2696 | chr2 | ENST00000263326.7 |
| IL37 | AATTCAAAAATGCACCTCCTGCAATTGTAATCTCGAGATTACAATTGCAGGAGGTGCA | 2697 | chr2 | ENST00000263326.7 |
| IL37 | AATTCAAAAAGTTCACACAAAGATCTTCTTTCTCGAGAAAGAAGATCTTTGTGTGAAC | 2698 | chr2 | ENST00000263326.7 |
| IL4 | AATTCAAAAAGCTGATCCGATTCCTGAAACCTCGAGGTTTCAGGAATCGGATCAGCT | 2699 | chr5 | ENST00000231449.6 |
| IL4 | AATTCAAAAACCACGGACACAAGTGCGATATCTCGAGATATCGCACTTGTGTCCGTGG | 2700 | chr5 | ENST00000231449.6 |
| IL4 | AATTCAAAAATAGCATGTGCCGGCAACTTTGCTCGAGCAAAGTTGCCGGCACATGCTA | 2701 | chr5 | ENST00000231449.6 |
| IL5 | AATTCAAAAAGCAAGAGTTTCTTGGTGTAATCTCGAGATTACACCAAGAAACTCTTGC | 2702 | chr5 | ENST00000231454.5 |
| IL5 | AATTCAAAAAGGGTACTGTGGAAAGACTATTCTCGAGAATAGTCTTTCCACAGTACCC | 2703 | chr5 | ENST00000231454.5 |
| IL5 | AATTCAAAAAGAAAGAGTCAGGCCTTAATTTCTCGAGAAATTAAGGCCTGACTCTTTC | 2704 | chr5 | ENST00000231454.5 |
| IL6 | AATTCAAAAAATGAGCGTTAGGACACTATTTCTCGAGAAATAGTGTCCTAACGCTCAT | 2705 | chr7 | ENST00000258743.9 |
| IL6 | AATTCAAAAAGAGTACCTCCAGAACAGATTTCTCGAGAAATCTGTTCTGGAGGTACTC | 2706 | chr7 | ENST00000258743.9 |
| IL6 | AATTCAAAAATGTGAAGCTGAGTTAATTTACTCGAGTAAATTAACTCAGCTTCACAT | 2707 | chr7 | ENST00000258743.9 |
| IL6R | AATTCAAAAAGCAGGCACTTACTACTAATAACTCGAGTTATTAGTAGTAAGTGCCTGC | 2708 | chr1 | ENST00000368485.7 |
| IL6R | AATTCAAAAATATCGGGCTGAACGGTCAAAGCTCGAGCTTTGACCGTTCAGCCCGATA | 2709 | chr1 | ENST00000368485.7 |
| IL6R | AATTCAAAAACTGGACCCTGTGGATGATAAACTCGAGTTTATCATCCACAGGGTCCAG | 2710 | chr1 | ENST00000368485.7 |
| IL6ST | AATTCAAAAACCGTGCATCGCACCTATTTACTCGAGTAAATAGGTGCGATGCACGGT | 2711 | chr5 | ENST00000336909.9 |
| IL6ST | AATTCAAAAACTTCAGCAGTACCTATAAAGCTCGAGCTTTATAGGTACTGCTGAAGT | 2712 | chr5 | ENST00000336909.9 |
| IL6ST | AATTCAAAAACGGCCAGAAGATCTACAATTACTCGAGTAATTGTAGATCTTCTGGCCG | 2713 | chr5 | ENST00000336909.9 |
| IL7 | AATTCAAAAAGCTCGCAAGTTGAGGCAATTTCTCGAGAAATTGCCTCAACTTGCGAGC | 2714 | chr8 | ENST00000263851.8 |
| IL7 | AATTCAAAAAGCTCACTATGAATCTATTATACTCGAGTATAATAGATTCATAGTGAGC | 2715 | chr8 | ENST00000263851.8 |
| IL7 | AATTCAAAAAGTGTTTCCTAAAGAGACTATTCTCGAGAATAGTCTCTTTAGGAAACAC | 2716 | chr8 | ENST00000263851.8 |
| IL9 | AATTCAAAAACCACCATGCAAACAAGATACCTCGAGGTATCTTGTTTGCATGGTGGT | 2717 | chr5 | ENST00000274520.1 |
| IL9 | AATTCAAAAAGAACAACAAGTGTCCATATTTCTCGAGAAATATGGACACTTGTTGTTC | 2718 | chr5 | ENST00000274520.1 |
| IL9 | AATTCAAAAACTGAAGAGTCTTCTGGAAATTCTCGAGAATTTCCAGAAGACTCTTCAG | 2719 | chr5 | ENST00000274520.1 |
| INHA | AATTCAAAAACCTCGGATGGAGGTTACTCTTCTCGAGAAGAGTAACCTCCATCCGAGG | 2720 | chr2 | ENST00000243786.2 |
| INHA | AATTCAAAAAGCAGCACTGTGCTTGTATCTACTCGAGTAGATACAAGCACAGTGCTGC | 2721 | chr2 | ENST00000243786.2 |
| INHA | AATTCAAAAATGGAGGTTACTCTTTCAAGTACTCGAGTACTTGAAAGAGTAACCTCCA | 2722 | chr2 | ENST00000243786.2 |
| INHBA | AATTCAAAAAGGCACTTTCCTACCCAATTACTCGAGTAATTGGGTAGGAAAGTGCCT | 2723 | chr7 | ENST00000242208.4 |
| INHBA | AATTCAAAAAGAGAATGGTGTACCCTTTATTCTCGAGAATAAAGGGTACACCATTCTC | 2724 | chr7 | ENST00000242208.4 |
| INHBA | AATTCAAAAAGACGCTGCACTTCGAGATTTCTCGAGAAATCTCGAAGTGCAGCGTCT | 2725 | chr7 | ENST00000242208.4 |
| INHBB | AATTCAAAAACAAATGGATGCGGTGACAAATCTCGAGATTTGTCACCGCATCCATTTG | 2726 | chr2 | ENST00000295228.3 |
| INHBB | AATTCAAAAAGCTGGAACGACTGGATCATAGCTCGAGCTATGATCCAGTCGTTCCAGC | 2727 | chr2 | ENST00000295228.3 |
| INHBB | AATTCAAAAATGATGAGTACAACATCGTCAACTCGAGTTGACGATGTTGTACTCATCA | 2728 | chr2 | ENST00000295228.3 |
| INHBC | AATTCAAAAATCAACCAGACTCGTCTTGATTCTCGAGAATCAAGACGAGTCTGGTTGA | 2729 | chr12 | ENST00000309668.2 |

TABLE 16-continued

3' to 5' (Reverse) shRNA sequences for Silencing of Cytokine/Chemokine
Genes to Reduce the Incidence of CRS

| Target Gene Symbol | shRNA Reverse Oligo Sequence | SEQ ID NO: | Location | Gene ID No. |
|---|---|---|---|---|
| INHBC | AATTCAAAAACAAGACTGACATACCTGACATCTCGAGATGTCAGGTATGTCAGTCTTG | 2730 | chr12 | ENST00000309668.2 |
| INHBC | AATTCAAAAACAGGCCAGTCTCATGTTCTTTCTCGAGAAAGAACATGAGACTGGCCTG | 2731 | chr12 | ENST00000309668.2 |
| INHBE | AATTCAAAAACTCCTCTACCTGGATCATAATCTCGAGATTATGATCCAGGTAGAGGAG | 2732 | chr12 | ENST00000266646.2 |
| INHBE | AATTCAAAAACCTGGGCTGGCATACCTTAACTCGAGTTAAGGTATGCCAGCCCAGGT | 2733 | chr12 | ENST00000266646.2 |
| INHBE | AATTCAAAAAGCAGCCCTTCCTAGAGCTTAACTCGAGTTAAGCTCTAGGAAGGGCTGC | 2734 | chr12 | ENST00000266646.2 |
| ITGA4 | AATTCAAAAACCAACGCTTCAGTGATCAATCCTCGAGGATTGATCACTGAAGCGTTGG | 2735 | chr2 | ENST00000397033.6 |
| ITGA4 | AATTCAAAAATGTAGAACACATCAAGCATTTCTCGAGAAATGCTTGATGTGTTCTACA | 2736 | chr2 | ENST00000397033.6 |
| ITGA4 | AATTCAAAAACATGATCTTGTGACATATTATCTCGAGATAATATGTCACAAGATCATG | 2737 | chr2 | ENST00000397033.6 |
| ITGAV | AATTCAAAAATTGAAGTGTACCCTAGCATTTCTCGAGAAATGCTAGGGTACACTTCAA | 2738 | chr2 | ENST00000261023.7 |
| ITGAV | AATTCAAAAACACTCCAAGAACATGACTATTCTCGAGAATAGTCATGTTCTTGGAGTG | 2739 | chr2 | ENST00000261023.7 |
| ITGAV | AATTCAAAAAGTGAGGTCGAAACAGGATAAACTCGAGTTTATCCTGTTTCGACCTCAC | 2740 | chr2 | ENST00000261023.7 |
| ITGB1 | AATTCAAAAATTTGTAGGAAGAGGGATAATACTCGAGTATTATCCCTCTTCCTACAAA | 2741 | chr10 | ENST00000302278.7 |
| ITGB1 | AATTCAAAAAGCCTTGCATTACTGCTGATATCTCGAGATATCAGCAGTAATGCAAGGC | 2742 | chr10 | ENST00000302278.7 |
| ITGB1 | AATTCAAAAAGCCTTGCATTACTGCTGATATCTCGAGATATCAGCAGTAATGCAAGGC | 2743 | chr10 | ENST00000302278.7 |
| ITGB3 | AATTCAAAAAGTCGTCAGATTCCAGTACTATCTCGAGATAGTACTGGAATCTGACGAC | 2744 | chr17 | ENST00000559488.5 |
| ITGB3 | AATTCAAAAAGTCGTCAGATTCCAGTACTATCTCGAGATAGTACTGGAATCTGACGAC | 2745 | chr17 | ENST00000559488.5 |
| ITGB3 | AATTCAAAAACCACGTCTACCTTCACCAATACTCGAGTATTGGTGAAGGTAGACGTGG | 2746 | chr17 | ENST00000559488.5 |
| KIT | AATTCAAAAAACTTCATCTAACGAGATTAAACTCGAGTTTAATCTCGTTAGATGAAGT | 2747 | chr4 | ENST00000288135.5 |
| KIT | AATTCAAAAAGCGACGAGATTAGGCTGTTATCTCGAGATAACAGCCTAATCTCGTCGC | 2748 | chr4 | ENST00000288135.5 |
| KIT | AATTCAAAAACGAGTTGGCCCTAGACTTAGCTCGAGCTAAGTCTAGGGCCAACTCGT | 2749 | chr4 | ENST00000288135.5 |
| KITLG | AATTCAAAAAGCAGGAATCGTGTGACTAATACTCGAGTATTAGTCACACGATTCCTGC | 2750 | chr12 | ENST00000228280.9 |
| KITLG | AATTCAAAAAGCAGGAATCGTGTGACTAATACTCGAGTATTAGTCACACGATTCCTGC | 2751 | chr12 | ENST00000228280.9 |
| KITLG | AATTCAAAAACCTATTTAATCCTCTCGTCAACTCGAGTTGACGAGAGGATTAAATAGG | 2752 | chr12 | ENST00000228280.9 |
| KLHL20 | AATTCAAAAAGCCAATACATGGAGGTTATATCTCGAGATATAACCTCCATGTATTGGC | 2753 | chr1 | ENST00000209884.4 |
| KLHL20 | AATTCAAAAAGCCGCAAGAACGACCACTAATCTCGAGATTAGTGGTCGTTCTTGCGGC | 2754 | chr1 | ENST00000209884.4 |
| KLHL20 | AATTCAAAAACACATTGTGAATCCCATATTTCTCGAGAAATATGGGATTCACAATGTG | 2755 | chr1 | ENST00000209884.4 |
| LEFTY1 | AATTCAAAAACAAGTTACCTCACCTAATTTCTCGAGAAATTAGGTGAGGTAACTTGT | 2756 | chr1 | ENST00000272134.5 |
| LEFTY1 | AATTCAAAAAGCCCAATGTGTCATTGTTTACTCGAGTAAACAATGACACATTGGGCT | 2757 | chr1 | ENST00000272134.5 |
| LEFTY1 | AATTCAAAAATCTCTAGTGAGCCCTGAATTTCTCGAGAAATTCAGGGCTCACTAGAGA | 2758 | chr1 | ENST00000272134.5 |
| LEFTY2 | AATTCAAAAAGTTACTCCATCCCAATTTAGCTCGAGCTAAATTGGGATGGAGTAACT | 2759 | chr1 | ENST00000366820.9 |
| LEFTY2 | AATTCAAAAACTAAGCACTTACGTGAGTAAACTCGAGTTTACTCACGTAAGTGCTTAG | 2760 | chr1 | ENST00000366820.9 |
| LEFTY2 | AATTCAAAAATAGGCGCCTGGTGTATCCATTCTCGAGAATGGATACACCAGGCGCCTA | 2761 | chr1 | ENST00000366820.9 |
| LIF | AATTCAAAAAGCAGTGCCAATGCCCTCTTTACTCGAGTAAAGAGGGCATTGGCACTGC | 2762 | chr22 | ENST00000249075.3 |
| LIF | AATTCAAAAACCGCATAGTCGTGTACCTTGCTCGAGCAAGGTACACGACTATGCGGT | 2763 | chr22 | ENST00000249075.3 |
| LIF | AATTCAAAAACAACAACCTGGACAAGCTATGCTCGAGCATAGCTTGTCCAGGTTGTTG | 2764 | chr22 | ENST00000249075.3 |
| LIFR | AATTCAAAAATGACTTGCGACTACGTCATTACTCGAGTAATGACGTAGTCGCAAGTCA | 2765 | chr5 | ENST00000263409.8 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
|---|---|---|---|---|
| LIFR | AATTCAAAAACTTCTGCAGATTCGATATTACTCGAGTAATATCGAATCTGCAGAAGT | 2766 | chr5 | ENST00000263409.8 |
| LIFR | AATTCAAAAAGTAGGCTCAGACATAACATTTCTCGAGAAATGTTATGTCTGAGCCTAC | 2767 | chr5 | ENST00000263409.8 |
| LTA | AATTCAAAAAGCCCTAGTACTGTCTTCTTTGCTCGAGCAAAGAAGACAGTACTAGGGC | 2768 | chr6 | ENST00000418386.2 |
| LTA | AATTCAAAAAGATCAAGTCACCGGAGCTTTCCTCGAGGAAAGCTCCGGTGACTTGATC | 2769 | chr6 | ENST00000418386.2 |
| LTA | AATTCAAAAAGCTCCCAGAAGATGGTGTATCCTCGAGGATACACCATCTTCTGGGAGC | 2770 | chr6 | ENST00000418386.2 |
| LTB | AATTCAAAAAGCGAGAGGGAAGACCTTCTTTCTCGAGAAAGAAGGTCTTCCCTCTCGC | 2771 | chr6 | ENST00000429299.2 |
| LTB | AATTCAAAAACGAGAGGGTGTACGTCAACATCTCGAGATGTTGACGTACACCCTCTCG | 2772 | chr6 | ENST00000429299.2 |
| LTB | AATTCAAAAAGACGAAGGAACAGGCGTTTCTCTCGAGAGAAACGCCTGTTCCTTCGTC | 2773 | chr6 | ENST00000429299.2 |
| LTBP1 | AATTCAAAAAGATGACCTGTGTCGATGTAAACTCGAGTTTACATCGACACAGGTCATC | 2774 | chr2 | ENST00000407925.5 |
| LTBP1 | AATTCAAAAAGGTGGAACAGTGCTGTTATTTCTCGAGAAATAACAGCACTGTTCCACC | 2775 | chr2 | ENST00000407925.5 |
| LTBP1 | AATTCAAAAACCGTTGAATACCGCCTTGAATCTCGAGATTCAAGGCGGTATTCAACGG | 2776 | chr2 | ENST00000407925.5 |
| LTBP3 | AATTCAAAAAGCATCCTCAATGGATGTGAAACTCGAGTTTCACATCCATTGAGGATGC | 2777 | chr11 | ENST00000322147.8 |
| LTBP3 | AATTCAAAAATGTTGTTCGGGTCGGAGATTTCTCGAGAAATCTCCGACCCGAACAACA | 2778 | chr11 | ENST00000322147.8 |
| LTBP3 | AATTCAAAAAAGCGCTTCAAGGTGGTCTTTGCTCGAGCAAAGACCACCTTGAAGCGCT | 2779 | chr11 | ENST00000322147.8 |
| LTBP4 | AATTCAAAAAGCTTCGACATGCCAGACTTTGCTCGAGCAAAGTCTGGCATGTCGAAGC | 2780 | chr19 | ENST00000308370.11 |
| LTBP4 | AATTCAAAAATGAAACACTACAGGGTGTATGCTCGAGCATACACCCTGTAGTGTTTCA | 2781 | chr19 | ENST00000308370.11 |
| LTBP4 | AATTCAAAAACAACCGGCTTTGAAAGAGTTACTCGAGTAACTCTTTCAAAGCCGGTTG | 2782 | chr19 | ENST00000308370.11 |
| MAF | AATTCAAAAATCAGTGGGATACGCCACATTTCTCGAGAAATGTGGCGTATCCCACTGA | 2783 | chr16 | ENST00000326043.4 |
| MAF | AATTCAAAAATTTATGGTGTGTGCAAGTAAACTCGAGTTTACTTGCACACACCATAAA | 2784 | chr16 | ENST00000326043.4 |
| MAF | AATTCAAAAAGTTAGAGAAGAAGGCTATTAACTCGAGTTAATAGCCTTCTTCTCTAAC | 2785 | chr16 | ENST00000326043.4 |
| MAF | AATTCAAAAATGTTAATGACTTCGATCTGATCTCGAGATCAGATCGAAGTCATTAACA | 2786 | chr16 | ENST00000326043.4 |
| MIF | AATTCAAAAACTACATCAACTATTACGACATCTCGAGATGTCGTAATAGTTGATGTAG | 2787 | chr22 | ENST00000215754.7 |
| MIF | AATTCAAAAACTACATCAACTATTACGACATCTCGAGATGTCGTAATAGTTGATGTAG | 2788 | chr22 | ENST00000215754.7 |
| MIF | AATTCAAAAAGACAGGGTCTACATCAACTATCTCGAGATAGTTGATGTAGACCCTGTC | 2789 | chr22 | ENST00000215754.7 |
| MINOS1- | AATTCAAAAAGCCAAGCTGCACAATTTAATACTCGAGTATTAAATTGTGCAGCTTGGC | 2790 | chr1 | ENST00000602662.1 |
| MINOS1- | AATTCAAAAAGCTGGCACTGTTCCCAGATAACTCGAGTTATCTGGGAACAGTGCCAGC | 2791 | chr1 | ENST00000602662.1 |
| MINOS1- | AATTCAAAAAGAAAGACCACTGGCAGAAACCTCGAGGTTTCTGCCAGTGGTCTTTCT | 2792 | chr1 | ENST00000602662.1 |
| MSTN | AATTCAAAAAGGCCCAACTATGGATATATTCTCGAGAATATATCCATAGTTGGGCCT | 2793 | chr2 | ENST00000260950.4 |
| MSTN | AATTCAAAAAGAGCTAGAAGGAGATCAAATTCTCGAGAATTTGATCTCCTTCTAGCTC | 2794 | chr2 | ENST00000260950.4 |
| MSTN | AATTCAAAAAGTATGCTTTAAAGTCTATTTCCTCGAGGAAATAGACTTTAAAGCATAC | 2795 | chr2 | ENST00000260950.4 |
| NAMPT | AATTCAAAAAGCGATAGCTATGACATTTATCTCGAGATAAATGTCATAGCTATCGCT | 2796 | chr7 | ENST00000222553.7 |
| NAMPT | AATTCAAAAAGTGAAGATCTAAGACATTTAACTCGAGTTAAATGTCTTAGATCTTCAC | 2797 | chr7 | ENST00000222553.7 |
| NAMPT | AATTCAAAAATACAAGGTTACTCACTATAAACTCGAGTTTATAGTGAGTAACCTTGTA | 2798 | chr7 | ENST00000222553.7 |
| NBL1 | AATTCAAAAAGCCAAGCTGCACAATTTAATACTCGAGTATTAAATTGTGCAGCTTGGC | 2799 | chr1 | ENST00000375136.7 |
| NBL1 | AATTCAAAAAGCTGGCACTGTTCCCAGATAACTCGAGTTATCTGGGAACAGTGCCAGC | 2800 | chr1 | ENST00000375136.7 |
| NBL1 | AATTCAAAAAGAAAGACCACTGGCAGAAACCTCGAGGTTTCTGCCAGTGGTCTTTCT | 2801 | chr1 | ENST00000375136.7 |
| NDP | AATTCAAAAACTGCTAAAGGTTACCGATTTCCTCGAGGAAATCGGTAACCTTTAGCAG | 2802 | chrX | ENST00000378062.5 |

TABLE 16-continued

3' to 5' (Reverse) shRNA sequences for Silencing of Cytokine/Chemokine
Genes to Reduce the Incidence of CRS

| Target Gene Symbol | shRNA Reverse Oligo Sequence | SEQ ID NO: | Location | Gene ID No. |
|---|---|---|---|---|
| NDP | AATTCAAAAACTCTGCATATTCTAGTAATAACTCGAGTTATTACTAGAATATGCAGAG | 2803 | chrX | ENST00000378062.5 |
| NDP | AATTCAAAAACGGACAGCTCATTCATAATGCTCGAGCATTATGAATGAGCTGTCCGT | 2804 | chrX | ENST00000378062.5 |
| NLRP7 | AATTCAAAAACCGTTCAAGGAAATTTCTATTCTCGAGAATAGAAATTTCCTTGAACGG | 2805 | chr19 | ENST00000328092.9 |
| NLRP7 | AATTCAAAAACGGGTCTCTAAGATGTCTTATCTCGAGATAAGACATCTTAGAGACCCG | 2806 | chr19 | ENST00000328092.9 |
| NLRP7 | AATTCAAAAACCTGCTCAGAAATCATAAATCTCGAGATTTATGATTTCTGAGCAGGT | 2807 | chr19 | ENST00000328092.9 |
| NODAL | AATTCAAAAAGTGCTCCTAGATCACCATAAACTCGAGTTTATGGTGATCTAGGAGCAC | 2808 | chr10 | ENST00000287139.7 |
| NODAL | AATTCAAAAACACCTATAGCTTTCATGTATTCTCGAGAATACATGAAAGCTATAGGTG | 2809 | chr10 | ENST00000287139.7 |
| NODAL | AATTCAAAAAGCATGCTGTATGTGGATAATGCTCGAGCATTATCCACATACAGCATGC | 2810 | chr10 | ENST00000287139.7 |
| NOG | AATTCAAAAAGGTCAGTATTATACGTTAAACTCGAGTTTAACGTATAATACTGACCT | 2811 | chr17 | ENST00000332822.4 |
| NOG | AATTCAAAAAATTCTGGTTGTTGCTAATAATCTCGAGATTATTAGCAACAACCAGAAT | 2812 | chr17 | ENST00000332822.4 |
| NOG | AATTCAAAAATGCGGAGGAAGTTACAGATGTCTCGAGACATCTGTAACTTCCTCCGCA | 2813 | chr17 | ENST00000332822.4 |
| NRG1 | AATTCAAAAAGATATACAGAGGCCTATAACCTCGAGGTTATAGGCCTCTGTGATATC | 2814 | chr8 | ENST00000287842.7 |
| NRG1 | AATTCAAAAAGGCTGATTCTGGAGAGTATATCTCGAGATATACTCTCCAGAATCAGCC | 2815 | chr8 | ENST00000287842.7 |
| NRG1 | AATTCAAAAAGACAGTGCCTCTGCCAATATCCTCGAGGATATTGGCAGAGGCACTGTC | 2816 | chr8 | ENST00000287842.7 |
| NRP1 | AATTCAAAAATATACTAGAATCACCGCATTTCTCGAGAAATGCGGTGATTCTAGTATA | 2817 | chr10 | ENST00000265371.8 |
| NRP1 | AATTCAAAAACAGCCTTGAATGCACTTATATCTCGAGATATAAGTGCATTCAAGGCTG | 2818 | chr10 | ENST00000265371.8 |
| NRP1 | AATTCAAAAACAGCCTTGAATGCACTTATATCTCGAGATATAAGTGCATTCAAGGCTG | 2819 | chr10 | ENST00000265371.8 |
| NRP2 | AATTCAAAAACGACTGCAAGTATGACTTTATCTCGAGATAAAGTCATACTTGCAGTCG | 2820 | chr2 | ENST00000357785.9 |
| NRP2 | AATTCAAAAACCGGATTGCTAATGAACAGATCTCGAGATCTGTTCATTAGCAATCCGG | 2821 | chr2 | ENST00000357785.9 |
| NRP2 | AATTCAAAAACCTCAACTTCAACCCTCACTTCTCGAGAAGTGAGGGTTGAAGTTGAGG | 2822 | chr2 | ENST00000357785.9 |
| OSM | AATTCAAAAACTTCCTCCTTTCCGTGTTTCCTCGAGGAAACACGGAAAGGAGGAAGT | 2823 | chr22 | ENST00000215781.2 |
| OSM | AATTCAAAAAGGACCGACTTTCCATTGATTCCTCGAGGAATCAATGGAAAGTCGGTCC | 2824 | chr22 | ENST00000215781.2 |
| OSM | AATTCAAAAATGGTCCTTGCACTCCTGTTTCCTCGAGGAAACAGGAGTGCAAGGACCA | 2825 | chr22 | ENST00000215781.2 |
| OSMR | AATTCAAAAATAACCTGACTCATCGAGTTTACTCGAGTAAACTCGATGAGTCAGGTTA | 2826 | chr5 | ENST00000274276.7 |
| OSMR | AATTCAAAAAGGAGAACCCTCACCTAATAACTCGAGTTATTAGGTGAGGGTTCTCCT | 2827 | chr5 | ENST00000274276.7 |
| OSMR | AATTCAAAAAGCACTCCATAAGGAATAATTTCTCGAGAAATTATTCCTTATGGAGTGC | 2828 | chr5 | ENST00000274276.7 |
| PARK7 | AATTCAAAAAGTAGCCGTGATGTGGTCATTTCTCGAGAAATGACCACATCACGGCTAC | 2829 | chr1 | ENST00000338639.9 |
| PARK7 | AATTCAAAAAGCAATTGTTGAAGCCCTGAATCTCGAGATTCAGGGCTTCAACAATTGC | 2830 | chr1 | ENST00000338639.9 |
| PARK7 | AATTCAAAAACTCTGAGAATCGTGTGGAAACTCGAGTTTCCACACGATTCTCAGAGT | 2831 | chr1 | ENST00000338639.9 |
| PDPN | AATTCAAAAAGCCTCTGGTATGAGAAATAAACTCGAGTTTATTTCTCATACCAGAGGC | 2832 | chr1 | ENST00000294489.10 |
| PDPN | AATTCAAAAAGTCCACGCGCAAGAACAAAGCTCGAGCTTTGTTCTTGCGCGTGGACT | 2833 | chr1 | ENST00000294489.10 |
| PDPN | AATTCAAAAATGACCCTGGTTGGAATCATAGCTCGAGCTATGATTCCAACCAGGGTCA | 2834 | chr1 | ENST00000294489.10 |
| PF4 | AATTCAAAAACGCTGAAGAATGGAAGGAACTCGAGTTTCCTTCCATTCTTCAGCGT | 2835 | chr4 | ENST00000296029.3 |
| PF4 | AATTCAAAAACCAACTGATAGCCACGCTGAACCTCGAGTTCAGCGTGGCTATCAGTTGG | 2836 | chr4 | ENST00000296029.3 |
| PF4 | AATTCAAAAACACGCTGAAGAATGGAAGGAACTCGAGTTCCTTCCATTCTTCAGCGTG | 2837 | chr4 | ENST00000296029.3 |
| PF4V1 | AATTCAAAAAGTTGTGGTATAGTCAATCTATCTCGAGATAGATTGACTATACCACAAC | 2838 | chr4 | ENST00000226524.3 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
|---|---|---|---|---|
| PF4V1 | AATTCAAAAAGCTGCCTAAGTGTGCACTTTCTCGAGAAAGTGCACACTTAGGCAGCT | 2839 | chr4 | ENST00000226524.3 |
| PF4V1 | AATTCAAAAACTGACACATCACAATTTCATACTCGAGTATGAAATTGTGATGTGTCAG | 2840 | chr4 | ENST00000226524.3 |
| PGLYRP1 | AATTCAAAAAGTGCCCACTCAGGTCACTTATCTCGAGATAAGTGACCTGAGTGGGCAC | 2841 | chr19 | ENST00000008938.4 |
| PGLYRP1 | AATTCAAAAACTTACGCTATGTGGTGGTATCCTCGAGGATACCACCACATAGCGTAAG | 2842 | chr19 | ENST00000008938.4 |
| PGLYRP1 | AATTCAAAAACATCAGCTTCATGGGCAACTACTCGAGTAGTTGCCCATGAAGCTGATG | 2843 | chr19 | ENST00000008938.4 |
| PLP2 | AATTCAAAAACCTGTCGGTGATTGAGATGATCTCGAGATCATCTCAATCACCGACAGG | 2844 | chrX | ENST00000376327.5 |
| PLP2 | AATTCAAAAACCTGTCGGTGATTGAGATGATCTCGAGATCATCTCAATCACCGACAGG | 2845 | chrX | ENST00000376327.5 |
| PLP2 | AATTCAAAAACGAAAGGGAATCCTCCTGTTTCTCGAGAAACAGGAGGATTCCCTTTCG | 2846 | chrX | ENST00000376327.5 |
| PPBP | AATTCAAAAAGGTGATGAATCTGCTGATTACTCGAGTAATCAGCAGATTCATCACCT | 2847 | chr4 | ENST00000296028.3 |
| PPBP | AATTCAAAAATGTTTCTGCCAAACTTCTTTACTCGAGTAAAGAAGTTTGGCAGAAACA | 2848 | chr4 | ENST00000296028.3 |
| PPBP | AATTCAAAAACTCCCAGGAAGGGTAGAATTTCTCGAGAAATTCTACCCTTCCTGGGAG | 2849 | chr4 | ENST00000296028.3 |
| PXDN | AATTCAAAAAGATTGCGACTGGACTCAAACCTCGAGGTTTGAGTCCAGTCGCAATCT | 2850 | chr2 | ENST00000252804.8 |
| PXDN | AATTCAAAAAGTTCCTGACGTCAGTCGAAATCTCGAGATTTCGACTGACGTCAGGAAC | 2851 | chr2 | ENST00000252804.8 |
| PXDN | AATTCAAAAAGAAGGATTCTTGACCATCAATCTCGAGATTGATGGTCAAGAATCCTTC | 2852 | chr2 | ENST00000252804.8 |
| RORC | AATTCAAAAACACCTCACAAATTGAAGTGATCTCGAGATCACTTCAATTTGTGAGGTG | 2853 | chr1 | ENST00000318247.6 |
| RORC | AATTCAAAAAGCCCTCATATTCCAACAACTTCTCGAGAAGTTGTTGGAATATGAGGGC | 2854 | chr1 | ENST00000318247.6 |
| RORC | AATTCAAAAAGCTTCTCAAAGCAGGAGCAATCTCGAGATTGCTCCTGCTTTGAGAAGC | 2855 | chr1 | ENST00000318247.6 |
| RORC | AATTCAAAAACGAGGATGAGATTGCCCTCTACTCGAGTAGAGGGCAATCTCATCCTCG | 2856 | chr1 | ENST00000318247.6 |
| SCG2 | AATTCAAAAACGACAAGGATCAAGAATTAGCTCGAGCTAATTCTTGATCCTTGTCGT | 2857 | chr2 | ENST00000305409.2 |
| SCG2 | AATTCAAAAACCTGTCTCTTATCCCTTTAATCTCGAGATTAAAGGGATAAGAGACAGG | 2858 | chr2 | ENST00000305409.2 |
| SCG2 | AATTCAAAAAGAAAGCAGCCCAGATTATAATCTCGAGATTATAATCTGGGCTGCTTTC | 2859 | chr2 | ENST00000305409.2 |
| SCGB3A1 | AATTCAAAAATCATAGAGGGCTCCCAGAAGTCTCGAGACTTCTGGGAGCCCTCTATGA | 2860 | chr5 | ENST00000292641.3 |
| SCGB3A1 | AATTCAAAAACCCGTGAACCACCTCATAGAGCTCGAGCTCTATGAGGTGGTTCACGGG | 2861 | chr5 | ENST00000292641.3 |
| SCGB3A1 | AATTCAAAAAGACTGGAGCATCTACACCTGACTCGAGTCAGGTGTAGATGCTCCAGTC | 2862 | chr5 | ENST00000292641.3 |
| SECTM1 | AATTCAAAAACACCAGAGAAATAACAGACAACTCGAGTTGTCTGTTATTTCTCTGGTG | 2863 | chr17 | ENST00000269389.7 |
| SECTM1 | AATTCAAAAACCATGACTCGAATATCTGAAACTCGAGTTTCAGATATTCGAGTCATGG | 2864 | chr17 | ENST00000269389.7 |
| SECTM1 | AATTCAAAAACCATGACTCGAATATCTGAAACTCGAGTTTCAGATATTCGAGTCATGG | 2865 | chr17 | ENST00000269389.7 |
| SLURP1 | AATTCAAAAAGTGCTTCCTGCAGGACCATTACTCGAGTAATGGTCCTGCAGGAAGCAC | 2866 | chr8 | ENST00000246515.1 |
| SLURP1 | AATTCAAAAAAGACCTCTGCAACTCGGAACTCTCGAGAGTTCCGAGTTGCAGAGGTCT | 2867 | chr8 | ENST00000246515.1 |
| SLURP1 | AATTCAAAAACTCAAGTGCTACACCTGCAAGCTCGAGCTTGCAGGTGTAGCACTTGAG | 2868 | chr8 | ENST00000246515.1 |
| SOSTDC1 | AATTCAAAAAGATGCCACAGAAATCCTTTATCTCGAGATAAAGGATTTCTGTGGCATC | 2869 | chr7 | ENST00000307068.4 |
| SOSTDC1 | AATTCAAAAAGGAACTGCGTTCCACCAAATACTCGAGTATTTGGTGGAACGCAGTTCC | 2870 | chr7 | ENST00000307068.4 |
| SOSTDC1 | AATTCAAAAATGAATCTTCACAGTAACATTTCTCGAGAAATGTTACTGTGAAGATTCA | 2871 | chr7 | ENST00000307068.4 |
| SP100 | AATTCAAAAAGAAGTGAGCCTGTGATCAATACTCGAGTATTGATCACAGGCTCACTTC | 2872 | chr2 | ENST00000340126.8 |
| SP100 | AATTCAAAAATATACGCTGCGGTGGATATACCTCGAGGTATATCCACCGCAGCGTATA | 2873 | chr2 | ENST00000340126.8 |
| SP100 | AATTCAAAAATCGTGATCTCATCACAAATAACTCGAGTTATTTGTGATGAGATCACGA | 2874 | chr2 | ENST00000340126.8 |
| SPI1 | AATTCAAAAAGCCCTATGACACGGATCTATACTCGAGTATAGATCCGTGTCATAGGGC | 2875 | chr11 | ENST00000378538.7 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
|---|---|---|---|---|
| SPI1 | AATTCAAAAAGAGCTTCGCCGAGAACAACTCTCGAGAGTTGTTCTCGGCGAAGCTCT | 2876 | chr11 | ENST00000378538.7 |
| SPI1 | AATTCAAAAACGGATCTATACCAACGCCAAACTCGAGTTTGGCGTTGGTATAGATCCG | 2877 | chr11 | ENST00000378538.7 |
| SPI1 | AATTCAAAAACCGTATGTAAATCAGATCTCCCTCGAGGGAGATCTGATTTACATACGG | 2878 | chr11 | ENST00000378538.7 |
| SPP1 | AATTCAAAAACCACAAGCAGTCCAGATTATACTCGAGTATAATCTGGACTGCTTGTGG | 2879 | chr4 | ENST00000237623.11 |
| SPP1 | AATTCAAAAACCGAGGTGATAGTGTGGTTTACTCGAGTAAACCACACTATCACCTCGG | 2880 | chr4 | ENST00000237623.11 |
| SPP1 | AATTCAAAAACTTCAGGGTTATGTCTATGTTCTCGAGAACATAGACATAACCCTGAAG | 2881 | chr4 | ENST00000237623.11 |
| TBX21 | AATTCAAAAAGCCCTAACTACAGTCGTTTACCTCGAGGTAAACGACTGTAGTTAGGGC | 2882 | ch17 | ENST00000177694.1 |
| TBX21 | AATTCAAAAACCTGTTGTGGTCCAAGTTTAACTCGAGTTAAACTTGGACCACAACAGG | 2883 | ch17 | ENST00000177694.1 |
| TBX21 | AATTCAAAAACGCTTCCAACACGCATATCTTCTCGAGAAGATATGCGTGTTGGAAGCG | 2884 | ch17 | ENST00000177694.1 |
| TBX21 | AATTCAAAAACAATGTGACCCAGATGATTGCTCGAGCAATCATCTGGGTCACATTGT | 2885 | ch17 | ENST00000177694.1 |
| TCAP | AATTCAAAAACTTTGTAGTTTGCCCAGAGTTCTCGAGAACTCTGGGCAAACTACAAAG | 2886 | chr17 | ENST00000309889.2 |
| TCAP | AATTCAAAAAGGCCATGGCTGCTTTGTAGTTCTCGAGAACTACAAAGCAGCCATGGCC | 2887 | chr17 | ENST00000309889.2 |
| TCAP | AATTCAAAAAGGTGGCTGAGATCACAAAGCACTCGAGTGCTTTGTGATCTCAGCCACC | 2888 | chr17 | ENST00000309889.2 |
| TGFB1 | AATTCAAAAAACTGCGGATCTCTGTGTCATTCTCGAGAATGACACAGAGATCCGCAGT | 2889 | chr19 | ENST00000221930.5 |
| TGFB1 | AATTCAAAAACCACAACGAAATCTATGACAACTCGAGTTGTCATAGATTTCGTTGTGG | 2890 | chr19 | ENST00000221930.5 |
| TGFB1 | AATTCAAAAACCACAACGAAATCTATGACAACTCGAGTTGTCATAGATTTCGTTGTGG | 2891 | chr19 | ENST00000221930.5 |
| TGFB2 | AATTCAAAAAGCGGCCTATTGCTTTAGAAATCTCGAGATTTCTAAAGCAATAGGCCGC | 2892 | chr1 | ENST00000366930.8 |
| TGFB2 | AATTCAAAAAGCTGGAGCATGCCCGTATTTACTCGAGTAAATACGGGCATGCTCCAGC | 2893 | chr1 | ENST00000366930.8 |
| TGFB2 | AATTCAAAAATTGCTGCCTACGTCCACTTTACTCGAGTAAAGTGGACGTAGGCAGCAA | 2894 | chr1 | ENST00000366930.8 |
| TGFB3 | AATTCAAAAACATTGCCAAACAGCGCTATATCTCGAGATATAGCGCTGTTTGGCAATG | 2895 | chr14 | ENST00000238682.7 |
| TGFB3 | AATTCAAAAAGCTCTAGGGAATCTGGATTATCTCGAGATAATCCAGATTCCCTAGAGC | 2896 | chr14 | ENST00000238682.7 |
| TGFB3 | AATTCAAAAACGGAATACTATGCCAAAGAAACTCGAGTTTCTTTGGCATAGTATTCCG | 2897 | chr14 | ENST00000238682.7 |
| TGFBR1 | AATTCAAAAAGCCTTGAGAGTAATGGCTAAACTCGAGTTTAGCCATTACTCTCAAGGC | 2898 | chr9 | ENST00000374994.8 |
| TGFBR1 | AATTCAAAAACTCATGTTGATGGTCTATATCCTCGAGGATATAGACCATCAACATGAG | 2899 | chr9 | ENST00000374994.8 |
| TGFBR1 | AATTCAAAAAGAAGTTGCTGTTAAGATATTCCTCGAGGAATATCTTAACAGCAACTTC | 2900 | chr9 | ENST00000374994.8 |
| TGFBR2 | AATTCAAAAACGTTCAGAAGTCGGTTAATAACTCGAGTTATTAACCGACTTCTGAACG | 2901 | chr3 | ENST00000295754.9 |
| TGFBR2 | AATTCAAAAACTCTAGGCTTTATCGTGTTTACTCGAGTAAACACGATAAAGCCTAGAG | 2902 | chr3 | ENST00000295754.9 |
| TGFBR2 | AATTCAAAAACTCAGGAAATGAGATTGATTTCTCGAGAAATCAATCTCATTTCCTGAG | 2903 | chr3 | ENST00000295754.9 |
| TGFBR3 | AATTCAAAAAGGAGTTGGTAAAGGGTTAATACTCGAGTATTAACCCTTTACCAACTCC | 2904 | chr1 | ENST00000212355.8 |
| TGFBR3 | AATTCAAAAATAATGGATTTCCGGGAGATATCTCGAGATATCTCCCGGAAATCCATTA | 2905 | chr1 | ENST00000212355.8 |
| TGFBR3 | AATTCAAAAACACACCCAGGGCTAGTATAAACTCGAGTTTATACTAGCCCTGGGTGTG | 2906 | chr1 | ENST00000212355.8 |
| THBS1 | AATTCAAAAAGTAGGTTATGATGAGTTTAATCTCGAGATTAAACTCATCATAACCTAC | 2907 | chr15 | ENST00000260356.5 |
| THBS1 | AATTCAAAAACGTGACTGTAAGATTGTAAATCTCGAGATTTACAATCTTACAGTCACG | 2908 | chr15 | ENST00000260356.5 |
| THBS1 | AATTCAAAAAGAGATCCCTAATCATCAAATTCTCGAGAATTTGATGATTAGGGATCTC | 2909 | chr15 | ENST00000260356.5 |
| THNSL2 | AATTCAAAAAGAGCCGATCAAGACTGTGTTTCTCGAGAAACACAGTCTTGATCGGCTC | 2910 | chr2 | ENST00000324166.6 |
| THNSL2 | AATTCAAAAAGCTGCCATTGAGAGTGTTCAACTCGAGTTGAACACTCTCAATGGCAGC | 2911 | chr2 | ENST00000324166.6 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
|---|---|---|---|---|
| THNSL2 | AATTCAAAAAGCTGCCATTGAGAGTGTTCAACTCGAGTTGAACACTCTCAATGGCAGC | 2912 | chr2 | ENST00000324166.6 |
| THPO | AATTCAAAAAGACCTCCGAGTCCTCAGTAAACTCGAGTTTACTGAGGACTCGGAGGTC | 2913 | chr3 | ENST00000204615.11 |
| THPO | AATTCAAAAAGCTAGCTCTTTGGTCTATTTCTCGAGAAATAGACCAAAGAGCTAGCT | 2914 | chr3 | ENST00000204615.11 |
| THPO | AATTCAAAAACAACCTCCAGCCTGGATATTCCTCGAGGAATATCCAGGCTGGAGGTTG | 2915 | chr3 | ENST00000204615.11 |
| TIMP1 | AATTCAAAAAGCACAGTGTTTCCCTGTTTATCTCGAGATAAACAGGGAAACACTGTGC | 2916 | chrX | ENST00000218388.8 |
| TIMP1 | AATTCAAAAAGCACAGTGTTTCCCTGTTTATCTCGAGATAAACAGGGAAACACTGTGC | 2917 | chrX | ENST00000218388.8 |
| TIMP1 | AATTCAAAAACAGACGGCCTTCTGCAATTCCTCGAGGAATTGCAGAAGGCCGTCTGT | 2918 | chrX | ENST00000218388.8 |
| TNF | AATTCAAAAAGAACCCAAGCTTAGAACTTTACTCGAGTAAAGTTCTAAGCTTGGGTTC | 2919 | chr6 | ENST00000449264.2 |
| TNF | AATTCAAAAAGGAGCCAGCTCCCTCTATTTACTCGAGTAAATAGGGGAGCTGGCTCC | 2920 | chr6 | ENST00000449264.2 |
| TNF | AATTCAAAAATGGCGTGGAGCTGAGAGATAACTCGAGTTATCTCTCAGCTCCACGCCA | 2921 | chr6 | ENST00000449264.2 |
| TNFRSF4 | AATTCAAAAAGCACGTGGTGTAACCTCAGAACTCGAGTTCTGAGGTTACACCACGTGC | 2922 | chr1 | ENST00000379236.3 |
| TNFRSF4 | AATTCAAAAACAGCAATAGCTCGGACGCAATCTCGAGATTGCGTCCGAGCTATTGCTG | 2923 | chr1 | ENST00000379236.3 |
| TNFRSF4 | AATTCAAAAAGACAGCTACAAGCCTGGAGTTCTCGAGAACTCCAGGCTTGTAGCTGTC | 2924 | chr1 | ENST00000379236.3 |
| TNFRSF4 | AATTCAAAAAGCTTCTACAACGACGTGGTCACTCGAGTGACCACGTCGTTGTAGAAGC | 2925 | chr1 | ENST00000379236.3 |
| TNFRSF11 | AATTCAAAAATGTTTACTTGCCCGGTTTAATCTCGAGATTAAACCGGGCAAGTAAACA | 2926 | chr18 | ENST00000586569.2 |
| TNFRSF11 | AATTCAAAAATGTACCAGTGAGAAGCATTATCTCGAGATAATGCTTCTCACTGGTACA | 2927 | chr18 | ENST00000586569.2 |
| TNFRSF11 | AATTCAAAAATGGGACGGTGCTGTAACAAATCTCGAGATTTGTTACAGCACCGTCCCA | 2928 | chr18 | ENST00000586569.2 |
| TNFRSF11 | AATTCAAAAAGAAAGCACTCACAGCTAATTTCTCGAGAAATTAGCTGTGAGTGCTTTC | 2929 | chr8 | ENST00000297350.8 |
| TNFRSF11 | AATTCAAAAAGATAAATGCTTGCTGCATAAACTCGAGTTTATGCAGCAAGCATTTATC | 2930 | chr8 | ENST00000297350.8 |
| TNFRSF11 | AATTCAAAAACCAGTGTGTGTTCATTGTAAACTCGAGTTTACAATGAACACACACTGG | 2931 | chr8 | ENST00000297350.8 |
| TNFRSF1A | AATTCAAAAAAGAACCAGTACCGGCATTATTCTCGAGAATAATGCCGGTACTGGTTCT | 2932 | chr12 | ENST00000162749.6 |
| TNFRSF1A | AATTCAAAAAGGAGCTGTTGGTGGGAATATACTCGAGTATATTCCCACCAACAGCTCC | 2933 | chr12 | ENST00000162749.6 |
| TNFRSF1A | AATTCAAAAACTTGAAGGAACTACTACTAAGCTCGAGCTTAGTAGTAGTTCCTTCAAG | 2934 | chr12 | ENST00000162749.6 |
| TNFRSF9 | AATTCAAAAAGCTCCGTTTCTCTGTTGTTAACTCGAGTTAACAACAGAGAAACGGAGC | 2935 | chr1 | ENST00000377507.7 |
| TNFRSF9 | AATTCAAAAACAAGAACACCATCCTACATAACTCGAGTTATGTAGGATGGTGTTCTTG | 2936 | chr1 | ENST00000377507.7 |
| TNFRSF9 | AATTCAAAAACAGTCCCTGTCCTCCAAATAGCTCGAGCTATTTGGAGGACAGGGACTG | 2937 | chr1 | ENST00000377507.7 |
| TNFSF9 | AATTCAAAAACAAGTTGGACCTGATATTTACTCGAGTAAATATCAAGGTCCAACTTG | 2938 | chr19 | ENST00000245817.4 |
| TNFSF9 | AATTCAAAAACTACTATGTCTTCTTTCAACTCTCGAGAGTTGAAAGAAGACATAGTAG | 2939 | chr19 | ENST00000245817.4 |
| TNFSF9 | AATTCAAAAACCCTTCACCGAGGTCGGAATACTCGAGTATTCCGACCTCGGTGAAGGG | 2940 | chr19 | ENST00000245817.4 |
| TNFSF9 | AATTCAAAAATGAGCTACAAAGAGGACACGACTCGAGTCGTGTCCTCTTTGTAGCTCA | 2941 | chr19 | ENST00000245817.4 |
| TNFSF10 | AATTCAAAAAAGAAATAGTTGTTGGTCTAAACTCGAGTTTAGACCAACAACTATTTCT | 2942 | chr3 | ENST00000241261.6 |
| TNFSF10 | AATTCAAAAAGTTATCCTGACCCTATATTGCTCGAGCAATATAGGGTCAGGATAACT | 2943 | chr3 | ENST00000241261.6 |
| TNFSF10 | AATTCAAAAAGACAAACAAATGGTCCAATATCTCGAGATATTGGACCATTTGTTTGTC | 2944 | chr3 | ENST00000241261.6 |
| TNFSF11 | AATTCAAAAACTAATGGTGTACGTCACTAAACTCGAGTTTAGTGACGTACACCATTAG | 2945 | chr13 | ENST00000398795.6 |
| TNFSF11 | AATTCAAAAACCGGATCAGGATGCAACATACCTCGAGGTATGTTGCATCCTGATCCGG | 2946 | chr13 | ENST00000398795.6 |
| TNFSF11 | AATTCAAAAAGCAGTATATTTCTTCGTTCTTCTCGAGAAGAACGAAGAAATATACTGC | 2947 | chr13 | ENST00000398795.6 |
| TNFSF12 | AATTCAAAAAGTATTCCCACTCTTATCTTACCTCGAGGTAAGATAAGAGTGGGAATAC | 2948 | chr17 | ENST00000293825.10 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
| --- | --- | --- | --- | --- |
| TNFSF12 | AATTCAAAAAGGGCATTGTGTTCACTGTACTCTCGAGAGTACAGTGAACACAATGCCC | 2949 | chr17 | ENST00000293825.10 |
| TNFSF12 | AATTCAAAAACAGATGGAGGTTACACAACTTCTCGAGAAGTTGTGTAACCTCCATCTG | 2950 | chr17 | ENST00000293825.10 |
| TNFSF12- | AATTCAAAAACCTCACCTACTTCGGACTCTTCTCGAGAAGAGTCCGAAGTAGGTGAGG | 2951 | chr17 | ENST00000293826.4 |
| TNFSF12- | AATTCAAAAACTGTACTGTCAGGTGCACTTTCTCGAGAAAGTGCACCTGACAGTACAG | 2952 | chr17 | ENST00000293826.4 |
| TNFSF12- | AATTCAAAAAGCGCAGGCAGATGGAGGTTACCTCGAGGTAACCTCCATCTGCCTGCGC | 2953 | chr17 | ENST00000293826.4 |
| TNFSF13 | AATTCAAAAACAGTTGCCCTCTGGTTGAGTTCTCGAGAACTCAACCAGAGGGCAACTG | 2954 | chr17 | ENST00000338784.8 |
| TNFSF13 | AATTCAAAAAATGGCTCTGCTGACCCAACAACTCGAGTTGTTGGGTCAGCAGAGCCAT | 2955 | chr17 | ENST00000338784.8 |
| TNFSF13 | AATTCAAAAACCCAACAAACAGAGCTGCAGACTCGAGTCTGCAGCTCTGTTTGTTGGG | 2956 | chr17 | ENST00000338784.8 |
| TNFSF13B | AATTCAAAAACCTGAAACACTACCCAATAATCTCGAGATTATTGGGTAGTGTTTCAGG | 2957 | chr13 | ENST00000375887.8 |
| TNFSF13B | AATTCAAAAACTACGCCATGGGACATCTAATCTCGAGATTAGATGTCCCATGGCGTAG | 2958 | chr13 | ENST00000375887.8 |
| TNFSF13B | AATTCAAAAAGTGACTTTGTTTCGATGTATTCTCGAGAATACATCGAAACAAAGTCAC | 2959 | chr13 | ENST00000375887.8 |
| TNFSF14 | AATTCAAAAATCCTGGGAGCAGCTGATACAACTCGAGTTGTATCAGCTGCTCCCAGGA | 2960 | chr19 | ENST00000599359.1 |
| TNFSF14 | AATTCAAAAAGACAGACCGACATCCCATTCACTCGAGTGAATGGGATGTCGGTCTGTC | 2961 | chr19 | ENST00000599359.1 |
| TNFSF14 | AATTCAAAAAATGGGTCTGACACGTGGAGAACTCGAGTTCTCCACGTGTCAGACCCAT | 2962 | chr19 | ENST00000599359.1 |
| TNFSF15 | AATTCAAAAAATTAAGACACTGATCACTAAACTCGAGTTTAGTGATCAGTGTCTTAAT | 2963 | chr9 | ENST00000374045.4 |
| TNFSF15 | AATTCAAAAAGTCGGAGACTACTTCATTTACTCGAGTAAATGAAGTAGTCTCCCGAC | 2964 | chr9 | ENST00000374045.4 |
| TNFSF15 | AATTCAAAAAACTATAGGAGGAGAGCAAATACTCGAGTATTTGCTCTCCTCCTATAGT | 2965 | chr9 | ENST00000374045.4 |
| TNFSF18 | AATTCAAAAACCTTCAGTTGGCTAATCTTTACTCGAGTAAAGATTAGCCAACTGAAGG | 2966 | chr1 | ENST00000404377.3 |
| TNFSF18 | AATTCAAAAACTGAACCTCCTTGCGTGAATACTCGAGTATTCACGCAAGGAGGTTCAG | 2967 | chr1 | ENST00000404377.3 |
| TNFSF18 | AATTCAAAAATGATACAAACTCTAACAAACCTCGAGGTTTGTTAGAGTTTGTATCAT | 2968 | chr1 | ENST00000404377.3 |
| TNFSF4 | AATTCAAAAAGTGGCCTCTCTGACTTACAAACTCGAGTTTGTAAGTCAGAGAGGCCAC | 2969 | chr1 | ENST00000281834.3 |
| TNFSF4 | AATTCAAAAAGCAGAACAACTCAGTCATCATCTCGAGATGATGACTGAGTTGTTCTGC | 2970 | chr1 | ENST00000281834.3 |
| TNFSF4 | AATTCAAAAAGCCAAGATTCGAGAGGAACAACTCGAGTTGTTCCTCTCGAATCTTGGC | 2971 | chr1 | ENST00000281834.3 |
| TNFSF8 | AATTCAAAAACTGTATGGTCTTGATCTATTCTCGAGAATAGATCAAGACCATACAGT | 2972 | chr9 | ENST00000223795.2 |
| TNFSF8 | AATTCAAAAACAAACTACACAGGGTATTAAACTCGAGTTTAATACCCTGTGTAGTTTG | 2973 | chr9 | ENST00000223795.2 |
| TNFSF8 | AATTCAAAAAGTGGATACATTCCAGTACATACTCGAGTATGTACTGGAATGTATCCAC | 2974 | chr9 | ENST00000223795.2 |
| TNFSF9 | AATTCAAAAACAAGTTGGACCTTGATATTTACTCGAGTAAATATCAAGGTCCAACTTG | 2975 | chr19 | ENST00000245817.4 |
| TNFSF9 | AATTCAAAAACTACTATGTCTTCTTTCAACTCTCGAGAGTTGAAAGAAGACATAGTAG | 2976 | chr19 | ENST00000245817.4 |
| TNFSF9 | AATTCAAAAACCCTTCACCGAGGTCGGAATACTCGAGTATTCCGACCTCGGTGAAGGG | 2977 | chr19 | ENST00000245817.4 |
| TRIM16 | AATTCAAAAAGCCGTTGTTCAGCGCAAATATCTCGAGATATTTGCGCTGAACAACGGC | 2978 | chr17 | ENST00000336708.11 |
| TRIM16 | AATTCAAAAAGCCGTTGTTCAGCGCAAATATCTCGAGATATTTGCGCTGAACAACGGC | 2979 | chr17 | ENST00000336708.11 |
| TRIM16 | AATTCAAAAACCGCATCAGGTGAACATCAAACTCGAGTTTGATGTTCACCTGATGCGG | 2980 | chr17 | ENST00000336708.11 |
| TSLP | AATTCAAAAAACTCAATGATAGCACCTAAACCTCGAGGTTTAGGTGCTATCATTGAGT | 2981 | chr5 | ENST00000344895.3 |
| TSLP | AATTCAAAAACGTCGCTTCAATCGACCTTTACTCGAGTAAAGGTCGATTGAAGCGACG | 2982 | chr5 | ENST00000344895.3 |
| TSLP | AATTCAAAAACCATCTTTATTATGGTCATATCTCGAGATATGACCATAATAAAGATGG | 2983 | chr5 | ENST00000344895.3 |
| TWSG1 | AATTCAAAAAGACTGTGTTGGTATGTGTAATCTCGAGATTACACATACCAACACAGTC | 2984 | chr18 | ENST00000262120.9 |

TABLE 16-continued

3' to 5' (Reverse) shRNA sequences for Silencing of Cytokine/Chemokine Genes to Reduce the Incidence of CRS

| Target Gene Symbol | shRNA Reverse Oligo Sequence | SEQ ID NO: | Location | Gene ID No. |
|---|---|---|---|---|
| TWSG1 | AATTCAAAAAGCGCCTTATTCCAGTGACAAACTCGAGTTTGTCACTGGAATAAGGCGC | 2985 | chr18 | ENST00000262120.9 |
| TWSG1 | AATTCAAAAAGAATCACTGAGCTGTAACAAACTCGAGTTTGTTACAGCTCAGTGATTC | 2986 | chr18 | ENST00000262120.9 |
| TXLNA | AATTCAAAAAGCACATACTGTGTGGACAATACTCGAGTATTGTCCACACAGTATGTGC | 2987 | chr1 | ENST00000373609.1 |
| TXLNA | AATTCAAAAATGCTGATGCAGACATTGAATACTCGAGTATTCAATGTCTGCATCAGCA | 2988 | chr1 | ENST00000373609.1 |
| TXLNA | AATTCAAAAAGCGAGGTATTCACCACATTCCTCGAGGAATGTGGTGAATACCTCGCT | 2989 | chr1 | ENST00000373609.1 |
| VASN | AATTCAAAAAGCTTGACTACGCCGACTTTGCTCGAGCAAAGTCGGCGTAGTCAAGCT | 2990 | chr16 | ENST00000304735.3 |
| VASN | AATTCAAAAAGCCAACAGGCTGCATGAAATCTCGAGATTTCATGCAGCCTGTTGGCT | 2991 | chr16 | ENST00000304735.3 |
| VASN | AATTCAAAAAGAGATCCTTTCCCATTTATTCCTCGAGGAATAAATGGGAAAGGATCTC | 2992 | chr16 | ENST00000304735.3 |
| VEGFA | AATTCAAAAACAAGATCCGCAGACGTGTAAACTCGAGTTTACACGTCTGCGGATCTTG | 2993 | chr6 | ENST00000425836.6 |
| VEGFA | AATTCAAAAACAAGATCCGCAGACGTGTAAACTCGAGTTTACACGTCTGCGGATCTTG | 2994 | chr6 | ENST00000425836.6 |
| VEGFA | AATTCAAAAAGCGCAAGAAATCCCGGTATAACTCGAGTTATACCGGGATTTCTTGCGC | 2995 | chr6 | ENST00000425836.6 |
| VSTM1 | AATTCAAAAAATGAATATGCGGCACTGAAAGCTCGAGCTTTCAGTGCCGCATATTCAT | 2996 | chr19 | ENST00000338372.6 |
| VSTM1 | AATTCAAAAACATTCCCAGAATGTGACATTTCTCGAGAAATGTCACATTCTGGGAATG | 2997 | chr19 | ENST00000338372.6 |
| VSTM1 | AATTCAAAAAGAGTGACCTATGCTGAGCTAACTCGAGTTAGCTCAGCATAGGTCACTC | 2998 | chr19 | ENST00000338372.6 |
| WFIKKN1 | AATTCAAAAATGCGCCCTGATCAGATGTATGCTCGAGCATACATCTGATCAGGGCGCA | 2999 | chr16 | ENST00000319070.2 |
| WFIKKN1 | AATTCAAAAAGGACGTGCTCAAGGATGACAACTCGAGTTGTCATCCTTGAGCACGTCC | 3000 | chr16 | ENST00000319070.2 |
| WFIKKN1 | AATTCAAAAAGTGCTGCATCAACGTGTGCTCGAGCACACACGTTGATGCAGCACT | 3001 | chr16 | ENST00000319070.2 |
| WFIKKN2 | AATTCAAAAATCAAGTTCTTGGGCACCAAGTCTCGAGACTTGGTGCCCAAGAACTTGA | 3002 | chr17 | ENST00000311378.4 |
| WFIKKN2 | AATTCAAAAATACAACCGCTGCTATATGGACCTCGAGGTCCATATAGCAGCGGTTGTA | 3003 | chr17 | ENST00000311378.4 |
| WFIKKN2 | AATTCAAAAACACCAGCTTGCTCAGATATTCCTCGAGGAATATCTGAGCAAGCTGGTG | 3004 | chr17 | ENST00000311378.4 |
| WNT1 | AATTCAAAAACTGTCGAGAAACGGCGTTTATCTCGAGATAAACGCCGTTTCTCGACAG | 3005 | chr12 | ENST00000293549.3 |
| WNT1 | AATTCAAAAAGACCTCGTCTACTTCGAGAAACTCGAGTTTCTCGAAGTAGACGAGGTC | 3006 | chr12 | ENST00000293549.3 |
| WNT1 | AATTCAAAAAGCCACGAGTTTGGATGTTGTACTCGAGTACAACATCCAAACTCGTGGC | 3007 | chr12 | ENST00000293549.3 |
| WNT2 | AATTCAAAAACCACAAATGGTCCCAATTAAGCTCGAGCTTAATTGGGACCATTTGTGG | 3008 | chr7 | ENST00000265441.7 |
| WNT2 | AATTCAAAAATCGGGAATCTGCCTTTGTTTACTCGAGTAAACAAAGGCAGATTCCCGA | 3009 | chr7 | ENST00000265441.7 |
| WNT2 | AATTCAAAAATTGACTATGGGATCAAATTTGCTCGAGCAAATTTGATCCCATAGTCAA | 3010 | chr7 | ENST00000265441.7 |
| WNT5A | AATTCAAAAACTCCCAGGACCCGCTTATTTACTCGAGTAAATAAGCGGGTCCTGGGAG | 3011 | chr3 | ENST00000264634.8 |
| WNT5A | AATTCAAAAACAAAGAATGCCAGTATCAATTCTCGAGAATTGATACTGGCATTCTTTG | 3012 | chr3 | ENST00000264634.8 |
| WNT5A | AATTCAAAAACCTGTTCAGATGTCAGAAGTACTCGAGTACTTCTGACATCTGAACAGG | 3013 | chr3 | ENST00000264634.8 |
| WNT7A | AATTCAAAAACATAGGAGAAGGCTCACAAATCTCGAGATTTGTGAGCCTTCTCCTATG | 3014 | chr3 | ENST00000285018.4 |
| WNT7A | AATTCAAAAAGGCGCAAGCATCATCTGTAACCTCGAGGTTACAGATGATGCTTGCGCC | 3015 | chr3 | ENST00000285018.4 |
| WNT7A | AATTCAAAAATCTTCGGGAAGGAGCTCAAAGCTCGAGCTTTGAGCTCCTTCCCGAAGA | 3016 | chr3 | ENST00000285018.4 |
| XCL1 | AATTCAAAAAGCTGTGCAATGGCAACAATTCTCGAGAATTGTTGCCATTGTCACAGC | 3017 | chr1 | ENST00000367818.3 |
| XCL1 | AATTCAAAAATTCAACTTGTCTCTATAATAGCTCGAGCTATTATAGAGACAAGTTGAA | 3018 | chr1 | ENST00000367818.3 |
| XCL1 | AATTCAAAAAGATTCTGGCTAGTGTCTATCCTCGAGGATAGACACTAGCCAGAATCT | 3019 | chr1 | ENST00000367818.3 |
| XCL2 | AATTCAAAAAACTGCCAGTTAGCAGAATCAACTCGAGTTGATTCTGCTAACTGGCAGT | 3020 | chr1 | ENST00000367819.2 |
| XCL2 | AATTCAAAAAGTAGGGAGTGAAGTCTCACATCTCGAGATGTGAGACTTCACTCCCTAC | 3021 | chr1 | ENST00000367819.2 |

TABLE 16-continued

3' to 5' (Reverse) shRNA sequences for Silencing of Cytokine/Chemokine
Genes to Reduce the Incidence of CRS

| Target Gene Symbol | shRNA Reverse Oligo Sequence | SEQ ID NO: | Location | Gene ID No. |
|---|---|---|---|---|
| XCL2 | AATTCAAAAAGAAATCCAACACCAGAAATAACTCGAGTTATTTCTGGTGTTGGATTTC | 3022 | chr1 | ENST00000367819.2 |
| ZFP36 | AATTCAAAAAGATCCGACCCTGATGAATATGCTCGAGCATATTCATCAGGGTCGGATC | 3023 | chr19 | ENST00000597629.1 |
| ZFP36 | AATTCAAAAAATCTGTCTCCTAGAATCTTATCTCGAGATAAGATTCTAGGAGACAGAT | 3024 | chr19 | ENST00000597629.1 |
| ZFP36 | AATTCAAAAACCCTTTATTTATGACGACTTTCTCGAGAAAGTCGTCATAAATAAAGGG | 3025 | chr19 | ENST00000597629.1 |

Example 16—Method of Making and Testing Cells Deficient in Specific Cytokine Expression Using Protein Expression Blockers (PEBL)—CAR19-GM-CSF PEBL Inject tumor in SCID-Beige mice (3e6 Raji containing Luciferase) if performing in vivo CRS experiment. This should be completed 3 weeks prior to infusion of CAR-T into mice.

The following sERteps may be taken to provide CRS resistance. A selectable marker is required to enrich for this gene modification as cytokines are secreted proteins, thus. This example describes the making of a cell CAR19-GM-CSF PEBL, in which blockade of GM-CSF secretion mitigates risk of CRS. As those of skill in the art will recognize, certain of the steps may be conducted sequentially or out of the order listed below, though perhaps leading to different efficiency.

Step 1: T Cell Activation (Day 0)

Purify T cells from leukapheresis chamber using Miltenyi juman PanT isolation kit. Resuspend in media. Count cells. Determine number of human T cell activation CD3/CD28 beands required to obtain 3:1 bead: cell ratio. Wash beads 2× with T cell media. Dilute cells at 1.256 cells/mL in hXcyte media. Add human T cell activation CD3/CD28 beads. Aliquot 4 ml/well of 1.256 cells/mL solution into 6-well plate. Incubate at 37° C.

Step 2: Transduction of T Cells with PEBL CAR (Day 1)

T cells are transduced with a CAR targeted to (i.e., that recognizes) one or more antigen or protein targets, for example with a Lentivirus containing a CAR construct targeting CD19, combined with the anti-GM-CSF PEBL. Expression from a polycistronic vector is preferable, allowing CD34 expression to mark both CAR and PEBL expression. However, expression can be achieved with the same viral vector expressing both the CAR and PEBL individually, or as independent transductions with separate vectors containing CAR and PEBL. Any other suitable method of transduction may be used, for example, AAV, retrovirus, etc, or through direct insertion of the CAR PEBL complex into a targeted location of the genome using homology directed repair and a donor vector containing the construct.

Step 3: Assessment of Td Efficiency (Day 10)

Take $5\times10^5$ cells from each sample and analyze by flow cytometry. Wash samples with RB. Add 3 μL of anti-CD34 PE antibody. Add 5 μL of CD3 APC and 2 μL of anti-FAB BV421 (detects CAR transduction). Wash. Perform flow cytometry. Cells should be CD34-positive indicating expression of CAR and PEBL from a polycistronic vector. Harvest T cells (Day 11).

Purification of CAR-T cells. CAR+ (CD34+) and GC-CSF deficient (PEBL+) cells can be enriched using a CD34-positive selection on the Miltenyi Automacs. This enriches the GC-CSF suppressed cells and enriches CAR+ cells.

Step 4: Assessment of CAR-T Activity

Inject $3\times10^7$ CAR-T cells per mouse I.P. Assess serum cytokine levels. (Day 12, Day 13, Day 14). Measure serum cytokine levels using Luminex multiplex profiling assay to check for elevations in CRS-related cytokines. Perform a 4-hour chromium release assay against target cells (Raji) to assess in vitro activity (Day 11).

PEBL constructs targeting GM-CSF are provided in FIG. 6 and Tables 17 and 18.

TABLE 17

Anti-GM-CSF PEBL Constructs (SEQ ID NOS 3071-3076, respectively)

| CD28 Leader | $V_L$ | Linker | $V_H$ | ER-Retention Domain | 2a | trCD34 |
|---|---|---|---|---|---|---|
| MALPVTALLLP LALLLHAARP (SEQ ID NO: 1) | DIELTQPPSVS VAPGQTARISC SGDNLPGKYVH WYQQKPGQAPV LVIYYDSNRPS GIPERFSGSNS GNTATLTISGT QAEDEADYYCQ SRTQTTIVFGG GTKLTVLGQ (SEQ ID NO: 3026) | GGGGS(n)n = 1, 2, 3, 4 (SEQ ID NO: 3069) | QVQLVESGGG LVQPGGSLRL SCAASGFTFS SHWMSWVRQA PGKGLEWVSN IWRGPYIYYA DSVKGRFTIS RDNSKNTLYL QMNSLRAEDT AVYYCARFQG YGGGFDYWGQ GTLVTVSS (SEQ ID NO: 3027) | EQKLISEEDLKD EL (SEQ ID NO: 3028) | | |

TABLE 17-continued

Anti-GM-CSF PEBL Constructs (SEQ ID NOS 3071-3076, respectively)

| CD28 Leader | V_L | Linker | V_H | ER-Retention Domain | 2a | trCD34 |
|---|---|---|---|---|---|---|
| MALPVTALLLP LALLLHAARP (SEQ ID NO: 1) | DIELTQPPSVS VAPGQTARISC SGDNLPGKYVH WYQQKPGQAPV LVIYYDSNRPS GIPERFSGSNS GNTATLTISGT QAEDEADYYCQ SRTQTTIVFGG GTKLTVLGQ (SEQ ID NO: 3026) | GGGGS(n)n = 1, 2, 3, 4 (SEQ ID NO: 3069) | QVQLVESGGG LVQPGGSLRL SCAASGFTFS SHWMSWVRQA PGKGLEWVSN IWRGPYIYYA DSVKGRFTIS RDNSKNTLYL QMNSLRAEDT AVYYCARFQG YGGGFDYWGQ GTLVTVSS (SEQ ID NO: 3027) | (GGGGS)4AEK DEL (SEQ ID NO: 3029) | | |
| MALPVTALLLP LALLLHAARP (SEQ ID NO: 1) | DIELTQPPSVS VAPGQTARISC SGDNLPGKYVH WYQQKPGQAPV LVIYYDSNRPS GIPERFSGSNS GNTATLTISGT QAEDEADYYCQ SRTQTTIVFGG GTKLTVLGQ (SEQ ID NO: 3026) | GGGGS(n)n = 1, 2, 3, 4 (SEQ ID NO: 3069) | QVQLVESGGG LVQPGGSLRL SCAASGFTFS SHWMSWVRQA PGKGLEWVSN IWRGPYIYYA DSVKGRFTIS RDNSKNTLYL QMNSLRAEDT AVYYCARFQG YGGGFDYWGQ GTLVTVSS (SEQ ID NO: 3027) | TTTPAPRPPTPA PTIASQPLSLRP EACRPAAGGAVH TRGLDFACDIYI WAPLAGTCGVLL LSLVITLYCNHR NLYKYKSRRSFI DEKKMP (SEQ ID NO: 3030) | | |
| MALPVTALLLP LALLLHAARP (SEQ ID NO: 1) | DIELTQPPSVS VAPGQTARISC SGDNLPGKYVH WYQQKPGQAPV LVIYYDSNRPS GIPERFSGSNS GNTATLTISGT QAEDEADYYCQ SRTQTTIVFGG GTKLTVLGQ (SEQ ID NO: 3026) | GGGGS(n)n = 1, 2, 3, 4 (SEQ ID NO: 3069) | QVQLVESGGG LVQPGGSLRL SCAASGFTFS SHWMSWVRQA PGKGLEWVSN IWRGPYIYYA DSVKGRFTIS RDNSKNTLYL QMNSLRAEDT AVYYCARFQG YGGGFDYWGQ GTLVTVSS (SEQ ID NO: 3027) | EQKLISEEDLKD EL (SEQ ID NO: 3028) | GSGATNFSLLK QAGDVEENPGP (SEQ ID NO: 3031) | MPRGWTALCLL SLLPSGFMSLD NNGTATPELPT QGTFSNVSTNV SYQETTTPSTL GSTSLHPVSQH GNEATTNITET TVKFTSTSVIT SVYGNTNSSVQ SQTSVISTVFT TPANVSTPETT LKPSLSPGNVS DLSTTSTSLAT SPTKPYTSSSP ILSDIKAEIKC SGIREVKLTQG ICLEQNKTSSC AEFKKDRGEGL ARVLCGEEQAD ADAGAQVCSLL LAQSEVRPQCL LLVLANRTEIS SKLQLMKKHQS DLKKLGILDFT EQDVASHQSYS QKTLIALVTSG ALLAVLGITGY FLMNRRSWSPI (SEQ ID NO: 3032) |
| MALPVTALLLP LALLLHAARP (SEQ ID NO: 1) | DIELTQPPSVS VAPGQTARISC SGDNLPGKYVH WYQQKPGQAPV LVIYYDSNRPS GIPERFSGSNS GNTATLTISGT QAEDEADYYCQ | GGGGS(n)n = 1, 2, 3, 4 (SEQ ID NO: 3069) | QVQLVESGGG LVQPGGSLRL SCAASGFTFS SHWMSWVRQA PGKGLEWVSN IWRGPYIYYA DSVKGRFTIS RDNSKNTLYL | (GGGGS)4AEK DEL (SEQ ID NO: 3029) | GSGATNFSLLK QAGDVEENPGP (SEQ ID NO: 3031) | MPRGWTALCLL SLLPSGFMSLD NNGTATPELPT QGTFSNVSTNV SYQETTTPSTL GSTSLHPVSQH GNEATTNITET TVKFTSTSVIT |

TABLE 17-continued

Anti-GM-CSF PEBL Constructs (SEQ ID NOS 3071-3076, respectively)

| CD28 Leader | V_L | Linker | V_H | ER-Retention Domain | 2a | trCD34 |
|---|---|---|---|---|---|---|
| | SRTQTTIVFGG GTKLTVLGQ (SEQ ID NO: 3026) | | QMNSLRAEDT AVYYCARFQG YGGGFDYWGQ GTLVTVSS (SEQ ID NO: 3027) | | | SVYGNTNSSVQ SQTSVISTVFT TPANVSTPETT LKPSLSPGNVS DLSTTSTSLAT SPTKPYTSSSP ILSDIKAEIKC SGIREVKLTQG ICLEQNKTSSC AEFKKDRGEGL ARVLCGEEQAD ADAGAQVCSLL LAQSEVRPQCL LLVLANRTEIS SKLQLMKKHQS DLKKLGILDFT EQDVASHQSYS QKTLIALVTSG ALLAVLGITGY FLMNRRSWSPI (SEQ ID NO: 3032) |
| MALPVTALLLP LALLLHAARP (SEQ ID NO: 1) | DIELTQPPSVS VAPGQTARISC SGDNLPGKYVH WYQQKPGQAPV LVIYYDSNRPS GIPERFSGSNS GNTATLTISGT QAEDEADYYCQ SRTQTTIVFGG GTKLTVLGQ (SEQ ID NO: 3026) | GGGGS(n)n = 1, 2, 3, 4 (SEQ ID NO: 3069) | QVQLVESGGG LVQPGGSLRL SCAASGFTFS SHWMSWVRQA PGKGLEWVSN IWRGPYIYYA DSVKGRFTIS RDNSKNTLYL QMNSLRAEDT AVYYCARFQG YGGGFDYWGQ GTLVTVSS (SEQ ID NO: 3027) | TTTPAPRPPTPA PTIASQPLSLRP EACRPAAGGAVH TRGLDFACDIYI WAPLAGTCGVLL LSLVITLYCNHR NLYKYKSRRSFI DEKKMP (SEQ ID NO: 3030) | GSGATNFSLLK QAGDVEENPGP (SEQ ID NO: 3031) | MPRGWTALCLL SLLPSGFMSLD NNGTATPELPT QGTFSNVSTNV SYQETTTPSTL GSTSLHPVSQH GNEATTNITET TVKFTSTSVIT SVYGNTNSSVQ SQTSVISTVFT TPANVSTPETT LKPSLSPGNVS DLSTTSTSLAT SPTKPYTSSSP ILSDIKAEIKC SGIREVKLTQG ICLEQNKTSSC AEFKKDRGEGL ARVLCGEEQAD ADAGAQVCSLL LAQSEVRPQCL LLVLANRTEIS SKLQLMKKHQS DLKKLGILDFT EQDVASHQSYS QKTLIALVTSG ALLAVLGITGY FLMNRRSWSPI (SEQ ID NO: 3032) |

TABLE 18

CD19 CAR with GM-CSF PEBL Constructs (SEQ ID NOS 3077-3082, respectively)

| CD8a Leader | CD19 V_H | Linker | CD19 V_L | CD8a Hinge | CD28tm | CD28 Co-stim | CD3z | 2a | CD8a Leader | V_L | Linker | V_H | ER-Retention Domain and Tag | 2a | Tag |
|---|---|---|---|---|---|---|---|---|---|---|---|---|---|---|---|
| MALPVT ALLLPL ALLLHA ARP (SEQ ID NO: 1) | DIQMTQTTS SLSASLGDR VTISCRASQ DISKYLNWY QQKPDGTVK LLIYHTSRL HSGVPSRFS GSGSGTDYS LTISNLEQE DIATYFCQQ GNTLPYTFG GGTKLEITR ADAAPTVSI FPPSSN (SEQ ID NO: 3033) | GGGGS4 (SEQ ID NO: 9) | EVKLQESGP GLVAPSQSL SVTCTVSGV SLPDYGVSW IRQPPRKGL EWLGVIWGS ETTYYNSAL KSRLTIIKD NSKSQVFLK MNSLQTDDT AIYYCAKHY YYGGSYAMD YWGQGTSVS (SEQ ID NO: 3034) | TTTPAPRPP TPAPTIASQ PLSLRPEAC RPAAGGAVH TRGLDFACD (SEQ ID NO: 3035) | FWVLVVVGG VLACYSLLV TVAFIIFWV (SEQ ID NO: 3036) | RSKRSRLLH SDYMNMTPR RPGPTRKHY QPYAPPRDF AAYRS (SEQ ID NO: 3037) | RVKFSRSA DAPAYKQG QNQLYNEL NLGRREEY DVLDKRRG RDPEMGK PRRKNPQE GLYNELQK DKMAEYAS EIGMKGER RGKGHDG LYQGLSTA TKDTYDAL HMQALPPR (SEQ ID NO: 3038) | GSGATNFS LLKQAGDV EENPGP (SEQ ID NO: 3031) | MALPVT ALLLPL ALLLHA ARP (SEQ ID NO: 1) | DIELQTPP SVSVAPGQ TARISCSG DNLPGKYV HWYQQKPG QAPVLVIY YDSNRPSG IPERFSGS NSGNTATL TISGTQAE DEADYYCQ SRTQTTIV FGGGTKLT VLGQ (SEQ ID NO: 3026) | GGGGS(n)n = 1, 2, 3, 4 (SEQ ID NO: 3069) | QVQLVESG GGLVQPGG SLRLSCAA SGFTFSSH WMSWVRQA PGKGLEWV SNIWRGPY IYYADSVK GRFTISRD NSKNTLYL QMNSLRAE DTAVYYCA RFQGYGGG FDYWGQGT LVTVSS (SEQ ID NO: 3027) | EQKLISEE DLKDEL (SEQ ID NO: 3028) | | |
| MALPVT ALLLPL ALLLHA ARP (SEQ ID NO: 1) | DIQMTQTTS SLSASLGDR VTISCRASQ DISKYLNWY QQKPDGTVK LLIYHTSRL HSGVPSRFS GSGSGTDYS LTISNLEQE DIATYFCQQ GNTLPYTFG GGTKLEITR ADAAPTVSI FPPSSN (SEQ ID NO: 3033) | GGGGS4 (SEQ ID NO: 9) | EVKLQEQGP GLVAPSQSL SVTCTVSGV SLPDYGVSW IRQPPRKGL EWLGVIWGS ETTYYNSAL KSRLTIIKD NSKSQVFLK MNSLQTDDT AIYYCAKHY YYGGSYAMD YWGQGTSVS (SEQ ID NO: 3034) | TTTPAPRPP TPAPTIASQ PLSLRPEAC RPAAGGAVH TRGLDFACD (SEQ ID NO: 3035) | FWVLVVVGG VLACYSLLV TVAFIIFWV (SEQ ID NO: 3036) | RSKRSRLLH SDYMNMTPR RPGPTRKHY QPYAPPRDF AAYRS (SEQ ID NO: 3037) | RVKFSRSA DAPAYKQG QNQLYNEL NLGRREEY DVLDKRRG RDPEMGK PRRKNPQE GLYNELQK DKMAEYAS EIGMKGER RRGKGHDG LYQGLSTA TKDTYDAL HMQALPPR (SEQ ID NO: 3038) | GSGATNFS LLKQAGDV EENPGP (SEQ ID NO: 3031) | MALPVT ALLLPL ALLLHA ARP (SEQ ID NO: 1) | DIELQTPP SVSVAPGQ TARISCSG DNLPGKYV HWYQQKPG QAPVLVIY YDSNRPSG IPERFSGS NSGNTATL TISGTQAE DEADYYCQ SRTQTTIV FGGGTKLT VLGQ (SEQ ID NO: 3026) | GGGGS(n)n = 1, 2, 3, 4 (SEQ ID NO: 3069) | QVQLVESG GGLVQPGG SLRLSCAA SGFTFSSH WMSWVRQA PGKGLEWV SNIWRGPY IYYADSVK GRFTISRD NSKNTLYL QMNSLRAE DTAVYYCA RFQGYGGG FDYWGQGT LVTVSS (SEQ ID NO: 3027) | (GGGGS)4 AEKDEL (SEQ ID NO: 3029) | | |
| MALPVT ALLLPL ALLLHA ARP (SEQ ID NO: 1) | DIQMTQTTS SLSASLGDR VTISCRASQ DISKYLNWY QQKPDGTVK LLIYHTSRL HSGVPSRFS GSGSGTDYS | GGGGS4 (SEQ ID NO: 9) | EVKLQEQGP GLVAPSQSL SVTCTVSGV SLPDYGVSW IRQPPRKGL EWLGVIWGS ETTYYNSAL KSRLTIIKD | TTTPAPRPP TPAPTIASQ PLSLRPEAC RPAAGGAVH TRGLDFACD (SEQ ID NO: 3035) | FWVLVVVGG VLACYSLLV TVAFIIFWV (SEQ ID NO: 3036) | RSKRSRLLH SDYMNMTPR RPGPTRKHY QPYAPPRDF AAYRS (SEQ ID NO: 3037) | RVKFSRSA DAPAYKQG QNQLYNEL NLGRREEY DVLDKRRG RDPEMGK PRRKNPQE GLYNELQK | GSGATNFS LLKQAGDV EENPGP (SEQ ID NO: 3031) | MALPVT ALLLPL ALLLHA ARP (SEQ ID NO: 1) | DIELQTPP SVSVAPGQ TARISCSG DNLPGKYV HWYQQKPG QAPVLVIY YDSNRPSG IPERFSGS | GGGGS(n)n = 1, 2, 3, 4 (SEQ ID NO: 3069) | QVQLVESG GGLVQPGG SLRLSCAA SGFTFSSH WMSWVRQA PGKGLEWV SNIWRGPY IYYADSVK | TTTPAPRP PTPAPTIA SQPLSLRP EACRPAAG AAVHTRGL DFACDIYI WAPLAGTC GVLLLSLV | | |

TABLE 18-continued

CD19 CAR with GM-CSF PEBL Constructs (SEQ ID NOS 3077-3082, respectively)

| CD8a Leader | CD19 V_H | Linker | CD19 V_L | CD8a Hinge | CD28tm | CD28 Co-stim | CD3z | 2a | CD8a Leader | V_L | Linker | V_H | ER-Retention Domain and Tag | 2a | Tag |
|---|---|---|---|---|---|---|---|---|---|---|---|---|---|---|---|
| | | | | | | | DKMAEAYS EIGMKGER RRGKGHDG LYQGLSTA TKDTYDAL HMQALPPR (SEQ ID NO: 3038) | | | NSGNTATL TISGTQAE DEADYYCQ SRTQTTIV FGGGTKLT VLGQ (SEQ ID NO: 3026) | | GRFTISRD NSKNTLYL QMNSLRAE DTAVYYCA RFQGYGGG FDYWGQGT LVTVSS (SEQ ID NO: 3027) | ITLYCNHR NLYKYKSR RSFIDEKK MP (SEQ ID NO: 3030) | | |
| MALPVT ALLLPL ALLLHA ARP (SEQ ID NO: 1) | DIQMTQTTS SLSASLGDR VTISCRASQ DISKYLNWY QQKPDGTVK LLIYHTSRL HSGVPSRFS GSGSGTDYS LTISNLEQE DIATYFCQQ GNTLPYTFG GGTKLEITR ADAAPTVSI FPPSSN (SEQ ID NO: 3033) | GGGGS (SEQ ID NO: 9) | DIQMTQTTS SLSASLGDR VTISCRASQ DISKYLNWY QQKPDGTVK LLIYHTSRL HSGVPSRFS GSGSGTDYS LTISNLEQE DIATYFCQQ GNTLPYTFG GGTKLEITR ADAAPTVSI FPPSSN (SEQ ID NO: 3033) | EVKLQESGP GLVAPSQSL SVTCTVSGV SLPDYGVSW IRQPPRKGL EWLGVIWGS ETTYYNSAL KSRLTIIKD NSKSQVFLK MNSLQTDDT AIYYCAKHY YYGGSYAMD YWGQGTSVS (SEQ ID NO: 3034) | TTTPAPRPP TPAPTIASQ PLSLRPEAC RPAAGGAVH TRGLDFACD (SEQ ID NO: 3035) | FWVLVVGG VLACYSLLV TVAFIIFWV (SEQ ID NO: 3036) | RSKRSRLLH SDYMNMTPR RPGPTRKHY QPYAPPRDF AAYRS (SEQ ID NO: 3037) | RVKFSRSA DAPAYKQG QNQLYNEL NLGRREEY DVLDKRRG RDPEMGGK PRRKNPQE GLYNELQK DKMAEAYS EIGMKGER RRGKGHDG LYQGLSTA TKDTYDAL HMQALPPR (SEQ ID NO: 3038) | GSGATNFS LLKQAGDV EENPGP (SEQ ID NO: 3031) | MALPVT ALLLPL ALLLHA ARP (SEQ ID NO: 1) | DIELQTPP SVSVAPGQ TARISCSG DNLPGKYV HWYQQKPG QAPVLVIY YDSNRPSG IPERFSGS NSGNTATL TISGTQAE DEADYYCQ SRTQTTIV FGGGTKLT VLGQ (SEQ ID NO: 3026) | GGGGS(n)= 1, 2, 3, 4 (SEQ ID NO: 3069) | QVQLVESG GGLVQPGG SLRLSCAA SGFTFSSH WMSWVRQA PGKGLEWV SNIWRGPY IYYADSVK GRFTISRD NSKNTLYL QMNSLRAE DTAVYYCA RFQGYGGG FDYWGQGT LVTVSS (SEQ ID NO: 3027) | EQKLISEE DLKDEL (SEQ ID NO: 3028) | GSGATN FSLLKQ AGDVEE NPGP (SEQ ID NO: 3031) | MPRGWTA LCLLSLL PSGFMSL DNNGTAT PELPTQG TFSNVST NVSYQET TTPSTLG STSLHPV SQHGNEA TTNITET TVKFTST SVITSVY GNTNSSV QSQTSVI STVFTTP ANVSTPE TTLKPSL SPGNVSD LSTTSTS LATSPTK PYTSSSP ILSDIKA EIKCSGI REVKLTQ GICLEQN KTSSCAE FKKDRGE GLARVLC GEEQADA DAGAQVC SLLLAQS EVRPQCL LLVLANR TEISSKL QLMKHQ |

TABLE 18-continued

CD19 CAR with GM-CSF PEBL Constructs (SEQ ID NOS 3077-3082, respectively)

| CD8a Leader | CD19 V$_H$ | Linker | CD19 V$_L$ | CD8a Hinge | CD28tm | CD28 Co-stim | CD3z | 2a | CD8a Leader | V$_L$ | Linker | V$_H$ | ER-Retention Domain and Tag | 2a | Tag |
|---|---|---|---|---|---|---|---|---|---|---|---|---|---|---|---|
| MALPVT ALLLPL ALLLHA ARP (SEQ ID NO: 1) | DIQMTQTTS SLSASLGDR VTISCRASQ DISKYLNWY QQKPDGTVK LLIYHTSRL HSGVPSRFS GSGSGTDYS LTISNLEQE DIATYFCQQ GNTLPYTFG GGTKLEITR ADAAPTVSI FPPSSN (SEQ ID NO: 3033) | GGGGS$_4$ (SEQ ID NO: 9) | EVKLQEQGP GLVAPSQSL SVTCTVSGV SLPDYGVSW IRQPPRKGL EWLGVIWGS ETTYYNSAL KSRLTIIKD NSKSQVFLK MNSLQTDDT AIYYCAKHY YYGGSYAMD YWGQGTSVS (SEQ ID NO: 3034) | TTTPAPRPP TPAPTIASQ PLSLRPEAC RPAAGGAVH TRGLDFACD (SEQ ID NO: 3035) | FWVLVVVGG VLACYSLLV TVAFIIFWV (SEQ ID NO: 3036) | RSKRSRLLH SDYMNMTPR RPGPTRKHY QPYAPPRDF AAYRS (SEQ ID NO: 3037) | RVKFSRSA DAPAYKQG QNQLYNEL NLGRREEY DVLDKRRG RDPEMGGK PRRKNPQE GLYNELQK DKMAEAYS EIGMKGER RRGKGHDG LYQGLSTA TKDTYDAL HMQALPPR (SEQ ID NO: 3038) | GSGATNFS LLKQAGDV EENPGP (SEQ ID NO: 3031) | MALPVT ALLLPL ALLLHA ARP (SEQ ID NO: 1) | DIELQTPP SVSVAPGQ TARISCSG DNLPGKYV HWYQQKPG QAPVLIIY YDSNRPSG IPERFSGS NSGNTATL TISGTQAE DEADYYCQ SRTQTTIV FGGGTKLT VLGQ (SEQ ID NO: 3026) | GGGGS(n) = 1, 2, 3, 4 (SEQ ID NO: 3069) | QVQLVESG GGLVQPGG SLRLSCAA SGFTFSSH WMSWVRQA PGKGLEWV SNIWRGPY IYYADSVK GRFTISRD NSKNTLYL QMNSLRAE DTAVYYCA RFQGYGGG FDYWGQGT LVTVSS (SEQ ID NO: 3027) | (GGGGS)$_4$ AEKDEL (SEQ ID NO: 3029) | GSGATN FSLLKQ AGDVEE NPGP (SEQ ID NO: 3031) | MPRGWTA LCLLSLL PSGFMSL DNNGTAT PELPTQG TFSNVST NVSYQET TTPSTLG STSLHPV SQHGNEA TTNIETT TVKFTST SVITSVY GNTNSSV QSQTSVI STVFTTP ANVSTPE TTLKPSL SPGNVSD LSTTSTS LATSPTK PYTSSSP ILSDIKA EIKCSGI REVKLTQ GICLEQN KTSSCAE FKKDRGE GLARVLC GEEQADA DAGAQVC SLLAQS EVRPQCL LLVLANR TEISSKL SDLKKLG ILDFTEQ DVASHQS YSQKTLI ALVTSGA LLAVLGI TGYFLMN RRSWSPI (SEQ ID NO: 10) |

TABLE 18-continued

CD19 CAR with GM-CSF PEBL Constructs (SEQ ID NOS 3077-3082, respectively)

| CD8a Leader | CD19 V_H | Linker | CD19 V_L | CD8a Hinge | CD28tm | CD28 Co-stim | CD3z | 2a | CD8a Leader | V_L | Linker | V_H | ER-Retention Domain and Tag | 2a | Tag |
|---|---|---|---|---|---|---|---|---|---|---|---|---|---|---|---|
| MALPVT ALLLPL ALLLHA ARP (SEQ ID NO: 1) | DIQMTQTTS SLSASLGDR VTISCRASQ DISKYLNWY QQKPDGTVK LLIYHTSRL HSGVPSRFS GSGSGTDYS LTISNLEQE DIATYFCQQ GNTLPYTFG GGTKLEITR ADAAPTVSI FPPSSN (SEQ ID NO: 3033) | GGGGS_4 (SEQ ID NO: 9) | EVKLQEQGP GLVAPSQSL SVTCTVSGV SLPDYGVSW IRQPPRKGL EWLGVIWGS ETTYYNSAL KSRLTIIKD NSKSQVFLK MNSLQTDDT AIYYCAKHY YYGGSYAMD YWGQGTSVS (SEQ ID NO: 3034) | TTTPAPRPP TPAPTIASQ PLSLRPEAC RPAAGGAVH TRGLDFACD (SEQ ID NO: 3035) | FWVLVVVGG VLACYSLLV TVAFIIFWV (SEQ ID NO: 3036) | RSKRSRLLH SDYMNMTPR RPGPTRKHY QPYAPPRDF AAYRS (SEQ ID NO: 3037) | RVKFSRSA DAPAYKQG QNQLYNEL NLGRREEY DVLDKRRG RDPEMGGK PRRKNPQE GLYNELQK DKMAEAYS EIGMKGER RRGKGHDG LYQGLSTA TKDTYDAL HMQALPPR (SEQ ID NO: 3038) | GSGATNFS LLKQAGDV EENPGP (SEQ ID NO: 3031) | MALPVT ALLLPL ALLLHA ARP (SEQ ID NO: 1) | DIELQTPP SVSVAPGQ TARISCSG DNLPGKYV HWYQQKPG QAPVLVIY YDSNRPSG IPERFSGS NSGNTATL TISGTQAE DEADYYCQ SRTQTTIV FGGGTKLT VLGQ (SEQ ID NO: 3026) | GGGGS(n) = 1, 2, 3, 4 (SEQ ID NO: 3069) | QVQLVESG GGLVQPGG SLRLSCAA SGFTFSSH WMSWVRQA PGKGLEWV SNIWRGPY IYYADSVK GRFTISRD NSKNTLYL QMNSLRAE DTAVYYCA RFQGYGGG FDYWGQGT LVTVSS (SEQ ID NO: 3027) | TTTPAPRP PTPAPTIA SQPLSLRP EACRPAAG AAVHTRGL DFACDIYI WAPLAGTC GVLLLSLV ITLYCNHR NLYKYKSR RSFIDEKK MP (SEQ ID NO: 3030) | GSGATN FSLLKQ AGDVEE NPGP (SEQ ID NO: 3031) | MPRGWTA LCLLSLL PSGFMSL DNNGTAT PELPTQG TFSNVST NVSYQET TTPSTLG STSLHPV SQHGNEA TTNITET TVKFTST SVITSVY GNTNSSV QSQTSVI STVFTTP ANVSTPE TTLKPSL SPGNVSD LSTTSTS LATSPTK PYTSSSP ILSDIKA EIKCSGI REVKLTQ QLMKKHQ SDLKKLG ILDFTEQ DVASHQS YSQKTLI ALVTSGA LLAVLGI TGYFLMN RRSWSPI (SEQ ID NO: 10) |

TABLE 18-continued

CD19 CAR with GM-CSF PEBL Constructs (SEQ ID NOS 3077-3082, respectively)

| CD8a Leader | CD19 V_H | Linker | CD19 V_L | CD8a Hinge | CD28tm | CD28 Co-stim | CD3z | 2a | CD8a Leader | V_L | Linker | V_H | ER-Retention Domain and Tag | 2a | Tag |
|---|---|---|---|---|---|---|---|---|---|---|---|---|---|---|---|
| | | | | | | | | | | | | | | | GICLEQN KTSSCAE FKKDRGE GLARVLC GEEQADA DAGAQVC SLLLAQS EVRPQCL LLVLANR TEISSKL QLMKKHQ SDLKKLG ILDFTEQ DVASHQS YSQKTLI ALVTSGA LLAVLGI TGYFLMN RRSWSPI (SEQ ID NO: 10) |

Example 17—In Vitro CRS Assay for Testing Efficacy of Inducing CRS after Deletion of GM-CSF in CART19

Cell lines: CD19 positive B-ALL cell line RAMOS was used to evaluate CRS in an in vitro assay. Prior to assay, RAMOS cells were stably transfected with GFP using lentiviral transduction and cultured in RPMI+10% FBS+Pen/Strep.

Isolation of normal donor monocytes and T cells: Primary human T cells and monocytes were isolated from normal healthy human donors. T cell cells were isolated from PBMC using CD4+CD8+ selection (Miltenyi Biotec) and monocytes were separated using Miltenyi biotec classical Monocyte Isolation beads according to the manufactures protocol.

T cell culture and CAR-T gene editing: T cells were subsequently resuspended at a concentration of $1 \times 10^6$ cells/mL in Xcyte media supplemented with 50 U/mL IL-2 and 10 ng/ml IL-15 in the presence of anti-CD3/CD28 beads (Bead to cell ratio 3:1). Twenty-four hours after initial stimulation, T cells were transfected with lentiviral vector encoding the CD19 CAR construct in the presence of polybrene (final conc. 6 μg/ml). Stimulatory beads were removed on day 2. CART19 cells were suspended at $4 \times 10^6$ T cells were electroporated in 100 μl buffer P3 with 15 μg spCas9 mRNA (Trilink CA.) and 20 μg of GM-CSF gRNA (Trilink) using a nucleofector 4D, program EO-115. Control CAR19 T cells were electroporated without GM-CSF gRNA. T-cells were subsequently evaluated at day 6 for CD34 (bicistronic marker of CAR-T) and intracellular GM-CSF expression using flowcytometry prior to co-culture assay.

Production of monocyte lineage cells: For iDC generation, monocytes ($1 \times 10^6$) were plated in 6 mLs of RPMI 1640 supplemented with supplemented with 0.1 mmol/L MEM Non-Essential Amino Acids, 2 mmol/L L-glutamine, 100 units/mL penicillin, 100 μg/mL streptomycin (Life Technologies) and 10% fetal calf serum (cR10). cR10 was subsequently supplemented with 0.2 μg/mL human IL-4 (Peptotec) and 0.2 μg/mL GM-CSF (Peptotec).

For macrophage and activated macrophage generation cR10 was supplemented with 10% human A/B serum instead of fetal calf serum (hR10). For activated macrophages hR10 medium was supplemented with 30 ng/ml of LPS. On day 4 cytokines and LPS were replenished. Macrophages, activated macrophages and iDC were harvested using 2 mmol/L EDTA (immature dendritic cells) on day 6 post-isolation. Twenty-four hours later, cells were harvested with 2 mmol/L EDTA and stained with CD45, CD80 and CD86 to confirm immature DC and mature DC differentiation.

Co-culture assay: CAR-T cells were combined at the following ratios in 200 μl per 96 well: 12.5K UCART-19 (with or with-out GM-CSF KO), Target, 50K Ramos cells (CD19+) and monocyte derived cells, 1K iDC or 5K macrophages or 5K activated macrophages.

Co-cultures were subsequently incubated for at 37° C. and 100 μl of assay supernatant was collected at 24 hr and 48 hr for cytokine analysis.

Measurement of Cytokine Levels

Cytokine concentration determination from culture supernatants was performed using IL-6 ELISA plate (R&D systems). Prior to analysis supernatant's were centrifuged at 300 g for 10 mins at 4° C. and subsequently diluted 1:10 in assay calibrator diluent. Measurements were performed using standard product protocols.

Figure 8:
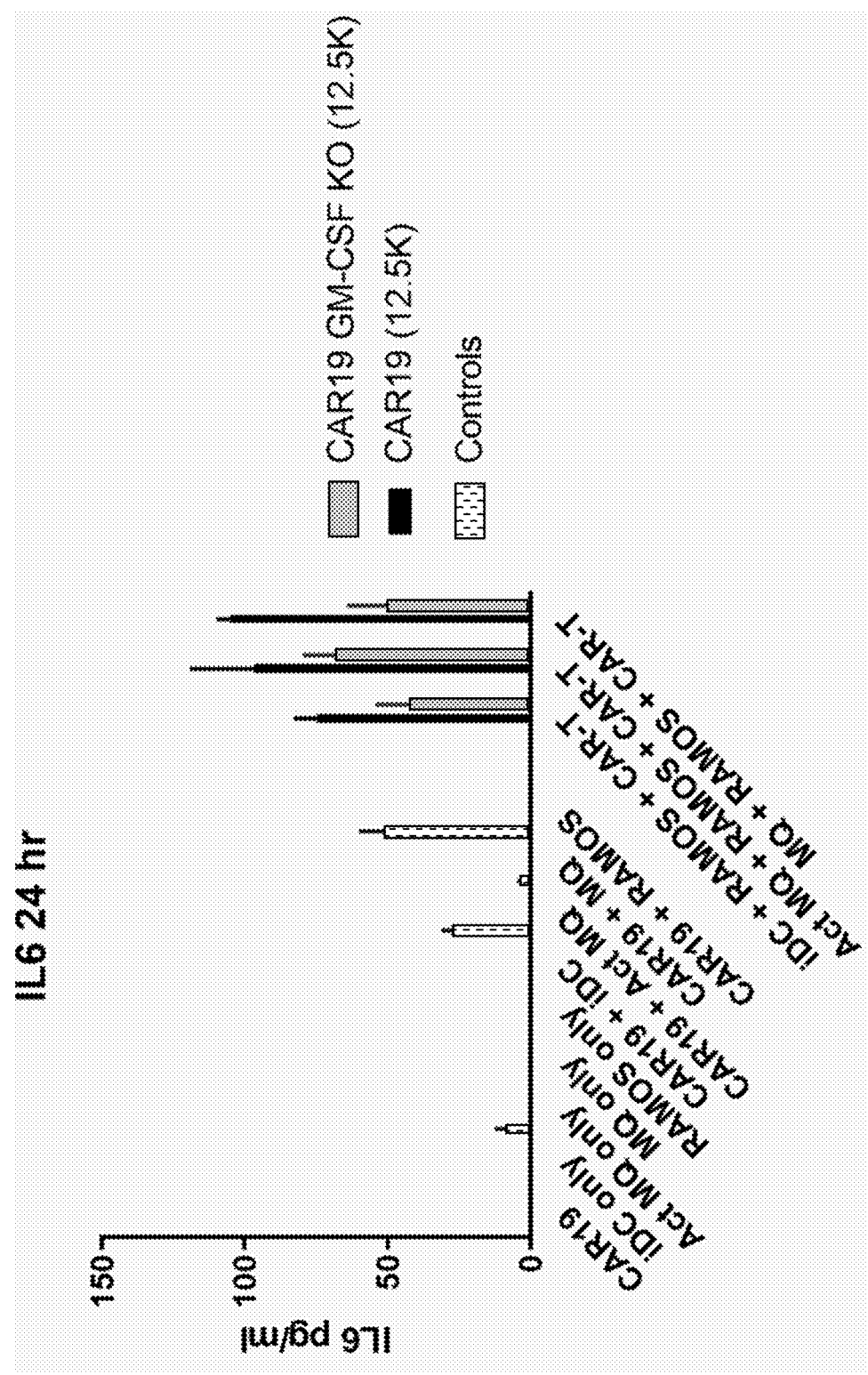
FIG. 8—Shows IL-6 expression in CAR19, iDC only, Act MQ only, MC only, RAMOS only, CAR19+iDC, CAR19+ActMQ, CAR19+MQ, CAR19+RAMOS, iDC+RAMOS+CAR-T, ActMQ+RAMOS+CAR-T, and MQ+RAMOS+CAR-T for CAR19 GM-CSF knock-out, CAR19, and controls at 24 hours.
Figure 10:
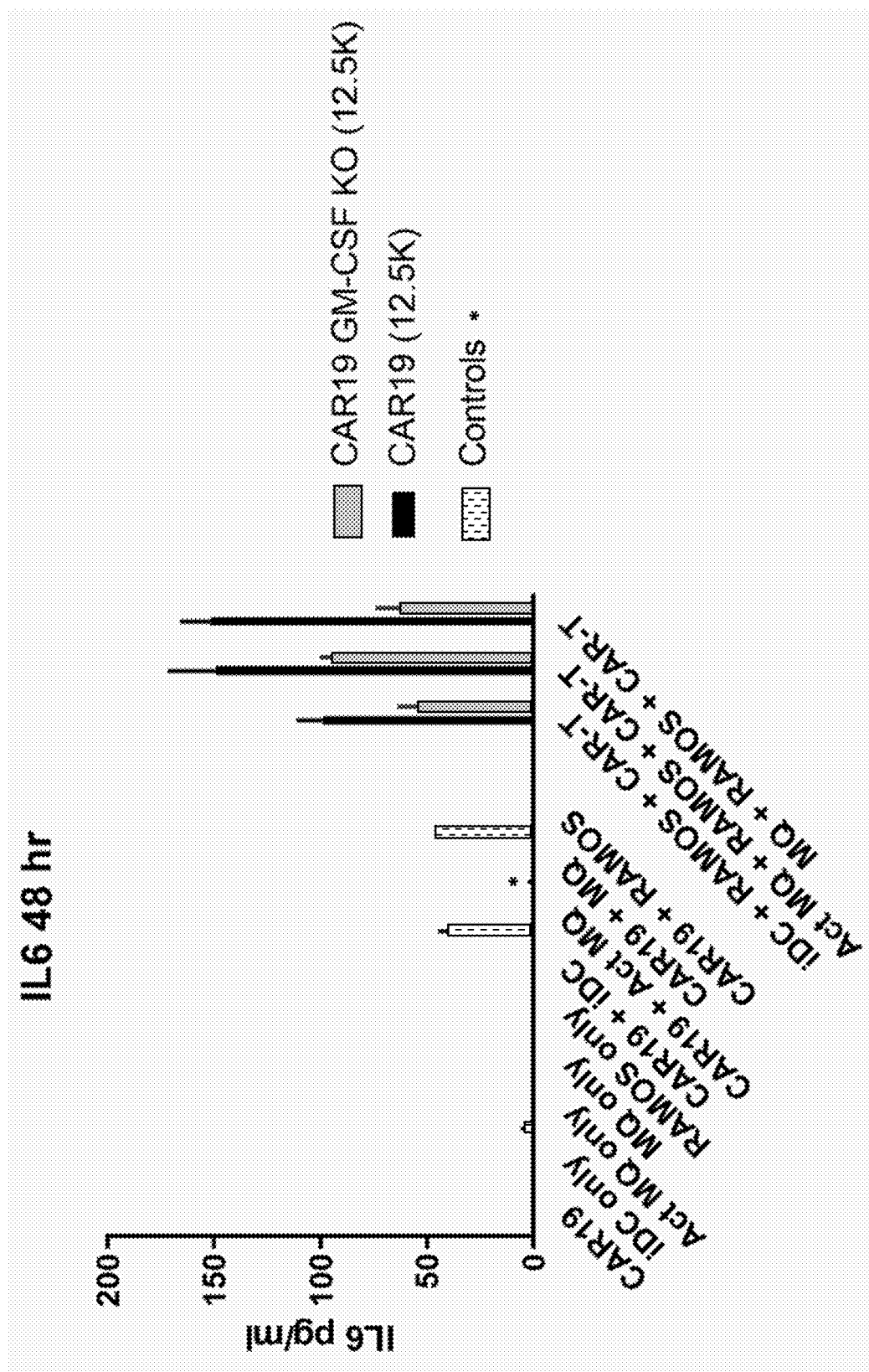
FIG. 10—Shows IL-6 expression in CAR19, iDC only, Act MQ only, MC only, RAMOS only, CAR19+iDC, CAR19+ActMQ, CAR19+MQ, CAR19+RAMOS, iDC+RAMOS+CAR-T, ActMQ+RAMOS+CAR-T, and MQ+RAMOS+CAR-T for CAR19 GM-CSF knock-out, CAR19, and controls at 48 hours.

GM-CSF deficient CART19 induced significantly lower il-6 expression across the different monocyte lineages. FIGS. 8 and 10

Example 18—In Vitro CRS Assay for Testing Efficacy of Inducing CRS after Deletion of GM-CSF in T Cells Isolation of normal donor monocytes and T cells: Primary human T cells and monocytes were isolated from normal healthy human donors. T cell cells were isolated from PBMC using CD4+CD8+ selection (Miltenyi Biotec) and monocytes were separated using Miltenyi Biotec classical Monocyte Isolation beads according to the manufactures protocol.

T cell culture and gene editing: T cells were subsequently resuspended at a concentration of $10^6$ cells/mL in Xcyte media supplemented with 50 U/mL IL-2 and 10 ng/ml IL-15 in the presence of anti-CD3/CD28 beads (Bead to cell ratio 3:1) (Life Technologies, catalog #111.32D). Twenty-four hours after initial stimulation. Stimulatory beads were removed on day 2. $4 \times 10^6$ T cells were electroporated in 100 μl buffer P3 with 15 μg spCas9 mRNA (Trilink CA.) and 20 μg of TRAC gRNA (Trilink) using a nucleofector 4D, program EO-115. Control CAR19 T cells were electroporated without GM-CSF gRNA. T-cells were subsequently evaluated at day 6 for GM-CSF expression prior to co-culture assay using flowcytometry.

Production of monocyte lineage cells: For iDC generation, monocytes ($1 \times 10^6$) were plated in 6 mLs of RPMI 1640 supplemented with supplemented with 0.1 mmol/L MEM Non-Essential Amino Acids, 2 mmol/L L-glutamine, 100 units/mL penicillin, 100 μg/mL streptomycin (Life Technologies) and 10% fetal calf serum (cR10). cR10 was subsequently supplemented with 0.2 μg/mL human IL-4 (Peptotec) and 0.2 μg/mL GM-CSF (Peptotec). On day 4 cytokines and LPS were replenished. IDC were harvested using 2 mmol/L EDTA (immature dendritic cells) on day 6 post-isolation.

Co-culture assay: T cells were combined at the following ratios in 200 μl per 96 well: 12.5K T cells (with or with-out GM-CSF KO), 50K anti-CD3/CD28 beads and 1K iDC Co-cultures were subsequently incubated for at 37° C. and 100 μl of assay supernatant was collected at 24 hr and 48 hr for cytokine analysis.

Measurement of cytokine levels: Cytokine concentration determination from culture supernatants was performed using IL-6 ELISA plate (R&D systems). Prior to analysis supernatants were centrifuged at 300×g for 10 mins at 4° C. and subsequently diluted 1:10 in assay calibrator diluent. Measurements were performed using standard product protocols.

Figure 7:
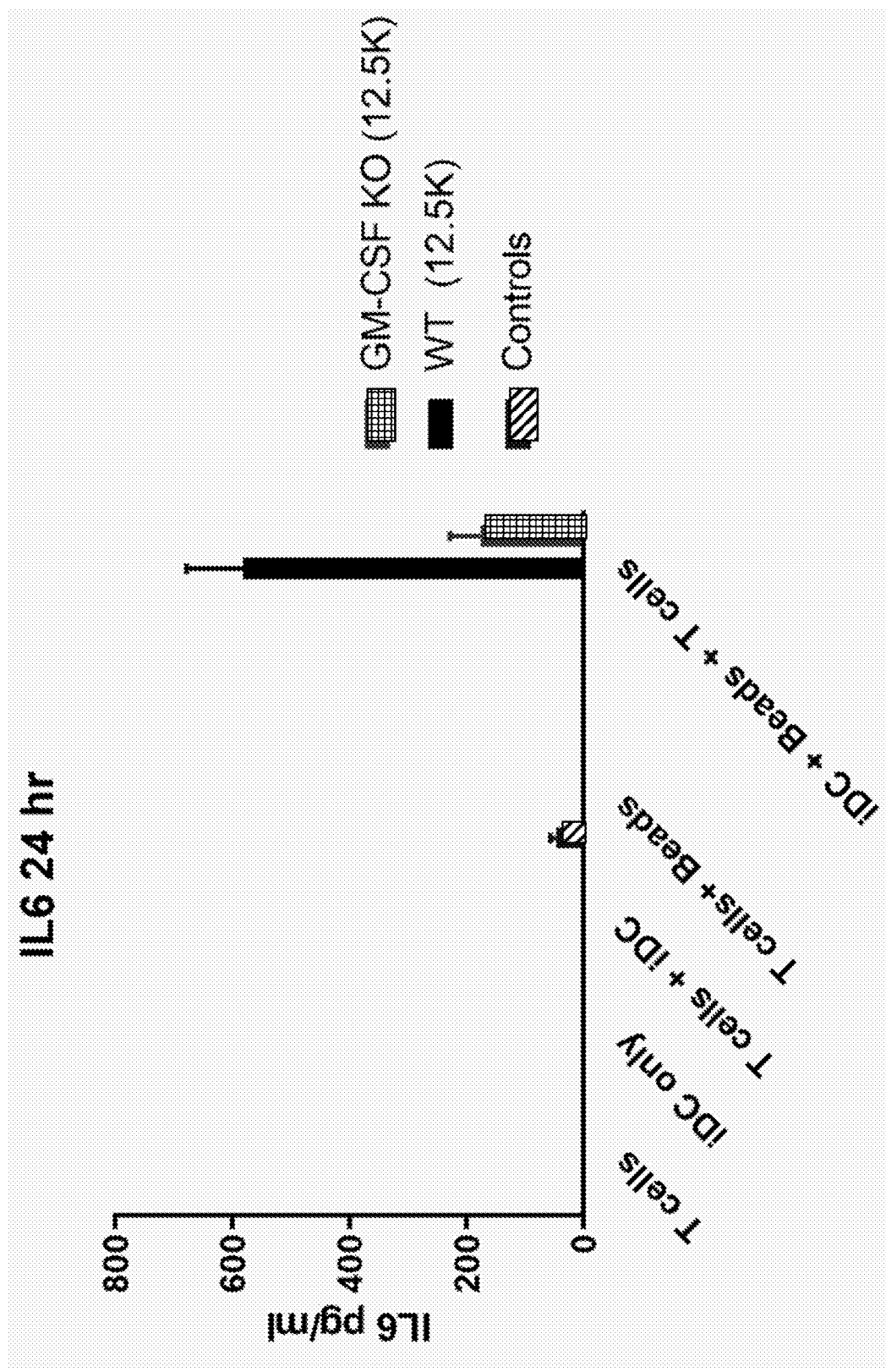
FIG. 7—Shows IL-6 expression in T cells, iDC cells, T cells+iDC, T cells+beads, and iDC+beads+ T cells for GM-CSF knock-out, wild-type, and controls at 24 hours.
Figure 9:
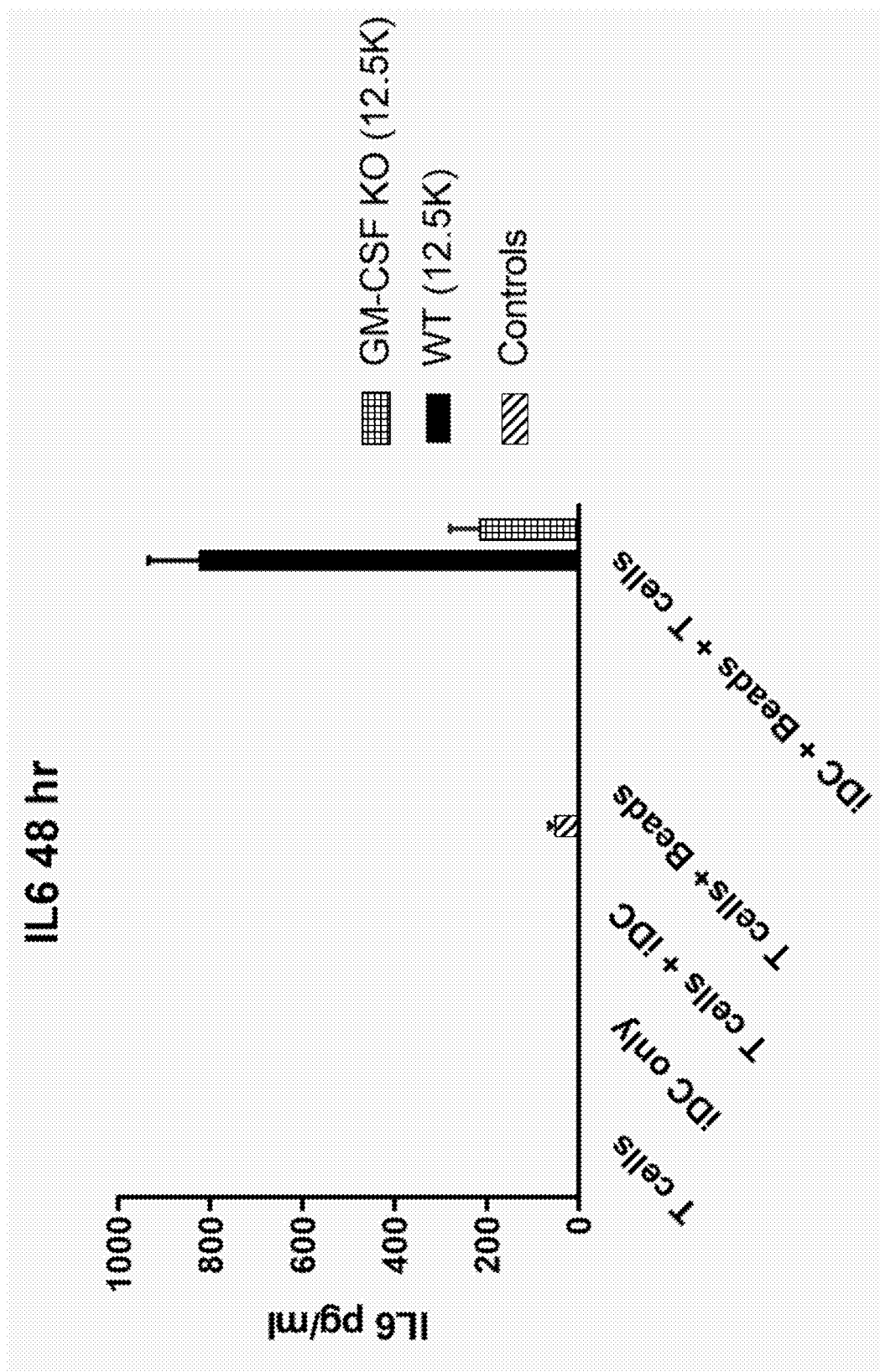
FIG. 9—Shows IL-6 expression in T cells, iDC cells, T cells+iDC, T cells+beads, and iDC+beads+ T cells for GM-CSF knock-out, wild-type, and controls at 48 hours.

Deletion of GM-CSF reduced IL-6 production >3-fold at 24 hrs (FIGS. 7 and 8) and >4-fold at 48 hrs (FIGS. 9 and 10) relative to non-edited T cells.

GM-CSF deficient T cells induced significantly lower IL-6 expression across the different monocyte lineages.

Example 19—Method for Making and Testing a Genome-Edited CAR-T Cell Deficient at Inducing CRS by Insertion of Selectable Marker into Gene Edited Locus Inject primary B-ALL ($2 \times 10^6$) in NSG mice if performing an in vivo CRS experiment. This should be completed 3 weeks prior to infusion of CAR-T into mice.

The following steps may be taken to provide a genome-edited, CRS-resistant, CAR-T cells. This example describes the making of a CD19CARTΔGMCSFΔCD3ε mutant IL-7R T cell, in which the deletion of GM-CSF mitigates risk of CRS, deletion of CD3e prevent TCR signaling and GvHD and the mutant IL-7R enhances proliferation of the CAR-T sufficiently to induce CRS in this model. Sequences encoding a mutant, constitutively active IL-7R sequence can be found in Table 19, or found in the art. As those of skill in the art will recognize, certain of the steps may be conducted sequentially or out of the order listed below, though perhaps leading to different efficiency.

Step 1: T Cell Activation (Day 0)

Purify T cells from a leukapheresis chamber using a Miltenyi human PanT isolation kit. Resuspend in media. Count cells. Determine the number of human T cell activation CD3/CD28 beads required to obtain a 3:1 bead: cell ratio. Wash beads 2× with T cell media. Dilute cells at 1.256 cells/mL in hXcyte media. Add human T cell activation CD3/CD28 beads. Aliquot 4 mL/well of 1.256 cell/mL solution into a 6 well plate. Incubate cells at 37° C.

Step 2: T Cell Transduction (Day 1)

CAR-T cells may then be transduced with one or more CARs targeted to (i.e., that recognizes) one or more targets, for example with a lentivirus containing a CAR construct. Any other suitable method of transduction may be used.

Step 3: CRISPR (Day 2)

In a CRS-resistant CAR-T cell, cytokine/chemokine/transcription factor genes or transcription factors may be deleted to prevent secretion of factors that induce secretion of cytokines from myeloid cells. Deletion may be accomplished by electroporating with Cas9 mRNA and gRNA against the target(s). Other techniques, however, could be used to suppress expression of the target. These include other genome editing techniques such as TALENs, RNA interference, and eliciting of internal binding of the antigen to prevent cell surface expression. Examples of gRNAs that may be used include those shown in Tables 8-10, and others known in the art.

| Sample ID | gRNA#1 | gRNA#2 | Cas9 | Nuecleofection Buffer P3 |
|---|---|---|---|---|
| UCART19 | 20 μg gGM-CSF | 20 μg gCD3ε | 15 μg Cas9 mRNA | 100 μl |

Cells are harvested, isolated, and purified, for example using magnetic selection with a labelled antibody-coated magnetic beads that bind to a cell-specific protein (available from, e.g., Miltenyi Biotec). For T cells, anti-CD3/CD28 beads could be used. Other purification techniques are known in the art and could be used.

TABLE 19

Sequences or Constitutively Expressing IL-7R

| CD8a Leader | CD19 V_L | Linker | CD19 V_H | CD8a Hinge | CD28tm | CD28 Co-stim | CD3z | 2a | Truncated CD34 | Truncated IL-7R ECD | IL-7 TMD | Trucated IL-7R ICD | Description |
|---|---|---|---|---|---|---|---|---|---|---|---|---|---|
| MALPVT ALLLPL ALLLHA ARP (SEQ ID NO: 1) | DIQMTQTT SSLSASLG DRVTISCR ASQDISKY LNWYQQKP DGTVKLLI YHTSRLHS GVPSRFSG SGSGTDYS LTISNLEQ QGNTLPYT FGGGTKLE ITRADAAP TVSIFPPS SN (SEQ ID NO: 3033) | GGGGS_4 (SEQ ID NO: 9) | EVKLQESGP GIVAPSQSL SVTCTVSGV SLPDYGVSW IRQPPRKGL EWLGVIWGS ETTYYNSAL KSRLKSRLT IIKDNSKSQ VFLKMNSLQ TDDTAIYYC AKHYYYGGS YAMDYWGQG TSVTVSS (SEQ ID NO: 3034) | TTTPAPRPP TPAPTIASQ PLSLRPEAC RPAAGGAVH TRGLDFACD (SEQ ID NO: 3035) | FWVLVVVG GVLACYSL LVTVAFII FWV (SEQ ID NO: 3036) | RSKRSRLLH SDYMNMTPR RPGPTRKHY QPYAPPRDF AAYRS (SEQ ID NO: 3037) | RVKFSRSA DAPAYKQG QNQLYNEL NLGRREEY DVLDKRRG RDPEMGGK PRRKNPQE GLYNELQK SQHGNEATT DKMAEAYS EIGMKGER RRGKGHDG LYQGLSTA TKDTYDAL HMQALPPR (SEQ ID NO: 3038) | GSGATNFS LLKQAGDV EENPGP (SEQ ID NO: 3031) | MPRGWTALC LLSLLPSGF MSLDNNGTA TPELPTQGT FSNVSTNVS YQETTTPST LGSTSLHPV SQHGNEATT NITETTVKF TSTSVITSV YGNTNSSVQ SQTSVISTV FTTPANVST PETTLKPSL LPSNVSDLS TTSTSLATS PTKPYTSSS PILSDIKAE IKCSGIREV KLTQGICLE QNKTSSCAE FKKDRGEGL ARVLCGEEQ ADADAGAQV CSLLIAQSE VRPQCLLIV LANRTEISS KLQLMKKHQ SDLKKLG (SEQ ID NO: 3039) | YREGANDFV VTFNTSHLQ KKYVKVLMH DVAYRQEKD ENKWTHVNL SSTKLTLLQ RKLQPAAMY EIKVRSIPD HYFKGFWSE WSPSYFRT PEINNSSGE MDPI (SEQ ID NO: 3040) | LLTCPTISI LSFFSVALL VILACVLW (SEQ ID NO: 3045) | KKRIKPIVW PSLPDHKKT LEHLCKKPR KNLNVSFNP ESFLDCQIH RVDDIQARD EVEGFLQDT FPQQLEESE KQRLGGDVQ SPNCPSEDV VITPESFGR DSSLTCLAG NVSACDAPI LSSSRSLDC RESGKNGPH VYQDLLLSL GTTNSTLPP PFSLQSGIL TLNPVAQGQ PILTSLGSN QEEAYVTMS SFYQNQ (SEQ ID NO: 3047) | IL7R with L5 and L6 elbows with CPT transmembrane T-ALL mutation insertion only |
| MALPVT ALLLPL ALLLHA ARP (SEQ ID NO: 1) | DIQMTQTT SSLSASLG DRVTISCR ASQDISKY LNWYQQKP DGTVKLLI YHTSRLHS GVPSRFSG SGSGTDYS LTISNLEQ QGNTLPYT FGGGTKLE ITRADAAP | GGGGS_4 (SEQ ID NO: 9) | EVKLQESGP GIVAPSQSL SVTCTVSGV SLPDYGVSW IRQPPRKGL EWLGVIWGS ETTYYNSAL KSRLKSRLT IIKDNSKSQ VFLKMNSLQ TDDTAIYYC AKHYYYGGS YAMDYWGQG | TTTPAPRPP TPAPTIASQ PLSLRPEAC RPAAGGAVH TRGLDFACD (SEQ ID NO: 3035) | FWVLVVVG GVLACYSL LVTVAFII FWV (SEQ ID NO: 3036) | RSKRSRLLH SDYMNMTPR RPGPTRKHY QPYAPPRDF AAYRS (SEQ ID NO: 3037) | RVKFSRSA DAPAYKQG QNQLYNEL NLGRREEY DVLDKRRG RDPEMGGK PRRKNPQE GLYNELQK SQHGNEATT DKMAEAYS EIGMKGER RRGKGHDG LYQGLSTA TKDTYDAL | GSGATNFS LLKQAGDV EENPGP (SEQ ID NO: 3031) | MPRGWTALC LLSLLPSGF MSLDNNGTA TPELPTQGT FSNVSTNVS YQETTTPST LGSTSLHPV SQHGNEATT NITETTVKF TSTSVITSV YGNTNSSVQ SQTSVISTV FTTPANVST | YREGANDFV VTFNTSHLQ KKYVKVLMH DVAYRQEKD ENKWTHVNL SCTKLTLLQ RKLQPAAMY EIKVRSIPD HYFKGFWSE WSPSYFRT PEINNSSGE MD (SEQ ID NO: 3045) | LLTCPTISI LSFFSVALL VILACVLW (SEQ ID NO: 3045) | KKRIKPIVW PSLPDHKKT LEHLCKKPR KNLNVSFNP ESFLDCQIH RVDDIQARD EVEGFLQDT FPQQLEESE KQRLGGDVQ SPNCPSEDV VITPESFGR DSSLTCLAG NVSACDAPI | IL7R with L5 and L6 elbows with CPT transmembrane T-ALL mutation insertion and S185C B-ALL mutation |

TABLE 19-continued

Sequences or Constitutively Expressing IL-7R

| CD8a Leader | CD19 V_L | Linker | CD19 V_H | CD8a Hinge | CD28tm | CD28 Co-stim | CD3z | 2a | Truncated CD34 | Truncated IL-7R ECD | IL-7 TMD | Trucated IL-7R ICD | Description |
|---|---|---|---|---|---|---|---|---|---|---|---|---|---|
| MALPVT ALLLPL ALLHA ARP (SEQ ID NO: 1) | TVSIFPPS SN (SEQ ID NO: 3033) | | TSVTVSS (SEQ ID NO: 3034) | | | | HMQALPPR (SEQ ID NO: 3038) | | PETTLKPSL LPSNVSDLS TTSTSLATS PTKPYTSSS PILSDIKAE IKCSGIREV KLTQGICLE QNKTSSCAE FKKDRGEGL ARVLCGEEQ ADADAGAQV CSLLLAQSE VRPQCLLLV LANRTEISS KLQLMKKHQ SDLKKLG (SEQ ID NO: 3039) | | | LSSSRSLDC RESGKNGPH VYQDLLLSL GTTNSTLPP PFSLQSGIL TLNPVAGQ PILTSLGSN QEEAYVTMS SFYQNQ (SEQ ID NO: 3047) | |
| MALPVT ALLLPL ALLHA ARP (SEQ ID NO: 1) | DIQMTQT SSLSASLG DRVTISCR ASQDISKY LNWYQQKP DGTVKLLI YHTSRLHS GVPSRFSG SGSGTDYS LTISNLEQ QGNTLPYT FGGGTKLE ITRADAAP TVSIFPPS SN (SEQ ID NO: 3033) | GGGGS4 (SEQ ID NO: 9) | EVKLQESGP GLVAPSQSL SVTCTVSGV SLPDYGVSW IRQPPRKGL EWLGVIWGS ETTYYNSAL KSRLKSRLT IIKDNSKSQ VFLKMNSLQ TDDTAIYYC AKHYYYGGS YAMDYWGQG TSVTVSS (SEQ ID NO: 3034) | TTTPAPRPP TPAPTIASQ PLSLRPEAC RPAAGGAVH TRGLDFACD (SEQ ID NO: 3035) | FWVLVVVG GVLACYSL LVTVAFI FWV (SEQ ID NO: 3036) | RSKRSRLLH SDYMNMTPR RPGPTRKHY QPYAPPRDF AAYRS (SEQ ID NO: 3037) | RVKFSRSA DAPAYKQG QNQLYNEL NLGRREEY DVLDKRRG RDPEMGGK PRRKNPQE GLYNELQK DKMAEAYS EIGMKGER RRGKGHDG LYQGLSTA TKDTYDAL HMQALPPR (SEQ ID NO: 3038) | GSGATNFS LLKQAGDV EENPGP (SEQ ID NO: 3031) | MPRGWTALC LLSLLPSGF MSLDNNGTA TPELPTQGT FSNVSTNVS YQETTTPST LGSTSLHPV SQHGNEATT NITETTVKF TSTSVITSV YGNTNSSVQ SQTSVISTV FTTPANVST PETTLKPSL LPSNVSDLS TTSTSLATS PTKPYTSSS PILSDIKAE IKCSGIREV KLTQGICLE | YREGANDFV VTFNTSHLQ KKYVKVLMH DVAYRQEKD ENKWTHVNL SCTKLTLLQ RKLQPAAMY EIKVRSIPD HYFKGFWSE WSPSYYFRT PEINNSSGE MD (SEQ ID NO: 3041) | LLTISILS FFSVALLV ILACVLM (SEQ ID NO: 3046) | KKRIKPIVW PSLPDHKKT LEHLCKKPR KNLNVSFNP ESFLDCQIH RVDDIQARD EVEGFLQDT FPQQLEESE KQRLGGDVQ SPNCPSEDV VITPESFGR DSSLITCLAG NVSACDAPI LSSSRSLDC RESGKNGPH VYQDLLLSL GTTNSTLPP PFSLQSGIL TLNPVAGQ PILTSLGSN | IL7R with L5 and L6 elbows with S185C B-ALL mutation only |

TABLE 19-continued

Sequences or Constitutively Expressing IL-7R

| CD8a Leader | CD19 V_L | Linker | CD19 V_H | CD8a Hinge | CD28tm | CD28 Co-stim | CD3z | 2a | Truncated CD34 | Truncated IL-7R ECD | IL-7 TMD | Trucated IL-7R ICD | Description |
|---|---|---|---|---|---|---|---|---|---|---|---|---|---|
| | | | | | | | | | QNKTSSCAE FKKDRGEGL ARVLCGEEQ ADADAGAQV CSLLIAQSE VRPQCLLLV LANRTEISS KLQLMKKHQ SDLKKLG (SEQ ID NO: 3039) | | | QEEAYVTMS SFYQNQ (SEQ ID NO: 3047) | |
| MALPVT ALLLPL ALLLHA ARP (SEQ ID NO: 1) | DIQMTQTT SSLSASLG DRVTISCR ASQDISKY LNWYQQKP DGTVKLLI YHTSRLHS GVPSRFSG SGSGTDYS LTISNLEQ QGNTLPYT FGGGTKLE ITRADAAP TVSIFPPS SN (SEQ ID NO: 3033) | GGGGS_4 (SEQ ID NO: 9) | EVKLQESGP GLVAPSQSL SVTCTVSGV SLPDYGVSW IRQPPRKGL EMLGVIWGS ETTYNSAL KSRLKSRLT IIKDNSKSQ VFLKMNSLQ TDDTAIYYC AKHYYYGGS YAMDYWGQG TSVTVSS (SEQ ID NO: 3034) | TTTPAPRPP TPAPTIASQ PLSLRPEAC RPAAGGAVH TRGLDFACD (SEQ ID NO: 3035) | FWVLVVVG GVLACYSL LVTVAFII FWV (SEQ ID NO: 3036) | RSKRSRLLH SDYMNMTPR RPGPTRKHY QPYAPPRDF AAYRS (SEQ ID NO: 3037) | RVKFSRSA DAPAYKQG QNQLYNEL NLGRREEY DVLDKRRG RDPEMGGK PRRKNPQE GLYNELQK DKMAEAYS EIGMKGER RRGKGHDG LYQGLSTA TKDTYDAL HMQALPPR (SEQ ID NO: 3038) | GSGATNFS LLKQAGDV EENPGP (SEQ ID NO: 3031) | | MPRGWTALC LLSLLPSGF MSLDNNGTA TPELPTQGT FSNVSTNVS YQETTPST LGSTSLHPV SQHGNEATT NITETTVKF TSTSVTSV YGNTNSSVQ SQTSVISTV FTTPANVST PETTLKPSL LPSNVSDLS TTSTSLATS PTKPYTSSS PILSDIKAE IKCSGIREV KLTQGICLE QNKTSSCAE FKKDRGEGL ARVLCGEEQ ADADAGAQV CSLLIAQSE VRPQCLLLV LANRTEISS KLQLMKKHQ SDLKKLG (SEQ ID NO: 3039) | YREGANDFV VTFNTSHLQ KKYVKVLMH DVAYRQEKD ENKWTHVNL SSTKLTLLQ RKLQPAAMY EIKVRSIPD HYFKGFWSE WSPSYYFRT PEINNSSGE MDPI (SEQ ID NO: 3040) | LLTISILSF FSVALIVIL ACVLW (SEQ ID NO: 46) | KKRIKPIVW PSLPDHKKT LEHLCKKPR KNLNVSFNP ESFLDCQIH RVDDIQARD EVEGFLQDT FPQQLEESE KQRLGGDVQ SPNCPSEDV VITPESFGR DSSLTCLAG NVSACDAPI LSSSRSLDC RESGKNGPH VYQDLLLSL GTTNSTLPP PFSLQSGIL TLNPVAQGQ PILTSLGSN QEEAYVTMS SFYQNQ (SEQ ID NO: 3047) | IL7R with L5 and L6 elbows WT |
| MALPVT ALLLPL ALLLHA | DIQMTQTT SSLSASLG DRVTISCR | GGGGS_4 (SEQ ID NO: 9) | EVKLQESGP GLVAPSQSL SVTCTVSGV | TTTPAPRPP TPAPTIASQ PLSLRPEAC | FWVLVVVG GVLACYSL LVTVAFII | RSKRSRLLH SDYMNMTPR RPGPTRKHY | RVKFSRSA DAPAYKQG QNQLYNEL | GSGATNFS LLKQAGDV EENPGP | | MPRGWTALC LLSLLPSGF MSLDNNGTA | VNLSSTKLT LLQRKLQPA AMYEIKVRS | LLTCPTISI LSFFSVALL VILACVLW | KKRIKPIVW PSLPDHKKT LEHLCKKPR | IL7R with L6 elbow only with CPT transmembrane T-ALL |

TABLE 19-continued

Sequences or Constitutively Expressing IL-7R

| CD8a Leader | CD19 V_L | Linker | CD19 V_H | CD8a Hinge | CD28tm | CD28 Co-stim | CD3z | 2a | Truncated CD34 | Truncated IL-7R ECD | IL-7 TMD | Trucated IL-7R ICD | Description |
|---|---|---|---|---|---|---|---|---|---|---|---|---|---|
| MALPVT ALLLPL ALLLHA ARP (SEQ ID NO: 1) | ASQDISKY LNWYQQKP DGTVKLLI YHTSRLHS GVPSRFSG SGSGTDYS LTISNLEQ QGNTLPYT FGGGTKLE ITRADAAP TVSIFPPS SN (SEQ ID NO: 3033) | | EVKLQESGP GLVAPSQSL SVTCTVSGV SLPDYGVSW IRQPPRKGL EWLGVIWGS ETTYYNSAL KSRLKSRLT IIKDNSKSQ VFLKMNSLQ TDDTAIYYC AKHYYYGGS YAMDYWGQG TSVTVSS (SEQ ID NO: 3034) | TTTPAPRPP TPAPTIASQ PLSLRPEAC (SEQ ID NO: 3035) | FWVLVVVG GVLACYSL LVTVAFII FWV (SEQ ID NO: 3036) | RSKRSRLLH SDYMNMTPR RPGPTRKHY QPYAPPRDF AAYRS (SEQ ID NO: 3037) | RVKFSRSA DAPAYKQG QNQLYNEL NLGRREEY DVLDKRRG RDPEMGGK PRRKNPQE GLYNELQK DKMAEAYS EIGMKGER RRGKGHDG LYQGLSTA TKDTYDAL HMQALPPR (SEQ ID NO: 3038) | GSGATNFS LLKQAGDV EENPGP (SEQ ID NO: 3031) | MPRGWTALC LLSLLPSGF MSLDNNGTA TPELPTQGT FSNVSTNVS YQETTTPST LGSTSLHPV SQHGNEATT NITETTVKF TSTSVITSV YGNTNSSVQ SQTSVISTV FTTPANVST PETTLKPSL LPSNVSDLS TTSTSLATS PTKPYTSSS PILSDIKAE | VNLSCTKLT LLQTKLQPA AMYEIKVRS IPDHYFKGF WSEWSPSYY FRTPEINNS SGEMDPI (SEQ ID NO: 3043) | LLTCPTISI LSFFSVALL VILACVLW (SEQ ID NO: 3045) | KKRIKPIVW PSLPDHKKT LEHLCKKPR KNLNVSFNP ESFLDCQIH RVDDIQARD EVEGFLQDT FPQQLEESE KQRLGGDVQ SPNCPSEDV VITPESFGR DSSLTCLAG NVSACDAPI LSSSRSLDC RESGKNGPH VYQDLLLSL GTTNSTLPP PFSLQSGIL | IL7R with L6 elbows with CPT trans- membrane T-ALL mutation insertion and S185C B-ALL mutation |

TABLE 19-continued

Sequences or Constitutively Expressing IL-7R

| CD8a Leader | CD19 V_L | Linker | CD19 V_H | CD8a Hinge | CD28tm | CD28 Co-stim | CD3z | 2a | Truncated CD34 | Truncated IL-7R ECD | IL-7 TMD | Trucated IL-7R ICD | Description |
|---|---|---|---|---|---|---|---|---|---|---|---|---|---|
| | | | | | | | | | IKCSGIREV KLTQGICLE QNKTSSCAE FKKDRGEGL ARVLCGEEQ ADADAGAQV CSLLIAQSE VRPQCLLLV LANRTEISS KLQLMKKHQ SDLKKLG (SEQ ID NO: 3039) | | | TLNPVAQGQ PILTSLGSN QEEAYVTMS SFYQNQ (SEQ ID NO: 3047) | |
| MALPVT ALLLPL ALLLHA ARP (SEQ ID NO: 1) | DIQMTQT SSLSASLG DRVTISCR ASQDISKY LNWYQQKP DGTVKLLI YHTSRLHS GVPSRFSG SGSGTDYS LTISNLEQ QGNTLPYT FGGGTKLE ITRADAAP TVSIFPPS SN (SEQ ID NO: 3033) | GGGGS_4 (SEQ ID NO: 9) | EVKLQESGP GLVAPSQSL SVTCTVSGV SLPDYGVSW IRQPPRKGL EMLGVIWGS ETTYYNSAL KSRLKSRLT IIKDNSKSQ VFLKMNSLQ TDDTAIYYC AKHYYYGGS YAMDYWGQG TSVTVSS (SEQ ID NO: 3034) | TTTPAPRPP TPAPTIASQ PLSLRPEAC RPAAGGAVH TRGLDFACD (SEQ ID NO: 3035) | FWLVVVG GVLACYSL LVTVAFII FWV (SEQ ID NO: 3036) | RSKRSRLLH SDYMNMTPR RPGPTRKHY QPYAPPRDF AAYRS (SEQ ID NO: 3037) | RVKFSRSA DAPAYKQG QNQLYNEL NLGRREEY DVLDKRRG RDPEMGGK PRRKNPQE GLYNELQK DKMAEAYS EIGMKGER RRGKGHDG LYQGLSTA TKDTYDAL HMQALPPR (SEQ ID NO: 3038) | GSGATNFS LLKQAGDV EENPGP (SEQ ID NO: 3031) | MPRGWTALC LLSLLPSGF MSLDNNGTA TPELPTQGT FSNVSTNVS YQETTTPST LGSTSLHPV SQHGNEATT NITETTVKF TSTSVITSV YGNTNSSVQ SQTSVISTV FTTPANVST PETTLKPSL LPSNVSDLS TTSTSLATS PTKPYTSSS PILSDIKAE IKCSGIREV KLTQGICLE QNKTSSCAE FKKDRGEGL ARVLCGEEQ ADADAGAQV CSLLIAQSE VRPQCLLLV LANRTEISS KLQLMKKHQ SDLKKLG (SEQ ID NO: 3039) | VNLSCTKLT LLQTKLQPA AMYEIKVRS IPDHYFKGF WSEWSPSYY FRTPEINNS SGEMDPI (SEQ ID NO: 3043) | LLTISILSF PSVALLVIL ACVLW (SEQ ID NO: 3046) | KKRIKPIVW PSLPDHKKT LEHLCKKPR KNLNVSFNP ESFLDCQIH RVDDIQARD EVEGFLQDT FPQQLEESE KQRLGGDVQ SPNCPSEDV VITPESFGR DSSLTCLAG NVSACDAPI LSSSRSLDC RESGKNGPH VYQDLLLSL GTTNSTLPP PFSLQSGIL TLNPVAQGQ PILTSLGSN QEEAYVTMS SFYQNQ (SEQ ID NO: 3047) | IL7R with L6 elbows with S185C B-ALL mutation only |

TABLE 19-continued

Sequences or Constitutively Expressing IL-7R

| CD8a Leader | CD19 V_L | Linker | CD19 V_H | CD8a Hinge | CD28tm | CD28 Co-stim | CD3z | 2a | Truncated CD34 | Truncated IL-7R ECD | IL-7 TMD | Trucated IL-7R ICD | Description |
|---|---|---|---|---|---|---|---|---|---|---|---|---|---|
| MALPVT ALLLPL ALLLHA ARP (SEQ ID NO: 1) | DIQMTQT SSLSASLG DRVTISCR ASQDISKY LNWYQQKP DGTVKLLI YHTSRLHS GVPSRFSG SGSGTDYS LTISNLEQ QGNTLPYT FGGGTKLE ITRADAAP TVSIFPPS SN (SEQ ID NO: 3033) | GGGGS₄ (SEQ ID NO: 9) | EVKLQESGP GLVAPSQSL SVTCTVSGV SLPDYGVSW IRQPPRKGL EWLGVIWGS ETTYYNSAL KSRLKSRLT IIKDNSKSQ VFLKMNSLQ TDDTAIYYC AKHYYYGGS YAMDYWGQG TSVTVSS (SEQ ID NO: 3034) | TTTPAPRPP TPAPTIASQ PLSLRPEAC RPAAGGAVH TRGLDFACD (SEQ ID NO: 3035) | FWVLVVVG GVLACYSL LVTVAFII FWV (SEQ ID NO: 3036) | RSKRSRLLH SDYMNMTPR RPGPTRKHY QPYAPPRDF AAYRS (SEQ ID NO: 3037) | RVKFSRSA DAPAYKQG QNQLYNEL NLGRREEY DVLDKRRG RDPEMGGK PRRKNPQE GLYNELQK DKMAEAYS EIGMKGER RRGKGHDG LYQGLSTA TKDTYDAL HMQALPPR (SEQ ID NO: 3038) | GSGATNFS LLKQAGDV EENPGP (SEQ ID NO: 3031) | MPRGWTALC LLSLLPSGF MSLDNNGTA TPELPTQGT FSNVSTNVS YQETTTPST LGSTSLHPV SQHGNEATT NITETTVKF TSTSVITSV YGNTNSSVQ SQTSVISTV FTTPANVST PETTLKPSL LPSNVSDLS TTSTSLATS PTKPYTSSS PILSDIKAE IKCSGIREV KLTQGICLE QNKTSSCAE FKKDRGEGL ARVLCGEEQ ADADAGAQV CSLLIAQSE VRPQCLLLV LANRTEISS KLQLMKKHQ SDLKKLG (SEQ ID NO: 3039) | VNLSSTKLT LLQRKLQPA AMYEIKVRS IPDHYFKGF WSEWSPSYY FRTPEINNS SGEMDPI (SEQ ID NO: 3042) | LLTISILSF FSVALLVIL ACVLW (SEQ ID NO: 3046) | KKRIKPIVW PSLPDHKKT LEHLCKKPR KNLNVSFNP ESFLDCQIH RVDDIQARD EVEGFLQDT FPQQLEESE KQRLGGDVQ SPNCPSEDV VITPESFGR DSSLTCLAG NVSACDAPI LSSSRSLDC RESGKNGPH VYQDLLLSL GTTNSTLPP PFSLQSGIL TLNPVAQGQ PILTSLGSN QEEAYVTMS SFYQNQ (SEQ ID NO: 3047) | Trucated IL-7R with L6 elbows WT |
| MALPVT ALLLPL ALLLHA ARP (SEQ ID NO: 1) | DIQMTQT SSLSASLG DRVTISCR ASQDISKY LNWYQQKP DGTVKLLI YHTSRLHS GVPSRFSG SGSGTDYS LTISNLEQ | GGGGS₄ (SEQ ID NO: 9) | EVKLQESGP GLVAPSQSL SVTCTVSGV SLPDYGVSW IRQPPRKGL EWLGVIWGS ETTYYNSAL KSRLKSRLT IIKDNSKSQ VFLKMNSLQ | TTTPAPRPP TPAPTIASQ PLSLRPEAC RPAAGGAVH TRGLDFACD (SEQ ID NO: 3035) | FWVLVVVG GVLACYSL LVTVAFII FWV (SEQ ID NO: 3036) | RSKRSRLLH SDYMNMTPR RPGPTRKHY QPYAPPRDF AAYRS (SEQ ID NO: 3037) | RVKFSRSA DAPAYKQG QNQLYNEL NLGRREEY DVLDKRRG RDPEMGGK PRRKNPQE GLYNELQK DKMAEAYS EIGMKGER | GSGATNFS LLKQAGDV EENPGP (SEQ ID NO: 3031) | MPRGWTALC LLSLLPSGF MSLDNNGTA TPELPTQGT FSNVSTNVS YQETTTPST LGSTSLHPV SQHGNEATT NITETTVKF TSTSVITSV | PEINNSSGE MDPI (SEQ ID NO: 3044) | LLTCPTISI LSFFSVALL VILACVLW (SEQ ID NO: 3045) | KKRIKPIVW PSLPDHKKT LEHLCKKPR KNLNVSFNP ESFLDCQIH RVDDIQARD EVEGFLQDT FPQQLEESE KQRLGGDVQ SPNCPSEDV | Trucated IL-7R with CPT T-ALL mutation. Lacking elbows and WSEWS motif (sugar bridge) (SEQ ID NO: 3070) |

TABLE 19-continued

Sequences or Constitutively Expressing IL-7R

| CD8a Leader | CD19 V_L | Linker | CD19 V_H | CD8a Hinge | CD28tm | CD28 Co-stim | CD3z | 2a | Truncated CD34 | Truncated IL-7R ECD | IL-7 TMD | Trucated IL-7R ICD | Description |
|---|---|---|---|---|---|---|---|---|---|---|---|---|---|
| | QGNTLPYT FGGGTKLE ITRADAAP TVSIFPPS SN (SEQ ID NO: 3033) | | TDDTAIYYC AKHYYYGGS YAMDYWGQG TSVTVSS (SEQ ID NO: 3034) | | | | RRGKGHDG LYQGLSTA TKDTYDAL HMQALPPR (SEQ ID NO: 3038) | | YGNTNSSVQ SQTSVLSTV FTTPANVST PETTLKPSL LPSNVSDLS TTSTSLATS PTKPYTSSS PILSDIKAE IKCSGIREV KLTQGICLE QNKTSSCAE FKKDRGEGL ARVLCGEEQ ADADAGAQV CSLLLAQSE VRPQCLLLV LANRTEISS KLQLMKKHQ SDLKKLG (SEQ ID NO: 3039) | | VITPESFGR DSSLTCLAG NVSACDAPI LSSSRSLDC RESGKNGPH VYQDLLLSL GTTNSTLPP PFSLQSGIL TLNPVAQGQ PILTSLGSN QEEAYVTMS SFYQNQ (SEQ ID NO: 3047) | |

Protocol-Nucleofection Using Nucleofector 4D:

Perform nucleofection protocol as described above (Example 6), using 20 μg of each gRNA (gGM-CSF and gCD38) to each tube of 15 μg Cas9 mRNA.

Step 4: Assessment of CRISPR Activity and Td Efficiency (Day 10)

Take $5\times10^5$ cells from each sample and analyze by flow cytometry. Wash samples with RB. Add 5 μl of CD3 APC and 2 μl of anti-FAB BV421 (detects CAR transduction). Wash. Perform Flow cytometry. Cells should be CD38-negative, CD34-positive and FAB+. Harvest T cells (Day 11).

Purification of CAR-T cells. TCR negative cells can be purified using TCRa/b negative selection to remove TCR positive cells.

Step 5: Assessment of CAR-T Activity In Vivo

Inject $5\times10^6$ CAR-T per mouse I.V. Assess serum cytokine levels (Day+1, +2, +3 +4, +5, +10, +15). Measure serum cytokine levels using Luminex multiplex cytokine profiling assay to check for elevations in CRS related cytokines. Perform a 4-hr chromium release assay against targets cells (Raji) to assess in vitro activity (Day 11). Monitor efficacy of tumor clearance using flow cytometry of blood to detect hCD45, CD19+ cells.

A modified gRNA protocol for T cell CRISPR and CAR-T transduction of UCART19 is provided below.

Day 0-T Cell Activation:

Purify T cells from a leukapheresis chamber using a Miltenyi human PanT isolation kit. Resuspend in media. Count cells. Determine the number of human T cell activation CD3/CD28 beads required to obtain a 3:1 bead: cell ratio. Wash beads 2× with T cell media. Dilute cells at 1.256 cells/mL in hXcyte media. Add human T cell activation CD3/CD28 beads T cells may then be transduced with one or more CARs targeted to (i.e., that recognizes) one or more targets, for example with a lentivirus containing a CAR construct. Any other suitable method of transduction may be used.

Day 2: $4\times10^6$ cells per reaction are used. EO-115-100 μl transfection volume is programmed, and the entire supplement added to the Nucleofector™ Solution P3. Cell culture plates are prepared by filling appropriate number of wells with desired volume of recommended culture media (2 ml in 6 well plate) and pre-incubating/equilibrating plates in a humidified 37° C./5% $CO_2$ incubator. Beads are magnetically removed (twice to ensure complete removal), then cells counted and cell density determined. The required number of cells are centrifuged at 90×g for 10 minutes at room temperature, the supernatant removed completely. Cells are then resuspended in PBS (1 ml) and transferred to a microcentrifuge tube, and the required number of cells centrifuged at 90×g for 10 minutes at room temperature. The supernatant is removed completely, and the cell pellet resuspended carefully in complete room temperature 4D Nucleofector™ Solution P3, $4\times10^6$ per 100 μl). Twenty μg of gRNA (gGM-CSF and gTRAC) are added to each tube of 15 μg Cas9 mRNA. Then 100 μl of cells is added to each tube of Cas9/gRNA, gently mixed and everything transferred into the Nucleocuvette™. The cuvette is gently tapped to remove bubbles. Electroporation is carried out using program (Human T cell stim EO-115). After run completion, the Nucleocuvette™ is carefully removed from the vessel from the retainer using a specialized tool. Cells are resuspended with pre-warmed medium. The media is then taken up from destination well, added to cuvette, and gently pipetted up and down two to three times. This is then transferred to well. This procedure is repeated with media from same well and incubated at 37° C.

Day 5: Assessment of CRISPR activity and Td efficiency. Samples of cells may then be assessed for transduction efficiency by taking a $5\times10^5$ cells from each sample and analyzing by flow cytometry. Samples are fix permeablised and anlaysed by FACS for CD3, CD34 and intracellular GM-CSF.

Assessment of Genetic Deletion.

To assess genetic deletion of GM-CSF and TRAC, $5\times10^5$ cells are harvested from each sample and their DNA extracted. Gene editing efficiency is assessed using target sequencing of the target loci using TIDE-analysis or deep sequencing.

Day 11

Bleed mice and measure tumor burden.

CD3 deplete T cells and inject into mice.

Inject mice with $5\times10^6$ CAR+ T cells/mouse.

Mouse groups are provided in Table 20 below:

TABLE 20

| Sample ID | Gene editing | Tumor | T cell source | CAR-T | CAR-T |
|---|---|---|---|---|---|
| A | — | $2\times10^6$/mouse | — | — | — |
| B | TRAC | $2\times10^6$/mouse | PanT | CAR19 + CD34 | $5\times10^6$/mouse |
| C | TRAC + GM-CSF | $2\times10^6$/mouse | PanT | CAR 19 CD34 | $5\times10^6$/mouse |
| D | TRAC | $2\times10^6$/mouse | PanT | CAR 19 + IL7r + CD34 | $5\times10^6$/mouse |
| E | TRAC + GM-CSF | $2\times10^6$/mouse | PanT | CAR 19 + IL7r + CD34 | $5\times10^6$/mouse |

Attune - CAR-T in vivo panel - CRS

| Detector | Bandpass (nm) | Antigen | Colour | Product # | Titer 50 μl blood or 500K in 100 μl |
|---|---|---|---|---|---|
| BL1 | 530/30 | | | | |
| BL2 | 695/40 | 7aad | 7AAd | | 1 ul |
| RL1 | 670/14 | CD19 | APC | BD555415 | 2 ul |
| RL2 | 720/30 | | | | |
| RL3 | 780/60 | CD4 | APC-H7 | BD560158 | 1 ul |
| VL1 | 450/40 | mCD45 | BV421 | BD563890 | 1 ul |
| VL2 | 525/50 | CD8 | BV510 | BD563256 | 4 ul |
| VL3 | 610/20 | | | | |
| VL4 | 660/20 | CD3 | BV650 | BD563852 | 2 ul |
| VL5 | 710/50 | | | | |
| VL6 | 780/60 | hCD45 | BV785 | BD563716 | 1 ul |
| YL1 | 585/16 | CD34 | PE | BD Pool PE | 2 ul |
| YL2 | 620/15 | | | | |
| YL3 | 780/60 | | | | |

Cytokine analysis and assessment of CRS is assed using Millipore luminex multiplex cytokine analysis.

Sequences for preparation of a vector as described herein include, but are not limited to, the following:

```
Left ITR of vector for insertion of CD34 into GM-CSF locus
                                                      SEQ ID NO: 3048
CCTGCAGGCAGCTGCGCGCTCGCTCGCTCACTGAGGCCGCCCGGGCGTCGGGCGACCTTTGGTCGCCCGGCCTCAGTGAGCGAGCGAGC

GCGCAGAGAGGGAGTGGCCAACTCCATCACTAGGGGTTCCT

Left Homology Arm of vector for insertion of CD34 into GM-CSF locus
                                                      SEQ ID NO: 3049
cctgagatggatgcagccacagccctggagccagcctgaagctcctggtgtcttctgggggctacatataggagtgtagtccgaacctc agaggggcaaacctgctctgcagagggaatcaaggttcacataaccagagaggggagtcactcaggaaggtggctccagagccaagagt cagactctgggtcccgacttgacccagccacaccccctctgaagcttgctgagagtggctgcagtctcgctgctggatgtgcacatggt ggtcattccctctgctcacaggggcaggggtccccccttactggactgaggttgcccctgctccaggtcctgggtgggagcccatgtg aactgtcagtggggcaggtctgtgagagctcccctcacactcaagtctctcacagtggccagagaagaggaaggctggagtcagaatga ggcaccagggcgggcatagcctgcccaaaggccctgggattacaggcaggatggggagccctatctaagtgtctcccacgcccaccc cagccattccaggccaggaagtccaaactgtgcccctcagagggaggggcagcctcaggcccattcagactgcccagggagggctgga gagccctcaggaaggcgggtgggtgggctgtcggttcttggaaaggttcattaatgaaaaccccaagcctgaccacctagggaaaagg ctcaccgttcccatgtgtggctgataaggggccaggagattccacagttcaggtagttccccgcctccctggcatttgtggtcaccat taatcatttcctctgtgtatttaagagctcttttgccagtgagcccaGTACACAGAGAGAAAGGCTAAAGTTCTCTGGAGGATGTGGCT GCAGAGCCTGCTGCTCTTGGGCACTGTGGCCTGCAGCATCTCTGCACCCGCCCGCTCGCCCAGCCCCAGCACGCAGCCCTGGGAGCATG

TGAATGCCATCCAGGAGGCCC

EFS promotor of vector for insertion of CD34 into GM-CSF locus
                                                      SEQ ID NO: 3050
GGCTCCGGTGCCCGTCAGTGGGCAGAGCGCACATCGCCCACAGTCCCCGAGAAGTTGGGGGGAGGGGTCGGCAATTGATCCGGTGCCTA GAGAAGGTGGCGCGGGGTAAACTGGGAAAGTGATGTCGTGTACTGGCTCCGCCTTTTTCCCGAGGGTGGGGGAGAACCGTATATAAGTG

CAGTAGTCGCCGTGAACGTTCTTTTTCGCAACGGGTTTGCCGCCAGAACACAGG trCD34 of vector for insertion of CD34 into GM-CSF locus
                                                      SEQ ID NO: 3051
atgccgcggggctggaccgcgctttgcttgctgagtttgctgcctttctgggttcatgagtcttgacaacaacggtactgctaccccaga gttacctacccagggaacattttcaaatgtttctacaaatgtatcctaccaagaaactacaacacctagtacccttggaagtaccagcc tgcacctgtgtctcaacatggcaatgaggccacaacaaacatcacagaaacgacagtcaaattcacatctacctctgtgataacctca gtttatggaaacacaaactcttctgtccagtcacagacctctgtaatcagcacagtgttcaccaccccagccaacgtttcaactccaga gacaaccttgaagcctagcctgtcacctggaaatgtttcagaccctttcaaccactagcactagccttgcaacatctcccactaaaccct atacatcatcttctcctatcctaagtgacatcaaggcagaaatcaaatgttcaggcatcagagaagtgaaattgactcagggcatctgc ctggagcaaaataagacctccagctgtgcggagtttaagaaggacaggggagagggcctggcccgagtgctgtgtggggaggagcaggc tgatgctgatgctggggcccaggtatgctccctgctccttgcccagtctgaggtgaggcctcagtgtctactgctggtcttggccaaca gaacagaaatttccagcaaactccaacttatgaaaaagcaccaatctgacctgaaaaagctggggatcctagatttcactgagcaagat gttgcaagccaccagagctattcccaaaagaccctgattgcactggtcacctcgggagccctgctggctgtcttgggcatcactggcta tttcctgatgaatcgccgcagctggagccccatttaa hGMB Poly A of vector for insertion of CD34 into GM-CSF locus
                                                      SEQ ID NO: 3052
ACGGGTGGCATCCCTGTGACCCCTCCCCAGTGCCTCTCCTGGCCCTGGAAGTTGCCACTCCAGTGCCCACCAGCCTTGTCCTAATAAAA TTAAGTTGCATCATTTTGTCTGACTAGGTGTCCTTCTATAATATTATGGGGTGGAGGGGGGTGGTATGGAGCAAGGGGCAAGTTGGGAA GACAACCTGTAGGGCCTGCGGGGTCTATTGGGAACCAAGCTGGAGTGCAGTGGCACAATCTTGGCTCACTGCAATCTCCGCCTCCTGGG TTCAAGCGATTCTCCTGCCTCAGCCTCCCGAGTTGTTGGGATTCCAGGCATGCATGACCAGGCTCAGCTAATTTTTGTTTTTTGGTAG AGACGGGGTTTCACCATATTGGCCAGGCTGGTCTCCAACTCCTAATCTCAGGTGATCTACCCACCTTGGCCTCCCAAATTGCTGGGATT

ACAGGCGTGAACCACTGCTCCCTTCCCTGTCCTTCTGATTTTGTAGGTAACCACGTGCGGACCGA
```

RHA of vector for insertion of CD34 into GM-CSF locus

SEQ ID NO: 3053

CGTCTCCTGAACCTGAGTAGAGACACTGCTGCTGAGATGgtaagtgagagaatgtgggcctgtgcctaggccacccagctggccctga ctggccacgcctgtcagcttgataacatgacattttccttttctacagAATGAAACAGTAGAAGTCATCTCAGAAATGTTTGACCTCCA Ggtaagatgcttctctctgacatagctttccagaagcccctgccctggggtggaggtggggactccattttagatggcaccacacaggg ttgtccactttctctccagtcagctggctgcaggaggaggggtagcaactgggtgctcaagaggctgctggccgtgccctatggcag tcacatgagctcctttatcagctgagcggccatgggcagacctagcattcaatggccaggagtcaccaggggacaggtggtaaagtggg ggtcacttcatgagacaggagctgtgggtttggggcgctcactgtgccccgagaccaagtcctgttgagacagtgctgactacagagag gcacagagggtttcaggaacaacccttgcccacccagcaggtccaggtgaggccccacccccctctccctgaatgatgggtgagagt cacctccttccctaaggctgggctcctctccaggtgccgctgagggtggcctgggcggggcagtgagaagggcaggttcgtgcctgcca tggacagggcagggtctatgactggacccagcctgtgcccctcccaagccctactcctgggggctgggggcagcagcaaaaaggagtgg tggagagttcttgtaccactgtgggcacttggccactgctcaccgacgaacgacattttccacagGAGCCGACCTGCCTACAGACCCGC CTGGAGCTGTACAAGCAGGGCCTGCGGGGCAGCCTCACCAAGCTCAAGGGCCCCTTGACCATGATGGCCAGCCACTACAAGCAGCACTG CCCTCCAACCCCGgtgagtgc Right ITR of vector for insertion of CD34 into GM-CSF locus

SEQ ID NO: 51

AGGAACCCCTAGTGATGGAGTTGGCCACTCCCTCTCTGCGCGCTCGCTCGCTCACTGAGGCCGGGCGACCAAAGGTCGCCCGACGCCCG

GGCTTTGCCCGGGCGGCCTCAGTGAGCGAGCGAGCGCGCAGCTGCCTGCAGG

Complete sequence of vector for insertion of CD34 into GM-CSF locus

SEQ ID NO: 3054

CCTGCAGGCAGCTGCGCGCTCGCTCGCTCACTGAGGCCGCCCGGGCGTCGGGCGACCTTTGGTCGCCCGGCCTCAGTGAGCGAGCGAGC

GCGCAGAGAGGGAGTGGCCAACTCCATCACTAGGGGTTCCTcctgagatggatgcagccacagccctggagccagcctgaagctcctgg tgtcttctgggggctacatataggagtgtagtccgaacctcagaggggcaaacctgctctgcagagggaatcaaggttcacataaccag agaggggagtcactcaggaaggtggctccagagccaagagtcagactctgggtcccgacttgacccagccacacccctctgaagcttg ctgagagtggctgcagtctcgctgctggatgtgcacatggtggtcattccctctgctcacaggggcagggtcccccttactggactg aggttgcccctgctccaggtcctgggtgggagcccatgtgaactgtcagtgggcaggtctgtgagagctcccctcacactcaagtct ctcacagtggccagagaagaggaaggctggagtcagaatgaggcaccagggcgggcatagcctgcccaaaggcccctgggattacaggc aggatggggagccctatctaagtgtctcccacgccccaccccagccattccaggccaggaagtccaaactgtgcccctcagagggaggg ggcagcctcaggcccattcagactgcccagggagggctggagagccctcaggaaggcgggtgggtgggctgtcggttcttggaaaggtt cattaatgaaaaccccaagcctgaccacctagggaaaaggctcaccgttcccatgtgtggctgataagggccaggagattccacagtt caggtagttcccccgcctccctggcattttgtggtcaccattaatcatttcctctgtgtatttaagagctcttttgccagtgagcccaG TACACAGAGAGAAAGGCTAAAGTTCTCTGGAGGATGTGGCTGCAGAGCCTGCTGCTCTTGGGCACTGTGGCCTGCAGCATCTCTGCACC CGCCCGCTCGCCCAGCCCCAGCACGCAGCCCTGGGAGCATGTGAATGCCATCCAGGAGGCCCGGCTCCGGTGCCCGTCAGTGGGCAGAG CGCACATCGCCCACAGTCCCCGAGAAGTTGGGGGGAGGGGTCGGCAATTGATCCGGTGCCTAGAGAAGGTGGCGCGGGGTAAACTGGGA AAGTGATGTCGTGTACTGGCTCCGCCTTTTTCCCGAGGGTGGGGGAGAACCGTATATAAGTGCAGTAGTCGCCGTGAACGTTCTTTTTC GCAACGGGTTTGCCGCCAGAACACAGGatgccgcggggctggaccgcgctttgcttgctgagtttgctgccttctgggttcatgagtct tgacaacaacggtactgctaccccagagttacctacccagggaacattttcaaatgtttctacaaatgtatcctaccaagaaactacaa cacctagtaccccttggaagtaccagcctgcaccctgtgtctcaacatggcaatgaggccacaacaaacatcacagaaacgacagtcaaa ttcacatctacctctgtgataacctcagtttatgaaacacaaactcttctgtccagtcacagacctctgtaatcagcacagtgttcac caccccagccaacgtttcaactccagagacaaccttgaagcctagcctgtcacctggaaatgtttcagacctttcaaccactagcacta gccttgcaacatctcccactaaaccctatacatcatcttctcctatcctaagtgacatcaaggcagaaatcaaatgttcaggcatcaga gaagtgaaattgactcagggcatctgcctggagcaaaataagacctccagctgtgcggagtttaagaaggacaggggagagggcctggc ccgagtgctgtgtgggaggagcaggctgatgctgatgctggggcccaggtatgctccctgctccttgcccagtctgaggtgaggcctc agtgtctactgctggtcttggccaacagaacagaaatttccagcaaactccaacttatgaaaaagcaccaatctgacctgaaaaagctg -continued

```
gggatcctagatttcactgagcaagatgttgcaagccaccagagctattcccaaaagaccctgattgcactggtcacctcgggagccct gctggctgtcttgggcatcactggctattcctgatgaatcgccgcagctggagccccatttaaACGGGTGGCATCCCTGTGACCCCTC CCCAGTGCCTCTCCTGGCCCTGGAAGTTGCCACTCCAGTGCCCACCAGCCTTGTCCTAATAAAATTAAGTTGCATCATTTTGTCTGACT AGGTGTCCTTCTATAATATTATGGGGTGGAGGGGGGTGGTATGGAGCAAGGGGCAAGTTGGGAAGACAACCTGTAGGGCCTGCGGGGTC TATTGGGAACCAAGCTGGAGTGCAGTGGCACAATCTTGGCTCACTGCAATCTCCGCCTCCTGGGTTCAAGCGATTCTCCTGCCTCAGCC TCCCGAGTTGTTGGGATTCCAGGCATGCATGACCAGGCTCAGCTAATTTTTGTTTTTTTGGTAGAGACGGGGTTTCACCATATTGGCCA GGCTGGTCTCCAACTCCTAATCTCAGGTGATCTACCCACCTTGGCCTCCCAAATTGCTGGGATTACAGGCGTGAACCACTGCTCCCTTC CCTGTCCTTCTGATTTTGTAGGTAACCACGTGCGGACCGACGTCTCCTGAACCTGAGTAGAGACACTGCTGCTGAGATGgtaagtgaga gaatgtgggcctgtgcctaggccacccagctggcccctgactggccacgcctgtcagcttgataacatgacattttccttttctacagA ATGAAACAGTAGAAGTCATCTCAGAAATGTTTGACCTCCAGgtaagatgcttctctctgacatagctttccagaagcccctgccctggg gtggaggtggggactccatttttagatggcaccacacaggggttgtccactttctctccagtcagctggctgcaggaggagggggtagcaa ctgggtgctcaagaggctgctggccgtgcccctatggcagtcacatgagctcctttatcagctgagcggccatgggcagacctagcatt caatggccaggagtcaccaggggacaggtggtaaagtgggggtcacttcatgagacaggagctgtgggtttggggcgctcactgtgccc cgagaccaagtcctgttgagacagtgctgactacagagaggcacagaggggtttcaggaacaaccttgcccacccagcaggtccaggt gaggccccaccccctctccctgaatgatggggtgagagtcacctccttccctaaggctgggctcctctccaggtgccgctgagggtgg cctgggcggggcagtgagaagggcaggttcgtgcctgccatggacagggcagggtctatgactggacccagcctgtgcccctcccaagc cctactcctgggggctgggggcagcagcaaaaaggagtggtggagagttcttgtaccactgtgggcacttggccactgctcaccgacga acgacattttccacagGAGCCGACCTGCCTACAGACCCGCCTGGAGCTGTACAAGCAGGGCCTGCGGGGCAGCCTCACCAAGCTCAAGG GCCCCTTGACCATGATGGCCAGCCACTACAAGCAGCACTGCCCTCCAACCCCGgtgagtgcAGGAACCCCTAGTGATGGAGTTGGCCAC TCCCTCTCTGCGCGCTCGCTCGCTCACTGAGGCCGGGCGACCAAAGGTCGCCCGACGCCCGGGCTTTGCCCGGGCGGCCTCAGTGAGCG

AGCGAGCGCGCAGCTGCCTGCAGG
``` left ITR of donor construct for inserting GFP into CD3ε locus

SEQ ID NO: 3048

```
CCTGCAGGCAGCTGCGCGCTCGCTCGCTCACTGAGGCCGCCCGGGCGTCGGGCGACCTTTGGTCGCCCGGCCTCAGTGAGCGAGCGAGC

GCGCAGAGAGGGAGTGGCCAACTCCATCACTAGGGGTTCCT
``` cloning remnants of donor construct for inserting GFP into CD3ε locus

SEQ ID NO: 3055

```
GCGGCCGCATCGATTGaattc
```

CD3 L homology arm of donor construct for inserting GFP into CD3ε locus

SEQ ID NO: 3056

```
AGGTAAGTCCACGAATCAGTGATTCAGTGGTGTGGAGAGCTTTATTTCTGAGAAGGCCAGTAGCGCTCCCTTCTGACAAGCAAATCTAA

GACCTGGATGACAGATGACTTCCTGCATTTGGTTGGTTCTTTTGTCATTCATATCTATCTGTAATACAGTTCTGGCTAATTTAAGAGGA

TAAGCTTGAAGACCTCTGGAATTTTTCGGCTTTAGGACTTTAAGGCTTTCTGAGCTTCAGTAGATCTAGATCTAGGAGCTCATGCTGGT

ATATTCTGAATCCGATGTATCTGAGTTACATCTATGAGCTACTTAATAAATATATCTATGAGCTAAATCTCATAGGCTAAGCATGAACC

TCACCTCCAAGACTCGGGGTTCCTAAATGGATGAGACCCTCTTTGGGAAGTCTTGTGGGCAGTGTCTAATTCCACTAGAAAAGTTTTAC

CTACAATTTAAACTTAAACCATGATATTTTCTTACTGCTGTTTCCTTTTTTCATTTTCAGGTGGTATTACACAGACACGTGAGTTTATT

GGTCTTTTATTTATGCCCTGTCTGAGGATGCAGATTGGTGGGTAGATGAGAAGGAACTGATTGAGAGAGATTAACCCCAAGAACTGATA

TCTTCCCAGCATTGCATTCTCAACTCCATTTTAGAAAGGTTCCAAATAGGGACTTCTGTGGGTTTTTCTTTACATCCATCTTACCCTTC

CCAAGTCCCCATGTCCCTGCGTAAACCCTAAAGCCACCTCTCAAAAGGTTCTCTAGTTCCCTTCAAGGTTCTCTAGTTCCCTTCATTCC

ACATATCTCCTCTTCCACACCCTCTAGCCAGTAGAGCTCCCTTCTGACAAGCAAGTCTAAGATCTAGATGACAGATGACTTCCTGCATT

TGGGTGGTTCTTTTGTCACTAATTTGCCTTTTCTAAAATTGTCCTGGTTTCTTCTGCCAATTTCCCTTCTTTCTCCCCAGCATATAAAG

TCTCCATCTCTGGAACCACA
```

CAR7 of donor construct for inserting GFP into CD3ε locus

SEQ ID NO: 3057 atggccttaccagtgaccgccttgctcctgccgctggccttgctgctccacgccgccaggccggatatccagatgacacagactacatc ctccctgtctgcctctctgggagacagagtcaccatcagttgcagtgcaagtcagggcattagcaattatttaaactggtatcagcaga aaccagatggaactgttaaactcctgatctattacacatcaagtttacactcaggagtcccatcaaggttcagtggcagtgggtctggg acagattattctctcaccatcagcaacctggaacctgaagatattgccacttattattgtcagcagtatagcaagcttccgtacacgtt cggaggggggaccaagctggaaataaaaacgtggtggtggtggttctggtggtggtggttctggcggcggcggctccggtggtggtggat ccgaggtgcaactggtggagtctgggggaggcttagtgaagcctggggggtccctgaaactctcctgtgcagcctctggactcactttc agtagctatgccatgtcttgggttcgccagactccagagaagaggctggagtgggtcgcatccattagtagtggtggtttcacctacta tccagacagtgtgaagggccgattcaccatctccagagataatgccaggaacatcctgtatctgcaaatgagcagtctgaggtctgagg acacggccatgtattactgtgcaagagacgaggtacgggggtacctcgatgtctggggcgcagggaccacggtcaccgtttccctagg GCTAGCaccacgacgccagcgccgcgaccaccaacaccggcgcccaccatcgcgtcgcagcccctgtccctgcgcccagaggcgtgccg gccagcggcgggggcgcagtgcacacgaggggctggacttcgcctgtgatttttgggtgctggtggtggttggtggagtcctggctt gctatagcttgctagtaacagtggcctttattattttctgggtgaggagtaagaggagcaggctcctgcacagtgactacatgaacatg actcccgcgccccgggcccaccogcaagcattaccagccctatgcccaccacgcgacttcgcagcctatcgctccagagtgaagtt cagcaggagcgcagacgcccccgcgtacaagcagggccagaaccagctctataacgagctcaatctaggacgaagagaggagtacgatg ttttggacaagagacgtggccgggaccctgagatgggggaaagccgagaaggaagaaccctcaggaaggcctgtacaatgaactgcag aaagataagatggcggaggcctacagtgagattgggatgaaaggcgagcgccggaggggcaaggggcacgatggcctttaccagggtct cagtacagccaccaaggacacctacgacgcccttcacatgcaggccctgccccctcgcCGGACCGATggaagcggagctactaacttca gcctgctgaagcaggctggagacgtggaggagaaccctggacctgtttctgaagccatgccgcggggctggaccgcgctttgcttgctg agtttgctgccttctgggttcatgagtcttgacaacaacggtactgctaccccagagttacctacccagggaacattttcaaatgtttc tacaaatgtatcctaccaagaaactacaacacctagtaccttggaagtaccagcctgcaccctgtgtctcaacatggcaatgaggcca caacaaacatcacagaaacgacagtcaaattcacatctacctctgtgataacctcagtttatggaaacacaaactcttctgtccagtca cagacctctgtaatcagcacagtgttcaccaccccagccaacgtttcaactccagagacaaccttgaagcctagcctgtcacctggaaa tgtttcagacctttcaaccactagcactagccttgcaacatctcccactaaaccctatacatcatcttctcctatcctaagtgacatca aggcagaaatcaaatgttcaggcatcagagaagtgaaattgactcagggcatctgcctggagcaaaataagacctccagctgtgcggag tttaagaaggacaggggagagggcctggcccgagtgctgtgtggggaggagcaggctgatgctgatgctggggcccaggtatgctccct gctccttgcccagtctgaggtgaggcctcagtgtctactgctggtcttggccaacagaacagaaatttccagcaaactccaacttatga aaaagcaccaatctgacctgaaaaagctggggatcctagatttcactgagcaagatgttgcaagccaccagagctattcccaaaagacc ctgattgcactggtcacctcgggagccctgctggctgtcttgggcatcactggctatttcctgatgaatcgccgcagctggagcccat ttaa GFP of donor construct for inserting into CD3ε locus

SEQ ID NO: 3058

ATGGTGAGCAAGGGCGAGGAGCTGTTCACCGGGGTGGTGCCCATCCTGGTCGAGCTGGACGGCGACGTAAACGGCCACAAGTTCAGCGT

GTCCGGCGAGGGCGAGGGCGATGCCACCTACGGCAAGCTGACCCTGAAGTTCATCTGCACCACCGGCAAGCTGCCCGTGCCCTGGCCCA

CCCTCGTGACCACCCTGACCTACGGCGTGCAGTGCTTCAGCCGCTACCCCGACCACATGAAGCAGCACGACTTCTTCAAGTCCGCCATG

CCCGAAGGCTACGTCCAGGAGCGCACCATCTTCTTCAAGGACGACGGCAACTACAAGACCCGCGCCGAGGTGAAGTTCGAGGGCGACAC

CCTGGTGAACCGCATCGAGCTGAAGGGCATCGACTTCAAGGAGGACGGCAACATCCTGGGGCACAAGCTGGAGTACAACTACAACAGCC

ACAACGTCTATATCATGGCCGACAAGCAGAAGAACGGCATCAAGGTGAACTTCAAGATCCGCCACAACATCGAGGACGGCAGCGTGCAG

CTCGCCGACCACTACCAGCAGAACACCCCCATCGGCGACGGCCCCGTGCTGCTGCCCGACAACCACTACCTGAGCACCCAGTCCGCCCT

GAGCAAAGACCCCAACGAGAAGCGCGATCACATGGTCCTGCTGGAGTTCGTGACCGCCGCCGGGATCACTCTCGGCATGGACGAGCTGT

ACAAGTAA

-continued hGMB poly A of donor construct for inserting GFP into CD3ε locus
SEQ ID NO: 3059
ACGGGTGGCATCCCTGTGACCCCTCCCCAGTGCCTCTCCTGGCCCTGGAAGTTGCCACTCCAGTGCCCACCAGCCTTGTCCTAATAAAA TTAAGTTGCATCATTTTGTCTGACTAGGTGTCCTTCTATAATATTATGGGGTGGAGGGGGGTGGTATGGAGCAAGGGGCAAGTTGGGAA GACAACCTGTAGGGCCTGCGGGGTCTATTGGGAACCAAGCTGGAGTGCAGTGGCACAATCTTGGCTCACTGCAATCTCCGCCTCCTGGG TTCAAGCGATTCTCCTGCCTCAGCCTCCCGAGTTGTTGGGATTCCAGGCATGCATGACCAGGCTCAGCTAATTTTTGTTTTTTTGGTAG AGACGGGGTTTCACCATATTGGCCAGGCTGGTCTCCAACTCCTAATCTCAGGTGATCTACCCACCTTGGCCTCCCAAATTGCTGGGATT

ACAGGCGTGAACCACTGCTCCCTTCCCTGTCCTTCTGATTTTGTAGGTAACCAC

CD3ε R homology ARM of donor construct for inserting GFP into CD3ε locus
SEQ ID NO: 3060
aGTAtaatattgacatgccctcagtatcctggatctgaaatactatggcaacacaatgataaaaacataggcggtgatgaggatgataa aaacataggcagtgatgaggatcacctgtcactgaaggaattttcagaattggagcaaagtggttattatgtctgctacccagaggaa gcaaaccagaagatgcgaacttttatctctacctgagggcaagagtgtgtgagaactgcatggagatggatgtgatgtcggtggccaca attgtcatagtggacatctgcatcactgggggcttgctgctgctggtttactactggagcaagaatagaaaggccaaggccaagcctgt gacacgaggagcgggtgctggcggcaggcaaaggggacaaaacaaggagaggccaccacctgttcccaacccagactatgagcccatcc ggaaaggccagcgggacctgtattctggcctgaatcagagacgcatctgaccctctggagaacactgcctcccgctggcccaggtctcc tctccagtcccctgcgactccctgtttcctgggctagtcttggaccccacgagagagaatcgttcctcagcctcatggtgaactcgcg ccctccagcctgatccccgctccctcctccctgccttctctgctggtacccagtcctaaaatattgctgcttcctcttcctttgaagc atcatcagtagtcacaccctcacagctggcctgccctcttgccaggatatttatttgtgctattcactccctttcctttggatgtaact tctccgttcagttccctccttttcttgcatgtaagttgtcccccatcccaaagtattccatctacttttctatcgccgtccccttttgc agccctctctggggatggactgggtaaatgttgacagaggccctgccccgttcacagatcctggccctgagccagccctgtgctcctcc ctcccccaacactccctaccaacc cloning remnants of donor construct for inserting GFP into CD3ε locus
SEQ ID NO: 3061
GCGgacCGAGCGGCCGC right ITR of donor construct for inserting GFP into CD3ε locus
SEQ ID NO: 3062
AGGAACCCCTAGTGATGGAGTTGGCCACTCCCTCTCTGCGCGCTCGCTCGCTCACTGAGGCCGGGCGACCAAAGGTCGCCCGACGCCCG

GGCTTTGCCCGGGCGGCCTCAGTGAGCGAGCGAGCGCGCAGCTGCCTGCAGG cloning remnants of donor construct for inserting GFP into CD3ε locus
SEQ ID NO: 3063
CCTGCAGGCAGCTGCGCGCTCGCTCGCTCACTGAGGCCGCCCGGGCGTCGGGCGACCTTTGGTCGCCCGGCCTCAGTGAGCGAGCGAGC GCGCAGAGAGGGAGTGGCCAACTCCATCACTAGGGGTTCCTGCGGCCGCATCGATTGaattcAGGTAAGTCCACGAATCAGTGATTCAG TGGTGTGGAGAGCTTTATTTCTGAGAAGGCCAGTAGCGCTCCCTTCTGACAAGCAAATCTAAGACCTGGATGACAGATGACTTCCTGCA TTTGGTTGGTTCTTTTGTCATTCATATCTATCTGTAATACAGTTCTGGCTAATTTAAGAGGATAAGCTTGAAGACCTCTGGAATTTTTC GGCTTTAGGACTTTAAGGCTTTCTGAGCTTCAGTAGATCTAGATCTAGGAGCTCATGCTGGTATATTCTGAATCCGATGTATCTGAGTT ACATCTATGAGCTACTTAATAAATATATCTATGAGCTAAATCTCATAGGCTAAGCATGAACCTCACCTCCAAGACTCGGGGTTCCTAAA TGGATGAGACCCTCTTTGGGAAGTCTTGTGGGCAGTGTCTAATTCCACTAGAAAAGTTTTACCTACAATTTAAACTTAAACCATGATAT TTTCTTACTGCTGTTTCCTTTTTTCATTTTCAGGTGGTATTACACAGACACGTGAGTTTATTGGTCTTTTATTTATGCCCTGTCTGAGG ATGCAGATTGGTGGGTAGATGAGAAGGAACTGATGAGAGAGATTAACCCCAAGAACTGATATCTTCCCAGCATTGCATTCTCAACTCC ATTTTAGAAAGGTTCCAAATAGGGACTTCTGTGGGTTTTTCTTTACATCCATCTTACCCTTCCCAAGTCCCCATGTCCCTGCGTAAACC CTAAAGCCACCTCTCAAAAGGTTCTCTAGTTCCCTTCAAGGTTCTCTAGTTCCCTTCATTCCACATATCTCCTCTTCCACACCCTCTAG CCAGTAGAGCTCCCTTCTGACAAGCAAGTCTAAGATCTAGATGACAGATGACTTCCTGCATTTGGGTGGTTCTTTTGTCACTAATTTGC CTTTTCTAAAATTGTCCTGGTTTCTTCTGCCAATTTCCCTTCTTTCTCCCCAGCATATAAAGTCTCCATCTCTGGAACCACAATGGTGA GCAAGGGCGAGGAGCTGTTCACCGGGGTGGTGCCCATCCTGGTCGAGCTGGACGGCGACGTAAACGGCCACAAGTTCAGCGTGTCCGGC GAGGGCGAGGGCGATGCCACCTACGGCAAGCTGACCCTGAAGTTCATCTGCACCACCGGCAAGCTGCCCGTGCCCTGGCCCACCCTCGT

```
GACCACCCTGACCTACGGCGTGCAGTGCTTCAGCCGCTACCCCGACCACATGAAGCAGCACGACTTCTTCAAGTCCGCCATGCCCGAAG
GCTACGTCCAGGAGCGCACCATCTTCTTCAAGGACGACGGCAACTACAAGACCCGCGCCGAGGTGAAGTTCGAGGGCGACACCCTGGTG
AACCGCATCGAGCTGAAGGGCATCGACTTCAAGGAGGACGGCAACATCCTGGGGCACAAGCTGGAGTACAACTACAACAGCCACAACGT
CTATATCATGGCCGACAAGCAGAAGAACGGCATCAAGGTGAACTTCAAGATCCGCCACAACATCGAGGACGGCAGCGTGCAGCTCGCCG
ACCACTACCAGCAGAACACCCCCATCGGCGACGGCCCCGTGCTGCTGCCCGACAACCACTACCTGAGCACCCAGTCCGCCCTGAGCAAA
GACCCCAACGAGAAGCGCGATCACATGGTCCTGCTGGAGTTCGTGACCGCCGCCGGGATCACTCTCGGCATGGACGAGCTGTACAAGTA
AACGGGTGGCATCCCTGTGACCCCTCCCCAGTGCCTCTCCTGGCCCTGGAAGTTGCCACTCCAGTGCCCACCAGCCTTGTCCTAATAAA
ATTAAGTTGCATCATTTTGTCTGACTAGGTGTCCTTCTATAATATTATGGGGTGGAGGGGGGTGGTATGGAGCAAGGGGCAAGTTGGGA
AGACAACCTGTAGGGCCTGCGGGGTCTATTGGGAACCAAGCTGGAGTGCAGTGGCACAATCTTGGCTCACTGCAATCTCCGCCTCCTGG
GTTCAAGCGATTCTCCTGCCTCAGCCTCCCGAGTTGTTGGGATTCCAGGCATGCATGACCAGGCTCAGCTAATTTTTGTTTTTTTGGTA
GAGACGGGGTTTCACCATATTGGCCAGGCTGGTCTCCAACTCCTAATCTCAGGTGATCTACCCACCTTGGCCTCCCAAATTGCTGGGAT
TACAGGCGTGAACCACTGCTCCCTTCCCTGTCCTTCTGATTTTGTAGGTAACCACaGTAtaatattgacatgccctcagtatcctggat
ctgaaatactatggcaacacaatgataaaaacataggcggtgatgaggatgataaaaacataggcagtgatgaggatcacctgtcactg
aaggaattttcagaattggagcaaagtggttattatgtctgctaccccagaggaagcaaaccagaagatgcgaacttttatctctacct
gagggcaagagtgtgtgagaactgcatggagatggatgtgatgtcggtggccacaattgtcatagtggacatctgcatcactgggggct
tgctgctgctggtttactactggagcaagaatagaaaggccaaggccaagcctgtgacacgaggagcgggtgctggcggcaggcaaagg
ggacaaaacaaggagaggccaccacctgttcccaacccagactatgagcccatccggaaaggccagcgggacctgtattctggcctgaa
tcagagacgcatctgaccctctggagaacactgcctcccgctggcccaggtctcctctccagtcccctgcgactccctgtttcctggg
ctagtcttggacccacgagagagaatcgttcctcagcctcatggtgaactcgcgccctccagcctgatccccgctccctcctccctg
ccttctctgctggtacccagtcctaaaatattgctgcttcctcttcctttgaagcatcatcagtagtcacaccctcacagctggcctgc
cctcttgccaggatatttatttgtgctattcactcccttcccttggatgtaacttctccgttcagttccctcctttcttgcatgtaa
gttgtcccccatcccaaagtattccatctactttctatcgccgtccccttttgcagccctctctggggatggactgggtaaatgttga
cagaggccctgcccgttcacagatcctggccctgagccagccctgtgctcctcctcccccaacactccctaccaaccGCGgacCGAG
CGGCCGCAGGAACCCCTAGTGATGGAGTTGGCCACTCCCTCTCTGCGCGCTCGCTCGCTCACTGAGGCCGGGCGACCAAAGGTCGCCCG
ACGCCCGGGCTTTGCCCGGGCGGCCTCAGTGAGCGAGCGAGCGCGCAGCTGCCTGCAGG
``` complete sequence of vector for insertion of GFP into CD3e locus

SEQ ID NO: 3064

```
CCTGCAGGCAGCTGCGCGCTCGCTCGCTCACTGAGGCCGCCCGGGCGTCGGGCGACCTTTGGTCGCCCGGCCTCAGTGAGCGAGCGAGC
GCGCAGAGAGGGAGTGGCCAACTCCATCACTAGGGGTTCCTGCGGCCGCATCGATTGaattcAGGTAAGTCCACGAATCAGTGATTCAG
TGGTGTGGAGAGCTTTATTTCTGAGAAGGCCAGTAGCGCTCCCTTCTGACAAGCAAATCTAAGACCTGGATGACAGATGACTTCCTGCA
TTTGGTTGGTTCTTTTGTCATTCATATCTATCTGTAATACAGTTCTGGCTAATTTAAGAGGATAAGCTTGAAGACCTCTGGAATTTTTC
GGCTTTAGGACTTTAAGGCTTTCTGAGCTTCAGTAGATCTAGATCTAGGAGCTCATGCTGGTATATTCTGAATCCGATGTATCTGAGTT
ACATCTATGAGCTACTTAATAAATATATCTATGAGCTAAATCTCATAGGCTAAGCATGAACCTCACCTCCAAGACTCGGGGTTCCTAAA
TGGATGAGACCCTCTTTGGGAAGTCTTGTGGGCAGTGTCTAATTCCACTAGAAAAGTTTTACCTACAATTTAAACTTAAACCATGATAT
TTTCTTACTGCTGTTTCCTTTTTTCATTTTCAGGTGGTATTACACAGACACGTGAGTTTATTGGTCTTTTATTTATGCCCTGTCTGAGG
ATGCAGATTGGTGGGTAGATGAGAAGGAACTGATTGAGAGAGATTAACCCCAAGAACTGATATCTTCCCAGCATTGCATTCTCAACTCC
ATTTTAGAAAGGTTCCAAATAGGGACTTCTGTGGGTTTTTCTTTACATCCATCTTACCCTTCCCAAGTCCCCATGTCCCTGCGTAAACC
CTAAAGCCACCTCTCAAAAGGTTCTCTAGTTCCCTTCAAGGTTCTCTAGTTCCCTTCATTCCACATATCTCCTCTTCCACACCCTCTAG
CCAGTAGAGCTCCCTTCTGACAAGCAAGTCTAAGATCTAGATGACAGATGACTTCCTGCATTTGGGTGGTTCTTTTGTCACTAATTTGC
CTTTTCTAAAATTGTCCTGGTTTCTTCTGCCAATTTCCCTTCTTTCTCCCCAGCATATAAAGTCTCCATCTCTGGAACCACAatggcct
taccagtgaccgccttgctcctgccgctggccttgctgctccacgccgccaggccggatatccagatgacacagactacatcctccctg
```

-continued tctgcctctctgggagacagagtcaccatcagttgcagtgcaagtcagggcattagcaattatttaaactggtatcagcagaaaccaga
tggaactgttaaactcctgatctattacacatcaagtttacactcaggagtcccatcaaggttcagtggcagtgggtctgggacagatt
attctctcaccatcagcaacctggaacctgaagatattgccacttattattgtcagcagtatagcaagcttccgtacacgttcggaggg
gggaccaagctggaaataaaacgtggtggtggtggttctggtggtggtggttctggcggcggcggctccggtggtggtggatccgaggt
gcaactggtggagtctgggggaggcttagtgaagcctgggggtccctgaaactctcctgtgcagcctctggactcactttcagtagct
atgccatgtcttgggttcgccagactccagagaagaggctggagtgggtcgcatccattagtagtggtggtttcacctactatccagac
agtgtgaagggccgattcaccatctccagagataatgccaggaacatcctgtatctgcaaatgagcagtctgaggtctgaggacacggc
catgtattactgtgcaagagacgaggtacgggggtacctcgatgtctggggcgcagggaccacggtcaccgtttcccctaggGCTAGCa
ccacgacgccagcgccgcgaccaccaacaccggcgcccaccatcgcgtcgcagcccctgtccctgcgcccagaggcgtgccggccagcg
gcggggggcgcagtgcacacgaggggctggacttcgcctgtgattttgggtgctggtggtggttggtggagtcctggcttgctatag
cttgctagtaacagtggcctttattattttctgggtgaggagtaagaggagcaggctcctgcacagtgactacatgaacatgactcccc
gccgcccgggcccacccgcaagcattaccagccctatgccccaccacgcgacttcgcagcctatcgctccagagtgaagttcagcagg
agcgcagacgcccccgcgtacaagcagggccagaaccagctctataacgagctcaatctaggacgaagagaggagtacgatgttttgga
caagagacgtggccgggaccctgagatgggggaaagccgagaaggaagaaccctcaggaaggcctgtacaatgaactgcagaaagata
agatggcggaggcctacagtgagattgggatgaaaggcgagcgccggaggggcaaggggcacgatggcctttaccagggtctcagtaca
gccaccaaggacacctacgacgcccttcacatgcaggccctgccccctcgcCGGACCGATggaagcggagctactaacttcagcctgct
gaagcaggctggagacgtggaggagaaccctggacctgtttctgaagccatgccgcggggctggaccgcgctttgcttgctgagtttgc
tgccttctgggttcatgagtcttgacaacaacggtactgctaccccagagttacctacccagggaacattttcaaatgtttctacaaat
gtatcctaccaagaaactacaacacctgtacccttggaagtaccagcctgcaccctgtgtctcaacatggcaatgaggccacaacaaa
catcacagaaacgacagtcaaattcacatctacctctgtgataacctcagtttatggaaacacaaactcttctgtccagtcacagacct
ctgtaatcagcacagtgttcaccaccccagccaacgtttcaactccagagacaaccttgaagcctagcctgtcacctggaaatgtttca
gacctttcaaccactagcactagccttgcaacatctcccactaaaccctatacatcatcttctcctatcctaagtgacatcaaggcaga
aatcaaatgttcaggcatcagagaagtgaaattgactcagggcatctgcctggagcaaaataagacctccagctgtgcggagtttaaga
aggacaggggagagggcctggcccgagtgctgtgtggggaggagcaggctgatgctgatgctggggcccaggtatgctccctgctcctt
gcccagtctgaggtgaggcctcagtgtctactgctggtcttggccaacagaacagaaatttccagcaaactccaacttatgaaaaagca
ccaatctgacctgaaaaagctggggatcctagatttcactgagcaagatgttgcaagccaccagagctattcccaaaagaccctgattg
cactggtcacctcgggagccctgctggctgtcttgggcatcactggctatttcctgatgaatcgccgcagctggagcccatttaaACG
GGTGGCATCCCTGTGACCCCTCCCCAGTGCCTCTCCTGGCCCTGGAAGTTGCCACTCCAGTGCCCACCAGCCTTGTCCTAATAAAATTA
AGTTGCATCATTTTGTCTGACTAGGTGTCCTTCTATAATATTATGGGGTGGAGGGGGGTGGTATGGAGCAAGGGGCAAGTTGGGAAGAC
AACCTGTAGGGCCTGCGGGGTCTATTGGGAACCAAGCTGGAGTGCAGTGGCACAATCTTGGCTCACTGCAATCTCCGCCTCCTGGGTTC
AAGCGATTCTCCTGCCTCAGCCTCCCGAGTTGTTGGGATTCCAGGCATGCATGACCAGGCTCAGCTAATTTTTGTTTTTTTGGTAGAGA
CGGGGTTTCACCATATTGGCCAGGCTGGTCTCCAACTCCTAATCTCAGGTGATCTACCCACCTTGGCCTCCCAAATTGCTGGGATTACA
GGCGTGAACCACTGCTCCCTTCCCTGTCCTTCTGATTTTGTAGGTAACCACaGTAtaatattgacatgccctcagtatcctggatctga
aatactatggcaacacaatgataaaaacataggcggtgatgaggatgataaaaacataggcagtgatgaggatcacctgtcactgaagg
aattttcagaattggagcaaagtggttattatgtctgctaccccagaggaagcaaaccagaagatgcgaacttttatctctacctgagg
gcaagagtgtgtgagaactgcatggagatggatgtgatgtcggtggccacaattgtcatagtggacatctgcatcactggggcttgct
gctgctggtttactactggagcaagaatagaaaggccaaggccaagcctgtgacacgaggagcgggtgctggcggcaggcaaaggggac
aaaacaaggagaggccaccacctgttcccaacccagactatgagcccatccggaaaggccagcgggacctgtattctggcctgaatcag
agacgcatctgaccctctggagaacactgcctcccgctggcccaggtctcctctccagtcccctgcgactccctgtttcctgggctag
tcttggaccccacgagagagaatcgttcctcagcctcatggtgaactcgcgcccctccagcctgatcccccgctccctcctccctgcctt
ctctgctggtacccagtcctaaaatattgctgcttcctcttccttttgaagcatcatcagtagtcacaccctcacagctggcctgccctc -continued

```
ttgccaggatatttatttgtgctattcactcccttcccttttggatgtaacttctccgttcagttccctcctttcttgcatgtaagttg tcccccatcccaaagtattccatctacttttctatcgccgtccccttttgcagccctctctggggatggactgggtaaatgttgacaga ggccctgcccgttcacagatcctggccctgagccagccctgtgctcctcctcccccaacactccctaccaaccGCGgacCGAGCGGC CGCAGGAACCCCTAGTGATGGAGTTGGCCACTCCCTCTCTGCGCGCTCGCTCGCTCACTGAGGCCGGGCGACCAAAGGTCGCCCGACGC

CCGGGCTTTGCCCGGGCGGCCTCAGTGAGCGAGCGAGCGCGCAGCTGCCTGCAGG
```

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

| | | | | | | | | | | | | | |
|---|---|---|---|---|---|---|---|---|---|---|---|---|---|
| E | 0.172 | 0.17 | 0.073 | 0.075 | 0.085 | 0.084 | 0.492 | 0.557 | 0.42 | 0.18 | 0.247 | 0.19 | 450 [Test] |
| | 0.046 | 0.045 | 0.044 | 0.046 | 0.045 | 0.045 | 0.05 | 0.053 | 0.05 | 0.048 | 0.048 | 0.047 | 540 [Ref] |
| | 0.698 | 0.691 | 0.161 | 0.161 | 0.222 | 0.216 | 2.46 | 2.796 | 2.054 | 0.735 | 1.107 | 0.794 | Pathlength |
| | 0.171 | 0.17 | 0.073 | 0.075 | 0.085 | 0.084 | 0.496 | 0.558 | 0.42 | 0.181 | 0.249 | 0.19 | 450 |
| | 0.046 | 0.046 | 0.045 | 0.047 | 0.045 | 0.045 | 0.05 | 0.053 | 0.051 | 0.048 | 0.049 | 0.047 | 540 |
| | 0.245 | 0.246 | 0.454 | 0.468 | 0.383 | 0.389 | 0.202 | 0.2 | 0.204 | 0.246 | 0.225 | 0.239 | Corrected [450] |
| | 0.066 | 0.066 | 0.277 | 0.291 | 0.204 | 0.209 | 0.02 | 0.019 | 0.025 | 0.066 | 0.044 | 0.059 | Corrected [540] |
| F | 0.127 | 0.124 | 0.07 | 0.074 | 0.075 | 0.072 | 0.148 | 0.143 | 0.128 | 0.102 | 0.115 | 0.121 | 450 [Test] |
| | 0.044 | 0.045 | 0.043 | 0.047 | 0.046 | 0.044 | 0.055 | 0.057 | 0.045 | 0.045 | 0.051 | 0.048 | 540 [Ref] |
| | 0.458 | 0.436 | 0.147 | 0.15 | 0.162 | 0.157 | 0.516 | 0.479 | 0.463 | 0.316 | 0.353 | 0.406 | Pathlength |
| | 0.127 | 0.124 | 0.07 | 0.074 | 0.075 | 0.072 | 0.147 | 0.144 | 0.129 | 0.102 | 0.116 | 0.12 | 450 |
| | 0.045 | 0.045 | 0.044 | 0.047 | 0.046 | 0.044 | 0.055 | 0.057 | 0.045 | 0.045 | 0.052 | 0.048 | 540 |
| | 0.277 | 0.283 | 0.475 | 0.493 | 0.465 | 0.462 | 0.286 | 0.3 | 0.278 | 0.323 | 0.328 | 0.296 | Corrected [450] |
| | 0.097 | 0.104 | 0.297 | 0.314 | 0.285 | 0.283 | 0.106 | 0.119 | 0.097 | 0.144 | 0.147 | 0.119 | Corrected [540] |
| G | 0.098 | 0.1 | 0.078 | 0.073 | 0.104 | 0.122 | 0.143 | 0.169 | 0.144 | 0.125 | 0.134 | 0.131 | 450 [Test] |
| | 0.044 | 0.044 | 0.046 | 0.044 | 0.045 | 0.05 | 0.049 | 0.049 | 0.05 | 0.05 | 0.045 | 0.046 | 540 [Ref] |
| | 0.301 | 0.313 | 0.179 | 0.161 | 0.326 | 0.398 | 0.523 | 0.667 | 0.523 | 0.415 | 0.493 | 0.469 | Pathlength |
| | 0.099 | 0.101 | 0.078 | 0.073 | 0.103 | 0.122 | 0.144 | 0.169 | 0.144 | 0.125 | 0.133 | 0.13 | 450 |
| | 0.044 | 0.044 | 0.046 | 0.044 | 0.045 | 0.05 | 0.05 | 0.049 | 0.05 | 0.05 | 0.045 | 0.045 | 540 |
| | 0.328 | 0.322 | 0.437 | 0.452 | 0.317 | 0.306 | 0.275 | 0.254 | 0.275 | 0.301 | 0.269 | 0.277 | Corrected [450] |
| | 0.148 | 0.142 | 0.259 | 0.272 | 0.138 | 0.127 | 0.095 | 0.074 | 0.096 | 0.12 | 0.091 | 0.096 | Corrected [540] |
| H | 0.082 | 0.087 | 0.113 | 0.12 | 0.074 | 0.081 | 0.165 | 0.169 | 0.15 | 0.103 | 0.122 | 0.119 | 450 [Test] |
| | 0.047 | 0.051 | 0.049 | 0.047 | 0.047 | 0.053 | 0.055 | 0.059 | 0.045 | 0.044 | 0.046 | 0.044 | 540 [Ref] |
| | 0.197 | 0.197 | 0.356 | 0.406 | 0.15 | 0.157 | 0.611 | 0.607 | 0.579 | 0.329 | 0.422 | 0.412 | Pathlength |
| | 0.082 | 0.087 | 0.113 | 0.12 | 0.074 | 0.081 | 0.165 | 0.169 | 0.15 | 0.103 | 0.122 | 0.118 | 450 |
| | 0.047 | 0.052 | 0.049 | 0.047 | 0.047 | 0.053 | 0.055 | 0.06 | 0.046 | 0.044 | 0.046 | 0.045 | 540 |
| | 0.415 | 0.443 | 0.316 | 0.296 | 0.493 | 0.516 | 0.27 | 0.279 | 0.259 | 0.314 | 0.289 | 0.288 | Corrected [450] |
| | 0.236 | 0.263 | 0.137 | 0.117 | 0.311 | 0.338 | 0.09 | 0.098 | 0.079 | 0.134 | 0.11 | 0.109 | Corrected [540] |

SEQUENCE LISTING

The patent contains a lengthy sequence listing. A copy of the sequence listing is available in electronic form from the USPTO web site (https://seqdata.uspto.gov/?pageRequest=docDetail&DocID=US12304941B2). An electronic copy of the sequence listing will also be available from the USPTO upon request and payment of the fee set forth in 37 CFR 1.19(b)(3).

What is claimed is:

1. A chimeric antigen receptor (CAR)-bearing effector T cell that is deficient in CD40LG.

2. The cell as recited in claim 1, wherein the CD40LG deficiency is effected by deletion or suppression of a gene encoding CD40LG, or by suppression of a gene transcript of CD40LG.

3. The cell as recited in claim 2, wherein the deletion or suppression of the gene encoding CD40LG effected by inserting a nucleic acid encoding the CAR into a locus of the CD40LG gene, or wherein the suppression of the gene transcript of CD40LG is effected by transfection of one or more types of small interfering RNAs (siRNA) or by transduction of one or more types of short hairpin RNAs (shRNA).

4. The cell as recited in claim 3, wherein the CAR is part of a construct that also includes a selectable marker chosen from a green fluorescence (GFP) gene, a YFP gene, a tCD34 gene, or a tEGFR gene.

5. The cell as recited in claim 2, wherein deletion or suppression is effected using CRISPR, Cas9-CRISPR, Transcription Activator-like Effector Nucleases (TALENs), Zinc Finger Nucleases (ZFNs), or Clustered Regularly Interspaced Short Palindromic Repeats (CRISPR).

6. The cell as recited in claim 5, wherein the Cas9 is delivered into the cell as mRNA or protein, and/or wherein a guide RNA (gRNA) targeting the gene to be deleted or suppressed is delivered contemporaneously with the Cas9.

7. The cell as recited in claim 6, wherein the gRNA targeting the gene comprises the nucleotide sequence set forth in one of SEQ ID NO: 252, SEQ ID NO: 253, and SEQ ID NO: 254.

8. The cell of claim 2, wherein:
the cell expresses at least one CAR, wherein the nucleic acid encoding the CAR is inserted into a locus of the CD40LG gene;
the gene encoding CD40LG is deleted or suppressed by a method chosen from Transcription Activator-like Effector Nucleases (TALENs), Zinc Finger Nucleases (ZFNs), and Clustered Regularly Interspaces Short Palindromic Repeats (CRISPR) editing;
CD40LG is suppressed by expression of an scFv with an endoplasmic reticulum (ER) binding tether to bind in the ER and prevent secretion;
the CD40LG gene transcript is suppressed by transfection of small interfering RNAs (siRNAs);
the CD40LG gene transcript is suppressed by transduction of short hairpin RNAs (shRNAs).

9. The cell as recited in claim 1, wherein the chimeric antigen receptor(s) specifically binds at least one antigen expressed on a malignant cell, a malignant T cell, a malignant B cell, a malignant mesothelial cell, or a malignant plasma cell.

10. The cell as recited in claim 9, wherein the at least one antigen expressed on a malignant cell is chosen from BCMA, CS1, CD38, CD138, CD19, CD33, CD123, CD371, CD117, CD135, Tim-3, CD5, CD7, CD2, CD4, CD3, CD79A, CD79B, APRIL, CD56, and CD1a; or
wherein the at least one antigen expressed on a malignant T cell is chosen from CD2, CD38, CD4, CD5, CD7, TCRA, and TCRβ; or
wherein the at least one antigen expressed on a malignant B cell is chosen from CD19, CD20, CD21, CD22, CD23, CD24, CD25, CD27, CD38, and CD45; or
wherein the at least one antigen expressed on a malignant mesothelial cell is mesothelin; or
wherein the at least one antigen expressed on a malignant plasma cell is chosen from BCMA, CS1, CD38, and CD19.

11. The cell as recited in claim 9, wherein the chimeric antigen receptor expresses the extracellular portion of the APRIL protein, the ligand for BCMA and TACI, effectively co-targeting both BCMA and TACI.

12. The cell as recited in claim 1, wherein endogenous T cell receptor mediated signaling is negligible in the cell.

13. The cell as recited in claim 12, wherein the cell does not induce alloreactivity, graft-versus-host disease, or fratricide.

14. A method of treatment of cancer in a patient, which has a reduced incidence of cytokine release syndrome and/or CAR-T associated neuropathy, comprising the administration of cells as recited in claim 1.

15. The method as recited in claim 14, wherein the cancer is a hematologic malignancy chosen from a T-cell malignancy, multiple myeloma, or acute myeloid leukemia (AML), or a solid tumor chosen from cervical cancer, pancreatic cancer, ovarian cancer, mesothelioma, or lung cancer.

* * * * *